(12) United States Patent
Zieler et al.

(10) Patent No.: US 8,614,089 B2
(45) Date of Patent: Dec. 24, 2013

(54) CENTROMERE SEQUENCES AND MINICHROMOSOMES

(75) Inventors: Helge Zieler, Encinitas, CA (US); Gary W. Rudgers, Indianapolis, IN (US); Gregory P. Copenhaver, Chapel Hill, NC (US); Daphne Preuss, Chicago, IL (US); Michael H. Pauly, Del Mar, CA (US)

(73) Assignee: Chromatin, Inc., Chicago, IL (US)

( * ) Notice: Subject to any disclaimer, the term of this patent is extended or adjusted under 35 U.S.C. 154(b) by 357 days.

(21) Appl. No.: 12/531,287

(22) PCT Filed: Mar. 14, 2008

(86) PCT No.: PCT/US2008/056993
§ 371 (c)(1),
(2), (4) Date: Jun. 21, 2010

(87) PCT Pub. No.: WO2008/112972
PCT Pub. Date: Sep. 18, 2008

(65) Prior Publication Data
US 2010/0297769 A1    Nov. 25, 2010

Related U.S. Application Data

(60) Provisional application No. 60/918,258, filed on Mar. 15, 2007, provisional application No. 60/951,351, filed on Jul. 23, 2007.

(51) Int. Cl.
*C12N 15/82* (2006.01)
*C12N 15/00* (2006.01)
*C12N 15/09* (2006.01)
*A01H 5/00* (2006.01)

(52) U.S. Cl.
USPC ........ 435/320.1; 435/419; 435/468; 800/278; 800/295

(58) Field of Classification Search
None
See application file for complete search history.

(56) References Cited

U.S. PATENT DOCUMENTS

| | | | |
|---|---|---|---|
| 4,889,806 A | 12/1989 | Olson et al. | |
| 5,270,201 A * | 12/1993 | Richards et al. | 435/418 |
| 5,288,625 A | 2/1994 | Hadlaczky et al. | |
| 5,316,931 A | 5/1994 | Donson et al. | |
| 5,491,076 A | 2/1996 | Carrington et al. | |
| 5,530,187 A | 6/1996 | Lamb et al. | |
| 5,589,379 A | 12/1996 | Kridl et al. | |
| 5,650,303 A | 7/1997 | Kridl et al. | |
| 5,695,967 A | 12/1997 | Van Bokkelen et al. | |
| 5,712,134 A | 1/1998 | Hadlaczky et al. | |
| 5,721,118 A | 2/1998 | Scheffler | |
| 5,733,744 A | 3/1998 | Hamilton | |
| 5,766,885 A | 6/1998 | Carrington et al. | |
| 5,773,705 A | 6/1998 | Vierstra et al. | |
| 5,866,793 A | 2/1999 | Baga et al. | |
| 5,869,294 A | 2/1999 | Harrington et al. | |
| 5,877,402 A | 3/1999 | Maliga et al. | |
| 5,891,625 A | 4/1999 | Buchardt et al. | |
| 5,891,691 A | 4/1999 | Hadlaczky et al. | |
| 5,925,808 A | 7/1999 | Oliver et al. | |
| 5,977,439 A | 11/1999 | Hamilton | |
| 5,977,441 A | 11/1999 | Oliver et al. | |
| 6,025,155 A | 2/2000 | Hadlaczky et al. | |
| 6,077,697 A | 6/2000 | Hadlaczky et al. | |
| 6,127,171 A | 10/2000 | Slilaty et al. | |
| 6,156,953 A | 12/2000 | Preuss et al. | |
| 6,162,963 A | 12/2000 | Kucherlapati et al. | |
| 6,265,211 B1 | 7/2001 | Choo et al. | |
| 6,277,608 B1 | 8/2001 | Hartley et al. | |
| 6,277,632 B1 | 8/2001 | Harney | |
| 6,291,243 B1 | 9/2001 | Fogarty et al. | |
| 6,337,431 B1 | 1/2002 | Tricoli et al. | |
| 6,348,353 B1 | 2/2002 | Harrington et al. | |
| 6,365,377 B1 | 4/2002 | Patten et al. | |
| 6,369,296 B1 | 4/2002 | Ratcliff et al. | |
| 6,376,234 B1 | 4/2002 | Grimsley et al. | |
| 6,376,745 B1 | 4/2002 | Atabekov et al. | |
| 6,388,168 B1 | 5/2002 | Maliga et al. | |
| 6,391,639 B1 | 5/2002 | Schenk et al. | |
| 6,455,315 B1 | 9/2002 | Baszczynski et al. | |
| 6,472,586 B1 | 10/2002 | Maliga et al. | |

(Continued)

FOREIGN PATENT DOCUMENTS

| | | |
|---|---|---|
| EP | 0 320 500 A2 | 6/1989 |
| EP | 0 338 266 A2 | 10/1989 |

(Continued)

OTHER PUBLICATIONS

Abdullah et al., Efficient plant regeneration from rice protoplasts through somatic embryogenesis, *BioTechnology*, 4: 1087-90 (1986).
Abel et al., Delay of disease development in transgenic plants that express the tobacco mosaic virus coat protein Gene, *Science*, 232: 738-43 (1986).
Adam et al., Retrofitting YACs for direct DNA transfer into plant cells, *Plant J.*, 11: 1349-58 (1997).
Alfenito et al., Molecular characterization of a maize B chromosome centric sequence, *Genetics*, 135: 589-97 (1993).
Alonso-Blanco et al., Development of AFLP based linkage map of Ler, Col and Cvi *Arabidopsis thaliana* ecotypes and construction of a Ler/Cvi recombinant inbred line population, *Plant J.*, 14: 259-71 (1998).

(Continued)

*Primary Examiner* — Brent T Page
(74) *Attorney, Agent, or Firm* — Marshall, Gerstein & Borun LLP

(57) ABSTRACT

The invention is generally related to methods of generating plants transformed with novel autonomous mini-chromosomes. Mini-chromosomes with novel compositions and structures are used to transform plants cells which are in turn used to generate the plant. Methods for generating the plant include methods for delivering the mini-chromosome into plant cell to transform the cell, methods for selecting the transformed cell, and methods for isolating plants transformed with the mini-chromosome. Plants generated in the present invention contain novel genes introduced into their genome by integration into existing chromosomes.

6 Claims, 5 Drawing Sheets

(56) References Cited

U.S. PATENT DOCUMENTS

| | | |
|---|---|---|
| 6,475,798 B2 | 11/2002 | Fogarty et al. |
| 6,495,318 B2 | 12/2002 | Harney |
| 6,514,693 B1 | 2/2003 | Lansdorp |
| 6,573,427 B1 | 6/2003 | Atabekov et al. |
| 2001/0008025 A1 | 7/2001 | Hadlaczky et al. |
| 2002/0028513 A1 | 3/2002 | Fogarty et al. |
| 2002/0034814 A1 | 3/2002 | Atabekov et al. |
| 2002/0059660 A1 | 5/2002 | Tricoli et al. |
| 2002/0072097 A1 | 6/2002 | Delcardayre et al. |
| 2002/0076811 A1 | 6/2002 | Okazaki et al. |
| 2002/0094574 A1 | 7/2002 | Hartley et al. |
| 2002/0108146 A1 | 8/2002 | Pang et al. |
| 2002/0111930 A1 | 8/2002 | Battles |
| 2002/0123053 A1 | 9/2002 | Luo et al. |
| 2002/0123145 A1 | 9/2002 | Ow |
| 2002/0128457 A1 | 9/2002 | Anderson et al. |
| 2002/0132348 A1 | 9/2002 | Bradshaw et al. |
| 2002/0151058 A1 | 10/2002 | Perkins et al. |
| 2002/0155530 A1 | 10/2002 | Szybalski et al. |
| 2002/0160410 A1 | 10/2002 | Hadlaczky et al. |
| 2002/0160970 A1 | 10/2002 | Hadlaczky et al. |
| 2002/0172997 A1 | 11/2002 | Hartley et al. |
| 2002/0174453 A1 | 11/2002 | Daniell et al. |
| 2002/0192819 A1 | 12/2002 | Hartley et al. |
| 2003/0003435 A1 | 1/2003 | DeJong et al. |
| 2003/0003466 A1 | 1/2003 | Harrington et al. |
| 2003/0022204 A1 | 1/2003 | Lansdorp |
| 2003/0032186 A1 | 2/2003 | Jorgensen et al. |
| 2003/0033617 A1 | 2/2003 | Hadlaczky et al. |
| 2003/0041353 A1 | 2/2003 | Daniell et al. |
| 2003/0049665 A1 | 3/2003 | Szybalski et al. |
| 2003/0064509 A1 | 4/2003 | Marynen et al. |
| 2003/0077804 A1 | 4/2003 | Byrd et al. |
| 2003/0083293 A1 | 5/2003 | Hadlaczky et al. |
| 2003/0084482 A1 | 5/2003 | Hall et al. |
| 2003/0088081 A1 | 5/2003 | Maliga et al. |
| 2003/0097678 A1 | 5/2003 | Kushinov et al. |
| 2003/0101480 A1 | 5/2003 | Hadlaczky et al. |
| 2003/0108914 A1 | 6/2003 | Hadlaczky |
| 2003/0124561 A1 | 7/2003 | Mach et al. |
| 2005/0268359 A1 | 12/2005 | Mach et al. |
| 2007/0271629 A1* | 11/2007 | Ananiev et al. .......... 800/278 |

FOREIGN PATENT DOCUMENTS

| | | |
|---|---|---|
| EP | 0 442 174 A1 | 8/1991 |
| EP | 0 552 829 A1 | 7/1993 |
| EP | 0 959 134 A1 | 11/1999 |
| EP | 1033405 A2 | 9/2000 |
| WO | WO-89/09219 A1 | 10/1989 |
| WO | WO-91/02066 A1 | 2/1991 |
| WO | WO-91/13994 A1 | 9/1991 |
| WO | WO-92/07080 A1 | 4/1992 |
| WO | WO-93/05165 A1 | 3/1993 |
| WO | WO-95/02319 A1 | 1/1995 |
| WO | WO-95/12669 A1 | 5/1995 |
| WO | WO-96/40965 A1 | 12/1996 |
| WO | WO-97/06250 A1 | 2/1997 |
| WO | WO-97/14026 A2 | 4/1997 |
| WO | WO-97/40183 A2 | 10/1997 |
| WO | WO-98/02562 A2 | 1/1998 |
| WO | WO-98/08964 A1 | 3/1998 |
| WO | WO-98/37223 A1 | 8/1998 |
| WO | WO-98/51790 A1 | 11/1998 |
| WO | WO-98/54342 A1 | 12/1998 |
| WO | WO-98/55637 A1 | 12/1998 |
| WO | WO-99/06581 A1 | 2/1999 |
| WO | WO-99/21977 A1 | 5/1999 |
| WO | WO-99/67374 A1 | 12/1999 |
| WO | WO-00/06715 A1 | 2/2000 |
| WO | WO-00/07431 A1 | 2/2000 |
| WO | WO-00/40723 A2 | 7/2000 |
| WO | WO-00/46350 A1 | 8/2000 |
| WO | WO-00/52155 A2 | 9/2000 |
| WO | WO-00/52183 A1 | 9/2000 |
| WO | WO-00/55325 A2 | 9/2000 |
| WO | WO-00/75289 A1 | 12/2000 |
| WO | WO-00/75299 A1 | 12/2000 |
| WO | WO-00/78985 A1 | 12/2000 |
| WO | WO-01/00858 A1 | 1/2001 |
| WO | WO-01/05962 A1 | 1/2001 |
| WO | WO-01/11020 A1 | 2/2001 |
| WO | WO-01/20011 A1 | 3/2001 |
| WO | WO-01/27241 A2 | 4/2001 |
| WO | WO-01/29241 A2 | 4/2001 |
| WO | WO-01/59091 A2 | 8/2001 |
| WO | WO-01/64024 A1 | 9/2001 |
| WO | WO-01/77357 A2 | 10/2001 |
| WO | WO-01/78976 A1 | 10/2001 |
| WO | WO-02/00842 A2 | 1/2002 |
| WO | WO-02/04629 A2 | 1/2002 |
| WO | WO-02/08409 A2 | 1/2002 |
| WO | WO-02/29068 A2 | 4/2002 |
| WO | WO-02/50288 A1 | 6/2002 |
| WO | WO-02/057464 A2 | 7/2002 |
| WO | WO-02/059296 A2 | 8/2002 |
| WO | WO-02/059330 A2 | 8/2002 |
| WO | WO-02/067655 A1 | 9/2002 |
| WO | WO-02/072849 A2 | 9/2002 |
| WO | WO-02/081710 A1 | 10/2002 |
| WO | WO-02/086144 A2 | 10/2002 |
| WO | WO-02/086146 A2 | 10/2002 |
| WO | WO-02/096923 A1 | 12/2002 |
| WO | WO-03/028014 A1 | 4/2003 |
| WO | WO-2005/010142 A2 | 2/2005 |
| WO | WO-2005/010187 A1 | 2/2005 |
| WO | WO-2005/083096 A1 | 9/2005 |
| WO | WO-2007/030510 A2 | 3/2007 |
| WO | WO-2007/137114 A2 | 11/2007 |

OTHER PUBLICATIONS

Ananiev et al., A knob-associated tandem repeat in maize capable of forming fold-back DNA segments:Are chromosome knobs megatransposons? *Proc. Natl. Acad. Sci. USA*, 95: 10785-90 (1998).

Ananiev et al., Chromosome-specific molecular organization of maize (*Zea mays* L.) centromeric regions, *Proc. Natl. Acad. Sci. USA*, 95: 13073-8 (1998).

Ananiev et al., Complex structure of knob DNA on maize chromosome 9: Retrotransposon invasion into heterochromatin, *Genetics*, 149: 2025-37 (1998).

Ananiev et al., Complex structure of knobs and centromeric regions in maize chromosomes, *Tsitol Genet.*, 34: 11-5 (2000).

Aragon-Alcaide et al., A cereal centromeric sequence, *Chromosoma*, 105: 261-8 (1996).

Araki et al., Site-specific recominanse, R, encoded by yeast plasmid pSR1, *J. Mol. Biol.*, 225: 25-37 (1992).

Areshchenkova et al., Long tomato microsatellites are predominantly associated with centromeric regions, *Genome*, 42: 536-44 (1999).

Armstrong et al., Physical mapping of DNA repetitive sequences to mitotic and meiotic chromosomes of *Brassica oleracea* var. *alboglabra* by fluorescence in situ hybridization, *Heredity*, 81: 666-73 (1998).

Barki-Golan et al., Studies on growth inhibition by lectins of penicillia and aspergilli, *Arch. Microbiol.*, 116: 119-24 (1978).

Baum et al., The centromeric K-type repeat and the central core are together sufficient to establish a functional schizosaccharomyces pombe centromere, *Molec. Biol. Cell*, 5: 747-61 (1994).

Bell et al., Assignment of 30 microsatellite loci to the linkage map of *Arabidopsis, Genomics*, 19: 137-44 (1994).

Bernal-Lugo et al., Changes in soluble carbohydrates during seed storage, *Plant Physiol.*, 98: 1207-10 (1992).

Berzal-Herranz et al., In vitro selection of active hairpin ribozymes by sequential RNA-catalyzed cleavage and ligation reactions, *Genes Dev.*, 6: 129-34 (1992).

Bevan et al., Clearing a path through the jungle: Progress in *Arabidopsis* genomics, *BioEssays*, 21: 110-20 (1999).

Bevan et al., Structure and transcription of the nopaline synthase gene region of T-DNA, *Nucl. Acids Res.*, 11: 369-85 (1983).

Birchler, Do these sequences make CENs yet? *Genome Res.*, 7: 1035-7 (1997).

(56) References Cited

OTHER PUBLICATIONS

Blackman et al., Maturation proteins and sugars in dessiccation tolerance of developing soybean seeds, *Plant Physiol.*, 100: 225-30 (1992).
Bloom, The Centromere frontier: Kinetochore components, microtubule-based motility, and the CEN-value paradox, *Cell*, 73: 621-4 (1993).
Bol et al., Plant pathogenesis-related proteins induced by virus infection, *Annu. Rev. Phytopath.*, 28: 113-38 (1990).
Bowler et al., Superoxide dismutase and stress tolerance, *Annu. Rev. Plant Physiol. Plant Mol. Biol.*, 43: 83-116 (1992).
Brandes et al., Multiple repetitive DNA sequences in the paracentromeric regions of *Arabidopsis thaliana* L., *Chromosome Res.*, 5: 238-46 (1997).
Branson et al., Potential for utilizing resistance from relatives of cultivated crops, *Proc. N. Cent. Branch Entomol. Soc. Am.*, 27: 91-5 (1972).
Brisson et al., Expression of a bacterial gene in plants by using a viral vector, *Nature*, 310: 511-6 (1984).
Broach et al., Transformation in yeast: Development of a hybrid cloning vector and isolation of the CAN1 gene, *Gene*, 8: 121-33 (1979).
Broekaert et al., A chitin-binding lectin from stinging nettle rhizomes with antifungal properties, *Science*, 245: 1100-2 (1989).
Broun et al., Characterization and genetic mapping of simple repeat sequences in the tomato genome, *Mol. Gen. Genet.*, 250: 39-49 (1996).
Buchowicz, Nuclear extrachromosomal DNA of higher plants, *Acta Biochim Pol.*, 44: 13-9 (1977).
Burke et al., Cloning of large segments of exogenous DNA into yeast by means of artificial chromosome vectors, *Science*, 236: 806-12 (1987).
Bytebier et al., T-DNA organization in tumor cultures and transgenic plants of the monocotyledon *Asparagus officinalis*, *Proc. Natl. Acad. Sci. USA*, 84: 5345-9 (1987).
Callis et al., Introns increase gene expression in cultured maize cells, *Genes Dev.*, 1: 1183-200 (1987).
Cambareri et al., Structure of the chromosome VII centromere region in *Neurospora crassa*: Degenerate transposons and simple repeats, *Molec. Cell. Biol.*, 18: 5465-77 (1998).
Campbell, The production and characterization of rodent and human hybridomas, *Lab. Tech. Biochem. Molec. Biol.*, 13: 75-83 (1984).
Capecchi, High efficiency transformation by direct microinjection of DNA into cultured mammalian cells, *Cell*, 22: 479-88 (1980).
Carbon et al., Centromere structure and function in budding and fission yeasts, *New Biologist*, 2: 10-9 (1990).
Carbon et al., Recombinant molecules: Impact on science and society, Raven Press: 335-78 (1977).
Carbon et al., Structural and functional analysis of a yeast centromere (CEN3), *J. Cell Sci.*, Suppl. 1, 43-58 (1984).
Carpenter et al., On the control of the distribution of meiotic exchange in *Drosophila melanogaster*, *Genetics*, 101: 81-9 (1982).
Cech et al., In vitro splicing of the ribosomal RNA precursor of tetrahymena: Involvement of a guanosine nucleotide in the excision of the intervening sequence, *Cell*, 27: 487-96 (1981).
Cepko et al., Construction and applications of a highly transmissible murine retrovirus shuttle vector, *Cell*, 37: 1053-62 (1984).
Chandler et al., Two regulatory genes of the maize anthocyanin pathway are homologous: Isolation of *B* utilizing *R* genomic sequences, *Plant Cell*, 1: 1175-83 (1989).
Chang et al., Restriction fragment length polymorphism linkage map for *Arabidopsis thaliana*, *Proc. Natl. Acad. Sci USA*, 85: 6856-60 (1988).
Charlesworth et al., The evolution of restricted recombination and the accumulation of repeated DNA sequences, *Genetics*, 112: 947-62 (1986).
Charlesworth et al., The evolutionary dynamics of repetitive DNA in eukaryotes, *Nature*, 371: 215-20 (1994).
Cheng et al., Functional rice centromeres are marked by a satellite repeat and a centromere-specific retrotransposon, *Plant Cell.*, 14: 1691-704 (2002).
Choi et al., Construction and characterization of a bacterial artificial chromosome library of *Arabidopsis thaliana*, *Plant Molec., Biol. Reporter*, 13: 124-9 (1995).
Choo, Turning on the centromere, *Nat. Genet.*, 18: 3-4 (1998).
Choo, Why is the centromere so cold? *Genome Res.*, 8: 81-2 (1998).
Chowrira et al., In vitro and in vivo comparison of hammerhead, hairpin, and hepatitis delta virus self-processing ribozyme cassettes, *J. Biol. Chem.*, 269: 25856-64 (1994).
Christou et al., Stable transformation of soybean callus by DNA-coated gold particles, *Plant Physiol.*, 87: 671-4 (1988).
Chu et al., Separation of large DNA molecules by contour-clamped homogenous electric fields, *Science*, 234: 1582-5 (1986).
Chye et al., Characterization of *TSCL*, a nonviral retroposon from *Arabidopsis thaliana*, *Plant Molec. Biol.*, 35: 893-904 (1997).
Clapp, Somatic gene therapy into hemotopoietic cells, *Clinics Perinatol.*, 20: 155-68 (1993).
Clarke et al., Analysis of centromeric DNA in the fission yeast *Schizosaccharomyces pombe*, *Proc. Natl. Acad. Sci. USA.*, 83:8253-7 (1986).
Clarke et al., Centromeres: Proteins, protein complexes, and repeated domains at centromeres of simple eukaryotes, *Genet. Dev.*, 8:212-8 (1998).
Clarke et al., Isolation of a yeast centromere and construction of functional small circular chromosomes, *Nature*, 287: 504-9 (1980).
Co et al., Generation of transgenic mice and germline transmission of a mammalian artificial chromosome introduced into embryos by pronuclear microinjection. *Chrom. Res.*, 8: 183-91 (2000).
Cohen et al., Construction of biologically functional bacterial plasmids in vitro, *Proc. Nat. Acad. Sci. USA*, 70: 3240-4 (1973).
Conkling et al., Isolation of transcriptionally regulated root-specific genes from tobacco, *Curr. Opin. Plant Physiol.*, 93: 1203-11 (1990).
Copenhaver et al., Assaying genome-wide recombination and centromere functions with *Arabidopsis* tetrads,*Proc. Natl. Acad. Sci. USA*, 95: 247-52 (1998).
Copenhaver et al., Centromeres in the genomic era: Unraveling paradoxes, *Plant Biol.*, 2: 104-8 (1999).
Copenhaver et al., Genetic definition and sequence analysis of *Arabidopsis* Centromeres, *Science*, 286: 2468-74 (1999).
Copenhaver et al., RFLP and physical mapping with an rDNA-specific endonuclease reveals that nucleolus organizer regions of *Arabidopsis thaliana* adjoin the telomeres on chromosomes 2 and 4, *Plant J.*, 9: 259-76 (1996).
Copenhaver et al., Tetrad analysis in higher plants: A budding technology, *Plant Physiol.*, 124: 7-16 (2000).
Copenhaver et al., Two-dimensional RFLP analyses reveal megabase-sized clusters of rRNA gene variants in *Arabidopsis thaliana*, suggesting local spreading of variants as the mode for gene homogenization during concerted evolution, *Plant J.*, 9: 273-82 (1996).
Copenhaver et al., Use of RFLPs larger than 100 kbp to map position and internal organization of the nucleolus organizer region on chromosome 2 in *Arabidopsis thaliana*, *Plant J.*, 7: 273-86 (1995).
Copenhaver, Using *Arabidopsis* to understand centromere function: Progress and prospects, *Chromosome Res.* 2993(11): 255-62 (2003).
Coxson et al., Pulse release of sugars and polyols from canopy bryophytes in tropical montane rain forest (Guadeloupe, French West Indies), *Biotropica*, 24: 121-33 (1992).
Creusot et al., The CIC Library: A large insert YAC library for genome mapping in *Arabidopsis thaliana*, *Plant J.*, 8: 763-70 (1995).
Cristou et al., Stable transformation of soybean callus by DNA-coated gold particles, *Plant Physiol.*, 87: 671-4 (1988).
Cuozzo et al., Viral protection in transgenic tobacco plants expressing the cucumber mosaic virus coat protein or its antisense RNA, *BioTechnology*, 6: 549-57 (1988).
Curiel et al., Adenovirus enhancement of transferrin-polylysine-mediated gene delivery, *Proc. Natl. Acad. Sci. USA*, 88: 8850-4 (1991).
Curiel et al., High-efficiency gene transfer mediated by adenovirus coupled to DNA-polylysine complexes, *Hum. Gen. Ther.*, 3:147-54 (1992).

(56) References Cited

OTHER PUBLICATIONS

Cutler et al., Winter flounder antifreeze protein improves the cold hardiness of plant tissues, *J. Plant Physiol.*, 135: 351-4 (1989).
Czapla et al., Effect of plant lectins on the larval development of European corn borer (*Lepidoptera: Pyralidae*) and southern corn rootworm (*Coleoptera: Chrysomelidae*), *J. Econ Entomol.*, 83: 2480-5 (1990).
Davies et al., Leaf senescence in a nonyellowing mutant of *Festuca pratensis*, *Plant Physiol.*, 93: 588-95 (1990).
Dawe et al., Centromeres put epigenetics in the driver's seat. *Trend Biochem. Sci.*, 31: 662-9 (2006).
Dellaporta et al., Molecular cloning of the maize R-nj allele by transposon tagging with Ac: Chromosome structure and function: impact of new concepts, 18th Stadler Genetics Symposium 11: 263-82 (1988).
Dennis et al., Knob heterochromatin homology in maize and its relatives, *J. Mol. Evol.*, 20: 341-50 (1984).
Depicker et al., A negative selection scheme for tobacco protoplast-derived cells expressing the T-DNA gene 2, *Plant Cell Reports*, 7: 63-6 (1988).
Di Laurenzio et al., The SCARECROW gene regulates an asymmetric cell division that is essential for generating the radial organization of the *Arabidopsis* Root, *Cell*, 86: 423-33 (1996).
Discussion with David Baltimore as Moderator, Recombinant Molecules: Impact on Science and Society: 337-352, New York (1977).
Donahue et al., The nucleotide sequence of the *HIS4* region of yeast, *Gene*, 18: 47-59 (1982).
Dong et al., Rice (*Oryza sativa*) centromeric regions consist of complex DNA, *Proc. Natl. Acad. Sci. USA*, 95: 8135-40 (1998).
Dure III et al., Common amino acid sequence domains among the LEA proteins of higher plants, *Plant Molec. Biol.*, 12: 475-86 (1989).
Dusart et al., A functional neo-centromere formed through activation of a latent human centromere and consisting of non-alpha satellite DNA, *Nat. Genet.*, 16: 144-53 (1997).
Earnshaw et al, Proteins of the inner and outer centromere of mitotic chromosomes, *Genome*, 31: 541-52 (1989).
Earnshaw et al., When is a centromere not a kinetochore? *J. Cell Sci.*, 99: 1-4 (1991).
Ebert et al., Identification of an essential upstream element in the nopaline synthase promoter by stable and transient assays, *Proc. Natl. Acad. Sci. USA*, 84: 5745-9 (1987).
Ecker, PFGE and YAC analysis of the *Arabidopsis* genome, *Methods* I: 186-94 (1990).
Eglitis et al., Retroviral vectors for introduction of genes into mammalian cells, *BioTechniques*, 6: 608-14 (1988).
Eglitis et al., Retroviral-mediated gene transfer into hemapoietic cells, *Avd. Exp. Med. Biol.*, 241: 19-27 (1988).
EMBL Accession No. AC138570, *Zea mays* genetic clone ZM16H10, finished contig 37375, complete sequence, Jan. 11, 2003.
EMBL Accession No. AC185251, *Zea mays* chromosome 4 clone CH201-478E6; ZMMBBc0478E06, Apr. 15, 2006.
EMBL Accession No. AY530257, *Zea mays* clone CentC42 centromeric repeat sequence, Feb. 28, 2004.
Enomoto et al., Mapping of the *pin* locus coding for a site-specific recombinase that causes flagellar-phase variation in *Escherichia coli* K-12, *J. Bacteriol.*, 156: 663-8 (1983).
Erdmann et al., Glycosylglycerol accumulation during salt acclimation of two unicellular cyanobacteria, *J. Gen. Microbiol.*, 138: 363-8 (1992).
Ferrin et al., Selective cleavage of human DNA: RecA-assisted restriction endonuclease (RARE) cleavage, *Science*, 254: 1494-7 (1991).
Fitzpatrick, Pleiotropic gene found in barley plant gene. *Engin. News*, 13(5): 1-22 (1993).
Fleig. et al., Functional selection for the centromere DNA from yeast chromosome VIII, *Nucl. Acids. Res.*, 23: 922-4 (1995).
Forster et al., Self-cleavage of plus and minus RNAs of a virusoid and a structural model for the active sites, *Cell*, 49: 211-20 (1987).
Fraley et al., The SEV system: A new disarmed TI plasmid vector system for plant transformation, *BioTechnology*, 3: 629-35 (1985).
Fransz et al., Cytogenetics for the model system *Arabidopsis thaliana*, *Plant J.*, 13: 867-76 (1998).
Fransz et al., Integrated cytogenetic map of chromosome arm 4S of *A. thaliana*: Structural organization of heterochromatic knob and centromere region, *Cell*, 100: 367-76 (2000).
Frary et al., Molecular mapping of the centromeres of tomato chromosomes 7 and 9, *Mol. Gen. Genet.*, 250: 295-304 (1996).
Fromm et al., Expression of genes transferred into monocot and dicot plant cells by electroporation, *Proc. Nat. Acad. Sci. USA*, 82: 5824-8 (1985).
Fromm et al., Stable transformation of maize after gene transfer by electroporation, *Nature*, 319: 791-3 (1986).
Fujimara et al, Regeneration of rice plants from protoplasts, *Plant Tissue Culture Letters*, 2: 74 (1985).
Fukui et al., Physical arrangement of retrotransposon-related repeats in centromeric regions of wheat, *Plant Cell Physiol.*, 42: 189-96 (2004).
Fynan et al., DNA vaccines: Protective immunizations by parenteral, mucosal, and gene-gun inoculations, *Proc. Natl. Acad. Sci. USA*, 90: 11478-82 (1993).
Ganal et al., A molecular and cytogenetic survey of major repeated DNA sequences in tomato (*Lycopersicon esculentum*), *Mol. Gen. Genet.*, 213: 262-8 (1988).
Gatehouse et al., Effect of seed lectins from *Phaseolus vulgaris* on the development of larvae of *Callosobruchus maculatus*; Mechanism of Toxicity, *J. Sci. Food. Agric.*, 35: 373-80 (1984).
Gefter et al., A simple method for polyethylene glycol-promoted hybridization of mouse myeloma cells, *Somatic Cell Genet*, 3: 231-6 (1977).
GenBank Accession No. AF139910.
GenBank Accession No. AF013103.
GenBank Accession No. AF049110.
GenBank Accession No. AF050437.
GenBank Accession No. AF050438.
GenBank Accession No. AF050452.
GenBank Accession No. AF050453.
GenBank Accession No. AF071126.
GenBank Accession No. AF078917.
GenBank Accession No. AF078922.
GenBank Accession No. AF078923.
GenBank Accession No. AF090447.
GenBank Accession No. AF123535.
GenBank Accession No. AF242891.
GenBank Accession No. AF273104.
GenBank Accession No. AF448416.
GenBank Accession No. AY129008.
GenBank Accession No. AY173950.
GenBank Accession No. AY321491.
GenBank Accession No. K01868.
GenBank Accession No. K02202.
GenBank Accession No. M35408.
GenBank Accession No. U39642.
GenBank Accession No. X01365.
Gerlach et al., Construction of a plant disease resistance gene from the satellite RNA of tobacco ringspot virus, *Nature*, 328: 802-5 (1987).
Gindullis et al., Construction and vharacterization of A BAC library for the molecular dissection of a single wild beet centromere and sugar beet (*Beta vulfaris*), *Genome Analysis*, 44: 846-55 (2001).
Gindullis et al., The large-scale organization of the centromeric region in beta species, *Genome Res.*, 11: 253-65 (2001).
Giordano et al., Identification by denaturing high-performance liquid chromatography of numerous polymorphisms in a candidate region for multiple sclerosis susceptibility, *Genomics*, 56: 247-53 (1999).
Goding (Ed.), *Monoclonal Antibodies: Principles and Practice*, Academic Press, Orlando, Florida, 60-74 (1986).
Golic et al., The FLP recombinase of yeast catalyzes site-specific recombination in the *Drosophila* genome, *Cell*, 59: 499-509 (1989).
Goring et al., Transformation of a partial nopaline synthase gene into tobacco suppresses the expression of a resident wild-type gene, *Proc. Natl. Acad. Sci. USA*, 88, 1770-4 (1991).
Graham et al., Transformation of rat cells by DNA of human adenovirus 5, *Virology*, 54: 536-9 (1973).

(56) References Cited

OTHER PUBLICATIONS

Grellet et al., Organization and evolution of a higher plant alphoid-like satellite DNA sequence, *J. Mol. Biol.*, 187: 495-507(1986).
Grill et al., Construction and characterization of a yeast artificial chromosome library of *Arabidopsis* which is suitable for chromosome walking, *Mol. Gen. Genet.*, 226: 484-90 (1991).
Guerrero et al., Turgo-responsive gene transcription and RNA levels increase rapidly when pea shoots are wilted. Sequence and expression of three inducible genes, *Plant Molec. Biol.*, 15:11-26 (1990).
Gupta et al., Increased resistance to oxidative stress in transgenic plants that overexpress chloroplastic Cu/Zn superoxide dismutase, *Proc. Natl. Acad. Sci. USA*, 90: 1629-33 (1993).
Gutierrez-Marcos et al., Three members of a novel small gene-family from *Arabidopsis thaliana* able to complement functionally an *Escherichia coli* mutant defective in PAPS reducatase activity encode proteins with a thioredoxin-like domain and APS reductase activity, *Proc. Natl. Acad. Sci USA*, 93: 13377-824 (1996).
Haaf et al., Integration of human satellite DNA into simian chromosomes: Centromere protein binding and disruption of normal chromosome segregation, *Cell*, 70: 681-96 (1992).
Hadlaczky et al., Centromere formation in mouse cells cotransformed with human DNA and a dominant marker gene, *Proc. Natl. Acad. Sci. USA*, 88: 8106-10 (1991).
Hall et al., The rapidly evolving field of plant centromeres, *Curr. Opin Plant Biol.*, 7108-14 (2002).
Hamilton et al., Stable transfer of intact high molecular weight DNA into plant chromosones, *Proc. Natl. Acad. Sci. USA*, 93: 9975-9(1996).
Hamilton, A binary BAC system for plant transformation with high-molecular-weight DNA, *Gene*, 4(200): 107-16 (1997).
Hammock et al., Expression and effects of the juvenile hormone esterase in a baculovirus vector, *Nature*, 344: 458-63 (1990).
Harrington et al., Formation of de novo centromeres and construction of first-generation human artificial microchromosomes, *Nat. Genet.*, 15: 345-54 (1997).
Harrison et al., Centromeric repetitive DNA sequences in the genus *Brassica, Theor. Appl. Genet*, 90:157-65 (1995).
Haseloff et al., Removal of a cryptic intron and subcellular localization of green fluorescent protein are required to mark transgenic *Arabidopsis* plants brightly, *Proc. Natl. Acad. Sci. USA*, 94: 2122-7 (1997).
Hauge et al., Mapping the *Arabidopsis* genome, *Symp. Society for Experimental Biology*, 45: 45-56 (1991).
Hegemann et al., The ceontromere of budding yeast, *BioEssays* 15: 451-60 (1998).
Heller et al., Mini-chromosomes derived from the human Y chromosome by telomere directed chromosome breakage, *Proc. Natl. Acad. Sci. USA*, 93:7125-30 (1996).
Hemenway et al., Analysis of the mechanism of protection in transgenic plants expressing the potato virus X coat protein or its antisense RNA, *EMBO J.*, 7: 1273-80 (1988).
Heslop-Harrison et al., Polymorphisms and genomic organization of repetitive DNA from centromeric regions of *Arabidopsis* chromosomes, *Plant Cell*, 11:31-42 (1999).
Hilder et al., A novel mechanism of insect resistance engineered into tobacco, *Nature*, 330: 160-3 (1987).
Hinchee et al., Production of transgenic soybean plants using *Agrobacterium*-mediated DNA transfer, *BioTechnology*, 6: 915-22 (1988).
Hoess et al., P1 site-specific recombination: Nucleotide sequence of the recombining sites, *Proc. Nat. Acad. Sci. USA*, 79: 3398-402 (1982).
Houben et al., DNA and proteins of plant centromeres, *Curr. Opin. Plant Biol.*, 6: 554-60 (2003).
Hsiao et al., High-frequency transformation of yeast by plasmids containing the cloned yeast ARG4 gene, *Proc. Natl. Acad. Sci. USA*, 76: 3829-33 (1979).
Hudakova et al., Sequence organization of barley centromeres, *Nucl. Acids Res.*, 29: 5029-35 (2001).
Hudspeth et al., Structure and expression of the maize gene encoding the phosphoenolpyruvate carboxylase isozyme involved in C4 photosynthesis, *Plant Molec. Biol.*, 12: 579-89 (1989).
Hwang et al., Identification and map position of YAC clones comprising one-third of the *Arabidopsis* genome, *Plant J.*, 1: 367-74 (1991).
Ikeda, et al., Genetic studies of avermectin biosynthesis in *Streptomyces avermitilis, J. Bacteriol.*, 16: 5615-21 (1987).
Ikeno, et al., Construction of YAC-based mammalian artificial chromosomes, *Nat. Biotechnol.*, 16: 431-9 (1998).
Ikuta et al., The alpha-amylase gene as a marker for gene cloning: Direct screening of recombinant clones, *BioTechnology*, 8: 241-2 (1990).
Inohara et al., Two genes, *atp*C1 and *atp*C2, for the subunit of *Arabidopsis thaliana* chloroplast ATP synthase, *J. Biol. Chem.*, 266: 7333-8 (1991).
Iwabuchi et al., Molecular and cytological characterization of repetitive DNS sequences in *Brassica. Theor. Appl. Genet.*, 81(3): 349-55 (1991).
Jiang et al., A conserved repetitive DNA element located in the centromeres of cereal chromosomes, *Proc. Natl. Acad. Sci. USA*, 93: 14210-3 (1996).
Jiang et al., A molecular view of plant centromeres, *Trends Plant Sci.*, 8: 570-5 (2003).
Jin et al., Maize-centromeres: Organization and functional adaptation in the genetic background of oat, department of horticulture, University of Wisconsin-Madison, Madison, Wisconsin 53706, USA, *Plant Cell*. 16:57-81 (2004).
Johnston et al., Gene gun transfection of animal cells and genetic immunization, *Meth. Cell Biol.*, 43: 353-63 (1994).
Jones et al., High level expression of introduced chimaeric genes in regenerated transformed plants, *EMBO J.* 4:2411-8 (1985).
Jones et al., T-DNA structure and gene expression in petunia plants transformed by *Agrobacterium tumafaciens* C58 derivatives, *Mol. Gen. Genet.*, 207: 478-85 (1987).
Jorgensen et al., T-DNA is organized predominantly in inverted repeat structures in plants transformed with *Agrobacterium tumafaciens* C58 derivatives, *Mol. Gen. Genet.*, 207: 471-7 (1987).
Jouanin et al., Localization and restriction maps of replication origin regions of the plasmids of *Agrobacterium rhizogenes* strain A$_4$, *Mol. Gen. Genet.*, 201: 370-4 (1985).
Joyce, RNA evolution and the origins of life, *Nature*, 338: 217-24 (1989).
Kaasen et al., Molecular cloning and physical mapping of the otsBA genes, which encode the osmoregulatory trehalose pathway of *Escherichia coli*: Evidence that transcription is activated by KatF (AppR), *J. Bacteriol.*, 174: 889-98 (1992).
Karpen, Position-effect variegation and the new biology of heterochromatin, *Curr. Opin. Genet. Dev.*, 4: 281-91 (1994).
Karsten et al., Polyolcontent of bostrychia and stictosiphonia (rhodomelaceae, rhodophyta) from field and culture, *Botanica Marina*, 35:11-9 (1992).
Kaszás et al., Misdivision analysis of centromere structure in maize, *EMBO J*. 15: 5246-55 (1996).
Kato et al., Foreign DNA introduced by calcium phosphate is integrated into repetitive DNA elements of the mouse L cell genome, *Molec. Cell Biol.* 6: 1787-95 (1986).
Katz et al., Cloning and expression of the tyrosinase gene from *Streptomyces antibioticus* in *Streptomyces lividans, J. Gen. Microbiol.*, 129: 2703-14 (1983).
Kim et al., Three-dimensional model of the active site of the self-splicing rRNA precursor of tetrahymena, *Proc. Natl. Acad. Sci. USA*, 84: 8788-92 (1987).
Kishii et al., A tandem repetitive sequence located in the centromeric region of common wheat (*Triticum aestivum*) chromosomes, *Chromosome Res.*, 9:417-28 (2001).
Klee et al., Vectors for transformation of higher plants, *BioTechnology*, 3: 637-42 (1985).
Klein et al., High-velocity microprojectiles for delivering nucleic acids into living cells, *Nature*, 327: 70-3 (1987).
Klein et al., Stable genetic transformation of intact nicotiana cells by the particle bombardment process, *Proc. Nat. Acad. Sci. USA*, 85: 8502-5 (1988).

(56) References Cited

OTHER PUBLICATIONS

Kohler et al., Continuous cultures of fused cells secreting antibody of predefined specificity, *Nature*, 256: 495-7 (1975).
Kohler et al., Derivation of specific antibody-producing tissue culture and tumor lines by cell fusion, *Eur. J. Immunol.*, 6: 511-9 (1976).
Kolchinsky et al., A major satellite DNA of soybean is a 92-base pairs tandem repeat, *Theor. Appl. Genet.*, 90: 621-6 (1995).
Konieczny et al., A procedure for mapping *Arabidopsis* mutations using co-dominant ectotype-specific PCR-based markers, *Plant J.*, 4: 403-10 (1993).
Konieczny et al., A superfamily of *Arabidopsis thaliana* retrotransposons, *Genetics*, 127: 801-9 (1991).
Koorneef et al., Trisomics in *Arabidopsis thaliana* and the location of linkage groups, *Genetica*, 61: 41-6 (1983).
Koorneef, Linkage map of *Arabidopsis thaliana*, *J. Heredity*, 74: 265-72 (1983).
Koorneef, The use of telotrisomics for centromere mapping in *Arabidopsis thaliana* (L.) Heynh., *Genetica*, 62: 33-40 (1983).
Koster et al., Sugars and desiccation tolerance in seeds, *Plant Physiol.*, 88: 829-32 (1988).
Kotani et al., Structural analysis and complete physical map of *Arabidopsis thaliana* chromosome 5 including centromeric telomeric regions, *DNA Res.*, 6: 381-6 (1999).
Kramer et al., Higher-accuracy method for measuring minichromosome stability in *Saccharomyces cerevisiae*. *Biotechniques*, 32: 1036-40 (2002).
Kuhn et al., Clustered tRNA genes in *Schizosaccharomyces pombe* centromeric DNA sequence repeats, *Proc. Natl. Acad. Sci. USA*, 88:1306-10 (1991).
Kumar et al., Plant retrotransposons. *Annu. Rev. Genet.*, 33: 479-532 (1999).
Kumekawa et al., The size and sequence organization of the centromeric region of *Arabiodpsis thaliana* chromosome 5, *DNA Res.*, 7: 315-21 (2000).
Kurata et al., Rice genome organization: The centromere and genome interactions, *Ann. Bot.*, 90: 427-35 (2002).
Kyte et al., A simple method for displaying the hydropathic character of a protein, *J. Mol. Biol.*, 157: 105-32 (1982).
Lakshmikumarin et al., Isolation and characterization of a highly repetitive DNA of *Brassica campestris*, *Plant Molec. Biol.*, 14: 447-8 (1990).
Lawton et al., Expression of a soybean-conclycinin gene under the control of the cauliflower mosaic virus 35S and 19S promoters in transformed petunia tissues, *Plant Molec. Biol.*, 9: 315-24 (1987).
Lechner et al., A 240 kd multisubunit protein complex, CBF3, is a major component of the budding yeast centromere, *Cell*, 64: 717-25 (1991).
Lee et al., Use of cloned *mtl* genes of *Escherichia coli* to introduce *mtl* deletion mutations into the chromosome, *J. Bacteriol.*, 153: 685-92 (1983).
Levings III, The Texas cytoplasm of maize: Cytoplasmic male sterility and disease susceptibility, *Science*, 250: 942-7 (1990).
Li et al., CUE1 : A mesophyll cell-specific positive regulator of light-controlled gene expression in *Arabidopsis*, *Plant Cell*, 7: 1599-610(1995).
Li et al., Direct electrophoretic detection of the allelic state of single DNA molecules in human sperm by using the polymerase chain reaction, *Proc. Natl. Acad. Sci. USA*, 87: 4580-4 (1990).
Lieber et al., Selection of efficient cleavage sites in target RNAs by using a ribozyme expression library, *Molec. Cell Biol.*, 15: 540-51 (1995).
Lin et al., Sequence and analysis of chromosome 2 of the plant *Arabidopsis thaliana*, *Nature*, 402: 761-8 (1999).
Liu et al., Complementation of plant mutants with large genomic DNA fragments by a transformation-competent artificial chromosome vector accelerates positional cloning, *Proc. Natl. Acad. Sci. USA*, 96: 6535-40 (1999).
Lohe et al., Return of the H-word (heterochromatin), *Curr. Opin. Genet. Dev.*, 5: 746-55 (1995).

Loomis et al., Cyroprotective capacity of end products of anaerobic metabolism, *J Exp. Zool.*, 252: 9-15 (1989).
Lorz et al., Gene transfer to cereal cells mediated by protoplast transformation, *Mol. Gen. Genet.*, 199: 178-82 (1985).
Louis, Corrected sequence for the right telomere of *Saccharomyces cerevisiae* chromosome III, *Yeast*, 10: 271-4 (1994).
Lu et al., High efficiency retroviral mediated gene transduction into single isolated immature and replatable CD34$^{3+}$ hemotopoietic stem/progenitor cells from human umbilical cord blood, *J. Exp. Med.*, 178: 2089-96 (1993).
Luo et al., Whole-genome fractionation rapidly purifies DNA from centromeric regions. *Nat. Methods.*, 1: 67-71 (2004).
Maeser et al., The gin recombinase of phase Mu Can catalyse site-specific recombination in plant protoplasts, *Mol. Gen. Genet.*, 230: 170-6 (1991).
Mahtani et al., Physical and genetic mapping of the human X chromosome centromere:Repression of recombination, *Genome Res.*, 8: 100-10 (1998).
Maloy, Experimental techniques in bacterial genetics , Jones and Bartlett, *Ann. N.Y. Acad. Sci.* 646 (1991).Table of Contents only.
Maluszynska et al., Localization of tandemly repeated DNA sequences in *Arabidopsis thaliana*, *Plant J.*, 1: 159-66 (1991).
Maluszynska et al., Molecular cytogenetics of the genus *Arabidopsis*:In situ localization of rDNA sites, chromosome numbers and diversity in centromeric heterochromatin, *Ann. Botany*, 71: 479-84 (1993).
Marcotte et al., Regulation of a wheat promoter by abscisic acid in rice protoplasts *Nature*, 335: 454 (1988).
Mariani et al., Induction of male sterility in plants by a chimaeric ribonuclease gene, *Nature*, 357: 737-41 (1990).
Marra et al., A map for sequence analysis of the *Arabidopsis thaliana* genome, *Nat. Genet.*, 22: 265-70 (1999).
Martinez-Zapater et al., A highly repeated DNA sequence in *Arabidopsis thaliana*, *Mol. Gen. Genet.*, 204: 417-23 (1986).
Matsuura et al., The *sre* gene (ORF459) encodes a site-specific recombinase responsible for integration of the R4 phage genome, *J. Baceteriol.*, 178:3374-6 (1996).
McCabe et al., Stable transformation of soybean (*Glycine Max*) by particle acceleration, *BioTechnology*, 6: 924-6 (1988).
Michel et al.., Modeling of the three-dimensional architecture of group I catalytic introns based on comparative sequence analysis, *J. Mol. Biol.*, 216:585-610 (1990).
Miller et al., Retrotransposon-related DNA sequences in the centromeres of grass chromosomes, *Genetics*, 150:1615-23 (1998).
Mortimer et al., Genetic mapping in *Saccharomyces cerevisiae*, Department of Biophysics and Medical Physics and Donner Laboratory, University of California at Berkeley:11-26 (1981).
Mozo et al., A complete BAC-based physical map of the *Arabidopsis thaliana* genome, *Nat., Genet.*, 22: 271-5 (1999).
Mozo et al., Construction and characterization of the IGF *Arabidopsis* BAC library, *Mol. Gen. Genet.*, 258: 562-70 (1998).
Mundy et al. Abscisic acid and water-stress induce the expression of a novel rice gene, *EMBO J.*, 7: 2279-86 (1988).
Murakami et al., The bialaphos biosynthetic genes of *Streptomyces hygroscopicus*:Molecular cloning and characterization of the gene cluster, *Mol. Gen. Genet.*, 205: 42-50 (1986).
Murata et al., Centromeric repetitive sequences in *Arabiidopsis thaliana*, *Jpn J. Genet.*, 69: 361-70 (1994).
Murata et al., Physical mapping of the 5S ribosomal RNA genes in *Arabidopsis thaliana* by multi-color fluorescence in situHybridization with Cosmid Clones, *Plant J.*, 12: 31-7 (1997).
Murdock et al., Biological effects of plant lectins on the *Cowpea weevil*, *Phytochemistry*, 29: 85-9 (1990).
Murphy et al., Localization of centromere function in a *Drosophila* minichromosome, *Cell*, 82: 599-609 (1995).
Murray et al., Construction of artificial chromosomes in yeast, *Nature*, 305: 189-93(1983).
Mysore et al., An *Arabidopsis* histone H2A mutant is deficient in *Agrobacterium* T-DNA integration, *Proc. Natl. Acad. Sci. USA*, 97: 948-53 (2000).
Mysore et al., *Arabidopsis* ecotypes and mutants that are recalcritant to *Agrobacterium* root transformation are susceptible to germ-line transformation, *Plant J.*, 21: 9-16 (2000).

(56) References Cited

OTHER PUBLICATIONS

Nagaki et al., Molecular and cytological analysis of large tracks of centrometic DNA reveal the structure and evolutionary dynamics of maize centromeres, *Genetics*, 163: 759-70 (2003).
Nagaki et al., Sequencing of a rice centromere uncovers active genes, *Nat. Genet.*, 36: 138-45 (2004).
Nakamura et al., Construction of an 800-KB contig in the near-centromeric region of the rice blast resistance gene *Pi-ta2* using a highly representative rice BAC library, *Mol Gen. Genet.*, 254: 611-20 (1997).
Napoli et al., Introduction of a chimeric chalcone synthase gene into petunia results in reversible co-suppression of homologous genes in trans, *Plant Cell*, 2: 279-98 (1990).
Negrutiu et al. Plant protoplasts as genetic tool: Selectable markers for developmental studies, *Int. J. Dev. Biol.*, 36: 73-84 (1992).
Nester et al., Crown gall: A molecular and physiological analysis, *Ann. Rev. Plant Physiol.*, 35: 387-413 (1984).
Nicklas, The forces that move chromosomes in mitosis, *Ann. Rev. Biophys. Biophys. Chem.*, 17: 431-49 (1988).
Nonomura et al., Organization of the 1.9-Kb repeat unit RCE1 in the centromeric region of rice chromosomes, *Mol. Gen. Genet*, 261: 1-10 (1999).
Nonomura et al., The centromere composition of multiple repetitive sequences on rice, *Chromosome* 5, 110: 284-91 (2001).
Noutoshi et al., Designing of plant artificial chromosome (PAC) by using the chlorella smallest chromosome as a model system, *Nucl. Acids Symp., Ser.* 37: 143-4 (1997).
Nussbaum et al., Construction and propagation of a defective simian virus 40 genome bearing an operator from bacteriophage, *Proc. Nat. Acad. Sci. USA.*, 73: 1068-72 (1976).
Odell et al., Identification of DNA sequences required for activity of the cauliflower mosaic virus 35S promoter, *Nature*, 313: 810-2 (1985).
Ohmori et al., Nucleotide sequence of the region required for maintenance of colicin E1 plasmid, *Mol. Gen. Genet.*, 176: 161-70 (1979).
Omirulleh et al., Activity of a chimeric promoter with the doubled CaMV 35S enhancer element in protoplast-derived cells and transgenic plants in maize, *Plant Molec. Biol.*, 21: 415-28 (1993).
Ow et al., Transient and stable expression of the firefly luciferase gene in plant cells and transgenic plants, *Science*, 234: 856-9 (1986).
Page et al., Characterization of a maize chromosome 4 centromeric sequence: Evidence for an evolutionary relationship with the B chromosome centromere, *Genetics*, 159: 291-301 (2001).
Palukaitis et al., Characterization of a viroid associated with avocado sunblotch disease, *Virology*, 99: 145-51 (1979).
Peacock et al., Highly repeated DNA sequence limited to knob heterochromatin in maize, *Proc. Natl. Acad. Sci. USA*, 78: 4490-4 (1981).
Pelissier et al., Athila, a new retroelement from *Arabidopsis thaliana.*, *Plant Mol. Biol.*, 29: 441-552 (1995).
Pelissier et al., DNA regions flanking the major *Arabidopsis thaliana* satellite are principally enriched in *Athila* retroelement sequences, *Genetica*, 97: 141-51 (1996).
Perkins, The detection of linkage in tetrad analysis, *Genetics*, 38: 187-97 (1953).
Perlak et al., Modification of the coding sequence enhances plant expression of insect control protein genes, *Proc. Natl. Acad. Sci USA*, 88: 3324-8 (1991).
Perriman et al., Extended target-site specificity for a hammerhead ribozyme, *Gene*, 113: 157-63 (1992).
Peterson et al., Production of transgenicmice with yeast artificial chromosomes, *TIG*, 13: 61-6 (1997).
Phi-Van et al., The chicken lysozyme 5' matrix attachment region increases transcription from a heterologous promoter in heterologous cells and dampens position effects on the expression of transfected genes, *Molec. Cell. Biol.*, 10: 2302-7 (1990).
Piatowski et al., Characterization of five abscisic acid-responsive cDNA clones isolated from the dessication-tolerant plant *Craterostigma plantagineum* and their relationship to other water-stress genes, *Plant Physiol.*, 94: 1682-8 (1990).

Potrykus et al., Direct gene transfer to cells of a graminaceous monocot, *Mol. Gen. Genet*. 199: 183-8 (1985).
Prasher et al., Cloning and expression of the cDNA coding for aequorin, a bioluminescent calcium-binding protein, *Biochem Biophys. Res. Commun.*, 126:1259-68 (1985).
Presting et al., A *Ty3/gypsy* retrotransposon-like sequence localizes to the centromeric regions of cereal chromosomes, *Plant J.*, 16:721-8 (1998).
Preuss et al., Tetrad analysis possible in *Arabidopsis* with mutation of the QUARTET (QRT) genes, *Science*, 264:1458-60 (1994).
Price et al., Systematic relationships of *Arabidopsis*: A molecular and morphological perspective, in Somerville, C. and Meyerowitz, E. (eds.), *Arabidopsis*, Cold Spring Harbor Press, New York (1995) pp. 7-19.
Prody et al., Autolytic processing of dimeric plant virus satellite RNA, *Science*, 231: 1577-80 (1986).
Puechberty, Genetic and physical analyses of the centromeric and pericentromeric regions of human chromosome 5: Recombination across 5cen, *Genomics*, 56: 274-87 (1999).
Rathore et al., Use of *bar* as a selectable marker gene and for the production of herbicide-resistant rice plants from protoplasts, *Plant Molec. Biol.*, 21: 871-84 (1993).
Rattner et al., The structure of the mammalian centromere, *BioEssays*, 13: 51-6 (1991).
Ravatn et al., Int-B13, An unusual site-specific recombinase of the bacteriophage P4 integrase family, is responsible for chromosomal insertion of the 105-kilobase *clc* element of *Pseudomonas* sp. strain B13, *J. Bacteriol.* 180: 5505-14 (1998).
Reed et al., Carbohydrate accumulation and osmotic stress in cyanobacteria, *J. Gen. Microbiol.*, 130: 1-4 (1984).
Reichel et al., Enhanced green fluorescence by the expression of an *Aequorea victoria* green fluorescent protein mutant in mono- and dicotyledonous plant cells, *Proc. Nat. Acad. Sci. USA*, 93: 5888-93 (1996).
Reinhold-Hurek et al., Self-splicing introns in tRNA genes of widely divergent bacteria, *Nature*, 357: 173-6 (1990).
Rensburg et al., Proline accumulation as drought-tolerance selection criterion:Its relationship to membrane integrity and chloroplast ultrastructure in nicotiana tabacum L., *J. Plant Physiol.*, 141: 188-94 (1993).
Richards et al., Isolation of a higher eukaryotic telomere from *Arabidopsis thaliana*, *Cell*, 53: 127-36 (1988).
Richards et al., Plant centromeres: Structure and control, *Curr. Opin. Plant Biol.*,1: 130-5 (1998).
Richards et al., The centomere region of *Arabidopsis thaliana* chromosome 1 contains telomere-similar sequences, *Nucl. Acids Res.*, 19: 3351-7 (1991).
Rieder, The formation, structure, and composition of the mammalian kinetochore and kinetochore fiber, New York State Department of Health, Division of Laboratories and Research, *Intl. Rev. Cytol.*79: 1-58 (1982).
Rogers et al., Improved vectors for plant transformation: Expression cassette vectors and new selectable markers, *Meth. Enzymol.*, 153: 253-77 (1987).
Rosenberg et al., RFLP subtraction: A method for making libraries of polymorphic markers, *Proc. Natl. Acad. Sci. USA*, 91: 6113-7 (1994).
Rosenfeld, Human artificial chromosomes get real, *Nat. Genet.*, 15:333-5 (1997).
Round et al., *Arabidopsis thaliana* centromere regions: Genetic map positions and repetitive DNA structure, *Genome Res.*, 7: 1045-53 (1997).
Sasnauskas et al., Molecular cloning and analysis of autonomous replicating sequence of *Candida maltosa*, *Yeast*, 8: 253-9 (1992).
Sauer, Functional expression of the *cre-lox* site-specific recombination system in the yeast *Saccharomyces cerevisiae*, *Molec. Cell Biol.*, 7: 2087-96 (1987).
Schmidt et al., Analysis of clones carrying repeated DNA sequences in two YAC libraries of *Arabidopsis thaliana* DNA, *Plant J.*, 5: 735-44 (1994).
Schmidt et al., Physical map and organization of *Arabidopsis thaliana* chromosome 4, *Science*, 270: 480-3 (1995).

(56) References Cited

OTHER PUBLICATIONS

Schwartz et al., New techniques for purifying large DNAs and studying their properties and packaging, Department of Human Genetics and Development, Columbia University: 189-195.
Schweizer et al., Species-specific DNA sequences for identification of somatic hybrids between *Lycopersicon esculentim* and *Solanum acaule*, *Theor. Appl. Genet.*, 75: 679-84 (1988).
Sears et al., Cytogenic studies in *Arabidopsis thaliana*, Department of Genetics, University of Missouri, *Can. J. Genet. Cytol.*, 12: 217-23 (1970).
Shagan et al., Nucleotide sequence of an *Arabidopsis thaliana* turgor-responsive cDNA clone encoding TMP-A, a transmembrane protein containing the major intrinsic protein motif, *Plant Physiol.*, 101: 1397-8 (1993).
Sheen et al., Green-flourescent protein as a new vital marker in plant cells, *Plant J.*, 8: 777-84 (1985).
Shizuya et al., Cloning and stable maintenance of 300-kilobase-pair fragments of human DNA in *Escherichia coli* using an F-factor-based vector. *Proc. Natl. Acad. Sci. USA*, 89: 8794-7 (1992).
Simoens et al., Characterization of highly repetitive sequences of *Arabidopsis thaliana*, *Nucl. Acids Res.*, 16: 6753-66 (1988).
Singh et al., Centromere mapping and orientation of the molecular linkage mao of rice (*Oryza sativa* L.), *Proc. Natl. Acad. Sci. USA*, 93: 6163-8 (1996).
Smith et al., Expression of truncated tomato polygalacturonase gene inhibits expression of the endogenous gene in transgenic plants, *Mol. Gen. Genet.*, 224: 447-81 (1990).
Smithies et al., Insertion of DNA sequences into the human chromosomal—globin locus by homologous recombination, *Nature*, 317: 230-4 (1985).
Smyth, New *Arabidopsis* mutations that result in all four products of meiosis being held together as a tetrad of fused pollen grains may facilitate genetic mapping and lead to new insights into pollen biology, *Curr. Biol.*, 4: 851-3 (1994).
Somerville et al., Plant functional genomics, *Science*, 285: 380-3 (1999).
Spielmann et al., T-DNA structure in transgenic tobacco plants with multiple independent integration sites, *Mol. Gen. Genet.*, 205: 34-43 (1986).
Stalker et al., Herbicide resistance in transgenic plants expressing a bacterial detoxification gene, *Science*, 242: 419-23 (1988).
Steif et al., A nuclear DNA attachment element mediates elevated and position-independent gene activity. *Nature*, 341: 343-5 (1989).
Stinchomb et al., Isolation and characterization of a yeast chromosomal replicator, *Nature*, 282: 39-43 (1979).
Stone et al., LEAFY COTYLEDON2 encodes a B3 domain transcription factor that induces embryo development, *Proc. Natl. Acad. Sci. USA*, 98:11806-11 (2001).
Stougaard, Substrate-dependent negative selection in plants using a bacterial cytosine deaminase gene, *Plant J.*, 3: 755-61 (1993).
Sullivan et al., Isolation and characterization of a maize chlorophyll a/b binding protein gene that produces high levels of mRNA in the dark, *Mol. Gen. Genet.*, 215: 431-40 (1980).
Sun et al., Human artificial episomal chromosomes for cloning large DNA fragments in human cells, *Nat. Genet.*, 8: 33-41 (1994).
Sun et al., Molecular structure of a functional drosophila centromere, *Cell*, 91: 1007-19 (1997).
Sutcliffe, Nucleotide sequence of the ampicillin resistance gene of *Escherichia coli* plasmid pBR322, *Proc. Natl. Acad. Sci. USA*, 75: 3737-41 (1978).
Symington et al., Meiotic recombination within the centromere of a yeast chromosome, *Cell*, 52: 237-40 (1988).
Symons, Avocado sunblotch viroid: Primary sequence and proposed secondary structure, *Nucl. Acids Res.*, 9: 6527-37 (1981).
Symons, Small catalytic RNAs, *Annu. Rev. Biochem.*, 61: 641-71 (1992).
Tarczynski et al., Expression of a bacerial mtID gene in transgenic tobacco leads to production and accumulation of mannitol, *Proc. Natl. Acad. Sci. USA*, 89: 2600-4 (1992).

Tarczynski et al., Stress protection of transgenic tobacco by production of the osmolyte mannitol, *Science*, 259: 508-10 (1993).
Tavoletti et al., Half tetrad analysis in alfalfa using multiple restriction fragment length polymorphism markers, *Proc. Natl. Acad. Sci. USA*, 93: 10918-22 (1996).
Thillet et al., Site-directed mutagenesis of mouse dihydrofolate reductase. Mutants with increased resistance to methotrexate and trimethoprim, *J. Biol. Chem.*, 263: 12500-8 (1988).
Thomas et al., High-frequency targeting of genes to specific sites in the mammalian genome, *Cell*, 44: 419-28 (1986).
Thomas et al., Viable molecular hybrids of bacteriophage lambda and eukaryotic DNA, *Proc. Nat. Acad. Sci. USA*, 71: 4579 (1974).
Thompson et al., A novel repetitive sequence associated with the centrometric regions of *Arabidopsis thaliana* chromosomes, *Mol. Gen. Genet.*, 253: 247-52 (1996).
Thompson et al., Decreased expression of BRCA1 accelerates growth and is often present during sporadic breast cancer progression, *Nat. Genet.*, 9: 444-50 (1995).
Thompson et al., Identification and distribution of seven classes of middle-repetitive DNA in the *Arabidopsis thaliana* genome, *Nucl. Acids Res.*, 24: 3017-22 (1996).
Tian et al., Expression of the green fluorescent protein gene in conifer tissues, *Plant Cell Reports*, 16: 267-71 (1997).
Tominaga, The site-specific recombinase encoded by pinD in *Shigella dysenteriae* is due to the presence of a defective Mu prophase, *Microbiol.*, 143: 2057-63 (1997).
Toriyama et al., Haploid and diploid plant regeneration from protoplasts of another callus in rice, *Theor Appl. Genet.*, 73: 16-9 (1986).
Tsay et al., Identification of a mobile endogenous transposon in *Arabidopsis thaliana*, *Science*, 260: 342-4 (1993).
Tugal et al., *Arabidopsis* 22-kilodalton peroxisomal membrane protein, nucleotide sequence analysis and biochemical characterization, *Plant Physiol.*, 120: 309-20 (1999).
Twell et al., Promoter analysis of genes that are coordinately expressed during pollen-specific enhancer sequences and shared regulatory elements, *Genes Dev.*, 5: 496-507 (1991).
Twell et al., Transient expression of chimeric genes delivered pollen by microprojectile bombardment, *Plant Physiol.*, 91: 1270-4 (1989).
Tyler-Smith et al., Localization of DNA sequences required for human centromere function through an analysis of rearranged Y chromosomes, *Nat. Genet.*, 5: 368-75 (1993).
Tyler-Smith et al., Mammalian chromosome structure, *Curr. Opin. Genet. Dev.*, 3: 390-7 (1993).
Uchimiya et al., Expression of a foreign gene in callus derived from DNA-treated protoplasts of rice, *Mol. Gen. Genet.*, 204: 204 (1986).
Vahedian et al., Genomic organization and evolution of the soybean SB92 satellite sequence, *Plant Molec. Biol.*, 29: 857-62 (1995).
Valvekens et al., *Agrobacterium tumefaciens*-mediated transformation of *Arabidopsis thaliana* root explants by using kanamycin selection, *Proc. Natl. Acad. Sci. USA*, 85: 5536-40 (1988).
Van Der Krol et al., Flavonoid genes in petunia: Addition of a limited number of gene copies may lead to a suppression of gene expression, *Plant Cell*, 2: 291-9 (1990).
Van't Hof et al., The size and number of replicon families of chromosomal DNA of *Arabidopsis thaliana*, *Chromosoma*, 68: 269-285 (1978).
Vasil et al., Herbicide resistant fertile transgenic wheat plants obtained by microprojectile bombardment of regenerable embryogenic callus, *BioTechnology*, 10: 667-74 (1992).
Vasil, Progress in the regeneration and genetic manipulation of cereal crops, *BioTechnology*, 6: 397-402 (1988).
Vernon et al., A novel methyl transferase induced by osmotic stress in the faculative halophyte *Mesembryanthemum crystallinum*, *EMBO J.* 11: 2077-85 (1992).
Voytas et al., A copia-like transposable element family in *Arabidopsis thaliana*, *Nature*, 336: 242-4 (1988).
Wagner et al., Coupling of adenovirus to transferrin-polylysine/DNA complexes greatly enhances receptor-mediated gene delivery and expression of transfected genes, *Proc. Natl. Acad. Sci. USA*, 89: 6099-103(1992).

(56) References Cited

OTHER PUBLICATIONS

Walker et al., DNA sequences required for anaerobic expression of the maize alcohol dehydrogenase 1 gene, *Proc. Nat. Acad. Sci. USA*, 84: 6624-8 (1987).

Wang et al., Characterization of cis-acting elements regulating transcription from the promoter of a constitutively active rice actin gene, *Molec. Cell Biol.*, 3399-406 (1992).

Weide et al., Paracentromeric sequences on tomato chromosome 6 show homology to human satellite III and to the mammalian CENP-B binding box, *Mol. Gen. Genet.*, 259: 190-7 (1998).

Wensink et al., A system for mapping DNA sequences in the chromosomes of *Drosophila melanogaster*, *Cell*, 3: 315-25 (1974).

Wevrick et al. Partial deletion of alpha satellite DNA associated with reduced amounts of the centromere protein CENP-B in a mitotically stable human chromosome rearrangement, *Molec. Cell Biol.*, 102: 6374-80 (1990).

Whitehouse et al., Mapping chromosome centromeres by the analysis of unordered tetrads, *Nature*, 4205: 893 (1950).

Wigler et al., Transfer of purified herpes virus thymidine kinase gene to cultured mouse cells, *Cell*, 11: 223-32 (1977).

Willard, Centromeres of mammalian chromosomes, *TIG* 6(12): 410-6 (1990).

Willard, Centromeres: The missing link in the development of human artificial chromosomes, *Genet. Dev.* 8: 219-25 (1998).

Wolter et al., Chilling sensitivity of *Arabidopsis thaliana* with genetically engineered membrane lipids, *EMBO J.*, 11: 4685-92 (1992).

Wong et al., Electric field mediated gene transfer, *Biochim. Biophys. Res. Commun.*, 107: 584-7 (1982).

Wright et al., Multiple non-LTR retrotransposons in the genome of *Arabidopsis thaliana*, *Genet.*, 142: 569-78 (1996).

Wu et al., Composition and structure of the centromeric region of rice chromosome 8, *Plant Cell*, 16: 967-76 (2004).

Xia et al., Genomic organization of the canreprepetitive DNA in *Brassica juncea*, *Plant Molec. Biol.*, 26: 817-32 (1994).

Xia et al., Structure and evolution of a highly repetitive DNA sequence from *Brassica napus*, *Plant Molec. Biol.*, 21: 213-24 (1993).

Xiang, et al. The Anti-*nptII* gene, *Plant Physiol.*, 102: 287-93 (1993).

Xu et al., Expression of a late embryogenesis abundant protein gene, HVA1, from barley confers tolerance to water deficit and salt stress in transgenic rice, *Plant Physiol.*, 110: 249-57 (1996).

Yamada et al., Plant regeneration from protoplast-derived callus of rice, *Plant Cell Rep.*, 4: 85 (1986).

Yamaguchi-Shinozaki et al., Molecular cloning and characterization of 9 cDNAs for genes that are responsive to a desiccation in *Arabidopsis thaliana*: Sequence analysis of one cDNA clone that encodes a putative transmembrane channel protein, *Plant Cell Physiol.*, 33: 217-24 (1992).

Yang et al., Maize sucrose synthase-1 promoter directs phloem cell-specific expression of gus gene in transgenic tobacco plants, *Proc. Natl. Acad. Sci. USA*, 87: 4144-8 (1990).

Yen et al., CENP-E, a novel human centomere-associated protein required for progression from metaphase to anaphase, *EMBO J.*, 10: 1245-54 (1991).

Young et al., A new approach for identifying and mapping structural genes in *Drosophila melanogaster*, Eukaryotic genetic systems ICNUCLA symposia on molecular and cellular biology VII: 315-31 (1977).

Yuan et al., Selection of guide sequences that direct efficient cleavage of mRNA by human ribonuclease P, *Science*, 263: 1269-73 (1994).

Yuan et al., Targeted cleavage of mRNA by human RNase P, *Proc. Natl. Acad. Sci. USA*, 89: 8006-10 (1992).

Zabel et al., Towards the construction of artificial chromosomes for tomato, 609-24.

Zatloukal et al., Transferinfection: A highly efficient way to express gene constructs in eukaryotic cells. *Ann. N.Y. Acad. Sci.*, 600: 136-153.

Zentgraf, Telomere-binding proteins of *Arabidopsis thaliana*, *Plant Molec. Biol.*, 27: 467-75 (1995).

Zhang et al., Molecular cloning, nucleotide sequence, and function of a site-specific recombinase encoded in the major pathogenicity island of *Salmonella typhi*, *Gene*, 202: 139-46 (1997).

Zukowski et al., Chromogenic identification of genetic regulatory signals in *Bacillus subtilis* based on expression of a cloned *Pseudomonas* gene, *Proc. Natl. Acad. Sci., USA*, 80: 1101-5 (1983).

Zuo et al., The *WUSCHEL* gene promotes vegetative-to-embryonic transition in *Arabidopsis*, *Plant J.*, 30:349-59 (2002).

Carlson et al., Meiotic transmission of an in vitro-assembled autonomous maize minichromosome. *PLoS Genet.*, 3(10): 1965-74 (2007).

EMBI Accession No. AC183942, *Zea mays* chromosome unknown clone CH201-2403; ZMMBBc0024003, *Sequencing in Progress*, 19 unordered pieces, dated Mar. 26, 2006.

EMBL Accession No. AC006161, *Arabidopsis thaliana* chromosome II section 37 of 255 of the complete sequence. Sequences from clones T12H3, T14A4. HTG, dated Dec. 11, 1998.

EMBL Accession No. AC006217, *Arabidopsis thaliana* chromosome II section 41 of 255 of the complete sequence. Sequence from clones T25N22, T13E11, dated Dec. 14, 1998.

EMBL Accession No. AC006586, *Arabidopsis thaliana* chromosome II section 50 of 255 of the complete sequence. Sequence from clones F7B19, T15D9, HTG, dated Mar. 11, 1999.

EMBL Accession No. AC012392, Genomic Sequence for *Arabidopsis thaliana* clone C17L7, Chromosome IV, complete sequence, dated Oct. 28, 1999.

EMBL Accession No. AF072897, *Arabidopsis thaliana* BAC T8A17 chromosome IV, complete sequence, dated Jun. 29, 1998.

EMBL Accession No. AF074021, *Arabidopsis thaliana* BAC F4H6, chromosome IV, complete sequence, dated Jul. 13, 1998.

EMBL Accession No. AF076274, *Arabidopsis thaliana* BAC T27D20, dated Jul. 8, 1998.

EMBL Accession No. AF162444, *Arabidopsis thaliana* BAC T32N4, dated Jun. 30, 1999.

EMBL Accession No. AY321491, *Zea mays* centromeric repeat CentC27, complete sequence, Jul. 21, 2003.

EMBL Accession No. AY530242, *Zea mays* clone CentC27 centromeric repeat sequence, Feb. 28, 2004.

EMBL Accession No. B97084, T31F11TR TAMU *Arabidopsis thaliana* genomic clone T31F11, genomic survey sequence, dated Apr. 3, 1998.

Genbank Accession No. AC169373.2, Sorghum bicolor clone SB_BBc0188M08, complete sequence, nucleotides 126110-132443, dated Mar. 1, 2006.

GenBank Accession No. AC196831.1, Sorghum bicolor clone SB_BBc0060K10, Working Draft Sequence, 6 unordered pieces, nucleotides 9604-9473, dated Jan. 17, 2007.

Lin et al., Sequence and analysis of chromosome 2 of plant *Arabidopsis thaliana*. *Nature*, 204(6763): 761-8 (1999).

Mayer et a l., Sequence and analysis of chromosome 4 of the plant *Arabidopsis thaliana*. *Nature* (London), 402(6763): 769-77 (1999).

Newman et al., Genes galore: A summary of methods for accessing results from large-scale partial sequencse of anonymous *Arabidopsis* cDNA clones. *Plant Physiol.*, 106: 1241-55 (1994).

Norris et al., The intron of *Arabidopsis thaliana* polyubiquitin gene is conserved in location and is a quantitative determinant of chimeric gene expression. *Plant Molec. Biol.*, 21: 895-906 (1993).

Sun et al., A model for the evolution of polyubiquitin genes from the study of *Adabidopsis thaliana* ecotypes. *Plant Molec. Biol.*, 34(5): 745-58 (1997).

Sun et al., Independent modulation of *Arabidopsis thaliana* polyubiquitin mRNAs in different organs and in response to enviromental changes. *Plant Journal*, 11(5): 1017-27 (1997).

Tsugeki et al., A transposon insertion in the *Arabidopsis* SSR16 gene causes an embryo-defective lethal mutation. *Plant Journal*, 10(3): 479-89 (1996).

* cited by examiner

FIG. 3
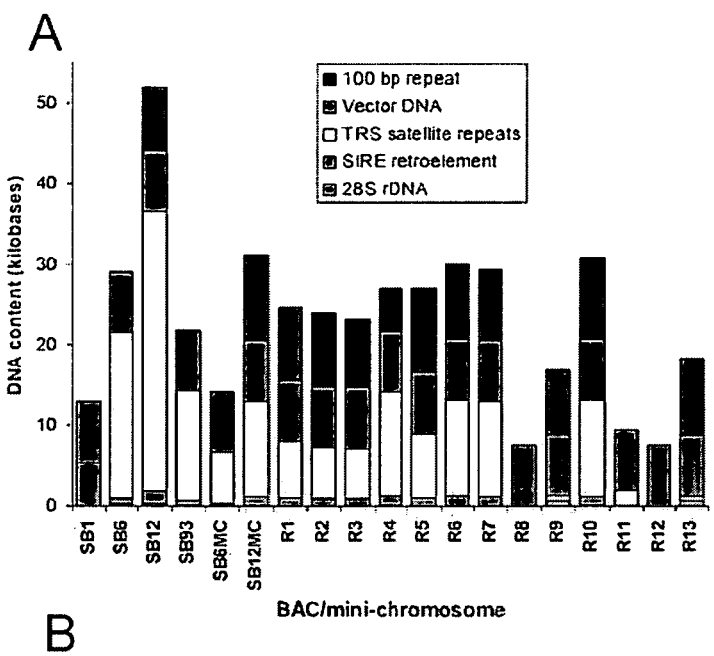
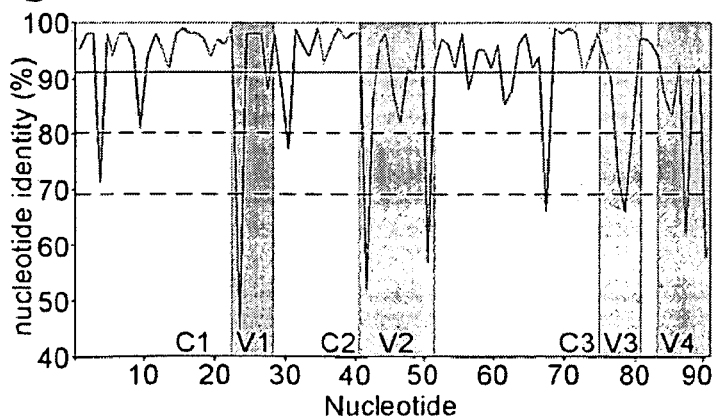

FIG. 4

Complete TRS, 100 bp repeat consensus sequences

1. TRS:

```
Soybean genomic  HAATTCAAAC GACAATAACT TTTTACTCGG ATGTCTGATT GAGTCCCGTA ATATATCGAG ACGCTCGAAA TTGAATDYTG AAGCTCTVAG C
SB12R2-3         AAAWTCAAAC GACAATAACT TTTDACTCGG ATGTCCGATT GWGTCCCGTA RTATATCGAG ACGCTCGWAA TTGAAAACAG AAGCTCTGAG M
6A-3             AAATTCAAAC GACAATAACT TTTDACTCGG ATGTCCGATT GWGTCCCGTA RTATATCGAG ACGCTCGWAA TTGAAAACAG AAGCTCTGAG M
6C-1             AAAWTCAAAC GACAATAACT TTTDACTCGG ATGTCCGATT GWGTCCCGTA RTATATCGAG ACGCTCGWAA TTGAAAACAG AAGCTCTRAG M
6C-9             AAAWTCAAAC GACAATAACT TTTDACTCGG ATGTCCGATT GWGTCCCGTA RTATATCGAG ACGCTCGWAA TTGAAAACWG AAGCTCTGAG M
```

2. 100 bp repeat:

```
Soybean genomic  TCCAGAGGCG GCGGGCCCGA TGACAAGCAG AGACCAAGTT TGGTCATTCT GCACCCAWGA TACGCGGAGA TACCTTAYGG TTATYCGCAC CCTTTT-GTC A
SB12R2-3         TCCAGAGGCG GCGGGCCCGA TGACAAGCAG AGACCAAGTT TGGTCATTCT GCACCCATGA TACGCGGAGA TACCTTATGG TTATTCGCAC CCTTTTTGTC A
6A-3             TCCAGAGGCG GCGGGCCCGA TGACAAGCAG AGACCAAGTT TGGTCATTCT GCACCCATGA TACGCGGAGA TACCTTATGG TTATTCGCAC CCTTTTTGTC A
6C-1             TCCAGAGGCG GCGGGCCCGA TGACAAGCAG AGACCAAGTT TGGTCATTCT GCACCCATGA TACGCGGAGA TACCTTATGG TTATTCGCAC CCTTTTTGTC A
6C-9             TCCAGAGGCG GCGGGCCCGA TGACAAGCAG AGACCAAGTT TGGTCATTCT GCACCCATGA TACGCGGAGA TACCTTATGG TTATTCGCAC CCTTTTTGTC A
```

FIG. 5

TCCACAGGCGGCGGGCCCGATGAYACGCGGAGAYACCTTAYGGTTATYCGCACCCTTKT
GTCATCCAGAGGCGGCGGGCCCGATGACAMGCRGAGAYMMMHDTWYGGTYATTCYGC
CACCCTTKTRTCA (SEQ ID NO: 101)

Soybean 127-bp consensus sequence

CENTROMERE SEQUENCES AND MINICHROMOSOMES

This application is a 371 application of PCT/US2008/056993, filed Mar. 14, 2008, which claims priority to U.S. Provisional Application No. 60/918,258, filed Mar. 15, 2007 and U.S. Provisional Patent Application No. 60/951,351, filed Jul. 23, 2007, both of which are incorporated by reference herein in their entirety.

Scientific work relating to the invention was supported by Grant No. R44GM069782-03 from the United States Institute of Health and Grant No. 70NANB3H3009 from the Advanced Technology Program of the United States National Institute of Standards and Technology. The United States government may have certain rights in the invention.

BACKGROUND OF THE INVENTION

Two general approaches are used for introduction of new genetic information ("transformation") into cells. One approach is to introduce the new genetic information as part of another DNA molecule, referred to as an "episomal vector," or "mini-chromosome", which can be maintained as an independent unit (an episome) apart from the host chromosomal DNA molecule(s). Episomal vectors contain all the necessary DNA sequence elements required for DNA replication and maintenance of the vector within the cell. Many episomal vectors are available for use in bacterial cells (for example, see Maniatis et al., "Molecular Cloning: a Laboratory Manual," Cold Spring Harbor Laboratory, Cold Spring Harbor, N.Y. 1982). However, only a few episomal vectors that function in higher eukaryotic cells have been developed. Higher eukaryotic episomal vectors were primarily based on naturally occurring viruses. In higher plant systems gemini viruses are double-stranded DNA viruses that replicate through a double-stranded intermediate upon which an episomal vector could be based, although the gemini virus is limited to an approximately 800 bp insert. Although an episomal plant vector based on the Cauliflower Mosaic Virus has been developed, its capacity to carry new genetic information also is limited (Brisson et al., Nature, 310:511, 1984.).

The other general method of genetic transformation involves integration of introduced DNA sequences into the recipient cell's chromosomes, permitting the new information to be replicated and partitioned to the cell's progeny as a part of the natural chromosomes. The introduced DNA usually is broken and joined together in various combinations before it is integrated at random sites into the cell's chromosome (see, for example Wigler et al., Cell, 11:223, 1977). Common problems with this procedure are the rearrangement of introduced DNA sequences and unpredictable levels of expression due to the location of the transgene in the genome or so called "position effect variegation" (Shingo et al., Mol. Cell. Biol., 6:1787, 1986). Further, unlike episomal DNA, integrated DNA cannot normally be precisely removed. A more refined form of integrative transformation can be achieved by exploiting naturally occurring viruses that integrate into the host's chromosomes as part of their life cycle, such as retroviruses (see Chepko et al., Cell, 37:1053, 1984).

One common genetic transformation method used in higher plants is based on the transfer of bacterial DNA into plant chromosomes that occurs during infection by the phytopathogenic soil bacterium *Agrobacterium* (see Nester et al., Ann. Rev. Plant Phys., 35:387-413, 1984). By substituting genes of interest for the naturally transferred bacterial sequences (called T-DNA), investigators have been able to introduce new DNA into plant cells. However, even this more "refined" integrative transformation system is limited in three major ways. First, DNA sequences introduced into plant cells using the *Agrobacterium* T-DNA system are frequently rearranged (see Jones et al., Mol. Gen. Genet., 207:478, 1987). Second, the expression of the introduced DNA sequences varies between individual transformants (see Jones et al., Embo J., 4:2411-2418, 1985). This variability is presumably caused by rearranged sequences and the influence of surrounding sequences in the plant chromosome (i.e., position effects), as well as methylation of the transgene. Finally, insertion of extra elements into the genome can disrupt the genes, promoters or other genetic elements necessary for normal plant growth and function.

Another widely used technique to genetically transform plants involves the use of microprojectile bombardment. In this process, a nucleic acid containing the desired genetic elements to be introduced into the plant is deposited on or in small metallic particles, e.g., tungsten, platinum, or preferably gold, which are then delivered at a high velocity into the plant tissue or plant cells. However, similar problems arise as with *Agrobacterium*-mediated gene transfer, and as noted above expression of the inserted DNA can be unpredictable and insertion of extra elements into the genome can disrupt and adversely impact plant processes.

One attractive alternative to commonly used methods of transformation is the use of an artificial chromosome. Artificial chromosomes are man-made linear or circular DNA molecules constructed in part from cis-acting DNA sequence elements that provide replication and partitioning of the constructed chromosomes (see Murray et al., Nature, 305:189-193, 1983). Desired elements include: (1) origin of replication, which are the sites for initiation of DNA replication, (2) Centromeres (site of kinetochore assembly and responsible for proper distribution of replicated chromosomes into daughter cells at mitosis or meiosis), and (3) if the chromosome is linear, telomeres (specialized DNA structures at the ends of linear chromosomes that function to stabilize the ends and facilitate the complete replication of the extreme termini of the DNA molecule). An additional desired element is a chromatin organizing sequence. It is well documented that centromere function is crucial for stable chromosomal inheritance in almost all eukaryotic organisms (reviewed in Nicklas 1988). The centromere accomplishes this by attaching, via centromere binding proteins, to the spindle fibers during mitosis and meiosis, thus ensuring proper gene segregation during cell divisions.

The essential chromosomal elements for construction of artificial chromosomes have been precisely characterized in lower eukaryotic species, and more recently in mouse and human. Autonomous replication sequences (ARSs) have been isolated from unicellular fungi, including *Saccharomyces cerevisiae* (brewer's yeast) and *Schizosaccharomyces pombe* (see Stinchcomb et al., 1979 and Hsiao et al., 1979). An ARS behaves like an origin of replication allowing DNA molecules that contain the ARS to be replicated in concert with the rest of the genome after introduction into the cell nuclei of these fungi. DNA molecules containing these sequences replicate, but in the absence of a centromere they are not partitioned into daughter cells in a controlled fashion that ensures efficient chromosome inheritance.

Artificial chromosomes have been constructed in yeast using the three cloned essential chromosomal elements (see Murray et al., Nature, 305:189-193, 1983). None of the essential components identified in unicellular organisms, however, function in higher eukaryotic systems. For example, a yeast CEN sequence will not confer stable inheritance upon vectors transformed into higher eukaryotes.

In contrast to the detailed studies done in yeast, less is known about the molecular structure of functional centromeric DNA of higher eukaryotes. Ultrastructural studies indicate that higher eukaryotic kinetochores, which are specialized complexes of proteins that form on the centromere during late prophase, are large structures (mammalian kinetochore plates are approximately 0.3 µm in diameter) which possess multiple microtubule attachment sites (reviewed in Rieder, 1982). It is therefore possible that the centromeric DNA regions of these organisms will be correspondingly large, although the minimal amount of DNA necessary for centromere function may be much smaller.

While the above studies have been useful in elucidating the structure and function of centromeres, it was not known whether information derived from lower eukaryotic or mammalian higher eukaryotic organisms would be applicable to plants. There exists a need for cloned centromeres from higher eukaryotic organisms, particularly plant organisms, which would represent a first step in production of artificial chromosomes. There further exists a need for plant cells, plants, seeds and progeny containing functional, stable, and autonomous artificial chromosomes capable of carrying a large number of different genes and genetic elements.

SUMMARY OF THE INVENTION

In one aspect, the present invention addresses mini-chromosomes comprising a centromere having one or more selected repeated nucleotide sequences, described in further detail herein. In some embodiments, such mini-chromosomes comprise a centromere comprising one or more selected repeated nucleotide sequences derived from *Zea mays* (corn).

In another aspect, the invention provides modified "adchromosomal" plants, e.g., *Zea mays* plants, containing functional, stable, autonomous mini-chromosomes. Such mini-chromosomes have been shown herein to be meiotically transmitted to progeny. The mini-chromosome of the invention preferably has a transmission efficiency during mitotic division of at least 90%, for example, at least 95% and/or a transmission efficiency during meiotic division of, e.g., at least 80%, at least 85%, at least 90% or at least 95%.

In one embodiment, the mini-chromosomes of the invention comprise a centromere comprising any one of (a) a repeated nucleotide sequence derived from (i.e. is a fragment or variant of) the sequence denoted as CentC, an exemplary sequence of which is provided as GenBank Accession No. AY1290008 (SEQ ID NO: 76), (b) a fragment derived from the sequence denoted as CRM, an exemplary sequence of which is provided as GenBank Accession No. AY129008 (SEQ ID NO: 77), (c) a fragment derived from the sequence denoted as CentA, an exemplary sequence of which is provided as GenBank Accession No. AF078917 (SEQ ID NO: 78), or (d) a repeated nucleotide sequence or fragment thereof derived from a retrotransposon, or combinations thereof. Such a sequence or fragment derived from CentC, CRM, CentA or a retrotransposon preferably hybridizes under highly selective conditions to a representative CentC, CRM, CentA or retrotransposon sequence, respectively, or retains at least 70%, 75%, 80%, 85%, 90% or 95% overall identity over the length of the sequence or fragment to a representative CentC, CRM CentA or retrotransposon sequence.

Particularly, the invention provides for mini-chromosomes comprising centromeres having the CentC repeated nucleotide sequence of SEQ ID NO: 70, SEQ ID NO: 71, SEQ ID NO: 91, SEQ ID NO: 92 or variants thereof, e.g. the variants provided in Tables 17 and 22. The invention further provides for mini-chromosomes comprising centromeres having a repeated nucleotide sequence that hybridizes to SEQ ID NO: 70, SEQ ID NO: 71, SEQ ID NO: 91 or SEQ ID NO: 92 under highly selective conditions comprising 0.02 M to 0.15 M NaCl at temperatures of about 50° C. to 70° C., or alternatively comprising hybridization at 65° C. and washing three times for 15 minutes with 0.25×SSC, 0.1% SDS at 65° C. Additional exemplary stringent hybridization conditions comprise 0.5×SSC and 0.25% SDS at 65° C. for 15 minutes, followed by a wash at 65° C. for a half hour. The invention also provides for mini-chromosomes comprising a repeated nucleotide sequence that is at least 70%, 75%, 80%, 85% 90% or 95% identical to SEQ ID NO: 70, SEQ ID NO: 71, SEQ ID NO" 91, or SEQ ID NO: 92. For example, a CentC variant may utilize any nucleotide displayed at a particular base position in Table 18 or 23 together with any nucleotide displayed at any other base position in Table 18 or 23 in any combination, provided that the sequence of the CentC variant retains overall identity over its length of at least 70% to SEQ ID NO: 70, SEQ ID NO: 71, SEQ ID NO: 91 or SEQ ID NO: 92, or would hybridize under highly selective conditions to SEQ ID NO: 70, SEQ ID NO: 71., SEQ ID NO: 91 or SEQ ID NO: 92

In another embodiment, the invention provides for mini-chromosomes comprising centromeres having a CRM repeated nucleotide sequence that is a fragment of SEQ ID NO: 77 or variant thereof. The invention also provides for mini-chromosomes comprising centromeres having a repeated nucleotide sequence that is a fragment of another retrotransposon sequence, such as the sequences of xilon, cinful, or ji (SEQ ID NOS: 93-95).

Such fragments of CRM and other retrotransposons preferably include at least 30, 40, 50, 60, 70, 80, 90, 100, 125, 150, 175, 200, 225, 250, 275, 300, 350, 400, 450, or 500 bp of CRM, most preferably at least 50 bp of the CRM sequence or the sequence of another retrotransposon. The invention further provides for mini-chromosomes comprising centromeres having a variant CRM or other retrotransposon repeated nucleotide sequence that hybridizes to SEQ ID NOS: 77 or other retrotransposon sequences under highly selective conditions comprising hybridization at 65° C. and washing three times for 15 minutes with 0.25×SSC, 0.1% SDS at 65° C. Additional exemplary stringent hybridization conditions comprise 0.02 M to 0.15 M NaCl at temperatures of about 50° C. to 70° C., or alternatively comprising 0.5× SSC and 0.25% SDS at 65° C. for 15 minutes, followed by a wash at 65° C. for a half hour. Exemplary fragments include nucleotides 1-515 (515 bp), nucleotides 1-930 (930 bp), nucleotides 1-1434 (1434 bp), nucleotides 1508-3791 (2284 bp), nucleotides 1508-5417 (3910 bp), nucleotides 2796-2890 (95 bp), nucleotides 2796-2893 (98 bp), nucleotides 4251-4744 (494 bp), nucleotides 4626-4772 (147 bp), nucleotides 4945-6236 (1295 bp), nucleotides 4983-5342 (360 bp), nucleotides 5487-5569 (83 bp), nucleotides 5757-6212 (456 bp), nucleotides 5765-7571 (1807 bp), nucleotides 6529-6653 (125 bp), nucleotides 6608-6658 (51 bp), nucleotides 6638-7571 (934 bp) and/or nucleotides 6640-7156 (517 bp) of SEQ ID NO: 77 or other retrotransposon sequence. The invention also provides for mini-chromosomes comprising a repeated nucleotide sequence that retains overall identity over its length of at least 70%, 75%, 80%, 85% 90% or 95% to SEQ ID NO: 77 or other retrotransposon sequences. The invention contemplates that these fragments range in size up to 26 bp, 51 bp, 56 bp, 83 bp, 91 bp, 95 bp, 98 bp, 100 bp, 125 bp, 147 bp, 360 bp, 456 bp, 494 bp, 515 bp, 517 bp, 930 bp, 934 bp, 1295 bp, 1434 bp, 1807 bp, 2284 bp, 3564 bp 3910 bp or 5452 bp in length.

The invention also provides for mini-chromosomes comprising centromeres having a CentA repeated nucleotide sequence that is a fragment of SEQ ID NO: 79 or variant thereof. Exemplary fragments of CentA are up to 512 bp or 513 bp in length (see Table 16 below) or range in size from 50 to 512 bp or 50 to 513 bp. The invention further provides for mini-chromosomes comprising centromeres having a variant CentA repeated nucleotide sequence that hybridizes to SEQ ID NO: 79 under highly selective conditions comprising hybridization at 65° C. and washing three times for 15 minutes with 0.25×SSC, 0.1% SDS at 65° C. Additional exemplary stringent hybridization conditions comprise 0.02 M to 0.15 M NaCl at temperatures of about 50° C. to 70° C., or alternatively comprising 0.5×SSC and 0.25% SDS at 65° C. for 15 minutes, followed by a wash at 65° C. for a half hour. The invention also provides for mini-chromosomes comprising a repeated nucleotide sequences that retains overall identity over its length of at least 70%, 75%, 80%, 85%, 90% or 95% to SEQ ID NO: 79.

The invention also provides for mini-chromosomes comprising centromeres having a retrotransposon sequence that is a fragment of any of SEQ ID NOS: 93, 94 or 95, or variant thereof. Exemplary fragments are at least 26 bp, 56 bp, 100 bp, 150 bp, 250 bp, 500 bp, and/or up to 1000 bp, 1327 bp, 2542 bp, 2616 bp, 3000 bp, 3564 bp, 3910 bp, 4000 bp, 5000 bp or 5452 bp in length. The invention further provides for mini-chromosomes comprising centromeres having a fragment or variant retrotransposon sequence that hybridizes to any one of SEQ ID NO: 93, 94 or 95 under highly selective conditions comprising hybridization at 65° C. and washing three times for 15 minutes with 0.25×SSC, 0.1% SDS at 65° C. Additional exemplary stringent hybridization conditions comprise 0.02 M to 0.15 M NaCl at temperatures of about 50° C. to 70° C., or alternatively comprising 0.5×SSC and 0.25% SDS at 65° C. for 15 minutes, followed by a wash at 65° C. for a half hour. The invention also provides for mini-chromosomes comprising a fragment or variant retrotransposon sequence that retains overall identity over its length of at least 70%, 75%, 80%, 85%, 90% or 95% to any one of SEQ ID NO: 93, 94 or 95.

The invention further provides for mini-chromosomes comprising centromeres comprising at least two repeated nucleotide sequences that hybridize under conditions comprising hybridization at 65° C. and followed by a wash in 0.5×SSC and 1% SDS for 15 minutes at 65° C., and two additional washes in the same wash solution at 65° C. for 30 minutes each to SEQ ID NO: 96 or 97. Alternatively, the hybridization conditions may comprise hybridization at 65° C. and washing three times for 15 minutes with 0.25×SSC, 0.1% SDS at 65° C.

In another embodiment, the centromeres of any of the preceding mini-chromosomes comprise a combination of two or more of the repeated nucleotides sequences described herein, including those derived from CentC, CRM, CentA or another retrotransposon sequences. The invention provides for mini-chromosomes having a centromere comprising (a) a first repeated nucleotide sequence derived from CentC that hybridizes under highly selective conditions comprising hybridization at 65° C. and washing three times for 15 minutes with 0.25×SSC, 0.1% SDS at 65° C. to the nucleotide sequence of either SEQ ID NO: 70, SEQ ID NO: 71, SEQ ID NO: 91 or SEQ ID NO: 92, and (b) a second repeated nucleotide sequence derived from CRM or another retrotransposon that hybridizes under highly selective conditions comprising hybridization at 65° C. and washing three times for 15 minutes with 0.25×SSC, 0.1% SDS at 65° C., to a retrotransposon nucleotide sequence of SEQ ID NO: 77 or the nucleotide sequence of another retrotransposon. Additional exemplary stringent hybridization conditions comprise 0.02 M to 0.15 M NaCl at temperatures of about 50° C. to 70° C., or alternatively comprising 0.5×SSC and 0.25% SDS at 65° C. for 15 minutes, followed by a wash at 65° C. for a half hour. Preferably the second repeated nucleotide sequence comprises at least 50 base pairs of SEQ ID NO: 77. Alternatively, the second nucleotide sequence is derived from CentA and can hybridize under highly selective conditions to the nucleotide sequence of SEQ ID NO: 79. As yet another alternative, the second nucleotide sequence is derived from a retrotransposon and can hybridize under highly selective conditions to the nucleotide sequence of any of SEQ ID NO: 93, 94 or 95. In particular, the invention contemplates mini-chromosomes having a centromere comprising the repeated nucleotide sequence of SEQ ID NO: 70 or a variant thereof and a 50 bp fragment of SEQ ID NO: 77. The invention also contemplates mini-chromosomes having a centromere comprising the repeated nucleotide sequence of SEQ ID NO: 71 or a variant thereof and a 50 bp fragment of SEQ ID NO: 77.

The invention further contemplates mini-chromosomes having centromeres comprising at least 300 bp, 400 bp, 500 bp, 750 bp, 1 kb, 1.5 kb, 2 kb, 2.5 kb, 3 kb, 3.5 kb, 4 kb, 4.5 kb, 5 kb, 5.5 kb, 6 kb, 6.5 kb, 7 kb, 10 kb, 25 kb, 50 kb, 100 kb, 150 kb, 190 kb or 200 kb of MMC1, ZB19, or ZB113.

The invention further contemplates that, for any of the contig fragments identified in any of the tables herein by their beginning and ending nucleotide numbers, isolated nucleic acids may be prepared (including single stranded or double stranded) that retain exact identity to the identified fragment or complement thereof, or that are further fragments or variants thereof that preferably retain ability to hybridize to the original identified fragment. Such isolated nucleic acids are used, e.g., as components of mini-chromosomes of the invention, as probes to isolate centromere sequences for use in mini-chromosomes of the invention, or for transcription of desired complementary strands.

The invention also contemplates mini-chromosomes having a centomere comprising one or more of the following simple repeat sequences: AT-rich repeat, $(GCA)_n$ repeat, GA-rich repeat, CT-rich repeat, T-rich or $(TTTTC)_n$ repeat.

In another embodiment, any of the preceding mini-chromosomes comprise centromeres having n copies of a repeated nucleotide sequence, wherein n is less than 1000, 500, 250, 100, 50, 30, 25, 20, 15, 10, 8, or 6. In exemplary embodiments, the centromeres of the mini-chromosomes of the invention comprise n copies of a repeated nucleotide sequence, wherein n is at least 5, 10, 15, or 20, 100 or 250.

In additional exemplary embodiments, the centromeres of the mini-chromosomes of the invention comprise n copies of a repeated nucleotide sequence where n ranges from 5 to 15, 5 to 25, 5 to 50, 5 to 100, 5 to 250, 5 to 500, 5 to 1000, 15 to 25, 15 to 50, 15 to 100, 15 to 250, 15 to 500, 15 to 1000, 25 to 50, 25 to 100, 25 to 250, 25 to 500, 25 to 1000, 50 to 100, 50 to 250, 50 to 500, 50 to 1000, 100 to 250, 100 to 500, 100 to 1000, 250 to 500, 250 to 1000, or 500 to 1000.

According to the rough sequence assembly described in Example 6, BAC clones ZB19 has long stretches of CentC repeat and BAC clone ZP113 has long stretches of CentC repeats and/or CRM repeats. For example, the BAC clone ZB19 has stretches of 50 copies of CentC repeats in about 7.5 kb of the nucleotide sequence of contig 30 (SEQ ID NO: 50) and 70 copies of CentC repeats in about 10.5 kb of the nucleotide sequence of contig 31 (SEQ ID NO: 51). The BAC clone ZB113 has stretches of 7 copies of CentC repeats in about 1 kb of the nucleotide sequence of contig 4 (SEQ ID NO: 55), 13 copies of CentC repeats in 1.5 kb of the nucleotide sequence of contig 8 (SEQ ID NO: 59), 24 copies of CentC repeats in about 3.5 kb of the nucleotide sequence of contig 11 (SEQ ID NO: 62), 70 copies of CentC repeats in about 10.7 kb of the nucleotide sequence of contig 15 (SEQ ID NO: 66), 85 copies of CentC repeats in about 13.5 kb of the nucleotide sequence of contig 17 (SEQ ID NO: 68), and 68 copies of CentC repeats in about 20 kb of the nucleotide sequence of contig 18 (SEQ ID NO: 69). In addition, BAC clone ZB113 has 10 copies of CRM repeats and 20 copies of CentC repeats in about 8.5 kb of the nucleotide sequence of contig 14 (SEQ ID NO: 65). BAC clone ZB113 has 11 copies of CRM repeat and 1 copies of CentA repeat in 15.5 kb of the nucleotide sequence of contig 16 (SEQ ID NO: 67). In addition mini-chromosome MMC1, described in Example 9, had 61.4+2.3 CentC repeats in about 9 kb of centromeric nucleotide sequence. These are examples of stretches of repeated nucleotide sequence in three functional mini-chromosomes.

The invention contemplates mini-chromosomes having a centromere comprising any of the following: at least 5, 6, 7, 8, 9 or 10 repeated nucleotide sequences in about 1.3 kb of nucleotide sequence, at least 15, 20, 25, 30, 35 or 37 repeated nucleotide sequences in about 5.5 kb of nucleotide sequence; at least 30, 35, 40, 45, 50, 55, 57, 60 or 61 repeated nucleotide sequences in about 9 kb of nucleotide sequence; or at least 40, 45, 50, 55, 60, 65, 70, 75 or 76 repeated nucleotide sequences in about 13.5 kb of nucleotide sequence.

In an embodiment of the invention, any of the preceding mini-chromosomes comprising a centromere having at least 5 consecutive repeated nucleotide sequences in head to tail orientation. The invention also provides for any of the preceding mini-chromosomes comprising a centromere having at least 5 repeated nucleotide sequences that are consecutive. Consecutive repeated nucleotide sequences may be in any orientation, e.g. head to tail, tail to tail, or head to head, and need not be directly adjacent to each other (e.g., may be 1-50 bp apart).

The invention further provides for any of the preceding mini-chromosomes comprising a centromere having at least 5 of the consecutive repeated nucleotide sequences separated by less than n number of nucleotides, wherein n ranges from 1 to 10, or 1 to 20, or 1 to 30, or 1 to 40, or 1 to 50 or wherein n is less than 10 bp or n is less than 20 bp or n is less than 30 bp or n is less than 40 bp or n is less than 50 bp.

In one embodiment, the mini-chromosomes of the invention are 1000 kilobases or less in length. In exemplary embodiments, the mini-chromosome is 600 kilobases or less in length or 500 kilobases or less in length.

In another embodiment, the mini-chromosomes of the invention comprises a site for site-specific recombination.

In another embodiment, the invention provides for the mini-chromosome, further comprising a centromeric nucleic acid insert that comprises artificially synthesized repeated nucleotide sequences. These artificially synthesized repeated nucleotide sequences may be derived from natural centromere sequences, combinations or fragments of natural centromere sequences including a combination of repeats of different lengths, a combination of different sequences, a combination of both different repeat lengths and different sequences, a combination of repeats from two or more plant species, a combination of different artificially synthesized sequences or a combination of natural centromere sequence(s) and artificially synthesized sequence(s).

The invention also provides for a mini-chromosome, wherein the mini-chromosome is derived from a donor clone or a centromere clone and has substitutions, deletions, insertions, duplications or arrangements of one or more nucleotides in the mini-chromosome compared to the nucleotide sequence of the donor clone or centromere clone. In one embodiment, the mini-chromosome is obtained by passage of the mini-chromosome through one or more hosts. In another embodiment, the mini-chromosome is obtained by passage of the mini-chromosome through two or more different hosts. The host may be selected from the group consisting of viruses, bacteria, yeasts, plants, prokaryotic organisms, or eukaryotic organisms. In another embodiment, the mini-chromosome is obtained from a donor clone by in vitro methods that introduce sequence variation during template-based replication of the donor clone, or its complementary sequence. In one embodiment this variation may be introduced by a DNA-dependent DNA polymerase. In a further embodiment a minichromosome derived by an in vitro method may be further modified by passage of the mini-chromosome through one or more hosts.

The invention also provides for a mini-chromosome, wherein the mini-chromosome comprises one or more exogenous nucleic acids. In further exemplary embodiments, the mini-chromosome comprises at least two or more, at least three or more, at least four or more, at least five or more or at least ten or more exogenous nucleic acids.

In one embodiment, at least one exogenous nucleic acid of any of the preceding mini-chromosomes of a plant is operably linked to a heterologous regulatory sequence functional in plant cells, including but not limited to a plant regulatory sequence. The invention also provides for exogenous nucleic acids linked to a non-plant regulatory sequence, such as an arthropod, viral, bacterial, vertebrate or yeast regulatory sequence.

In another embodiment, the mini-chromosome comprises an exogenous nucleic acid that confers herbicide resistance, insect resistance, disease resistance, or stress resistance on the plant. The invention provides for mini-chromosomes comprising an exogenous nucleic acid that confers resistance to phosphinothricin or glyphosate herbicide. Nonlimiting examples include an exogenous nucleic acid that encodes a phosphinothricin acetyltransferase, glyphosate acetyltransferase, acetohydroxyadic synthase or a mutant enoylpyruvylshikimate phosphate (EPSP) synthase. Nonlimiting examples of exogenous nucleic acids that confer insect resistance include a *Bacillus thuringiensis* toxin gene or *Bacillus cereus* toxin gene. In related embodiments, the mini-chromosome comprises an exogenous nucleic acid conferring herbicide resistance, an exogenous nucleic acid conferring insect resistance, and at least one additional exogenous nucleic acid.

The invention further provides for mini-chromosomes comprising an exogenous nucleic acid that confers resistance to drought, heat, chilling, freezing, excessive moisture, ultraviolet light, ionizing radiation, toxins, pollution, mechanical stress or salt stress. The invention also provides for a mini-chromosome that comprises an exogenous nucleic acid that confers resistance to a virus, bacteria, fungi or nematode.

The invention provides for mini-chromosomes comprising an exogenous nucleic acid selected from the group consisting of a nitrogen fixation gene, a plant stress-induced gene, a nutrient utilization gene, a gene that affects plant pigmentation, a gene that encodes an antisense or ribozyme molecule, a gene encoding a secretable antigen, a toxin gene, a receptor gene, a ligand gene, a seed storage gene, a hormone gene, an enzyme gene, an interleukin gene, a clotting factor gene, a cytokine gene, an antibody gene, a growth factor gene, a transcription factor gene, a transcriptional repressor gene, a DNA-binding protein gene, a recombination gene, a DNA replication gene, a programmed cell death gene, a kinase gene, a phosphatase gene, a G protein gene, a cyclin gene, a cell cycle control gene, a gene involved in transcription, a gene involved in translation, a gene involved in RNA processing, a gene involved in RNAi, an organellar gene, a intracellular trafficking gene, an integral membrane protein gene, a transporter gene, a membrane channel protein gene, a cell wall gene, a gene involved in protein processing, a gene involved in protein modification, a gene involved in protein degradation, a gene involved in metabolism, a gene involved in biosynthesis, a gene involved in assimilation of nitrogen or other elements or nutrients, a gene involved in controlling carbon flux, gene involved in respiration, a gene involved in photosynthesis, a gene involved in light sensing, a gene involved in organogenesis, a gene involved in embryogenesis, a gene involved in differentiation, a gene involved in meiotic drive, a gene involved in self incompatibility, a gene involved in development, a gene involved in nutrient, metabolite or mineral transport, a gene involved in nutrient, metabolite or mineral storage, a calcium-binding protein gene, or a lipid-binding protein gene.

The invention also provides for a mini-chromosome comprising an exogenous enzyme gene selected from the group consisting of a gene that encodes an enzyme involved in metabolizing biochemical wastes for use in bioremediation, a gene that encodes an enzyme for modifying pathways that produce secondary plant metabolites, a gene that encodes an enzyme that produces a pharmaceutical, a gene that encodes an enzyme that improves changes the nutritional content of a plant, a gene that encodes an enzyme involved in vitamin synthesis, a gene that encodes an enzyme involved in carbohydrate, polysaccharide or starch synthesis, a gene that encodes an enzyme involved in mineral accumulation or availability, a gene that encodes a phytase, a gene that encodes an enzyme involved in fatty acid, fat or oil synthesis, a gene that encodes an enzyme involved in synthesis of chemicals or plastics, a gene that encodes an enzyme involved in synthesis of a fuel and a gene that encodes an enzyme involved in synthesis of a fragrance, a gene that encodes an enzyme involved in synthesis of a flavor, a gene that encodes an enzyme involved in synthesis of a pigment or dye, a gene that encodes an enzyme involved in synthesis of a hydrocarbon, a gene that encodes an enzyme involved in synthesis of a structural or fibrous compound, a gene that encodes an enzyme involved in synthesis of a food additive, a gene that encodes an enzyme involved in synthesis of a chemical insecticide, a gene that encodes an enzyme involved in synthesis of an insect repellent, or a gene controlling carbon flux in a plant.

In another embodiment of the invention, any of the preceding mini-chromosomes comprise a telomere.

The invention also provides embodiments wherein any of the preceding mini-chromosomes are linear or circular.

In one embodiment, the invention provides for adchromosomal *Zea mays* (corn) plants and/or corn plant cells comprising any of the preceding mini-chromosomes. The invention also provides for corn plant tissue and corn seed obtained from the corn plants of the invention.

In another embodiment, the invention provides for adchromosomal plants comprising any of the preceding mini-chromosomes. In addition, the invention provides for plant cells, tissues and seeds obtained from the adchromosomal plants.

In one embodiment of the invention, any of the preceding adchromosomal plants are a monocotyledon. In another embodiment of the invention, any of the preceding adchromosomal plants are a dicotyledone. The invention also provides that the adchromosomal plants of the invention are, e.g., crop plants, cereal plants, vegetable crops, field crops, fruit and vine crops, wood or fiber crops or ornamental plants.

Another embodiment of the invention is a part of any of the preceding adchromosomal plants. Exemplary plant parts of the invention include a pod, root, cutting, tuber, stem, stalk, fruit, berry, nut, flower, leaf, bark, wood, epidermis, vascular tissue, organ, protoplast, crown, callus culture, petiole, petal, sepal, stamen, stigma, style, bud, meristem, cambium, cortex, pith, sheath, silk or embryo. Other exemplary plant parts are a meiocyte or gamete or ovule or pollen or endosperm of any of the preceding adchromosomal plants. Other exemplary plant parts are a seed, embryo or propagule of any of the preceding adchromosomal plants.

An embodiment of the invention is a progeny of any of the preceding adchromosomal plants of the invention. These progeny of the invention may be the result of self-breeding, cross-breeding, apomyxis or clonal propagation. In exemplary embodiments, the invention also provides for progeny that comprise a mini-chromosome that is descended from a parental mini-chromosome that contained a centromere less than about 200 kilobases in length, less than 150 kilobases, less than 100 kilobases, less than 85 kilobases in length, less than about 50 kilobases in length, less than about 30 kb in length, less than about 20 kb in length, less than about 12 kilobases in length, less than about 10 kb in length, less than about 7 kb in length, less than about 5 kb in length, or less than about 2 kb in length.

In another aspect, the invention provides for methods of making a mini-chromosome for use in any of the preceding adchromosomal plants of the invention. These methods comprise identifying a centromere nucleotide sequence in a genomic DNA library using a multiplicity of diverse probes, and constructing a mini-chromosome comprising the centromere nucleotide sequence. These methods may further comprise determining hybridization scores for hybridization of the multiplicity of diverse probes to genomic clones within the genomic nucleic acid library, determining a classification for genomic clones within the genomic nucleic acid library according to the hybridization scores for at least two of the diverse probes, and selecting one or more genomic clones within one or more classifications for constructing the mini-chromosome.

In exemplary embodiments, the step of determining a classification for genomic clones within the genomic nucleic acid library may utilize the hybridization scores for at least 3, 4, 5, 6, 7, 8, 9, 10, 11, 12, 13, 14, 15, 16, 17, 18, 19, 20, 21, 22, 23, 24, 25, 26, 27, 28, 29 or 30 or more different probes. A classification may comprise a pattern of high, medium or low hybridization scores to various probes.

Exemplary embodiments of probes useful in this method include a probe that hybridizes to the centromere region of a chromosome, a probe that hybridizes to satellite repeat DNA, a probe that hybridizes to retroelement or retrotransposon DNA, a probe that hybridizes to portions of genomic DNA that are heavily methylated, a probe that hybridizes to arrays of tandem repeats in genomic DNA, a probe that hybridizes to telomere DNA or a probe that hybridizes to a pseudogene. Other exemplary probes include, a probe that hybridizes to ribosomal DNA, a probe that hybridizes to mitochondrial DNA, or a probe that hybridizes to chloroplast DNA, for which preferably a classification comprises a low hybridization score for hybridization to said probe.

Another aspect of the invention provides for methods of using any of the preceding adchromosomal plants for a food product, a pharmaceutical product or chemical product, according to which a suitable exogenous nucleic acid is expressed in adchromosomal plants or plant cells and the plant or plant cells are grown. The plant may secrete the product into its growth environment or the product may be contained within the plant, in which case the plant is harvested and desirable products are extracted.

Thus, the invention contemplates methods of using any of the preceding adchromosomal plants to produce a modified food product, for example, by growing a plant that expresses a exogenous nucleic acid that alters the nutritional content of the plant, and harvesting or processing the corn plant.

The invention also contemplates methods of using any of the preceding adchromosomal plants to produce a recombinant protein, by growing a plant comprising a mini-chromosome that comprises an exogenous nucleic acid encoding the recombinant protein. Optionally the plant is harvested and the desired recombinant protein is isolated from the plant. Exemplary recombinant proteins include pharmaceutical proteins or industrial enzymes.

The invention also contemplates methods of using any of the preceding adchromosomal plants to produce a recombinant protein, by growing a plant comprising a mini-chromosome that comprises an exogenous nucleic acid encoding an enzyme involved in synthesis of the chemical product. Optionally the plant is harvested and the desired chemical product is isolated from the plant. Exemplary chemical products include pharmaceutical products.

BRIEF DESCRIPTION OF DRAWING

FIG. 3 shows the alignment of *Glycine max* (soybean) consensus centromere satellite repeats. Repeats isolated at random from the genome (consensus classes ChrGm1 (SEQ ID NO: 98) and ChrGm2 (SEQ ID NO: 99), and the consensus repeat isolated from SB12MC (SEQ ID NO: 97) are compared; bases showing a significant difference are shaded.

FIG. 4 shows an alignment of the TRS repeat and the novel 100 bp repeat obtained from soybean genomic DNA, and the mini-chromosomes SB12R2-2, SB6A-3, SBC-1 and SBC-9.

FIG. 5 shows the soybean 127 bp consensus sequence.

SEQUENCES OF THE INVENTION

Figure 1:
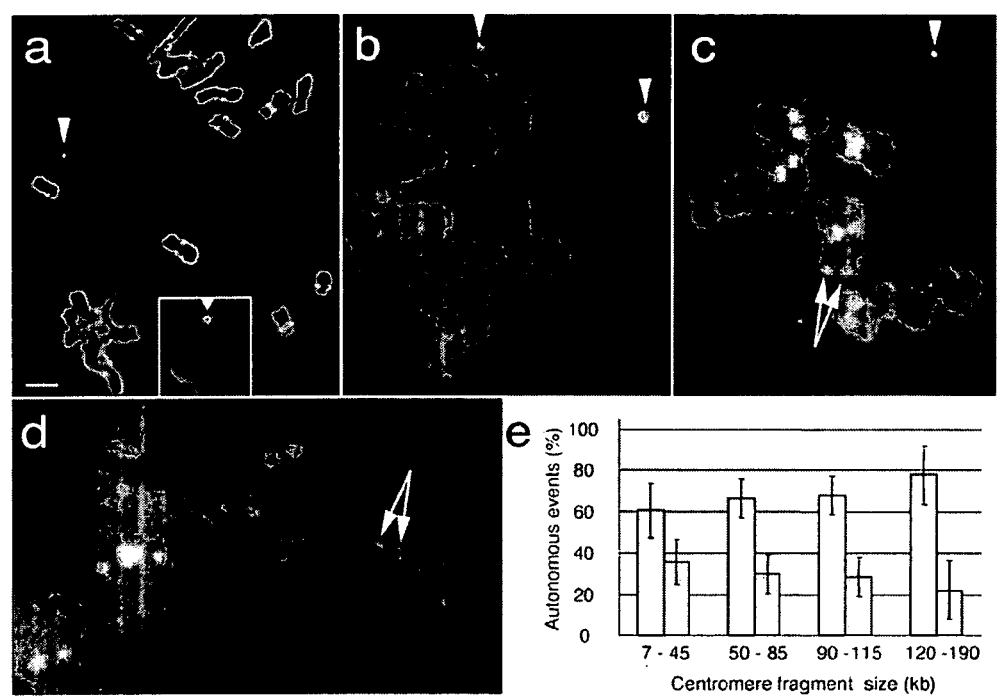
FIG. 1 depicts generation of autonomous mini-chromosomes. Panels A-D depict metaphase chromosome spreads labeled with FISH probes specific for the DsRed and nptII gene cassette or centromere sequences; DNA is stained with DAPI; autonomous mini-chromosomes (arrowheads); integrated constructs appear as pairs of FISH signals (arrows); size bar, 5 µm. (a-b) MMC1 event V-1; (a) T1 plant, (b) T2 plant; (c) event V-4 with autonomous and integrated copies of MMC1; (d) pCHR758 (non-centromeric control). Panel E depicts centromere fragments across a wide size range enable autonomous mini-chromosome inheritance. For each size category, the percentage of transformation events (total=48) that yielded only an autonomous mini-chromosomes (white bars) or both an autonomous and integrated mini-chromosomes in the same cell (grey bars) is shown; error bars=standard error.

The following table indicates the identity of the SEQ ID NOs in the sequence listing:
SEQ ID NOS: 1-6—*Drosophila melanogaster* promoter sequences
SEQ ID NOS: 7-20 *Saccharomyces cerevisia* promoter sequences SEQ ID NOS: 21-51—contigs 1-31 of ZB19
SEQ ID NOS: 52-69—contigs 1-18 of ZB113
SEQ ID NO 70—Consensus repeat sequence of CentC from ZB19
SEQ ID NO 71—Consensus repeat sequence of CentC from ZB113
SEQ ID NO 72—Consensus repeat sequence of repeat SmOTOT00200215.1 from ZB113
SEQ ID NO 73—Consensus repeat sequence of repeat SmOTOT00200215.2 from ZB113
SEQ ID NO 74—Consensus repeat sequence of repeat SmOTOT00200480 from ZB113
SEQ ID NO 75—Consensus repeat sequence of repeat SmOTOT00200588 from ZB113
SEQ ID NO: 76—Full length sequence of CentC (GenBank Accession no. AY321491)
SEQ ID NO: 77—Full length sequence of CRM (GenBank Accession no. AY129008)
SEQ ID NO: 78—Full length sequence of CentA (GenBank Accession no. AF078917)
SEQ ID NOS: 79-89—Additional sequences from ZB19 and ZB113
SEQ ID NO: 90—Sequence of MMC1
SEQ ID NO: 91—Assembled MMC1 sequence
SEQ ID NO: 92:—Consensus sequence of MMC1 Cent C repeats
SEQ ID NO: 93: Retrotransposon nucleotide sequence
SEQ ID NO: 94: Retrotransposon nucleotide sequence
SEQ ID NO: 95: Retrotransposon nucleotide sequence
SEQ ID NO: 96: Novel contiguous nucleotide sequence of SB12MC centromeric insert
SEQ ID NO: 97: Novel 100 bp nucleotide repeat sequence of SB12MC
SEQ ID NO: 98: Soybean consensus repeat sequence CrGm1
SEQ ID NO: 99: Soybean consensus repeat sequence CrGm2
SEQ ID NO: 99: Soybean TRS repeat sequence
SEQ ID NO: 100: Full length sequence of MMC1 (Genbank Accession No. EU053446)

DETAILED DESCRIPTION OF THE INVENTION

While this invention is susceptible of embodiment in many different forms, and will be described herein in detail, specific embodiments thereof with the understanding that the present disclosure is to be considered as an exemplification of the principles of the invention and is not intended to limit the invention to the specific embodiments illustrated.

The invention provides novel, functional, stable, autonomous mini-chromosomes. Such mini-chromosomes have been shown herein to be meiotically transmitted to progeny. The invention also provides for adchromosomal plants, particularly *Zea mays* plants, described in further detail herein, comprising a mini-chromosome, wherein said mini-chromosome preferably has a transmission efficiency during mitotic division of at least 90%, for example, at least 95%. Additionally, these adchromosomal plants may comprise a mini-chromosome having a transmission efficiency during meiotic division of, e.g., at least 80%, at least 85%, at least 90% or at least 95%.

One aspect of the invention is related to plants containing functional, stable, autonomous mini-chromosomes, preferably carrying one or more nucleic acids exogenous to the cell. Such plants carrying mini-chromosomes are contrasted to transgenic plants whose genome has been altered by chromosomal integration of an exogenous nucleic acid. Preferably, expression of the exogenous nucleic acid, either constitutively or in response to a signal which may be a challenge or a stimulus, e.g. tissue specific expression or time specific expression, results in an altered phenotype of the plant.

The invention provides for mini-chromosomes comprising at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 60, 70, 80, 90, 100, 110, 120, 130, 140, 150, 250, 500, 1000 or more exogenous nucleic acids.

The invention contemplates that any plants, including but not limited to monocots, dicots, gymnosperm, field crops, vegetable crops, fruit and vine crops, or any specific plants named herein, may be modified by carrying autonomous mini-chromosomes as described herein. A related aspect of the invention is plant parts or plant tissues, including pollen, silk, endosperm, ovule, seed, embryo, pods, roots, cuttings, tubers, stems, stalks, fruit, berries, nuts, flowers, leaves, bark, whole plant, plant cell, plant organ, protoplast, cell culture, or any group of plant cells organized into a structural and functional unit, any cells of which carry mini-chromosomes.

A related aspect of the invention is adchromosomal plant parts or plant tissues, including pollen, silk, endosperm, ovule, seed, embryo, pods, roots, cuttings, tubers, stems, stalks, crown, callus culture, petiole, petal, sepal, stamen, stigma, style, bud, fruit, berries, nuts, flowers, leaves, bark, wood, whole plant, plant cell, plant organ, protoplast, cell culture, or any group of plant cells organized into a structural and functional unit. In one preferred embodiment, the exogenous nucleic acid is primarily expressed in a specific location or tissue of a plant, for example, epidermis, vascular tissue, meristem, cambium, cortex, pith, leaf, sheath, flower, root or seed. Tissue-specific expression can be accomplished with, for example, localized presence of the mini-chromosome, selective maintenance of the mini-chromosome, or with promoters that drive tissue-specific expression.

Another related aspect of the invention is meiocytes, pollen, ovules, endosperm, seed, somatic embryos, apomyctic embryos, embryos derived from fertilization, vegetative propagules and progeny of the originally adchromosomal plant and of its filial generations that retain the functional, stable, autonomous mini-chromosome. Such progeny include clonally propagated plants, embryos and plant parts as well as filial progeny from self- and cross-breeding, and from apomyxis.

Preferably the mini-chromosome is transmitted to subsequent generations of viable daughter cells during mitotic cell division with a transmission efficiency of at least 60%, 70%, 80%, 85%, 90%, 95%, 96%, 97%, 98%, or 99%. More preferably, the mini-chromosome is transmitted to viable gametes during meiotic cell division with a transmission efficiency of at least 60%, 70%, 80%, 85%, 90%, 95%, 96%, 97%, 98%, or 99% when more than one copy of the mini-chromosome is present in the gamete mother cells of the plant. Preferably, the mini-chromosome is transmitted to viable gametes during meiotic cell division with a transmission frequency of at least 20%, 30%, 40%, 45%, 46%, 47%, 48%, or 49% when one copy of the mini-chromosome is present in the gamete mother cells of the plant. For production of seeds via sexual reproduction or by apomyxis the mini-chromosome is preferably transferred into at least 60%, 70%, 80%, 85%, 90%, 95%, 96%, 97%, 98%, or 99% of viable embryos when cells of the plant contain more than one copy of the mini-chromosome. For production of seeds via sexual reproduction or by apomyxis from plants with one mini-chromosome per cell, the mini-chromosome is preferably transferred into at least 20%, 30%, 40%, 45%, 46%, 47%, 48%, or 49% of viable embryos.

Preferably, a mini-chromosome that comprises an exogenous selectable trait or exogenous selectable marker can be employed to increase the frequency in subsequent generations of adchromosomal cells, tissues, gametes, embryos, endosperm, seeds, plants or progeny. More preferably, the frequency of transmission of mini-chromosomes into viable cells, tissues, gametes, embryos, endosperm, seeds, plants or progeny can be at least 95%, 96%, 97%, 98%, 99% or 99.5% after mitosis or meiosis by applying a selection that favors the survival of adchromosomal cells, tissues, gametes, embryos, endosperm, seeds, plants or progeny over such cells, tissues, gametes, embryos, endosperm, seeds, plants or progeny lacking the mini-chromosome.

Transmission efficiency may be measured as the percentage of progeny cells or plants that carry the mini-chromosome as measured by one of several assays taught herein including detection of reporter gene fluorescence, PCR detection of a sequence that is carried by the mini-chromosome, RT-PCR detection of a gene transcript for a gene carried on the mini-chromosome, Western analysis of a protein produced by a gene carried on the mini-chromosome, Southern analysis of the DNA (either in total or a portion thereof) carried by the mini-chromosome, fluorescence in situ hybridization (FISH) or in situ localization by repressor binding, to name a few. Any assay used to detect the presence of the mini-chromosome (or a portion of the mini-chromosome) may be used to measure the efficiency of a parental cell or plant transmits the mini-chromosome to its progeny. Efficient transmission as measured by some benchmark percentage should indicate the degree to which the mini-chromosome is stable through the mitotic and meiotic cycles.

Plants of the invention may also contain chromosomally integrated exogenous nucleic acid in addition to the autonomous mini-chromosomes. The adchromosomal plants or plant parts, including plant tissues of the invention may include plants that have chromosomal integration of some portion of the mini-chromosome (e.g. exogenous nucleic acid or centromere sequences) in some or all cells the plant. The plant, including plant tissue or plant cell is still characterized as adchromosomal despite the occurrence of some chromosomal integration. In one aspect of the invention, the autonomous mini-chromosome can be isolated from integrated exogenous nucleic acid by crossing the adchromosomal plant containing the integrated exogenous nucleic acid with plants producing some gametes lacking the integrated exogenous nucleic acid and subsequently isolating offspring of the cross, or subsequent crosses, that are adchromosomal but lack the integrated exogenous nucleic acid. This independent segregation of the mini-chromosome is one measure of the autonomous nature of the mini-chromosome.

Another aspect of the invention relates to methods for producing and isolating such adchromosomal plants containing functional, stable, autonomous mini-chromosomes.

In one embodiment, the invention contemplates improved methods for isolating native centromere sequences. In another embodiment, the invention contemplates methods for generating variants of native or artificial centromere sequences by passage through bacterial or plant or other host cells.

In a further embodiment, the invention contemplates methods for delivering the mini-chromosome into plant cells or tissues to transform the cells or tissues, optionally detecting mini-chromosome presence or assessing mini-chromosome performance, and optionally generating a plant from such cells or tissues.

Exemplary assays for assessing mini-chromosome performance include lineage-based inheritance assays, use of chromosome loss agents to demonstrate autonomy, exonucleas digestion, global mitotic mini-chromosome inheritance assays (sectoring assays) with or without the use of agents inducing chromosomal loss, assays measuring expression levels of marker genes in the mini-chromosome over time and space in a plant, physical assays for separation of autonomous mini-chromosomes from endogenous nuclear chromosomes of plants, molecular assays demonstrating conserved mini-chromosome structure, such as PCR, Southern blots, mini-chromosome rescue, cloning and characterization of mini-chromosome sequences present in the plant, cytological assays detecting mini-chromosome presence in the cell's genome (e.g. FISH) and meiotic mini-chromosome inheritance assays, which measure the levels of mini-chromosome inheritance into a subsequent generation of plants via meiosis and gametes, embryos, endosperm or seeds.

Another aspect of the invention relates to methods for using such adchromosomal plants containing a mini-chromosome for producing food products, pharmaceutical products and chemical products by appropriate expression of exogenous nucleic acid(s) contained within the mini-chromosome(s).

Mini-chromosomes containing centromeres from one plant species, when inserted into plant cells of a different species or even a different genus or family, can be stable, functional and autonomous. Thus, another aspect of the invention is an adchromosomal plant comprising a functional, stable, autonomous mini-chromosome that contains centromere sequence derived from *Zea mays*.

Yet another aspect of the invention provides novel autonomous mini-chromosomes with novel compositions and structures which are used to transform plant cells which are in turn used to generate a plant (or multiple plants). Exemplary mini-chromosomes of the invention are contemplated to be of a size 2000 kb or less in length. Other exemplary sizes of mini-chromosomes include less than or equal to, e.g., 1500 kb, 1000 kb, 900 kb, 800 kb, 700 kb, 600 kb, 500 kb, 450 kb, 400 kb, 350 kb, 300 kb, 250 kb, 200 kb, 150 kb, 100 kb, 80 kb, 60 kb, 40 kb or 35 kb in length.

In a related aspect, novel centromere compositions as characterized by sequence content, size or other parameters are provided. Preferably, the minimal size of centromeric sequence is utilized in mini-chromosome construction. Exemplary sizes include a centromeric nucleic acid insert derived from a portion of plant genomic DNA, that is less than or equal to 1000 kb, 900 kb, 800 kb, 700 kb, 600 kb, 500 kb, 400 kb, 300 kb, 200 kb, 190 kb, 150 kb, 100 kb, 95 kb, 90 kb, 85 kb, 80 kb, 75 kb, 70 kb, 65 kb, 60 kb, 55 kb, 50 kb, 45 kb, 40 kb, 35 kb, 30 kb, 25 kb, 20 kb, 17 kb, 15 kb, 12 kb, 10 kb, 7, kb, 6.4 kb, 5 kb, or 2 kb in length. Exemplary inserts may range in size 80 kb to 100 kb, 7 kb to 190 kb, 7 kb to 12 kb, 5 kb to 10 kb, 3 kb to 10 kb, 3 kb to 7 kb, 5 kb to 7 kb. For example, rescued functional variant soybean centromeric sequences have been shown to be less than 30 kb in size. Moreover, as little as 7 kb of maize sequence has been shown to provide centromere function. Another related aspect is the novel structure of the mini-chromosome, particularly structures lacking bacterial sequences, e.g., required for bacterial propagation.

In exemplary embodiments, the invention also contemplates mini-chromosomes or other vectors comprising fragments or variants of the genomic DNA inserts of the BAC clones [identified as ZB19, or ZB113] deposited on Feb. 23, 2005 with the American Type Culture Collection (ATCC), P.O. Box 1549 Manassas, Va. 20108, USA, under Accession Nos. PTA-6604 and, PTA-6605, respectively], or fragments of SEQ ID NO: 90, fragments of SEQ ID NO: 91 or fragments of SEQ ID NO: 100, naturally occurring descendants thereof, that retain the ability to segregate during mitotic or meiotic division as described herein, as well as adchromosomal plants or parts containing these mini-chromosomes. Other exemplary embodiments include mini-chromosomes or other vectors comprising fragments or variants of the genomic DNA inserts of any of the BAC clones identified herein including MMC1, or descendants thereof, and fragments or variants of the centromeric nucleic acid inserts of any of the vectors or mini-chromosomes identified herein.

In other exemplary embodiments, the invention contemplates mini-chromosomes or other vectors comprising centromeric nucleotide sequence that when hybridized to 1, 2, 3, 4, 5, 6, 7, 8 or more of the probes described in the examples herein, under hybridization conditions described herein, e.g. low, medium or high stringency, provides relative hybridization scores as described in the examples herein. Exemplary stringent hybridization conditions comprise hybridization at 65° C. and washing three times for 15 minutes with 0.25× SSC, 0.1% SDS at 65° C. Additional exemplary stringent hybridization conditions comprise hybridization in 0.02 M to 0.15 M NaCl at temperatures of about 50° C. to 70° C. or 0.5×SSC 0.25% SDS at 65° for 15 minutes, followed by a wash at 65 degrees for a half hour or hybridization at 65° C. for 14 hours followed by 3 washings with 0.5×SSC, 1% SDS at 65° C. Preferably the probes for which relative hybridization scores are described herein as 5/10 or greater are used, and a hybridization signal greater than background for one or more of these probes is used to select clones. Adchromosomal plants or parts containing such mini-chromosomes are contemplated.

The invention contemplates mini-chromosomes having centromeres comprising at least 50 bp of the contig segments identified in Tables 14 and 18 as homologous to any of the following sequences: Mo17 locus bz (GenBank Accession No. AY664416), rust resistance gene rp3-1 (GenBank Accession No. AY5704035), coliphage phi-X174 (Genbank Accession No. J02482), 40S ribosomal protein S8 (GenBank Accession No. AY530951), gag-pol (GenBank Accession No. AF464738), retrotransposon (GenBank Accession No. AY574035), Mo17 locus 9008 (GenBank Accession No. AY664418), alpha zein gene cluster (GenBank Accession No. AF090447), Mo17 locus 9009 (GenBank Accession No. AY664419), B73 locus 9002 (GenBank Accession No. AY664413), *Magnaporthe grisea* (GenBank Accession No. XM_367004), yeast 26S ribosomal RNA (GenBank Accession No. AY046113), Tn1 (GenBank Accession No. AF162223), and polynucleotides having the sequence of any of SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88 and SEQ ID NO: 89. The invention also contemplates mini-chromosomes having a centromere comprising a fragment or a variant of any of these nucleotide sequences.

The advantages of the present invention include: provision of an autonomous, independent genetic linkage group for accelerating breeding; lack of disruption of host genome; multiple gene "stacking" of large an potentially unlimited numbers of genes; uniform genetic composition exogenous DNA sequences in plant cells and plants containing autonomous mini-chromosomes; defined genetic context for predictable gene expression; higher frequency occurrence and recovery of plant cells and plants containing stably maintained exogenous DNA due to elimination of inefficient integration step; and the ability to eliminate mini-chromosomes in any tissues.

I. Composition of Mini-Chromosomes and Mini-Chromosome Construction

The mini-chromosome vector of the present invention may contain a variety of elements, including (1) sequences that function as plant centromeres, (2) one or more exogenous nucleic acids, including, for example, plant-expressed genes, (3) sequences that function as an origin of replication, which may be included in the region that functions as plant centromere, (4) optionally, a bacterial plasmid backbone for propagation of the plasmid in bacteria, (5) optionally, sequences that function as plant telomeres, (6) optionally, additional "stuffer DNA" sequences that serve to separate the various components on the mini-chromosome from each other, (7) optionally "buffer" sequences such as MARs or SARs, (8) optionally marker sequences of any origin, including but not limited to plant and bacterial origin, (9) optionally, sequences that serve as recombination sites, and (10) "chromatin packaging sequences" such as cohesion and condensing binding sites.

The mini-chromosomes of the present invention may be constructed to include various components which are novel, which include, but are not limited to, the centromere comprising novel repeating centromeric sequences, as described in further detail below.

Novel Centromere Compositions

The centromere in the mini-chromosome of the present invention may comprise novel repeating centromeric sequences.

Exemplary embodiments of centromere nucleic acid sequences according to the present invention include fragments or variants of the genomic DNA inserts of the BAC clones [identified as ZB19, or ZB113 deposited on Feb. 23, 2005 with the American Type Culture Collection (ATCC), P.O. Box 1549 Manassas, Va. 20108, USA, under Accession Nos. PTA-6604 and PTA-6605, respectively], MMC1, or SB12MC, that retain the ability to segregate during mitotic or meiotic division as described herein. Variants of such sequences include artificially produced modifications as described herein and modifications produced via passaging through one or more bacterial, plant or other host cells as described herein.

The invention optionally excludes from the claims any soybean centromere sequence that would hybridize to the soybean centromere sequences disclosed in the following patent publications that are incorporated in their entirety herein: U.S. Pat. No. 7,119,250, U.S. Pat. No. 7,193,128 and WO 2005/083096.

Vectors comprising one, two, three, four, five, six, seven, eight, nine, ten, 15 or 20 or more of the elements contained in any of the exemplary vectors described in the examples below are also contemplated.

The invention specifically contemplates the alternative use of fragments or variants (mutants) of any of the nucleic acids described herein that retain the desired activity, including nucleic acids that function as centromeres, nucleic acids that function as promoters or other regulatory control sequences, or exogenous nucleic acids. Variants may have one or more additions, substitutions or deletions of nucleotides within the original nucleotide sequence or consensus sequence. Variants include nucleic acid sequences that are at least 50%, 55%, 60, 65, 70, 75, 80, 81, 82, 83, 84, 85, 86, 87, 88, 89, 90, 91, 92, 93, 94, 95, 96, 97, 98, 99, or 100% identical to the original nucleic acid sequence. Variants also include nucleic acid sequences that hybridize under low, medium, high or very high stringency conditions to the original nucleic acid sequence. Similarly, the specification also contemplates the alternative use of fragments or variants of any of the polypeptides described herein.

The comparison of sequences and determination of percent identity between two nucleotide sequences can be accomplished using a mathematical algorithm. In a preferred embodiment, the percent identity between two amino acid sequences is determined using the Needleman and Wunsch (1970) J. Mol. Biol. 48:444-453 algorithm which has been incorporated into the GAP program in the GCG software package, using either a Blossum 62 matrix or a PAM250 matrix. Preferably parameters are set so as to maximize the percent identity.

As used herein, the term "hybridizes under low stringency, medium stringency, and high stringency conditions" describes conditions for hybridization and washing. Guidance for performing hybridization reactions can be found in Current Protocols in Molecular Biology (1989) John Wiley & Sons, N.Y., 6.3.1-6.3.6, which is incorporated by reference. Aqueous and non-aqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.5× SSC, 0.1% SDS, at least at 50° C.; 2) medium stringency hybridization conditions in 6×SSC at about 45° C., followed by one or more washes in 0.2×SSC, 0.1% SDS at 55° C.; 3) high stringency hybridization conditions are hybridization at 65° C. and washing three times for 15 minutes with 0.25× SSC, 0.1% SDS at 65° C. Additional exemplary stringent hybridization conditions comprise 6×SSC at about 45° C., followed by one or more washes in 0.2×SSC, 0.1% SDS at 65° C. Other exemplary highly selective or stringent hybridization conditions comprise 0.02 M to 0.15 M NaCl at temperatures of about 50° C. to 70° C. or 0.5×SSC 0.25% SDS at 65° for 15 minutes, followed by a wash at 65 degrees for a half hour.

Mini-Chromosome Sequence Content and Structure

Plant-expressed genes from non-plant sources may be modified to accommodate plant codon usage, to insert preferred motifs near the translation initiation ATG codon, to remove sequences recognized in plants as 5' or 3' splice sites, or to better reflect plant GC/AT content. Plant genes typically have a GC content of more than 35%, and coding sequences which are rich in A and T nucleotides can be problematic. For example, ATTTA motifs may destabilize mRNA; plant polyadenylation signals such as AATAAA at inappropriate positions within the message may cause premature truncation of transcription; and monocotyledons may recognize AT-rich sequences as splice sites.

Each exogenous nucleic acid or plant-expressed gene may include a promoter, a coding region and a terminator sequence, which may be separated from each other by restriction endonuclease sites or recombination sites or both. Genes may also include introns, which may be present in any number and at any position within the transcribed portion of the gene, including the 5' untranslated sequence, the coding region and the 3' untranslated sequence. Introns may be natural plant introns derived from any plant, or artificial introns based on the splice site consensus that has been defined for plant species. Some intron sequences have been shown to enhance expression in plants. Optionally the exogenous nucleic acid may include a plant transcriptional terminator, non-translated leader sequences derived from viruses that enhance expression, a minimal promoter, or a signal sequence controlling the targeting of gene products to plant compartments or organelles.

The coding regions of the genes can encode any protein, including but not limited to visible marker genes (for example, fluorescent protein genes, other genes conferring a visible phenotype to the plant) or other screenable or selectable marker genes (for example, conferring resistance to antibiotics, herbicides or other toxic compounds or encoding a protein that confers a growth advantage to the cell expressing the protein) or genes which confer some commercial or agronomic value to the adchromosomal plant. Multiple genes can be placed on the same mini-chromosome vector, limited only by the number of restriction endonuclease sites or site-specific recombination sites present in the vector. The genes may be separated from each other by restriction endonuclease sites, homing endonuclease sites, recombination sites or any combinations thereof. Any number of genes can be present.

The mini-chromosome vector may also contain a bacterial plasmid backbone for propagation of the plasmid in bacteria such as *E. coli, A. tumefaciens,* or *A. rhizogenes*. The plasmid backbone may be that of a low-copy vector or in other embodiments it may be desirable to use a mid to high level copy backbone. In one embodiment of the invention, this backbone contains the replicon of the F' plasmid of *E. coli*. However, other plasmid replicons, such as the bacteriophage P1 replicon, or other low-copy plasmid systems such as the RK2 replication origin, may also be used. The backbone may include one or several antibiotic-resistance genes conferring resistance to a specific antibiotic to the bacterial cell in which the plasmid is present. Bacterial antibiotic-resistance genes include but are not limited to kanamycin-, ampicillin-, chloramphenicol-, streptomycin-, spectinomycin-, tetracycline- and gentamycin-resistance genes.

The mini-chromosome vector may also contain plant telomeres. An exemplary telomere sequence is TTTAGGG or its complement. Telomeres are specialized DNA structures at the ends of linear chromosomes that function to stabilize the ends and facilitate the complete replication of the extreme termini of the DNA molecule (Richards et. al., Cell. 1988 Apr. 8; 53(1):127-36; Ausubel et al., Current Protocols in Molecular Biology, Wiley & Sons, 1997).

Additionally, the mini-chromosome vector may contain "stuffer DNA" sequences that serve to separate the various components on the mini-chromosome (centromere, genes, telomeres) from each other. The stuffer DNA may be of any origin, prokaryotic or eukaryotic, and from any genome or species, plant, animal, microbe or organelle, or may be of synthetic origin. The stuffer DNA can range from 100 bp to 10 Mb in length and can be repetitive in sequence, with unit repeats from 10 to 1,000,000 bp. Examples of repetitive sequences that can be used as stuffer DNAs include but are not limited to: rDNA, satellite repeats, retroelements, transposons, pseudogenes, transcribed genes, microsatellites, tDNA genes, short sequence repeats and combinations thereof. Alternatively, the stuffer DNA can consist of unique, non-repetitive DNA of any origin or sequence. The stuffer sequences may also include DNA with the ability to form boundary domains, such as but not limited to scaffold attachment regions (SARs) or matrix attachment regions (MARs). The stuffer DNA may be entirely synthetic, composed of random sequence. In this case, the stuffer DNA may have any base composition, or any A/T or G/C content. For example, the G/C content of the stuffer DNA could resemble that of the plant (~30-40%), or could be much lower (0-30%) or much higher (40-100%). Alternatively, the stuffer sequences could be synthesized to contain an excess of any given nucleotide such as A, C, G or T. Different synthetic stuffers of different compositions may also be combined with each other. For example a fragment with low G/C content may be flanked or abutted by a fragment of medium or high G/C content, or vice versa.

In one embodiment of the invention, the mini-chromosome has a circular structure without telomeres. In another embodiment, the mini-chromosome has a circular structure with telomeres. In a third embodiment, the mini-chromosome has a linear structure with telomeres, as would result if a "linear" structure were to be cut with a unique endonuclease, exposing the telomeres at the ends of a DNA molecule that contains all of the sequence contained in the original, closed construct with the exception of the an antibiotic-resistance gene. In a fourth embodiment of the invention, the telomeres could be placed in such a manner that the bacterial replicon, backbone sequences, antibiotic-resistance genes and any other sequences of bacterial origin and present for the purposes of propagation of the mini-chromosome in bacteria, can be removed from the plant-expressed genes, the centromere, telomeres, and other sequences by cutting the structure with an unique endonuclease. This results in a mini-chromosome from which much of, or preferably all, bacterial sequences have been removed. In this embodiment, bacterial sequence present between or among the plant-expressed genes or other mini-chromosome sequences would be excised prior to removal of the remaining bacterial sequences by cutting the mini-chromosome with a homing endonuclease and re-ligating the structure such that the antibiotic-resistance gene has been lost. The unique endonuclease site may be the recognition sequence of a homing endonuclease. Alternatively, the endonucleases and their sites can be replaced with any specific DNA cutting mechanism and its specific recognition site such as rare-cutting endonuclease or recombinase and its specific recognition site, as long as that site is present in the mini-chromosomes only at the indicated positions.

Various structural configurations are possible by which mini-chromosome elements can be oriented with respect to each other. A centromere can be placed on a mini-chromosome either between genes or outside a cluster of genes next to one telomere or next to the other telomere. Stuffer DNAs can be combined with these configurations to place the stuffer sequences inside the telomeres, around the centromere between genes or any combination thereof. Thus, a large number of alternative mini-chromosome structures are possible, depending on the relative placement of centromere DNA, genes, stuffer DNAs, bacterial sequences, telomeres, and other sequences. The sequence content of each of these variants is the same, but their structure may be different depending on how the sequences are placed. These variations in architecture are possible both for linear and for circular mini-chromosomes.

Exemplary Centromere Components

Centromere components may be isolated or derived from native plant genome, for example, modified through recombinant techniques or through the cell-based techniques described below. Alternatively, wholly artificial centromere components may be constructed using as a general guide the sequence of native centromeres. Combinations of centromere components derived from natural sources and/or combinations of naturally derived and artificial components are also contemplated. As noted above, centromere sequence from one taxonomic plant species has been shown to be functional in another taxonomic plant species, genus and family.

In one embodiment, the centromere contains n copies of a repeated nucleotide sequence obtained by the methods disclosed herein; wherein n is at least 2. In another embodiment, the centromere contains n copies of interdigitated repeats. An interdigitated repeat is a DNA sequence that consists of two distinct repetitive elements that combine to create a unique permutation. Potentially any number of repeat copies capable of physically being placed on the recombinant construct could be included on the construct, including about 5, 10, 15, 20, 30, 50, 75, 100, 150, 200, 300, 400, 500, 750, 1,000, 1,500, 2,000, 3,000, 5,000, 7,500, 10,000, 20,000, 30,000, 40,000, 50,000, 60,000, 70,000, 80,000, 90,000 and about 100,000, including all ranges in-between such copy numbers. Moreover, the copies, while largely identical, can vary from each other. Such repeat variation is commonly observed in naturally occurring centromeres. The length of the repeat may vary, but will preferably range from about 20 bp to about 360 bp, from about 20 bp to about 250 bp, from about 50 bp to about 225 bp, from about 75 bp to about 210 bp, such as a 92 bp repeat, a 97 bp repeat and a 100 bp repeat, from about 100 bp to about 205 bp, from about 125 bp to about 200 bp, from about 150 bp to about 195 bp, from about 160 bp to about 190 and from about 170 bp to about 185 bp including about 180 bp.

The invention contemplates that two or more of these repeated nucleotide sequences, or similar repeated nucleotide sequences, may be oriented head to tail within the centromere. The term "head to tail" refers to multiple consecutive copies of the same or similar repeated nucleotide sequence (e.g., at least 70% identical) that are in the same 5'-3' orientation. The invention also contemplates that two or more of these repeated nucleotide sequences may be consecutive within the centromere. The term "consecutive" refers to the same or similar repeated nucleotide sequences (e.g., at least 70% identical) that follow one after another without being interrupted by other significant sequence elements. Such consecutive repeated nucleotide sequences may be in any orientation, e.g. head to tail, tail to tail, or head to head, and may be separated by n number of nucleotides, wherein n ranges from 1 to 10, or 1 to 20, or 1 to 30, or 1 to 40, or 1 to 50. Exemplary repeated nucleotide sequences derived from corn, and identified by the methods described herein, are CentC, CRM and CentA. An exemplary sequence of CentC is provided as GenBank Accession No. AY1290008 (SEQ ID NO: 76). The consensus sequence of CentC derived from BAC clone ZB19 is set out as SEQ ID NO: 70, and the consensus sequence of CentC derived from BAC clone ZB113 is set out as SEQ ID NO: 71. Variants of these CentC consensus sequences within the BAC clones were identified and are set out in Tables 17 and 22. Exemplary repeated nucleotide sequences derived from soybean, and identified by the methods described herein are set out as SEQ ID NOS: 96, 97, 98 and 99.

An exemplary sequence of CRM is provided as GenBank Accession No. AY129008 (SEQ ID NO: 77). The fragments of SEQ ID NO: 77 that are observed within the BAC clone ZB113 are as follows: nucleotides 1-515, nucleotides 1-930, nucleotides 1-1434, nucleotides 1508-3791, nucleotides 1508-5417, nucleotides 2796-2890, nucleotides 2796-2893, nucleotides 4251-4744, nucleotides 4626-4772, nucleotides 4945-6236, nucleotides 4983-5342, nucleotides 5487-5569, nucleotides 5757-6212, nucleotides 5765-7571, nucleotides 6529-6653, nucleotides 6608-6658, nucleotides 6638-7571 and/or nucleotides 6640-7156 of SEQ ID NO: 77. An exemplary sequence of CentA is provided as GenBank Accession No. AF078917 (SEQ ID NO: 78). The fragment of SEQ ID NO: 78 that are observed in the BAC clone ZB113 are as follows comprise nucleotides 9589-10101 of SEQ ID NO: 37. (contig 16).

Modification of Centromeres Isolated from Native Plant Genome

Modification and changes may be made in the centromeric DNA segments of the current invention and still obtain a functional molecule with desirable characteristics. The following is a discussion based upon changing the nucleic acids of a centromere to create an equivalent, or even an improved, second generation molecule.

In particular embodiments of the invention, mutated centromeric sequences are contemplated to be useful for increasing the utility of the centromere. It is specifically contemplated that the function of the centromeres of the current invention may be based in part of in whole upon the secondary structure of the DNA sequences of the centromere, modification of the DNA with methyl groups or other adducts, and/or the proteins which interact with the centromere. By changing the DNA sequence of the centromere, one may alter the affinity of one or more centromere-associated protein(s) for the centromere and/or the secondary structure or modification of the centromeric sequences, thereby changing the activity of the centromere. Alternatively, changes may be made in the centromeres of the invention which do not affect the activity of the centromere. Changes in the centromeric sequences which reduce the size of the DNA segment needed to confer centromere activity are contemplated to be particularly useful in the current invention, as would changes which increased the fidelity with which the centromere was transmitted during mitosis and meiosis.

Modification of Centromeres by Passage Through Bacteria, Plant or Other Hosts or Processes In the methods of the present invention, the resulting mini-chromosome DNA sequence may also be a derivative of the parental clone or centromere clone having substitutions, deletions, insertions, duplications and/or rearrangements of one or more nucleotides in the nucleic acid sequence. Such nucleotide mutations may occur individually or consecutively in stretches of 1, 2, 3, 4, 5, 10, 20, 40, 80, 100, 200, 400, 800, 1000, 2000, 4000, 8000, 10000, 50000, 100000, and about 200000, including all ranges in-between.

Variations of mini-chromosomes may arise through passage of mini-chromosomes through various hosts including virus, bacteria, yeast, plant or other prokaryotic or eukaryotic organism and may occur through passage of multiple hosts or individual host. Variations may also occur by replicating the mini-chromosome in vitro.

Derivatives may be identified through sequence analysis, or variations in mini-chromosome molecular weight through electrophoresis such as, but not limited to, CHEF gel analysis, column or gradient separation, or any other methods used in the field to determine and/or analyze DNA molecular weight or sequence content. Alternately, derivatives may be identified by the altered activity of a derivative in conferring centromere function to a mini-chromosome.

Exemplary Exogenous Nucleic Acids Including Plant-Expressed Genes

Of particular interest in the present invention are exogenous nucleic acids which when introduced into plants will alter the phenotype of the plant, a plant organ, plant tissue, or portion of the plant. Exemplary exogenous nucleic acids encode polypeptides involved in one or more important biological properties in plants. Other exemplary exogenous nucleic acids alter expression of exogenous or endogenous genes, either increasing or decreasing expression, optionally in response to a specific signal or stimulus.

As used herein, the term "trait" can refer either to the altered phenotype of interest or the nucleic acid which causes the altered phenotype of interest.

One of the major purposes of transformation of crop plants is to add some commercially desirable, agronomically important traits to the plant. Such traits include, but are not limited to, herbicide resistance or tolerance; insect (pest) resistance or tolerance; disease resistance or tolerance (viral, bacterial, fungal, nematode or other pathogens); stress tolerance and/or resistance, as exemplified by resistance or tolerance to drought, heat, chilling, freezing, excessive moisture, salt stress, mechanical stress, extreme acidity, alkalinity, toxins, UV light, ionizing radiation or oxidative stress; increased yields, whether in quantity or quality; enhanced or altered nutrient acquisition and enhanced or altered metabolic efficiency; enhanced or altered nutritional content and makeup of plant tissues used for food, feed, fiber or processing; physical appearance; male sterility; drydown; standability; prolificacy; starch quantity and quality; oil quantity and quality; protein quality and quantity; amino acid composition; modified chemical production; altered pharmaceutical or nutraceutical properties; altered bioremediation properties; increased biomass; altered growth rate; altered fitness; altered biodegradability; altered $CO_2$ fixation; presence of bioindicator activity; altered digestibility by humans or animals; altered allergenicity; altered mating characteristics; altered pollen dispersal; improved environmental impact; altered nitrogen fixation capability; the production of a pharmaceutically active protein; the production of a small molecule with medicinal properties; the production of a chemical including those with industrial utility; the production of nutraceuticals, food additives, carbohydrates, RNAs, lipids, fuels, dyes, pigments, vitamins, scents, flavors, vaccines, antibodies, hormones, and the like; and alterations in plant architecture or development, including changes in developmental timing, photosynthesis, signal transduction, cell growth, reproduction, or differentiation. Additionally one could create a library of an entire genome from any organism or organelle including mammals, plants, microbes, fungi, or bacteria, represented on mini-chromosomes.

In one embodiment, the modified plant may exhibit increased or decreased expression or accumulation of a product of the plant, which may be a natural product of the plant or a new or altered product of the plant. Exemplary products include an enzyme, an RNA molecule, a nutritional protein, a structural protein, an amino acid, a lipid, a fatty acid, a polysaccharide, a sugar, an alcohol, an alkaloid, a carotenoid, a propanoid, a phenylpropanoid, or terpenoid, a steroid, a flavonoid, a phenolic compound, an anthocyanin, a pigment, a vitamin or a plant hormone. In another embodiment, the modified plant has enhanced or diminished requirements for light, water, nitrogen, or trace elements. In another embodiment the modified plant has an enhance ability to capture or fix nitrogen from its environment. In yet another embodiment, the modified plant is enriched for an essential amino acid as a proportion of a protein fraction of the plant. The protein fraction may be, for example, total seed protein, soluble protein, insoluble protein, water-extractable protein, and lipid-associated protein. The modification may include overexpression, underexpression, antisense modulation, sense suppression, inducible expression, inducible repression, or inducible modulation of a gene.

A brief summary of exemplary improved properties and polypeptides of interest for either increased or decreased expression is provided below.

(i) Herbicide Resistance

A herbicide resistance (or tolerance) trait is a characteristic of a modified plant that is resistant to dosages of an herbicide that is typically lethal to a non-modified plant. Exemplary herbicides for which resistance is useful in a plant include glyphosate herbicides, phosphinothricin herbicides, oxynil herbicides, imidazolinone herbicides, dinitroaniline herbicides, pyridine herbicides, sulfonylurea herbicides, bialaphos herbicides, sulfonamide herbicides and glufosinate herbicides. Other herbicides would be useful as would combinations of herbicide genes on the same mini-chromosome.

The genes encoding phosphinothricin acetyltransferase (bar), glyphosate tolerant EPSP synthase genes, glyphosate acetyltransferase, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are good examples of herbicide resistant genes for use in transformation. The bar gene codes for an enzyme, phosphinothricin acetyltransferase (PAT), which inactivates the herbicide phosphinothricin and prevents this compound from inhibiting glutamine synthetase enzymes. The enzyme 5 enolpyruvylshikimate 3 phosphate synthase (EPSP Synthase), is normally inhibited by the herbicide N (phosphonomethyl)glycine (glyphosate). However, genes are known that encode glyphosate resistant EPSP synthase enzymes. These genes are particularly contemplated for use in plant transformation. The deh gene encodes the enzyme dalapon dehalogenase and confers resistance to the herbicide dalapon. The bxn gene codes for a specific nitrilase enzyme that converts bromoxynil to a non herbicidal degradation product. The glyphosate acetyl transferase gene inactivates the herbicide glyphosate and prevents this compound from inhibiting EPSP synthase.

Polypeptides that may produce plants having tolerance to plant herbicides include polypeptides involved in the shikimate pathway, which are of interest for providing glyphosate tolerant plants. Such polypeptides include polypeptides involved in biosynthesis of chorismate, phenylalanine, tyrosine and tryptophan.

(ii) Insect Resistance

Potential insect resistance (or tolerance) genes that can be introduced include *Bacillus thuringiensis* toxin genes or Bt genes (Watrud et al., In: Engineered Organisms and the Environment, 1985). Bt genes may provide resistance to lepidopteran or coleopteran pests such as European Corn Borer (ECB). Preferred Bt toxin genes for use in such embodiments include the CryIA(b) and CryIA(c) genes. Endotoxin genes from other species of *B. thuringiensis* which affect insect growth or development also may be employed in this regard.

It is contemplated that preferred Bt genes for use in the mini-chromosomes disclosed herein will be those in which the coding sequence has been modified to effect increased expression in plants, and for example, in monocot plants. Means for preparing synthetic genes are well known in the art and are disclosed in, for example, U.S. Pat. No. 5,500,365 and U.S. Pat. No. 5,689,052, each of the disclosures of which are specifically incorporated herein by reference in their entirety. Examples of such modified Bt toxin genes include a synthetic Bt CryIA(b) gene (Perlak et al., Proc. Natl. Acad. Sci. USA, 88:3324-3328, 1991), and the synthetic CryIA(c) gene termed 1800b (PCT Application WO 95/06128). Some examples of other Bt toxin genes known to those of skill in the art are given in Table 1 below.

TABLE 1

*Bacillus thuringiensis* Endotoxin Genes[a]

| New Nomenclature | Old Nomenclature | GenBank Accession |
|---|---|---|
| Cry1Aa | CryIA(a) | M11250 |
| Cry1Ab | CryIA(b) | M13898 |
| Cry1Ac | CryIA(c) | M11068 |
| Cry1Ad | CryIA(d) | M73250 |
| Cry1Ae | CryIA(e) | M65252 |

TABLE 1-continued

Bacillus thuringiensis Endotoxin Genes[a]

| New Nomenclature | Old Nomenclature | GenBank Accession |
|---|---|---|
| Cry1Ba | CryIB | X06711 |
| Cry1Bb | ET5 | L32020 |
| Cry1Bc | PEG5 | Z46442 |
| Cry1Bd | CryE1 | U70726 |
| Cry1Ca | CryIC | X07518 |
| Cry1Cb | CryIC(b) | M97880 |
| Cry1Da | CryID | X54160 |
| Cry1Db | PrtB | Z22511 |
| Cry1Ea | CryIE | X53985 |
| Cry1Eb | CryIE(b) | M73253 |
| Cry1Fa | CryIF | M63897 |
| Cry1Fb | PrtD | Z22512 |
| Cry1Ga | PrtA | Z22510 |
| Cry1Gb | CryH2 | U70725 |
| Cry1Ha | PrtC | Z22513 |
| Cry1Hb |  | U35780 |
| Cry1Ia | CryV | X62821 |
| Cry1Ib | CryV | U07642 |
| Cry1Ja | ET4 | L32019 |
| Cry1Jb | ET1 | U31527 |
| Cry1K |  | U28801 |
| Cry2Aa | CryIIA | M31738 |
| Cry2Ab | CryIIB | M23724 |
| Cry2Ac | CryIIC | X57252 |
| Cry3A | CryIIIA | M22472 |
| Cry3Ba | CryIIIB | X17123 |
| Cry3Bb | CryIIIB2 | M89794 |
| Cry3C | CryIIID | X59797 |
| Cry4A | CryIVA | Y00423 |
| Cry4B | CryIVB | X07423 |
| Cry5Aa | CryVA(a) | L07025 |
| Cry5Ab | CryVA(b) | L07026 |
| Cry6A | CryVIA | L07022 |
| Cry6B | CryVIB | L07024 |
| Cry7Aa | CryIIIC | M64478 |
| Cry7Ab | CryIIICb | U04367 |
| Cry8A | CryIIIE | U04364 |
| Cry8B | CryIIIG | U04365 |
| Cry8C | CryIIIF | U04366 |
| Cry9A | CryIG | X58120 |
| Cry9B | CryIX | X75019 |
| Cry9C | CryIH | Z37527 |
| Cry10A | CryIVC | M12662 |
| Cry11A | CryIVD | M31737 |
| Cry11B | Jeg80 | X86902 |
| Cry12A | CryVB | L07027 |
| Cry13A | CryVC | L07023 |
| Cry14A | CryVD | U13955 |
| Cry15A | 34 kDa | M76442 |
| Cry16A | cbm71 | X94146 |
| Cry17A | cbm71 | X99478 |
| Cry18A | CryBP1 | X99049 |
| Cry19A | Jeg65 | Y08920 |
| Cyt1Aa | CytA | X03182 |
| Cyt1Ab | CytM | X98793 |
| Cyt2A | CytB | Z14147 |
| Cyt2B | CytB | U52043 |

[a]N. Crickmore, D. R. Zeigler, J. Feitelson, E. Schnepf, J. Van Rie, D. Lereclus, J. Baum, and D. H. Dean. Microbiology and Molecular Biology Reviews (1998) Vol 62: 807-813 (and updated on the internet at Professor Crickmore's internet site at the University of Sussex, School of Life Sciences.

Protease inhibitors also may provide insect resistance (Johnson et al., Proc Natl Acad Sci USA. 1989 December; 86(24): 9871-9875.), and will thus have utility in plant transformation. The use of a protease inhibitor II gene, pinII, from tomato or potato is envisioned to be particularly useful. Even more advantageous is the use of a pinII gene in combination with a Bt toxin gene, the combined effect of which has been discovered to produce synergistic insecticidal activity. Other genes which encode inhibitors of the insect's digestive system, or those that encode enzymes or co factors that facilitate the production of inhibitors, also may be useful. This group may be exemplified by oryzacystatin and amylase inhibitors such as those from wheat and barley.

Amylase inhibitors are found in various plant species and are used to ward off insect predation via inhibition of the digestive amylases of attacking insects. Several amylase inhibitor genes have been isolated from plants and some have been introduced as exogenous nucleic acids, conferring an insect resistant phenotype that is potentially useful ("Plants, Genes, and Crop Biotechnology" by Maarten J. Chrispeels and David E. Sadava (2003) Jones and Bartlett Press).

Genes encoding lectins may confer additional or alternative insecticide properties. Lectins are multivalent carbohydrate binding proteins which have the ability to agglutinate red blood cells from a range of species. Lectins have been identified recently as insecticidal agents with activity against weevils, ECB and rootworm (Murdock et al., Phytochemistry, 29:85-89, 1990, Czapla & Lang, J. Econ. Entomol., 83:2480-2485, 1990). Lectin genes contemplated to be useful include, for example, barley and wheat germ agglutinin (WGA) and rice lectins (Gatehouse et al., J. Sci. Food. Agric., 35:373-380, 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated that the expression of juvenile hormone esterase, directed towards specific insect pests, also may result in insecticidal activity, or perhaps cause cessation of metamorphosis (Hammock et al., Nature, 344:458-461, 1990).

Genes which encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant plants. Genes that code for activities that affect insect molting, such as those affecting the production of ecdysteroid UDP glucosyl transferase, also fall within the scope of the useful exogenous nucleic acids of the present invention.

Genes that code for enzymes that facilitate the production of compounds that reduce the nutritional quality of the host plant to insect pests also are encompassed by the present invention. It may be possible, for instance, to confer insecticidal activity on a plant by altering its sterol composition. Sterols are obtained by insects from their diet and are used for hormone synthesis and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti nutritional effects on insects and to reduce the nutritional quality of their diet. Therefore, further embodiments of the invention concern modified plants with enhanced lipoxygenase activity which may be resistant to insect feeding.

*Tripsacum dactyloides* is a species of grass that is resistant to certain insects, including corn root worm. It is anticipated that genes encoding proteins that are toxic to insects or are involved in the biosynthesis of compounds toxic to insects will be isolated from *Tripsacum* and that these novel genes will be useful in conferring resistance to insects. It is known that the basis of insect resistance in *Tripsacum* is genetic, because said resistance has been transferred to *Zea mays* via sexual crosses (Branson and Guss, Proceedings North Central Branch Entomological Society of America, 27:91-95, 1972). It is further anticipated that other cereal, monocot or dicot plant species may have genes encoding proteins that are toxic to insects which would be useful for producing insect resistant plants.

Further genes encoding proteins characterized as having potential insecticidal activity also may be used as exogenous nucleic acids in accordance herewith. Such genes include, for example, the cowpea trypsin inhibitor (CpTI; Hilder et al., Nature, 330:160-163, 1987) which may be used as a rootworm deterrent; genes encoding avermectin (Avermectin and Abamectin., Campbell, W. C., Ed., 1989; Ikeda et al., J. Bacteriol., 169:5615-5621, 1987) which may prove particularly useful as a corn rootworm deterrent; ribosome inactivating protein genes; and even genes that regulate plant structures. Modified plants including anti insect antibody genes and genes that code for enzymes that can convert a non toxic insecticide (pro insecticide) applied to the outside of the plant into an insecticide inside the plant also are contemplated.

Polypeptides that may improve plant tolerance to the effects of plant pests or pathogens include proteases, polypeptides involved in anthocyanin biosynthesis, polypeptides involved in cell wall metabolism, including cellulases, glucosidases, pectin methylesterase, pectinase, polygalacturonase, chitinase, chitosanase, and cellulose synthase, and polypeptides involved in biosynthesis of terpenoids or indole for production of bioactive metabolites to provide defense against herbivorous insects. It is also anticipated that combinations of different insect resistance genes on the same minichromosome will be particularly useful.

Vegetative Insecticidal Proteins (VIP) are a relatively new class of proteins originally found to be produced in the vegetative growth phase of the bacterium, Bacillus cereus, but do have a spectrum of insect lethality similar to the insecticidal genes found in strains of Bacillus thuriengensis. Both the vip1a and vip3A genes have been isolated and have demonstrated insect toxicity. It is anticipated that such genes may be used in modified plants to confer insect resistance ("Plants, Genes, and Crop Biotechnology" by Maarten J. Chrispeels and David E. Sadava (2003) Jones and Bartlett Press).

(iii) Environment or Stress Resistance

Improvement of a plant's ability to tolerate various environmental stresses such as, but not limited to, drought, excess moisture, chilling, freezing, high temperature, salt, and oxidative stress, also can be effected through expression of novel genes. It is proposed that benefits may be realized in terms of increased resistance to freezing temperatures through the introduction of an "antifreeze" protein such as that of the Winter Flounder (Cutler et al., J. Plant Physiol., 135:351-354, 1989) or synthetic gene derivatives thereof. Improved chilling tolerance also may be conferred through increased expression of glycerol 3 phosphate acetyltransferase in chloroplasts (Wolter et al., The EMBO J., 4685-4692, 1992). Resistance to oxidative stress (often exacerbated by conditions such as chilling temperatures in combination with high light intensities) can be conferred by expression of superoxide dismutase (Gupta et al., 1993), and may be improved by glutathione reductase (Bowler et al., Ann Rev. Plant Physiol., 43:83-116, 1992). Such strategies may allow for tolerance to freezing in newly emerged fields as well as extending later maturity higher yielding varieties to earlier relative maturity zones.

It is contemplated that the expression of novel genes that favorably affect plant water content, total water potential, osmotic potential, or turgor will enhance the ability of the plant to tolerate drought. As used herein, the terms "drought resistance" and "drought tolerance" are used to refer to a plant's increased resistance or tolerance to stress induced by a reduction in water availability, as compared to normal circumstances, and the ability of the plant to function and survive in lower water environments. In this aspect of the invention it is proposed, for example, that the expression of genes encoding for the biosynthesis of osmotically active solutes, such as polyol compounds, may impart protection against drought. Within this class are genes encoding for mannitol L phosphate dehydrogenase (Lee and Saier, 1982) and trehalose 6 phosphate synthase (Kaasen et al., J. Bacteriology, 174:889-898, 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski et al., Science, 259:508-510, 1993, Tarczynski et al Proc. Natl. Acad. Sci. USA, 89:1-5, 1993).

Similarly, the efficacy of other metabolites in protecting either enzyme function (e.g., alanopine or propionic acid) or membrane integrity (e.g., alanopine) has been documented (Loomis et al., J. Expt. Zoology, 252:9-15, 1989), and therefore expression of genes encoding for the biosynthesis of these compounds might confer drought resistance in a manner similar to or complimentary to mannitol. Other examples of naturally occurring metabolites that are osmotically active and/or provide some direct protective effect during drought and/or desiccation include fructose, erythritol (Coxson et al., Biotropica, 24:121-133, 1992), sorbitol, dulcitol (Karsten et al., Botanica Marina, 35:11-19, 1992), glucosylglycerol (Reed et al., J. Gen. Microbiology, 130:1-4, 1984; Erdmann et al., J. Gen. Microbiology, 138:363-368, 1992), sucrose, stachyose (Koster and Leopold, Plant Physiol., 88:829-832, 1988; Blackman et al., Plant Physiol., 100:225-230, 1992), raffinose (Bernal Lugo and Leopold, Plant Physiol., 98:1207-1210, 1992), proline (Rensburg et al., J. Plant Physiol., 141: 188-194, 1993), glycine betaine, ononitol and pinitol (Vernon and Bohnert, The EMBO J., 11:2077-2085, 1992). Continued canopy growth and increased reproductive fitness during times of stress will be augmented by introduction and expression of genes such as those controlling the osmotically active compounds discussed above and other such compounds. Currently preferred genes which promote the synthesis of an osmotically active polyol compound are genes which encode the enzymes mannitol 1 phosphate dehydrogenase, trehalose 6 phosphate synthase and myoinositol 0 methyltransferase.

It is contemplated that the expression of specific proteins also may increase drought tolerance. Three classes of Late Embryogenic Abundant (LEA) Proteins have been assigned based on structural similarities (see Dure et al., Plant Molecular Biology, 12:475-486, 1989). All three classes of LEAs have been demonstrated in maturing (e.g. desiccating) seeds. Within these 3 types of LEA proteins, the Type II (dehydrin type) have generally been implicated in drought and/or desiccation tolerance in vegetative plant parts (e.g. Mundy and Chua, The EMBO J., 7:2279-2286, 1988; Piatkowski et al., Plant Physiol., 94:1682-1688, 1990; Yamaguchi Shinozaki et al., Plant Cell Physiol., 33:217-224, 1992). Expression of a Type III LEA (HVA 1) in tobacco was found to influence plant height, maturity and drought tolerance (Fitzpatrick, Gen. Engineering News, 22:7, 1993). In rice, expression of the HVA 1 gene influenced tolerance to water deficit and salinity (Xu et al., Plant Physiol., 110:249-257, 1996). Expression of structural genes from any of the three LEA groups may therefore confer drought tolerance. Other types of proteins induced during water stress include thiol proteases, aldolases or transmembrane transporters (Guerrero et al., Plant Molecular Biology, 15:11-26, 1990), which may confer various protective and/or repair type functions during drought stress. It also is contemplated that genes that effect lipid biosynthesis and hence membrane composition might also be useful in conferring drought resistance on the plant.

Many of these genes for improving drought resistance have complementary modes of action. Thus, it is envisaged that combinations of these genes might have additive and/or synergistic effects in improving drought resistance in plants. Many of these genes also improve freezing tolerance (or resistance); the physical stresses incurred during freezing and drought are similar in nature and may be mitigated in similar fashion. Benefit may be conferred via constitutive expression of these genes, but the preferred means of expressing these novel genes may be through the use of a turgor induced promoter (such as the promoters for the turgor induced genes described in Guerrero et al., Plant Molecular Biology, 15:11-26, 1990 and Shagan et al., Plant Physiol., 101:1397-1398, 1993 which are incorporated herein by reference). Spatial and temporal expression patterns of these genes may enable plants to better withstand stress.

It is proposed that expression of genes that are involved with specific morphological traits that allow for increased water extractions from drying soil would be of benefit. For example, introduction and expression of genes that alter root characteristics may enhance water uptake. It also is contemplated that expression of genes that enhance reproductive fitness during times of stress would be of significant value. For example, expression of genes that improve the synchrony of pollen shed and receptiveness of the female flower parts, e.g., silks, would be of benefit. In addition it is proposed that expression of genes that minimize kernel abortion during times of stress would increase the amount of grain to be harvested and hence be of value.

Given the overall role of water in determining yield, it is contemplated that enabling plants to utilize water more efficiently, through the introduction and expression of novel genes, will improve overall performance even when soil water availability is not limiting. By introducing genes that improve the ability of plants to maximize water usage across a full range of stresses relating to water availability, yield stability or consistency of yield performance may be realized.

Polypeptides that may improve stress tolerance under a variety of stress conditions include polypeptides involved in gene regulation, such as serine/threonine-protein kinases, MAP kinases, MAP kinase kinases, and MAP kinase kinase kinases; polypeptides that act as receptors for signal transduction and regulation, such as receptor protein kinases; intracellular signaling proteins, such as protein phosphatases, GTP binding proteins, and phospholipid signaling proteins; polypeptides involved in arginine biosynthesis; polypeptides involved in ATP metabolism, including for example ATPase, adenylate transporters, and polypeptides involved in ATP synthesis and transport; polypeptides involved in glycine betaine, jasmonic acid, flavonoid or steroid biosynthesis; and hemoglobin. Enhanced or reduced activity of such polypeptides in modified plants will provide changes in the ability of a plant to respond to a variety of environmental stresses, such as chemical stress, drought stress and pest stress.

Other polypeptides that may improve plant tolerance to cold or freezing temperatures include polypeptides involved in biosynthesis of trehalose or raffinose, polypeptides encoded by cold induced genes, fatty acyl desaturases and other polypeptides involved in glycerolipid or membrane lipid biosynthesis, which find use in modification of membrane fatty acid composition, alternative oxidase, calcium-dependent protein kinases, LEA proteins or uncoupling protein.

Other polypeptides that may improve plant tolerance to heat include polypeptides involved in biosynthesis of trehalose, polypeptides involved in glycerolipid biosynthesis or membrane lipid metabolism (for altering membrane fatty acid composition), heat shock proteins or mitochondrial NDK.

Other polypeptides that may improve tolerance to extreme osmotic conditions include polypeptides involved in proline biosynthesis.

Other polypeptides that may improve plant tolerance to drought conditions include aquaporins, polypeptides involved in biosynthesis of trehalose or wax, LEA proteins or invertase.

(iv) Disease Resistance

It is proposed that increased resistance (or tolerance) to diseases may be realized through introduction of genes into plants, for example, into monocotyledonous plants such as maize. It is possible to produce resistance to diseases caused by viruses, viroids, bacteria, fungi and nematodes. It also is contemplated that control of mycotoxin producing organisms may be realized through expression of introduced genes. Resistance can be affected through suppression of endogenous factors that encourage disease-causing interactions, expression of exogenous factors that are toxic to or otherwise provide protection from pathogens, or expression of factors that enhance the plant's own defense responses.

Resistance to viruses may be produced through expression of novel genes. For example, it has been demonstrated that expression of a viral coat protein in a modified plant can impart resistance to infection of the plant by that virus and perhaps other closely related viruses (Cuozzo et al., Bio/Technology, 6:549-553, 1988, Hemenway et al., The EMBO J., 7:1273-1280, 1988, Abel et al., Science, 232:738-743, 1986). It is contemplated that expression of antisense genes targeted at essential viral functions may also impart resistance to viruses. For example, an antisense gene targeted at the gene responsible for replication of viral nucleic acid may inhibit replication and lead to resistance to the virus. It is believed that interference with other viral functions through the use of antisense genes also may increase resistance to viruses. Further, it is proposed that it may be possible to achieve resistance to viruses through other approaches, including, but not limited to the use of satellite viruses.

It is proposed that increased resistance to diseases caused by bacteria and fungi may be realized through introduction of novel genes. It is contemplated that genes encoding so called "peptide antibiotics," pathogenesis related (PR) proteins, toxin resistance, or proteins affecting host pathogen interactions such as morphological characteristics will be useful. Peptide antibiotics are polypeptide sequences which are inhibitory to growth of bacteria and other microorganisms. For example, the classes of peptides referred to as cecropins and magainins inhibit growth of many species of bacteria and fungi. It is proposed that expression of PR proteins in plants, for example, monocots such as maize, may be useful in conferring resistance to bacterial disease. These genes are induced following pathogen attack on a host plant and have been divided into at least five classes of proteins (Bol, Linthorst, and Cornelissen, 1990). Included amongst the PR proteins are beta 1,3 glucanases, chitinases, and osmotin and other proteins that are believed to function in plant resistance to disease organisms. Other genes have been identified that have antifungal properties, e.g., UDA (stinging nettle lectin), or hevein (Broakaert et al., 1989; Barkai Golan et al., 1978).

It is known that certain plant diseases are caused by the production of phytotoxins. It is proposed that resistance to these diseases would be achieved through expression of a novel gene that encodes an enzyme capable of degrading or otherwise inactivating the phytotoxin. It also is contemplated that expression of novel genes that alter the interactions between the host plant and pathogen may be useful in reducing the ability of the disease organism to invade the tissues of the host plant, e.g., an increase in the waxiness of the leaf cuticle or other morphological characteristics.

Polypeptides useful for imparting improved disease responses to plants include polypeptides encoded by cercosporin induced genes, antifungal proteins and proteins encoded by R-genes or SAR genes.

Agronomically important diseases caused by fungal phytopathogens include: glume or leaf blotch, late blight, stalk/head rot, rice blast, leaf blight and spot, corn smut, wilt, sheath blight, stem canker, root rot, blackleg or kernel rot.

Exemplary plant viruses include tobacco or cucumber mosaic virus, ringspot virus, necrosis virus, maize dwarf mosaic virus, etc. Specific fungal, bacterial and viral pathogens of major crops include, but are not limited to:

RICE: rice brown spot fungus (*Cochliobolus miyabeanus*), rice blast fungus—*Magnaporthe grisea* (*Pyricularia grisea*), *Magnaporthe salvinii* (*Sclerotium oryzae*), *Xanthomomas oryzae* pv. *oryzae*, *Xanthomomas oryzae* pv. *oryzicola*, *Rhizoctonia* spp. (including but not limited to *Rhizoctonia solani*, *Rhizoctonia oryzae* and *Rhizoctonia oryzae-sativaes*), *Pseudomonas* spp. (including but not limited to *Pseudomonas plantarii*, *Pseudomonas avenae*, *Pseudomonas glumae*, *Pseudomonas fuscovaginae*, *Pseudomonas alboprecipitans*, *Pseudomonas syringae* pv. *panici*, *Pseudomonas syringae* pv. *syringae*, *Pseudomonas syringae* pv. *oryzae* and *Pseudomonas syringae* pv. *aptata*), *Erwinia* spp. (including but not limited to *Erwinia herbicola*, *Erwinia amylovaora*, *Erwinia chrysanthemi* and *Erwinia carotovora*), *Achyla* spp. (including but not limited to *Achyla conspicua* and *Achyia klebsiana*), *Pythium* spp. (including but not limited to *Pythium dissotocum*, *Pythium irregulare*, *Pythium arrhenomanes*, *Pythium myriotylum*, *Pythium catenulatum*, *Pythium graminicola* and *Pythium spinosum*), *Saprolegnia* spp., *Dictyuchus* spp., *Pythiogeton* spp., *Phytophthora* spp., *Alternaria padwickii*, *Cochliobolus miyabeanus*, *Curvularia* spp. (including but not limited to *Curvularia lunata*, *Curvularia affinis*, *Curvularia clavata*, *Curvularia eragrostidis*, *Curvularia fallax*, *Curvularia geniculata*, *Curvularia inaequalis*, *Curvularia intermedia*, *Curvularia oryzae*, *Curvularia oryzae-sativae*, *Curvularia pallescens*, *Curvularia senegalensis*, *Curvularia tuberculata*, *Curvularia uncinata* and *Curvularia verruculosa*), *Sarocladium oryzae*, *Gerlachia oryzae*, *Fusarium* spp. (including but not limited *Fusarium graminearum*, *Fusarium nivale* and to different pathovars of *Fusarium monoliforme*, including pvs. *fujikuroi* and *zeae*), *Sclerotium rolfsii*, *Phoma exigua*, *Mucor fragilis*, *Trichoderma viride*, *Rhizopus* spp., *Cercospora oryzae*, *Entyloma oryzae*, *Dreschlera gigantean*, *Scierophthora macrospora*, *Mycovellosiella oryzae*, *Phomopsis oryzae-sativaes*, *Puccinia graminis*, *Uromyces coronatus*, *Cylindrocladium scoparium*, *Sarocladium oryzae*, *Gaeumannomyces graminis* pv. *graminis*, *Myrothecium verrucaria*, *Pyrenochaeta oryzae*, *Ustilaginoidea virens*, *Neovossia* spp. (including but not limited to *Neovossia horrida*), *Tilletia* spp., *Balansia oryzae-sativae*, *Phoma* spp. (including but not limited to *Phoma sorghina*, *Phoma insidiosa*, *Phoma glumarum*, *Phoma glumicola* and *Phoma oryzina*), *Nigrospora* spp. (including but not limited to *Nigrospora oryzae*, *Nigrospora sphaerica*, *Nigrospora panici* and *Nigrospora padwickii*), *Epiococcum nigrum*, *Phyllostica* spp., *Wolkia decolorans*, *Monascus purpureus*, *Aspergillus* spp., *Penicillium* spp., *Absidia* spp., *Mucor* spp., *Chaetomium* spp., *Dematium* spp., *Monilia* spp., *Streptomyces* spp., *Syncephalastrum* spp., *Verticillium* spp., *Nematospora coryli*, *Nakataea sigmoidea*, *Cladosporium* spp., *Bipolaris* spp., *Coniothyrium* spp., *Diplodia oryzae*, *Exserophilum rostratum*, *Helococera oryzae*, *Melanomma glumarum*, *Metashaeria* spp., *Mycosphaerella* spp., *Oidium* spp., *Pestalotia* spp., *Phaeoseptoria* spp., *Sphaeropsis* spp., *Trematosphaerella* spp., rice black-streaked dwarf virus, rice dwarf virus, rice gall dwarf virus, barley yellow dwarf virus, rice grassy stunt virus, rice hoja blanca virus, rice necrosis mosaic virus, rice ragged stunt virus, rice stripe virus, rice stripe necrosis virus, rice transitory yellowing virus, rice tungro bacilliform virus, rice tungro spherical virus, rice yellow mottle virus, rice tarsonemid mite virus, Echinochloa hoja blanca virus, Echinochloa ragged stunt virus, orange leaf mycoplasma-like organism, yellow dwarf mycoplasma-like organism, *Aphelenchoides besseyi*, *Ditylenchus angustus*, *Hirschmanniella* spp., *Criconemella* spp., *Meloidogyne* spp., *Heterodera* spp., *Pratylenchus* spp., *Hoplolaimus indicus*.

SOYBEANS: *Phytophthora sojae*, *Fusarium solani* f. sp. *Glycines*, *Macrophomina phaseolina*, *Fusarium*, *Pythium*, *Rhizoctonia*, *Phialophora gregata*, *Sclerotinia sclerotiorum*, *Diaporthe phaseolorum* var. *sojae*, *Colletotrichum truncatum*, *Phomopsis longicolla*, *Cercospora kikuchii*, *Diaporthe phaseolonum* var. *meridionalis* (and var. *caulivora*), *Phakopsora pachyrhyzi*, *Fusarium solani*, *Microsphaera diffusa*, *Septoria glycines*, *Cercospora kikuchii*, *Macrophomina phaseolina*, *Sclerotinia sclerotiorum*, *Corynespora cassiicola*, *Rhizoctonia solani*, *Cercospora sojina*, *Phytophthora megasperma* fsp. *glycinea*, *Macrophomina phaseolina*, *Fusarium oxysporum*, *Diapothe phaseolorum* var. *sojae* (*Phomopsis sojae*), *Diaporthe phaseolorum* var. *caulivora*, *Sclerotium rolfsii*, *Cercospora kikuchii*, *Cercospora sojina*, *Peronospora manshurica*, *Colletotrichum dematium* (*Colletotichum truncatum*), *Corynespora cassiicola*, *Phyllosticta sojicola*, *Alternaria alternata*, *Pseudomonas syringae* p.v. *glycinea*, *Xanthomonas campestris* p.v. *phaseoli*, *Microspaera diffusa*, *Fusarium semitectum*, *Phialophora gregata*, Soybean mosaic virus, *Glomerella glycines*, Tobacco Ring spot virus, Tobacco Streak virus, *Phakopsora pachyrhyzi*, *Pythium aphanidermatum*, *Pythium ultimum*, *Pythium dearyanum*, Tomato spotted wilted virus, *Heterodera glycines*, *Fusarium solani*, Soybean cyst and root knot nematodes.

CORN: *Fusarium moniliforme* var. *subglutinans*, *Erwinia stewartii*, *Fusarium moniliforme*, *Gibberella zeae* (*Fusarium Graminearum*), *Stenocarpella maydi* (*Diplodia maydis*), *Pythium irregulare*, *Pythium debaryanum*, *Pythium graminicola*, *Pythium splendens*, *Pythium ultimum*, *Pythium aphanidermatum*, *Aspergillus flavus*, *Bipolaris maydis* O, T (*cochliobolus heterostrophus*), *Helminthosporium carbonum* I, II, and III (*Cochliobolus carbonum*), *Exserohilum turcicum* I, II and III, *Helminthosporium pedicellatum*, *Physoderma maydis*, *Phyllosticta maydis*, Kabatie-maydis, *Cercospora sorghi*, *Ustilago maydis*, *Puccinia sorghi*, *Puccinia polysora*, *Macrophomina phaseolina*, *Penicillium oxalicum*, *Nigrospora oryzae*, *Cladosporium herbarum*, *Curvularia lunata*, *Curvularia inaequalis*, *Curvularia pallescens*, *Clavibacter michiganese* subsp. *Nebraskense*, *Trichoderma viride*, Maize dwarf Mosaic Virus A and B, Wheat Streak Mosaic Virus, Maize Chlorotic Dwarf Virus, *Claviceps sorghi*, *Pseudonomas avenae*, *Erwinia chrysantemi* p.v. *Zea*, *Erwinia corotovora*, *Cornstun spiroplasma*, *Diplodia macrospora*, *Sclerophthora macrospora*, *Peronosclerospora sorghi*, *Peronoscherospora philippinesis*, *Peronosclerospora* maydis, Peronosclerospora sacchari, Spacelotheca reiliana, Physopella zea, Cephalosporium maydis, Caphalosporium acremonium, Maize Chlorotic Mottle Virus, High Plains Virus, Maize Mosaic Virus, Maize Rayado Fino Virus, Maize Streak Virus, Maize Stripe Virus, Maize Rought Dwarf Virus:

WHEAT: *Pseudomonas syringae* p.v. *atrofaciens*, *Urocystis agropyri*, *Xanthomonas campestris* p.v. *translucens*, *Pseudomonas syringae* p.v. *syringae*, *Alternaria alternata*, *Cladosporium herbarum*, *Fusarium graminearum*, *Fusarium avenaceum*, *Fusarium culmorum*, *Ustilago tritici*, *Ascochyta tritici*, *Cephalosporium gramineum*, *Collotetrichum graminicola*, *Erysiphe graminis* f. sp. *Tritici*, *Puccinia graminis* f. sp. *Tritici*, *Puccinia recondite* f. sp. *tritici*, *puccinia striiformis*, *Pyrenophora triticirepentis*, *Septoria nodorum*, *Septoria tritici*, *Spetoria avenae*, *Pseudocercosporella herpotrichoides*, *Rhizoctonia solani*, *Rhizoctonia cerealis*, *Gaeumannomyces graminis* var. *tritici*, *Pythium aphanidermatum*, *Pythium arrhenomanes*, *Pythium ultimum*, *Bipolaris sorokiniana*, Barley Yellow Dwarf Virus, Brome Mosaic Virus, Soil Borne Wheat Mosaic Virus, Wheat Streak Virus, Wheat Spindle Streak Virus, American Wheat Striate Virus, *Claviceps purpurea*, *Tilletia tritici*, *Tilletia laevis*, *Pstilago tritici*, *Tilletia indica*, *Rhizoctonia solani*, *Pythium arrhenomannes*, *Pythium gramicola*, *Pythium aphanidermatum*, High Plains Virus, European Wheat Striate Virus:

CANOLA: *Albugo candida*, *Alternaria brassicae*, *Leptosharia maculans*, *Rhizoctonia solani*, *Sclerotinia sclerotiorum*, *Mycospaerella brassiccola*, *Pythium ultimum*, *Peronospora parasitica*, *Fusarium roseum*, *Fusarium oxysporum*, *Tilletia foetida*, *Tilletia caries*, *Alternaria alternata*:

SUNFLOWER: *Plasmophora halstedii*, *Scherotinia sclerotiorum*, Aster Yellows, *Septoria helianthi*, *Phomopsis helianthi*, *Alternaria helianthi*, *Alternaria zinniae*, *Botrytis cinera*, *Phoma macdonaldii*, *Macrophomina phaseolina*, *Erysiphe cichoracearum*, *Phizopus oryzae*, *Rhizopus arrhizus*, *Rhizopus stolonifer*, *Puccinia helianthi*, *Verticillium Dahliae*, *Erwinia carotovorum* p.v. *carotovora*, *Cephalosporium acremonium*, *Phytophthora cryptogea*, *Albugo tragopogonis*.

SORGHUM: *Exserohilum turcicum*, *Colletotrichum graminicola* (*Glomerella graminicola*), *Cercospora sorghi*, *Gloeocercospora sorghi*, *Ascochyta sorghi*, *Pseudomonas syringae* p.v. *syringae*, *Xanthomonas campestris* p.v. *holcicola*, *Pseudomonas andropogonis*, *Puccinia purpurea*, *Macrophomina phaseolina*, *Periconia circinata*, *Fusarium moniliforme*, *Alternaria alternate*, *Bipolaris sorghicola*, *Helminthosporium sorghicola*, *Curvularia lunata*, *Phoma insidiosa*, *Pseudomonas avenae* (*Pseudomonas alboprecipitans*), *Ramulispora sorghi*, *Ramulispora sorghicola*, *Phyllachara sacchari Sporisorium relianum* (*Sphacelotheca reliana*), *Sphacelotheca cruenta*, *Sporisorium sorghi*, Sugarcane mosaic H, Maize Dwarf Mosaic Virus A & B, *Claviceps sorghi*, *Rhizoctonia solani*, *Acremonium strictum*, *Sclerophthona macrospora*, *Peronosclerospora sorghi*, *Peronosclerospora philippinensis*, *Sclerospora graminicola*, *Fusarium graminearum*, *Fusarium Oxysporum*, *Pythium arrhenomanes*, *Pythium graminicola*.

ALFALFA: *Clavibater michiganensis* subsp. *Insidiosum*, *Pythium ultimum*, *Pythium irregulare*, *Pythium splendens*, *Pythium debaryanum*, *Pythium aphanidermatum*, *Phytophthora megasperma*, *Peronospora trifoliorum*, *Phoma medicaginis* var. *medicaginis*, *Cercospora medicaginis*, *Pseudopeziza medicaginis*, *Leptotrochila medicaginis*, *Fusarium oxysporum*, *Rhizoctonia solani*, *Uromyces striatus*, *Colletotrichum trifolii* race 1 and race 2, *Leptosphaerulina briosiana*, *Stemphylium botryosum*, *Stagonospora meliloti*, *Sclerotinia trifoliorum*, Alfalfa Mosaic Virus, *Verticillium albo-atrum*, *Xanthomonas campestris* p.v. *alfalfae*, *Aphanomyces euteiches*, *Stemphylium herbarum*, *Stemphylium alfalfae*.

(v) Plant Agronomic Characteristics

Two of the factors determining where crop plants can be grown are the average daily temperature during the growing season and the length of time between frosts. Within the areas where it is possible to grow a particular crop, there are varying limitations on the maximal time it is allowed to grow to maturity and be harvested. For example, a variety to be grown in a particular area is selected for its ability to mature and dry down to harvestable moisture content within the required period of time with maximum possible yield. Therefore, crops of varying maturities are developed for different growing locations. Apart from the need to dry down sufficiently to permit harvest, it is desirable to have maximal drying take place in the field to minimize the amount of energy required for additional drying post harvest. Also, the more readily a product such as grain can dry down, the more time there is available for growth and kernel fill. It is considered that genes that influence maturity and/or dry down can be identified and introduced into plant lines using transformation techniques to create new varieties adapted to different growing locations or the same growing location, but having improved yield to moisture ratio at harvest. Expression of genes that are involved in regulation of plant development may be especially useful.

It is contemplated that genes may be introduced into plants that would improve standability and other plant growth characteristics. Expression of novel genes in plants which confer stronger stalks, improved root systems, or prevent or reduce ear droppage or shattering would be of great value to the farmer. It is proposed that introduction and expression of genes that increase the total amount of photoassimilate available by, for example, increasing light distribution and/or interception would be advantageous. In addition, the expression of genes that increase the efficiency of photosynthesis and/or the leaf canopy would further increase gains in productivity. It is contemplated that expression of a phytochrome gene in crop plants may be advantageous. Expression of such a gene may reduce apical dominance, confer semidwarfism on a plant, or increase shade tolerance (U.S. Pat. No. 5,268,526). Such approaches would allow for increased plant populations in the field.

(vi) Nutrient Utilization

The ability to utilize available nutrients may be a limiting factor in growth of crop plants. It is proposed that it would be possible to alter nutrient uptake, tolerate pH extremes, mobilization through the plant, storage pools, and availability for metabolic activities by the introduction of novel genes. These modifications would allow a plant, for example, maize to more efficiently utilize available nutrients. It is contemplated that an increase in the activity of, for example, an enzyme that is normally present in the plant and involved in nutrient utilization would increase the availability of a nutrient or decrease the availability of an antinutritive factor. An example of such an enzyme would be phytase. It is further contemplated that enhanced nitrogen utilization by a plant is desirable. Expression of a glutamate dehydrogenase gene in plants, e.g., *E. coli* gdhA genes, may lead to increased fixation of nitrogen in organic compounds. Furthermore, expression of gdhA in plants may lead to enhanced resistance to the herbicide glufosinate by incorporation of excess ammonia into glutamate, thereby detoxifying the ammonia. It also is contemplated that expression of a novel gene may make a nutrient source available that was previously not accessible, e.g., an enzyme that releases a component of nutrient value from a more complex molecule, perhaps a macromolecule.

Polypeptides useful for improving nitrogen flow, sensing, uptake, storage and/or transport include those involved in aspartate, glutamine or glutamate biosynthesis, polypeptides involved in aspartate, glutamine or glutamate transport, polypeptides associated with the TOR (Target of Rapamycin) pathway, nitrate transporters, nitrate reductases, amino transferases, ammonium transporters, chlorate transporters or polypeptides involved in tetrapyrrole biosynthesis.

Polypeptides useful for increasing the rate of photosynthesis include phytochrome, ribulose bisphosphate carboxylase-oxygenase, Rubisco activase, photosystem I and II proteins, electron carriers, ATP synthase, NADH dehydrogenase or cytochrome oxidase.

Polypeptides useful for increasing phosphorus uptake, transport or utilization include phosphatases or phosphate transporters.

(vii) Male Sterility

Male sterility is useful in the production of hybrid seed. It is proposed that male sterility may be produced through expression of novel genes. For example, it has been shown that expression of genes that encode proteins, RNAs, or peptides that interfere with development of the male inflorescence and/or gametophyte result in male sterility. Chimeric ribonuclease genes that express in the anthers of transgenic tobacco and oilseed rape have been demonstrated to lead to male sterility (Mariani et al., Nature, 347:737-741, 1990).

A number of mutations were discovered in maize that confer cytoplasmic male sterility. One mutation in particular, referred to as T cytoplasm, also correlates with sensitivity to Southern corn leaf blight. A DNA sequence, designated TURF 13 (Levings, Science, 250:942-947, 1990), was identified that correlates with T cytoplasm. It is proposed that it would be possible through the introduction of TURF 13 via transformation, to separate male sterility from disease sensitivity. As it is necessary to be able to restore male fertility for breeding purposes and for grain production, it is proposed that genes encoding restoration of male fertility also may be introduced.

(viii) Altered Nutritional Content

Genes may be introduced into plants to improve or alter the nutrient quality or content of a particular crop. Introduction of genes that alter the nutrient composition of a crop may greatly enhance the feed or food value. For example, the protein of many grains is suboptimal for feed and food purposes, especially when fed to pigs, poultry, and humans. The protein is deficient in several amino acids that are essential in the diet of these species, requiring the addition of supplements to the grain. Limiting essential amino acids may include lysine, methionine, tryptophan, threonine, valine, arginine, and histidine. Some amino acids become limiting only after corn is supplemented with other inputs for feed formulations. The levels of these essential amino acids in seeds and grain may be elevated by mechanisms which include, but are not limited to, the introduction of genes to increase the biosynthesis of the amino acids, decrease the degradation of the amino acids, increase the storage of the amino acids in proteins, or increase transport of the amino acids to the seeds or grain.

Polypeptides useful for providing increased seed protein quantity and/or quality include polypeptides involved in the metabolism of amino acids in plants, particularly polypeptides involved in biosynthesis of methionine/cysteine and lysine, amino acid transporters, amino acid efflux carriers, seed storage proteins, proteases, or polypeptides involved in phytic acid metabolism.

The protein composition of a crop may be altered to improve the balance of amino acids in a variety of ways including elevating expression of native proteins, decreasing expression of those with poor composition, changing the composition of native proteins, or introducing genes encoding entirely new proteins possessing superior composition.

The introduction of genes that alter the oil content of a crop plant may also be of value. Increases in oil content may result in increases in metabolizable-energy-content and density of the seeds for use in feed and food. The introduced genes may encode enzymes that remove or reduce rate-limitations or regulated steps in fatty acid or lipid biosynthesis. Such genes may include, but are not limited to, those that encode acetyl-CoA carboxylase, ACP-acyltransferase, alpha-ketoacyl-ACP synthase, or other well known fatty acid biosynthetic activities. Other possibilities are genes that encode proteins that do not possess enzymatic activity such as acyl carrier protein. Genes may be introduced that alter the balance of fatty acids present in the oil providing a more healthful or nutritive feedstuff. The introduced DNA also may encode sequences that block expression of enzymes involved in fatty acid biosynthesis, altering the proportions of fatty acids present in crops.

Genes may be introduced that enhance the nutritive value of crops, or of foods derived from crops by increasing the level of naturally occurring phytosterols, or by encoding for proteins to enable the synthesis of phytosterols in crops. The phytosterols from these crops can be processed directly into foods, or extracted and used to manufacture food products.

Genes may be introduced that enhance the nutritive value of the starch component of crops, for example by increasing the degree of branching, resulting in improved utilization of the starch in livestock by delaying its metabolism. Additionally, other major constituents of a crop may be altered, including genes that affect a variety of other nutritive, processing, or other quality aspects. For example, pigmentation may be increased or decreased.

Carbohydrate metabolism may be altered, for example by increased sucrose production and/or transport. Polypeptides useful for affecting on carbohydrate metabolism include polypeptides involved in sucrose or starch metabolism, carbon assimilation or carbohydrate transport, including, for example sucrose transporters or glucose/hexose transporters, enzymes involved in glycolysis/gluconeogenesis, the pentose phosphate cycle, or raffinose biosynthesis, or polypeptides involved in glucose signaling, such as SNF1 complex proteins.

Feed or food crops may also possess sub-optimal quantities of vitamins, antioxidants or other nutraceuticals, requiring supplementation to provide adequate nutritive value and ideal health value. Introduction of genes that enhance vitamin biosynthesis may be envisioned including, for example, vitamins A, E, B12, choline, or the like. Mineral content may also be sub-optimal. Thus genes that affect the accumulation or availability of compounds containing phosphorus, sulfur, calcium, manganese, zinc, or iron among others would be valuable.

Numerous other examples of improvements of crops may be used with the invention. The improvements may not necessarily involve grain, but may, for example, improve the value of a crop for silage. Introduction of DNA to accomplish this might include sequences that alter lignin production such as those that result in the "brown midrib" phenotype associated with superior feed value for cattle. Other genes may encode for enzymes that alter the structure of extracellular carbohydrates in the stover, or that facilitate the degradation of the carbohydrates in the non-grain portion of the crop so that it can be efficiently fermented into ethanol or other useful carbohydrates.

It may be desirable to modify the nutritional content of plants by reducing undesirable components such as fats, starches, etc. This may be done, for example, by the use of exogenous nucleic acids that encode enzymes which increase plant use or metabolism of such components so that they are present at lower quantities. Alternatively, it may be done by use of exogenous nucleic acids that reduce expression levels or activity of native plant enzymes that synthesize such components.

Likewise the elimination of certain undesirable traits may improve the food or feed value of the crop. Many undesirable traits must currently be eliminated by special post-harvest processing steps and the degree to which these can be engineered into the plant prior to harvest and processing would provide significant value. Examples of such traits are the elimination of anti-nutritionals such as phytates and phenolic compounds which are commonly found in many crop species. Also, the reduction of fats, carbohydrates and certain phytohormones may be valuable for the food and feed industries as they may allow a more efficient mechanism to meet specific dietary requirements.

In addition to direct improvements in feed or food value, genes also may be introduced which improve the processing of crops and improve the value of the products resulting from the processing. One use of crops is via wetmilling. Thus novel genes that increase the efficiency and reduce the cost of such processing, for example by decreasing steeping time, may also find use. Improving the value of wetmilling products may include altering the quantity or quality of starch, oil, corn gluten meal, or the components of gluten feed. Elevation of starch may be achieved through the identification and elimination of rate limiting steps in starch biosynthesis by expressing increased amounts of enzymes involved in biosynthesis or by decreasing levels of the other components of crops resulting in proportional increases in starch.

Oil is another product of wetmilling, the value of which may be improved by introduction and expression of genes. Oil properties may be altered to improve its performance in the production and use of cooking oil, shortenings, lubricants or other oil-derived products or improvement of its health attributes when used in the food-related applications. Novel fatty acids also may be synthesized which upon extraction can serve as starting materials for chemical syntheses. The changes in oil properties may be achieved by altering the type, level, or lipid arrangement of the fatty acids present in the oil. This in turn may be accomplished by the addition of genes that encode enzymes that catalyze the synthesis of novel fatty acids (e.g. fatty acid elongases, desaturases) and the lipids possessing them or by increasing levels of native fatty acids while possibly reducing levels of precursors or breakdown products. Alternatively, DNA sequences may be introduced which slow or block steps in fatty acid biosynthesis resulting in the increase in precursor fatty acid intermediates. Genes that might be added include desaturases, epoxidases, hydratases, dehydratases, or other enzymes that catalyze reactions involving fatty acid intermediates. Representative examples of catalytic steps that might be blocked include the desaturations from stearic to oleic acid or oleic to linolenic acid resulting in the respective accumulations of stearic and oleic acids. Another example is the blockage of elongation steps resulting in the accumulation of C8 to C12 saturated fatty acids.

Polypeptides useful for providing increased seed oil quantity and/or quality include polypeptides involved in fatty acid and glycerolipid biosynthesis, beta-oxidation enzymes, enzymes involved in biosynthesis of nutritional compounds, such as carotenoids and tocopherols, or polypeptides that increase embryo size or number or thickness of aleurone.

Polypeptides involved in production of galactomannans or arabinogalactans are of interest for providing plants having increased and/or modified reserve polysaccharides for use in food, pharmaceutical, cosmetic, paper and paint industries.

Polypeptides involved in modification of flavonoid/isoflavonoid metabolism in plants include cinnamate-4-hydroxylase, chalcone synthase or flavones synthase. Enhanced or reduced activity of such polypeptides in modified plants will provide changes in the quantity and/or speed of flavonoid metabolism in plants and may improve disease resistance by enhancing synthesis of protective secondary metabolites or improving signaling pathways governing disease resistance.

Polypeptides involved in lignin biosynthesis are of interest for increasing plants' resistance to lodging and for increasing the usefulness of plant materials as biofuesls.

(ix) Production or Assimilation of Chemicals or Biological

It may further be considered that a modified plant prepared in accordance with the invention may be used for the production or manufacturing of useful biological compounds that were either not produced at all, or not produced at the same level, in the corn plant previously. Alternatively, plants produced in accordance with the invention may be made to metabolize or absorb and concentrate certain compounds, such as hazardous wastes, thereby allowing bioremediation of these compounds.

The novel plants producing these compounds are made possible by the introduction and expression of one or potentially many genes with the constructs provided by the invention. The vast array of possibilities include but are not limited to any biological compound which is presently produced by any organism such as proteins, nucleic acids, primary and intermediary metabolites, carbohydrate polymers, enzymes for uses in bioremediation, enzymes for modifying pathways that produce secondary plant metabolites such as falconoid or vitamins, enzymes that could produce pharmaceuticals, and for introducing enzymes that could produce compounds of interest to the manufacturing industry such as specialty chemicals and plastics. The compounds may be produced by the plant, extracted upon harvest and/or processing, and used for any presently recognized useful purpose such as pharmaceuticals, fragrances, and industrial enzymes to name a few.

(x) Other Characteristics

Cell cycle modification: Polypeptides encoding cell cycle enzymes and regulators of the cell cycle pathway are useful for manipulating growth rate in plants to provide early vigor and accelerated maturation. Improvements in quality traits, such as seed oil content, may also be obtained by expression of cell cycle enzymes and cell cycle regulators. Polypeptides of interest for modification of cell cycle pathway include cycling and EIF5α pathway proteins, polypeptides involved in polyamine metabolism, polypeptides which act as regulators of the cell cycle pathway, including cyclin-dependent kinases (CDKs), CDK-activating kinases, cell cycle-dependent phosphatases, CDK-inhibitors, Rb and Rb-binding proteins, or transcription factors that activate genes involved in cell proliferation and division, such as the E2F family of transcription factors, proteins involved in degradation of cyclins, such as cullins, and plant homologs of tumor suppressor polypeptides.

Plant growth regulators: Polypeptides involved in production of substances that regulate the growth of various plant tissues are of interest in the present invention and may be used to provide modified plants having altered morphologies and improved plant growth and development profiles leading to improvements in yield and stress response. Of particular interest are polypeptides involved in the biosynthesis, or degradation of plant growth hormones, such as gibberellins, brassinosteroids, cytokinins, auxins, ethylene or abscisic acid, and other proteins involved in the activity, uptake and/or transport of such polypeptides, including for example, cytokinin oxidase, cytokinin/purine permeases, F-box proteins, G-proteins or phytosulfokines.

Transcription factors in plants: Transcription factors play a key role in plant growth and development by controlling the expression of one or more genes in temporal, spatial and physiological specific patterns. Enhanced or reduced activity of such polypeptides in modified plants will provide significant changes in gene transcription patterns and provide a variety of beneficial effects in plant growth, development and response to environmental conditions. Transcription factors of interest include, but are not limited to myb transcription factors, including helix-turn-helix proteins, homeodomain transcription factors, leucine zipper transcription factors, MADS transcription factors, transcription factors having AP2 domains, zinc finger transcription factors, CCAAT binding transcription factors, ethylene responsive transcription factors, transcription initiation factors or UV damaged DNA binding proteins.

Homologous recombination: Increasing the rate of homologous recombination in plants is useful for accelerating the introgression of transgenes into breeding varieties by backcrossing, and to enhance the conventional breeding process by allowing rare recombinants between closely linked genes in phase repulsion to be identified more easily. Polypeptides useful for expression in plants to provide increased homologous recombination include polypeptides involved in mitosis and/or meiosis, DNA replication, nucleic acid metabolism, DNA repair pathways or homologous recombination pathways including for example, recombinases, nucleases, proteins binding to DNA double-strand breaks, single-strand DNA binding proteins, strand-exchange proteins, resolvases, ligases, helicases and polypeptide members of the RAD52 epistasis group.

Non-Protein-Expressing Exogenous Nucleic Acids

Plants with decreased expression of a gene of interest can also be achieved, for example, by expression of antisense nucleic acids, dsRNA or RNAi, catalytic RNA such as ribozymes, sense expression constructs that exhibit cosuppression effects, aptamers or zinc finger proteins.

Antisense RNA reduces production of the polypeptide product of the target messenger RNA, for example by blocking translation through formation of RNA:RNA duplexes or by inducing degradation of the target mRNA. Antisense approaches are a way of preventing or reducing gene function by targeting the genetic material as disclosed in U.S. Pat. Nos. 4,801,540; 5,107,065; 5,759,829; 5,910,444; 6,184,439; and 6,198,026, all of which are incorporated herein by reference. In one approach, an antisense gene sequence is introduced that is transcribed into antisense RNA that is complementary to the target mRNA. For example, part or all of the normal gene sequences are placed under a promoter in inverted orientation so that the 'wrong' or complementary strand is transcribed into a non-protein expressing antisense RNA. The promoter used for the antisense gene may influence the level, timing, tissue, specificity, or inducibility of the antisense inhibition.

Autonomous mini-chromosomes may contain exogenous DNA bounded by recombination sites, for example lox-P sites, that can be recognized by a recombinase, e.g. Cre, and removed from the mini-chromosome. In cases where there is a homologous recombination site or sites in the host genomic DNA, the exogenous DNA excised the mini-chromosome may be integrated into the genome at one of the specific recombination sites and the DNA bounded by the recombination sites will become integrated into the host DNA. The use of a mini-chromosome as a platform for DNA excision or for launching such DNA integration into the host genome may include in vivo induction of the expression of a recombinase encoded in the genomic DNA of a transgenic host, or in a mini-chromosome or other episome.

RNAi gene suppression in plants by transcription of a dsRNA is described in U.S. Pat. No. 6,506,559, U.S. patent application Publication No. 2002/0168707, WO 98/53083, WO 99/53050 and WO 99/61631, all of which are incorporated herein by reference. The double-stranded RNA or RNAi constructs can trigger the sequence-specific degradation of the target messenger RNA. Suppression of a gene by RNAi can be achieved using a recombinant DNA construct having a promoter operably linked to a DNA element comprising a sense and anti-sense element of a segment of genomic DNA of the gene, e.g., a segment of at least about 23 nucleotides, more preferably about 50 to 200 nucleotides where the sense and anti-sense DNA components can be directly linked or joined by an intron or artificial DNA segment that can form a loop when the transcribed RNA hybridizes to form a hairpin structure.

Catalytic RNA molecules or ribozymes can also be used to inhibit expression of the target gene or genes or facilitate molecular reactions. Ribozymes are targeted to a given sequence by hybridization of sequences within the ribozyme to the target mRNA. Two stretches of homology are required for this targeting, and these stretches of homologous sequences flank the catalytic ribozyme structure. It is possible to design ribozymes that specifically pair with virtually any target mRNA and cleave the target mRNA at a specific location, thereby inactivating it. A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include Tobacco Ringspot Virus (Prody et al., *Science*, 231:1577-1580, 1986), Avocado Sunblotch Viroid (Palukaitis et al., *Virology*, 99:145-151, 1979; Symons, *Nucl. Acids Res.*, 9:6527-6537, 1981), and Lucerne Transient Streak Virus (Forster and Symons, *Cell*, 49:211-220, 1987), and the satellite RNAs from velvet tobacco mottle virus, Solanum nodiflorum mottle virus and subterranean clover mottle virus. The design and use of target RNA-specific ribozymes is described in Haseloff, et al., Nature 334:585-591 (1988). Several different ribozyme motifs have been described with RNA cleavage activity (Symons, *Annu. Rev. Biochem.*, 61:641-671, 1992). Other suitable ribozymes include sequences from RNase P with RNA cleavage activity (Yuan et al., *Proc. Natl. Acad. Sci. USA*, 89:8006-8010, 1992; Yuan and Altman, *Science*, 263:1269-1273, 1994; U.S. Pat. Nos. 5,168,053 and 5,624,824), hairpin ribozyme structures (Berzal-Herranz et al., *Genes and Devel.*, 6:129-134, 1992; Chowrira et al., *J. Biol. Chem.*, 269:25856-25864, 1994) and Hepatitis Delta virus based ribozymes (U.S. Pat. No. 5,625,047). The general design and optimization of ribozyme directed RNA cleavage activity has been discussed in detail (Haseloff and Gerlach, 1988, Nature. 1988 Aug. 18; 334 (6183):585-91, Chowrira et al., J. Biol. Chem., 269:25856-25864, 1994).

Another method of reducing protein expression utilizes the phenomenon of cosuppression or gene silencing (for example, U.S. Pat. Nos. 6,063,947; 5,686,649; or 5,283,184; each of which is incorporated herein by reference). Cosuppression of an endogenous gene using a full-length cDNA sequence as well as a partial cDNA sequence are known (for example, Napoli et al., Plant Cell 2:279-289 [1990]; van der Krol et al., Plant Cell 2:291-299 [1990]; Smith et al., Mol. Gen. Genetics 224:477-481 [1990]). The phenomenon of cosuppression has also been used to inhibit plant target genes in a tissue-specific manner.

In some embodiments, nucleic acids from one species of plant are expressed in another species of plant to effect cosuppression of a homologous gene. The introduced sequence generally will be substantially identical to the endogenous sequence intended to be repressed, for example, about 65%, 80%, 85%, 90%, or preferably 95% or greater identical. Higher identity may result in a more effective repression of expression of the endogenous sequence. A higher identity in a shorter than full length sequence compensates for a longer, less identical sequence. Furthermore, the introduced sequence need not have the same intron or exon pattern, and identity of non-coding segments will be equally effective. Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence.

Yet another method of reducing protein activity is by expressing nucleic acid ligands, so-called aptamers, which specifically bind to the protein. Aptamers may be obtained by the SELEX (Systematic Evolution of Ligands by EXponential Enrichment) method. See U.S. Pat. No. 5,270,163, incorporated herein by reference. In the SELEX method, a candidate mixture of single stranded nucleic acids having regions of randomized sequence is contacted with the protein and those nucleic acids having an increased affinity to the target are selected and amplified. After several iterations a nucleic acid with optimal affinity to the polypeptide is obtained and is used for expression in modified plants.

A zinc finger protein that binds a polypeptide-encoding sequence or its regulatory region is also used to alter expression of the nucleotide sequence. Transcription of the nucleotide sequence may be reduced or increased. Zinc finger proteins are, for example, described in Beerli et al. (1998) PNAS 95:14628-14633, or in WO 95/19431, WO 98/54311, or WO 96/06166, all incorporated herein by reference.

Other examples of non-protein expressing sequences specifically envisioned for use with the invention include tRNA sequences, for example, to alter codon usage, and rRNA variants, for example, which may confer resistance to various agents such as antibiotics.

It is contemplated that unexpressed DNA sequences, including novel synthetic sequences, could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from unlabelled germplasm.

Exemplary Plant Promoters, Regulatory Sequences and Targeting Sequences

Exemplary classes of plant promoters are described below.

Constitutive Expression promoters: Exemplary constitutive expression promoters include the ubiquitin promoter (e.g., sunflower—Binet et al. Plant Science 79: 87-94 (1991); maize—Christensen et al. Plant Molec. Biol. 12: 619-632 (1989); and *Arabidopsis*—Callis et al., J. Biol. Chem. 265: 12486-12493 (1990) and Norris et al., Plant Mol. Biol. 21: 895-906 (1993)); the CaMV 35S promoter (U.S. Pat. Nos. 5,858,742 and 5,322,938); or the actin promoter (e.g., rice—U.S. Pat. No. 5,641,876; McElroy et al. Plant Cell 2: 163-171 (1990), McElroy et al. Mol. Gen. Genet. 231: 150-160 (1991), and Chibbar et al. Plant Cell Rep. 12: 506-509 (1993)).

Inducible Expression promoters: Exemplary inducible expression promoters include the chemically regulatable tobacco PR-1 promoter (e.g., tobacco—U.S. Pat. No. 5,614, 395; *Arabidopsis*—Lebel et al., Plant J. 16: 223-233 (1998); maize—U.S. Pat. No. 6,429,362). Various chemical regulators may be employed to induce expression, including the benzothiadiazole, isonicotinic acid, and salicylic acid compounds disclosed in U.S. Pat. Nos. 5,523,311 and 5,614,395. Other promoters inducible by certain alcohols or ketones, such as ethanol, include, for example, the alcA gene promoter from *Aspergillus nidulans* (Caddick et al. (1998) Nat. Biotechnol 16:177-180). A glucocorticoid-mediated induction system is described in Aoyama and Chua (1997) The Plant Journal 11: 605-612 wherein gene expression is induced by application of a glucocorticoid, for example a dexamethasone. Another class of useful promoters are water-deficit-inducible promoters, e.g. promoters which are derived from the 5' regulatory region of genes identified as a heat shock protein 17.5 gene (HSP 17.5), an HVA22 gene (HVA22), and a cinnamic acid 4-hydroxylase (CA4H) gene of *Zea mays*. Another water-deficit-inducible promoter is derived from the rab-17 promoter as disclosed by Vilardell et al., Plant Molecular Biology, 17(5):985-993, 1990. See also U.S. Pat. No. 6,084,089 which discloses cold inducible promoters, U.S. Pat. No. 6,294,714 which discloses light inducible promoters, U.S. Pat. No. 6,140,078 which discloses salt inducible promoters, U.S. Pat. No. 6,252,138 which discloses pathogen inducible promoters, and U.S. Pat. No. 6,175,060 which discloses phosphorus deficiency inducible promoters.

As another example, numerous wound-inducible promoters have been described (e.g. Xu et al. Plant Molec. Biol. 22: 573-588 (1993), Logemann et al. Plant Cell 1: 151-158 (1989), Rohrmeier & Lehle, Plant Molec. Biol. 22: 783-792 (1993), Firek et al. Plant Molec. Biol. 22: 129-142 (1993), Warner et al. Plant J. 3: 191-201 (1993)). Logemann describe 5' upstream sequences of the potato wun1 gene. Xu et al. show that a wound-inducible promoter from the dicotyledon potato (pin2) is active in the monocotyledon rice. Rohrmeier & Lehle describe maize Wip1 cDNA which is wound induced and which can be used to isolate the cognate promoter. Firek et al. and Warner et al. have described a wound-induced gene from the monocotyledon *Asparagus officinalis*, which is expressed at local wound and pathogen invasion sites.

Tissue-Specific Promoters: Exemplary promoters that express genes only in certain tissues are useful according to the present invention. For example root specific expression may be attained using the promoter of the maize metallothionein-like (MTL) gene described by de Framond (FEBS 290: 103-106 (1991)) and also in U.S. Pat. No. 5,466,785, incorporated herein by reference. U.S. Pat. No. 5,837,848 discloses a root specific promoter. Another exemplary promoter confers pith-preferred expression (see Int'l. Pub. No. WO 93/07278, herein incorporated by reference, which describes the maize trpA gene and promoter that is preferentially expressed in pith cells). Leaf-specific expression may be attained, for example, by using the promoter for a maize gene encoding phosphoenol carboxylase (PEPC) (see Hudspeth & Grula, Plant Molec Biol 12: 579-589 (1989)). Pollen-specific expression may be conferred by the promoter for the maize calcium-dependent protein kinase (CDPK) gene which is expressed in pollen cells (WO 93/07278). U.S. Pat. Appl. Pub.

No. 20040016025 describes tissue-specific promoters. Pollen-specific expression may be conferred by the tomato LAT52 pollen-specific promoter (Bate et. al., Plan mol Biol. 1998 July; 37(5):859-69).

See also U.S. Pat. No. 6,437,217 which discloses a root-specific maize RS81 promoter, U.S. Pat. No. 6,426,446 which discloses a root specific maize RS324 promoter, U.S. Pat. No. 6,232,526 which discloses a constitutive maize A3 promoter, U.S. Pat. No. 6,177,611 which discloses constitutive maize promoters, U.S. Pat. No. 6,433,252 which discloses a maize L3 oleosin promoter that are aleurone and seed coat-specific promoters, U.S. Pat. No. 6,429,357 which discloses a constitutive rice actin 2 promoter and intron, U.S. patent application Pub. No. 20040216189 which discloses an inducible constitutive leaf specific maize chloroplast aldolase promoter.

Optionally a plant transcriptional terminator can be used in place of the plant-expressed gene native transcriptional terminator. Exemplary transcriptional terminators are those that are known to function in plants and include the CaMV 35S terminator, the tml terminator, the nopaline synthase terminator and the pea rbcS E9 terminator. These can be used in both monocotyledons and dicotyledons.

Various intron sequences have been shown to enhance expression, particularly in monocotyledonous cells. For example, the introns of the maize Adh1 gene have been found to significantly enhance expression. Intron 1 was found to be particularly effective and enhanced expression in fusion constructs with the chloramphenicol acetyltransferase gene (Callis et al., Genes Develop. 1: 1183-1200 (1987)). The intron from the maize bronze1 gene also enhances expression. Intron sequences have been routinely incorporated into plant transformation vectors, typically within the non-translated leader. U.S. Patent Application Publication 2002/0192813 discloses 5', 3' and intron elements useful in the design of effective plant expression vectors.

A number of non-translated leader sequences derived from viruses are also known to enhance expression, and these are particularly effective in dicotyledonous cells. Specifically, leader sequences from Tobacco Mosaic Virus (TMV, the "omega-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693-8711 (1987); Skuzeski et al. Plant Molec. Biol. 15: 65-79 (1990)). Other leader sequences known in the art include but are not limited to: picornavirus leaders, for example, EMCV leader (Encephalomyocarditis 5' noncoding region) (Elroy-Stein, O., Fuerst, T. R., and Moss, B. PNAS USA 86:6126-6130 (1989)); potyvirus leaders, for example, TEV leader (Tobacco Etch Virus) (Allison et al., 1986); MDMV leader (Maize Dwarf Mosaic Virus); Virology 154:9-20); human immunoglobulin heavy-chain binding protein (BiP) leader, (Macejak, D. G., and Sarnow, P., Nature 353: 90-94 (1991); untranslated leader from the coat protein mRNA of alfalfa mosaic virus (AMV RNA 4), (Jobling, S. A., and Gehrke, L., Nature 325:622-625 (1987); tobacco mosaic virus leader (TMV), (Gallie et al., Molecular Biology of RNA, pages 237-256 (1989); or Maize Chlorotic Mottle Virus leader (MCMV) (Lommel et al., Virology 81:382-385 (1991). See also, Della-Cioppa et al., Plant Physiology 84:965-968 (1987).

A minimal promoter may also be incorporated. Such a promoter has low background activity in plants when there is no transactivator present or when enhancer or response element binding sites are absent. One exemplary minimal promoter is the Bz1 minimal promoter, which is obtained from the bronze1 gene of maize. Roth et al., Plant Cell 3: 317 (1991). A minimal promoter may also be created by use of a synthetic TATA element. The TATA element allows recognition of the promoter by RNA polymerase factors and confers a basal level of gene expression in the absence of activation (see generally, Mukumoto (1993) Plant Mol Biol 23: 995-1003; Green (2000) Trends Biochem Sci 25: 59-63).

Sequences controlling the targeting of gene products also may be included. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104-15109 (1988)). These signal sequences can be fused to heterologous gene products to effect the import of heterologous products into the chloroplast (van den Broeck, et al. Nature 313: 358-363 (1985)). DNA encoding for appropriate signal sequences can be isolated from the 5' end of the cDNAs encoding the RUBISCO protein, the CAB protein, the EPSP synthase enzyme, the GS2 protein or many other proteins which are known to be chloroplast localized. Other gene products are localized to other organelles such as the mitochondrion and the peroxisome (e.g. Unger et al. Plant Molec. Biol. 13: 411-418 (1989)). Examples of sequences that target to such organelles are the nuclear-encoded ATPases or specific aspartate amino transferase isoforms for mitochondria. Targeting cellular protein bodies has been described by Rogers et al. (Proc. Natl. Acad. Sci. USA 82: 6512-6516 (1985)). In addition, amino terminal and carboxy-terminal sequences are responsible for targeting to the ER, the apoplast, and extracellular secretion from aleurone cells (Koehler & Ho, Plant Cell 2: 769-783 (1990)). Additionally, amino terminal sequences in conjunction with carboxy terminal sequences are responsible for vacuolar targeting of gene products (Shinshi et al. Plant Molec. Biol. 14: 357-368 (1990)).

Another possible element which may be introduced is a matrix attachment region element (MAR), such as the chicken lysozyme A element (Stief, 1989), which can be positioned around an expressible gene of interest to effect an increase in overall expression of the gene and diminish position dependent effects upon incorporation into the plant genome (Stief et al., Nature, 341:343, 1989; Phi-Van et al., Mol. Cell. Biol., 10:2302-2307.1990).

Use of Non-Plant Promoter Regions Isolated from *Drosophila melanogaster* and *Saccharomyces cerevisiae* to Express Genes in Plants The promoter in the mini-chromosome of the present invention can be derived from plant or non-plant species. In one embodiment, the nucleotide sequence of the promoter is derived from non-plant species for the expression of genes in plant cells, including but not limited to dicotyledon plant cells such as tobacco, tomato, potato, soybean, canola, sunflower, alfalfa, cotton and *Arabidopsis*, or monocotyledonous plant cell, such as wheat, maize, rye, rice, turf grass, oat, barley, sorghum, millet, and sugarcane. In one embodiment, the non-plant promoters are constitutive or inducible promoters derived from insect, e.g., *Drosophila melanogaster* or yeast, e.g., *Saccharomyces cerevisiae*. Table 2 lists the promoters from *Drosophila melanogaster* and *Saccharomyces cerevisiae* that are used to derive the examples of non-plant promoters in the present invention. Promoters derived from any animal, protist, or fungi are also contemplated. SEQ ID NOS: 1-20, or fragments, mutants, hybrid or tandem promoters thereof, are examples of promoter sequences derived from *Drosophila melanogaster* or *Saccharomyces cerevisiae*. These non-plant promoters can be operably linked to nucleic acid sequences encoding polypeptides or non-protein-expressing sequences including, but not limited to, antisense RNA and ribozymes, to form nucleic acid constructs, vectors, and host cells (prokaryotic or eukaryotic), comprising the promoters.

TABLE 2a

*Drosophila melanogaster* Promoters
(Information obtained from the Flybase Tweedie et al.,
The FlyBase Consortium, Nucleic Acids Research (2009) 37: D555-D559)

| SEQ ID NO: | SSymbol | Flybase ID | Standard promoter gene name | Gene Product | Chromosome |
|---|---|---|---|---|---|
| 1 | Pgd | FBgn0004654 | Phosphogluconate dehydrogenase | 6-phosphogluconate dehydrogenase | X |
| 2 | Grim | FBgn0015946 | grim | grim-P138 | 3 |
| 3 | Uro | FBgn0003961 | Urate oxidase | Uro-P1 | 2 |
| 4 | Sna | FBgn0003448 | snail | sna-P1 | 2 |
| 5 | Rh3 | FBgn0003249 | Rhodopsin 3 | Rh3 | 3 |
| 6 | Lsp-1 γ | FBgn0002564 | Larval serum protein 1 γ | Lsp1γ-P1 | 3 |

TABLE 2b

*Saccharomyces cerevisiae* Promoters
(partial reference: Cherry et al., D Nature 1997 387(6632 Suppl): 67-73.
Genetic and physical maps of *Saccharomyces cerevisiae*))

| Seq ID NO: | Symbol | Systematic Name | Standard promoter gene name | Gene Product | Chromosome |
|---|---|---|---|---|---|
| 7 | Tef-2 | YBR118W | TEF2 (Translation elongation factor promoter) | Translation elongation factor EF-1 alpha | 2 |
| 8 | Leu-1 | YGL009C | LEU1 (LEUcine biosynthesis) | isopropylmalate isomerase | 7 |
| 9 | Met16 | YPR167C | METhionine requiring | 3'phosphoadenylyl sulfate reductase | 16 |
| 10 | Leu-2 | YCL018W | LEU2 (leucine biosynthesis) | beta-IPM (isopropylmalate) dehydrogenase | 3 |
| 11 | His-4 | YCL030C | HIS4 (HIStidine requiring) | histidinol dehydrogenase | 3 |
| 12 | Met-2 | YNL277W | MET2 (methionine requiring) | L-homoserine-O-acetyltransferase | 14 |
| 13 | Ste-3 | YKL178C | STE3 (alias DAF2 Sterile) | a-factor receptor | 11 |
| 14 | Arg-1 | YOL058W | ARG1 (alias ARG10 ARGinine requiring) | arginosuccinate synthetase | 15 |
| 15 | Pgk-1 | YCR012W | PGK1 (phosphoglycerate kinase) | Phosphoglycer-ate kinase | 3 |
| 16 | GPD-1 | YDL022W | GPD1 (alias DAR1/HOR1/OSG1/OSR5: glycerol-3-phosphate dehydrogenase activity | glycerol-3-phosphate dehydrogenase | 4 |
| 17 | ADH1 | YOL086C | ADH1 (alias ADC1) | alcohol dehydrogenase | 15 |
| 18 | GPD-2 | YOL059W | GPD2 (alias GPD3: glycerol-3-phosphate dehydrogenase activity | glycerol-3-phosphate dehydrogenase | 15 |
| 19 | Arg-4 | YHR018C | ARGinine requiring | Arginine-succinate lyase | 8 |
| 20 | Yat-1 | YAR035W | YAT-1 (carnitine acetyltransferase) | carnitine acetyltransferase | 1 |

In the mini-chromosomes of the present invention, the promoter may be a mutant of the promoters having a substitution, deletion, and/or insertion of one or more nucleotides in the nucleic acid sequence of SEQ ID NOS: 1 to 20, hybrid or tandem promoters.

The techniques used to isolate or clone a nucleic acid sequence comprising a promoter of interest are known in the art and include isolation from genomic DNA. The cloning procedures may involve excision or amplification, for example by polymerase chain reaction, and isolation of a desired nucleic acid fragment comprising the nucleic acid sequence encoding the promoter, insertion of the fragment into a vector molecule, and incorporation of the recombinant vector into the plant cell.

Definitions

The term "adchromosomal" plant or plant part as used herein means a plant or plant part that contains functional, stable and autonomous mini-chromosomes. Adchromosomal plants or plant parts may be chimeric or not chimeric (chimeric meaning that mini-chromosomes are only in certain portions of the plant, and are not uniformly distributed throughout the plant). An adchromosomal plant cell contains at least one functional, stable and autonomous mini-chromosome.

The term "autonomous" as used herein means that when delivered to plant cells, at least some mini-chromosomes are transmitted through mitotic division to daughter cells and are episomal in the daughter plant cells, i.e. are not chromosomally integrated in the daughter plant cells. Daughter plant cells that contain autonomous mini-chromosomes can be selected for further replication using, for example, selectable or screenable markers. During the introduction into a cell of a mini-chromosome, or during subsequent stages of the cell cycle, there may be chromosomal integration of some portion or all of the DNA derived from a mini-chromosome in some cells. The mini-chromosome is still characterized as autonomous despite the occurrence of such events if a plant may be regenerated that contains episomal descendants of the mini-chromosome distributed throughout its parts, or if gametes or progeny can be derived from the plant that contain episomal descendants of the mini-chromosome distributed through its parts.

As used herein, a "centromere" is any DNA sequence that confers an ability to segregate to daughter cells through cell division. In one context, this sequence may produce a transmission efficiency to daughter cells ranging from about 1% to about 100%, including to about 5%, 10%, 20%, 30%, 40%, 50%, 60%, 70%, 80%, 90% or about 95% of daughter cells. Variations in such a transmission efficiency may find important applications within the scope of the invention; for example, mini-chromosomes carrying centromeres that confer 100% stability could be maintained in all daughter cells without selection, while those that confer 1% stability could be temporarily introduced into a transgenic organism, but be eliminated when desired. In particular embodiments of the invention, the centromere may confer stable transmission to daughter cells of a nucleic acid sequence, including a recombinant construct comprising the centromere, through mitotic or meiotic divisions, including through both meiotic and meiotic divisions. A plant centromere is not necessarily derived from plants, but has the ability to promote DNA transmission to daughter plant cells.

As used herein, the term "circular permutations" refer to variants of a sequence that begin at base n within the sequence, proceed to the end of the sequence, resume with base number one of the sequence, and proceed to base n−1. For this analysis, n may be any number less than or equal to the length of the sequence. For example, circular permutations of the sequence ABCD are: ABCD, BCDA, CDAB, and DABC.

The term "co-delivery" as used herein refers to the delivery of two nucleic acid segments to a cell. In co-delivery of plant growth inducing genes and mini-chromosomes, the two nucleic acid segments are delivered simultaneously using the same delivery method. Alternatively, the nucleic acid segment containing the growth inducing gene, optionally as part of an episomal vector, such as a viral vector or a plasmid vector, may be delivered to the plant cells before or after delivery of the mini-chromosome, and the mini-chromosome may carry an exogenous nucleic acid that induces expression of the earlier-delivered growth inducing gene. In this embodiment, the two nucleic acid segments may be delivered separately at different times provided the encoded growth inducing factors are functional during the appropriate time period.

The term "coding sequence" is defined herein as a nucleic acid sequence that is transcribed into mRNA which is translated into a polypeptide when placed under the control of promoter sequences. The boundaries of the coding sequence are generally determined by the ATG start codon located at the start of the open reading frame, near the 5' end of the mRNA, and TAG, TGA or TAA stop codons at the end of the coding sequence, near the 3' end f the mRNA, and in some cases, a transcription terminator sequence located just downstream of the open reading frame at the 3' end of the mRNA. A coding sequence can include, but is not limited to, genomic DNA, cDNA, semisynthetic, synthetic, or recombinant nucleic acid sequences.

As used herein the term "consensus" refers to a nucleic acid sequence derived by comparing two or more related sequences. A consensus sequence defines both the conserved and variable sites between the sequences being compared. Any one of the sequences used to derive the consensus or any permutation defined by the consensus may be useful in construction of mini-chromosomes.

The term "exogenous" when used in reference to a nucleic acid, for example, is intended to refer to any nucleic acid that has been introduced into a recipient cell, regardless of whether the same or similar nucleic acid is already present in such a cell. Thus, as an example, "exogenous DNA" can include an additional copy of DNA that is already present in the plant cell, DNA from another plant, DNA from a different organism, or a DNA generated externally, such as a DNA sequence containing an antisense message of a gene, or a DNA sequence encoding a synthetic or modified version of a gene. An "exogenous gene" can be a gene not normally found in the host genome in an identical context, or an extra copy of a host gene. The gene may be isolated from a different species than that of the host genome, or alternatively, isolated from the host genome but operably linked to one or more regulatory regions which differ from those found in the unaltered, native gene.

The term "functional" as used herein to describe a mini-chromosome means that when an exogenous nucleic acid is present within the mini-chromosome the exogenous nucleic acid can function in a detectable manner when the mini-chromosome is within a plant cell; exemplary functions of the exogenous nucleic acid include transcription of the exogenous nucleic acid, expression of the exogenous nucleic acid, regulatory control of expression of other exogenous nucleic acids, recognition by a restriction enzyme or other endonuclease, ribozyme or recombinase; providing a substrate for DNA methylation, DNA glycolation or other DNA chemical modification; binding to proteins such as histones, helix-loop-helix proteins, zinc binding proteins, leucine zipper proteins, MADS box proteins, topoisomerases, helicases, transposases, TATA box binding proteins, viral protein, reverse transcriptases, or cohesins; providing an integration site for homologous recombination; providing an integration site for a transposon, T-DNA or retrovirus; providing a substrate for RNAi synthesis; priming of DNA replication; aptamer binding; or kinetochore binding. If multiple exogenous nucleic acids are present within the mini-chromosome, the function of one or preferably more of the exogenous nucleic acids can be detected under suitable conditions permitting function thereof.

As used herein, a "library" is a pool of cloned DNA fragments that represents some or all DNA sequences collected, prepared or purified from a specific source. Each library may contain the DNA of a given organism inserted as discrete restriction enzyme generated fragments or as randomly sheared fragments into many thousands of plasmid vectors. For purposes of the present invention, *E. coli*, yeast, and *Salmonella* plasmids are particularly useful for propagating the genome inserts from other organisms. In principle, any gene or sequence present in the starting DNA preparation can be isolated by screening the library with a specific hybridization probe (see, for example, Young et al., In: Eukaryotic Genetic Systems ICN-UCLA Symposia on Molecular and Cellular Biology, VII, 315-331, 1977).

As used herein, the term "linker" refers to a DNA molecule, generally up to 50 or 60 nucleotides long and composed of two or more complementary oligonucleotides that have been synthesized chemically, or excised or amplified from existing plasmids or vectors. In a preferred embodiment, this fragment contains one, or preferably more than one, restriction enzyme site for a blunt cutting enzyme and/or a staggered cutting enzyme, such as BamHI. One end of the linker is designed to be ligatable to one end of a linear DNA molecule and the other end is designed to be ligatable to the other end of the linear molecule, or both ends may be designed to be ligatable to both ends of the linear DNA molecule.

As used herein, a "mini-chromosome" is a recombinant DNA construct including a centromere and capable of transmission to daughter cells. A mini-chromosome may remain separate from the host genome (as episomes) or may integrate into host chromosomes. The stability of this construct through cell division could range between from about 1% to about 100%, including about 5%, 10%, 20%, 30%, 40%, 50%, 60%, 70%, 80%, 90% and about 95%. The mini-chromosome construct may be a circular or linear molecule. It may include elements such as one or more telomeres, origin of replication sequences, stuffer sequences, buffer sequences, chromatin packaging sequences, linkers and genes. The number of such sequences included is only limited by the physical size limitations of the construct itself. It could contain DNA derived from a natural centromere, although it may be preferable to limit the amount of DNA to the minimal amount required to obtain a transmission efficiency in the range of 1-100%. The mini-chromosome could also contain a synthetic centromere composed of tandem arrays of repeats of any sequence, either derived from a natural centromere, or of synthetic DNA. The mini-chromosome could also contain DNA derived from multiple natural centromeres. The mini-chromosome may be inherited through mitosis or meiosis, or through both meiosis and mitosis. As used herein, the term mini-chromosome specifically encompasses and includes the terms "plant artificial chromosome" or "PLAC," or engineered chromosomes or microchromosomes and all teachings relevant to a PLAC or plant artificial chromosome specifically apply to constructs within the meaning of the term mini-chromosome.

The term "non-protein expressing sequence" or "non-protein coding sequence" is defined herein as a nucleic acid sequence that is not eventually translated into protein. The nucleic acid may or may not be transcribed into RNA. Exemplary sequences include ribozymes or antisense RNA.

The term "operably linked" is defined herein as a configuration in which a control sequence, e.g., a promoter sequence, directs transcription or translation of another sequence, for example a coding sequence. For example, a promoter sequence could be appropriately placed at a position relative to a coding sequence such that the control sequence directs the production of a polypeptide encoded by the coding sequence.

"Phenotype" or "phenotypic trait(s)", as used herein, refers to an observable property or set of properties resulting from the expression of a gene. The set of properties may be observed visually or after biological or biochemical testing, and may be constantly present or may only manifest upon challenge with the appropriate stimulus or activation with the appropriate signal.

The term "plant," as used herein, refers to any type of plant. Exemplary types of plants are listed below, but other types of plants will be known to those of skill in the art and could be used with the invention. Modified plants of the invention include, for example, dicots, gymnosperm, monocots, mosses, ferns, horsetails, club mosses, liverworts, hornworts, red algae, brown algae, gametophytes and sporophytes of pteridophytes, and green algae.

The term "crop plant" refers to plants grown for agricultural or commercial rather than experimental purposes and specifically excludes *Arabidopsis thaliana*. Some plants grown for experimental purposes may take on commercial importance when used to produce pharmaceutical or chemical products. Centromeres "derived from crop plants" according to the present invention specifically exclude centromeres that are fragments of naturally occurring *Arabidopsis thaliana* centromeres or naturally occurring descendants thereof. Centromeres derived from crop plants include variants (mutants) of *Arabidopsis thaliana* centromeres, or artificial centromeres synthesized based on nucleotide sequences of *Arabidopsis thaliana* centromeres.

A common class of plants exploited in agriculture are vegetable crops, including artichokes, kohlrabi, arugula, leeks, asparagus, lettuce (e.g., head, leaf, romaine), bok Choy, malanga, broccoli, melons (e.g., muskmelon, watermelon, crenshaw, honeydew, cantaloupe), brussels sprouts, cabbage, cardoni, carrots, napa, cauliflower, okra, onions, celery, parsley, chick peas, parsnips, chicory, chinese cabbage, peppers, collards, potatoes, cucumber plants (marrows, cucumbers), pumpkins, cucurbits, radishes, dry bulb onions, rutabaga, eggplant, salsify, escarole, shallots, endive, garlic, spinach, green onions, squash, greens, beet (sugar beet or fodder beet), sweet potatoes, swiss chard, horseradish, tomatoes, kale, turnips, or spices.

Other types of plants frequently finding commercial use include fruit and vine crops such as apples, grapes, apricots, cherries, nectarines, peaches, pears, plums, prunes, quince, almonds, chestnuts, filberts, pecans, pistachios, walnuts, citrus, blueberries, boysenberries, cranberries, currants, loganberries, raspberries, strawberries, blackberries, grapes, avocados, bananas, kiwi, persimmons, pomegranate, pineapple, tropical fruits, pomes, melon, mango, papaya, or lychee.

Modified wood and fiber or pulp plants of particular interest include, but are not limited to maple, oak, cherry, mahogany, poplar, aspen, birch, beech, spruce, fir, kenaf, pine, walnut, cedar, redwood, chestnut, *acacia*, bombax, alder, *eucalyptus, catalpa*, mulberry, persimmon, ash, honeylocust, sweetgum, privet, sycamore, *magnolia*, sourwood, cottonwood, mesquite, buckthorn, locust, willow, elderberry, teak, linden, bubinga, basswood or elm.

Modified flowers and ornamental plants of particular interest, include, but are not limited to, roses, petunias, pansy, peony, olive, begonias, violets, *phlox*, nasturtiums, irises, lilies, orchids, *vinca, philodendron*, poinsettias, *opuntia, cyclamen*, magnolia, dogwood, azalea, redbud, boxwood, *Viburnum*, maple, elderberry, *hosta*, agave, asters, sunflower, pansies, *hibiscus*, morning glory, *alstromeria, zinnia, geranium, Prosopis, artemesia, clematis, delphinium, dianthus, gallium, coreopsis, iberis, lamium*, poppy, lavender, *leucophyllum, sedum, salvia, verbascum, digitalis, penstemon*, savory, *pythrethrum*, or *oenothera*. Modified nut-bearing trees of particular interest include, but are not limited to pecans, walnuts, macadamia nuts, hazelnuts, almonds, or pistachios, cashews, pignolas or chestnuts.

Many of the most widely grown plants are field crop plants such as evening primrose, meadow foam, corn (field, sweet, popcorn), hops, jojoba, peanuts, rice, safflower, small grains (barley, oats, rye, wheat, etc.), sorghum, tobacco, kapok, leguminous plants (beans, lentils, peas, soybeans), oil plants (rape, mustard, poppy, olives, sunflowers, coconut, castor oil plants, cocoa beans, groundnuts, oil palms), fibre plants (cotton, flax, hemp, jute), lauraceae (cinnamon, camphor), or plants such as coffee, sugarcane, cocoa, tea, or natural rubber plants.

Still other examples of plants include bedding plants such as flowers, cactus, succulents or ornamental plants, as well as trees such as forest (broad-leaved trees or evergreens, such as conifers), fruit, ornamental, or nut-bearing trees, as well as shrubs or other nursery stock.

Modified crop plants of particular interest in the present invention include, but are not limited to, soybean (*Glycine max*), cotton, canola (also known as rape), wheat, sunflower, sorghum, alfalfa, barley, safflower, millet, rice, tobacco, fruit and vegetable crops or turfgrasses. Exemplary cereals include maize, wheat, barley, oats, rye, millet, sorghum, rice triticale, secale, einkorn, spelt, emmer, teff, milo, flax, gramma grass, *Tripsacum* sp., or teosinte. Oil-producing plants include plant species that produce and store triacylglycerol in specific organs, primarily in seeds. Such species include soybean (*Glycine max*), rapeseed or canola (including *Brassica napus*, *Brassica rapa* or *Brassica campestris*), *Brassica juncea*, *Brassica carinata*, sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) or peanut (*Arachis hypogaea*).

The term "plant part" as used herein includes pollen, silk, endosperm, ovule, seed, embryo, pods, roots, cuttings, tubers, stems, stalks, fruit, berries, nuts, flowers, leaves, bark, wood, whole plant, plant cell, plant organ, epidermis, vascular tissue, protoplast, cell culture, crown, callus culture, petiole, petal, sepal, stamen, stigma, style, bud, meristem, cambium, cortex, pith, sheath or any group of plant cells organized into a structural and functional unit. In one preferred embodiment, the exogenous nucleic acid is expressed in a specific location or tissue of a plant, for example, epidermis, vascular tissue, meristem, cambium, cortex, pith, leaf, sheath, flower, root or seed.

The term "promoter" is defined herein as a DNA sequence that allows the binding of RNA polymerase (including but not limited to RNA polymerase I, RNA polymerase II and RNA polymerase III from eukaryotes) and directs the polymerase to a downstream transcriptional start site of a nucleic acid sequence encoding a polypeptide to initiate transcription. RNA polymerase effectively catalyzes the assembly of messenger RNA complementary to the appropriate DNA strand of the coding region.

A "promoter operably linked to a heterologous gene" is a promoter that is operably linked to a gene that is different from the gene to which the promoter is normally operably linked in its native state. Similarly, an "exogenous nucleic acid operably linked to a heterologous regulatory sequence" is a nucleic acid that is operably linked to a regulatory control sequence to which it is not normally linked in its native state.

The term "hybrid promoter" is defined herein as parts of two or more promoters that are fused together to generate a sequence that is a fusion of the two or more promoters, which is operably linked to a coding sequence and mediates the transcription of the coding sequence into mRNA.

The term "tandem promoter" is defined herein as two or more promoter sequences each of which is operably linked to a coding sequence and mediates the transcription of the coding sequence into mRNA.

The term "constitutive active promoter" is defined herein as a promoter that allows permanent stable expression of the gene of interest.

The term "Inducible promoter" is defined herein as a promoter induced by the presence or absence of biotic or an abiotic factor.

The term "polypeptide" does not refer to a specific length of the encoded product and, therefore, encompasses peptides, oligopeptides, and proteins. The term "exogenous polypeptide" is defined as a polypeptide which is not native to the plant cell, a native polypeptide in which modifications have been made to alter the native sequence, or a native polypeptide whose expression is quantitatively altered as a result of a manipulation of the plant cell by recombinant DNA techniques.

As used herein, the term "pseudogene" refers to a non-functional copy of a protein-coding gene; pseudogenes found in the genomes of eukaryotic organisms are often inactivated by mutations and are thus presumed to be non-essential to that organism; pseudogenes of reverse transcriptase and other open reading frames found in retroelements are abundant in the centromeric regions of *Arabidopsis* and other organisms and are often present in complex clusters of related sequences.

As used herein the term "regulatory sequence" refers to any DNA sequence that influences the efficiency of transcription or translation of any gene. The term includes, but is not limited to, sequences comprising promoters, enhancers and terminators.

As used herein the term "repeated nucleotide sequence" refers to any nucleic acid sequence of at least 25 bp present in a genome or a recombinant molecule, other than a telomere repeat, that occurs at least two or more times and that are preferably at least 80% identical either in head to tail or head to head orientation either with or without intervening sequence between repeat units.

As used herein, the term "retroelement" or "retrotransposon" refers to a genetic element related to retroviruses that disperse through an RNA stage; the abundant retroelements present in plant genomes contain long terminal repeats (LTR retrotransposons) and encode a polyprotein gene that is processed into several proteins including a reverse transcriptase. Specific retroelements (complete or partial sequences) can be found in and around plant centromeres and can be present as dispersed copies or complex repeat clusters. Individual copies of retroelements may be truncated or contain mutations; intact retroelements are rarely encountered.

As used herein the term "satellite DNA" refers to short DNA sequences (typically <1000 bp) present in a genome as multiple repeats, mostly arranged in a tandemly repeated fashion, as opposed to a dispersed fashion. Repetitive arrays of specific satellite repeats are abundant in the centromeres of many higher eukaryotic organisms.

As used herein, a "screenable marker" is a gene whose presence results in an identifiable phenotype. This phenotype may be observable under standard conditions, altered conditions such as elevated temperature, or in the presence of certain chemicals used to detect the phenotype. The use of a screenable marker allows for the use of lower, sub-killing antibiotic concentrations and the use of a visible marker gene to identify clusters of transformed cells, and then manipulation of these cells to homogeneity. Preferred screenable markers of the present include genes that encode fluorescent proteins that are detectable by a visual microscope such as the fluorescent reporter genes DsRed, ZsGreen, ZsYellow, AmCyan, Green Fluorescent Protein (GFP). An additional preferred screenable marker gene is lac.

Alternative methods of screening for adchromosomal plant cells may involve use of relatively low, sub-killing concentrations of a selection agent (e.g. sub-killing antibiotic concentrations), and also involve use of a screenable marker (e.g., a visible marker gene) to identify clusters of modified cells carrying the screenable marker, after which these screenable cells are manipulated to homogeneity. As used herein, a "selectable marker" is a gene whose presence results in a clear phenotype, and most often a growth advantage for cells that contain the marker. This growth advantage may be present under standard conditions, altered conditions such as elevated temperature, specialized media compositions, or in the presence of certain chemicals such as herbicides or antibiotics. Use of selectable markers is described, for example, in Broach et al. Gene, 8:121-133, 1979. Examples of selectable markers include the thymidine kinase gene, the cellular adenine phosphoribosyltransferase gene and the dihydrylfolate reductase gene, hygromycin phosphotransferase genes, the bar gene, neomycin phosphotransferase genes and phosphomannose isomerase, among others. Preferred selectable markers in the present invention include genes whose expression confer antibiotic or herbicide resistance to the host cell, or proteins allowing utilization of a carbon source not normally utilized by plant cells. Expression of one of these markers should be sufficient to enable the maintenance of a vector within the host cell, and facilitate the manipulation of the plasmid into new host cells. Of particular interest in the present invention are proteins conferring cellular resistance to kanamycin, G 418, paramomycin, hygromycin, bialaphos, and glyphosate for example, or proteins allowing utilization of a carbon source, such as mannose, not normally utilized by plant cells.

The term "stable" as used herein means that the mini-chromosome can be transmitted to daughter cells over at least 8 mitotic generations. Some embodiments of mini-chromosomes may be transmitted as functional, autonomous units for less than 8 mitotic generations, e.g. 1, 2, 3, 4, 5, 6, or 7. Preferred mini-chromosomes can be transmitted over at least 8, 9, 10, 11, 12, 13, 14, 15, 16, 17, 18, 18, 19, 20, 21, 22, 23, 24, 25, 26, 27, 28, 29 or 30 generations, for example, through the regeneration or differentiation of an entire plant, and preferably are transmitted through meiotic division to gametes. Other preferred mini-chromosomes can be further maintained in the zygote derived from such a gamete or in an embryo or endosperm derived from one or more such gametes. A "functional and stable" mini-chromosome is one in which functional mini-chromosomes can be detected after transmission of the mini-chromosomes over at least 8 mitotic generations, or after inheritance through a meiotic division. During mitotic division, as occurs occasionally with native chromosomes, there may be some non-transmission of mini-chromosomes; the mini-chromosome may still be characterized as stable despite the occurrence of such events if an adchromosomal plant that contains descendants of the mini-chromosome distributed throughout its parts may be regenerated from cells, cuttings, propagules, or cell cultures containing the mini-chromosome, or if an adchromosomal plant can be identified in progeny of the plant containing the mini-chromosome.

As used herein, a "structural gene" is a sequence which codes for a polypeptide or RNA and includes 5' and 3' ends. The structural gene may be from the host into which the structural gene is transformed or from another species. A structural gene will preferably, but not necessarily, include one or more regulatory sequences which modulate the expression of the structural gene, such as a promoter, terminator or enhancer. A structural gene will preferably, but not necessarily, confer some useful phenotype upon an organism comprising the structural gene, for example, herbicide resistance. In one embodiment of the invention, a structural gene may encode an RNA sequence which is not translated into a protein, for example a tRNA or rRNA gene.

As used herein, the term "telomere" or "telomere DNA" refers to a sequence capable of capping the ends of a chromosome, thereby preventing degradation of the chromosome end, ensuring replication and preventing fusion to other chromosome sequences. Telomeres can include naturally occurring telomere sequences or synthetic sequences. Telomeres from one species may confer telomere activity in another species. An exemplary telomere DNA is a heptanucleotide telomere repeat TTTAGGG (and its complement) found in the majority of plants.

"Transformed," "transgenic," "modified," and "recombinant" refer to a host organism such as a plant into which an exogenous or heterologous nucleic acid molecule has been introduced, and includes meiocytes, seeds, zygotes, embryos, endosperm, or progeny of such plant that retain the exogenous or heterologous nucleic acid molecule but which have not themselves been subjected to the transformation process.

When the phrase "transmission efficiency" of a certain percent is used, transmission percent efficiency is calculated by measuring mini-chromosome presence through one or more mitotic or meiotic generations. It is directly measured as the ratio (expressed as a percentage) of the daughter cells or plants demonstrating presence of the mini-chromosome to parental cells or plants demonstrating presence of the mini-chromosome. Presence of the mini-chromosome in parental and daughter cells is demonstrated with assays that detect the presence of an exogenous nucleic acid carried on the mini-chromosome. Exemplary assays can be the detection of a screenable marker (e.g. presence of a fluorescent protein or any gene whose expression results in an observable phenotype), a selectable marker, or PCR amplification of any exogenous nucleic acid carried on the mini-chromosome.

Constructing Mini-Chromosomes by Site-Specific Recombination

Plant mini-chromosomes may be constructed using site-specific recombination sequences (for example those recognized by the bacteriophage P1 Cre recombinase, or the bacteriophage lambda integrase, or similar recombination enzymes). A compatible recombination site, or a pair of such sites, is present on both the centromere containing DNA clones and the donor DNA clones. Incubation of the donor clone and the centromere clone in the presence of the recombinase enzyme causes strand exchange to occur between the recombination sites in the two plasmids; the resulting mini-chromosomes contain centromere sequences as well as mini-chromosome vector sequences. The DNA molecules formed in such recombination reactions is introduced into *E. coli*, other bacteria, yeast or plant cells by common methods in the field including, but not limited to, heat shock, chemical transformation, electroporation, particle bombardment, whiskers, or other transformation methods followed by selection for marker genes including chemical, enzymatic, color, or other marker present on either parental plasmid, allowing for the selection of transformants harboring mini-chromosomes.

II. Methods of Detecting and Characterizing Mini-Chromosomes in Plant Cells or of Scoring Mini-Chromosome Performance in Plant Cells:

Identification of Candidate Centromere Fragments by Probing BAC Libraries

Centromere clones are identified from a large genomic insert library such as a Bacterial Artificial Chromosome library. Probes are labeled using nick-translation in the presence of radioactively labeled dCTP, dATP, dGTP or dTTP as in, for example, the commercially available Rediprime kit (Amersham) as per the manufacturer's instructions. Other labeling methods familiar to those skilled in the art could be substituted. The libraries are screened and deconvoluted. Genomic clones are screened by probing with small centromere-specific clones. Other embodiments of this procedure would involve hybridizing a library with other centromere sequences. Of the BAC clones identified using this procedure, a representative set are identified as having high hybridization signals to some probes, and optionally low hybridization signals to other probes. These are selected, the bacterial clones grown up in cultures and DNA prepared by methods familiar to those skilled in the art such as alkaline lysis. The DNA composition of purified clones is surveyed using for example fingerprinting by digesting with restriction enzymes such as, but not limited to, HinfI or HindIII. In a preferred embodiment the restriction enzyme cuts within the tandem centromere satellite repeat (see below). A variety of clones showing different fingerprints are selected for conversion into mini-chromosomes and inheritance testing. It can also be informative to use multiple restriction enzymes for fingerprinting or other enzymes which can cleave DNA.

Fingerprinting Analysis of BACs and Mini-Chromosomes

Centromere function may be associated with large tandem arrays of satellite repeats. To assess the composition and architecture of the centromere BACs, the candidate BACs are digested with a restriction enzyme, such as HindIII, which cuts with known frequency within the consensus sequence of the unit repeat of the tandemly repeated centromere satellite. Digestion products are then separated by agarose gel electrophoresis. Large insert clones containing a large array of tandem repeats will produce a strong band of the unit repeat size, as well as less intense bands at 2× and 3× the unit repeat size, and further multiples of the repeat size. These methods are well-known and there are many possible variations known to those skilled in the art.

Determining Sequence Composition of Mini-Chromosomes by Shotgun Cloning/Sequencing, Sequence Analysis To determine the sequence composition of the mini-chromosome, the insert is sequenced. To generate DNA suitable for sequencing mini-chromosomes are fragmented, for example by using a random shearing method (such as sonication, nebulization, etc). Other fragmentation techniques may also be used such as enzymatic digestion. These fragments are then cloned into a plasmid vector and sequenced. The resulting DNA sequence is trimmed of poor-quality sequence and of sequence corresponding to the plasmid vector. The sequence is then compared to the known DNA sequences using an algorithm such as BLAST to search a sequence database such as GenBank.

To determine the consensus of the satellite repeat in the mini-chromosome, the sequences containing satellite repeat are aligned using a DNA sequence alignment program such as ContigExpress from Vector NTI. The sequences may also be aligned to previously determined repeats for that species. The sequences are trimmed to unit repeat length using the consensus as a template. Sequences trimmed from the ends of the alignment are realigned with the consensus and further trimmed until all sequences are at or below the consensus length. The sequences are then aligned with each other. The consensus is determined by the frequency of a specific nucleotide at each position; if the most frequent base is three times more frequent than the next most frequent base, it was considered the consensus.

Methods for determining consensus sequence are well known in the art, see, e.g., U.S. Pat. App. Pub. No. 20030124561; Hall & Preuss (2002). These methods, including DNA sequencing, assembly, and analysis, are well-known and there are many possible variations known to those skilled in the art. Other alignment parameters may also be useful such as using more or less stringent definitions of consensus.

Non-Selective Mini-Chromosome Mitotic Inheritance Assays

The following list of assays and potential outcomes illustrates how various assays can be used to distinguish autonomous events from integrated events.

Assay #1: Transient Assay

Mini-chromosomes are tested for their ability to become established as chromosomes and their ability to be inherited in mitotic cell divisions. In this assay, mini-chromosomes are delivered to plant cells, for example suspension cells in liquid culture. The cells used can be at various stages of growth. In this example, a population in which some cells were undergoing division was used. The mini-chromosome is then assessed over the course of several cell divisions, by tracking the presence of a screenable marker, e.g. a visible marker gene such as a fluorescent protein. Mini-chromosomes that are inherited well may show an initial delivery into many single cells; after several cell divisions, these single cells divide to form clusters of mini-chromosome-containing cells. Other exemplary embodiments of this method include delivering mini-chromosomes to other mitotic cell types, including roots and shoot meristems.

Assay #2: Non-Lineage Based Inheritance Assays on Modified Transformed Cells and Plants Mini-chromosome inheritance is assessed on modified cell lines and plants by following the presence of the mini-chromosome over the course of multiple cell divisions. An initial population of mini-chromosome containing cells is assayed for the presence of the mini-chromosome, by the presence of a marker gene, including but not limited to a fluorescent protein, a colored protein, a protein assayable by histochemical assay, and a gene affecting cell morphology. All nuclei are stained with a DNA-specific dye including but not limited to DAPI, Hoechst 33258, OliGreen, Giemsa YOYO, or TOTO, allowing a determination of the number of cells that do not contain the mini-chromosome. After the initial determination of the percent of cells carrying the mini-chromosome, the cells are allowed to divide over the course of several cell divisions. The number of cell divisions, n, is determined by a method including but not limited to monitoring the change in total weight of cells, and monitoring the change in volume of the cells or by directly counting cells in an aliquot of the culture. After a number of cell divisions, the population of cells is again assayed for the presence of the mini-chromosome. The loss rate per generation is calculated by the equation:

$$\text{Loss rate per generation} = 1 - (F/I)^{1/n}$$

The population of mini-chromosome-containing cells may include suspension cells, roots, leaves, meristems, flowers, or any other tissue of modified plants, or any other cell type containing a mini-chromosome.

These methods are well-known and there are many possible variations known to those skilled in the art; they have been used before with human cells and yeast cells.

Assay #3: Lineage Based Inheritance Assays on Modified Cells and Plants

Mini-chromosome inheritance is assessed on modified cell lines and plants by following the presence of the mini-chromosome over the course of multiple cell divisions. In cell types that allow for tracking of cell lineage, including but not limited to root cell files, trichomes, and leaf stomata guard cells, mini-chromosome loss per generation does not need to be determined statistically over a population, it can be discerned directly through successive cell divisions. In other manifestations of this method, cell lineage can be discerned from cell position, or methods including but not limited to the use of histological lineage tracing dyes, and the induction of genetic mosaics in dividing cells.

In one simple example, the two guard cells of the stomata are daughters of a single precursor cell. To assay mini-chromosome inheritance in this cell type, the epidermis of the leaf of a plant containing a mini-chromosome is examined for the presence of the mini-chromosome by the presence of a marker gene, including but not limited to a fluorescent protein, a colored protein, a protein assayable by histochemical assay, and a gene affecting cell morphology. The number of loss events in which one guard cell contains the mini-chromosome (L) and the number of cell divisions in which both guard cells contain the mini-chromosome (B) are counted. The loss rate per cell division is determined as L/(L+B). Other lineage-based cell types are assayed in similar fashion. These methods are well-known and there are many possible variations known to those skilled in the art; they have been used before with yeast cells.

Lineal mini-chromosome inheritance may also be assessed by examining root files or clustered cells in callus over time. Changes in the percent of cells carrying the mini-chromosome will indicate the mitotic inheritance.

Assay #4: Inheritance Assays on Modified Cells and Plants in the Presence of Chromosome Loss Agents Any of the above three assays can be done in the presence of chromosome loss agents (including but not limited to colchicine, colcemid, caffeine, etopocide, nocodazole, oryzalin, trifluran). It is likely that an autonomous mini-chromosome will prove more susceptible to loss induced by chromosome loss agents; therefore, autonomous mini-chromosomes should show a lower rate of inheritance in the presence of chromosome loss agents. These methods have been used to study chromosome loss in fruit flies and yeast; there are many possible variations known to those skilled in the art.

III. Transformation of Plant Cells and Plant Regeneration

Various methods may be used to deliver DNA into plant cells. These include biological methods, such as *Agrobacterium, E. coli*, and viruses, physical methods such as biolistic particle bombardment, nanocopoiea device, the Stein beam gun, silicon carbide whiskers and microinjection, electrical methods such as electroporation, and chemical methods such as the use of poly-ethylene glycol and other compounds known to stimulate DNA uptake into cells. Examples of these techniques are described by Paszkowski et al., EMBO J. 3: 2717-2722 (1984), Potrykus et al., Mol. Gen. Genet. 199: 169-177 (1985), Reich et al., Biotechnology 4: 1001-1004 (1986), and Klein et al., Nature 327: 70-73 (1987). Transformation using silicon carbide whiskers, e.g. in maize, is described in Brisibe, J. Exp. Bot. 51(343):187-196 (2000) and Dunwell, Methods Mol. Biol. 111:375-82 (1999) and U.S. Pat. No. 5,464,765.

Agrobacterium-Mediated Delivery

*Agrobacterium*-mediated transformation is one method for introducing a desired genetic element into a plant. Several *Agrobacterium* species mediate the transfer of a specific DNA known as "T-DNA" that can be genetically engineered to carry a desired piece of DNA into many plant species. Plasmids used for delivery contain the T-DNA flanking the nucleic acid to be inserted into the plant. The major events marking the process of T-DNA mediated pathogenesis are induction of virulence genes, processing and transfer of T-DNA.

There are three common methods to transform plant cells with *Agrobacterium*. The first method is co-cultivation of *Agrobacterium* with cultured isolated protoplasts. This method requires an established culture system that allows culturing protoplasts and plant regeneration from cultured protoplasts. The second method is transformation of cells or tissues with *Agrobacterium*. This method requires (a) that the plant cells or tissues can be modified by *Agrobacterium* and (b) that the modified cells or tissues can be induced to regenerate into whole plants. The third method is transformation of seeds, apices or meristems with *Agrobacterium*. This method requires exposure of the meristematic cells of these tissues to *Agrobacterium* and micropropagation of the shoots or plan organs arising from these meristematic cells.

Those of skill in the art are familiar with procedures for growth and suitable culture conditions for *Agrobacterium* as well as subsequent inoculation procedures. Liquid or semi-solid culture media can be used. The density of the *Agrobacterium* culture used for inoculation and the ratio of *Agrobacterium* cells to explant can vary from one system to the next, as can media, growth procedures, timing and lighting conditions.

Transformation of dicotyledons using *Agrobacterium* has long been known in the art, and transformation of monocotyledons using *Agrobacterium* has also been described. See, WO 94/00977 and U.S. Pat. No. 5,591,616, both of which are incorporated herein by reference. See also, Negrotto et al., Plant Cell Reports 19: 798-803 (2000), incorporated herein by reference.

A number of wild-type and disarmed strains of *Agrobacterium tumefaciens* and *Agrobacterium rhizogenes* harboring Ti or Ri plasmids can be used for gene transfer into plants. Preferably, the *Agrobacterium* hosts contain disarmed Ti and Ri plasmids that do not contain the oncogenes that cause tumorigenesis or rhizogenesis. Exemplary strains include *Agrobacterium tumefaciens* strain C58, a nopaline-type strain that is used to mediate the transfer of DNA into a plant cell, octopine-type strains such as LBA4404 or succinamopine-type strains, e.g., EHA101 or EHA105. The use of these strains for plant transformation has been reported and the methods are familiar to those of skill in the art.

U.S. Application No. 20040244075 published Dec. 2, 2004 describes improved methods of *Agrobacterium*-mediated transformation. The efficiency of transformation by *Agrobacterium* may be enhanced by using a number of methods known in the art. For example, the inclusion of a natural wound response molecule such as acetosyringone (AS) to the *Agrobacterium* culture has been shown to enhance transformation efficiency with *Agrobacterium tumefaciens* (Shahla et al., (1987) Plant Molec. Biol. 8:291-298). Alternatively, transformation efficiency may be enhanced by wounding the target tissue to be modified or transformed. Wounding of plant tissue may be achieved, for example, by punching, maceration, bombardment with microprojectiles, etc. (See e.g., Bidney et al., (1992) Plant Molec. Biol. 18:301-313).

In addition, a recent method described by Broothaerts, et. al. (Nature 433: 629-633, 2005) expands the bacterial genera that can be used to transfer genes into plants. This work involved the transfer of a disarmed Ti plasmid without T-DNA and another vector with T-DNA containing the marker enzyme beta-glucuronidase, into three different bacteria. Gene transfer was successful and this method significantly expands the tools available for gene delivery into plants.

Microprojectile Bombardment Delivery

Another widely used technique to genetically transform plants involves the use of microprojectile bombardment. In this process, a nucleic acid containing the desired genetic elements to be introduced into the plant is deposited on or in small dense particles, e.g., tungsten, platinum, or preferably 1 micron gold particles, which are then delivered at a high velocity into the plant tissue or plant cells using a specialized biolistics device. Many such devices have been designed and constructed; one in particular, the PDS1000/He sold by Bio-Rad, is the instrument most commonly used for biolistics of plant cells. The advantage of this method is that no specialized sequences need to be present on the nucleic acid molecule to be delivered into plant cells; delivery of any nucleic acid sequence is theoretically possible.

For the bombardment, cells in suspension are concentrated on filters or solid culture medium. Alternatively, immature embryos, seedling explants, or any plant tissue or target cells may be arranged on solid culture medium. The cells to be bombarded are positioned at an appropriate distance below the microprojectile stopping plate.

Various biolistics protocols have been described that differ in the type of particle or the manner in which DNA is coated onto the particle. Any technique for coating microprojectiles that allows for delivery of transforming DNA to the target cells may be used. For example, particles may be prepared by functionalizing the surface of a gold oxide particle by providing free amine groups. DNA, having a strong negative charge, will then bind to the functionalized particles.

Parameters such as the concentration of DNA used to coat microprojectiles may influence the recovery of transformants containing a single copy of the transgene. For example, a lower concentration of DNA may not necessarily change the efficiency of the transformation but may instead increase the proportion of single copy insertion events. In this regard, ranges of approximately 1 ng to approximately 10 μg (10,000 ng), approximately 5 ng to 8 μg or approximately 20 ng, 50 ng, 100 ng, 200 ng, 500 ng, 1 μg, 2 μg, 5 μg, or 7 μg of transforming DNA may be used per each 1.0-2.0 mg of starting 1.0 micron gold particles.

Other physical and biological parameters may be varied, such as manipulation of the DNA/microprojectile precipitate, factors that affect the flight and velocity of the projectiles, manipulation of the cells before and immediately after bombardment (including osmotic state, tissue hydration and the subculture stage or cell cycle of the recipient cells), the orientation of an immature embryo or other target tissue relative to the particle trajectory, and also the nature of the transforming DNA, such as linearized DNA or intact supercoiled plasmids. One may particularly wish to adjust physical parameters such as DNA concentration, gap distance, flight distance, tissue distance, and helium pressure.

The particles delivered via biolistics can be "dry" or "wet." In the "dry" method, the mini-chromosome DNA-coated particles such as gold are applied onto a macrocarrier (such as a metal plate, or a carrier sheet made of a fragile material such as mylar) and dried. The gas discharge then accelerates the macrocarrier into a stopping screen, which halts the macrocarrier but allows the particles to pass through; the particles then continue their trajectory until they impact the tissue being bombarded. For the "wet" method, the droplet containing the mini-chromosome DNA-coated particles is applied to the bottom part of a filter holder, which is attached to a base which is itself attached to a rupture disk holder used to hold the rupture disk to the helium egress tube for bombardment. The gas discharge directly displaces the DNA/gold droplet from the filter holder and accelerates the particles and their DNA cargo into the tissue being bombarded. The wet biolistics method has been described in detail elsewhere but has not previously been applied in the context of plants (Mialhe et al., Mol Mar Biol Biotechnol. 4(4):275-83, 1995). The concentrations of the various components for coating particles and the physical parameters for delivery can be optimized using procedures known in the art.

A variety of plant cells/tissues are suitable for transformation, including immature embryos, scutellar tissue, suspension cell cultures, immature inflorescence, shoot meristem, epithelial peels, nodal explants, callus tissue, hypocotyl tissue, cotyledons, roots, and leaves, meristem cells, and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspore-derived embryos, roots, hypocotyls, cotyledons and the like. Those cells which are capable of proliferating as callus also are recipient cells for genetic transformation.

Any suitable plant culture medium can be used. Examples of suitable media would include but are not limited to MS-based media (Murashige and Skoog, Physiol. Plant, 15:473-497, 1962) or N6-based media(Chu et al., Scientia Sinica 18:659, 1975) supplemented with additional plant growth regulators including but not limited to auxins such as picloram (4-amino-3,5,6-trichloropicolinic acid), 2,4-D (2,4-dichlorophenoxyacetic acid), naphalene-acetic acid (NAA) and dicamba (3,6-dichloroanisic acid), cytokinins such as BAP (6-benzylaminopurine) and kinetin, and gibberellins. Other media additives can include but are not limited to amino acids, macroelements, iron, microelements, vitamins and organics, carbohydrates, undefined media components such as casein hydrolysates, an appropriate gelling agent such as a form of agar, a low melting point agarose or Gelrite if desired. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Examples of such media would include but are not limited to Murashige and Skoog (Mursahige and Skoog, Physiol. Plant, 15:473-497, 1962), N6 (Chu et al., Scientia Sinica 18:659, 1975), Linsmaier and Skoog (Linsmaier and Skoog, Physio. Plant., 18:100, 1965), Uchimiya and Murashige (Uchimiya and Murashige, Plant Physiol. 15:473, 1962), Gamborg's B5 media (Gamborg et al., Exp. Cell Res., 50:151, 1968), D medium (Duncan et al., Planta, 165:322-332, 1985), Mc-Cown's Woody plant media (McCown and Lloyd, HortScience 6:453, 1981), Nitsch and Nitsch (Nitsch and Nitsch, Science 163:85-87, 1969), and Schenk and Hildebrandt (Schenk and Hildebrandt, Can. J. Bot. 50:199-204, 1972) or derivations of these media supplemented accordingly. Those of skill in the art are aware that media and media supplements such as nutrients and growth regulators for use in transformation and regeneration and other culture conditions such as light intensity during incubation, pH, and incubation temperatures can be varied.

Those of skill in the art are aware of the numerous modifications in selective regimes, media, and growth conditions that can be varied depending on the plant system and the selective agent. Typical selective agents include but are not limited to antibiotics such as geneticin (G418), kanamycin, paromomycin or other chemicals such as glyphosate or other herbicides. Consequently, such media and culture conditions disclosed in the present invention can be modified or substituted with nutritionally equivalent components, or similar processes for selection and recovery of transgenic events, and still fall within the scope of the present invention.

Mini-Chromosome Delivery without Selection

The Mini-chromosome is delivered to plant cells or tissues, e.g., plant cells in suspension to obtain stably modified callus clones for inheritance assay. Suspension cells are maintained in a growth media, for example Murashige and Skoog (MS) liquid medium containing an auxin such as 2,4-dichlorophenoxyacetic acid (2,4-D). Cells are bombarded using a particle bombardment process, such as the helium-driven PDS-1000/He system, and propagated in the same liquid medium to permit the growth of modified and non-modified cells. Portions of each bombardment are monitored for formation of fluorescent clusters, which are isolated by micromanipulation and cultured on solid medium. Clones modified with the mini-chromosome are expanded and homogenous clones are used in inheritance assays, or assays measuring mini-chromosome structure or autonomy.

Mini-Chromosome Transformation with Selectable Marker Gene

Isolation of mini-chromosome-modified cells in bombarded calluses or explants can be facilitated by the use of a selectable marker gene. The bombarded tissues are transferred to a medium containing an appropriate selective agent for a particular selectable marker gene. Such a transfer usually occurs between 0 and about 7 days after bombardment. The transfer could also take place any number of days after bombardment. The amount of selective agent and timing of incorporation of such an agent in selection medium can be optimized by using procedures known in the art. Selection inhibits the growth of non-modified cells, thus providing an advantage to the growth of modified cells, which can be further monitored by tracking the presence of a fluorescent marker gene or by the appearance of modified explants (modified cells on explants may be green under light in selection medium, while surrounding non-modified cells are weakly pigmented). In plants that develop through shoot organogenesis (e.g. *Brassica*, tomato or tobacco), the modified cells can form shoots directly, or alternatively, can be isolated and expanded for regeneration of multiple shoots transgenic for the mini-chromosome. In plants that develop through embryogenesis (e.g. corn or soybean), additional culturing steps may be necessary to induce the modified cells to form an embryo and to regenerate in the appropriate media.

Useful selectable marker genes are well known in the art and include, for example, herbicide and antibiotic resistance genes including but not limited to neomycin phosphotransferase II (conferring resistance to kanamycin, paramomycin and G418), hygromycin phosphotransferase (conferring resistance to hygromycin), 5-enolpyruvylshikimate-3-phosphate synthase (EPSPS, conferring resistance to glyphosate), phosphinothricin acetyltransferase (conferring resistance to phosphinothricin/bialophos), MerA (conferring resistance to mercuric ions). Selectable marker genes may be transformed using standard methods in the art.

The first step in the production of plants containing novel genes involves delivery of DNA into a suitable plant tissue (described in the previous section) and selection of the tissue under conditions that allow preferential growth of any cells containing the novel genes. Selection is typically achieved with a selectable marker gene present in the delivered DNA, which may be a gene conferring resistance to an antibiotic, herbicide or other killing agent, or a gene allowing utilization of a carbon source not normally metabolized by plant cells. For selection to be effective, the plant cells or tissue need to be grown on selective medium containing the appropriate concentration of antibiotic or killing agent, and the cells need to be plated at a defined and constant density. The concentration of selective agent and cell density are generally chosen to cause complete growth inhibition of wild type plant tissue that does not express the selectable marker gene; but allowing cells containing the introduced DNA to grow and expand into adchromosomal clones. This critical concentration of selective agent typically is the lowest concentration at which there is complete growth inhibition of wild type cells, at the cell density used in the experiments. However, in some cases, sub-killing concentrations of the selective agent may be equally or more effective for the isolation of plant cells containing mini-chromosome DNA, especially in cases where the identification of such cells is assisted by a visible marker gene (e.g., fluorescent protein gene) present on the mini-chromosome.

In some species (e.g., tobacco or tomato), a homogenous clone of modified cells can also arise spontaneously when bombarded cells are placed under the appropriate selection. An exemplary selective agent is the neomycin phosphotransferase II (nptII) marker gene, which is commonly used in plant biotechnology and confers resistance to the antibiotics kanamycin, G418 (geneticin) and paramomycin. In other species, or in certain plant tissues or when using particular selectable markers, homogeneous clones may not arise spontaneously under selection; in this case the clusters of modified cells can be manipulated to homogeneity using the visible marker genes present on the mini-chromosomes as an indication of which cells contain mini-chromosome DNA.

Regeneration of Adchromosomal Plants from Explants to Mature, Rooted Plants

For plants that develop through shoot organogenesis (e.g. *Brassica*, tomato and tobacco), regeneration of a whole plant involves culturing of regenerable explant tissues taken from sterile organogenic callus tissue, seedlings or mature plants on a shoot regeneration medium for shoot organogenesis, and rooting of the regenerated shoots in a rooting medium to obtain intact whole plants with a fully developed root system. These plants are potted in soil and grown to maturity in a greenhouse.

For plant species, such corn and soybean, regeneration of a whole plant occurs via an embryogenic step that is not necessary for plant species where shoot organogenesis is efficient. In these plants the explant tissue is cultured on an appropriate media for embryogenesis, and the embryo is cultured until shoots form. The regenerated shoots are cultured in a rooting medium to obtain intact whole plants with a fully developed root system. These plants are potted in soil and grown to maturity in a greenhouse.

Explants are obtained from any tissues of a plant suitable for regeneration. Exemplary tissues include hypocotyls, internodes, roots, cotyledons, petioles, cotyledonary petioles, leaves and peduncles, prepared from sterile seedlings or mature plants.

Explants are wounded (for example with a scalpel or razor blade) and cultured on a shoot regeneration medium (SRM) containing Murashige and Skoog (MS) medium as well as a cytokinin, e.g., 6-benzylaminopurine (BA), and an auxin, e.g., α-naphthaleneacetic acid (NAA), and an anti-ethylene agent, e.g., silver nitrate ($AgNO_3$). For example, 2 mg/L of BA, 0.05 mg/L of NAA, and 2 mg/L of $AgNO_3$ can be added to MS medium for shoot organogenesis. The most efficient shoot regeneration is obtained from longitudinal sections of internode explants.

Shoots regenerated via organogenesis are rooted in a MS medium containing low concentrations of an auxin such as NAA. Plants are potted and grown in a greenhouse to sexual maturity for seed harvest.

To regenerate a whole plant with a mini-chromosome, explants are pre-incubated for 1 to 7 days (or longer) on the shoot regeneration medium prior to bombardment with mini-chromosome (see below). Following bombardment, explants are incubated on the same shoot regeneration medium for a recovery period up to 7 days (or longer), followed by selection for transformed shoots or clusters on the same medium but with a selective agent appropriate for a particular selectable marker gene (see below).\

Method of Co-Delivering Growth Inducing Genes to Facilitate Isolation of Adchromosomal Plant Cell Clones Another method used in the generation of cell clones containing mini-chromosomes involves the co-delivery of DNA containing genes that are capable of activating growth of plant cells, or that promote the formation of a specific organ, embryo or plant structure that is capable of self-sustaining growth. In one embodiment, the recipient cell receives simultaneously the mini-chromosome, and a separate DNA molecule encoding one or more growth promoting, organogenesis-promoting, embryogenesis-promoting or regeneration-promoting genes. Following DNA delivery, expression of the plant growth regulator genes stimulates the plant cells to divide, or to initiate differentiation into a specific organ, embryo, or other cell types or tissues capable of regeneration. Multiple plant growth regulator genes can be combined on the same molecule, or co-bombarded on separate molecules. Use of these genes can also be combined with application of plant growth regulator molecules into the medium used to culture the plant cells, or of precursors to such molecules that are converted to functional plant growth regulators by the plant cell's biosynthetic machinery, or by the genes delivered into the plant cell.

The co-bombardment strategy of mini-chromosomes with separate DNA molecules encoding plant growth regulators transiently supplies the plant growth regulator genes for several generations of plant cells following DNA delivery. During this time, the mini-chromosome may be stabilized by virtue of its centromere, but the DNA molecules encoding plant growth regulator genes, or organogenesis-promoting, embryogenesis-promoting or regeneration-promoting genes will tend to be lost. The transient expression of these genes, prior to their loss, may give the cells containing mini-chromosome DNA a sufficient growth advantage, or sufficient tendency to develop into plant organs, embryos or a regenerable cell cluster, to outgrow the non-modified cells in their vicinity, or to form a readily identifiable structure that is not formed by non-modified cells. Loss of the DNA molecule encoding these genes will prevent phenotypes from manifesting themselves that may be caused by these genes if present through the remainder of plant regeneration. In rare cases, the DNA molecules encoding plant growth regulator genes will integrate into the host plant's genome or into the mini-chromosome.

Alternatively the genes promoting plant cell growth may be genes promoting shoot formation or embryogenesis, or giving rise to any identifiable organ, tissue or structure that can be regenerated into a plant. In this case, it may be possible to obtain embryos or shoots harboring mini-chromosomes directly after DNA delivery, without the need to induce shoot formation with growth activators supplied into the medium, or lowering the growth activator treatment necessary to regenerate plants. The advantages of this method are more rapid regeneration, higher transformation efficiency, lower background growth of non-modified tissue, and lower rates of morphologic abnormalities in the regenerated plants (due to shorter and less intense treatments of the tissue with chemical plant growth activators added to the growth medium).

Determination of Mini-Chromosome Structure an Autonomy in Adchromosomal Plants and Tissues The structure and autonomy of the mini-chromosome in adchromosomal plants and tissues can be determined by methods including but not limited to: conventional and pulsed-field Southern blot hybridization to genomic DNA from modified tissue subjected or not subjected to restriction endonuclease digestion, dot blot hybridization of genomic DNA from modified tissue hybridized with different mini-chromosome specific sequences, mini-chromosome rescue, exonucleas activity, PCR on DNA from modified tissues with probes specific to the mini-chromosome, or Fluorescence In Situ Hybridization to nuclei of modified cells. Table 3 below summarizes these methods.

TABLE 3

| Assay | Assay details | Potential outcome | Interpretation |
| --- | --- | --- | --- |
| Southern blot | Restriction digest of genomic DNA* compared to purified mini-C | Native sizes and pattern of bands | Autonomous or integrated via CEN fragment |
| | | Altered sizes or pattern of bands | Integrated or rearranged |
| CHEF gel Southern blot | Restriction digest of genomic DNA compared to purified mini-C | Native sizes and pattern of bands | Autonomous or integrated via CEN fragment |
| | | Altered sizes or pattern of bands | Integrated or rearranged |
| | Native genomic DNA (no digest) | Mini-C band migrating ahead of genomic DNA | Autonomous circles or linears present in plant |
| | | Mini-C band co-migrating with genomic DNA | Integrated |
| | | >1 mini-C bands observed | Various possibilities |
| Exonuclease assay | Exonuclease digestion of genomic DNA followed by detection of circular mini-chromosome by PCR, dot blot, or restriction digest (optional), electrophoresis and southern blot (useful for circular mini-chromosomes) | Signal strength close to that w/o exonuclease | Autonomous circles present |
| | | No signal or signal strength lower that w/o exonuclease | Integrated |

TABLE 3-continued

| Assay | Assay details | Potential outcome | Interpretation |
|---|---|---|---|
| Mini-chromosome rescue | Transformation of plant genomic DNA into E. coli followed by selection for antibiotic resistance genes on mini-C | Colonies isolated only from mini-C plants with mini-Cs, not from controls; mini-C structure matches that of the parental mini-C | Autonomous circles present, native mini-C structure |
| | | Colonies isolated only from mini-C plants with mini-Cs, not from controls; mini-C structure different from parental mini-C | Autonomous circles present, rearranged mini-C structure OR mini-Cs integrated via centromere fragment |
| | | Colonies observed both in mini-C-modified plants and in controls | Various possibilities |
| PCR | PCR amplification of various parts of the mini-chromosome | All mini-C parts detected by PCR | Complete mini-C sequences present in plant |
| | | Subset of mini-c parts detected by PCR | Partial mini-C sequences present in plant |
| FISH | Detection of mini-chromosome sequences in mitotic or meiotic nuclei by fluorescence in situ hybridization | Mini-C sequences detected, free of genome | autonomous |
| | | Mini-C sequences detected, associated with genome | integrated |
| | | Mini-C sequences detected, both free and associated with genome | Both autonomous and integrated mini-C sequences present |
| | | No mini-C sequences detected | Mini-C DNA not visible by FISH |

*Genomic DNA refers to total DNA extracted from plants containing a mini-chromosome Furthermore, mini-chromosome structure can be examined by characterizing mini-chromosomes 'rescued' from adchromosomal cells. Circular mini-chromosomes that contain bacterial sequences for their selection and propagation in bacteria can be rescued from an adchromosomal plant or plant cell and re-introduced into bacteria. If no loss of sequences has occurred during replication of the mini-chromosome in plant cells, the mini-chromosome is able to replicate in bacteria and confer antibiotic resistance. Total genomic DNA is isolated from the adchromosomal plant cells by any method for DNA isolation known to those skilled in the art, including but not limited to a standard cetyltrimethylammonium bromide (CTAB) based method (Current Protocols in Molecular Biology (1994) John Wiley & Sons, N.Y., 2.3) The purified genomic DNA is introduced into bacteria (e.g., E. coli) using methods familiar to one skilled in the art (for example heat shock or electroporation). The transformed bacteria are plated on solid medium containing antibiotics to select bacterial clones modified with mini-chromosome DNA. Modified bacterial clones are grown up, the plasmid DNA purified (by alkaline lysis for example), and DNA analyzed by restriction enzyme digestion and gel electrophoresis or by sequencing. Because plant-methylated DNA containing methylcytosine residues will be degraded by wild-type strains of E. coli, bacterial strains (e.g. DH10B) deficient in the genes encoding methylation restriction nucleases (e.g. the mcr and mrr gene loci in E. coli) are best suited for this type of analysis. Mini-chromosome rescue can be performed on any plant tissue or clone of plant cells modified with a mini-chromosome.

Mini-Chromosome Autonomy Demonstration by In Situ Hybridization (ISH)

To assess whether the mini-chromosome is autonomous from the native plant chromosomes, or has integrated into the plant genome, In Situ Hybridization is carried out (Fluorescent In Situ Hybridization or FISH is particularly well suited to this purpose). In this assay, mitotic or meiotic tissue, such as root tips or meiocytes from the anther, possibly treated with metaphase arrest agents such as colchicines is obtained, and standard FISH methods are used to label both the centromere and sequences specific to the mini-chromosome. For example, a Zea centromere is labeled using a probe from a sequence that labels all Zea centromeres, attached to one fluorescent tag (Molecular Probes Alexafluor 568, for example), and sequences specific to the mini-chromosome are labeled with another fluorescent tag (Alexafluor 488, for example). All centromere sequences are detected with the first tag; only mini-chromosomes are detected with both the first and second tag. Chromosomes are stained with a DNA-specific dye including but not limited to DAPI, Hoechst 33258, OliGreen, Giemsa YOYO, and TOTO. An autonomous mini-chromosome is visualized as a body that shows hybridization signal with both centromere probes and mini-chromosome specific probes and is separate from the native chromosomes.

Determination of Gene Expression Levels

The expression level of any gene present on the mini-chromosome can be determined by methods including but not limited to one of the following. The mRNA level of the gene can be determined by Northern Blot hybridization, Reverse Transcriptase-Polymerase Chain Reaction, binding levels of a specific RNA-binding protein, in situ hybridization, or dot blot hybridization.

The protein level of the gene product can be determined by Western blot hybridization, Enzyme-Linked Immunosorbant Assay (ELISA), fluorescent quantitation of a fluorescent gene product, enzymatic quantitation of an enzymatic gene product, immunohistochemical quantitation, or spectroscopic quantitation of a gene product that absorbs a specific wavelength of light.

Use of Exonuclease to Isolate Circular Mini-Chromosome DNA from Genomic DNA:

Exonucleases may be used to obtain pure mini-chromosome DNA, suitable for isolation of mini-chromosomes from E. coli or from plant cells. The method assumes a circular structure of the mini-chromosome. A DNA preparation containing mini-chromosome DNA and genomic DNA from the source organism is treated with exonuclease, for example lambda exonuclease combined with *E. coli* exonuclease I, or the ATP-dependent exonuclease (Qiagen Inc). Because the exonuclease is only active on DNA ends, it will specifically degrade the linear genomic DNA fragments, but will not affect the circular mini-chromosome DNA. The result is mini-chromosome DNA in pure form. The resultant mini-chromosome DNA can be detected by a number of methods for DNA detection known to those skilled in the art, including but not limited to PCR, dot blot followed by hybridization analysis, and southern blot followed by hybridization analysis. Exonuclease treatment followed by detection of resultant circular mini-chromosome may be used as a method to determine mini-chromosome autonomy.

Structural Analysis of Mini-Chromosomes by BAC-End Sequencing:

BAC-end sequencing procedures, known to those skilled in the art, can be applied to characterize mini-chromosome clones for a variety of purposes, such as structural characterization, determination of sequence content, and determination of the precise sequence at a unique site on the chromosome (for example the specific sequence signature found at the junction between a centromere fragment and the vector sequences). In particular, this method is useful to prove the relationship between a parental mini-chromosome and the mini-chromosomes descended from it and isolated from plant cells by mini-chromosome rescue, described above.

Methods for Scoring Meiotic Mini-Chromosome Inheritance

A variety of methods can be used to assess the efficiency of meiotic mini-chromosome transmission. In one embodiment of the method, gene expression of genes encoded by the mini-chromosome (marker genes or non-marker genes) can be scored by any method for detection of gene expression known to those skilled in the art, including but not limited to visible methods (e.g. fluorescence of fluorescent protein markers, scoring of visible phenotypes of the plant), scoring resistance of the plant or plant tissues to antibiotics, herbicides or other selective agents, by measuring enzyme activity of proteins encoded by the mini-chromosome, or measuring non-visible plant phenotypes, or directly measuring the RNA and protein products of gene expression using microarray, northern blots, in situ hybridization, dot blot hybridization, RT-PCR, western blots, immunoprecipitation, Enzyme-Linked Immunosorbant Assay (ELISA), immunofluorescence and radio-immunoassays (RIA). Gene expression can be scored in the post-meiotic stages of microspore, pollen, pollen tube or female gametophyte, or the post-zygotic stages such as embryo, seed, or progeny seedlings and plants. In another embodiment of the method, the mini-chromosome can de directly detected or visualized in post-meiotic, zygotic, embryonal or other cells in by a number of methods for DNA detection known to those skilled in the art, including but not limited to fluorescence in situ hybridization, in situ PCR, PCR, southern blot, or by mini-chromosome rescue described above.

FISH Analysis of Mini-Chromosome Copy Number in Meiocytes, Roots or Other Tissues of Adchromosomal Plants The copy number of the mini-chromosome can be assessed in any cell or plant tissue by In Situ Hybridization (Fluorescent In Situ Hybridization or FISH is particularly well suited to this purpose). In an exemplary assay, standard FISH methods are used to label the centromere, using a probe which labels all chromosomes with one fluorescent tag (Molecular Probes Alexafluor 568, for example), and to label sequences specific to the mini-chromosome with another fluorescent tag (Alexafluor 488, for example). All centromere sequences are detected with the first tag; only mini-chromosomes are detected with both the first and second tag. Nuclei are stained with a DNA-specific dye including but not limited to DAPI, Hoechst 33258, OliGreen, Giemsa YOYO, and TOTO. Mini-chromosome copy number is determined by counting the number of fluorescent foci that label with both tags.

Induction of Callus and Roots from Adchromosomal Plants Tissues for Inheritance Assays Mini-chromosome inheritance is assessed using callus and roots induced from transformed plants. To induce roots and callus, tissues such as leaf pieces are prepared from adchromosomal plants and cultured on a Murashige and Skoog (MS) medium containing a cytokinin, e.g., 6-benzylaminopurine (BA), and an auxin, e.g., α-naphthaleneacetic acid (NAA). Any tissue of an adchromosomal plant can be used for callus and root induction, and the medium recipe for tissue culture can be optimized using procedures known in the art.

Clonal Propagation of Adchromosomal Plants

To produce multiple clones of plants from a mini-chromosome-transformed plant, any tissue of the plant can be tissue-cultured for shoot organogenesis using regeneration procedures described under the section regeneration of plants from explants to mature, rooted plants (see above). Alternatively, multiple auxiliary buds can induced from a mini-chromosome-modified plant by excising the shoot tip, which can be rooted and subsequently be grown into a whole plant; each auxiliary bud can be rooted and produce a whole plant.

Scoring of Antibiotic- or Herbicide Resistance in Seedlings and Plants (Progeny of Self- and Out-Crossed Transformants Progeny seeds harvested from mini-chromosome-modified plants can be scored for antibiotic- or herbicide resistance by seed germination under sterile conditions on a growth media (for example Murashige and Skoog (MS) medium) containing an appropriate selective agent for a particular selectable marker gene. Only seeds containing the mini-chromosome can germinate on the medium and further grow and develop into whole plants. Alternatively, seeds can be germinated in soil, and the germinating seedlings can then be sprayed with a selective agent appropriate for a selectable marker gene. Seedlings that do not contain mini-chromosome do not survive; only seedlings containing mini-chromosome can survive and develop into mature plants.

Genetic Methods for Analyzing Mini-Chromosome Performance:

In addition to direct transformation of a plant with a mini-chromosome, plants containing a mini-chromosome can be prepared by crossing a first plant containing the functional, stable, autonomous mini-chromosome with a second plant lacking the mini-chromosome.

Fertile plants modified with mini-chromosomes can be crossed to other plant lines or plant varieties to study mini-chromosome performance and inheritance. In the first embodiment of this method, pollen from an adchromosomal plant can be used to fertilize the stigma of a non-adchromosomal plant. Mini-chromosome presence is scored in the progeny of this cross using the methods outlines in the preceding section. In the second embodiment, the reciprocal cross is performed by using pollen from a non-adchromosomal plant to fertilize the flowers of a adchromosomal plant. The rate of mini-chromosome inheritance in both crosses can be used to establish the frequencies of meiotic inheritance in male and female meiosis. In the third embodiment of this method, the progeny of one of the crosses just described are back-crossed to the non-adchromosomal parental line, and the progeny of this second cross are scored for the presence of genetic markers in the plant's natural chromosomes as well as the mini-chromosome. Scoring of a sufficient marker set against a sufficiently large set of progeny allows the determination of linkage or co-segregation of the mini-chromosome to specific chromosomes or chromosomal loci in the plant's genome. Genetic crosses performed for testing genetic linkage can be done with a variety of combinations of parental lines; such variations of the methods described are known to those skilled in the art.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

Example 1

Corn Centromere Discovery

BAC Library Construction

Two Bacterial Artificial Chromosome (BAC) libraries were constructed from corn genomic DNA. The corn genomic DNA was isolated from corn variety B73 and digested with the restriction enzymes BstYI or MboI. These enzymes were chosen because they are methylation insensitive and therefore can be used to enrich BAC libraries for centromere DNA sequences.

Probe Identification and Selection

Twenty-three groups of corn repetitive genomic or plastid sequences, including specific centromere-localized sequences, were initially compiled as candidate probes for hybridization with the BAC libraries (Table 4). These probes represented various classes of corn repetitive sequences including satellite repeats (heterochromatic/centromere-specific), retroelements, rDNA, B chromosome-specific repeats, chloroplast and mitochondrion DNA, hypermethylated or hypomethylated DNA fractions, and telomeric DNA.

TABLE 4

Maize Repetitive Sequences and Bac Library Probes

| Class | Class Name | Primers | Description | Reference | Comment | GenBank accession |
|---|---|---|---|---|---|---|
| 1 | CR (centromeric retrotransposable) element | CRJM-001 and 002 | gypsy-type localized to cen of all cereals. CentC and CRM co-IP with CEN H3 | Aragon-Alcaide et al 1996, Jiang et al 1996, Zhong et al 2002 | aka CRM, pSau3A9 (from *sorghum*), CRR (from rice) | AY1290008 |
| 2 | CentA | CHR 15 and 16 | centromere retrotransposon, includes MCS1A and B | | AF082532 Similar sequence | AF078917 |
| 3 | Huck | CRJM-005 and 006 | Ty3/gypsy | Meyers et al 2001 | (most frequent) | AF050438 |
| 4 | Grande | CRJM-056 and 057 | Ty3/gypsy | Meyers et al 2001 | | AF050437 |
| 5 | Cinful | CRJM-007 and 008 | Ty3/gypsy | Meyers et al 2001 | | AF049110 |
| 6 | Ji/Prem2 | LTR-5 CRJM-011 and 012 gag CRJM-013 and 014 | Ty1/copia | Meyers et al 2001 | | from alpha zein seq |
| 7 | Opie | | Ty1/copia | Meyers et al 2001 | 5' LTR | AF050453 |
| 8 | Tekay | CRJM-009 and 010 | | | 3' LTR | AF050452 |
| 9 | alpha zein | | | | | AF090447 |
| 10 | adh | | | | | AF123535 |
| 11 | bz | | | | | AF448416 |
| 12 | knob 180 | CHR 11 and 12 | | | many sequences| | gi|168710| gb|M32521.1| MZEZMA |
| 13 | MZEHETRO | CRJM-015 and 016 | maize heterochromatic repeat (knob) | Peacock et al PNAS. 78, 4490-4494 (1981) | | M35408 |
| 14 | TR-1(knob 360) | CHR 13 and 14 | Knob-specific | Hsu et al 2002 | 3 lengths, multi types. Type 1 BLASTs to all 3. Cuts w/RI | AF071126 |
| 15 | CentC | CHR 17 and 18 | 156 bp | Ananiev et al 1998 | all match well | AY321491 (Cent C27) AF078923 158a AF078922 156a |
| | | CRJM-019 and 020 | | | | |
| 16 | Cent4 | CRJM-021 and 022 | Chromosome 4 repeat homologous to B-chromosome cen repeat | Page et al, 2001 | | AF242891 |
| 17 | pZmBs and K5 | S67586 | B-specific repeats; B73 has no B chromosomes | Alfenito and Birchler 1993; Kaszas and Birchler 1993, 1998 | | AY173950 |
| 18 | rDNA | CRJM-023 and 024 | maize intergenic spacer | | | AF013103 |
| | | CRJM-025 and 026 | maize 5S | | | AF273104 |
| | | CRJM-027 and 028 | maize 17S | | | K0220 |

TABLE 4-continued

Maize Repetitive Sequences and Bac Library Probes

| Class | Class Name | Primers | Description | Reference | Comment | GenBank accession |
|---|---|---|---|---|---|---|
| 19 | chloroplast | CHHZ211 and 212 | Arabidiosis | | | |
| | | CRJM-030 and 031 | maize xpl rDNAs | | | X01365 |
| 20 | mito | CHHZ214 and 215 | Arabidiosis | | | |
| | | CRJM-032 and 033 | maize mito 26S rDNA | | | K01868 |
| 21 | hypermethylated fraction | purified | | | complex mixture | |
| 22 | hypomethylated fraction | purified | | | complex mixture | |
| 23 | telomere | | sub-telomeric repeat | U39641 | | U39642 |

Twelve probes were picked to interrogate the BAC libraries. These probes represent different groups of commonly found repetitive sequences in the corn genome. The twelve probes selected are shown in Tables 3 and 4 and were: CentC (#15), Cent4 (#16), MZEHETRO (#13), TR-1 (#14), CentA (#2), CR (#1), Huck (#3), Grande (#4), 17S rDNA (#18), 5S rDNA (#18); B cen (#17), and xplmito (#19 and #20). The primers used to amplify these probes are identified in Table 5. Probes were prepared and labeled with standard molecular methods.

each clone. Scores of 1 to 10 (based on the hybridization intensities, with 10 being the strongest hybridization) were imported into a relational database, for classification. The database contained a total of 24 tables, 12 from each library used in the interrogation. Each table contained the hybridization scores of each BAC clone from the BstY1 or MboI library, to one of the 12 probes. Data analysis was carried out using standard SQL (Structured Query Language) routines to find BACs that contain different groups of repetitive sequences.

TABLE 5

Classification of maize BAC Clones Containing Centromeric DNA

| | | Probe Hybridization Range | | | | | | | | | | | |
|---|---|---|---|---|---|---|---|---|---|---|---|---|---|
| Class | Class Properties | CentC | CentA | CR | Huck | Grande | 17S rDNA | Cent4 | TR-1 | MZE HETRO | 5S rDNA | B cen | xplmito | # clones identified |
| I | HiC LoA | >=7 | <7 | <7 | <7 | <6 | N/A | N/A | N/A | N/A | N/A | N/A | N/A | 61 |
| II | HiC HiA | >=7 | >=6 | <7 | <=10 | <=10 | N/A | N/A | N/A | N/A | N/A | N/A | N/A | 61 |
| III | HiCR HiC | >=7 | <6 | >=6 | <=10 | <=10 | N/A | N/A | N/A | N/A | N/A | N/A | N/A | 30 |
| IV | HiA HiC HiCR | >=7 | >6 | >=6 | <=10 | <=10 | N/A | N/A | N/A | N/A | N/A | N/A | N/A | 30 |
| V | HiC Hi17s | >=7 | >0 | >0 | >0 | >0 | >5 | N/A | N/A | N/A | N/A | N/A | N/A | 30 |
| VI | Hi4 | >0 | >0 | >0 | >0 | N/A | N/A | >5 | N/A | N/A | N/A | N/A | N/A | 17 |
| VII | HiTr1 LoHe | >0 | >0 | N/A | N/A | N/A | >0 | N/A | >6 | <6 | N/A | N/A | N/A | 31 |
| VIII | LoTr1 HiHe | >0 | >0 | N/A | N/A | N/A | >0 | N/A | <5 | >7 | N/A | N/A | N/A | 31 |
| IX | HiTr1 HiHe | >0 | >0 | N/A | N/A | N/A | >0 | N/A | >6 | >6 | N/A | N/A | N/A | 24 |
| Total | | | | | | | | | | | | | | 315 |

*Values represent hybridization intensities of an individual BAC to each probe on a scale of 1 to 10. Values were normalized.

Library Interrogation and Data Analysis

The BAC clones from the libraries were spotted onto filters for further analysis. The filters were hybridized with each of the 12 probes to identify specific BAC clones that contain DNA from the group of sequences represented by the probe(s). Exemplary hybridization conditions: hybridization at 65° C. and washing three times for 15 minutes with 0.25×SSC, 0.1% SDS at 65° C. Additional exemplary stringent hybridization conditions comprise 0.5×SSC 0.25% SDS at 65 degrees for 15 minutes, followed by a wash at 65 degrees for a half hour.

A total of 92,160 BAC clones from the two libraries (36,864 BAC clones from 2 filters from the BstYI library and 55,296 clones from 3 filters from the MboI library) were interrogated with each of the 12 probes described above, and the hybridization intensities of the BAC clones with each probe were scanned to quantitate hybridization intensity for Classification and Selection of BAC Clones for Mini-Chromosome Construction BAC clones containing centromeric/heterochromatic DNA were identified by their hybridization scores to different probes. The goal was to select BAC clones that contained a diverse set of various repetitive sequences. Nine classes of centromeric BAC clones were eventually chosen to cover the broadest possible range of centromeric/heterochromatic sequences for mini-chromosome construction. Detailed descriptions of each class and probe hybridization values for each class are shown in Table 5.

Class I (HiC LoA) BAC clones had strong hybridization to probe CentC, but low hybridization to CentA, CR, Huck and Grande. Class II (HiC HiA) BAC clones had strong hybridization to both CentC and CentA, but low hybridization to CR. Class III (HiCR HiC) BAC clones had strong hybridization to both CentC and CR, but low hybridization to CentA.

Class IV (HiA HiC HiCR) BAC clones had strong hybridization to CentC, CentA, and CR. Class V (HiC Hills) BAC clones had strong hybridization to CentC and 17S rDNA. Class VI (Hi4) BAC clones had strong hybridization to Cent4. Class VII (HiTr1 LoHet) BAC clones had strong hybridization to TR-1 but low hybridization to MZEHETRO. Class VIII (LoTr1 HiHet) BAC clones had strong hybridization to MZEHETRO but low hybridization to TR-1. Class IX (HiTr1 HiHet) BAC clones had strong hybridization to both TR-1 and MZEHETRO.

A number of representative clones from each class were chosen to yield a total of 315 BAC clones for further analysis by restriction digest fingerprinting. The number of clones chosen in each class is shown in Table 5.

The 315 BAC clones were fingerprinted based on restriction sites found in the centromere specific sequence(s). Fingerprinting was used to evaluate the sequence composition of the large numbers of BAC clones and to compare their similarity to each other by comparing the restriction enzyme digest fragment patterns. A sequence with a tandem repeated sequence will show a single intense band of unit repeat size when digested with a restriction enzyme that cuts within the unit repeat. Second, BAC clones with similar sequences will show similar patterns of restriction fragments in a digest.

BAC DNA was extracted from bacteria using methods familiar to those in the art. Restriction enzymes HpaII and MspI were used to digest BAC clones in Classes I through VI, and restriction enzyme NdeI was used to digest BAC clones in classes VII through IX.

*Z. mays* BACs ZB19 and ZB113 were deposited with the American Type Culture Collection (ATCC) on Feb. 22, 2005 and assigned accession nos. PTA-6604 and PTA-6605. ZB19 was classified as "class 1" or "HiCLoA when characterized with the restriction endonucleases HpaII, MspI and fingerprint class CL/SL, sm. ZB113 was classified as "class 4" or "HiA, HiC and HiCR and fingerprint class CL/SL.

Example 2

Construction of Maize Mini-Chromosomes

The 315 BAC clones identified in Example 1 were grown up and DNA was extracted for mini-chromosome construction using NucleoBond™ Purification Kit (Clontech). To determine the molecular weight of centromere fragments in the BAC libraries, a frozen sample of bacteria harboring a BAC clone was grown in selective liquid media and the BAC DNA harvested using a standard alkaline lysis method. The recovered BAC DNA was restriction digested and resolved on an agarose gel. Centromere fragment size was determined by comparing to a molecular weight standard.

For each BAC, two types of mini-chromosomes were generated, differing only by the promoter used to express the DsRed gene. Corn ADH promoter was used to express DsRed in mini-chromosomes constructed with pCHR667 and the *Arabidopsis* UBQ10 promoter was used to express DsRed in mini-chromosomes constructed with pCHR758. Mini-chromosome genetic elements within the pCHR667 and pCHR758 vectors are set out in Tables 6 and 7, respectively.

TABLE 6

Donor Components of pCHR667

| Genetic Element | Size (base pair) | Location (bp) | Details |
|---|---|---|---|
| ADH Corn Promoter | 1189 | 14-1202 | PCR amplified maize promoter alcohol dehydrogenase 1 (ADH-1) for expression of DsRed in maize (used primers CRJM-42/43) |
| Maize ADH Intron | 579 | 1216-1794 | PCR amplified maize ADH intron with AUG mutation for stabilization of DsRed2 gene transcript and increase protein expression level (used primers CRJM-72/73) |
| DsRed2 + NLS | 780 | 1817-2596 | Nuclear localized red fluorescent protein from *Discosoma* sp. (Matz, M et. al *Nat Biotechnol* 1999 Dec; 17(12): 1227). |
| ADH Terminator | 203 | 2725-2927 | Amplified maize terminator using primers CRJM-46/47 |
| Bacterial Kanamycin | 817 | 3066-3882 | Bacterial kanamycin selectable marker |
| Rps16A terminator | 489 | 4065-4553 | Amplified from *Arabidopsis thaliana* 40S ribosomal protein S16 (At2g09990) for termination of NptII gene |
| NPTII | 795 | 4617-5411 | Neomycin phosphotransferase II plant selectable marker |
| UBQ10 intron | 359 | 5439-5798 | PCR amplified *Arabidopsis thaliana* intron from UBQ10 gene (At4g05320) for stabilization of NptII gene transcript and increase protein expression level |
| YAT1 yeast promoter | 2000 | 5812-7811 | PCR amplified YAT1 promoter from chromosome I of *Saccharomyces cerevisiae* for expression of NptII in maize |
| LoxP | 34 | 10341-10374 and 7829-7862 | Recombination site for Cre mediated recombination (Arenski et. al 1983, Abremski et. al 1984) |

TABLE 7

Donor Components of pCHR758

| Genetic Element | Size (base pair) | Location (bp) | Details |
|---|---|---|---|
| UBQ10 promoter | 2038 | 14-2051 | *Arabidopsis thaliana* poly-ubiquitin promoter (At4g05320) |
| DsRed2 + NLS | 780 | 2088-2867 | Nuclear localized red fluorescent protein from *Discosoma* sp. (Matz, M et. al *Nat Biotechnol* 1999 Dec; 17(12): 1227). |
| Pyruvate kinase terminator | 332 | 3002-3333 | *Arabidopsis thaliana* pyruvate kinase terminator (At5g52920) |
| Bacterial Kanamycin | 817 | 3478-4294 | Bacterial kanamycin selectable marker |
| Rps16A terminator | 489 | 4477-4965 | Amplified from *Arabidopsis thaliana* 40S ribosomal protein S16 (At2g09990) for termination of NptII gene |
| NPTII | 795 | 5029-5823 | Neomycin phosphotransferase II plant selectable marker |
| UBQ10 intron | 359 | 5851-6210 | PCR amplified *Arabidopsis thaliana* intron from UBQ10 gene (At4g05320) for stabilization of NptII gene transcript and increase protein expression level |
| YAT1 yeast promoter | 2000 | 6224-8223 | PCR amplified YAT1 promoter from chromosome I of *Saccharomyces cerevisiae* for expression of NptII in maize |

TABLE 7-continued

Donor Components of pCHR758

| Genetic Element | Size (base pair) | Location (bp) | Details |
|---|---|---|---|
| LoxP | 34 | 8243-8276 & 10755-10788 | Recombination site for Cre mediated recombination (Arenski et. al 1983, Abremski et. al 1984) |

Corn mini-chromosomes were constructed by following a two-step procedure: Step 1: Preparation of donor DNA for retrofitting with BAC centromere vectors and Step 2: Cre-Lox Recombination-BAC and Donor DNA to generate the mini-chromosome. A total of 230 corn mini-chromosomes were constructed using this assembly process, and were subsequently tested in several different corn cell lines.

Preparation of Donor DNA for Retrofitting

Cre recombinase-mediated exchange was used to construct mini-chromosomes by combining the plant centromere fragments cloned in pBeloBAC11 with a donor plasmid (i.e. pCHR667 or pCHR758, Tables 7 & 8). The recipient BAC vector carrying the plant centromere fragment contained a loxP recombination site; the donor plasmid contained two such sites, flanking the sequences to be inserted into the recipient BAC.

Cre recombinase-mediated exchange was used to construct mini-chromosomes by combining the plant centromere fragments cloned in pBeloBAC11 with a donor plasmid (i.e. pCHR667 & pCHR758, Table 6 & 7). The recipient BAC vector carrying the plant centromere fragment contained a loxP recombination site; the donor plasmid contained two such sites, flanking the sequences to be inserted into the recipient BAC. Mini-chromosomes were constructed using a two-step method. First, the donor plasmid was linearized to allow free contact between the two loxP site; in this step the backbone of the donor plasmid is eliminated. In the second step, the donor molecules were combined with centromere BACs and were treated with Cre recombinase, generating circular mini-chromosomes with all the components of the donor and recipient DNA. Mini-chromosomes were delivered into *E. coli* and selected on medium containing kanamycin and chloramphenicol. Only vectors that successfully cre recombined and contained both selectable markers survived in the medium. Mini-chromosomes were extracted from bacteria and restriction digested to verify DNA composition and calculate centromere insert size.

To determine the molecular weight of the centromere fragments in the mini-chromosomes, three bacterial colonies from each transformation event were independently grown in selective liquid media and the mini-chromosome DNA harvested using a standard alkaline lysis method. The recovered mini-chromosome was restriction digested and resolved on an agarose gel. Centromere fragment size was determined by comparing to a molecular weight standard. If variation in centromere size was noted, the mini-chromosome with the largest centromere insert was used for further experimentation. Selection of Corn Cell Clones Stably Containing Mini-chromosome DNA Functional Testing of Mini-Chromosomes Using Transient Assays Maize mini-chromosomes were tested in several corn cell lines including PC1117, HiII, and BMS, and the procedure was optimized for antibiotic selection, cell pre-treatments, and bombardment conditions. All assays were transient and fluorescent cells were counted at several time points. Preliminary results identified several mini-chromosomes that successfully generated fluorescent cell clusters.

Example 3

Mini-Chromosome Delivery into Maize Cells

Various methods have been used to deliver DNA into plant cells. These include biological methods, such as viruses, physical methods such as biolistic particle bombardment and silicon carbide whiskers, electrical methods such as electroporation, and chemical methods such as the use of polyethylene glycol and other compounds known to stimulate DNA uptake into cells. Biolistic particle bombardment have been the methods that have found most widespread use in plant biotechnology.

Biolistic Particle Delivery of Mini-Chromosomes

A biolistic particle delivery method was used to transfer corn mini-chromosomes into a number of different corn tissues including suspension cells, plate-grown calli, and immature embryos. For the purpose of transient delivery or selection of stable cell culture modified with a corn mini-chromosome, suspension cells were used for delivery using wet or dry gold delivery methods. An example of such a suspension culture is the publicly available line, PC1117.

Wet Bombardment

A biolistic delivery method using wet gold particles kept in an aqueous DNA suspension was adapted from the teachings of Milahe and Miller (Biotechniques 16: 924-931, 1994) and used to transform corn cells. To prepare the wet gold particles for bombardment, 1.0 μm gold particles were washed by mixing with 100% ethanol on a vortex followed by spinning the particles in a microfuge at 4000 rpm in order to remove supernatant. Subsequently, the gold particles were washed with sterile distilled water three times, followed by spinning in a microfuge to remove supernatant. The washed gold particles are resuspend in sterile distilled water at a final concentration of 90 mg per ml and stored at 4° C. until use. For bombardment, the gold particle suspension (90 mg/ml) was then mixed rapidly with 1 μg/μl DNA solution (in $dH_2O$ or TE), 2.5 M $CaCl_2$, and 1 M spermidine. DNA/gold mixture was left at room temperature and used for bombardment within 2-4 hours.

For bombardment of corn cells, the cells were harvested by centrifugation (1200 rpm for 2 minutes) on the day of bombardment. The cells were plated onto 50 mm circular polyester screen cloth disks placed on petri plates with solid medium. The solid medium used was the same medium that the cells are normally grown in, plus 0.26% gelrite, or 0.6% tissue culture agar, added before autoclaving. Approximately 1.5 ml packed cells were placed on each filter disk, and spread out in a very even spot approximately 1 inch in diameter.

Bombardment of the cells was carried out in the BioRad PDS-1000/He Biolistic Particle Delivery System (BioRad). The DNA/gold suspension was resuspended and immediately inserted onto the grid of the filter holder. A 50 mm circular polyester screen cloth disk with the cells was placed into a fresh 60 mm petri dish with the same medium and the cells were covered with a 10×10 cm square of sterile nylon or Dacron chiffon netting. A metal cylinder was inserted into the petri dish and used to push the netting down to the bottom of the dish. This weight prevents the cells from being dislodged from the plate during bombardment. The petri dish containing the cells was then placed onto the sample holder, and positioned in the sample chamber of the gene gun and bombarded with the DNA/gold suspension. After the bombardment, the cells were scraped off the filter circle in the petri dish containing solid medium with a sterile spatula and transferred to fresh medium in a 125 ml blue-capped glass bottle. The bottles were transferred onto a shaker and grown while shaking at 150 rpm.

Suspensions of the maize cell line PC117 were bombarded with wet gold particles containing DNA from BAC clones ZB10, ZB18, ZB19 and ZB99. After bombardment, all cells were returned to liquid culture and allowed to grow for three days prior to plating in selection media. Subsequently, the transfected cells were grown in selection medium containing various concentrations of antibiotics. The selection media contained either an increasing concentration of kanamycin (25, 50, 75, 100, 125 and 150 µg/ml) or G418 (10, 20, 35, 50, 75 and 100 µg/ml). The growth of clones in the selection medium indicated expression of the selection gene within the mini-chromosome and suggests a functional centromere within the mini-chromosome. These results are summarized in Table 8.

TABLE 8

| Construct | # bombardments | # clones isolated |
|---|---|---|
| ZB10R2-1 | 2 | 0 |
| ZB18R3-1 | 2 | 0 |
| ZB19R2-1 | 12 | 9 |
| ZB99R1-1 | 12 | 1 |

Dry Bombardment

A biolistic delivery method using dry gold particles was also carried out to deliver mini-chromosomes to corn embryos. For this method, 5 µg of mini-chromosome DNA was precipitated onto 3 mg of sterilized and washed 0.6µ gold particles. The DNA-containing gold particles were resuspended in cold sterile water containing 2.5 M $CaCl_2$. The mixture was lightly vortexed, and then filter-sterilized 0.1 M Spermidine (free base) was added to the mixture. Subsequently, the mixture was lightly vortexed and allowed to precipitate on ice for an hour, with vortexing about every 10 minutes. The precipitated DNA was then washed with 100% ethanol, resuspended in 100% ethanol which was allowed to fully evaporate prior to bombardment.

Immature embryos were excised onto N6 based medium (Chu's N6 medium with 25 µM silver nitrate) 3-5 days prior to day of bombardment. The embryos were osmotically adjusted approximately 4 hours prior to bombardment. This osmotic medium is composed of Chu's N6 Basal medium with the addition of 25 µM silver nitrate, 36.4 g/l sorbitol, and 36.4 g/l mannitol. Embryos were arranged scutellar side up in an open ring that had the same diameter as the plate stage in the gun.

The embryos were bombarded using the BioRad PDS-1000/He Biolistic Particle Delivery System. For this bombardment, the rupture disk rating was 1100 psi with one shot per plate of embryos. The distance from the rupture disk to the macrocarrier was ¼ inch. After bombardment, the plates of embryos were incubated in a dark incubator overnight at 27° C. The following day, the bombarded tissue was transferred to selection medium, Chu's N6 with 200-250 mg/l Paromomycin or 25-35 mg/l G418 (Geneticin), and cultured in the dark. During this transfer, any emerging coleoptiles were removed from the immature embryos.

Approximately 2-3 weeks after bombardment, all tissue was transferred to fresh selective medium at a higher selection pressure of 250-300 mg/l Paromomycin or 35-50 mg/l G418. At this transfer, the callus was separated into approximately 2-3 mm sements. The callus that was proliferating and showed dsRed activity after at least two subcultures was regenerated. Regeneration was initiated when the amount of healthy callus suggested that a minimum of three plants can be regenerated from that event.

For regeneration, the callus was transferred to R1 medium (MS medium with 20 g/l sucrose and 5 mg/l 6-benzyl-aminopurine). Plates were then incubated at 27° C. in the dark for 3-7 days. Tissue was then moved to R2 medium (MS medium with 60 g/l sucrose) with either 10 mg/l G418 or 50 mg/l Paromomycin and placed under low light at 26° C. When leaf tissue reached the top of the petri dish, developing plantlets were transferred to R3 medium (MS medium with 15 gl/l sucrose) with either 10 mg/l G418 or 50 mg/l under higher light intensity at 26° C. to continue plant growth and allow substantial root development. Plantlets were then transferred into moistened soilless mix under a humi-dome to maintain high humidity in a growth chamber for one week prior to being transplanted into the greenhouse.

Example 4

Selection of Corn Cell Clones Stably Containing Mini-Chromosome DNA

Use of Visible Marker Genes

The presence of visible marker genes allowed for visual selection of Corn cells stably containing mini-chromosome DNA because any modified cells or cell clusters were readily identified by virtue of fluorescent protein expression. In addition, the use of fluorescent protein expression allowed for the use of sub-killing concentrations of selective agent during growth of plant tissue on selective medium. This flexibility allowed for the use of a wider range of antibiotic concentrations than possible in the absence of a visible marker gene, without having to consider the amount of background growth observed in wild type plant tissue. As a result, the adchromosomal cell clones were isolated with use of certain selectable marker genes, and under conditions that might not be effective in standard selection experiments as practiced in the industry. These selections were typically done at lower antibiotic concentrations than practiced elsewhere, and resulted in higher levels of background growth. Fluorescent cell clusters can be visually identified after one to several weeks of growth on selective media. Clusters of cells stably containing mini-chromosomes were identified by visual observation of fluorescence in the cells in a darkened room.

Manipulation of Adchromosomal Tissue to Homogeneity

After identifying clusters of fluorescent cells, physical manipulations were carried out to allow for the preferential expansion of cells harboring the delivered mini-chromosomes. Non-fluorescent tissue surrounding the fluorescent clusters was trimmed to avoid overgrowth of fluorescent cells by non-fluorescent ones, while retaining a minimum tissue size capable of rapid growth. These manipulations were performed under sterile conditions with the use of a fluorescence stereomicroscope that allows for visualization of the fluorescent cells and cell clumps in the larger pieces of tissue. In between the mechanical purification steps, the tissue was allowed to grow on appropriate media, either in the presence or absence of selection. Over time, a pure population of fluorescent cells was obtained.

Method of Co-Delivering Growth Inducing Genes to Facilitate Isolation of Adchromosomal Plant Cell Clones Another method used in the generation of cell clones containing mini-chromosomes involved the co-delivery of DNA containing genes that are capable of activating growth of plant cells. In this method, the cell receiving DNA receives simultaneously the mini-chromosome, and a separate NA molecule encoding one or more growth promoting genes. Following DNA delivery, expression of the plant growth regulator genes stimulates the plant cells to divide, or to initiate differentiation into a specific organ, embryo, or other cell types or tissues capable of regeneration. Multiple plant growth regulator genes are combined on the same molecule, or co-bombarded on separate molecules. Use of these genes can also be combined with application of plant growth regulator molecules into the medium used to culture the plant cells, or of precursors to such molecules that are converted to functional plant growth regulators by the plant cell's biosynthetic machinery, or by the genes delivered into the plant cell.

The co-bombardment strategy of mini-chromosomes with separate DNA molecules encoding plant growth regulators transiently supplies the plant growth regulator genes for several generations of plant cells following DNA delivery. During this time, the mini-chromosome may be stabilized by virtue of its centromere, but the DNA molecules encoding plant growth regulator genes will tend to be lost. In rare cases, the DNA molecules encoding plant growth regulator genes will integrate into the host plant's genome or into the mini-chromosome.

Example 5

Regeneration of Adchromosomal Corn Plants

A total of 125 corn mini-chromosomes were prepared as described herein and are shown in Table 9.

TABLE 9

| BAC Number ZB | Mini-chromosome Number | | Bac Number ZB | Mini-chromosome Number | |
|---|---|---|---|---|---|
| | 667 donor vector | 758 donor vector | | 667 donor vector | 758 donor vector |
| 5 | ZB5R1-1 | | 30 | | ZB130R2-1 |
| 6 | ZB6R1-1 | ZB6R2-1 | 31 | | ZB131R2-2 |
| 7 | ZB7R1-1 | ZB7R2-2 | 37 | | ZB137R2-3 |
| 8 | ZB8R1-2 | ZB8R2-1 | 44 | | ZB144R2-1 |
| 9 | ZB9R1-1 | | 45 | | ZB145R2-2 |
| 10 | ZB10R2-1 | ZB10R3-1 | 46 | | ZB146R2-1 |
| 13 | ZB13R1-1 | ZB13R2-1 | 47 | | ZB147R2-2 |
| 14 | ZB14R1-1 | ZB14R2-1 | 50 | | ZB150R2-1 |
| 18 | ZB18R2-1 | ZB18R3-1 | 56 | ZB156R1-1 | ZB156R2-1 |
| 19 | ZB19R1-1 | ZB19R2-1 | 57 | ZB157R1-2 | |
| 20 | ZB20R1-1 | | 58 | ZB158R1-2 | ZB158R2-3 |
| 21 | ZB21R2-1 | | 67 | | ZB167R2-1 |
| 24 | ZB24R2-1 | | 75 | ZB175R1-1 | ZB175R2-1 |
| 25 | | ZB25R2-1 | 77 | ZB177R1-1 | ZB177R2-1 |
| 29 | ZB29R1-1 | | 78 | ZB178R1-1 | ZB178R2-1 |
| 32 | | ZB32R3-1 | 99 | ZB199R1-1 | ZB199R2-1 |
| 34 | | ZB34R3-1 | 07 | ZB207R1-1 | |
| 44 | | ZB44R2-2 | 11 | ZB211R3-1 | |
| 49 | | ZB49R2-1 | 32 | ZB232R1-1 | ZB232R2-1 |
| 64 | ZB64R1-1 | ZB64R2-2 | 33 | ZB233R1-1 | ZB233R2-1 |
| 65 | ZB65R1-1 | | 35 | ZB235R1-1 | ZB235R2-1 |
| 66 | ZB66R1-1 | | 38 | | ZB238R2-1 |
| 71 | ZB71R1-3 | | 43 | | ZB243R2-1 |
| 72 | ZB72R1-2 | | 48 | | ZB248R2-1 |
| 73 | ZB73R1-3 | ZB73R2-1 | 53 | | ZB253R2-1 |
| 80 | | ZB80R2-1 | 58 | ZB258R2-1 | ZB258R3-2 |
| 81 | | ZB81R2-1 | 59 | ZB259R2-2 | |
| 82 | ZB82R1-2 | ZB82R2-1 | 60 | ZB260R2-2 | |
| 94 | ZB94R1-1 | ZB94R2-1 | 61 | ZB261R2-1 | |
| 96 | ZB96R1-1 | ZB96R2-1 | 65 | ZB265R2-1 | |
| 98 | ZB98R1-3 | ZB98R2-1 | 71 | | ZB271R3-2 |
| 99 | ZB99R1-1 | ZB99R2-1 | 79 | | ZB279R3-1 |
| 100 | ZB100R1-2 | ZB100R2-3 | 82 | | ZB282R2-2 |
| 101 | ZB101R1-2 | ZB101R2-2 | 91 | | ZB291R3-1 |
| | | ZB104R2-1 | 93 | ZB293R1-1 | |
| 105 | ZB105R1-1 | ZB105R2-1 | 95 | ZB295R1-3 | ZB295R2-1 |
| 106 | ZB106R1-1 | ZB106R2-2 | 96 | ZB296R1-2 | ZB296R2-1 |
| 108 | ZB108R1-2 | ZB108R2-1 | 97 | ZB297R1-3 | ZB297R2-2 |
| 109 | ZB109R1-1 | ZB109R2-1 | 98 | ZB298R1-1 | |
| 113 | ZB113R1-1 | ZB113R2-1 | 05 | ZB305R1-2 | ZB305R2-1 |
| 120 | ZB120R1-1 | | 08 | ZB308R1-1 | ZB308R2-2 |
| 122 | ZB122R1-3 | ZB122R2-1 | | | |
| 123 | ZB123R1-1 | | | | |
| 124 | ZB124R1-1 | | | | |
| 129 | | ZB129R2-2 | | | |

The biolistic delivery method described above was used to deliver the mini-chromosomes into a number of different corn tissues including suspension cells, plate-grown calli, and immature embryos. For the purpose of transient delivery or selection of stable cell culture modified with a corn mini-chromosome, suspension cells were used for delivery using wet or dry gold delivery methods. An example of such a suspension culture is the publicly available line, PC1117.

To obtain trans-chromosomal corn plants modified with corn mini-chromosomes, standard protocols for corn tissue culture and transformation are followed. Such protocols include the Maize Embryo/Callus Bombardment Protocols available at Iowa Statue University, College of Agriculture web site.

The transformation process involves the preparation of regenerable tissues such as immature embryos from corn cultivars such as HiII, pre-culture of embryos on an auxin-enriched medium, delivery of miniC's into immature embryos or embryogenic calli, selection and isolation of fluorescent cell clusters, expansion of cell clusters and formation of transchromosomal embryos, maturation and regeneration of embryos into whole plants.

Example 6

Sequence Analysis of Centromeres

Two BAC clones (ZB19 and ZB113) were sequenced and the centromere sequences were analyzed using conventional methods. Briefly, the BAC DNA was purified from *E. coli*, sheared and cloned into standard cloning vectors to create a shotgun library. Clones in the library were sequenced as reads 500-900 bp in length. Individual reads were trimmed to remove sequence of poor quality (phred score of <20) and to remove sequences derived from the cloning vector used to generate the shotgun library. The remaining sequence information was then filtered to remove *E. coli* sequences, which inevitably contaminate the BAC DNA prep, and sequences corresponding to the known vector component of each mini-chromosome.

The filtered reads and sequences were then analyzed with a variety of tools to establish sequence content and to locate repetitive DNA sequences. Contig assemblies were recomputed with phredPhrap. The following programs were used extensively: phred/phrap and consed (Ewing B, Green P: Basecalling of automated sequencer traces using phred. II. Error probabilities. Genome Research 8:186-194 (1998); Ewing B, Hillier L, Wendl M, Green P: Basecalling of automated sequencer traces using phred. I. Accuracy assessment. Genome Research 8:175-185 (1998); Gordon, David. "Viewing and Editing Assembled Sequences Using Consed", in Current Protocols in Bioinformatics, A. D. Baxevanis and D. B. Davison, eds, New York: John Wiley & Co., 2004, 11.2.1-11.2.43; Gordon D, Desmarais C, Green P: Automated finishing with Autofinish. Genome Res 11:614-625 (2001); and Gordon D, Abajian C, Green P: Consed: a graphical tool for sequence finishing. Genome Research 8:195-202 (1998), and ReapeatMasker (available at the Institute of Systems Biology website). The following databases were used to identify maize sequences: Genbank, RepeatMasker Libraries (repeatmaskerlibraries20050523.tar.gz), TIGR databases "characterized.sub.—02202004.fasta", "uncharacterized-.sub.—02202004.fasta", "RECON_prediction.sub.—02202004.fasta" which are accessible at the TIGR web site.

As described in detail below, repeat CentC is highly represented in the sequence of both ZB19 and ZB113. These fingerprint analysis classified BAC clone ZB19 as "class 1" or "HiC,LoA" and BAC clone ZB113 as "class 4" or "HiA, HiC and HiCR" (see Table 5 above). The repeated sequence CRM was also highly represented in ZB113.

The full length sequence of CentC is set out in GenBank Accession No. AY321491 (SEQ ID NO: 76). The full length sequence of CRM is set out in GenBank Accession No. AY129008 (SEQ ID NO: 77). The full length sequence of CentA is set out in Genbank Accession No. AF078917 (SEQ ID NO: 78).

Characterization of ZB19

The nucleotide sequence of ZB19 was assembled into 31 contigs with a combined trimmed length of 64 kb. ZB19 contigs numbered 1-31 correspond to SEQ ID NOS: 21-51, respectively.

When examining all contigs, only the two largest contigs, 30 and 31, showed significant numbers of high and low quality matches among various sequencing reads. Alternatively, all but three contigs (16, 17 and 22) show nearly complete matches to TIGR maize database entries. Large numbers of sequence regions within contig 30 have significant matches to sequence regions in contig 31. Given the small number of inconsistent forward/reverse pairs, this does not suggest a misassembly but rather that both contigs 30 and 31 share large numbers of common maize sequence. Other distinct sequence similarities were evident between contigs 7 and 29, and contigs 17 and 22.

The sequence analysis of ZB19 indicated that 0.47% of the sequence is simple repeats and low complexity sequence (e.g. AT-rich, (CGA)n, GA-rich and CT-rich), 14% vector sequence, 1.15% *E. coli* sequence, 83% sequence is present in the TIGR maize database, 1.10% uncharacterized sequence and 28.91% CentC repeat. About 19.4 kb of the sequence was true repeat sequences, meaning those sequences are repeated within the BAC ZB19 sequence.

ZB19 has 39 simple repeat bases (0.06%) and 257 low complexity bases (0.39%) contained within contigs 16, 24, 25, and 28. This low simple repeat content is summarized in Table 10.

TABLE 10

ZB19 Simple Repeat Content

| Contig (length) | Contig Match begin | end | length | % diverge | Simple repeat |
|---|---|---|---|---|---|
| ZB19.Contig16 (2303) | 1572 | 1597 | 25 | 0 | AT_rich |
| ZB19.Contig24 (2816) | 708 | 747 | 39 | 17.5 | (CGA)n |
| ZB19.Contig25 (2997) | 60 | 87 | 27 | 3.6 | AT_rich |
| ZB19.Contig25 (2997) | 2518 | 2552 | 34 | 11.4 | GA-rich |
| ZB19.Contig28 (3308) | 1121 | 1292 | 171 | 32.4 | CT-rich |
| | | | 296 | | |
| | | | 0.47% | | |

The ZB19 contigs are set out as SEQ ID NOS: 21-51 respectively. These contigs were compared to the NCBI database at the National Institute of Health Web Site using BLAST. Results of the BLAST comparison are set out in Table 11.

TABLE 11

ZB19 Genbank Homology

| Contig (length) | Contig Alignment | | | | Genbank | | | |
| | begin | end | length | % id | begin | end | Accession # | Homologous feature |
|---|---|---|---|---|---|---|---|---|
| ZB19.Contig1 (1500) | 1 | 1500 | 1501 | 97.07 | 191344 | 189846 | AY664416 | Mo17 locus bz |
| ZB19.Contig2 (1708) | 545 | 1451 | 918 | 86.06 | 14246 | 13335 | AY574035 | rust resistance rp3-1 |
| ZB19.Contig3 (118) | 1 | 118 | 118 | 100 | 4877 | 4760 | J02482 | Coliphage phi-X174 |
| ZB19.Contig4 (194) | 1 | 194 | 194 | 100 | 980 | 1173 | J02482 | Coliphage phi-X174 |
| ZB19.Contig5 (1176) | 28 | 1148 | 1122 | 97.15 | 8181 | 7060 | AY664416 | Mo17 locus bz |
| ZB19.Contig6 (731) | | | | | | | "NA" | "pCHR758mcv" |
| ZB19.Contig7 (1325) | 560 | 1311 | 756 | 92.33 | 3387 | 2633 | AY530951 | 40S ribosomal protein S8 |
| ZB19.Contig8 (77) | | | | | | | "NA" | "low quality" |
| ZB19.Contig9 (153) | | | | | | | "NA" | "*E coli*" |

TABLE 11-continued

ZB19 Genbank Homology

| Contig (length) | Contig Alignment | | | | Genbank | | | |
|---|---|---|---|---|---|---|---|---|
| | begin | end | length | % id | begin | end | Accession # | Homologous feature |
| ZB19.Contig10 (1424) | 23 | 1412 | 1396 | 91.55 | 42422 | 41034 | AF464738 | putative gag-pol |
| ZB19.Contig11 (78) | | | | | | | "NA" | "*E coli*" |
| ZB19.Contig12 (1743) | 561 | 1532 | 974 | 90.04 | 40272 | 41239 | AY574035 | rust resistance rp3-1 |
| ZB19.Contig13 (1528) | 853 | 1301 | 449 | 91.31 | 1 | 448 | AY574035 | retrotransposon |
| ZB19.Contig14 (460) | | | | | | | "NA" | "*E coli*" |
| ZB19.Contig15 (234) | 1 | 234 | 234 | 99.57 | 669 | 436 | J02482 | Coliphage phi-X174 |
| ZB19.Contig16 (2303) | | | | | | | "NA" | "pCHR758mcv" |
| ZB19.Contig17 (1638) | | | | | | | "NA" | "pCHR758mcv" |
| ZB19.Contig18 (1869) | 132 | 1719 | 1590 | 84.97 | 37117 | 35528 | AY664418 | Mo17 locus 9008 |
| ZB19.Contig19 (2133) | 1055 | 2109 | 1055 | 97.63 | 309950 | 308897 | AF090447 | alpha zein gene cluster |
| ZB19.Contig20 (1536) | 93 | 1505 | 1422 | 83.97 | 400455 | 401871 | AY664419 | Mo17 locus 9009 |
| ZB19.Contig21 (1614) | 261 | 1556 | 1296 | 96.91 | 238900 | 237606 | AY664418 | Mo17 locus 9008 |
| ZB19.Contig22 (2563) | | | | | | | "NA" | "pCHR758mcv" |
| ZB19.Contig23 (2753) | 695 | 2625 | 1938 | 85.19 | 33521 | 35457 | AY664418 | Mo17 locus 9008 |
| ZB19.Contig23 (2753) | 187 | 680 | 496 | 82.26 | 32998 | 33492 | AY664418 | Mo17 locus 9008 |
| ZB19.Contig23 (2753) | 31 | 148 | 119 | 82.35 | 170387 | 170505 | AY664418 | Mo17 locus 9008 |
| ZB19.Contig24 (2816) | 748 | 2788 | 2046 | 96.19 | 308241 | 306197 | AF090447 | alpha zein gene cluster |
| ZB19.Contig24 (2816) | 136 | 707 | 572 | 94.76 | 308852 | 308282 | AF090447 | alpha zein gene cluster |
| ZB19.Contig25 (2997) | 31 | 770 | 746 | 86.6 | 113462 | 114199 | AY574035 | rust resistance rp3-1 |
| ZB19.Contig25 (2997) | 849 | 1560 | 720 | 86.67 | 104886 | 105601 | AY574035 | rust resistance rp3-1 |
| ZB19.Contig26 (2897) | 482 | 2861 | 2380 | 91.18 | 89258 | 86886 | AY664416 | Mo17 locus bz |
| ZB19.Contig26 (2897) | 35 | 463 | 430 | 93.72 | 93544 | 93117 | AY664416 | Mo17 locus bz |
| ZB19.Contig27 (2305) | 38 | 2822 | 2790 | 92.29 | 75093 | 72309 | AY664416 | Mo17 locus bz |
| ZB19.Contig28 (3308) | 157 | 2297 | 2142 | 91.83 | 116223 | 118359 | AY664413 | B73 locus 9002 |
| ZB19.Contig28 (3308) | 2308 | 2372 | 65 | 92.31 | 118385 | 118446 | AY664413 | B73 locus 9002 |
| ZB19.Contig29 (4998) | 27 | 1161 | 1135 | 96.3 | 189722 | 188588 | AY664416 | Mo17 locus bz |
| ZB19.Contig29 (4998) | 1161 | 1429 | 271 | 93.36 | 195008 | 195276 | AY664416 | Mo17 locus bz |
| ZB19.Contig29 (4998) | 1430 | 2298 | 870 | 92.41 | 31346 | 30482 | AY664416 | Mo17 locus bz |
| ZB19.Contig29 (4998) | 2094 | 4994 | 2903 | 92.08 | 30851 | 27961 | AY664416 | Mo17 locus bz |
| ZB19.Contig30 (8151) | | | | | | | "NA" | "CentC-like TIGR identified" |
| ZB19.Contig31 (10813) | | | | | | | "NA" | "CentC-like TIGR identified" |

The identity, distribution and frequency of repeats within the centromere sequences of ZB19 are set out in Table 12. The repeats were identified by comparing the contigs to the TIGR maize database of the Institute of Genomic Research Web Site. Results of this comparison is summarized in Table 12. Percent divergence is defined as the percentage of a sequence (% of the total number of nucleotides) that is different from another sequence, with nucleotide mismatches are classified as differences.

Nearly all of contigs 4, 8, 11, 14, 15 and 18 match repeat elements without gaps apart from 155 bases on the 5' end of contig 2, a 454 bp gap in the middle of cotnig 16 and the 3' 1071 bp of contig 17. Sequence regions from ZB19 are identified by 75 named TIGR maize sequence database records. Among these, 23 records are CentC variants and many are multiply represented. The remaining 52 records are not CentC and are either uniquely represented or mutiply represented by non-overlapping fragments.

TABLE 12

TIGR Maize Sequence Content in ZB19

| Contig (length) | Contig Match | | | | Maize repeat DB | TIGR |
|---|---|---|---|---|---|---|
| | begin | end | length | % diverge | identifier | homology |
| ZB19.Contig1 (1500) | 1 | 1447 | 1446 | 15.2 | SiTERTOOT0149 | put. retrotrans. |
| ZB19.Contig1 (1500) | 1152 | 1483 | 331 | 13 | SgTERTOOT03898 | put. retrotrans. |
| ZB19.Contig2 (1708) | 30 | 205 | 175 | 17.8 | SgCMCMOOT00130 | centromere-related |
| ZB19.Contig2 (1708) | 212 | 1474 | 1262 | 11.8 | SmOTOT00101839 | family_4154_C17 |
| ZB19.Contig2 (1708) | 1475 | 1700 | 225 | 17 | SgTERTOOT30294 | put. retrotrans. |
| ZB19.Contig2 (1708) | 1475 | 1676 | 201 | 15.2 | SgTERTOOT31072 | put. retrotrans. |
| ZB19.Contig5 (1176) | 10 | 121 | 111 | 9.8 | SgTERTOOT01453 | put. retrotrans. |
| ZB19.Contig5 (1176) | 22 | 1148 | 1126 | 4.7 | SiTERTOOT0208 | put. retrotrans. |
| ZB19.Contig5 (1176) | 977 | 1169 | 192 | 19.2 | SgTERT00100386 | put. retrotrans. |
| ZB19.Contig7 (1325) | 30 | 606 | 576 | 4.9 | SgTERTOOT19733 | put. retrotrans. |
| ZB19.Contig7 (1325) | 560 | 1325 | 765 | 5.6 | SgTERTOOT00141 | put. retrotrans. |
| ZB19.Contig10 (1424) | 12 | 117 | 105 | 9.5 | SgTERTOOT00426 | put. retrotrans. |
| ZB19.Contig10 (1424) | 23 | 1421 | 1398 | 7.1 | SiTERTOOT0207 | put. retrotrans. |
| ZB19.Contig12 (1743) | 1 | 218 | 217 | 5.5 | SiTERTOOT0090 | put. retrotrans. |
| ZB19.Contig12 (1743) | 219 | 1590 | 1371 | 10.9 | SgTERTOOT03659 | put. retrotrans. |
| ZB19.Contig12 (1743) | 1589 | 1743 | 154 | 22.1 | SgTERTOOT29480 | put. retrotrans. |
| ZB19.Contig13 (1528) | 21 | 105 | 84 | 28.2 | SmOTOT00101761 | family_3909_C1 |
| ZB19.Contig13 (1528) | 43 | 805 | 762 | 13.8 | SmOTOT00200539 | family_18_C52 |
| ZB19.Contig13 (1528) | 688 | 819 | 131 | 13.6 | SmOTOT00200521 | family_18_C35 |
| ZB19.Contig13 (1528) | 822 | 1528 | 706 | 5 | SiTERTOOT0162 | put. retrotrans. |

TABLE 12-continued

TIGR Maize Sequence Content in ZB19

| Contig (length) | Contig Match begin | end | length | % diverge | Maize repeat DB identifier | TIGR homology |
|---|---|---|---|---|---|---|
| ZB19.Contig18 (1869) | 16 | 347 | 331 | 9.3 | SmOTOT00201263 | family_457_C3 |
| ZB19.Contig18 (1869) | 33 | 417 | 384 | 20 | SmOTOT00100906 | family_21444_C1 |
| ZB19.Contig18 (1869) | 418 | 1175 | 757 | 13.2 | SiTERTOOT0109 | put. retrotrans. |
| ZB19.Contig18 (1869) | 418 | 1083 | 665 | 8.4 | SgTERTOOT23750 | put. retrotrans. |
| ZB19.Contig18 (1869) | 986 | 1848 | 862 | 32 | SgTERTOOT01238 | put. retrotrans. |
| ZB19.Contig19 (2133) | 1055 | 2109 | 1054 | 2.3 | SiTERTOOT0192 | put. retrotrans. |
| ZB19.Contig20 (1536) | 23 | 1319 | 1296 | 18.9 | SiTERTOOT0103 | put. retrotrans. |
| ZB19.Contig20 (1536) | 1320 | 1508 | 188 | 9.5 | SmOTOT00101322 | family_2963_C1 |
| ZB19.Contig21 (1614) | 51 | 647 | 596 | 21.1 | SgTERTOOT16518 | put. retrotrans. |
| ZB19.Contig21 (1614) | 131 | 1608 | 1477 | 5.3 | SiTERTOOT0172 | put. retrotrans. |
| ZB19.Contig23 (2753) | 7 | 63 | 56 | 13.2 | SmOTOT00200682 | family_21_C7 |
| ZB19.Contig23 (2753) | 22 | 189 | 167 | 10.7 | SmOTOT00100741 | family_1920_C6 |
| ZB19.Contig23 (2753) | 190 | 547 | 357 | 26.1 | SgTERTOOT18326 | put. retrotrans. |
| ZB19.Contig23 (2753) | 250 | 399 | 149 | 7.5 | SmOTOT00200636 | family_20_C20 |
| ZB19.Contig23 (2753) | 399 | 632 | 233 | 9 | SmOTOT00201628 | family_73_C1 |
| ZB19.Contig23 (2753) | 640 | 1305 | 665 | 32.8 | SgTERTOOT02327 | put. retrotrans. |
| ZB19.Contig23 (2753) | 710 | 1116 | 406 | 32.4 | SgTERTOOT26280 | put. retrotrans. |
| ZB19.Contig23 (2753) | 804 | 1364 | 560 | 31.6 | SiTERTOOT0139 | put. retrotrans. |
| ZB19.Contig23 (2753) | 1050 | 1247 | 197 | 14.1 | SmOTOT00201653 | family_766_C5 |
| ZB19.Contig23 (2753) | 1271 | 1403 | 132 | 15.8 | SmOTOT00201649 | family_766_C1 |
| ZB19.Contig23 (2753) | 1405 | 1691 | 286 | 11.8 | SmOTOT00201691 | family_79_C1 |
| ZB19.Contig23 (2753) | 1756 | 2702 | 946 | 35.8 | SgTERTOOT00119 | put. retrotrans. |
| ZB19.Contig23 (2753) | 1903 | 2039 | 136 | 13.1 | SmOTOT00200145 | family_1251_C1 |
| ZB19.Contig23 (2753) | 2230 | 2626 | 396 | 31.8 | SgTERTOOT00404 | put. retrotrans. |
| ZB19.Contig24 (2816) | 14 | 2788 | 2774 | 6 | SiTERTOOT0192 | put. retrotrans. |
| ZB19.Contig25 (2997) | 22 | 2767 | 2745 | 21.6 | SiTERTOOT0310 | put. retrotrans. |
| ZB19.Contig25 (2997) | 2498 | 2970 | 472 | 25.4 | SgTERTOOT26929 | put. retrotrans. |
| ZB19.Contig25 (2997) | 2875 | 2981 | 106 | 15.9 | SgTERTOOT08404 | put. retrotrans. |
| ZB19.Contig26 (2897) | 28 | 463 | 435 | 2.8 | SgTERTOOT22255 | put. retrotrans. |
| ZB19.Contig26 (2897) | 480 | 2871 | 2391 | 3.7 | SiTERTOOT0162 | put. retrotrans. |
| ZB19.Contig27 (2845) | 7 | 2823 | 2816 | 6.3 | SiTERTOOT0162 | put. retrotrans. |
| ZB19.Contig28 (3308) | 27 | 2368 | 2341 | 18.9 | SiTERTOOT0157 | put. retrotrans. |
| ZB19.Contig29 (4998) | 29 | 1161 | 1132 | 21.8 | SiTERTOOT0310 | put. retrotrans. |
| ZB19.Contig29 (4998) | 1162 | 1429 | 267 | 2.6 | SgTERTOOT17469 | put. retrotrans. |
| ZB19.Contig29 (4998) | 1430 | 4994 | 3564 | 8.7 | SiTERTOOT0170 | put. retrotrans. |
| ZB19.Contig29 (4998) | 2032 | 4998 | 2966 | 1.9 | SiTERTOOT0172 | put. retrotrans. |
| ZB19.Contig30 (8151) | 74 | 233 | 159 | 31.8 | SiTERTOOT0296 | put. retrotrans. |
| ZB19.Contig30 (8151) | 368 | 500 | 132 | 6 | SgCMCM00200161 | CentC |
| ZB19.Contig30 (8151) | 501 | 655 | 154 | 2.6 | SgCMCM00200034 | CentC |
| ZB19.Contig30 (8151) | 656 | 810 | 154 | 5.8 | SgCMCM00200282 | CentC |
| ZB19.Contig30 (8151) | 811 | 966 | 155 | 5.8 | SgCMCM00200175 | Cent |
| ZB19.Contig30 (8151) | 967 | 1121 | 154 | 3.2 | SgCMCM00200034 | CentC |
| ZB19.Contig30 (8151) | 1122 | 1276 | 154 | 6.5 | SgCMCM00200356 | CentC |
| ZB19.Contig30 (8151) | 1277 | 1431 | 154 | 5.8 | SgCMCM00200034 | CentC |
| ZB19.Contig30 (8151) | 1432 | 1587 | 155 | 3.9 | SgCMCM00200282 | CentC |
| ZB19.Contig30 (8151) | 1588 | 1743 | 155 | 5.8 | SgCMCM00200175 | CentC |
| ZB19.Contig30 (8151) | 1744 | 1898 | 154 | 4.5 | SgCMCM00200034 | CentC |
| ZB19.Contig30 (8151) | 1899 | 2053 | 154 | 3.2 | SgCMCM00200034 | CentC |
| ZB19.Contig30 (8151) | 2054 | 2208 | 154 | 3.9 | SgCMCM00200356 | CentC |
| ZB19.Contig30 (8151) | 2209 | 2363 | 154 | 4.5 | SgCMCM00200034 | CentC |
| ZB19.Contig30 (8151) | 2364 | 2518 | 154 | 3.2 | SgCMCM00200356 | CentC |
| ZB19.Contig30 (8151) | 2519 | 2674 | 155 | 3.9 | SgCMCM00200228 | CentC |
| ZB19.Contig30 (8151) | 2675 | 2829 | 154 | 3.2 | SgCMCM00200034 | CentC |
| ZB19.Contig30 (8151) | 2830 | 2984 | 154 | 3.2 | SgCMCM00200145 | CentC |
| ZB19.Contig30 (8151) | 2985 | 3139 | 154 | 3.9 | SgCMCM00200034 | CentC |
| ZB19.Contig30 (8151) | 3140 | 3295 | 155 | 1.9 | SgCMCM00200034 | CentC |
| ZB19.Contig30 (8151) | 3296 | 3452 | 156 | 1.9 | SgCMCM00200034 | CentC |
| ZB19.Contig30 (8151) | 3453 | 3607 | 154 | 3.9 | SgCMCM00200034 | CentC |
| ZB19.Contig30 (8151) | 3608 | 3763 | 155 | 1.9 | SgCMCM00200034 | CentC |
| ZB19.Contig30 (8151) | 3764 | 3918 | 154 | 4.5 | SgCMCM00200034 | CentC |
| ZB19.Contig30 (8151) | 3919 | 4073 | 154 | 1.9 | SgCMCM00200034 | CentC |
| ZB19.Contig30 (8151) | 4074 | 4227 | 153 | 2.6 | SgCMCM00200092 | CentC |
| ZB19.Contig30 (8151) | 4228 | 4382 | 154 | 3.9 | SgCMCM00200034 | CentC |
| ZB19.Contig30 (8151) | 4383 | 4538 | 155 | 2.6 | SgCMCM00200034 | CentC |
| ZB19.Contig30 (8151) | 4539 | 4693 | 154 | 3.9 | SgCMCM00200034 | CentC |
| ZB19.Contig30 (8151) | 4694 | 4848 | 154 | 2.6 | SgCMCM00200034 | CentC |
| ZB19.Contig30 (8151) | 4849 | 5003 | 154 | 3.9 | SgCMCM00200356 | CentC |
| ZB19.Contig30 (8151) | 5004 | 5158 | 154 | 5.8 | SgCMCM00200034 | CentC |
| ZB19.Contig30 (8151) | 5159 | 5314 | 155 | 4.5 | SgCMCM00200526 | CentC |
| ZB19.Contig30 (8151) | 5315 | 5468 | 153 | 3.9 | SgCMCM00200034 | CentC |
| ZB19.Contig30 (8151) | 5469 | 5624 | 155 | 5.8 | SgCMCM00200034 | CentC |
| ZB19.Contig30 (8151) | 5625 | 5779 | 154 | 3.2 | SgCMCM00200228 | CentC |
| ZB19.Contig30 (8151) | 5780 | 5934 | 154 | 3.2 | SgCMCM00200034 | CentC |
| ZB19.Contig30 (8151) | 5935 | 6089 | 154 | 3.9 | SgCMCM00200145 | CentC |

TABLE 12-continued

TIGR Maize Sequence Content in ZB19

| Contig (length) | Contig Match | | | | Maize repeat DB identifier | TIGR homology |
|---|---|---|---|---|---|---|
| | begin | end | length | % diverge | | |
| ZB19.Contig30 (8151) | 6090 | 6244 | 154 | 3.9 | SgCMCM00200034 | CentC |
| ZB19.Contig30 (8151) | 6245 | 6399 | 154 | 4.5 | SgCMCM00200145 | CentC |
| ZB19.Contig30 (8151) | 6400 | 6555 | 155 | 3.2 | SgCMCM00200034 | CentC |
| ZB19.Contig30 (8151) | 6556 | 6710 | 154 | 4.5 | SgCMCM00200034 | CentC |
| ZB19.Contig30 (8151) | 6711 | 6865 | 154 | 1.9 | SgCMCM00200034 | CentC |
| ZB19.Contig30 (8151) | 6866 | 7020 | 154 | 3.9 | SgCMCM00200356 | CentC |
| ZB19.Contig30 (8151) | 7021 | 7175 | 154 | 4.5 | SgCMCM00200009 | CentC |
| ZB19.Contig30 (8151) | 7176 | 7330 | 154 | 2.6 | SgCMCM00200228 | CentC |
| ZB19.Contig30 (8151) | 7331 | 7485 | 154 | 5.2 | SgCMCM00200034 | CentC |
| ZB19.Contig30 (8151) | 7486 | 7640 | 154 | 5.2 | SgCMCM00200026 | CentC |
| ZB19.Contig30 (8151) | 7642 | 7796 | 154 | 1.9 | SgCMCM00200034 | CentC |
| ZB19.Contig30 (8151) | 7797 | 7952 | 155 | 4.5 | SgCMCM00200034 | CentC |
| ZB19.Contig30 (8151) | 7954 | 8107 | 153 | 4.6 | SgCMCM00200372 | CentC |
| ZB19.Contig31 (10813) | 23 | 167 | 144 | 4.8 | SgCMCM00200030 | CentC |
| ZB19.Contig31 (10813) | 168 | 322 | 154 | 3.9 | SgCMCM00200356 | CentC |
| ZB19.Contig31 (10813) | 323 | 477 | 154 | 2.6 | SgCMCM00200034 | CentC |
| ZB19.Contig31 (10813) | 478 | 632 | 154 | 3.9 | SgCMCM00200034 | CentC |
| ZB19.Contig31 (10813) | 633 | 788 | 155 | 2.6 | SgCMCM00200034 | CentC |
| ZB19.Contig31 (10813) | 789 | 943 | 154 | 3.2 | SgCMCM00200034 | CentC |
| ZB19.Contig31 (10813) | 944 | 1098 | 154 | 3.9 | SgCMCM00200145 | CentC |
| ZB19.Contig31 (10813) | 1100 | 1254 | 154 | 3.9 | SgCMCM00200034 | CentC |
| ZB19.Contig31 (10813) | 1255 | 1409 | 154 | 2.6 | SgCMCM00200228 | CentC |
| ZB19.Contig31 (10813) | 1410 | 1565 | 155 | 5.8 | SgCMCM00200034 | CentC |
| ZB19.Contig31 (10813) | 1566 | 1720 | 154 | 3.9 | SgCMCM00200356 | CentC |
| ZB19.Contig31 (10813) | 1721 | 1875 | 154 | 2.6 | SgCMCM00200034 | CentC |
| ZB19.Contig31 (10813) | 1876 | 2031 | 155 | 4.5 | SgCMCM00200034 | CentC |
| ZB19.Contig31 (10813) | 2032 | 2186 | 154 | 2.6 | SgCMCM00200034 | CentC |
| ZB19.Contig31 (10813) | 2187 | 2342 | 155 | 5.1 | SgCMCM00200034 | CentC |
| ZB19.Contig31 (10813) | 2343 | 2497 | 154 | 3.9 | SgCMCM00200090 | CentC |
| ZB19.Contig31 (10813) | 2498 | 2649 | 151 | 3.3 | SgCMCM00200260 | CentC |
| ZB19.Contig31 (10813) | 2650 | 2804 | 154 | 1.9 | SgCMCM00200356 | CentC |
| ZB19.Contig31 (10813) | 2805 | 2959 | 154 | 1.9 | SgCMCM00200034 | CentC |
| ZB19.Contig31 (10813) | 2960 | 3114 | 154 | 4.5 | SgCMCM00200034 | CentC |
| ZB19.Contig31 (10813) | 3115 | 3270 | 155 | 3.2 | SgCMCM00200034 | CentC |
| ZB19.Contig31 (10813) | 3271 | 3425 | 154 | 3.2 | SgCMCM00200034 | CentC |
| ZB19.Contig31 (10813) | 3426 | 3580 | 154 | 2.6 | SgCMCM00200034 | CentC |
| ZB19.Contig31 (10813) | 3581 | 3734 | 153 | 3.9 | SgCMCM00200159 | CentC |
| ZB19.Contig31 (10813) | 3735 | 3890 | 155 | 4.5 | SgCMCM00200034 | CentC |
| ZB19.Contig31 (10813) | 3891 | 4045 | 154 | 1.9 | SgCMCM00200034 | CentC |
| ZB19.Contig31 (10813) | 4047 | 4201 | 154 | 5.2 | SgCMCM00200026 | CentC |
| ZB19.Contig31 (10813) | 4202 | 4356 | 154 | 3.2 | SgCMCM00200090 | CentC |
| ZB19.Contig31 (10813) | 4357 | 4513 | 156 | 2.6 | SgCMCM00200034 | CentC |
| ZB19.Contig31 (10813) | 4514 | 4668 | 154 | 6.5 | SgCMCM00200179 | CentC |
| ZB19.Contig31 (10813) | 4669 | 4823 | 154 | 3.2 | SgCMCM00200034 | CentC |
| ZB19.Contig31 (10813) | 4824 | 4978 | 154 | 5.2 | SgCMCM00200034 | CentC |
| ZB19.Contig31 (10813) | 4979 | 5133 | 154 | 3.9 | SgCMCM00200034 | CentC |
| ZB19.Contig31 (10813) | 5135 | 5289 | 154 | 5.2 | SgCMCM00200026 | CentC |
| ZB19.Contig31 (10813) | 5290 | 5444 | 154 | 3.2 | SgCMCM00200090 | CentC |
| ZB19.Contig31 (10813) | 5445 | 5601 | 156 | 2.6 | SgCMCM00200034 | CentC |
| ZB19.Contig31 (10813) | 5602 | 5756 | 154 | 6.5 | SgCMCM00200179 | CentC |
| ZB19.Contig31 (10813) | 5757 | 5911 | 154 | 3.2 | SgCMCM00200034 | CentC |
| ZB19.Contig31 (10813) | 5912 | 6066 | 154 | 5.2 | SgCMCM00200034 | CentC |
| ZB19.Contig31 (10813) | 6068 | 6221 | 153 | 3.9 | SgCMCM00200034 | CentC |
| ZB19.Contig31 (10813) | 6222 | 6376 | 154 | 4.5 | SgCMCM00200356 | CentC |
| ZB19.Contig31 (10813) | 6377 | 6533 | 156 | 7.1 | SgCMCM00200282 | CentC |
| ZB19.Contig31 (10813) | 6534 | 6686 | 152 | 5.9 | SgCMCM00200026 | CentC |
| ZB19.Contig31 (10813) | 6687 | 6840 | 153 | 4.5 | SgCMCM00200090 | CentC |
| ZB19.Contig31 (10813) | 6841 | 6995 | 154 | 3.9 | SgCMCM00200034 | CentC |
| ZB19.Contig31 (10813) | 6996 | 7150 | 154 | 2.6 | SgCMCM00200104 | CentC |
| ZB19.Contig31 (10813) | 7151 | 7305 | 154 | 3.2 | SgCMCM00200034 | CentC |
| ZB19.Contig31 (10813) | 7306 | 7460 | 154 | 3.2 | SgCMCM00200356 | CentC |
| ZB19.Contig31 (10813) | 7461 | 7616 | 155 | 4.5 | SgCMCM00200034 | CentC |
| ZB19.Contig31 (10813) | 7617 | 7771 | 154 | 3.9 | SgCMCM00200145 | CentC |
| ZB19.Contig31 (10813) | 7772 | 7925 | 153 | 3.2 | SgCMCM00200034 | CentC |
| ZB19.Contig31 (10813) | 7926 | 8081 | 155 | 2.6 | SgCMCM00200034 | CentC |
| ZB19.Contig31 (10813) | 8083 | 8236 | 153 | 4.5 | SgCMCM00200356 | CentC |
| ZB19.Contig31 (10813) | 8237 | 8392 | 155 | 5.8 | SgCMCM00200282 | CentC |
| ZB19.Contig31 (10813) | 8393 | 8547 | 154 | 3.2 | SgCMCM00200034 | CentC |
| ZB19.Contig31 (10813) | 8548 | 8703 | 155 | 3.9 | SgCMCM00200258 | CentC |
| ZB19.Contig31 (10813) | 8704 | 8859 | 155 | 3.9 | SgCMCM00200058 | CentC |
| ZB19.Contig31 (10813) | 8860 | 9015 | 155 | 4.5 | SgCMCM00200034 | CentC |
| ZB19.Contig31 (10813) | 9016 | 9170 | 154 | 3.9 | SgCMCM00200090 | CentC |
| ZB19.Contig31 (10813) | 9171 | 9324 | 153 | 3.9 | SgCMCM00200034 | CentC |
| ZB19.Contig31 (10813) | 9325 | 9479 | 154 | 4.5 | SgCMCM00200228 | CentC |

TABLE 12-continued

TIGR Maize Sequence Content in ZB19

| Contig (length) | Contig Match | | | | Maize repeat DB identifier | TIGR homology |
|---|---|---|---|---|---|---|
| | begin | end | length | % diverge | | |
| ZB19.Contig31 (10813) | 9480 | 9634 | 154 | 3.2 | SgCMCM00200034 | CentC |
| ZB19.Contig31 (10813) | 9635 | 9789 | 154 | 1.3 | SgCMCM00200092 | CentC |
| ZB19.Contig31 (10813) | 9790 | 9917 | 127 | 3.1 | SgCMCM00200234 | CentC |
| ZB19.Contig31 (10813) | 9914 | 10011 | 97 | 2.1 | SgCMCM00200032 | CentC |
| ZB19.Contig31 (10813) | 10012 | 10165 | 153 | 2.6 | SgCMCM00200034 | CentC |
| ZB19.Contig31 (10813) | 10167 | 10320 | 153 | 3.2 | SgCMCM00200356 | CentC |
| ZB19.Contig31 (10813) | 10325 | 10476 | 151 | 2.6 | SgCMCM00200150 | CentC |
| ZB19.Contig31 (10813) | 10477 | 10631 | 154 | 2.6 | SgCMCM00200034 | CentC |
| ZB19.Contig31 (10813) | 10632 | 10785 | 153 | 4.5 | SgCMCM00200092 | CentC |

The contigs of ZB19 consist of sequence that is not repeated within the library apart from all of contig 31 and all but the very 5' end of contig 30 and perhaps a small ~400 base repeat in the middle of contig 29. The repeat regions extend approximately 8 and 10 kb in contigs 30 and 31, respectively. Since the repeated regions are apparent both when compared to self and the reverse complement, the larger repeat region consists of many smaller repeat regions that occur both in the forward and reverse direction.

The consensus sequence of the CentC repeat present in ZB19 is set out as SEQ ID NO: 70. The variants of the CentC repeats present in ZB19 are set out in Table 13 where the most common base is indicated. Where the most common base occurs less than 60% of the time, the percent occurence of each base is reported.

TABLE 13

| CentC consensus and Variation in ZB19 | |
|---|---|
| 1 | T |
| 2 | G (C: 4/G: 96) |
| 3 | G (A: 9/G: 91) |
| 4 | T (A: 3/T: 97) |
| 5 | T (C: 4/T: 96) |
| 6 | C (C: 81/G: 3/T: 16) |
| 7 | C (A: 3/C: 85/G: 1/T: 11) |
| 8 | G (A: 5/G: 95) |
| 9 | G (A: 2/G: 97) |
| 10 | T (G: 1/T: 99) |
| 11 | G (G: 98/T: 2) |
| 12 | G (C: 1/G: 99) |
| 13 | C (A: 1/C: 99) |
| 14 | A (A: 94/C: 3/G: 2) |
| 15 | A (A: 97/C: 2/G: 1) |
| 16 | A (A: 98/G: 2) |
| 17 | A |
| 18 | A (A: 99/C: 1/—: 1) |
| 19 | C (A: 2/C: 97/T: 1) |
| 20 | T (A: 4/C: 3/T: 94) |
| 21 | C (C: 91/T: 9) |
| 22 | G (A: 7/G: 90/T: 3) |
| 23 | T (C: 2/T: 98) |
| 24 | G (C: 3/G: 93/—: 4) |
| 25 | C (A: 4/C: 90/G: 1/T: 4) |
| 26 | H(A: 24/C: 3/T: 55/—: 18) |
| 27 | T (A: 2/G: 3/T: 95) |
| 28 | T (A: 1/G: 1/T: 99) |
| 29 | D(A: 12/G: 27/T: 53/—: 8) |
| 30 | W(A: 48/T: 52) |
| 31 | M(A: 55/C: 1/—: 44) |
| 32 | T (A: 4/C: 1/T: 92/—: 3) |
| 33 | T(T: 1/—: 99) |
| 34 | G |
| 35 | C (C: 99/T: 1) |
| 36 | A |
| 37 | C (A: 3/C: 97) |
| 38 | Y(C: 26/T: 3/—: 71) |

TABLE 13-continued

| CentC consensus and Variation in ZB19 | |
|---|---|
| 39 | C (C: 99/—: 1) |
| 40 | C (C: 93/G: 1/T: 1/—: 4) |
| 41 | C (C: 79/G: 2/T: 2/—: 18) |
| 42 | G (A: 3/C: 1/G: 96) |
| 43 | A (A: 99/G: 1) |
| 44 | C (A: 3/C: 95/T: 3) |
| 45 | A |
| 46 | C (A: 1/C: 96/T: 3) |
| 47 | C |
| 48 | C (C: 97/G: 1/T: 3) |
| 49 | G(G: 1/—: 99) |
| 50 | G (A: 3/G: 92/T: 5) |
| 51 | T (A: 2/T: 98) |
| 52 | T (T: 99) |
| 53 | T (G: 2/T: 98) |
| 54 | T (C: 1/T: 98/—: 1) |
| 55 | C (C: 91/T: 9/—: 1) |
| 56 | G (A: 1/G: 99) |
| 57 | G (A: 10/G: 90) |
| 58 | G(G: 1/—: 99) |
| 59 | A (A: 97/T: 3) |
| 60 | A (A: 99/T: 1) |
| 61 | T |
| 62 | G (A: 4/G: 96) |
| 63 | G |
| 64 | G (A: 3/G: 89/T: 8) |
| 65 | T |
| 66 | G |
| 67 | A |
| 68 | C (C: 96/T: 4) |
| 69 | G (A: 4/G: 96) |
| 70 | T (C: 1/T: 99) |
| 71 | G |
| 72 | C (C: 93/G: 2/T: 5) |
| 73 | G (A: 4/G: 90/T: 6) |
| 74 | G (A: 6/G: 94) |
| 75 | C |
| 76 | A (A: 95/G: 5) |
| 77 | A |
| 78 | C (A: 1/C: 99) |
| 79 | G (A: 3/G: 97) |
| 80 | A |
| 81 | A |
| 82 | A |
| 83 | T |
| 84 | T (A: 1/G: 1/T: 99) |
| 85 | G (A: 4/G: 96) |
| 86 | C (A: 3/G: 94/T: 3) |
| 87 | G (A: 3/G: 97) |
| 88 | C (A: 2/C: 91/G: 1/T: 5/—: 2) |
| 89 | G (A: 4/G: 96) |
| 90 | A (A: 98/T: 2) |
| 91 | A |
| 92 | A (A: 99/C: 1) |
| 93 | C |
| 94 | C (A: 4/C: 96) |
| 95 | A |

TABLE 13-continued

CentC consensus and Variation in ZB19

| | |
|---|---|
| 96 | C (A: 1/C: 96/T: 3) |
| 97 | C (A: 3/C: 92/T: 5) |
| 98 | C (A: 1/C: 99) |
| 99 | C (A: 25/C: 74/—: 1) |
| 100 | A |
| 101 | A |
| 102 | C(C: 3/—: 97) |
| 103 | A |
| 104 | C (A: 1/C: 99/T: 1) |
| 105 | A (A: 97/T: 3) |
| 106 | A(A: 1/—: 99) |
| 107 | T |
| 108 | G (A: 1/G: 94/T: 4) |
| 109 | A (A: 64/C: 1/G: 26/T: 8) |
| 110 | G |
| 111 | T (G: 1/T: 99) |
| 112 | T |
| 113 | T (T: 98/—: 2) |
| 114 | T (T: 98/—: 2) |
| 115 | G (A: 3/G: 94/T: 3/—: 1) |
| 116 | G |
| 117 | A (A: 99/G: 1) |
| 118 | C |
| 119 | C (A: 2/C: 96/T: 3) |
| 120 | T (A: 3/T: 97) |
| 121 | A (A: 90/G: 1/T: 9) |
| 122 | A (A: 99/T: 1) |
| 123 | A |
| 124 | G (C: 1/G: 99) |
| 125 | T (C: 1/T: 99) |
| 126 | A |
| 127 | G (A: 4/G: 96) |
| 128 | T (G: 1/T: 99) |
| 129 | G (A: 2/G: 92/T: 6) |
| 130 | G (G: 72/T: 28) |
| 131 | A |
| 132 | T (G: 6/T: 94) |
| 133 | T (C: 1/T: 99) |
| 134 | G (C: 3/G: 97) |
| 135 | G (A: 2/C: 3/G: 95/T: 1) |
| 136 | G (G: 97/T: 3) |
| 137 | C (A: 2/C: 98) |
| 138 | A (A: 97/C: 2/G: 1) |
| 139 | T |
| 140 | G (A: 3/G: 96/T: 1) |
| 141 | T |
| 142 | T |
| 143 | C (C: 94/T: 6) |
| 144 | G (A: 4/G: 94/T: 3) |
| 145 | T (T: 99) |
| 146 | T |
| 147 | G |
| 148 | C (C: 97/T: 3) |
| 149 | G (A: 2/G: 97/—: 1) |
| 150 | A (A: 96/C: 4) |
| 151 | A (A: 97/T: 3) |
| 152 | A |
| 153 | A |
| 154 | A |
| 155 | C (A: 4/C: 67/G: 3/T: 25/—: 1) |
| 156 | G (A: 13/G: 84/—: 3) |
| 157 | A |
| 158 | A (A: 98/T: 2) |
| 159 | G (G: 99/T: 1) |
| 160 | A |
| 161 | A |
| 162 | A (A: 99/G: 1) |
| 163 | T (C: 1/G: 1/T: 97) |
| 164 | G (C: 1/G: 99) |
| 165 | R(A: 45/G: 55) |
| 166 | T |
| 167 | T |
| 168 | C |
| 169 | Y(C: 41/T: 59) |
| 170 | G (A: 30/G: 70) |
| 171 | G (A: 14/G: 86) |
| 172 | T |
| 153 | mean length |
| 3.8 | std |

Characterization of ZB113

The nucleotide sequence of ZB113 was assembled into 18 contigs with a combined trimmed length of 90 kb. ZB113 contigs 1-18 correspond to SEQ ID NOS: 52-69, respectively.

All but three contigs (9, 12, and 13c) of ZB113 showed significant numbers of mostly high and some low quality matches to various sequencing reads; and all but contigs 12 and 13 showed significant matches to TIGR maize database entries. With the large numbers of inconsistent forward/reverse pairs present within the contigs there may be a number of misassemblies present. Notably, contig 17 might be falsely assembled sequence fragments belonging to contigs 14, 15, and 18. Many large regions of similarity exist between the contigs. Notably, an approximately 1.3 kb region on the 3' end of contig 18 is present several times on the 5' end of contig 18 as well as covering nearly all of contigs 15 and 17, and the 3' half of contig 14.

The sequence analysis of ZB19 indicated that 0.23% of the sequence is simple repeats and low complexity sequence (e.g. AT-rich, T-rich and (TTTTC)n), 17% vector sequence, 78% sequence is present in the TIGR maize database, 4.40% uncharacterized sequence, 47.55% CentC repeat, 0.57% CentA repeat and 31.73% of CRM repeat. About 42.3 kb of the sequence was true repeat sequence, meaning those sequences are repeated within the BAC ZB19 sequence.

ZB113 has 64 simple repeat bases (0.07%) and 145 low complexity bases (0.16%) contained within contigs 12, 13, 16, and 18. This low simple repeat content is summarized in Table 14.

TABLE 14

ZB113 Simple Repeat Content

| Contig (length) | Contig Match | | | | Simple repeat |
|---|---|---|---|---|---|
| | begin | end | length | % diverge | |
| ZB113.Contig12 (5594) | 1466 | 1488 | 22 | 0 | AT_rich |
| ZB113.Contig12 (5594) | 2391 | 2423 | 32 | 0 | AT_rich |
| ZB113.Contig13 (5111) | 3730 | 3755 | 25 | 0 | AT_rich |
| ZB113.Contig16 (15540) | 3933 | 3995 | 62 | 22.2 | T-rich |
| ZB113.Contig18 (20048) | 16200 | 16263 | 63 | 11.3 | (TTTTC)n |
| | | | 204 | | |

The ZB113 contigs are set out as SEQ ID NOS: 52-69, respectively. These contigs were compared to the NCBI database at the National Institute of Health Web Site using BLAST. Results of the BLAST comparison are set out in Table 15.

TABLE 15

ZB113 GenBank Homology

| Contig (length) | Contig Alignment | | | | Genbank | | | |
|---|---|---|---|---|---|---|---|---|
| | begin | end | length | % id | begin | end | Accession # | Homologous feature |
| ZB113.Contig1 (864) | | | | | | | "NA" | "pCHR758mcv" |
| ZB113.Contig2 (835) | 366 | 547 | 182 | 96.15 | 27727 | 27546 | AC116034 | *Zea mays* clone |
| ZB113.Contig2 (835) | 587 | 703 | 117 | 99.15 | 21738 | 21622 | AC116034 | *Zea mays* clone |
| ZB113.Contig2 (835) | 743 | 835 | 93 | 91.4 | 21581 | 21491 | AC116034 | *Zea mays* clone |
| ZB113.Contig2 (835) | 234 | 279 | 46 | 100 | 27870 | 27825 | AC116034 | *Zea mays* clone |
| ZB113.Contig2 (835) | 168 | 215 | 48 | 97.92 | 28900 | 28853 | AC116034 | *Zea mays* clone |
| ZB113.Contig2 (835) | 317 | 344 | 28 | 100 | 27917 | 27890 | AC116034 | *Zea mays* clone |
| ZB113.Contig3 (903) | 137 | 732 | 598 | 97.99 | 1 | 597 | XM_367004 | *Magnaporthe grisea* |
| ZB113.Contig4 (1110) | | | | | | | "NA" | "CentC-like TIGR identified" |
| ZB113.Contig5 (586) | | | | | | | "NA" | "pCHR758mcv" |
| ZB113.Contig6 (857) | | | | | | | "NA" | "pCHR758mcv" |
| ZB113.Contig7 (119) | 20 | 95 | 76 | 96.05 | 264 | 339 | AY046113 | yeast 26S ribosomal RNA |
| ZB113.Contig8 (1510) | | | | | | | "NA" | "CentC-like TIGR identified" |
| ZB113.Contig9 (1785) | | | | | | | "NA" | "pCHR758mcv" |
| ZB113.Contig10 (867) | 1 | 831 | 831 | 98.92 | 8132 | 8957 | AF162223 | Tn10 |
| ZB113.Contig11 (3369) | | | | | | | "NA" | "CentC-like TIGR identified" |
| ZB113.Contig12 (5594) | | | | | | | "NA" | "pCHR758mcv" |
| ZB113.Contig13 (5111) | | | | | | | "NA" | "pCHR758mcv" |
| ZB113.Contig14 (8559) | 57 | 4643 | | | | | "NA" | "CRM retrotrans-like TIGR identified" |
| ZB113.Contig14 (8559) | 4643 | 7938 | | | | | "NA" | "CentC-like TIGR identified" |
| ZB113.Contig14 (8559) | 7937 | 8511 | | | | | "NA" | "CRM retrotrans-like TIGR identified" |
| ZB113.Contig15 (10771) | | | | | | | "NA" | "CentC-like TIGR identified" |
| ZB113.Contig16 (15540) | 37 | 9786 | | | | | "NA" | "CRM retrotrans-like TIGR identified" |
| ZB113.Contig16 (15540) | 9589 | 10101 | | | | | "NA" | "CentA-like TIGR identified" |
| ZB113.Contig16 (15540) | 9916 | 12079 | | | | | "NA" | "CRM retrotrans-like TIGR identified" |
| ZB113.Contig16 (15540) | 12080 | 12436 | | | | | "NA" | "pCHR758mcv" |
| ZB113.Contig16 (15540) | 12533 | 14274 | | | | | "NA" | "CRM retrotrans-like TIGR identified" |
| ZB113.Contig16 (15540) | 14274 | 15203 | | | | | "NA" | "pCHR758mcv" |
| ZB113.Contig16 (15540) | 15203 | 15404 | | | | | "NA" | "CRM retrotrans-like TIGR identified" |
| ZB113.Contig16 (15540) | 15404 | 15540 | | | | | "NA" | "pCHR758mcv" |
| ZB113.Contig17 (14443) | | | | | | | "NA" | "CentC-like TIGR identified" |
| ZB113.Contig18 (20048) | 57 | 7388 | | | | | "NA" | "CentC-like TIGR identified" |
| ZB113.Contig18 (20048) | 7389 | 10554 | | | | | "NA" | "CRM retrotrans-like TIGR identified" |
| ZB113.Contig18 (20048) | 10512 | 10664 | | | | | "No Match" | None |
| ZB113.Contig18 (20048) | 10633 | 20015 | | | | | "NA" | "CentC-like TIGR identified" |

The identity, distribution and frequency of repeats within the centromere sequences of ZB113 is set out in Table 16. The contigs were also compared to the TIGR maize database at the Institute of Genomic Research Web Site. Results of this comparison are summarized in Table 16. Sequence regions from ZB113 are identified by 54 named TIGR maize sequence database records. Among these, 38 records are CentC variants and many are multiply represented. The remaining 16 records are not CentC and are either uniquely represented or multiply represented by non-overlapping fragments, apart from SmO-TOT00200141, SmOTOT00200215, SmOTOT00200264, SmOTOT00200480, SmOTOT00201588.

TABLE 17

ZB113 TIGR Maize Sequence Content

| Contig (length) | Contig Match | | | | Maize Repeat DB | TIGR |
|---|---|---|---|---|---|---|
| | begin | end | length | % diverge | Identifier | homology |
| ZB113.Contig2 (835) | 156 | 384 | 228 | 2.2 | SmOTOT00200480 | family_1868_C1 |
| ZB113.Contig2 (835) | 390 | 698 | 308 | 1.9 | SmOTOT00200215 | family_1380_C2 |
| ZB113.Contig2 (835) | 700 | 748 | 48 | 2.1 | SmOTOT00200303 | family_14706_C1 |
| ZB113.Contig2 (835) | 745 | 835 | 90 | 6.7 | SmOTOT00200264 | family_1431_C3 |
| ZB113.Contig4 (1110) | 78 | 233 | 155 | 3.2 | SgCMCM00200034 | CentC |
| ZB113.Contig4 (1110) | 234 | 369 | 135 | 4.4 | SgCMCM00200034 | CentC |
| ZB113.Contig4 (1110) | 370 | 524 | 154 | 1.9 | SgCMCM00200228 | CentC |
| ZB113.Contig4 (1110) | 525 | 678 | 153 | 1.3 | SgCMCM00200173 | CentC |
| ZB113.Contig4 (1110) | 679 | 833 | 154 | 2.6 | SgCMCM00200034 | CentC |
| ZB113.Contig4 (1110) | 834 | 988 | 154 | 1.3 | SgCMCM00200228 | CentC |
| ZB113.Contig4 (1110) | 989 | 1060 | 71 | 0 | SgCMCM00200173 | CentC |
| ZB113.Contig8 (1510) | 5 | 37 | 32 | 3 | SgCMCM00200269 | CentC |
| ZB113.Contig8 (1510) | 38 | 192 | 154 | 1.9 | SgCMCM00200034 | CentC |
| ZB113.Contig8 (1510) | 193 | 346 | 153 | 1.9 | SgCMCM00200228 | CentC |
| ZB113.Contig8 (1510) | 347 | 501 | 154 | 1.9 | SgCMCM00200034 | CentC |
| ZB113.Contig8 (1510) | 502 | 656 | 154 | 1.9 | SgCMCM00200228 | CentC |
| ZB113.Contig8 (1510) | 657 | 811 | 154 | 1.3 | SgCMCM00200099 | CentC |
| ZB113.Contig8 (1510) | 812 | 966 | 154 | 3.2 | SgCMCM00200034 | CentC |
| ZB113.Contig8 (1510) | 967 | 1122 | 155 | 1.3 | SgCMCM00200530 | CentC |

TABLE 17-continued

ZB113 TIGR Maize Sequence Content

| Contig (length) | Contig Match begin | end | length | % diverge | Maize Repeat DB Identifier | TIGR homology |
|---|---|---|---|---|---|---|
| ZB113.Contig8 (1510) | 1123 | 1277 | 154 | 3.9 | SgCMCM00200058 | CentC |
| ZB113.Contig8 (1510) | 1279 | 1433 | 154 | 2.6 | SgCMCM00200034 | CentC |
| ZB113.Contig8 (1510) | 1434 | 1471 | 37 | 13.2 | SgCMCM00200214 | CentC |
| ZB113.Contig8 (1510) | 1434 | 1467 | 33 | 8.8 | SgCMCM00200257 | CentC |
| ZB113.Contig8 (1510) | 1434 | 1460 | 26 | 0 | SgCMCM00200350 | CentC |
| ZB113.Contig10 (867) | 1 | 831 | 830 | 0.5 | SmOTOT00102689 | family_7207_C1 |
| ZB113.Contig11 (3369) | 52 | 177 | 125 | 1.6 | SgCMCM00200034 | CentC |
| ZB113.Contig11 (3369) | 178 | 332 | 154 | 1.9 | SgCMCM00200034 | CentC |
| ZB113.Contig11 (3369) | 333 | 486 | 153 | 2.6 | SgCMCM00200017 | CentC |
| ZB113.Contig11 (3369) | 487 | 641 | 154 | 1.9 | SgCMCM00200034 | CentC |
| ZB113.Contig11 (3369) | 642 | 797 | 155 | 1.3 | SgCMCM00200099 | CentC |
| ZB113.Contig11 (3369) | 798 | 954 | 156 | 3.8 | SgCMCM00200014 | CentC |
| ZB113.Contig11 (3369) | 958 | 1115 | 157 | 5.8 | SgCMCM00200034 | CentC |
| ZB113.Contig11 (3369) | 1116 | 1270 | 154 | 2.6 | SgCMCM00200034 | CentC |
| ZB113.Contig11 (3369) | 1271 | 1425 | 154 | 1.9 | SgCMCM00200034 | CentC |
| ZB113.Contig11 (3369) | 1426 | 1579 | 153 | 1.9 | SgCMCM00200228 | CentC |
| ZB113.Contig11 (3369) | 1580 | 1735 | 155 | 1.9 | SgCMCM00200228 | CentC |
| ZB113.Contig11 (3369) | 1736 | 1890 | 154 | 2.6 | SgCMCM00200228 | CentC |
| ZB113.Contig11 (3369) | 1891 | 2046 | 155 | 0.6 | SgCMCM00200095 | CentC |
| ZB113.Contig11 (3369) | 2047 | 2201 | 154 | 1.3 | SgCMCM00200228 | CentC |
| ZB113.Contig11 (3369) | 2202 | 2358 | 156 | 1.9 | SgCMCM00200026 | CentC |
| ZB113.Contig11 (3369) | 2359 | 2513 | 154 | 2.6 | SgCMCM00200034 | CentC |
| ZB113.Contig11 (3369) | 2514 | 2669 | 155 | 2.6 | SgCMCM00200034 | CentC |
| ZB113.Contig11 (3369) | 2670 | 2824 | 154 | 0 | SgCMCM00200228 | CentC |
| ZB113.Contig11 (3369) | 2825 | 2979 | 154 | 1.9 | SgCMCM00200228 | CentC |
| ZB113.Contig11 (3369) | 2980 | 3135 | 155 | 0.6 | SgCMCM00200095 | CentC |
| ZB113.Contig11 (3369) | 3136 | 3290 | 154 | 2.6 | SgCMCM00200034 | CentC |
| ZB113.Contig11 (3369) | 3291 | 3328 | 37 | 13.2 | SgCMCM00200214 | CentC |
| ZB113.Contig11 (3369) | 3291 | 3324 | 33 | 8.8 | SgCMCM00200257 | CentC |
| ZB113.Contig11 (3369) | 3291 | 3317 | 26 | 0 | SgCMCM00200095 | CentC |
| ZB113.Contig14 (8559) | 57 | 1862 | 1805 | 0.6 | SiCMCMOOT0036 | CRM |
| ZB113.Contig14 (8559) | 1895 | 2046 | 151 | 1.3 | SmOTOT00201588 | family_6912_C1 |
| ZB113.Contig14 (8559) | 2035 | 2541 | 506 | 24.5 | SiCMCMOOT0036 | CRM |
| ZB113.Contig14 (8559) | 2524 | 3249 | 725 | 1.4 | SmOTOT00200264 | family_1431_C3 |
| ZB113.Contig14 (8559) | 3179 | 3581 | 402 | 23 | SmOTOT00101933 | family_4330_C5 |
| ZB113.Contig14 (8559) | 3296 | 3604 | 308 | 1.9 | SmOTOT00200215 | family_1380_C2 |
| ZB113.Contig14 (8559) | 3610 | 4066 | 456 | 2.5 | SmOTOT00200480 | family_1868_C1 |
| ZB113.Contig14 (8559) | 3968 | 4277 | 309 | 25.4 | SiCMCMOOT0036 | CRM |
| ZB113.Contig14 (8559) | 4245 | 4643 | 398 | 0.8 | SmOTOT00200141 | family_1241_C3 |
| ZB113.Contig14 (8559) | 4643 | 5076 | 433 | 3 | SgTERTOOT02246 | put. retrotrans. |
| ZB113.Contig14 (8559) | 5077 | 5234 | 157 | 2.6 | SgCMCM00200102 | CentC |
| ZB113.Contig14 (8559) | 5235 | 5390 | 155 | 0.6 | SgCMCM00200099 | CentC |
| ZB113.Contig14 (8559) | 5391 | 5545 | 154 | 1.9 | SgCMCM00200034 | CentC |
| ZB113.Contig14 (8559) | 5546 | 5700 | 154 | 1.9 | SgCMCM00200228 | CentC |
| ZB113.Contig14 (8559) | 5701 | 5855 | 154 | 1.9 | SgCMCM00200228 | CentC |
| ZB113.Contig14 (8559) | 5856 | 6011 | 155 | 1.3 | SgCMCM00200095 | CentC |
| ZB113.Contig14 (8559) | 6012 | 6166 | 154 | 3.9 | SgCMCM00200034 | CentC |
| ZB113.Contig14 (8559) | 6167 | 6321 | 154 | 1.9 | SgCMCM00200034 | CentC |
| ZB113.Contig14 (8559) | 6322 | 6476 | 154 | 0.7 | SgCMCM00200228 | CentC |
| ZB113.Contig14 (8559) | 6477 | 6631 | 154 | 1.9 | SgCMCM00200228 | CentC |
| ZB113.Contig14 (8559) | 6632 | 6787 | 155 | 0.6 | SgCMCM00200095 | CentC |
| ZB113.Contig14 (8559) | 6788 | 6942 | 154 | 1.9 | SgCMCM00200228 | CentC |
| ZB113.Contig14 (8559) | 6943 | 7097 | 154 | 1.9 | SgCMCM00200034 | CentC |
| ZB113.Contig14 (8559) | 7098 | 7252 | 154 | 1.9 | SgCMCM00200034 | CentC |
| ZB113.Contig14 (8559) | 7253 | 7409 | 156 | 2.5 | SgCMCM00200026 | CentC |
| ZB113.Contig14 (8559) | 7410 | 7565 | 155 | 0.6 | SgCMCM00200095 | CentC |
| ZB113.Contig14 (8559) | 7566 | 7720 | 154 | 1.9 | SgCMCM00200034 | CentC |
| ZB113.Contig14 (8559) | 7721 | 7875 | 154 | 1.9 | SgCMCM00200034 | CentC |
| ZB113.Contig14 (8559) | 7876 | 7938 | 62 | 3.2 | SgCMCM00200356 | CentC |
| ZB113.Contig14 (8559) | 7937 | 8511 | 574 | 11.5 | SiCMCMOOT0036 | put. retrotrans. |
| ZB113.Contig16 (15540) | 37 | 5452 | 5415 | 1.7 | SiCMCMOOT0036 | put. retrotrans. |
| ZB113.Contig16 (15540) | 5453 | 8994 | 3541 | 25.8 | SiCMCMOOT0036 | put. retrotrans. |
| ZB113.Contig16 (15540) | 8955 | 9353 | 398 | 0.8 | SmOTOT00200141 | family_1241_C3 |
| ZB113.Contig16 (15540) | 9317 | 9520 | 203 | 28.6 | SiCMCMOOT0033 | centromeric repeat |
| ZB113.Contig16 (15540) | 9532 | 9786 | 254 | 17.7 | SgTERTOOT02246 | put. retrotrans. |
| ZB113.Contig16 (15540) | 9589 | 10101 | 512 | 17.1 | SiTERTOOT0090 | CentA |
| ZB113.Contig16 (15540) | 9916 | 12079 | 2163 | 21.6 | SiCMCMOOT0036 | CRM |
| ZB113.Contig16 (15540) | 12533 | 12567 | 34 | 6.1 | SmOTOT00101153 | family_26265_C1 |
| ZB113.Contig16 (15540) | 12537 | 12812 | 275 | 17.4 | SmOTOT00102620 | family_68_C5 |
| ZB113.Contig16 (15540) | 12815 | 13013 | 198 | 18.6 | SmOTOT00100244 | family_1167_C2 |
| ZB113.Contig15 (10771) | 62 | 216 | 154 | 1.9 | SgCMCM00200224 | CentC |
| ZB113.Contig15 (10771) | 217 | 371 | 154 | 1.3 | SgCMCM00200034 | CentC |
| ZB113.Contig15 (10771) | 372 | 526 | 154 | 3.2 | SgCMCM00200034 | CentC |
| ZB113.Contig15 (10771) | 527 | 682 | 155 | 2.6 | SgCMCM00200034 | CentC |

TABLE 17-continued

ZB113 TIGR Maize Sequence Content

| Contig (length) | Contig Match | | | | Maize Repeat DB | TIGR |
| --- | --- | --- | --- | --- | --- | --- |
| | begin | end | length | % diverge | Identifier | homology |
| ZB113.Contig15 (10771) | 683 | 837 | 154 | 1.9 | SgCMCM00200228 | CentC |
| ZB113.Contig15 (10771) | 838 | 994 | 156 | 1.9 | SgCMCM00200026 | CentC |
| ZB113.Contig15 (10771) | 995 | 1150 | 155 | 1.3 | SgCMCM00200095 | CentC |
| ZB113.Contig15 (10771) | 1151 | 1305 | 154 | 3.2 | SgCMCM00200034 | CentC |
| ZB113.Contig15 (10771) | 1306 | 1460 | 154 | 1.9 | SgCMCM00200034 | CentC |
| ZB113.Contig15 (10771) | 1461 | 1615 | 154 | 1.9 | SgCMCM00200228 | CentC |
| ZB113.Contig15 (10771) | 1616 | 1770 | 154 | 1.3 | SgCMCM00200228 | CentC |
| ZB113.Contig15 (10771) | 1771 | 1926 | 155 | 0.6 | SgCMCM00200095 | CentC |
| ZB113.Contig15 (10771) | 1927 | 2081 | 154 | 2.6 | SgCMCM00200034 | CentC |
| ZB113.Contig15 (10771) | 2082 | 2236 | 154 | 1.9 | SgCMCM00200034 | CentC |
| ZB113.Contig15 (10771) | 2237 | 2391 | 154 | 2.6 | SgCMCM00200228 | CentC |
| ZB113.Contig15 (10771) | 2392 | 2547 | 155 | 0.6 | SgCMCM00200095 | CentC |
| ZB113.Contig15 (10771) | 2548 | 2702 | 154 | 2.6 | SgCMCM00200034 | CentC |
| ZB113.Contig15 (10771) | 2703 | 2857 | 154 | 1.9 | SgCMCM00200034 | CentC |
| ZB113.Contig15 (10771) | 2858 | 3012 | 154 | 0.7 | SgCMCM00200228 | CentC |
| ZB113.Contig15 (10771) | 3013 | 3167 | 154 | 1.3 | SgCMCM00200228 | CentC |
| ZB113.Contig15 (10771) | 3168 | 3323 | 155 | 0.6 | SgCMCM00200095 | CentC |
| ZB113.Contig15 (10771) | 3324 | 3478 | 154 | 1.9 | SgCMCM00200034 | CentC |
| ZB113.Contig15 (10771) | 3479 | 3633 | 154 | 1.9 | SgCMCM00200034 | CentC |
| ZB113.Contig15 (10771) | 3634 | 3788 | 154 | 0.7 | SgCMCM00200228 | CentC |
| ZB113.Contig15 (10771) | 3789 | 3943 | 154 | 1.3 | SgCMCM00200228 | CentC |
| ZB113.Contig15 (10771) | 3944 | 4099 | 155 | 1.3 | SgCMCM00200095 | CentC |
| ZB113.Contig15 (10771) | 4100 | 4254 | 154 | 2.6 | SgCMCM00200034 | CentC |
| ZB113.Contig15 (10771) | 4255 | 4409 | 154 | 1.9 | SgCMCM00200034 | CentC |
| ZB113.Contig15 (10771) | 4410 | 4564 | 154 | 0.7 | SgCMCM00200228 | CentC |
| ZB113.Contig15 (10771) | 4565 | 4719 | 154 | 0.7 | SgCMCM00200034 | CentC |
| ZB113.Contig15 (10771) | 4720 | 4874 | 154 | 1.9 | SgCMCM00200228 | CentC |
| ZB113.Contig15 (10771) | 4875 | 5029 | 154 | 1.9 | SgCMCM00200228 | CentC |
| ZB113.Contig15 (10771) | 5030 | 5185 | 155 | 1.3 | SgCMCM00200095 | CentC |
| ZB113.Contig15 (10771) | 5186 | 5340 | 154 | 3.2 | SgCMCM00200034 | CentC |
| ZB113.Contig15 (10771) | 5341 | 5495 | 154 | 1.3 | SgCMCM00200034 | CentC |
| ZB113.Contig15 (10771) | 5496 | 5649 | 153 | 1.3 | SgCMCM00200002 | CentC |
| ZB113.Contig15 (10771) | 5650 | 5806 | 156 | 1.3 | SgCMCM00200026 | CentC |
| ZB113.Contig15 (10771) | 5807 | 5961 | 154 | 1.9 | SgCMCM00200034 | CentC |
| ZB113.Contig15 (10771) | 5962 | 6115 | 153 | 0 | SgCMCM00200530 | CentC |
| ZB113.Contig15 (10771) | 6116 | 6270 | 154 | 4.5 | SgCMCM00200058 | CentC |
| ZB113.Contig15 (10771) | 6272 | 6426 | 154 | 3.2 | SgCMCM00200034 | CentC |
| ZB113.Contig15 (10771) | 6427 | 6581 | 154 | 1.3 | SgCMCM00200034 | CentC |
| ZB113.Contig15 (10771) | 6582 | 6737 | 155 | 1.9 | SgCMCM00200099 | CentC |
| ZB113.Contig15 (10771) | 6738 | 6891 | 153 | 1.3 | SiCMCM0020001 | CentC |
| ZB113.Contig15 (10771) | 6892 | 7048 | 156 | 1.3 | SgCMCM00200026 | CentC |
| ZB113.Contig15 (10771) | 7049 | 7203 | 154 | 1.3 | SgCMCM00200034 | CentC |
| ZB113.Contig15 (10771) | 7204 | 7358 | 154 | 1.3 | SgCMCM00200034 | CentC |
| ZB113.Contig15 (10771) | 7359 | 7513 | 154 | 2.6 | SgCMCM00200034 | CentC |
| ZB113.Contig15 (10771) | 7514 | 7668 | 154 | 1.3 | SgCMCM00200017 | CentC |
| ZB113.Contig15 (10771) | 7669 | 7825 | 156 | 1.3 | SgCMCM00200026 | CentC |
| ZB113.Contig15 (10771) | 7826 | 7980 | 154 | 2.6 | SgCMCM00200034 | CentC |
| ZB113.Contig15 (10771) | 7981 | 8135 | 154 | 1.9 | SgCMCM00200034 | CentC |
| ZB113.Contig15 (10771) | 8136 | 8290 | 154 | 1.9 | SgCMCM00200034 | CentC |
| ZB113.Contig15 (10771) | 8291 | 8445 | 154 | 1.3 | SgCMCM00200228 | CentC |
| ZB113.Contig15 (10771) | 8446 | 8600 | 154 | 1.9 | SgCMCM00200228 | CentC |
| ZB113.Contig15 (10771) | 8601 | 8757 | 156 | 0.6 | SgCMCM00200026 | CentC |
| ZB113.Contig15 (10771) | 8758 | 8912 | 154 | 2.6 | SgCMCM00200034 | CentC |
| ZB113.Contig15 (10771) | 8913 | 9067 | 154 | 1.9 | SgCMCM00200034 | CentC |
| ZB113.Contig15 (10771) | 9068 | 9223 | 155 | 2.6 | SgCMCM00200228 | CentC |
| ZB113.Contig15 (10771) | 9224 | 9378 | 154 | 2.6 | SgCMCM00200034 | CentC |
| ZB113.Contig15 (10771) | 9379 | 9533 | 154 | 1.9 | SgCMCM00200099 | CentC |
| ZB113.Contig15 (10771) | 9534 | 9688 | 154 | 2.6 | SgCMCM00200034 | CentC |
| ZB113.Contig15 (10771) | 9689 | 9842 | 153 | 0 | SgCMCM00200530 | CentC |
| ZB113.Contig15 (10771) | 9843 | 9997 | 154 | 3.9 | SgCMCM00200058 | CentC |
| ZB113.Contig15 (10771) | 9999 | 10153 | 154 | 3.2 | SgCMCM00200034 | CentC |
| ZB113.Contig15 (10771) | 10154 | 10308 | 154 | 1.3 | SgCMCM00200034 | CentC |
| ZB113.Contig15 (10771) | 10309 | 10464 | 155 | 1.9 | SgCMCM00200034 | CentC |
| ZB113.Contig15 (10771) | 10465 | 10619 | 154 | 3.2 | SgCMCM00200044 | CentC |
| ZB113.Contig15 (10771) | 10620 | 10759 | 139 | 9.1 | SgCMCM00200311 | CentC |
| ZB113.Contig15 (10771) | 10620 | 10726 | 106 | 3.7 | SgCMCM00200152 | CentC |
| ZB113.Contig17 (14443) | 1 | 91 | 90 | 9.9 | SgCMCM00200454 | CentC |
| ZB113.Contig17 (14443) | 13 | 91 | 78 | 0 | SgCMCM00200530 | CentC |
| ZB113.Contig17 (14443) | 92 | 246 | 154 | 1.9 | SgCMCM00200099 | CentC |
| ZB113.Contig17 (14443) | 247 | 402 | 155 | 1.3 | SgCMCM00200099 | CentC |
| ZB113.Contig17 (14443) | 403 | 561 | 158 | 2.6 | SgCMCM00200102 | CentC |
| ZB113.Contig17 (14443) | 562 | 716 | 154 | 2.6 | SgCMCM00200034 | CentC |
| ZB113.Contig17 (14443) | 717 | 870 | 153 | 1.3 | SgCMCM00200173 | CentC |
| ZB113.Contig17 (14443) | 871 | 1025 | 154 | 1.9 | SgCMCM00200228 | CentC |

TABLE 17-continued

ZB113 TIGR Maize Sequence Content

| Contig (length) | Contig Match | | | | Maize Repeat DB Identifier | TIGR homology |
|---|---|---|---|---|---|---|
| | begin | end | length | % diverge | | |
| ZB113.Contig17 (14443) | 1026 | 1161 | 135 | 4.4 | SgCMCM00200034 | CentC |
| ZB113.Contig17 (14443) | 1162 | 1317 | 155 | 2.6 | SgCMCM00200034 | CentC |
| ZB113.Contig17 (14443) | 1318 | 1472 | 154 | 1.3 | SgCMCM00200034 | CentC |
| ZB113.Contig17 (14443) | 1473 | 1627 | 154 | 1.9 | SgCMCM00200034 | CentC |
| ZB113.Contig17 (14443) | 1628 | 1782 | 154 | 0.7 | SgCMCM00200034 | CentC |
| ZB113.Contig17 (14443) | 1783 | 1937 | 154 | 1.3 | SgCMCM00200224 | CentC |
| ZB113.Contig17 (14443) | 1938 | 2093 | 155 | 2.6 | SgCMCM00200014 | CentC |
| ZB113.Contig17 (14443) | 2094 | 2249 | 155 | 1.3 | SgCMCM00200102 | CentC |
| ZB113.Contig17 (14443) | 2250 | 2405 | 155 | 1.9 | SgCMCM00200079 | CentC |
| ZB113.Contig17 (14443) | 2406 | 2560 | 154 | 2.6 | SgCMCM00200228 | CentC |
| ZB113.Contig17 (14443) | 2561 | 2715 | 154 | 0 | SgCMCM00200034 | CentC |
| ZB113.Contig17 (14443) | 2716 | 2870 | 154 | 3.2 | SgCMCM00200034 | CentC |
| ZB113.Contig17 (14443) | 2871 | 3025 | 154 | 1.9 | SgCMCM00200224 | CentC |
| ZB113.Contig17 (14443) | 3026 | 3180 | 154 | 2.6 | SgCMCM00200034 | CentC |
| ZB113.Contig17 (14443) | 3181 | 3337 | 156 | 1.9 | SgCMCM00200026 | CentC |
| ZB113.Contig17 (14443) | 3338 | 3492 | 154 | 1.3 | SgCMCM00200228 | CentC |
| ZB113.Contig17 (14443) | 3493 | 3647 | 154 | 1.3 | SgCMCM00200228 | CentC |
| ZB113.Contig17 (14443) | 3648 | 3802 | 154 | 1.9 | SgCMCM00200034 | CentC |
| ZB113.Contig17 (14443) | 3803 | 3957 | 154 | 3.2 | SgCMCM00200034 | CentC |
| ZB113.Contig17 (14443) | 3958 | 4114 | 156 | 0.6 | SgCMCM00200026 | CentC |
| ZB113.Contig17 (14443) | 4115 | 4269 | 154 | 0.7 | SgCMCM00200228 | CentC |
| ZB113.Contig17 (14443) | 4270 | 4424 | 154 | 1.3 | SgCMCM00200228 | CentC |
| ZB113.Contig17 (14443) | 4425 | 4579 | 154 | 6.5 | SgCMCM00200224 | CentC |
| ZB113.Contig17 (14443) | 4580 | 4734 | 154 | 0.7 | SgCMCM00200224 | CentC |
| ZB113.Contig17 (14443) | 4735 | 4894 | 159 | 0 | SgCMCM00200500 | CentC |
| ZB113.Contig17 (14443) | 4895 | 5049 | 154 | 2.6 | SgCMCM00200068 | CentC |
| ZB113.Contig17 (14443) | 5050 | 5204 | 154 | 0.7 | SgCMCM00200228 | CentC |
| ZB113.Contig17 (14443) | 5205 | 5359 | 154 | 0.7 | SgCMCM00200228 | CentC |
| ZB113.Contig17 (14443) | 5360 | 5515 | 155 | 1.3 | SgCMCM00200034 | CentC |
| ZB113.Contig17 (14443) | 5516 | 5670 | 154 | 1.3 | SgCMCM00200228 | CentC |
| ZB113.Contig17 (14443) | 5671 | 5826 | 155 | 0.6 | SgCMCM00200095 | CentC |
| ZB113.Contig17 (14443) | 5827 | 5981 | 154 | 1.3 | SgCMCM00200228 | CentC |
| ZB113.Contig17 (14443) | 5982 | 6136 | 154 | 1.9 | SgCMCM00200228 | CentC |
| ZB113.Contig17 (14443) | 6137 | 6292 | 155 | 0.6 | SgCMCM00200095 | CentC |
| ZB113.Contig17 (14443) | 6293 | 6447 | 154 | 1.3 | SgCMCM00200228 | CentC |
| ZB113.Contig17 (14443) | 6448 | 6602 | 154 | 0.7 | SgCMCM00200228 | CentC |
| ZB113.Contig17 (14443) | 6603 | 6757 | 154 | 1.9 | SgCMCM00200034 | CentC |
| ZB113.Contig17 (14443) | 6758 | 6912 | 154 | 1.3 | SgCMCM00200034 | CentC |
| ZB113.Contig17 (14443) | 6913 | 7067 | 154 | 2.6 | SgCMCM00200034 | CentC |
| ZB113.Contig17 (14443) | 7068 | 7224 | 156 | 1.3 | SgCMCM00200026 | CentC |
| ZB113.Contig17 (14443) | 7225 | 7379 | 154 | 0 | SgCMCM00200228 | CentC |
| ZB113.Contig17 (14443) | 7380 | 7533 | 153 | 1.9 | SgCMCM00200228 | CentC |
| ZB113.Contig17 (14443) | 7534 | 7688 | 154 | 1.9 | SgCMCM00200034 | CentC |
| ZB113.Contig17 (14443) | 7689 | 7843 | 154 | 2.6 | SgCMCM00200034 | CentC |
| ZB113.Contig17 (14443) | 7844 | 7998 | 154 | 2.6 | SgCMCM00200034 | CentC |
| ZB113.Contig17 (14443) | 8000 | 8154 | 154 | 3.9 | SgCMCM00200058 | CentC |
| ZB113.Contig17 (14443) | 8155 | 8310 | 155 | 1.3 | SgCMCM00200530 | CentC |
| ZB113.Contig17 (14443) | 8311 | 8465 | 154 | 3.2 | SgCMCM00200034 | CentC |
| ZB113.Contig17 (14443) | 8466 | 8621 | 155 | 0.6 | SgCMCM00200099 | CentC |
| ZB113.Contig17 (14443) | 8622 | 8780 | 158 | 2.6 | SgCMCM00200102 | CentC |
| ZB113.Contig17 (14443) | 8781 | 8935 | 154 | 1.9 | SgCMCM00200034 | CentC |
| ZB113.Contig17 (14443) | 8936 | 9089 | 153 | 0 | SgCMCM00200173 | CentC |
| ZB113.Contig17 (14443) | 9090 | 9244 | 154 | 0.7 | SgCMCM00200228 | CentC |
| ZB113.Contig17 (14443) | 9245 | 9399 | 154 | 1.9 | SgCMCM00200034 | CentC |
| ZB113.Contig17 (14443) | 9400 | 9554 | 154 | 1.9 | SgCMCM00200034 | CentC |
| ZB113.Contig17 (14443) | 9555 | 9709 | 154 | 1.9 | SgCMCM00200034 | CentC |
| ZB113.Contig17 (14443) | 9710 | 9864 | 154 | 0.7 | SgCMCM00200034 | CentC |
| ZB113.Contig17 (14443) | 9865 | 10017 | 152 | 1.3 | SgCMCM00200026 | CentC |
| ZB113.Contig17 (14443) | 10018 | 10171 | 153 | 1.3 | SgCMCM00200002 | CentC |
| ZB113.Contig17 (14443) | 10172 | 10327 | 155 | 1.3 | SgCMCM00200099 | CentC |
| ZB113.Contig17 (14443) | 10328 | 10482 | 154 | 2.6 | SgCMCM00200034 | CentC |
| ZB113.Contig17 (14443) | 10483 | 10637 | 154 | 0.7 | SgCMCM00200034 | CentC |
| ZB113.Contig17 (14443) | 10638 | 10794 | 156 | 1.3 | SgCMCM00200026 | CentC |
| ZB113.Contig17 (14443) | 10795 | 10948 | 153 | 1.3 | SgCMCM00200005 | CentC |
| ZB113.Contig17 (14443) | 10949 | 11104 | 155 | 1.3 | SgCMCM00200099 | CentC |
| ZB113.Contig17 (14443) | 11105 | 11259 | 154 | 1.3 | SgCMCM00200034 | CentC |
| ZB113.Contig17 (14443) | 11260 | 11414 | 154 | 2.6 | SgCMCM00200034 | CentC |
| ZB113.Contig17 (14443) | 11416 | 11570 | 154 | 3.9 | SgCMCM00200058 | CentC |
| ZB113.Contig17 (14443) | 11571 | 11724 | 153 | 0 | SgCMCM00200530 | CentC |
| ZB113.Contig17 (14443) | 11725 | 11879 | 154 | 1.9 | SgCMCM00200034 | CentC |
| ZB113.Contig17 (14443) | 11880 | 12035 | 155 | 0.6 | SgCMCM00200099 | CentC |
| ZB113.Contig17 (14443) | 12036 | 12194 | 158 | 2.6 | SgCMCM00200102 | CentC |
| ZB113.Contig17 (14443) | 12195 | 12351 | 156 | 3.2 | SgCMCM00200026 | CentC |
| ZB113.Contig17 (14443) | 12352 | 12506 | 154 | 0.7 | SgCMCM00200228 | CentC |

TABLE 17-continued

ZB113 TIGR Maize Sequence Content

| Contig (length) | Contig Match | | | | Maize Repeat DB Identifier | TIGR homology |
|---|---|---|---|---|---|---|
| | begin | end | length | % diverge | | |
| ZB113.Contig17 (14443) | 12507 | 12661 | 154 | 1.3 | SgCMCM00200228 | CentC |
| ZB113.Contig17 (14443) | 12662 | 12816 | 154 | 3.9 | SgCMCM00200224 | CentC |
| ZB113.Contig17 (14443) | 12817 | 12911 | 94 | 3.2 | SgCMCM00200025 | CentC |
| ZB113.Contig17 (14443) | 12911 | 13372 | 461 | 3 | SgTERTOOT02573 | put. retrotrans. |
| ZB113.Contig18 (20048) | 57 | 212 | 155 | 0.6 | SgCMCM00200095 | CentC |
| ZB113.Contig18 (20048) | 213 | 367 | 154 | 3.2 | SgCMCM00200034 | CentC |
| ZB113.Contig18 (20048) | 368 | 522 | 154 | 1.9 | SgCMCM00200034 | CentC |
| ZB113.Contig18 (20048) | 523 | 677 | 154 | 1.3 | SgCMCM00200228 | CentC |
| ZB113.Contig18 (20048) | 678 | 832 | 154 | 2.6 | SgCMCM00200228 | CentC |
| ZB113.Contig18 (20048) | 833 | 988 | 155 | 0.6 | SgCMCM00200095 | CentC |
| ZB113.Contig18 (20048) | 989 | 1143 | 154 | 3.2 | SgCMCM00200034 | CentC |
| ZB113.Contig18 (20048) | 1144 | 1298 | 154 | 1.3 | SgCMCM00200034 | CentC |
| ZB113.Contig18 (20048) | 1299 | 1453 | 154 | 2.6 | SgCMCM00200034 | CentC |
| ZB113.Contig18 (20048) | 1454 | 1609 | 155 | 1.9 | SgCMCM00200079 | CentC |
| ZB113.Contig18 (20048) | 1610 | 1765 | 155 | 1.3 | SgCMCM00200102 | CentC |
| ZB113.Contig18 (20048) | 1766 | 1921 | 155 | 0 | SgCMCM00200099 | CentC |
| ZB113.Contig18 (20048) | 1922 | 2077 | 155 | 2.6 | SgCMCM00200014 | CentC |
| ZB113.Contig18 (20048) | 2078 | 2232 | 154 | 2.6 | SgCMCM00200224 | CentC |
| ZB113.Contig18 (20048) | 2233 | 2387 | 154 | 1.9 | SgCMCM00200017 | CentC |
| ZB113.Contig18 (20048) | 2388 | 2542 | 154 | 2.6 | SgCMCM00200034 | CentC |
| ZB113.Contig18 (20048) | 2543 | 2697 | 154 | 2.6 | SgCMCM00200017 | CentC |
| ZB113.Contig18 (20048) | 2698 | 2852 | 154 | 1.9 | SgCMCM00200034 | CentC |
| ZB113.Contig18 (20048) | 2853 | 3007 | 154 | 0.7 | SgCMCM00200228 | CentC |
| ZB113.Contig18 (20048) | 3008 | 3161 | 153 | 0 | SgCMCM00200173 | CentC |
| ZB113.Contig18 (20048) | 3162 | 3317 | 155 | 1.9 | SgCMCM00200156 | CentC |
| ZB113.Contig18 (20048) | 3318 | 3473 | 155 | 0 | SgCMCM00200167 | CentC |
| ZB113.Contig18 (20048) | 3474 | 3629 | 155 | 3.2 | SgCMCM00200014 | CentC |
| ZB113.Contig18 (20048) | 3630 | 3784 | 154 | 2.6 | SgCMCM00200017 | CentC |
| ZB113.Contig18 (20048) | 3785 | 3940 | 155 | 0 | SgCMCM00200034 | CentC |
| ZB113.Contig18 (20048) | 3941 | 4096 | 155 | 1.3 | SgCMCM00200104 | CentC |
| ZB113.Contig18 (20048) | 4097 | 4251 | 154 | 1.3 | SgCMCM00200034 | CentC |
| ZB113.Contig18 (20048) | 4252 | 4406 | 154 | 1.3 | SgCMCM00200169 | CentC |
| ZB113.Contig18 (20048) | 4407 | 4562 | 155 | 2.6 | SgCMCM00200034 | CentC |
| ZB113.Contig18 (20048) | 4563 | 4718 | 155 | 2.6 | SgCMCM00200102 | CentC |
| ZB113.Contig18 (20048) | 4719 | 4874 | 155 | 0 | SgCMCM00200099 | CentC |
| ZB113.Contig18 (20048) | 4875 | 5027 | 152 | 2 | SgCMCM00200005 | CentC |
| ZB113.Contig18 (20048) | 5028 | 5183 | 155 | 1.9 | SgCMCM00200095 | CentC |
| ZB113.Contig18 (20048) | 5184 | 5339 | 155 | 1.3 | SgCMCM00200034 | CentC |
| ZB113.Contig18 (20048) | 5340 | 5494 | 154 | 0.7 | SgCMCM00200034 | CentC |
| ZB113.Contig18 (20048) | 5495 | 5649 | 154 | 0.7 | SgCMCM00200034 | CentC |
| ZB113.Contig18 (20048) | 5650 | 5804 | 154 | 0 | SgCMCM00200169 | CentC |
| ZB113.Contig18 (20048) | 5805 | 5959 | 154 | 1.9 | SgCMCM00200224 | CentC |
| ZB113.Contig18 (20048) | 5960 | 6115 | 155 | 1.3 | SiCMCM0020001 | CentC |
| ZB113.Contig18 (20048) | 6116 | 6271 | 155 | 3.2 | SgCMCM00200034 | CentC |
| ZB113.Contig18 (20048) | 6272 | 6426 | 154 | 2.6 | SgCMCM00200034 | CentC |
| ZB113.Contig18 (20048) | 6427 | 6581 | 154 | 3.2 | SgCMCM00200169 | CentC |
| ZB113.Contig18 (20048) | 6582 | 6737 | 155 | 1.9 | SgCMCM00200034 | CentC |
| ZB113.Contig18 (20048) | 6738 | 6892 | 154 | 3.2 | SgCMCM00200034 | CentC |
| ZB113.Contig18 (20048) | 6893 | 7047 | 154 | 1.9 | SgCMCM00200034 | CentC |
| ZB113.Contig18 (20048) | 7048 | 7202 | 154 | 4.5 | SgCMCM00200034 | CentC |
| ZB113.Contig18 (20048) | 7203 | 7388 | 185 | 1.1 | SgCMCM00200225 | CentC |
| ZB113.Contig18 (20048) | 7389 | 7548 | 159 | 0 | SgCMCM00200500 | CentC |
| ZB113.Contig18 (20048) | 7549 | 7703 | 154 | 0.7 | SgCMCM00200224 | CentC |
| ZB113.Contig18 (20048) | 7704 | 7858 | 154 | 0.7 | SgCMCM00200005 | CentC |
| ZB113.Contig18 (20048) | 7859 | 7951 | 92 | 4.3 | SgCMCM00200012 | CentC |
| ZB113.Contig18 (20048) | 7952 | 8370 | 418 | 2 | SmOTOT00200141 | family_1241_C3 |
| ZB113.Contig18 (20048) | 8338 | 8646 | 308 | 25.2 | SiCMCMOOT0036 | CRM |
| ZB113.Contig18 (20048) | 8549 | 8927 | 378 | 5.5 | SmOTOT00200480 | family_1868_C1 |
| ZB113.Contig18 (20048) | 8789 | 8949 | 160 | 4.5 | SmOTOT00200480 | family_1868_C1 |
| ZB113.Contig18 (20048) | 8955 | 9262 | 307 | 2.9 | SmOTOT00200215 | family_1380_C2 |
| ZB113.Contig18 (20048) | 8974 | 9371 | 397 | 25.5 | SmOTOT00101933 | family_4330_C5 |
| ZB113.Contig18 (20048) | 9309 | 10034 | 725 | 2.2 | SmOTOT00200264 | family_1431_C3 |
| ZB113.Contig18 (20048) | 10017 | 10554 | 537 | 27.1 | SiCMCMOOT0036 | CRM |
| ZB113.Contig18 (20048) | 10512 | 10664 | 152 | 26.4 | SmOTOT00201588 | family_6912_C1 |
| ZB113.Contig18 (20048) | 10633 | 13769 | 3136 | 25.3 | SiCMCMOOT0036 | CRM |
| ZB113.Contig18 (20048) | 13802 | 13931 | 129 | 0.8 | SmOTOT00101774 | family_3931_C1 |
| ZB113.Contig18 (20048) | 13932 | 17719 | 3787 | 2.5 | SiCMCMOOT0036 | CRM |
| ZB113.Contig18 (20048) | 17718 | 17780 | 62 | 4.8 | SgCMCM00200021 | CentC |
| ZB113.Contig18 (20048) | 17781 | 17936 | 155 | 1.9 | SgCMCM00200095 | CentC |
| ZB113.Contig18 (20048) | 17937 | 18091 | 154 | 1.9 | SgCMCM00200228 | CentC |
| ZB113.Contig18 (20048) | 18092 | 18246 | 154 | 1.9 | SgCMCM00200034 | CentC |
| ZB113.Contig18 (20048) | 18247 | 18401 | 154 | 1.9 | SgCMCM00200034 | CentC |
| ZB113.Contig18 (20048) | 18402 | 18556 | 154 | 2.6 | SgCMCM00200034 | CentC |
| ZB113.Contig18 (20048) | 18557 | 18711 | 154 | 0.7 | SgCMCM00200034 | CentC |

TABLE 17-continued

ZB113 TIGR Maize Sequence Content

| Contig (length) | Contig Match begin | end | length | % diverge | Maize Repeat DB Identifier | TIGR homology |
|---|---|---|---|---|---|---|
| ZB113.Contig18 (20048) | 18712 | 18868 | 156 | 1.3 | SgCMCM00200026 | CentC |
| ZB113.Contig18 (20048) | 18869 | 19022 | 153 | 1.3 | SiCMCM0020001 | CentC |
| ZB113.Contig18 (20048) | 19023 | 19177 | 154 | 1.3 | SgCMCM00200099 | CentC |
| ZB113.Contig18 (20048) | 19178 | 19333 | 155 | 2.6 | SgCMCM00200014 | CentC |
| ZB113.Contig18 (20048) | 19334 | 19489 | 155 | 0.6 | SgCMCM00200099 | CentC |
| ZB113.Contig18 (20048) | 19490 | 19647 | 157 | 3.9 | SgCMCM00200058 | CentC |
| ZB113.Contig18 (20048) | 19648 | 19802 | 154 | 3.2 | SgCMCM00200044 | CentC |
| ZB113.Contig18 (20048) | 19803 | 19958 | 155 | 0.6 | SgCMCM00200099 | CentC |
| ZB113.Contig18 (20048) | 19959 | 20015 | 56 | 8.8 | SgCMCM00200457 | CentC |
| ZB113.Contig18 (20048) | 19959 | 20000 | 41 | 2.4 | SgCMCM00200498 | CentC |

The ZB113 contigs 4, 8, 11, 15, and 17 consist of nearly all repeated sequence, contig 14 has an approximately 4 kb stretch of repeated sequence within its 3' half, and contig 18 has a 5 kb and 3 kb of repeated sequence on its 5' and 3' ends. The repeated regions are apparent both when compared to self and the reverse complement, therefore the larger repeat regions consists of many smaller repeat regions that occur both in the forward and reverse direction.

The consensus sequence of the CentC repeat represented in ZB113 is set out as SEQ ID NO: 71. The variants of the CentC repeats present in ZB113 are set out in Table 17 where the most common base is indicated. Where the most common base occurs less than 60% of the time, the percent occurence of each base is reported.

TABLE 17

ZB113 CentC consensus sequence and variants

| | |
|---|---|
| 1 | C |
| 2 | C |
| 3 | A |
| 4 | T |
| 5 | T (G: 0/T: 100) |
| 6 | T (C: 2/G: 0/T: 98) |
| 7 | C (A: 0/C: 92/T: 8) |
| 8 | T (A: 0/C: 0/T: 100) |
| 9 | T (C: 1/G: 1/T: 98/—: 0) |
| 10 | C (A: 1/C: 84/G: 3/T: 12) |
| 11 | G (A: 1/G: 97/T: 2) |
| 12 | T |
| 13 | T |
| 14 | T (G: 0/T: 100) |
| 15 | T (A: 0/T: 100) |
| 16 | T (C: 0/T: 100) |
| 17 | K(G: 0/T: 0/—: 99) |
| 18 | C (A: 0/C: 95/G: 1/T: 3/—: 0) |
| 19 | G (A: 6/C: 0/G: 89/T: 5) |
| 20 | C (A: 0/C: 78/G: 0/T: 21) |
| 21 | M(A: 2/C: 1/—: 97) |
| 22 | A(A: 2/—: 98) |
| 23 | A (A: 99/C: 0/—: 0) |
| 24 | A (A: 97/C: 1/—: 2) |
| 25 | C (C: 90/G: 3/T: 5/—: 2) |
| 26 | G (A: 3/G: 97) |
| 27 | A (A: 97/G: 3/T: 0) |
| 28 | A (A: 98/G: 0/T: 0/—: 1) |
| 29 | C (A: 1/C: 75/G: 1/—: 23) |
| 30 | V(A: 8/C: 2/G: 0/—: 90) |
| 31 | M(A: 0/C: 17/—: 83) |
| 32 | M(A: 17/C: 6/—: 78) |
| 33 | A (A: 75/—: 25) |
| 34 | T (G: 0/T: 99/—: 0) |
| 35 | G (C: 0/G: 99/T: 0) |
| 36 | C (C: 100/T: 0) |
| 37 | C (A: 1/C: 98/G: 0/T: 1) |
| 38 | C (A: 2/C: 84/G: 7/T: 5/—: 2) |

TABLE 17-continued

ZB113 CentC consensus sequence and variants

| | |
|---|---|
| 39 | B(C: 1/G: 0/T: 0/—: 98) |
| 40 | H(A: 0/C: 0/T: 0/—: 99) |
| 41 | A (A: 100/C: 0/G: 0) |
| 42 | A (A: 99/T: 1) |
| 43 | T (C: 3/T: 97) |
| 44 | C (A: 0/C: 83/G: 0/T: 1/—: 15) |
| 45 | C (C: 99/G: 0/T: 0) |
| 46 | N(A: 0/C: 16/G: 0/T: 0/—: 83) |
| 47 | A (A: 99/C: 1) |
| 48 | C (C: 97/G: 2/T: 1) |
| 49 | T (A: 0/C: 0/T: 99) |
| 50 | W(A: 50/T: 50) |
| 51 | A (A: 99/C: 1/T: 1) |
| 52 | C (C: 99/T: 1) |
| 53 | T (A: 0/T: 100) |
| 54 | T (A: 1/T: 99/—: 0) |
| 55 | T (T: 100/—: 0) |
| 56 | W(A: 1/T: 1/—: 98) |
| 57 | A(A: 0/—: 100) |
| 58 | A (A: 99/G: 1) |
| 59 | G (A: 0/C: 6/G: 94) |
| 60 | G (A: 7/C: 0/G: 92/T: 1/—: 0) |
| 61 | D(A: 1/G: 0/T: 1/—: 99) |
| 62 | T (A: 0/C: 0/T: 99) |
| 63 | C (A: 8/C: 91/G: 0/T: 1) |
| 64 | C (C: 99/T: 0/—: 0) |
| 65 | A (A: 99/C: 0/G: 0/—: 0) |
| 66 | A (A: 99/C: 0/G: 0) |
| 67 | A (A: 100/T: 0) |
| 68 | A |
| 69 | A(A: 2/—: 98) |
| 70 | C (A: 0/C: 99/T: 1) |
| 71 | T (C: 0/T: 100) |
| 72 | C (C: 100/T: 0) |
| 73 | A (A: 100/G: 0) |
| 74 | T (A: 0/C: 0/G: 0/T: 99) |
| 75 | K(G: 35/T: 1/—: 64) |
| 76 | G (A: 0/G: 64/T: 35/—: 0) |
| 77 | T (A: 0/C: 0/G: 0/T: 64/—: 35) |
| 78 | T |
| 79 | T (G: 1/T: 99/—: 0) |
| 80 | G (A: 1/C: 0/G: 88/T: 8/—: 4) |
| 81 | G (A: 5/G: 95) |
| 82 | G (A: 1/G: 94/T: 5) |
| 83 | G (A: 2/G: 98) |
| 84 | D(A: 0/G: 2/T: 3/—: 95) |
| 85 | T (A: 0/G: 5/T: 95) |
| 86 | G (A: 0/C: 0/G: 99) |
| 87 | G (A: 2/C: 0/G: 94/T: 3) |
| 88 | D(A: 0/G: 0/T: 8/—: 91) |
| 89 | T |
| 90 | T (G: 0/T: 100) |
| 91 | T (C: 1/T: 89/—: 10) |
| 92 | C (A: 0/C: 95/G: 0/T: 4) |
| 93 | G (A: 6/C: 0/G: 86/T: 8) |
| 94 | C (A: 1/C: 98/G: 1/T: 1) |

TABLE 17-continued

ZB113 CentC consensus sequence and variants

| | |
|---|---|
| 95 | G (A: 37/C: 0/G: 63) |
| 96 | C (A: 1/C: 99/G: 0/T: 0) |
| 97 | A (A: 99/T: 1) |
| 98 | A (A: 94/G: 6/T: 0) |
| 99 | R(A: 0/G: 0/—: 99) |
| 100 | T |
| 101 | T (G: 0/T: 100) |
| 102 | T |
| 103 | C (A: 0/C: 81/G: 1/T: 18/—: 0) |
| 104 | G (A: 0/C: 0/G: 97/T: 2) |
| 105 | R(A: 0/G: 1/—: 99) |
| 106 | T(T: 1/—: 99) |
| 107 | T (G: 0/T: 100) |
| 108 | T (A: 0/T: 100) |
| 109 | G (C: 0/G: 99/T: 0) |
| 110 | T (C: 16/T: 84) |
| 111 | C (A: 0/C: 99/T: 0) |
| 112 | G (A: 4/C: 0/G: 96) |
| 113 | C (A: 0/C: 99/G: 1) |
| 114 | A (A: 98/G: 1/T: 0) |
| 115 | C (A: 0/C: 97/T: 3) |
| 116 | G (A: 1/G: 99) |
| 117 | T |
| 118 | C (C: 97/T: 3) |
| 119 | T(T: 0/—: 100) |
| 120 | C(C: 0/—: 100) |
| 121 | A |
| 122 | C |
| 123 | C (C: 93/T: 7) |
| 124 | C (C: 99/T: 1) |
| 125 | A |
| 126 | T (A: 0/T: 100) |
| 127 | T (G: 0/T: 100) |
| 128 | T(T: 0/—: 100) |
| 129 | C |
| 130 | C (C: 69/G: 0/T: 31) |
| 131 | G (A: 1/G: 99) |
| 132 | A |
| 133 | A |
| 134 | A |
| 135 | A |
| 136 | M(A: 1/C: 25/—: 74) |
| 137 | C (A: 1/C: 72/G: 18/—: 10) |
| 138 | G (A: 1/G: 96/T: 3) |
| 139 | G (A: 5/G: 95) |
| 140 | G (G: 75/T: 8/—: 17) |
| 141 | T (C: 0/T: 100) |
| 142 | G (A: 24/G: 76) |
| 143 | T (C: 0/T: 100) |
| 144 | C (C: 97/G: 2/T: 0) |
| 145 | G (A: 14/G: 86) |
| 146 | G (G: 83/T: 11/—: 6) |
| 147 | G (A: 4/G: 96/T: 0) |
| 148 | K(G: 55/T: 8/—: 37) |
| 149 | K(G: 4/T: 0/—: 96) |
| 150 | T(G: 1/T: 99) |
| 151 | G (A: 0/G: 100) |
| 152 | C (A: 4/C: 96) |
| 153 | A (A: 100/T: 0) |
| 154 | T (A: 0/C: 1/T: 99) |
| 155 | A |
| 156 | C (A: 3/C: 68/—: 29) |
| 157 | A |
| 158 | A (A: 96/G: 4) |
| 159 | A |
| 160 | G |
| 161 | C |
| 162 | A (A: 99/T: 1) |
| 163 | C |
| 164 | G (A: 1/G: 99) |
| 165 | A (A: 97/C: 3) |
| 166 | G (A: 1/G: 98/—: 1) |
| 167 | T |
| 168 | T (G: 1/T: 99) |
| 169 | T |
| 170 | T |
| 171 | T |
| 172 | G (G: 99/T: 1) |
| 173 | T(T: 0/—: 100) |
| 174 | C |
| 175 | C |
| 176 | A |
| 177 | C (C: 98/G: 2) |
| 178 | C (A: 2/C: 97/T: 1) |
| 179 | G (A: 3/G: 97) |
| 180 | G |
| 181 | A |
| 182 | A |
| 183 | C |
| 184 | C (C: 99/T: 1) |
| 185 | A |
| 186 | T |
| 187 | C |
| 188 | T |
| mean length | 155 |
| stdev | 1.5 |

The sequence of the CRM retrotransposon (SEQ ID NO: 76) was blasted against the contigs of ZB113 and filtered for hits with alignment lengths greater than 50 to determine the representation of CRM in ZB113. The representation of CRM within ZB113 is summarized in Table 18.

TABLE 18

CRM Fragments in ZB113

| Contig | CRM begin | CRM end | % identity | Contig match begin | Contig match end |
|---|---|---|---|---|---|
| ZB113.fasta.screen.Contig14 | 1 | 930 | 99.3 | 933 | 1862 |
| ZB113.fasta.screen.Contig14 | 1 | 515 | 99.8 | 7937 | 8451 |
| ZB113.fasta.screen.Contig14 | 2796 | 2893 | 91.1 | 2132 | 2035 |
| ZB113.fasta.screen.Contig14 | 5765 | 7571 | 90.9 | 57 | 1862 |
| ZB113.fasta.screen.Contig14 | 6640 | 7156 | 83.7 | 7936 | 8451 |
| ZB113.fasta.screen.Contig16 | 1 | 1434 | 99.4 | 5452 | 4019 |
| ZB113.fasta.screen.Contig16 | 1508 | 5417 | 99.6 | 3947 | 37 |
| ZB113.fasta.screen.Contig16 | 4251 | 4744 | 99.3 | 6565 | 7058 |
| ZB113.fasta.screen.Contig16 | 4626 | 4772 | 80.1 | 12043 | 11897 |
| ZB113.fasta.screen.Contig16 | 4945 | 6236 | 80.8 | 11724 | 10433 |
| ZB113.fasta.screen.Contig16 | 4983 | 5342 | 80.0 | 7297 | 7656 |
| ZB113.fasta.screen.Contig16 | 5487 | 5569 | 80.6 | 7801 | 7883 |
| ZB113.fasta.screen.Contig16 | 5757 | 6213 | 85.7 | 8071 | 8527 |
| ZB113.fasta.screen.Contig16 | 6529 | 6653 | 86.8 | 10140 | 10016 |
| ZB113.fasta.screen.Contig16 | 6608 | 6658 | 82.4 | 8922 | 8972 |
| ZB113.fasta.screen.Contig16 | 6638 | 7572 | 84.3 | 5455 | 4522 |
| ZB113.fasta.screen.Contig18 | 1 | 1434 | 99.0 | 17719 | 16288 |
| ZB113.fasta.screen.Contig18 | 1508 | 3791 | 99.4 | 16214 | 13932 |
| ZB113.fasta.screen.Contig18 | 2796 | 2890 | 99.7 | 10426 | 10520 |
| ZB113.fasta.screen.Contig18 | 4251 | 4744 | 80.3 | 11782 | 12275 |
| ZB113.fasta.screen.Contig18 | 4983 | 5342 | 79.8 | 12514 | 12873 |
| ZB113.fasta.screen.Contig18 | 5487 | 5569 | 80.6 | 13018 | 13100 |
| ZB113.fasta.screen.Contig18 | 5757 | 6213 | 88.0 | 13288 | 13744 |
| ZB113.fasta.screen.Contig18 | 6640 | 7572 | 82.1 | 17720 | 16789 |

Five unique repeats were identified in the nucleotide sequence of ZB113 (SmOTOT00200141, SmOTOT00200215 (2 variants), SmOTOT00200264, SmOTOT00200480, SmOTOT00201588 and analyzed for variation in a manner similar to CentC. The repeat SmOTOT00200141 was too large for analysis with source reads matching a wide variety of locations. The consensus sequence of SmOTOT00200215 are set out as SEQ ID NO: 72 and SEQ ID NO: 73. The consensus of SmOTOT00200480 is set out as SEQ ID NO: 74. The consensus of SmOTOT00201588 is set out as SEQ ID NO: 75. The variants of the unique repeats are set out in Tables 18-20 respectively where the most common base is indicated. Where the most common base occurs less than 60% of the time, the percent occurence of each base is reported.

The sequences were queried against GenBank, which returned no feature specific hit. SmOTOT00200215.1 (SEQ ID NO: 72) and SmOTOT00200480 (SEQ ID NO: 74) and SmOTOT00201588 (SEQ ID NO: 75) matched a clone from Zea mays (AC116034), and SmOTOT00200215.2 (SEQ ID NO: 73) returned no matches.

TABLE 19

| SmOTOT00200215.1 Variation in ZB113 | |
|---|---|
| 1 | T |
| 2 | T |
| 3 | T |
| 4 | C |
| 5 | A |
| 6 | T |
| 7 | C |
| 8 | C |
| 9 | C |
| 10 | G |
| 11 | G |
| 12 | T |
| 13 | C |
| 14 | G |
| 15 | T |
| 16 | T |
| 17 | T |
| 18 | T |
| 19 | T |
| 20 | A |
| 21 | G (A: 17/G: 83) |
| 22 | A |
| 23 | A |
| 24 | C |
| 25 | A |
| 26 | T |
| 27 | A |
| 28 | A |
| 29 | C |
| 30 | T |
| 31 | T |
| 32 | G |
| 33 | A |
| 34 | G |
| 35 | G |
| 36 | T |
| 37 | A |
| 38 | C |
| 39 | C |
| 40 | T |
| 41 | T |
| 42 | C |
| 43 | C |
| 44 | G |
| 45 | T |
| 46 | A |
| 47 | A |
| 48 | A |
| 49 | C |
| 50 | C |
| 51 | G |
| 52 | G |
| 53 | G |
| 54 | C |
| 55 | A |
| 56 | T |
| 57 | A |
| 58 | A |
| 59 | C |
| 60 | T |
| 61 | T |
| 62 | T |
| 63 | T |
| 64 | C |
| 65 | G |
| 66 | C |
| 67 | T |
| 68 | C |
| 69 | G |

TABLE 19-continued

| SmOTOT00200215.1 Variation in ZB113 | |
|---|---|
| 70 | G |
| 71 | G |
| 72 | T |
| 73 | G |
| 74 | T |
| 75 | C |
| 76 | C |
| 77 | A |
| 78 | A |
| 79 | A |
| 80 | A |
| 81 | A |
| 82 | A |
| 83 | T |
| 84 | C |
| 85 | T |
| 86 | G |
| 87 | A |
| 88 | A |
| 89 | A |
| 90 | T |
| 91 | T |
| 92 | T |
| 93 | T |
| 94 | T |
| 95 | A |
| 96 | T (C: 17/T: 83) |
| 97 | A |
| 98 | G |
| 99 | G |
| 100 | A |
| 101 | G |
| 102 | C |
| 103 | T |
| 104 | A (A: 83/T: 17) |
| 105 | G |
| 106 | T |
| 107 | T |
| 108 | G |
| 109 | A |
| 110 | C |
| 111 | A |
| 112 | C |
| 113 | C |
| 114 | A |
| 115 | T |
| 116 | T |
| 117 | C |
| 118 | T (G: 17/T: 83) |
| 119 | G |
| 120 | A |
| 121 | G |
| 122 | G |
| 123 | C |
| 124 | C |
| 125 | G |
| 126 | G |
| 127 | C |
| 128 | C |
| 129 | A |
| 130 | A |
| 131 | A |
| 132 | C |
| 133 | T |
| 134 | C (C: 83/G: 17) |
| 135 | A |
| 136 | C |
| 137 | C |
| 138 | T |
| 139 | A (A: 83/T: 17) |
| 140 | C (C: 83/T: 17) |
| 141 | G |
| 142 | G |
| 143 | T |
| 144 | C |
| 145 | T |
| 146 | G |
| 147 | T |

TABLE 19-continued

| SmOTOT00200215.1 Variation in ZB113 | |
|---|---|
| 148 | T |
| 149 | T |
| 150 | G |
| 151 | G |
| 152 | G |
| 153 | G |
| 154 | T |
| 155 | T |
| 156 | C |
| 157 | G |
| 158 | A |
| mean length | 156 |
| stdev | 2.9 |

TABLE 20

| SmOTOT00200215.2 Variation in ZB113 | |
|---|---|
| 1 | A |
| 2 | C |
| 3 | A |
| 4 | A |
| 5 | A |
| 6 | C |
| 7 | C |
| 8 | G |
| 9 | A |
| 10 | G |
| 11 | T |
| 12 | C |
| 13 | A |
| 14 | A |
| 15 | C |
| 16 | G |
| 17 | G |
| 18 | Y(C: 50/T: 50) |
| 19 | C |
| 20 | G (G: 80/T: 20) |
| 21 | T |
| 22 | T (C: 40/T: 60) |
| 23 | T (C: 20/T: 80) |
| 24 | C |
| 25 | C (C: 80/T: 20) |
| 26 | T (G: 17/T: 83) |
| 27 | T |
| 28 | G (G: 67/T: 33) |
| 29 | T (A: 33/T: 67) |
| 30 | T (G: 17/T: 83) |
| 31 | T |
| 32 | T |
| 33 | T (C: 17/T: 83) |
| 34 | C (C: 67/T: 33) |
| 35 | T (C: 33/T: 67) |
| 36 | C (C: 83/G: 17) |
| 37 | C (C: 67/T: 33) |
| 38 | T |
| 39 | T |
| 40 | C (C: 83/G: 17) |
| 41 | G |
| 42 | G |
| 43 | T |
| 44 | T |
| 45 | A (A: 67/T: 17/—: 17) |
| 46 | A(A: 17/—: 83) |
| 47 | C(C: 17/—: 83) |
| 48 | C (A: 17/C: 67/G: 17) |
| 49 | G |
| 50 | A |
| 51 | A |
| 52 | A |
| 53 | A |
| 54 | A |
| 55 | A |
| 56 | A |
| 57 | A |

TABLE 20-continued

| SmOTOT00200215.2 Variation in ZB113 | |
|---|---|
| 58 | A |
| 59 | C |
| 60 | A (A: 83/C: 17) |
| 61 | G (A: 17/G: 83) |
| 62 | V(A: 33/C: 33/G: 33) |
| 63 | A |
| 64 | A |
| 65 | A |
| 66 | A |
| 67 | A |
| 68 | A |
| 69 | A |
| 70 | A |
| 71 | A |
| 72 | A(A: 33/—: 67) |
| 73 | M(A: 17/C: 17/—: 67) |
| 74 | C (A: 17/C: 83) |
| 75 | A |
| 76 | A |
| 77 | A |
| 78 | C |
| 79 | C |
| 80 | G |
| 81 | A |
| 82 | G |
| 83 | T |
| 84 | C |
| 85 | M(A: 17/C: 17/—: 67) |
| 86 | A |
| 87 | A |
| 88 | C |
| 89 | G (G: 67/—: 33) |
| 90 | A (A: 67/—: 33) |
| 91 | C (C: 67/—: 33) |
| 92 | C (C: 67/—: 33) |
| 93 | G (G: 67/—: 33) |
| 94 | G(G: 17/—: 83) |
| 95 | C(C: 17/—: 83) |
| 96 | C(C: 17/—: 83) |
| 97 | C (C: 83/T: 17) |
| 98 | T |
| 99 | T (C: 17/T: 83) |
| 100 | C |
| 101 | C |
| 102 | T |
| 103 | T |
| 104 | G |
| 105 | T |
| 106 | T |
| 107 | T |
| 108 | T |
| 109 | T |
| 110 | C |
| 111 | T |
| 112 | C |
| 113 | C |
| 114 | T |
| 115 | T |
| 116 | C |
| 117 | G |
| 118 | G |
| 119 | T |
| 120 | T |
| 121 | A |
| 122 | C |
| 123 | D(A: 50/G: 33/T: 17) |
| 124 | T |
| 125 | A (A: 67/C: 33) |
| 126 | A |
| 127 | A |
| 128 | A |
| 129 | A |
| 130 | A |
| 131 | A |
| 132 | A |
| 133 | C |
| 134 | A |
| 135 | G |

TABLE 20-continued

SmOTOT00200215.2 Variation in ZB113

| | |
|---|---|
| 136 | A |
| 137 | A (A: 67/—: 33) |
| 138 | A (A: 67/—: 33) |
| 139 | C (C: 67/—: 33) |
| 140 | A (A: 67/—: 33) |
| 141 | A (A: 67/—: 33) |
| 142 | A |
| 143 | A |
| 144 | A |
| 145 | A |
| 146 | A |
| 147 | A |
| 148 | A |
| 149 | G |
| 150 | A |
| 151 | A (A: 67/T: 33) |
| 152 | A |
| 153 | A |
| 154 | C |
| 155 | G |
| 156 | A |
| 157 | A |
| 158 | G |
| 159 | G |
| 160 | A |
| 161 | G |
| 162 | A |
| 163 | A |
| 164 | G (A: 33/G: 67) |
| 165 | G |
| 166 | G |
| 167 | A |
| 168 | T |
| 169 | A |
| 170 | C |
| 171 | G |
| 172 | G |
| 173 | T |
| 174 | T |
| 175 | G |
| 176 | T |
| 153 | |
| 3.6 | |

TABLE 21

SmOTOT00200480 Variation in ZB113

| | |
|---|---|
| 1 | G |
| 2 | A |
| 3 | C |
| 4 | G |
| 5 | T |
| 6 | A |
| 7 | A |
| 8 | C |
| 9 | C |
| 10 | G |
| 11 | A |
| 12 | A |
| 13 | G |
| 14 | G |
| 15 | A |
| 16 | G |
| 17 | A |
| 18 | A |
| 19 | A |
| 20 | A |
| 21 | A |
| 22 | Y(C: 50/T: 50) |
| 23 | A |
| 24 | A |
| 25 | G |
| 26 | G |
| 27 | A |

TABLE 21-continued

SmOTOT00200480 Variation in ZB113

| | |
|---|---|
| 28 | R(A: 50/G: 50) |
| 29 | A |
| 30 | C |
| 31 | G |
| 32 | A |
| 33 | T |
| 34 | G |
| 35 | T |
| 36 | T |
| 37 | G |
| 38 | A |
| 39 | C |
| 40 | T |
| 41 | C |
| 42 | G |
| 43 | G |
| 44 | T |
| 45 | T |
| 46 | T |
| 47 | G |
| 48 | T |
| 49 | G |
| 50 | G |
| 51 | Y(C: 50/T: 50) |
| 52 | G |
| 53 | T |
| 54 | G |
| 55 | A |
| 56 | T |
| 57 | C |
| 58 | A |
| 59 | A |
| 60 | A |
| 61 | Y(C: 50/T: 50) |
| 62 | G |
| 63 | G |
| 64 | R(A: 50/G: 50) |
| 65 | A |
| 66 | G |
| 67 | A |
| 68 | T |
| 69 | G |
| 70 | R(A: 50/G: 50) |
| 71 | T |
| 72 | G |
| 73 | G |
| 74 | C |
| 75 | G |
| 76 | G |
| 77 | C |
| 78 | G |
| 79 | C |
| 80 | T |
| 81 | A |
| 82 | G |
| 83 | G |
| 84 | R(A: 50/G: 50) |
| 85 | T |
| 86 | T |
| 87 | T |
| 88 | G |
| 89 | A |
| 90 | A |
| 91 | T |
| 92 | G |
| 93 | G |
| 94 | T |
| 95 | G |
| 96 | G |
| 97 | A |
| 98 | A |
| 99 | G |
| 100 | A |
| 101 | A |
| 102 | C |
| 103 | A |
| 104 | C |
| 105 | A |

TABLE 21-continued

SmOTOT00200480 Variation in ZB113

| Position | Base |
|---|---|
| 106 | A |
| 107 | T |
| 108 | G |
| 109 | C |
| 110 | A |
| 111 | A |
| 112 | C |
| 113 | C |
| 114 | A |
| 115 | G |
| 116 | C |
| 117 | A |
| 118 | A |
| 119 | C |
| 120 | A |
| 121 | A |
| 122 | R(A: 50/G: 50) |
| 123 | K(G: 50/T: 50) |
| 124 | R(A: 50/G: 50) |
| 125 | A |
| 126 | A(A: 50/—: 50) |
| 127 | C |
| 128 | G |
| 129 | C |
| 130 | G |
| 131 | A |
| 132 | A |
| 133 | A |
| 134 | G |
| 135 | C |
| 136 | A |
| 137 | C |
| 138 | A |
| 139 | C |
| 140 | A |
| 141 | A |
| 142 | A |
| 143 | T |
| 144 | T |
| 145 | C |
| 146 | A |
| 147 | A |
| 148 | C |
| 149 | A |
| 150 | A |
| 151 | T |
| 152 | G |
| 153 | C |
| 154 | A |
| 155 | G |
| 156 | A |
| 157 | T |
| 158 | T |
| 159 | A |
| 160 | T |
| 161 | T |
| 162 | G |
| 163 | A |
| 164 | A |
| 165 | A |
| 166 | G |
| 167 | A |
| 168 | A |
| 169 | A |
| 170 | G |
| 171 | T |
| 172 | G |
| 173 | Y(C: 50/T: 50) |
| 174 | G |
| 175 | A |
| 176 | G |
| 177 | G |
| 178 | C |
| 179 | T |
| 180 | C |
| 181 | A |
| 182 | A |
| 183 | A |
| 184 | A |
| 185 | G |
| 186 | G |
| 187 | G |
| 188 | T |
| 189 | G |
| 190 | C |
| 191 | T |
| 192 | G |
| 193 | G |
| 192 | 0.55 |

Summary

The sequence analysis described above demonstrates that BAC ZB19 is enriched for CentC and BAC ZB113 is enriched for CentC and CRM. The frequency of these repeats is particular to the BACs of the invention and is not a representation of the natural occurrence of these repeats in the maize genome. The relative frequency of sequences within the entire maize genome database (TIGR web site) having homology to CentC or CRM was compared to the frequency in ZB19 and ZB113. CentC hit the maize genome (300 Mb) 530 times over a total aligned length of 70 kb. CRM hit the maize genome 860 times over a total aligned length of 336 kb. The proportion of CentC and CRM in ZB19 and ZB119 as compared to the maize genome is summarized in Table 22.

TABLE 22

| | CentC | CRM |
|---|---|---|
| ZB19 | 28.91 | 0.00 |
| ZB113 | 47.55 | 31.73 |
| maize genome | 0.02 | 0.11 |

Example 7

Additional Corn Centromere Discovery and Mini-Chromosome Construction

Identification of Centromere DNA and Mini-Chromosome Construction.

A Bacterial Artificial Chromosome (BAC) library was constructed from corn genomic DNA. The corn genomic DNA was isolated from corn variety B73 and digested with the restriction enzyme MboI.

Six of the probes listed in Table 4 were used to interrogate the BAC library. The six probes were: CRM (#1), CentA (#2), MZEHETRO (#13), CentC (#15), Cent (#16) and TR-1 (#14). The primers used to amplify these probes are also identified in Table 4. Probes were prepared and labeled with $^{32}$P using standard molecular methods.

The BAC clones were spotted onto nitrocellulose filters for further analysis. The filters were hybridized with each of the $^{32}$P labeled probes to identify specific BAC clones that contain DNA from the group of sequences represented by the probe(s). The labeled probes were hybridized for 14 hours at 65° C. and washed with 0.5×SSC, 1% SDS three times at 65° C. To identify clones carrying centromere DNA, phosphorimager scans of each hybridization experiment were digitally assembled into a MySQL database. BAC clones with strong hybridization signals to one or more of the repetitive sequences were selected for mini-chromosome construction.

To construct the mini-chromosomes, a high copy number plasmid (pCHR758) carrying the *Arabidopsis* UBQ10 promoter (GenBank accession No. AL161503) fused to DsRed (Clonetech cat#632408) and the yeast YAT1 promoter fused to nptII (GenBank accession numbers L28920 and U35136, respectively) was constructed as described in Example 2 Mini-chromosome genetic elements within the pCHR758 vector are set out in Table 7.

Mini-Chromosome Delivery and Propagation in Plants.

Mini-chromosomes grown in *E. coli* were purified using alkaline lysis or cesium chloride protocols and delivered to embryogenic H99 maize tissues by biolistic bombardment of DNA-coated gold particles as described in Frame et al. *In Vitro Cell. Dev. Biol. Plant.* 36: 21-29, 2000 and in Example 3 above. Transformed events were identified by selection on Chu's N6 medium containing G418 Sulfate (PhytoTechnology Laboratories) or Paromomycin (Sigma) and regenerated. Transformed plants were subsequently grown without selection in a soilless mix (Sunshine LC1) in a greenhouse (16 h days, 26-28° C.). Seedlings were grown in 48-well flats (2 sq ft) with one plant per well to the V3 (third leaf) developmental stage and then transplanted into 1.6 gallon pots containing 1:1:1 soil:peat:perlite and grown to maturity. Plants subjected to stress conditions were maintained in 48-well flats for 60 days with watering limited to once per day. Mini-chromosome containing plants were advanced through generations by backcrossing to corn variety H99, outcrossing to public maize inbreds such as B73, and by self-pollination or sibling-mating.

Fluorescence Assays

Mini-chromosome gene expression was confirmed by detecting DsRed gene expression via fluorescence assays. Leaf 3 (V2 stage of development) was sampled across its entire width (minimally 2500 cells per sample) and fluorescence was detected using a Zeiss SV-11 dissecting microscope equipped with a rhodamine filter cube (excitation: D540/25; dichroic 565LP; emission: D605/55). Background autofluorescence was detected with a GFP filter cube (excitation: BP 470/40; beamsplitter: FT495; emission: BP 525/50); bonafide DsRed fluorescence was not detectable at this excitation wavelength. DsRed expression in pollen was determined after fixing florets in 95% ethanlol. Aceto-carmine staining was subsequently used to assess pollen viability.

Example 8

Evaluation of Autonomous Mini-Chromosomes

To evaluate whether the candidate mini-chromosomes were maintained autonomously, fluorescence in situ hybridization (FISH) was performed on mitotic metaphase chromosome spreads from root tips. FISH was performed essentially as described in Kato et al. *Proc. Natl. Acad. Sci. U.S.A.* 101: 13554-13559, 2004, using probes labeled with Alexa488 (pCHR758, Molecular Probes) and Alexa568 (CentC, Roche).

For FISH, root tips were collected approximately 10 days after transplanting regenerated T0 plants to soil or after germination (T1-T4 plants). Sampled roots (3-6 per plant) were moistened and exposed to nitrous oxide at 150 psi for 2.5 hours to arrest chromosomes in metaphase as described in Kato *Biotech. Histochem* 74: 160-166, 1999. Roots were fixed in 90% acetic acid, and spread onto poly-lysine coated glass slides by squashing thin cross sections. Following hybridization, slides were counter-stained with DAPI (0.04 mg/ml) and ≥15 metaphase cells were evaluated per plant using a Zeiss Axio-Imager equipped with rhodamine, FITC, and DAPI filter sets (excitation BP 550/24, emission BP 605/70; excitation BP 470/40, emission: BP525/50; and excitation G 365, emission BP 445/50, respectively).

Extra-chromosomal signals were only considered to indicate autonomous mini-chromosomes if ≥70% of the images (n≥15 cells analyzed) showed co-localization of the Alexa488 and Alexa568 signals within 1 nuclear diameter of the endogenous metaphase maize chromosomes. Gray-scale images were captured in each panel, merged and adjusted with pseudo-color using Zeiss AxioVision (Version 4.5) software; fluorescent signals from doubly labeled mini-chromosomes were detected in both the red and green channels.

Integrated constructs resulted in two FISH signals, each on a replicated metaphase chromatid. Mini-chromosomes were considered autonomous when i) ≥70% of the cells examined (n≥15) contained signals that were clearly distinct from the DAPI-stained host chromosomes, ii) integrated signals were not detected, and iii) the fluorescent probe corresponding to the mini-chromosome-encoded genes co-localized with the probe to repetitive centromeric DNA, suggesting an intact construct and making it unlikely that the signal was due to noise.

Based on these criteria, 47/52 (90%) of the transformed constructs (104 events) were able to form an autonomous mini-chromosome and 43/52 (with centromeric inserts ranging in size from 7 to 190 kb) gave rise to plants that contained only one autonomous mini-chromosome (Table 23). This unexpectedly high rate of recovering autonomous mini-chromosomes suggests that embryogenic maize tissue readily established mini-chromosomes from purified DNA and that the BAC clones that yielded transformed plants contained sequences that efficiently promote mini-chromosome formation. The efficiency of forming an autonomous mini-chromosomes increased slightly, although not significantly (t-test), as the size of the genomic DNA insert increased. As described below, mini-chromosomes were often efficiently inherited; nonetheless, mini-chromosome integration was detected only during the initial transformation event, and not in subsequent generations (T1 through T4, 0/312 metaphase spreads, 33 plants). One of these mini-chromosomes (denoted herein as "MMC1") is described in detail below.

TABLE 23

Mini-chromosome transformation events and FISH analysis

| Construct[a] | Explants[b] | Transformation Events | Analyzed by FISH | Autonomous | Integrated | Autonomous and integrated |
|---|---|---|---|---|---|---|
| 1 | 264 | 10 | 9 | 5 | — | 4 |
| 2 | 87 | 2 | 2 | 2 | — | — |
| 3 | 87 | 1 | 1 | 1 | — | — |
| 4 | 150 | 13 | 1 | 1 | — | — |
| 5 | 25 | 1 | 1 | — | 1 | — |
| 6 | 150 | 8 | 3 | 3 | — | — |
| 7 | 204 | 22 | 10 | 4 | — | 6 |

TABLE 23-continued

Mini-chromosome transformation events and FISH analysis

| Construct[a] | Explants[b] | Transformation Events | Analyzed by FISH | Autonomous | Integrated | Autonomous and integrated |
|---|---|---|---|---|---|---|
| 8 | 134 | 6 | 1 | 1 | — | — |
| 9 | 54 | 4 | 1 | — | — | 1 |
| 10 | 54 | 2 | 1 | — | 1 | — |
| 11 | 54 | 1 | 1 | — | 1 | — |
| 12 | 54 | 2 | 1 | 1 | — | — |
| 13 | 50 | 3 | 1 | 1 | — | — |
| 14 | 50 | 3 | 1 | — | — | 1 |
| 15 | 50 | 3 | 2 | 1 | — | 1 |
| 16 | 168 | 7 | 1 | 1 | — | — |
| 17 | 50 | 4 | 2 | — | — | 2 |
| 18 | 50 | 6 | 4 | 3 | — | 1 |
| 19 | 50 | 2 | 1 | 1 | — | — |
| 20 | 200 | 5 | 5 | 4 | — | 1 |
| 21 | 50 | 1 | 1 | 1 | — | — |
| 22 | 50 | 1 | 1 | 1 | — | — |
| 23 | 50 | 1 | 1 | 1 | — | — |
| 24 | 40 | 1 | 1 | 1 | — | — |
| 25 | 60 | 1 | 1 | 1 | — | — |
| 26 | 60 | 1 | 1 | 1 | — | — |
| 27 | 60 | 2 | 1 | 1 | — | — |
| 28 | 126 | 6 | 1 | 1 | — | — |
| 29 | 65 | 3 | 1 | 1 | — | — |
| 30 | 126 | 2 | 1 | 1 | — | — |
| 31 | 126 | 4 | 2 | 1 | — | 1 |
| 32 | 168 | 10 | 5 | 4 | — | 1 |
| 33 | 294 | 15 | 2 | 2 | — | — |
| 34 | 168 | 1 | 1 | 1 | — | — |
| 35 | 126 | 12 | 5 | 3 | — | 2 |
| 36 | 126 | 7 | 2 | 1 | — | 1 |
| 37 | 110 | 6 | 2 | 1 | — | 1 |
| 38 | 126 | 6 | 1 | 1 | — | — |
| 39 | 126 | 8 | 2 | 2 | — | — |
| 40 | 126 | 1 | 1 | 1 | — | — |
| 41 | 168 | 6 | 1 | 1 | — | — |
| 42 | 126 | 4 | 2 | 1 | — | 1 |
| 43 | 206 | 2 | 1 | — | 1 | — |
| 44 | 126 | 2 | 1 | 1 | — | — |
| 45 | 126 | 6 | 5 | 3 | 1 | 1 |
| 46 | 126 | 7 | 2 | 1 | — | 1 |
| 47 | 126 | 2 | 2 | 2 | — | — |
| 48 | 126 | 10 | 3 | 1 | — | 2 |
| 49 | 206 | 1 | 1 | — | 1 | — |
| 50 | 126 | 3 | 1 | 1 | — | — |
| 51 | 126 | 6 | 1 | — | — | 1 |
| 52 | 126 | 2 | 2 | 2 | — | — |
| Total | 5882 | 245 | 104 | 69 | 6 | 29 |

For MMC1, 5/9 independent transformation events yielded only an autonomous chromosome (FIGS. 1a, b); 4/9 generated both integrated and autonomous copies (FIG. 1c). Control transformations performed with a DsRed/nptII plasmid lacking a centromere-derived insert (pCHR758) integrated into a native chromosome (7/7 events, FIG. 1d). MMC1 contains a 19 kb insert that hybridized to sequences typically located in the centromeric regions of native maize chromosomes; 42 other mini-chromosomes (with inserts ranging in size from 7 to 190 kb) also gave rise to plants that contained only an autonomous mini-chromosomes. The efficiency of forming an autonomous mini-chromosomes increased slightly, although not significantly, as the size of the genomic DNA insert increased (FIG. 1e). While this study did not explore the interactions between mini-chromosome DNA inserts and kinetochore or spindle proteins, hereafter these fragments are denoted as "centromeric", based on the typical genomic location of the sequences they contain.

The ability of the mini-chromosome fragments to confer inheritance by crossing T0 transformants to wild-type, growing the progeny without selection and monitoring nuclear-localized DsRed fluorescence was examined. Typically, only one mini-chromosome per cell (monosomic) was observed, therefore it was expected that these T0 plants would behave as hemizygotes; if the mini-chromosome obeyed Mendelian inheritance, then such crosses would yield DsRed progeny in a 1:1 ratio. Ten T0 plants carrying only an autonomous MMC1 copy (derived from 3 events) were crossed to wild-type pollen. The significance of MMC1 inheritance data was determined with a chi-square goodness of fit test. Differences from Mendelian segregation (based on a 1:1 segregation ratio in crosses to wild-type and a 3:1 segregation ratio in self crosses or crosses to sibling plants) were considered significant at $P<0.05$ (or a chi-square value greater than 3.84). Mendelian inheritance ratios were observed in most hemizygous plants from the T1 (female: 208:249; $P>0.05$; male: 39:50; $P>0.05$) and T2 (female: 40:44; $P>0.05$) generations (Table 24).

TABLE 24

| Construct | Event | Parental Generation | % Loss, Female | No. Progeny (T0 crosses) | % Loss Male | No. Progeny (T0 crosses) |
|---|---|---|---|---|---|---|
| MMC1 | V-1 | T0 | 0 | 172 (4) | nt | |
| | | T1 | 0 | 457 (10) | 0 | 89 (3) |
| | | T1[c] | 100 | 48 (1) | 100 | 35 (2) |
| | | T2 | 0 | 84 (4) | nt | |
| MMC1 | Q-1 | T0 | 0 | 36 (3) | nt | |
| MMC1 | Q-2 | T0 | 52 | 138 (3) | nt | |
| pCHR758 | 1 | T0 | 0 | 237 (8) | nt | |

The "percent loss female" or "percent loss male" represents the difference between the expected (hemizygous locus) and observed numbers of DsRed+ progeny, expressed as a percent of the expected DsRed+ progeny. Ratios insignificantly different from expectations ($x^2$ P>0.05) are indicated as 0. The "number of progeny" represents plants visually scored for DsRed expression; parentheses, the number of parental crosses that gave rise to these progeny. Crosses derived from a single V-1 plant that demonstrated sectoring in the T1 generation; loss was confirmed by PCR. nt=not tested. Two of these events (V-1 and Q-1), transmitted DsRed to T1 offspring at ratios that did not differ significantly from Mendelian predictions (hemizygous locus, P>0.05; 78:94 and 17:19; Table 24 and 25). In the third MMC1 event (Q-2), a 52% reduction in DsRed+ progeny compared to expectations (33:105; P<0.001) was observed (Table 25), which suggested genetic instability.

lacked DsRed sequences, indicating that the this variation was not due to silencing of gene expression. PCR reactions were carried out on genomic DNA isolated from young plants; quantitative PCR (qPCR) reactions were performed in triplicate using a BioRad Chromo4 machine with TaqMan primers and probes (Sigma-Genosys). Amplification was achieved by incubating at 95° C. for 3 minutes, and 39 cycles of 95° C. for 15 seconds and 59° C. for 48 seconds with a 1 second reduction per cycle. Copy number determinations were made by comparing qPCR signals from a control plasmid containing one copy of the maize Adh1 gene (GenBank X04049) and DsRed to the signals obtained from mini-chromosome-containing plants. This analysis confirmed this variation was not due to silencing; it could result from in planta modifications of the centromeric insert or from epigenetic effects that led to less robust segregation (Dawe et al. *TRENDS Biochem. Sci.* 31: 662-669, 2006). As expected, performing a similar analysis of 6 events carrying an integrated pCHR758 backbone yielded Mendelian inheritance ratios (118:140 DsRed+:DsRed; P>0.05).

FISH analysis showed that T1 plants from event V-1 retained an autonomous MMC: a DsRed-containing episome was present in 80% of root metaphase cells (n=44), a detection level consistent with previous artificial chromosome studies (Co et al., Chrom Res 8: 183-191, 2000). DsRed expression was consistently observed in nearly every cell from these plants (see below), and therefore it is concluded that the absence of an mini-chromosome FISH signal in 20% of root cells likely represents the challenges of retaining and

TABLE 25

Meiotic Inheritance of MMC1

| Construct | Event | Generation | Female[a] | Male[a] | Expected Progeny Ratio | Observed Progeny Ratio (P value)[b] | % loss[c] |
|---|---|---|---|---|---|---|---|
| MMC1 | V-1 | T0 | MMC1 (M) | WT | 1:1 | 78:94 (0.75) | 9.3 |
| | | T1 | MMC1 (M) | WT | 1:1 | 118:149 (0.06) | 12 |
| | | T1 | WT | MMC1 (M) | 1:1 | 31:48 (0.06) | 21.5 |
| | | T1[d] | MMC1 (M) | WT | 1:1 | 0:48 (*) | 100 |
| | | T1[d] | WT | MMC1 (M) | 1:1 | 0:35 (*) | 100 |
| | | T1 | MMC1 (M) | MMC1 (M) | 3:1 | 61:86 (*) | 44.7 |
| | | T2 | MMC1 (M) | WT | 1:1 | 67:65 (0.86) | 0 |
| | | T2 | MMC1 (M) | MMC1 (M) | 3:1 | 82:35 (0.22) | 6.6 |
| | | T2 | WT | MMC1 (D) | 1:0 | 184:18 (NA) | 8.9 |
| | | T2 | MMC1 (D) | MMC1 (D) | 1:0 | 48:0 (NA) | 0 |
| | | T3 | MMC1 (M) | WT | 1:1 | 38:37 (0.91) | 0 |
| | | T3 | MMC1 (M) | MMC1 (M) | 3:1 | 80:33 (0.3) | 5.6 |
| MMC1 | Q-1 | T0 | MMC1 (M) | WT | 1:1 | 17:19 (0.74) | 5.6 |
| MMC1 | Q-2 | T0 | MMC1 (M) | WT | 1:1 | 33:105 (*) | 52 |
| pCHR758 | 1 | T0 | pCHR758 (M) | WT | 1:1 | 118:119 (0.95) | 0.4 |

In Table 25, "M" refers to monosomic for MMC1, "D" refers to disomic for MMC1, "WT" refers to wild-type maize. The P value calculations in Table 25 were based on Chi-Square distributions with 1 degree of freedom. P values significantly different from expectations ($x^2$ P<0.05) are indicated with an asterisk in Table 25. P values were not calculated for expectations of 1:0 and are noted as NA. Loss rates were calculated as the difference between the expected and observed numbers of DsRed positive progeny, and are expressed as percent of the expected (assuming Mendelian assortment). For crosses derived from a single V-1 plant that demonstrated sectoring in the T1 generation; loss was confirmed by PCR.

PCR analysis of the progeny from this cross was carried out to confirm that the plants lacking DsRed expression also detecting every MMC throughout the FISH protocol. To monitor MMC1 inheritance in subsequent generations and through both male and female gametes, T1 and T2 plants were crossed to wild-type and monitored DsRed transmission. A series of crosses with T1, T2, and T3 plants derived from event V-1 were carried out and DsRed transmission was monitored. When male or female monosomic MMC1 plants were crossed to wild-type, DsRed segregation was not significantly different from Mendelian inheritance ratios (1:1).

Hemizygous T1 plant derived from event V-1 were also self-pollinated to generate a T2 plant that likely carried two copies of MMC1 (a homozygous disome). Crossing pollen from this T2 plant onto 5 different maize inbreds yielded 165 DsRed+:16 DsRed− offspring (P>0.05 for disomy). Similarly, self-pollinating another potentially disomic T2 plant produced 48 DsRed⁺: 0 DsRed⁻ offspring (P>0.05 for disomy). Quantitative PCR analysis of these T2 plants confirmed disomy with 2.00 and 1.90 (standard error=0.08) DsRed copies per cell, respectively.

For most autonomous mini-chromosomes, nuclear DsRed expression was observed in every leaf cell, indicating stability through mitosis. In some cases, however, sectors that lacked DsRed expression were found; these were generally limited to a few cell files. In reproductive tissues such sectors could lead to aberrant meiotic mini-chromosome segregation. For example, one exceptional T1 plant from event V-1 had prominent mitotic DsRed leaf sectors, and none of the male or female offspring from this plant contained DsRed (female: 0:48; male 0:35; Table 23); the absence of DsRed-encoding DNA in these progeny was confirmed by PCR, supporting the view that this mini-chromosome was indeed autonomous. Interestingly, the leaf tissue of this plant had prominent mitotic DsRed leaf sectors, suggesting a high rate of MMC instability.

When T2 and T3 hemizygous plants derived from event V-1 were self-pollinated, DsRed⁺ inheritance was observed in a ratio that did not significantly differ from a 3:1 Mendelian pattern. However, in a second case of non-Mendelian assortment, a self-cross in the T1 generation yielded a 1:1 DsRed⁺ inheritance ratio, suggesting loss of MMC1 from either the male or female floral tissue. Nonetheless, this cross was useful for generating plants that potentially carried two copies of MMC1 (homozygous disomes). Crossing pollen from a candidate T2 disome onto 5 different maize inbreds yielded 184 DsRed⁺:18 DsRed⁻ offspring (P>0.05 for disomy). Similarly, self-pollinating potentially disomic T2 or T3 plants produced 48:0 and 24:0 DsRed⁺:DsRed⁻ offspring, respectively. Quantitative PCR analysis of the potentially disomic T2 plants confirmed 2.00 and 1.90 (standard error=0.08) DsRed copies per cell, respectively.

In total, mitotic sectors of DsRed expression from MMC1 were detected in 3.6% of T0 plants (n=56), 3.0% of T1 plants (n=404), 1.9% of T2 plants (n=837), and no T3 plants (n=738). The reduced sectoring frequency as plants advanced through generations suggests a gradual increase in mini-chromosome stability due to changes in DNA composition, epigenetic modifications, or copy number in mitotic cells. It was also observed that 60 days of crowding and drought stress did not appreciably alter MMC1 stability; DsRed expression was found in every T2 and T3 plant from event V-1 grown under stress (151 and 159 plants respectively). Moreover, pollen from stressed hemizygous T2 plants demonstrated Mendelian DsRed segregation (281:238 DsRed⁺:DsRed⁻; P>0.05).

Importantly, mini-chromosome integration was detected only during the initial transformation event, and not in subsequent generations (T1-T4, 0/312 metaphase spreads, 33 plants). Mini-chromosome structural alterations sometimes occurred during transformation, often involving the centromeric insert, rather than the gene cassette. Additional rearrangements were typically not detected after the T1 generation (n=5), although the repetitive nature of the centromeric fragment made it impossible to thoroughly evaluate its structure. To assess the structure of MMC1 through generations, Southern blot analysis was performed with probing to detect all of the unique sequence bands contained in the min-chromosome construct.

For Southern blots, genomic DNA was isolated from young leaf tissue using a Nucleobond Plant Genomic DNA extraction kit (Clontech Corp). 10 µg of DNA was digested with BglII (New England Biolabs), separated on a 0.7% agarose gel, vacuum transferred to a nylon membrane (Amersham BioSciences) and probed with a mixture of non-overlapping pCHR758 fragments labeled with ³²P (Rediprime II, Amersham BioSciences). Hybridization was performed overnight at 65° C. and blots were washed 3 times (15 minutes each) with 0.25×SSC, 0.1% SDS, 65° C.; signals were detected with a Storm phosphorimager. Southern blot analysis showed centromeric alterations in event V-1 that were transmitted from the T1 parent to the T2 progeny. Event Q-2 suffered a larger alteration of the centromeric fragments, potentially explaining its reduced meiotic stability. In contrast, an event carrying both integrated and autonomous MMC1 copies (V-4) showed a more complicated pattern, as did plants carrying integrated pCHR758. As expected for independently assorting loci, when plants from event V-4 were crossed to wild-type, the autonomous and integrated copies segregated: FISH evaluation of DsRed-expressing T2 plants yielded a 1:4:2 ratio (autonomous:autonomous and integrated:integrated).

Taken together, these experiments support the conclusion that MMC1 was maintained as an autonomous chromosome: It remains distinct from host chromosomes, it is structurally stable through generations, the genes it carries are expressed and transmitted through meiosis and mitosis, and, in some cases, it can be lost from the genome at a frequency higher than that of a native chromosome.

Example 9

Sequence Analysis of MMC1

MMC1 was sequenced to an average of 30× coverage by shotgun sequencing (Lark Technologies, Inc., TX) and 454 Technology (454 Life Sciences, Conn.) and assembled with Phred/Phrap; a small gap was closed by primer walking, using direct dye-terminator cycling sequencing of MMC1. Quantitative dot-blotting was used to calculate the total size of the CentC array. Briefly, two sets of blots, each containing samples in triplicate were hybridized with CentC(CC) and vector specific (V) probes separately. Signals for each spot were captured with a Storm phosphorimager and CC/V ratios were calculated. Plasmids with the vector sequence and 1, 3 and 8 copies of a cloned CentC repeat were used as standards. MMC1 assembly was verified by restriction mapping with panels of enzymes (BamHI, BmgBI, EcoRI and HindIII); this data was consistent with the calculated size of the CentC array. BLASTN was used to assess sequence similarity, GENSCAN to predict promoters and open reading frames, and Repeat Finder to analyze CentC satellites.

Hybridization of the maize genomic library determined that MMC1 contained a high percentage of CentC, and sequence analysis confirmed the presence of 61.4±2.3 CentC copies arranged in an uninterrupted 9 kb tandem array SEQ ID NO: 100). The repetitive nature of CentC made a precise assembly of this array challenging; therefore rare DNA polymorphisms within the repeats were used to aid in sequence assembly, and confirmed the overall length of the array (approximately 9 kb) with restriction enzyme digestion and gel electrophoresis. CentC repeat alignments showed that each base is conserved at an average frequency of 96.1% (FIGS. 2b,c), a level consistent with previously reported plant satellite conservation (Hall et al. *Genetics* 170: 1913-1927, 2005). Clustering algorithms failed to detect higher order repeat arrangements in MMC1.

Figure 2:
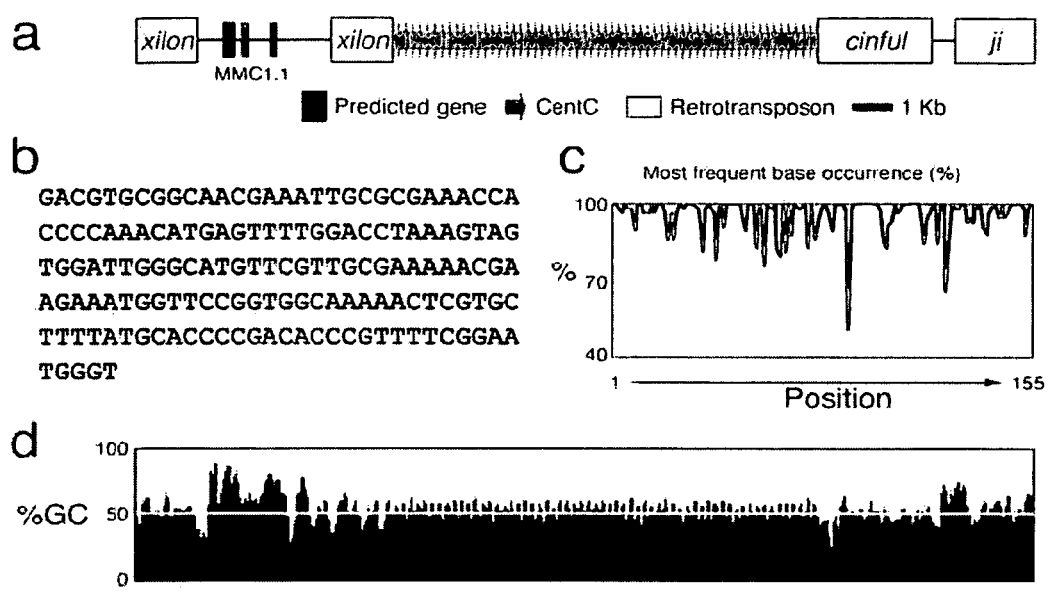
FIG. 2 depicts sequence analysis of the MMC1 centromeric fragment. Panel A shows the assembled sequence (SEQ ID NO: 91). Panel B shows the consensus sequence of ~60 MMC1 CentC repeats (SEQ ID NO: 92). Panel C depicts the occurrence of the most frequent base (%) for each nucleotide in the CentC consensus. Panel D shows the 50 bp sliding window analysis of MMC1 GC content; white line, genomic average=49.5%.

While the maize genome has an average GC content of 49.5%, the 5.6 and 4.8 kb regions flanking the CentC array of MMC1 reach 88% and 70% GC, respectively (FIG. 2d). Overall, the GC content of the MMC1 centromeric insert is 48%; by comparison the *Arabidopsis* and rice centromere DNA averages 35-40% and 39-48%, respectively (Copenhaver et al. *Science* 286: 2468-. MMC1 encodes four regions with similarity to retrotransposons xilon, cinful, or ji (Kumar et al. *Annu. Rev. Genet.* 33:479-532, 1999), as well as a 453 bp open reading frame (MMC1.1) that potentially encodes a novel protein of unknown function, complete with a promoter and poly-A signal (FIG. 2a). BLAST searches of GenBank revealed no evidence for MMC1.1 expression, but transcripts >95% identical to CentC and to the MMC1 retrotransposons were abundant. The centromere-specific histone CENH3 binds to transcripts corresponding to CentC and to the retrotransposon CRM, suggesting a role for these RNAs in centromere function (Topp et al. *Proc. Natl. Acad. Sci, USA,* 101: 15986-15991, 2004); it is possible xilon, cinful, or ji transcripts play a similar role. Retrotransposons also can nucleate the formation of heterochromatin that can spread to nearby regions (Talbert et al. *Nat. Rev. Genet.* 7: 793-803, 2006), although MMC1-encoded DsRed and nptII were readily expressed, despite their separation of 3.3 and 6.2 kb, respectively, from retrotransposons.

Example 10

Soybean Centromere Discovery and Mini-Chromosome Assembly and Construction

BAC Library Construction

A soybean BAC library (Williams 82 genotype) was obtained from Clemson University Genomics Institute (CUGI, Clemson, S.C.) and filters were hybridized with probes labeled by using the Rediprime kit (Amersham Biosciences, Piscataway, N.J.). 18,432 genomic clones were screened, and of these, 358 hybridized strongly to the centromere satellite. Two hundred of these BACs were digested with ApoI or HinfI, enzymes that cut within the tandem centromere satellite repeat.

Probe Identification and Selection

Large DNA fragments from soybean centromeres were identified by probing the BAC library with highly methylated genomic DNA (Luo et al. *Nature Methods* 1, 67-71 2004) and the 92 bp satellite repeat (Vahedian et al., *Plant Mol Biol* 29, 857-862, 1995). 358 out of 18,432 BAC clones screened contained significant quantities of this satellite. Clones that hybridized poorly to 5S rDNA or retroelement probes (Genbank X06044 and AF186186, respectively) were chosen for further analysis. The BAC clones from the library were interrogated with each of the probes described above using the following hybridization conditions: hybridization at 65° C. and followed by a wash in 0.5×SSC and 1% SDS for 15 minutes at 65° C., and two additional washes in the same wash solution at 65° C. for 30 minutes each.

To identify clones with homogenous, tandem satellite arrays the BACs were digested with restriction enzymes predicted to cut once within each unit repeat; BACs yielding a predominant 92 bp band, with multimeric bands at 184 and 276 bp were selected for assembly into mini-chromosomes. Mini-chromosomes constructed using the inserts contained in the BAC clones denoed as SB6 and SB12 (100 and 80 kbp, respectively), are described below. The inserts of these BACs primarily contained satellite arrays.

Cre recombinase-mediated exchange was used to combine the large centromere fragments with a pair of plant-expressed marker genes. The BAC vector carrying the centromere fragments contains a loxP recombination site (Shizuya et al., *Proc Natl Acad Sci USA* 89, 8794-8797,1992); a second vector (pCHR151) contained a pair of complementary loxP sites flanking two plant-expressed genes, each with a promoter, coding sequence and terminator. Nuclear localized DsRed, a convenient cell-autonomous red fluorescent protein as a visible marker. The bacterial MerA gene, conferring resistance to mercuric ions was used as a selectable marker.

Using purified cre recombinase in vitro, the pCHR151 was combined with clones SB6 and SB12, generating circular, recombinant molecules containing DsRed, MerA, the low-copy bacterial backbone and a centromere DNA fragment. The resulting mini-chromosomes are denoted herein as SB6MC and SB12MC, respectively. Due to the tendency of the tandem satellite arrays to recombine into smaller arrays, mini-chromosomes containing different sizes of centromere fragments were often obtained. Mini-chromosome SB6MC and SB12MC containing smaller centromere inserts (22 and 27 kb respectively) were chosen for further analysis.

Testing Mini-Chromosome Function

To test the ability of the mini-chromosomes to remain autonomous and be stably inherited, circular mini-chromosome DNA was delivered into soybean suspension cells with biolistic particle bombardment, propagated the cells in non-selective medium, and visually monitored the cultures for inheritance of DsRed as described above. Traditional plant transformation procedures produce a large number of transient transformation events, only a small number of which become stable through integration of the delivered DNA into a host chromosome. In contrast, it was predicted that the centromere sequences present on the mini-chromosomes would allow non-integrated DNA to be inherited, producing larger numbers of cells stably carrying the introduced constructs.

The inheritance of each mini-chromosome was followed by monitoring the expansion of fluorescent cell clusters in non-selective medium over five generations after bombardment (4, 11, and 19 days, ~3-4 days per cell division). Soybean cells were grown on solid medium containing 2.6% gelrite in the dark at 24° C. Fluorescent cell populations were harvested from plates and plated onto the same medium; cells were sub-cultured onto fresh plates every two weeks. Cell fluorescence was measured by spreading cells on microscope slides and counting fluorescent and total cells. This assay was facilitated by the tendency of plant cell suspensions to grow in aggregates of ~100-1000 cells derived from the same progenitor cell(s). The plasmid pCHR151 lacking centromere DNA yielded only transient events that were rapidly lost, and few clusters of fluorescent cells were detected. The mini-chromosomes SB6MC and SB12MC were inherited at a higher frequency and stabilized a larger number of initial events, yielding numerous fluorescent cell clusters. A control mini-chromosome (SB1 MC), containing a non-centromere-derived insert, was poorly maintained and never gave rise to fluorescent clusters.

To examine the potential for long-term mini-chromosome inheritance, cell clusters carrying the construct were isolated by plating mixed cell cultures on selective medium containing $HgCl_2$; resistant cell clones expanded and were manipulated to homogeneity. Additional lines were isolated in the absence of selection by micro-manipulating fluorescent cell clusters. In total, 10 lines containing SB6MC and 1 line containing SB12MC wer isolated. However, lines carrying the control constructs pCHR151 or SB1MC were not derived, confirming that centromere DNA increases the probability of obtaining stable events. Therefore, the SB12MC cell line was chosen for further study.

The mitotic stability of SB12MC was measured by isolating cell clusters homogeneous for DsRed expression and growing them for 3-4 generations in the absence of selection. The fraction of cells expressing DsRed after unselected growth was determined for several independent populations, and the chromosome loss rate per generation (X) was calculated using the formula $X=1-(F/I)1/N$ where N is the number of generations, and I and F are the initial and final fractions of DsRed containing cells (Kramer et al., *Biotechniques* 32, 1036, 1038, 1040, 2002). About 0.05 loss events per generation for a cell line carrying SB12MC (Table 24) were observed, which was similar to that reported previously for human mini-chromosomes (Harrington et al., *Nat Genet.* 15, 345-355, 1997). These rates could reflect loss of the mini-chromosome, silencing of DsRed expression, or both.

TABLE 24

Mini-chromosome loss rate of SB12MC

| Exp't[a] | Fraction MC[b] | Generations[c] | Loss rate |
|---|---|---|---|
| 1 | 0.74 | 3.41 | 0.085 |
| 2 | 0.82 | 3.55 | 0.053 |
| 3 | 0.81 | 3.60 | 0.056 |
| 4 | 0.89 | 4.03 | 0.029 |
| 5 | 0.89 | 3.98 | 0.030 |
|   |      | Average | 0.051 ± 0.023 |

[a]independent sub-clones from the same cell line, assayed in parallel
[b]fraction of cells containing mini-chromosomes: number of red fluorescent nuclei/number of DAPI-stained nuclei; ≥200 cells from each clone were counted
[c]determined by $\log_2$ of the ratio of weight between initial and final samples Mini-Chromosome Autonomy.

As a direct demonstration of mini-chromosome autonomy, circular constructs were recovered from fluorescent soybean cell lines that had been propagated for 5 months (~25 generations) following bombardment. Genomic DNA was extracted from a cell line containing SB12MC using the CTAB method (Gelvin et al. *Curr Opin Biotechnol* 9, 227-232, 1991), and the DNA was treated with a highly processive ATP-dependent exonuclease (Qiagen USA), resulting in degradation of all linear DNA fragments including those derived from host chromosomes. Surviving DNA molecules were introduced into *E. coli* and transformants were selected on antibiotic-containing medium.

Genomic DNA from unmodified soybean cells did not result in any antibiotic-resistant colonies, while DNA purified from the line containing mini-chromosomes yielded 13 independent modified colonies (2 from exonuclease-treated DNA and 11 from untreated DNA, R1-R13). DNA was extracted from each transformed *E. coli* clone and characterized by gel electrophoresis and sequencing. While the vector backbone of the rescued mini-chromosomes was typically unchanged (9/13 transformants). One clone with minor changes and three clones with more extreme rearrangements were detected. It is unclear whether these rearrangements occurred within the plant cells or during re-introduction into *E. coli*. The centromere insert size in the recovered clones was more variable, probably reflecting expansion and contraction of repetitive element arrays. Nevertheless, most centromere inserts were within ±10 kb of the parental construct. BAC-end sequencing demonstrated that 11/13 of the recovered clones retained the same DNA sequence junctions at the centromere cloning boundaries as the parental molecule (600/600 bp sequenced at each junction), including two of the mini-chromosomes with altered vector sequences.

Fluorescence in situ hybridization (FISH) was carried out to examine mini-chromosome autonomy and copy number as described in Schwarzzacher and Heslop-Harrison (*Practical in situ Hybridization*. Springer-Verlag, New York 2000). Cells containing mini-chromosomes were arrested in metaphase, spread on slides and probed with labeled soybean centromere satellite DNA (red) and mini-chromosome vector sequences. Mini-chromosomes were considered autonomous when metaphase cells contained co-localized hybridization signals (from two probes) that were separate from the host chromosomes, and lacked corresponding integrated signals. Most cells examined in this study contained one or two autonomous mini-chromosomes; similar signals were not detected in non-transgenic controls. In cells hybridizing to both the centromere and vector probes, only one autonomous mini-chromosome was identified; similar signals were not detected in non-transgenic controls. Only a subset of the native centromeres were labeled, suggesting that the satellite sequence used as a probe is chromosome-specific. Strong vector hybridization signals were not detected within the host chromosomes, this was consistent with a high degree of mini-chromosome autonomy and the absence of associated integration events.

Satellite Sequences from Mini-Chromosomes

The identified soybean mini-chromosomes defined DNA sequences sufficient for centromere activity. The sequence content of the centromere-containing BAC clones and the mini-chromosomes derived from them with quantitative dot blots, using probes that correspond to i) vector sequences, ii) soybean satellites, iii) the SIRE retroelement, and iv) 28S rDNA, all of which are highly repetitive sequences present in the soybean centromeric region. BAC SB1 lacked centromere activity and has a high rDNA content with undetectable satellite and retroelement sequences. By contrast, the mini-chromosome derivatives of SB6 and SB12 had similar compositions, with 6.4 and 11.8 kb of centromere satellite, respectively. The recovered SB12 derivatives retained the parental composition (R4, R6, R7, R10), had a two-fold decrease in satellite (R1, R2, R3, R5), or had little or no satellite (R8, R9, R11, R12, R13). Satellite sequences may have been eliminated in the plant cells, or in the process of recovery into bacterial cells. The SIRE retroelements present in SB12 were retained in most of the derivatives, suggesting little selective pressure to eliminate this sequence during growth of the modified cell culture. In addition, each mini-chromosome also contained ~8.5 kb of gene sequence from pCHR151.

DNA sequencing of SB12MC (1.4-fold insert coverage) revealed ~80% of the insert was composed of tandem satellite repeats (Genbank U11026 and Z26334), ~9.9% was made up of retroelement-related sequences, and ~10.1% represented novel, contiguous sequence (SEQ ID NO: 96). The same analysis also produced 1.6-fold vector sequence coverage, indicating little if any cloning bias against fragments from the centromere. Individual satellite repeats showed an average of 91.3% (s.d.=11.3%) identity to each other, with specific regions showing significantly higher and lower levels of variability. Comparing the satellite repeat consensus from SB12MC to that obtained from random satellite sequences (CrGm1 and CrGm2; SEQ ID NOS: 98 and 99, respectively) identified several bases that differed significantly ($\chi^2$ test, $P<0.05$). The SB12MC satellite repeats showed an average length of 91.07±0.40 bp, similar to the CrGm2 91-base consensus and differing from the CrGm1 92-base consensus. FIG. 3 shows an alignment of these consensus sequences.

In addition to the 92-bp soybean satellite, an array of a novel 100 bp repeat was identified in SB12MC (~8 kb, 15.7%) (SEQ ID NO: 97) but not in SB6MC. The 100 bp repeat has no sequence similarity to any known soybean satellite. Interestingly, while TRS satellite were unstable through cycles of cell divisions in both plant and *E. coli* cells, the size of 100 bp satellite track remained around 8 kb in BAC, mini-chromosome and rescued mini-chromosomes, with the exception of being completely lost in R8, R11 and R12.

The invention is claimed as follows:

1. An isolated mini-chromosome comprising a centromere, wherein the centromere comprises
   (a) at least two first repeated nucleotide sequences comprising any one of: the nucleotide sequence of SEQ ID NO: 90, the nucleotide sequence of SEQ ID NO: 91, the nucleotide sequence of SEQ ID NO: 97; or the nucleotide sequence of SEQ ID NO: 100;
   (b) at least a second nucleotide sequence comprising a retrotransposon.

2. The mini-chromosome of 1 wherein the retroposon nucleotide sequence is 95% identical to the retrotransposon nucleotide sequence of CRM (SEQ ID NO: 77), xilon (SEQ ID NO: 93), cinful (SEQ ID NO: 94) or ji (SEQ ID NO: 95).

3. The minichromosome of claim 1, further comprising at least one exogenous nucleic acid.

4. The minichromosome of claim 1, wherein the minichromosome is circular.

5. The minichromosome of claim 1, wherein the minichromosome exhibits a segregation efficiency in corn cells of at least 60%.

6. A plant cell comprising a minichromosome of claim 1.

* * * * *

SEQUENCE LISTING

<160> NUMBER OF SEQ ID NOS: 100

<210> SEQ ID NO 1
<211> LENGTH: 2139
<212> TYPE: DNA
<213> ORGANISM: Drosophila melanogaster

<400> SEQUENCE: 1

| | | | | | | |
|---|---|---|---|---|---|---|
| gttgtccgca | gcggagatgc | aactgatgca | acccacattt | cagatcaccg | acaacgtgca | 60 |
| gcgcggcaac | tacgccactc | tgaccgacaa | ggatgtggcg | catttcgagc | agctcctggg | 120 |
| caagaacttc | gtgctcactg | aggacctgga | gggatacaac | atctgcttcc | ttaagaggat | 180 |
| tcgaggtagg | ttgtgtaacc | aaattcattc | acattcgtgt | gcccttaat | gaatttctcc | 240 |
| gatgaattgc | ttcaaccagg | caacagcaag | ttggtgctta | agcccggaag | cacggcggag | 300 |
| gtggccgcca | tcctgaagta | ctgcaacgag | cgtcgtttgg | cggtggtgcc | gcagggcggg | 360 |
| aacacaggtc | tagtgggcgg | atccgtgccg | atctgcgacg | agattgtcct | ttctctagcg | 420 |
| cgcctgaaca | aggtgttatc | cgtggacgag | gtcaccggca | ttgctgtcgt | ggaggcgggc | 480 |
| tgcatcctgg | agaacttcga | tcagagggcc | agagaggtgg | gcttgacggt | gccactggac | 540 |
| ctgggcgcca | aggccagttg | ccacatcggg | ggcaatgtgt | ccacaaacgc | gggcggagtg | 600 |
| cgggtggtgc | gttacggcaa | tctgcacggc | tctgttttgg | gcgtggaggc | ggtgctggcc | 660 |
| accggtcagg | tgctggacct | tatgtccaac | ttcaagaagg | acaacaccgg | ctaccacatg | 720 |
| aagcacttgt | tcataggatc | cgagggcact | ctgggcgtgg | tcacgaagct | ttcgatgctc | 780 |
| tgcccccatt | cctcgcgagc | ggtgaacgtg | gccttcatcg | gcctgaactc | cttcgacgat | 840 |
| gtgctgaaga | cttttgtcag | tgccaagcgt | aatctgggcg | agattctaag | ctcctgcgag | 900 |
| ctgattgacg | agcgggcctt | gaacaccgcc | ctcgagcagt | tcaagttcct | gaagtgagtt | 960 |
| gcgccacctt | tgtcttctct | gagcgttacc | aatcctgttc | acaaacttat | ttcccatagc | 1020 |
| tcccccattt | cgggatttcc | cttctacatg | ctcatcgaga | cctcgggcag | caacggtgac | 1080 |
| cacgacgagg | agaagatcaa | ccagttcatt | ggggacggta | tggagcgtgg | cgagatccag | 1140 |
| gatggcaccg | taaccggtga | tcccggcaag | gtgcaggaga | tctggaagat | ccgcgaaatg | 1200 |
| gtgccgctgg | gtctgatcga | gaagagcttc | tgcttcaagt | acgacatctc | gctgcctctg | 1260 |
| cgggacttct | acaacattgt | ggacgtgatg | cgagagaggt | gcggtcccct | ggccacagtt | 1320 |
| gtctgcggat | acggccatct | gggggactct | aatctgcacc | tgaacgtctc | ctgcgaggag | 1380 |
| tttaacggcg | agatctacaa | gcgggtcgaa | cccttcgtct | acgagtacac | ctccaagctg | 1440 |
| aagggcagca | ttagtgcgga | gcacggcatt | ggcttcctga | agaaggacta | cctgcactac | 1500 |
| tccaaggacc | cggtggccat | ggctacatg | cgcgagatga | agaagctgct | ggaccccaac | 1560 |
| agcatcctca | atccctataa | ggtgcttaac | tgaaggcttc | tacctaatag | attctatttt | 1620 |
| ttttgtttgt | gtgtaatttt | cataaccta | taatacagaa | atggcattag | aagtgaattt | 1680 |
| tgttaacttg | tgaagttaaa | aaggaccatc | atatttggca | cgaaaccaat | gggcaaaact | 1740 |
| tacttataaa | atagtccgaa | aaaatagtat | ataccagttt | ttacagtacc | acattatagg | 1800 |
| tactcggagg | taataataga | aaaaacacta | tctttgcatt | tactgttaca | ctacgaagca | 1860 |
| ctatatttag | tagcagtact | cattagagtc | cactcacaaa | attagcacca | accggcagta | 1920 |
| attggtcaag | gatcggcgat | agcttcaaac | tccgaagttc | aaagtcaaac | tgccgccctg | 1980 |
| cgaaagcttc | gcgagtggag | cttttctgca | cttatcgata | gctaacattg | tggcgcgact | 2040 |

```
atcgatcgac gagctgccgc ttaacagtgc catatataga ttgtaacatt agaagctcaa    2100
atcattgttg gagcacaaac cacaaagaac acacgaaac                           2139

<210> SEQ ID NO 2
<211> LENGTH: 2191
<212> TYPE: DNA
<213> ORGANISM: Drosophila melanogaster

<400> SEQUENCE: 2
aaaatatttc acctcatttt ccgcacacca tttataagca aagttacccc caacccataa      60
cttttatggt aagtaataca gaccctccaa gttcggcaaa tcgataccca gcgaccttga     120
gcttgacatt tatatatatg ccagaatata acgaccacgt gctgtcaact gtgtcaggaa     180
aagctcaccc acactttctt tggaggagct gtgctcccta aacgaatttc attgtcaagg     240
tcgcacgcac aaaaatgaag aggaaaagct gaatgtgggt ggaaatgccg gccggcacga     300
ccttgaagcc agttgggtga gaaataaaaa gcttttgccg gtaggagact tgtgaacat      360 cacccacaag tggcggactt ggccttggcg atggccttgt tggagctccc tcagcaaaaa     420
tgttacatag ggggaggaaa taagctcaat tggctttatg ctttccgctc cctggaagtc     480
cttttctgga atgttaaagt gttaaatgac atttattgaa catttgggac agaggaggag     540
ataatacaat atacttgtct aattaaaaaa aatcgttatt atgatttatt ccatatgtaa     600
gattttaatt catcatgatt gtaaataaat tatataaaac aaattcaata aatttacatt     660
attgataaaa tttatttttt catgaaatta tacccaaaaa ttattctcaa ttttttcttat    720 aatcagtttt gcataagtat actttcttca taccctctca ccacagccac tgctttcttg    780
actttgcaac tatccgggaa cagcttatca taatggatga gctgcagcta acggaaaatg    840
ggggagctgg gatcaaacat tttccaaggt tgaaattgtc gtcagcataa tgtttgaggg    900
agctggattc gcgttagctt gaaggtcaat ccatttgggt gccctttgtt atggtcaagt    960
ttaaggctgc aataggggga atcttcaagg accattacgc aaggttttcg catcaaagat   1020
ttgccgtgca agcttttga gttgaaggat gcttaacttg aaagcgggtt agtggttcca    1080
agagatttta ggtgaaggag actccgctgt tttgaaatat attaagtatg taagaagta    1140 tactataaat aacccaaagt gatacaatgt aagaaaagat ctcgttggtc cctggtataa   1200
atttgtttgc cattaatgaa tattgaaaat aataattata ctaataatag gtacaataag   1260
caagattaaa ttgcatttaa tcaccaaaaa tcagtttcta tgcgaaccaa aatgtcataa   1320
caaacaattg ttgattcatc cgtagtgaaa tccaagttcg aaattcgaaa tgagcatacg   1380
acgaccaaac ttcccctcaa aattgctaga ctcagctaga gcaagtacgc ccaagttaac   1440
ccctgaaatt cgaatgaat tcgatgccgc gcttcgaaca acgaaatccc aaagagctta   1500
cgttttattt gacgtagcac tcttacgtga atgattttc cccaattccg ctctcatttc    1560
ccgagtctct caccgcttct cagccacttt cccaccccct ttctagttcc gaagtaaagg   1620
taacaaaggc agccgtgtct ttggggtggt aaactggcgg tggtggtggc acattgtcag   1680
tggtgtgggt tcctgtggtt ggtggttcaa ttggttggtt gttggcataa acaaagcaca   1740
cacacaatac acacaaactc ccgggggtg gtggaaattg ggagggtgac attcactgcg    1800
agagaggaac tcgcttccta taggaaagta caaagagagc tatttataa atgtgactgc    1860 agcaaggata tttacagtca gtccactctg aaacctcgac gagagaacat tgaataacaa   1920
gcggaagcga aaagcgcagt tgaaagtccg tcaaaaagcg acaagtttcc tcgttcgttt   1980
tcccgccaaa tgagtcagaa aaattttcca agtgctcgat acgaaacata aagacttaca   2040
```

-continued

| | |
|---|---|
| agacttaaag tgcaagcagt gaatggaata tattattcct cagcgatatt gaaatcaaac | 2100 |
| attaaaaata tatgctacac taaagttata tattttttta aagattcata cgttttgtaa | 2160 |
| aatcacattt tgtattaaat taaataccgc c | 2191 |

<210> SEQ ID NO 3
<211> LENGTH: 2035
<212> TYPE: DNA
<213> ORGANISM: Drosophila melanogaster

<400> SEQUENCE: 3

| | |
|---|---|
| tgggtgcgtc gcaggtttca ctggaaaaca atttgcactt ttgtttgtgg agtcgacaac | 60 |
| aaaagcattc acttgtctaa gactctctca ttcataactc gcactttagt tcactgaacc | 120 |
| gcacgcaaaa ctttggggcg gacaacatgt tttcgaggtg ccaaaagctt cataaaacta | 180 |
| ccaatccatt agattaaatt ccaggcggta catcttttgg ggatgattca tgtggcaggg | 240 |
| gttctctact cgtttacaat catatcatca tcttcaagat catatagttt atcatatcag | 300 |
| tagagtacta caatataatg cataaactaa gccaataaac tttatgacgc gtgcttatgc | 360 |
| gaaagtaaac tttattatca aatttactta accgtgaaat caaaaccttt atataaacac | 420 |
| gaatattatt atctttgcta aataaaactc tcgcttaaca aacaatgaca cttcaattcc | 480 |
| aacatagagt ttatcttaag ccaataacca aaaacggaac ttacataact tgccaacaaa | 540 |
| catatgaata tagctatttc ggatcgtggg agaccattat gcatacaagg cacgctccta | 600 |
| aaaaccgtgt taaacaaata tatgtcaaat gtatatctta aaaaagcgcg cacatatctt | 660 |
| ttgaaatatc ttcacccaga gtatgtatga gattaaactg gattagcact aagccacagc | 720 |
| ttctgtagat agaaatttta tgcagagagt agattatttg gctgctgagc aatttgacca | 780 |
| ccacaagata gcagagaaca tctgacattt tctatatcca tataataaaa ctgacttaac | 840 |
| actaagctga gtggtatgt ttaaatcctc cagctaataa atcgagacta aacgccctat | 900 |
| cttatagtga tatataatag tatctatatg tgtattgtca tttactgttt atgagtattt | 960 |
| gaaaaaacca ttctatattt tataggttag ttaataaata ttttgatata catatgtaga | 1020 |
| ttggctcaca cgtacttatg acccactaca taataaaatt gttttgtttt ttaatagaat | 1080 |
| aatggtttat aaaagttta gactcacacg gaaatgataa actctttgca aatacagctt | 1140 |
| tcattttatt acaaattgca ctctttcaga tctgcagttg ctatgccaac cttttattcc | 1200 |
| ctttactaaa agggtatact aggcttactg aacagtatgt aactggtaaa gtaaagcgtt | 1260 |
| tccgattcta taaattatat atctaaactt ttgatcagtc gaatccatct gaacacattc | 1320 |
| tgtcacatta gattattcca gaaactcaac ttaaacatgt gtattttta agaccattat | 1380 |
| caaggatatt aaaaatggtc tcctaaaatt taataaacaa agtgtcaca tcaaatttaa | 1440 |
| gacgtaaatt aatatttttt ttctatggtg aaataattgt tattttccaa tgttgtgaaa | 1500 |
| taataaatgt atcttttcaa cgcacacatt ttcaaggttt taataataat agtgactcgt | 1560 |
| gcgtgaataa gagagaaatt aagattttaa aaaagaataa aattcagaga tgtgatctgt | 1620 |
| aaaaattatt taccaattt catttacccc cgaaagtgat gctaatggtt aaaacggcat | 1680 |
| ttgcgactta tctcctacgt aatattgcaa aaataaggat ttggttagat gagtgtgaag | 1740 |
| taaacaagat gcaagttttt ggagatagaa aacatagcct tgagtcttgg tcatgtttac | 1800 |
| ttggcaccag gccgcgatta tcagcgctac tagtcgtaat ttgagttaga ccttaatac | 1860 |
| tctaagtgag agtgatgata tacgatttcc cagccacttg cttttctacga aatgcgctaa | 1920 |
| aaaaaatccc taactacaca aagatttgtg ttgttatcca ggtgttctga tataaaaggc | 1980 |

-continued

```
ggcaaggaaa ttgatggcat catcagtatc aaagtgagag tgattgcagt cacac        2035
```

<210> SEQ ID NO 4
<211> LENGTH: 2136
<212> TYPE: DNA
<213> ORGANISM: Drosophila melanogaster

<400> SEQUENCE: 4

```
atgggacggt cctattctca gcaaaaattg acaagaacaa caacaatgtc tatggaaaat     60
cgaacttcat cccagcacct gcagaaatcc cgagcgagtc ggggaaaaag tatttaaccc    120
ccgaaagggt tttccccaaa ataatgaagt aatgaatgaa gcgaaaaaca ctggccgcca    180
atctacctaa tactaatgag cgggccaacc cgaccaggaa ttttttgcaag tcaggtactt    240
caacggatat atgggttcga caagtgcgga ttttcccgcg acatcaatga ggacttggcc    300
gggttatccg cggtgctcat cgggcaattc cgcggccgag gacttcatcg tagtgatcat    360
taggtagata tgtgcatgga tgtgacatgg cgatcattgc gcggaataac acacgtaata    420
accgagatat ccgggatgac ccaccaggta ggatgtgagg acatatagaa accccccagc    480
cagttttttcc actcgtcgtg gcttgttttg cttgagtttc gctgactgcg taattggata    540
agatgggaaa ttactttaaa tccttcgctg atccacatcc ggacattcgt cgaaggaaaa    600
tccattgcag ggaaatacga aatgaaatg cggctgggtt attggctcga catttcccat    660
cttccctcac gccattggtt gcaggatcgc ggggaattgg aattccgcgc tggaatttt    720
tgtcacctct tgggtttatc aaacttttg ggtttgctat ggatttttttc caattttacc    780
accgcgcctg gtttttttttt tttgacgacg cggaaaatcg gacttggcta tgcgggcttg    840
tctgtttttc cgggtacaaa gtctgcatgt cagcctccat gcgggagtgg gagttgggaa    900
agtttcccat cgatagttgg agggggtggct gaaagtctg gaggtgctag ctgggaaagt    960
tgtgtgtgcg cgatgaggca aggagtcaaa gatcagggga gttggaaagc gagaattgtg   1020
ggaatcgtcc aggactcagc tggatgctga ggggcagtat gatttttttt acgttatcaa   1080
tcgaattgat tttaagacag cagaacttca catactaata agatgaccat gggattagtt   1140
aaaatgtgta actcgtattc gaatcgtcat tctttcacgg accaatcgtg ggaacaggag   1200
atctcttcga tccaagctca caggagactt gacactcttc gtctattcct tgtcaagttt   1260
ttaatgacat ctcctatgcc ctgagctatg ttttcctagc tctcatcgat cgctgccaat   1320
gagccactgg agatgatcca taagtcagcg tagagtgcac cccagagttg acacttggtg   1380
tctcggaatt cggctcatta tcagtgctat ttttggaaca cctctctgcg aaggtgtcat   1440
ttttgtcagt gcgtatcgct caggttcaac tccccaccaa aaaccgaatt tagagcatcg   1500
gcagatgtac ttgaagcact caatctaagt gaggaaacca ccccatgaac gaagagtact   1560
aggagtccta tttgactcgt gcttaaaaat agaaaattac ttagggtgat ccataggtag   1620
ggaggcgata ttgtaacttg catttcggac ccggacctgc acgagttatt acgggtgggt   1680
tgtgagcgta tcgggaaatt ggagagccac cagatctgtc ataacttata cggggatcc   1740
ttattcctgg gagggtgcgc ctgcgtctgc tcttccgaga gagaggtggg aaatggagga   1800
agagagagag agagagagtg agagagcagg tagagggaag tgagggaaat acgcaataag   1860
ggtatgggaa aagtgctgtt gttgttgcta ggtagcgacg cacacgtgcg agtgtttttc   1920
tgttttgaag aagaaccacc accaaatggc gacacgggcg tcggcagagg cgcagagttc   1980
cgggtataaa agagcgtgct cgactgttga acctgtcacag ccacctcagc tctcgttgag   2040
aacgcaacca ccgctctata ctcgatcccg aactatataa ctcgcctctc gatcgccgat   2100
```

-continued

```
ctcccgattt acccatctcg atcagtaccg gaaacc                              2136
```

<210> SEQ ID NO 5
<211> LENGTH: 2015
<212> TYPE: DNA
<213> ORGANISM: Drosophila melanogaster

<400> SEQUENCE: 5

```
atttggctcc ccatcgccat cggttgctcc aatgacacta gggaattgtg ggccgccgac      60
agctgtcctt aattacatgg aaatccacac tagattcgtg cccctcgccc cgtactcgca     120
gccgaagtcc ccacagagtc attcaccttg ccaccaccaa aaaaaaaacg aaagcaactg     180
aaggaaaagt tcgattcgaa ggctgaggga taccctttaaa ggcccatttc ccggcttcgt    240
aaatcacatt tagttagcca tttagactac agcaagtctt ttaagataca ctgcaaaata    300
aataccatta cattaataga agtgtcatgt catcggtctg tattttttgtt accacagaat    360
agacttacat atatgataaa aaaatgttca acaataagtt acatcggtag ccaattctat    420
agatttaatt ccttacgaat atagtttcgt tggaatactc aatttgtaat tgtaattaat    480
tataattatt ataattttaa gaatttatat aagtaactaa aagacacggc agacacagaa    540
tgaaaacact ctatgttagg gaatgcaaaa aaacgtggcg gaagccaaaa ggcgcaagca    600
aaaatcgaaa ccaagtgaat ataacatatt atttcaacag gcaactcatt cagcatataa    660
tattaccacc catggagctt tatgtagttg atgtacgtag tctatgatgt ggagcccacg    720
ttggcggaac tgggaatggg gattgggggtt tgagagctgt ggtaaattgg ggggttgaag    780
tatcaagggt ttgggttctg tagacctgcg gaatcgaggt gaataagcga agaacacatt    840
cacacacact aaaaggcaaa caaagggaaa tcaatctttg tacatacttt tagcatatgc    900
acacgtatga tctccaccca cttttccctc ccaatgaaac aaacacacac acacatgcaa    960
ggccgtacgt ttgtatatgt gtgcggttgt cggcttttgcc gggaattggg gaatatttgc   1020
atgcctttgt gtactttttc catatgattt atgacctaaa ttgttgctgc tcgcgcacat   1080
ataattacac acacatcgct gtggccatgt gtgtgtgtgt cgtcttggga cgcgcgccaa   1140
agtatgctac acttttttgtt ttatgagtta ataagtaggc gtggccccag cccaattgct   1200
acactctgat tatggcaccg gatacccaga tagacgccca tccaccccac tgtaagatgg   1260
gggaatttcc aaacctatat gtatgtgcag atcagatagg atagcacaga acttttttaaa   1320
gtacactttt ggggcacgca atttagaaaa tgtacctcgg tgtcggagaa attattttttaa   1380
aagtcgactg aaccacctcg ttccatatgg agaagtctac gagttcaagt ttaatggagc   1440
agctgactgc actgaatttt gtagtttaat acacaaatcc gcaaattgca tctcacttca   1500
aatagcctgg tacatagtat ctactaacat aactcatatt aaaataaagc aaccaaccag   1560
agggccgaag ttctattaat aaaactaata tttaactatt atatatacat tttatttact   1620
tggtacgctt atgataacct tcgaaagaga accaacacaa tacgctttgt catttgaaaa   1680
ataaatatgc tgtaactact ttacaaggtg aaactcttgt cagaagataa gaggctaggt   1740
aagttgatta ttcaatcagt ttacttactg caacccaaaa tggtcactgc actaaccttc   1800
agatgagctg cactacaccc tcaatcgaga atcaatgcaa acgcagtgcc agcgaaaatg   1860
tcagcaaggg attaggccaa tcccaaacgg gtaatcccgc tgcgacaatg ctaatccaat   1920
tccgatgggc cgtataaaag ccccaagctg ggctggctgt gatttcgtct tggcccgcag   1980
accggagcat ggagtccggt aacgtgtcgt cgagc                              2015
```

<210> SEQ ID NO 6

<211> LENGTH: 2082
<212> TYPE: DNA
<213> ORGANISM: Drosophila melanogaster

<400> SEQUENCE: 6

```
atcgatgacg gcatcggctt gacctctcgg agtacgtttg attttataga acaagttttc      60
tcctttctta tactataagg aaaaattata aaaattgctg aaaatgaaac atggctagaa     120
ttcgttttt aacatttttt caatctgaga aaaaatttcc gattagtctt aaaataacta     180
aaccaattcg tatacccgtt aatcgtagaa gaaaatgaa attcatataa taagtagatg     240
gatttgctga cccggtgagg tatatatgta ttcctgaaca tgatcagtaa acgagtcgat     300
ctggccttat ccgtatgaac gtcgagatct cgggaaatac aaaagctaga aggttgagat     360
taagtatgca gattctagaa gaagacgcag cgcaagtttg cgactacgct gaatctactg     420
ctaaaaactg ccacgcccac acttcttaag aatttgattt attttcacaa gctgaggaac     480
ggtagggtcg aggaactcga ctacaacgtt ctgccttgtt tatttcttaa caaaaactta     540
gtagccgttt gggttggaaa ccacctgacc ttaggtctgg tagcagttat ttaatttatt     600
ttttttattt tatacaactt gctcgctgtt tgttcccct agccctgaaa cacaagctgt     660
caaacggtgg aggtgataag tctaatgaat gcgataagct ttatttcaat tcgcaatttt     720
cgtgtggcat tttggcaaaa aaaaaaactc gtcggacata catgttgcca caaacataaa     780
gtgaatacat aatgttgggt gaacgactca tacacgattg tggcaaatca aattctttta     840
acacgggacg gggaaaggcg agtgaagata ttttagcata tatttagcac atctgttaaa     900
tccattttt tactctccgt tttcggccag atatggttag aaaagaaaaa aattagtaca     960
taccccata tataataaga aaaaagaga gagtcagcag aagtacgggg agcttaagtg     1020
tagcaatcag aacatcacaa atagtaaata aattaataat aataataatc atatccaaaa    1080
atattttat tcctaaccta tcgcattgtt acatcgaggg tgaaattcaa aatagacaaa    1140
aagttgggga ataaaatgtg aaaaaagtgg taaaatgttt aatagtgtgg gcgttactgt   1200
tttgtcggtg tgaggtgcgt ggccaccaaa gtgttttttgg tataacgata gaaattggta   1260
agacaaacaa tattgcgaag aaaacccgaa gcatttttaa aaagtgcgaa cgtggcagtt    1320
ttaagggttt gtgggcgtgg caataatttt tggcaattcg ataaaaatgt acaggaccaa    1380
atatatgaag aaatataaaa tattttttcaa aatgacagcc agcaaccata catatatata   1440
aataaatgtc ggagacccct ccttctacct gtaacatact tttccacgaa tctagtattg    1500
gttgatatat aattatgctg tgtataagac caaaatcagt gtacatttcc attggattca    1560
ccaaccggat ggttccggat ggtaatgcaa atattcatc taagaaacga aaacacctag     1620
aattaaacct gaactgatat gacttatgca catatcagtg aggtgggcag ttcaaagcaa    1680
tcacgatgct ccaagttatt atcgcagtgc agtgaaaaat tcacagtcac cgtcgccaat    1740
tgccaataaa gatcggccat tatacaacag aaccgcgttg aagacgatcg acgaggtcgt    1800
gggtcttatc ttatcaccac ctgaattgag gcatgcctcc agaatgacga gggcatccga    1860
agataatgtg gcccgctatt ttcggccggg actggaccta tgcgacgacc tatgctgatg    1920
acgggagtct gccgctgata tggtgcaatg caaggctcca gtcgggggta taaaagaccc    1980
agtttcggtg cagtcaagac aacagacttt aggtgttggt cgttgagcga accaaagccg    2040
gagcagttga ggaaccaaag aatagcagcg agaggaccaa gg                       2082
```

<210> SEQ ID NO 7
<211> LENGTH: 1999
<212> TYPE: DNA

<213> ORGANISM: Saccharomyces cerevisia

<400> SEQUENCE: 7

```
tgtagggacc caaatccaat tgtagtagtt accttgatta tggttggctt gtccttcgat      60
agttttgcct tttccaaagc gctagaaatg gattccatat cgtcgtctcc tttatcgact     120
tccatgactt cccaaccata tgcctcgtat cgcttcaaaa catcttcgtc gaacgagtac     180
gaggttttac cgtcaatgga aatgctatta ctgtcataaa acgtaatcaa gttacccaat     240
tgcagatgtc ccgctaagga agaggtctcc gaagaaacac cctcttgtaa gcaaccatcc     300
cctacaatag caaacgtata tgagtcggaa atgggaaagc catcctcgtt ataagtggcg     360
gcaaagttgg cctgcgctat tgccatacca acagcatttg agataccctg gcctagcgga     420
ccggaagtga tttccactcc cgctgagtgg aattctggat gacccggtgt ccttgagttt     480
acttgtctaa attgtctcaa gtcctcgata gagtaatcgt atcctaatag atggagcatt     540
gagtacagaa gagcgcatga gtgaccgttc gacagaacaa acctgtctct attgatccaa     600
tgttcattgt tagggttaca gcgcagttgc ttgaaaatta catgggcaac tggtgccaat     660
cctagtggtg cacctgggtg gccagattgt gcgctttcca cctggtcaac ggaaagtaat     720
cttaaagtgg aaaccgcaag tttatcaatg tcggagaact gtgccatttt tttgttcttt     780
ttttgattag taaggtataa tcgtctacgt agaggttaca aatcgaagac tacagtaaga     840
ggggacaagc caattgaata tacgactgaa ataaatggaa taattctgca ttattacact     900
cgtttatata tccaaacagg tgatctggta ttctcttgac aacgaatgaa gctccctata     960
ttcgacactc cttattcagg actcctccca acaaggagaa gtaggtgttc cttgagctac    1020
cctttaaagc tggggagatg agcttgccct tcctgtcatc gccattatga cgagaaaagt    1080
aaaacatgta gaataaggtc cacccaaaca tgtccgagca atgacgttat atatcgtgtt    1140
ccctgttcaa agcatggcat atgtgccatt aaaggcgaat ttttgtccct agcaaaggag    1200
agacagcgag ccaccattaa gaagtgactt gaaagcaagc gaaatagct acacatatat     1260
atcaatatat tgacctataa acccaaaatg tgaaagaaat ttgataggtc aagatcaatg    1320
taaacaatta ctttgttatg tagagttttt ttagctacct atattccacc ataacatcaa    1380
tcatgcggtt gctggtgtat ttaccaataa tgtttaatgt atatatatat atatatatat    1440
ggggccgtat acttacatat agtagatgtc aagcgtaggc gcttcccctg ccggctgtga    1500
ggcgccata accaaggtat ctatagaccg ccaatcagca aactacctcc gtacattcat    1560
gttgcaccca cacatttata cacccagacc gcgacaaatt acccataagg ttgtttgtga    1620
cggcgtcgta caagagaacg tgggaacttt ttaggctcac caaaaaagaa agaaaaaata    1680
cgagttgctg acagaagcct caagaaaaaa aaaattcttc ttcgactatg ctggaggcag    1740
agatgatcga gccggtagtt aactatatat agctaaattg gttccatcac cttctttttct   1800
ggtgtcgctc cttctagtgc tatttctggc ttttcctatt tttttttttc catttttctt    1860
tctctctttc taatatataa attctcttgc attttctatt tttctctcta tctattctac    1920
ttgtttattc ccttcaaggt tttttttttaa ggagtacttg tttttagaat atacggtcaa    1980
cgaactataa ttaactaaa                                                1999
```

<210> SEQ ID NO 8
<211> LENGTH: 2001
<212> TYPE: DNA
<213> ORGANISM: Saccharomyces cerevisia

<400> SEQUENCE: 8

```
tctgctatta ttgatgcttt gaagacctcc agacaaattt ttcacagaat gtactcttac      60
gttgtttacc gtattgcttt gtctctacat ttggaaatct tcttgggtct atggattgct     120
attttggata actctttgga cattgatttg attgttttca tcgctatttt cgctgatgtt     180
gctactttgg ctattgctta cgataatgct ccttactctc aaagcccgt taaatggaac      240 ctaccaagat tatggggtat gtctattatt ttgggcatag ttttagctat aggttcttgg     300
attaccttga ctactatgtt cttaccaaag ggtggtatta tccaaaactt cggtgctatg     360
aacggtatta tgttcttgca aatttccttg actgaaaact ggttgatttt cattaccaga     420
gctgctggtc cattctggtc ttctatccca tcctggcaat ggctggtgc cgtcttcgct      480 gtcgacatca tcgctaccat gtttacctta ttcggttggt ggtctgaaaa ctggactgat     540
attgttactg tcgtccgtgt ctggatctgg tctatcggta tcttctgtgt tttgggtggt     600
ttctactacg aaatgtccac ttctgaagcc tttgacagat tgatgaacgg taagccaatg     660
aaggaaaaga gtctaccag aagtgtcgaa gacttcatgg ctgctatgca aagagtctct     720
actcaacacg aaaaggaaac ctaatcctgt tgaagtagca tttaatcata atttttgtca     780 catttttaatc aacttgattt ttctggttta attttttctaa tttaattttt aatttttta    840 tcaatgggaa ctgatacact aaaaagaatt aggagccaac aagaataagc cgcttatttc     900
ctactagagt ttgcttaaaa tttcatctcg aattgtcatt ctaatatttt atccacacac     960
acaccttaaa attttagat aaatggcat caactcttag cttcacacac acacacacac      1020
cgaagctggt tgttttattt gatttgatat aattggtttc tctggatggt acttttttctt    1080 tcttggttat ttcctatttt aaaatatgaa acgcacacaa gtcataatta ttctaataga    1140
gcacaattca caacacgcac atttcaactt taatattttt ttagaaacac tttatttagt    1200
ctaattctta atttttaata tataatgc acacacacta atttattcat taattttta      1260 ttgagtagga tttgaaaata tttggtatct ttgcaagatg tttgtataga gggacaaaga    1320
atcgtcttta ttatggtcaa ggctttacgt cataatagtt cctgcccagc tcttctataa    1380
tactttaaag atctcttctc gtttgctcca tttggaagtc tcgcttacgt ttatgcgccc    1440
atacagacac tcaagataca cacttacatg aacgtataca aatttactaa cactacttga    1500
aaatatgaac cacagtacat catattaaga cgtagtattc gatgattgaa ggccgcctcc    1560
gcgaaatacc tttactgatt ttgccggtta atcgcatcga aatttcttca tcacaagaaa    1620
gcaaacaaat cgccaggcca ttctacaagt ttccttttct tatgaagatg taaaagctac    1680
taaggcgtca ttactctaga tgactcagtt tagtctgacc ttctatagta tactaccctg    1740
gcgctatgat gatgagcggt tcttttattg cggaaacgaa aattccggga ccggcgaaat    1800
ttgcccggtt ttgtccgtaa ccggcttcat gagtcggctt caatagtagt tgaatactta    1860
tttaaacagc agaacttaac tcactcatca cgctgtttcc gctgaatttt ctcaaaatat    1920
ctaagcagtc aacaaatata aagaatattg aaattgacag ttttttgtcgc tatcgatttt    1980 tattatttgc tgttttaaat c                                             2001
```

<210> SEQ ID NO 9  
<211> LENGTH: 2000  
<212> TYPE: DNA  
<213> ORGANISM: Saccharomyces cerevisia

<400> SEQUENCE: 9

```
ccaaatcatt cttattcggt ttccagacgg taacaatacc ctcgcccatc ccacacaaaa      60
gggtatctgc tacttcggga tcgacgaaac aaccacaaag aacttcgtcc tcctgatcat     120
```

```
cgctgatcaa aatttttacca tcctcgtttc cagctacgtt cggtttggca tctttgtcgc    180
gaacgtcaaa ataagctaac gttgtctggc ccaaagaaat gaatttatat gcagatcttt    240
tatcaaagtg gaaaatatcg ttgatagagt cgccaaaatg tatcgaacga atggaatttg    300
ataatgccaa gttttccgag tttattacgt gtatattacc ggattcatcg cctattaaaa    360
tgaatgggtg agtttgagag gcgcataatt tcgtaaattt atcattttttt ttctcttcag    420 aattaaacag tgagcttaag tttaccttttt gacgacttt gccggtcata gtattggcct    480 ttttttaaaac attatccgat ccaacagaaa aaatattgtc acctttagaa tcaaagcaca    540
tggcacggac actacccttta tgtcttttag tcttccaaag tgttttttacg cccaagtctt    600 catctttttcc tgtttgctttt tgttgctgtt gttcttcaat atcaacaaat ttcaaatctc    660
cagtttctag gtctatatct aatctaatcc aagggcatac acctttctttt gcatccttgc    720 ctgtagttgc agtgtcaatt ctacgtctac gatctaggtg cgattgcaac ttagcggggt    780
cataacgatg gcacacaata tgtcctgtac caaagccagt tattataatg ggcagttcag    840
gatgtaaaag agactggaaa atgggagctt ttaatgatag taattctaga atgggcaggt    900
ttgttgaatc gacaacatct gttttttttt tgctctttgc catagctgat gcgtggattg    960 tttctaatttt cccagctgct tcctcttcca attgtggcga tgatgccatg atttctatgt   1020 taaaatttttt ctaaccatga aatttttttt ttctagcgag aaaaaaaatc agaaaaatta   1080
ctattagtga gtattggaga cattgtcaat gggagatgtt ctctttataa tatcttcaac   1140 aggttcttttc aactctggaa attcatccac aatcttgtca gcaagtgaat ctcttaattg   1200
cttcaatcca tgcatcttgc ctctttgata ttggttggat cttcttatgg cttccacgaa   1260
ctctcttgtg taaatatctg gatttctacc gtcctcaatg tattgaacaa cttccaaggg   1320
aatgtccacc ttagacaagc tggattgagg atcgttgctt ctcacgttca gcttgtacaa   1380
gcgatccaca tttctttgca agttggtgat cattcccttg gtggcttctg gagtaccagg   1440
aaaatcatat atcgagacac ctaattcaac gaaggactca ataatcgaag ccacttggtc   1500
ttgagtagtg gccagttctt gctgcaattg ttcattgtta gtgctgtttc cattcatctt   1560
atcggtttat ttttctatat atttgcctct ttctcaaaca ggagttagta gttaaaagta   1620
cgaagttctt gttctttaat gcgcgctgac aaaagaattg gataaaagag aatggtgggg   1680
ggacaagaag gaaatttgtc ctagtttaac atgaatggca tcttgttacc gggtggacat   1740
cacctattga ttctaaatat ctttacggtt tatcatactg ttctttattc cgtcgttatt   1800 cttttttattt ttatcatcat ttcacgtggc tagtaaaaga aaagccacaa catgactcag   1860
caaatctcga caaagtaaaa gctcatagag atagtattat attgatataa aaaaagtata   1920
ctgtactgtt tgtaacctttt tcaatgcttt aagatcaaaa ctaaggccag caaaggtatc   1980
aacccatagc aactcataaa                                                 2000
```

<210> SEQ ID NO 10
<211> LENGTH: 2001
<212> TYPE: DNA
<213> ORGANISM: Saccharomyces cerevisia

<400> SEQUENCE: 10

```
gaaaccatta aatcatattt aataaattgt tgcgacatgc aagaagttcg cggatggtca     60
tgcgtattta agaatagtca agtaacaatt tgcttattcg ttgatgatat gatattattc    120
agcaaagact taaatgcaaa taagaaaatc ataacaacac tcaagaaaca atacgataca    180
aagataataa atctgggtga aagtgataac gaaattcagt acgacatact tggattagag    240
```

-continued

| | |
|---|---|
| atcaaatatc aaagaagcaa gtacatgaaa ttaggtatgg aaaaatcctt gacagaaaaa | 300 |
| ttacccaaac taaacgtacc tttgaaccca aaaggaaaga aacttagagc tccaggtcaa | 360 |
| ccaggtcatt atatagacca ggatgaacta gaaatagatg aagatgaata caaagagaaa | 420 |
| gtacatgaaa tgcaaaagtt gattggtcta gcttcatatg ttggatataa atttagattt | 480 |
| gacttactat actacatcaa cacattgctc aaccatatac tattcccctc taggcaagtt | 540 |
| ttagacatga catatgagtt aatacaattc atgtgggaca ctagagataa acaattaata | 600 |
| tggcacaaaa acaaacctac caagccagat aataaactag tcgcaataag cgatgcttca | 660 |
| tatggtaacc aaccatatta caagtcacaa attggtaaca ttttcctact caacggaaaa | 720 |
| gtgattggag␣gaaagtcgac␣aaaggcttcg␣ttaacatgca␣cttcaactac␣agaagcagaa | 780 |
| atacacgcgg tcagtgaagc tattccgcta ttgaataacc tcagtcacct tgtgcaagaa | 840 |
| cttaacaaga aaccaattat taaaggctta cttactgata gtagatcaac gatcagtata | 900 |
| attaagtcta caaatgaaga gaaatttaga aacagatttt ttggcacaaa ggcaatgaga | 960 |
| cttagagatg aagtatcagg taataattta tacgtatact acatcgagac caagaagaac | 1020 |
| attgctgatg tgatgacaaa acctcttccg ataaaaacat ttaaactatt aactaacaaa | 1080 |
| tggattcatt agatctatta cattatgggt ggtatgttgg aataaaaatc aactatcatc | 1140 |
| tactaactag tatttacgtt actagtatat tatcatatac ggtgttagaa gatgacgcaa | 1200 |
| atgatgagaa atagtcatct aaattagtgg aagctgaaac gcaaggattg ataatgtaat | 1260 |
| aggatcaatg aatattaaca tataaaatga tgataataat atttatagaa ttgtgtagaa | 1320 |
| ttgcagattc cctttatgg attcctaaat cctcgaggag aacttctagt atatctacat | 1380 |
| acctaatatt attgccttat taaaaatgga atcccaacaa ttcatcaaa atccacattc | 1440 |
| tcttcaaaat caattgtcct gtacttcctt gttcatgtgt gttcaaaaac gttatattta | 1500 |
| taggataatt atactctatt tctcaacaag taattggttg tttggccgag cggtctaagg | 1560 |
| cgcctgattc aagaaatatc ttgaccgcag ttaactgtgg gaatactcag gtatcgtaag | 1620 |
| atgcaagagt tcgaatctct tagcaaccat tattttttc ctcaacataa cgagaacaca | 1680 |
| caggggcgct atcgcacaga atcaaattcg atgactggaa attttttgtt aatttcagag | 1740 |
| gtcgcctgac gcatatacct ttttcaactg aaaaattggg agaaaaagga aaggtgagag | 1800 |
| ccgcggaacc ggcttttcat atagaataga gaagcgttca tgactaaatg cttgcatcac | 1860 |
| aatacttgaa gttgacaata ttatttaagg acctattgtt ttttccaata ggtggttagc | 1920 |
| aatcgtctta ctttctaact tttcttacct tttacatttc agcaatatat atatatatat | 1980 |
| ttcaaggata taccattcta a | 2001 |

```
<210> SEQ ID NO 11
<211> LENGTH: 2001
<212> TYPE: DNA
<213> ORGANISM: Saccharomyces cerevisia

<400> SEQUENCE: 11
```

| | |
|---|---|
| cactaccacc actacggttg tccatgacgt atcctgcgat tttttgaatt aatgattcaa | 60 |
| tagttgacat ttgctcgtca ttgggggttcg actgagctgc ggatgtcaac ttcgcaacag | 120 |
| cttctgcatg gttccttga gaaaaatgag actcagcctc tgagattaac ttatccgtat | 180 |
| ccatttcaga tctttgctat acgtttgtat cgctatatgt acgttctttt aatgaacttt | 240 |
| ctcctttctt tatcgtgtag cttgcttggg tatcttttaa tgagttgcgg acagtgagat | 300 |
| ttttcagaag ggcaattggc caagacacca aaaacgtttg gacgagacag gcatcaaagg | 360 |

```
acaaggtaaa aggcgttgag ctgtggctgg ctgtgtatgc gtttgaaata ccatggatag    420
atatcaaaga aagataggat gtttcataca aatcccaaat ttggggcgcg gacaactgaa    480
atacgtgggt ccagtggaca cgaaagctgg aatgtttgct ggtgtagact tacttgccaa    540
cattggtaag aacgatggat cattcatggg gaagaagtat tttcaaacag agtatcctca    600
aagtggacta tttatccagt tgcaaaaagt cgcatcattg atcgagaagg catcgatatc    660
gcaaacctcg agaagaacga cgatggaacc gctatcaata cccaaaaaca gatctattgt    720
gaggctcact aaccagttct ctcccatgga tgatcctaaa tcccccacac ccatgagaag    780
tttccggatc accagtcggc acagcggtaa tcaacagtcg atggaccagg aggcatcgga    840
tcaccatcaa cagcaagaat ttggttacga taacagagaa gacagaatgg aggtcgactc    900
tatcctgtca tcagacagaa aggctaatca caacaccacc agcgattgga aaccggacaa    960
tggccacatg aatgacctca atagcagcga agttacaatt gaattacgag aagcccaatt   1020
gaccatcgaa aagctacaaa ggaaacaact acactacaaa aggctactcg atgaccaaag   1080
aatggtcctc gaagaagtgc aaccgacttt tgataggtat gaagccacaa tacaagaaag   1140
agagaaagag atagaccatc tcaagcaaca attggagctc gaacgcagac agcaagccaa   1200
acaaaagcag ttttttgacg ctgagaatga acagctactt gctgtcgtaa gccaactaca   1260
cgaagagatc aaagaaaacg aagagagaaa tctttctcat aatcaaccca ctggtgccaa   1320
cgaagatgtc gaactcctga aaaacagct ggaacaatta cgcaacatag aagaccaatt   1380
tgagttacac aagacaaagt gggctaaaga acgcgaacaa ttgaaaatgc ataacgattc   1440
gctcagtaaa gaataccaaa atttgagcaa ggaactattt ttgacaaaac cacaagattc   1500
ctcatcggaa gaggtggcat ccttaacgaa aaaacttgaa gaggctaatg aaaaaatcaa   1560
acagttggaa caggctcaag cacaaacagc cgtggaatcg ttgccaattt tcgaccccc    1620
tgcaccagtc gataccacgg caggaagaca acagtggtgt gagcattgcg atacgatggg   1680
tcataataca gcagaatgcc cccatcacaa tcctgacaac cagcagttct tctaggcagt   1740
cgaactgact ctaatagtga ctccggtaaa ttagttaatt aattgctaaa cccatgcaca   1800
gtgactcacg tttttttatc agtcattcga tatagaaggt aagaaaagga tatgactatg   1860
aacagtagta tactgtgtat ataatagata tggaacgtta tattcacctc cgatgtgtgt   1920
tgtacataca taaaaatatc atagcacaac tgcgctgtgt aatagtaata caatagtttta   1980
caaaattttt tttctgaata c                                             2001

<210> SEQ ID NO 12
<211> LENGTH: 2001
<212> TYPE: DNA
<213> ORGANISM: Saccharomyces cerevisia

<400> SEQUENCE: 12
acaatgagga gaacatgcc gttttacaag aattaaatag tttaacccaa agaattaatg     60
aactaggcat ggaaagtata aattcaaact ccgattcgga cagaataaac gggtcatatt    120
cacaagtgga ttttggtaac aataacgacg aggacgatat gaacctgttc gacccagatt    180
ttatggcaca agaccaattg cgtgctgaag aaagagacta caacaaggat gatagaacac    240
ccttagctaa ggtccctgcg gccttttcaat caactggatt gggcataacc cccgatgacg    300
atatcgagag acaatacata acggaacaca gatcacgaca tgaagtgcca aagcggtctc    360
ccgagaaacc ctccaacccg ctggaaatag gtaacccata cgcgaaacct ggcacaaggt    420
tgaataccac tcacacccac agcaaaactg atcgtagcat tacccctcag aggggccagc    480
```

| | |
|---|---|
| cagtcccatc aggccagcag atttcctcct acgtgcagcc agcaaacatt aatagtccta | 540 |
| acaaaatgta tggtgcaaac aactcggcaa tgggttcgcc caggaatcca agacgagag | 600 |
| cgccaccagg tccatacaat cagggatgga ataaccgccc ctcgccttca aatatttacc | 660 |
| aacgtcctca tccctcagat acacaaccac aagcatatca tctccccgga aacccatact | 720 |
| caacggggaa caggccaaac atgcaagcgc aatatcaccc gcagcaggtg cccatgccta | 780 |
| tcctgcagca gcccaatcgc ccgtaccaac cttatgcgat gaatacgcac atgggctctc | 840 |
| ctggcggata tgctggggca gcaccaccat ttcagccagc taacgtcaac tacaatacta | 900 |
| ggcctcagca gccatggcct acacctaact caccatccgc acactaccgt ccgccccta | 960 |
| acctgaacca gcctcaaaac ggtagtgctg gttactatcg tccgccggca ccacaattgc | 1020 |
| aaaactccca agcccgtcca caaagaagg acggattctc acgttcatg ccatctgcaa | 1080 |
| ctacgaagaa cccatatgcc cagtaactcg accgactggt tgtaatttta caaaagaga | 1140 |
| gacaattaag aaaagaaaca agcgccaggc ttccgtatcc cagttttca tctcactttc | 1200 |
| tgggcacgat tgtaataata cttcatgata ataactaaac tatataagta gtgtctcatc | 1260 |
| cgtaaaatata catttagaca gattcttgta ttttctccgg gcaattttta acttttttc | 1320 |
| tgttagggca catgacactt gcctattatg gacagccagt aaagatgtgc catatattgc | 1380 |
| ccccttacg ctctctgcca gtattagtgg gaaaaaaaaa actgaaaaaa aaaaatcgc | 1440 |
| agactactaa taatcacgtg atatttcttt tcactctctt cataaagttg ctaaaaacac | 1500 |
| acaatcgaat gagcctctga gcagtataaa ttgtacttca aagcactagt catgaaaaac | 1560 |
| gcttacatta gttcagtttg tcaaggttat gctattactt gtacttattt cttgctattg | 1620 |
| ttagtggctc cccacattga cgtattttca cgtgatgcgc ctcactgcgg aaggcgccac | 1680 |
| acattgcctg caaaaaattg tggatgcact catttgatag taaactaagt catgttaatc | 1740 |
| gtttggattt ggcacacacc cacaaatata cacattacat atatatatat attcaaaata | 1800 |
| cagctgcgtc caatagatga gcttccgctt cgttgtacaa cctacctgct atcttgttca | 1860 |
| cggatatttc ttgcttttaa taaacaaag taactctaga acagtcaagt cttcgataat | 1920 |
| ttttttagtc acagggtccg tctaaagttt ctctttattt ggaataatag aaaagaaaga | 1980 |
| aaaaaacgta gtataaaagg a | 2001 |

<210> SEQ ID NO 13
<211> LENGTH: 2000
<212> TYPE: DNA
<213> ORGANISM: Saccharomyces cerevisia

<400> SEQUENCE: 13

| | |
|---|---|
| aaggatggca ataccccaat cggaggaact cgaacacttc agtatctgtg tcttctagtg | 60 |
| agtctttagc ggaagttatt cagccatctt ccttcaaaag tgggagtagt tcattgcatt | 120 |
| atctatcgtt ttctatctca agccaacctg gttcgtacgg ttcttggttc aacaaaaggc | 180 |
| caacaatttc tcagttcttt caaccaagcc cttcttaaaa acacaacgag tcgtgggaga | 240 |
| ggctgcaaac aactgctgga atatgcaaa ggacttcaag ttcgtcttct ttgcagcaag | 300 |
| caacctccag gttatcacta accactccgc aacaatcacc gtctatcagc gaatatgatg | 360 |
| agtatccttg gatgggcaca cctggctctc ctaatgttgg agatgtgtct cacgcacccc | 420 |
| cattggttaa gaatatatca tataaatttc cactaaagaa cgttgagttg aaagagatt | 480 |
| gccaaaggat ctctcaggat gatctttttgg atgaggcttt tgaaagaata tgtcagccct | 540 |
| ctttggctga ccttaattcc acttacgaaa ttttttccagg taactcttct tatgcggata | 600 |

```
ttttgactac tgattctgat attgatgatg gcttgatgaa taaacctctg gaactattgc        660
cgaaatatac aatgtattta acccatttta acaattttt  ccagttgcaa gcatgtcctg        720
ctggtcaaga atcagagagc agaataacaa attctatgaa gattgacctg ttaaaggcgg        780
attacacaag aagtctatta gtatcgttac gttcaaggga cattagggat gtcgcattga        840
aaagagagtt tactggcaat aacaacaata acagcaacca gaatatctat gatgagaatt        900
ttgtcggaaa aaggaagtac gtgttgaaac agaagaccag aaaaatcttt tcctgtggca        960
agattggcaa gctaagtact agtttggaaa actgcgttaa ttttgttgaa aatagtataa       1020
agagtgcaat gatgttatat gatgataatg gaatagatag tgagcttcgc gattcagaag       1080
ctttacggat ttttttcatct cttgttcatt attgtaatgc aggttaatgt tttctccttc      1140
tttacatgtt taatatattc caagttacct aagaggtgta cgatatttt ttcttttata        1200 tatatgattt tctctattca tttttagtt tttttgata cataagcgaa tcgcacattg         1260
cgcaacttca atttgttgat tcgccaaagt attcttacca taaacaacc attcgttgct        1320 ttacccttc gtaatcattt accgtgataa ccataatcag aaacttatta tttcagccta       1380
gtagaccggc caagcaggcc ttgtaatgtt tctcttgatt gcttgaatct tttaagcagc      1440
caaatctttc caaaaaaatg caattatcag aacaaaacta tttaaggtga cttctccgta      1500
tttacaccac cagaagcgtt ctggctcccc ttttctctaa acgttaaaca ttttacaatt      1560
gaaatgttac caatcctata ttattgtacc acattgccag atttatgaac tctgggtatg     1620
ggtgctaatt ttcgttagaa gcgctggtac aattttctct gtcattgtga cactaattag     1680
gaaacttctc gactatcaat gtgtaaatga aggaataatg gcggaaactt tgaaactttg    1740
tcaataattg catcattgga tgcgtttcat ttggccgtta tcacggagag gcagagttct     1800
ctccacaatt tgggcagaag tctttttgaaa agacatatat atatatatat atgtatatga    1860
gtggatgctt aagtaagaa taatttctga attcccaagt attcattttg tgcagtattc      1920
acatattcta ttttattgct ttttaacttt agaggcaatt aaattgtgt aggaaaggca      1980 aaatactatc aaaattttcc                                                  2000
```

<210> SEQ ID NO 14
<211> LENGTH: 2001
<212> TYPE: DNA
<213> ORGANISM: Saccharomyces cerevisia

<400> SEQUENCE: 14

```
ttgccttcaa gatctacttt cctaagaaga tcattattac aaacacaact gcactcaaag         60
atgactgctc atactaatat caaacagcac aaacactgtc atgaggacca tcctatcaga       120
agatcggact ctgccgtgtc aattgtacat ttgaaacgtg cgcccttcaa ggttacagtg       180
attggttctg gtaactgggg gaccaccatc gccaaagtca ttgcggaaaa cacagaattg       240
cattcccata tcttcgagcc agaggtgaga atgtgggttt tgatgaaaa gatcggcgac        300 gaaaatctga cggatatcat aaatacaaga caccagaacg ttaaatatct acccaatatt      360
gacctgcccc ataatctagt ggccgatcct gatctttttac actccatcaa gggtgctgac     420
atccttgttt tcaacatccc tcatcaattt ttaccaaaca tagtcaaaca attgcaaggc      480
cacgtggccc ctcatgtaag ggccatctcg tgtctaaaag ggttcgagtt gggctccaag      540
ggtgtgcaat tgctatcctc ctatgttact gatgagttag gaatccaatg tggcgcacta      600
tctggtgcaa acttggcacc ggaagtggcc aaggagcatt ggtccgaaac caccgtggct     660
taccaactac caaaggatta tcaaggtgat ggcaaggatg tagatcataa gattttgaaa      720
```

```
ttgctgttcc acagacctta cttccacgtc aatgtcatcg atgatgttgc tggtatatcc    780
attgccggtg ccttgaagaa cgtcgtggca cttgcatgtg gtttcgtaga aggtatggga    840
tggggtaaca atgcctccgc agccattcaa aggctgggtt taggtgaaat tatcaagttc    900
ggtagaatgt ttttcccaga atccaaagtc gagacctact atcaagaatc cgctggtgtt    960
gcagatctga tcaccacctg ctcaggcggt agaaacgtca aggttgccac atacatggcc   1020
aagaccggta agtcagcctt ggaagcagaa aaggaattgc ttaacggtca atccgcccaa   1080
gggataatca catgcagaga agttcacgag tggctacaaa catgtgagtt gacccaagaa   1140
ttcccattat tcgaggcagt ctaccagata gtctacaaca acgtccgcat ggaagaccta   1200
ccggagatga ttgaagagct agacatcgat gacgaataga cactctcccc cccctcccc    1260
ctctgatctt tcctgttgcc tctttttccc ccaaccaatt tatcattata acaagttct    1320
acaactacta ctagtaacat tactacagtt attataattt tctattctct ttttctttaa   1380
gaatctatca ttaacgttaa tttctatata tacataacta ccattataca cgctattatc   1440
gtttacatat cacatcaccg ttaatgaaag atacgacacc ctgtacacta acacaattaa   1500
ataatcgcca taaccttttc tgttatctat agcccttaaa gctgtttctt cgagcttttt   1560
cactgcagta attctccaca tgggcccagc cactgagata agagcgctat gttagtcact   1620
actgacggct ctccagtcat ttatgtgatt ttttagtgac tcatgtcgca tttggcccgt   1680
tttttttccgc tgtcgcaacc tatttccatt aacggtgccg tatggaagag tcatttaaag   1740
gcaggagaga gagattactc atcttcattg gatcagattg atgactgcgt acggcagata   1800
gtgtaatctg agcagttgcg agacccagac tggcactgtc tcaatagtat attaatgggc   1860
atacattcgt actcccttgt tcttgcccac agttctctct ctctttactt cttgtatctt   1920
gtctccccat tgtgcagcga taaggaacat tgttctaata tacacggata caaaagaaat   1980
acacataatt gcataaaata c                                              2001

<210> SEQ ID NO 15
<211> LENGTH: 1999
<212> TYPE: DNA
<213> ORGANISM: Saccharomyces cerevisia

<400> SEQUENCE: 15
ttttgtaaga aattattcac cgcatcttca tctggcaaac gaatgggaga ctttgaggaa     60
cccaatccat ttctgaataa cggagattta gaaatgtaaa aggtagcaaa tgtaaaaagt    120
gccaggacca tcacagcagt caatgccaac accaatttcc cttgccatga cactgttgga    180
tcttttgaag gagatttgta acctggaatc tcactataat gaacacattc accggattca    240
cacttcaaag taatataagg gtcaccaaac acggtcaata tcaaatcatt catagaaggc    300
tcactgaatt tacattgcct tgtttctaaa tcacagctga aatctcctgg cccttttatt    360
gtctctgtca ggaaatccga gatatctata gaccccttag caccacacaa cacagtgtcg    420
ggaacgcatt tgcattgaac gtcattacac ttataatggg aggtattctg ttccaagtcg    480
tattcaaagg cacaatcact taagccacaa tagaagcttt ctaactgatc tatccaaaac    540
tgaaaattac attcttgatt aggtttatca caggcaaatg taatttgtgg tattttgccg    600
ttcaaaatct gtagaatttt tcattggtc acattacaac ctgaaaatac tttatctaca    660
atcataccat tcttataaca tgtcccctta atactaggat caggcatgaa cgcatcacag    720
acaaaatctt cttgacaaac gtcacaattg atccctcccc atccgttatc acaatgacag    780
gtgtcatttt gtgctcttat gggacgatcc ttattaccgc tttcatccgg tgatagaccg    840
```

-continued

```
ccacagaggg gcagagagca atcatcacct gcaaacccct ctatacactc acatctacca      900
gtgtacgaat tgcattcaga aaactgtttg cattcaaaaa taggtagcat acaattaaaa      960
catggcgggc atgtatcatt gcccttatct tgtgcagtta gacgcgaatt tttcgaagaa     1020
gtaccttcaa agaatggggt cttatcttgt tttgcaagta ccactgagca ggataataat     1080
agaaatgata atatactata gtagagataa cgtcgatgac ttcccatact gtaattgctt     1140
ttagttgtgt attttagtg tgcaagtttc tgtaaatcga ttaattttt tttctttcct       1200
cttttattta accttaattt ttatttaga ttcctgactt caactcaaga cgcacagata      1260
ttataacatc tgcataatag gcatttgcaa gaattactcg tgagtaagga aagagtgagg     1320
aactatcgca tacctgcatt taaagatgcc gatttgggcg cgaatccttt attttggctt     1380
caccctcata ctattatcag ggccagaaaa aggaagtgtt tccctccttc ttgaattgat     1440
gttaccctca taaagcacgt ggcctcttat cgagaaagaa attaccgtcg ctcgtgattt     1500
gtttgcaaaa agaacaaaac tgaaaaaacc cagacacgct cgacttcctg tcttcctatt     1560
gattgcagct tccaatttcg tcacacaaca aggtcctagc gacggctcac aggttttgta    1620
acaagcaatc gaaggttctg gaatggcggg aaagggttta gtaccacatg ctatgatgcc    1680
cactgtgatc tccagagcaa agttcgttcg atcgtactgt tactctctct ctttcaaaca    1740
gaattgtccg aatcgtgtga caacaacagc ctgttctcac acactctttt cttctaacca    1800
aggggtggt ttagtttagt agaacctcgt gaaacttaca tttacatata tataaacttg     1860
cataaattgg tcaatgcaag aaatacatat ttggtctttt ctaattcgta gttttcaag    1920
ttcttagatg ctttcttttt ctcttttta cagatcatca aggaagtaat tatctacttt    1980
ttacaacaaa tataaaaca                                                  1999

<210> SEQ ID NO 16
<211> LENGTH: 1999
<212> TYPE: DNA
<213> ORGANISM: Saccharomyces cerevisia

<400> SEQUENCE: 16
aaacaaatgg caaaaataac gggcttcacc attgttcctg tatggtgtat tagaacatag       60
ctgaaaatac ttctgcctca aaaaagtgtt aaaaaaaaga ggcattatat agaggtaaag      120
cctacaggcg caagataaca catcaccgct ctccccctc tcatgaaaag tcatcgctaa      180
agaggaacac tgaaggttcc cgtaggttgt ctttggcaca aggtagtaca tggtaaaaac      240
tcaggatgga ataattcaaa ttcaccaatt tcaacgtccc ttgtttaaaa agaaaagaat      300
ttttctcttt aaggtagcac taatgcatta tcgatgatgt aaccattcac acaggttatt      360
tagcttttga tccttgaacc attaattaac ccagaaatag aaattaccca agtggggctc      420
tccaacacaa tgagaggaaa ggtgactttt taaggggggcc agaccctgtt aaaaacccttt     480
gatggctatg taataatagt aaattaagtg caaacatgta agaaagattc tcggtaacga      540
ccatacaaat attgggcgtg tggcgtagtc ggtagcgcgc tcccttagca tgggagaggt      600
ctccggttcg attccggact cgtccaaatt attttttact ttccgcggtg ccagagatgca     660
gacgtggcca actgtgtctg ccgtcgcaaa atgatttgaa ttttgcgtcg cgcacgtttc      720
tcacgtacat aataagtatt tcatacagt tctagcaaga cgaggtggtc aaaatagaag       780
cgtcctatgt tttacagtac aagacagtcc atactgaaat gacaacgtac ttgacttttc      840
agtatttct ttttctcaca gtctggttat ttttgaaagc gcacgaaata tatgtaggca      900
agcattttct gagtctgctg acctctaaaa ttaatgctat tgtgcacctt agtaacccaa      960
```

-continued

```
ggcaggacag ttaccttgcg tggtgttact atggccggaa gcccgaaaga gttatcgtta   1020
ctccgattat tttgtacagc tgatgggacc ttgccgtctt catttttttt tttttttcacc  1080
tatagagccg ggcagagctg cccggcttaa ctaagggccg gaaaaaaaac ggaaaaaaga   1140
aagccaagcg tgtagacgta gtataacagt atatctgaca cgcacgtgat gaccacgtaa   1200
tcgcatcgcc cctcacctct cacctctcac cgctgactca gcttcactaa aaaggaaaat   1260
atatactctt tcccaggcaa ggtgacagcg gtccccgtct cctccacaaa ggcctctcct   1320
ggggtttgag caagtctaag tttacgtagc ataaaaattc tcggattgcg tcaaataata   1380
aaaaaagtaa ccccacttct acttctacat cggaaaaaca ttccattcac atatcgtctt   1440
tggcctatct tgttttgtcc tcggtagatc aggtcagtac aaacgcaaca cgaaagaaca   1500
aaaaaagaag aaaacagaag gccaagacag ggtcaatgag actgttgtcc tcctactgtc   1560
cctatgtctc tggccgatca cgcgccattg tccctcagaa acaaatcaaa cacccacacc   1620
ccgggcaccc aaagtcccca cccacaccac caatacgtaa acggggcgcc cctgcaggc    1680
cctcctgcgc gcggcctccc gccttgcttc tctcccttc cttttctttt tccagttttc   1740
cctattttgt cccttttttcc gcacaacaag tatcagaatg ggttcatcaa atctatccaa   1800
cctaattcgc acgtagactg gcttggtatt ggcagtttcg tagttatata tatactacca   1860
tgagtgaaac tgttacgtta ccttaaattc tttctcccctt taattttctt ttatcttact   1920
ctcctacata agacatcaag aaacaattgt atattgtaca cccccccct ccacaaacac    1980
aaatattgat aatataaag                                                1999

<210> SEQ ID NO 17
<211> LENGTH: 2009
<212> TYPE: DNA
<213> ORGANISM: Saccharomyces cerevisia

<400> SEQUENCE: 17
ggatgagaaa cgagtgcggt ttcgagagta gatattcaac ccacccgaag tagccttcag    60
gaactggttc cgttctctct tcctccggaa tagtctgaat gtccttaaga gaccgtggct   120
cgtatactct tctattcttg ggccgcaata gcaaaaagag ccagacaaac acgacggcgg   180
taagaccgta gataatcagg gttgaaatga acgccgaagt cgaagaactg tcagccatag   240
tacgtatgtg ctataaatat ctaacctttc gctgctttga atatgatgtg ctcaaatata   300
acttaatata atagtataac aaaaaggagt actatttgct aaatatcgta gacgtagtag   360
acatagtaaa tacaataaag gatagataac caagaaccca catcaagcga atacatacat   420
atatatatac tcgatgtata catgtttcta agcacttgcg cacatacgta tttaaagtat   480
ttcagggaga ttaacgtatt aaaacaagaa gagggttgac tacatcacga tgagggggat   540
cgaagaaatg atggtaaatg aaataggaaa tcaaggagca tgaaggcaaa agacaaatat   600
aagggtcgaa cgaaaaataa agtgaaaagt gttgatatga tgtatttggc tttgcggcgc   660
cgaaaaaacg agtttacgca attgcacaat catgctgact ctgtggcgga cccgcgctct   720
tgccggcccg gcgataacgc tgggcgtgag gctgtgcccg gcggagtttt ttgcgcctgc   780
attttccaag gtttaccctg cgctaagggg cgagattgga gaagcaataa gaatgccggt   840
tgggggttgcg atgatgacga ccacgacaac tggtgtcatt atttaagttg ccgaaagaac   900
ctgagtgcat ttgcaacatg agtatactag aagaatgagc caagacttgc gagacgcgag   960
tttgccggtg gtgcgaacaa tagagcgacc atgaccttga aggtgagacg cgcataaccg  1020
ctagagtact ttgaagagga aacagcaata gggttgctac cagtataaat agacaggtac  1080
```

```
atacaacact ggaaatggtt gtctgtttga gtacgctttc aattcatttg ggtgtgcact    1140
ttattatgtt acaatatgga agggaacttt acacttctcc tatgcacata tattaattaa    1200
agtccaatgc tagtagagaa ggggggtaac acccctccgc gctcttttcc gattttttc     1260 taaaccgtgg aatatttcgg atatccttt gttgtttccg ggtgtacaat atggacttcc     1320
tcttttctgg caaccaaacc catacatcgg gattcctata ataccttcgt tggtctccct    1380
aacatgtagg tggcggaggg gagatataca atagaacaga taccagacaa gacataatgg    1440
gctaaacaag actacaccaa ttacactgcc tcattgatgg tggtacataa cgaactaata    1500
ctgtagccct agacttgata gccatcatca tatcgaagtt tcactaccct ttttccattt    1560
gccatctatt gaagtaataa taggcgcatg caacttcttt tcttttttt tcttttctct     1620 ctcccccgtt gttgtctcac catatccgca atgacaaaaa aatgatggaa gacactaaag    1680
gaaaaaatta acgacaaaga cagcaccaac agatgtcgtt gttccagagc tgatgagggg    1740
tatctcgaag cacacgaaac ttttttcctc cttcattcac gcacactact ctctaatgag    1800
caacggtata cggccttcct tccagttact tgaatttgaa ataaaaaaaa gtttgctgtc    1860
ttgctatcaa gtataaatag acctgcaatt attaatcttt tgtttcctcg tcattgttct    1920
cgttcccttt cttccttgtt tcttttttctg cacaatattt caagctatac caagcataca   1980
atcaactatc tcatatacaa tgtctatcc                                     2009

<210> SEQ ID NO 18
<211> LENGTH: 1943
<212> TYPE: DNA
<213> ORGANISM: Saccharomyces cerevisia

<400> SEQUENCE: 18
ggcagtcatc aggatcgtag gagataagca ccctgacaag taacatgccg atgaagttgt      60
ttggttcatt gggcaaaaaa atcgggattc tagaaaaccc tgagttgaag attttttcga    120
cagttttatc gtctaggatg gtatcggcac tcattgtgaa cacgttttca atcggagtca    180
tgatttcctc aaccctcttt gcctttagat ccaaaacagc agagatgatt gtaacttcgt    240
ctttagtcaa ccgttccacc cccatggtcc tatgcaaggt gaccaaagtc tttaagccgg    300
attttttgta catcgtacca tgatcttcac ccagcatata gtccaggaga gtcgcgatcg    360
gatatgcgac tgggtacatc agatacatca gtacaagaac aaaggggcag aagaatgccc    420
caacttgcag cccgtatta acacagacac tctgcggaat aatttcaccg aagatcacaa    480
ttagaatagt tgacgacact acagcctgcc aaccaccccc aagacacctg tccaaaacaa    540
taggcaatgt ttcgttggtt ataacattag aaagcagcag tgtgactaga acccaatgct    600
tccccctaga tattaggtca agcacccgct tggccagttt cttttcagaa ttcgagcctg    660
aagtgctgat taccttcagg tagacttcat cttgacccat caaccccagc gtcaatcctg    720
caaatacacc acccagcagc actaggatga tagagataat atagtacgtg gtaacgcttg    780
cctcatcacc tacgctatgg ccggaatcgg caacatccct agaattgagt acgtgtgatc    840
cggataacaa cggcagtgaa tatatcttcg gtatcgtaaa gatgtgatat aagatgatgt    900 ataccccaatg aggagcgcct gatcgtgacc tagaccttag tggcaaaaac gacatatcta    960
ttatagtggg gagagtttcg tgcaaataac agacgcagca gcaagtaact gtgacgatat    1020
caactctttt tttattatgt aataagcaaa caagcacgaa tggggaaagc ctatgtgcaa    1080
tcaccaaggt cgtccctttt ttcccatttg ctaatttaga atttaaagaa accaaaagaa    1140
tgaagaaaga aaacaaatac tagccctaac cctgacttcg tttctatgat aatacccctgc   1200
```

```
tttaatgaac ggtatgccct agggtatatc tcactctgta cgttacaaac tccggttatt    1260
ttatcggaac atccgagcac ccgcgccttc ctcaacccag gcaccgcccc caggtaaccg    1320
tgcgcgatga gctaatcctg agccatcacc caccccaccc gttgatgaca gcaattcggg    1380
agggcgaaaa ataaaaactg gagcaaggaa ttaccatcac cgtcaccatc accatcatat    1440
cgccttagcc tctagccata gccatcatgc aagcgtgtat cttctaagat tcagtcatca    1500
tcattaccga gtttgttttc cttcacatga tgaagaaggt ttgagtatgc tcgaaacaat    1560
aagacgacga tggctctgcc attgttatat tacgcttttg cggcgaggtg ccgatgggtt    1620
gctgagggga agagtgttta gcttacggac ctattgccat tgttattccg attaatctat    1680
tgttcagcag ctcttctcta ccctgtcatt ctagtatttt tttttttttt ttttggtttt    1740 acttttttt cttcttgcct tttttcttg ttactttttt tctagttttt tttccttcca    1800
ctaagctttt tccttgattt atccttgggt tcttctttct actcctttag attttttttt    1860
tatatattaa ttttaagtt tatgtatttt ggtagattca attctctttc cctttccttt    1920
tccttcgctc cccttcctta tca    1943

<210> SEQ ID NO 19
<211> LENGTH: 2001
<212> TYPE: DNA
<213> ORGANISM: Saccharomyces cerevisia

<400> SEQUENCE: 19
tgacaacgag taccaggaaa tcagtgcttc tgctttgaag aaggctcgta agggctgtga      60
tggtttgaag aaaaaggcag tcaagcaaaa ggaacaggag ttgaagaaac aacaaaaaga     120
ggcagaaaat gctgccaagc aattgtctgc tttgaatatc accattaagg aggacgaatc     180
gctaccagct gccattaaga ctagaattta tgactcttat tccaaggtcg acaaagagt     240 taaggtttcc ggttggatcc atagattacg ttctaacaag aaggttatttt tcgtcgtcct     300 cagagacgga tctggtttca ttcaatgtgt cttgtccggt gatttggcat ggctcaaca     360 aactttggac ctgactttgg aatccaccgt tactctgtac ggtaccatag tcaaattgcc     420
tgagggtaaa accgctccag gtggtgttga attgaatgtc gactattacg aagttgtagg     480
tttggccccc ggtggtgaag actcctttac aaacaaaatc gcagagggct cagacccttc     540
tttactgttg gaccaacgtc atttggcctt gagaggagat gccttgtctg cagtcatgaa     600
agtccgtgct gctctactga aaagcgttag acgtgtttat gatgaagaac atttgacaga     660
agttacccca ccatgtatgg tgcaaactca agtcgaaggt ggttccactt tgttcaagat     720
gaactattac ggcgaggaag cttacttgac ccaaagttcc caattatatt tagaaacctg     780
tttggcctcc ctaggtgatg tttataccat ccaagaatct ttcagagctg aaaagtccca     840
cacaagaaga catttgtccg aatatacccca tatcgaagct gaattggcct tcttgactttt    900 cgacgatcta ttcaacatat tgaaacttt gatcgtcaaa tccgtgcaat acgttttgga     960
agacccaatt gctggcccac tcgtaaaaca attgaatcca aactttaagg ctccaaaggc    1020
tccattcatg agattacagt acaaggatgc cattacctgg ttgaacgaac acgacatcaa    1080
gaacgaagag ggcgaagact ttaaatttgg tgacgatatt gcagaagctg ctgaaagaaa    1140
gatgaccgat accatcggcg tcccaatctt tttgacgaga ttcccagtag aaatcaagtc    1200
tttctacatg aagcgttgtt ctgacgaccc ccgcgtcact gaatccgtcg acgttttgat    1260
gccaaacgtt ggtgaaatca ctggtggttc tatgagaatc gacgacatgg acgaactaat    1320
ggcagggttt aagcgtgagg gtattgatac cgacgcctac tactggttca ttgaccaaag    1380
```

```
aaaatacggt acttgcccac atggtggtta cggtatcggt accgaacgta ttttagcctg    1440
gttgtgtgac agattcactg tcagagactg ttccttgtat ccacgtttca gcggtagatg    1500
taagccatga tctttagtta ctgaagagta cgtgagcgct cacatatata caaatattta    1560
taccgattaa tatttacgtt cctccctctc tctaattatt cattgattta ttcaagaatt    1620
agcgttataa caataaatgg ttggcgcagg caattaattt ttctttactc ttccaaaccc    1680
tctgttaacg acaatcaaat aacctgatct gccaaggctc catcatatct ggcctagaac    1740
agtttttttt tttcgattat ttgttcgttc ttgtggtggt tactcattgg cagaatcccg    1800
aaaatcatga ttagtagatg aatgactcac tttttggata agctggcgca aattgaaaca    1860
tgtgaaaaaa aaaaaaaagg attataaaag gtcagcgaag cacagaactc tgagataaga    1920
ctacctttct ttagctaggg gagaatattc gcaattgaag agctcaaaag caggtaacta    1980
tataacaaga ctaaggcaaa c                                              2001

<210> SEQ ID NO 20
<211> LENGTH: 1999
<212> TYPE: DNA
<213> ORGANISM: Saccharomyces cerevisia

<400> SEQUENCE: 20
tcctaaggac atattccgtt cgtacttgag ttattggatc tatgaaatcg ctcgctatac      60
accagtcatg attttgtccc tggtaatagg ggttttggtt ttattaatta tatttttaa     120 tgacaacgaa gcttgtgttt tcaattctgc aatatttgct tttacttctc ttgtaggttt     180
gttaataata ttaagtgatg gtaatccaaa gctagtcagt cgtcgaaatt ttaggaccga     240
gcttttagtg gatgtcatca cacgtaaacc ggcggtagaa gggaaagaat ggaggatcat     300
cacatacaac atgaaccaat atttgtttaa tcatgggcaa tggcatactc cgtattactt     360
ttacagcgat gaggattgct accgttattt tctacgcctt gttgagggag taacccccaa     420
gaagcaaaca gccacgtcaa ttggcaattc tccggtcacc gctaagcctg aagatgccat     480
cgagtcagct tctcctagtt ccagactgaa ttatcaaaac ttttttgctca aggcagcgga     540 gatcgaacga caagctcagg aaaattactg gcgaaggcgg catcccaata tcgatgcgct     600
tcttaaaaag acggaatagc ttagagacac taccatacgt aaagcgaaca taaactagag     660
tatgatatat aatcagcact aactggccgg aaaacggccg aaggaagcct cgaaaagtcg     720
attcgtgttg gacccatttg ctgaacaaag tggttcattg cctacctatt atggtagtag     780
tcgtgataat cgtgtggttg gttttgtcaa cggtgcattt gcattttcat gacaataaac     840
cttgcgtttt cgttctcggg atattacttt ccctccactt cttttcgcctc aatagctcct     900 ataagcattc tcagggcgta tgtcggtgat cgagatttcc aagcaagctt ttagtggaaa     960
tcatcgcgcg caagccagcg gtaaagggaa aagaacggag gacgattaca tacaagatga    1020
acgaataaat aaattaataa taaataataa taaaagtac agtagcatta aatattatta     1080
agtttaatga ttaaaaattg gttaattgtc aagaaaatct aaggtattaa taaataaata    1140
atactatgac aacttgcagc gaaagcatca gccccaatga aaattaatca gaattgaatc    1200
tgagcgtatt tatttgataa cggtttacgt aactgttgga ataaaaatca actatcatct    1260
actaactagt gttacgttac ctagtatatt atcatatacg gtgttagaag atgacgcaaa    1320
tgatgagaaa tagtcatcgt tttcaacgga agctgaaata caaggattga taatgtaata    1380
ggatcaatga atatcaacat ataaaacgat gataataata tttatagaat tgtgtagaat    1440
tgcagattcc cttttatgga ttcctaaatc ctcgagaaga acttctagta tatctacgta    1500
```

```
cctaatatta ttgccttatt aaaaatggaa tcccaacaat tatctcaaaa ttcccccaat    1560
tctcatcagt aacaccccac cccgtattac ttttaccgtg atgaagattg gcatcgttac    1620
tttctaaacg taggacgtgc ggaatgacaa aaccatcagc agtgtcacga tctctccagt    1680
cacaatggca atcatgagtg catagtccaa agtaaagggg caaggaaaag catgattgaa    1740
aggactcccc atctggactc tatatgtcat cagcggctaa aaaaaagcat atagcacaac    1800
atcagcatca gcatcagcac tagagtcatc ggcccggcgg tccgcggtca tccccgcgga    1860 cttttccgtcc gcccggcggg ctgtatcagc gtcaactgga acgcgcatat atatacaaga    1920
cacacataac atagaagcac acccacgaca ataaccacac gacaataacc acacccgccc    1980 accccctcctt tccgtatac                                                1999

<210> SEQ ID NO 21
<211> LENGTH: 1500
<212> TYPE: DNA
<213> ORGANISM: Zea mays

<400> SEQUENCE: 21
tgtcctattc atttataact tactaccccg cattacttac ttgaaaccta aggattgact      60
agctttacac tttactttat ccttgatgac cttatgggct gttatggtta gcactctgct     120
attgccttaa cttaatcaat gaacatgatg tgactattta tgatactgtt atcctgatga     180
tgttgatgat cttgtgatac tctagggggc tcaggctgtt tcctgagtac ctctccgtaa     240
ggacttgttc gttgagagac cacccgggat aacagtacaa ccatgagggt gaaatgggat     300
gcccttagct gattaattag atgaactaga ggtgtagttg cttagccgtc gtgccgtcaa     360
tggggtccag gcacagtgct tgctctgccg aggctgagtg ccgaggttct ttcgttttgc     420
tctttgttag tcactctcct gcggggaggg gtactgtgtt tatcaaactg gagaaaccta     480
acgggcagct atggtctcta gggaatcttt gtaaaagcta cgtagtgatg ccctgccgga     540
ccacctaggt agtggtcaat ggggattagc tctccccggg tagaaaggga atcatgactc     600
atgggtaaag tgtgcaacct ctgcagaggg tagtgaaact ggtatatcag ctgtgctcac     660
ggttaagagc agccttggga tcctctttga ttagagatac agatggttcg agatacaagg     720
attatgttat ggttttggtt cgactatgat gatgatgttc ctcgatgagg aaatggttta     780
cgggttgtta aatgctaaaa tctggcttct actaatgata aatacctgac caactaaaag     840
caactgcttg agcctaaccc cacataaagc tagtccactt cagccaaacg ggacatttgc     900
tgagtacgtt gatgtgtact catccttgct ttaccacaaa aacaccaggt tgtccgcatt     960
gtaaccactg ctcaggagaa ggtgaagccg tggaaggaga cttccaggag ttccaagact    1020
acgacgaatt ctaggtgtgg gttggcggca accccccagtc agctacctgt gaaggcctta    1080
tctttactgc gtttcgctag cactttgatt tacctgttaa acaatgact atgtggatgt     1140 ctatgactct gtgatgtaat aagttaatac tcttttatgt tattattcga gcactgtgcg    1200
atgatgttca tttatgtaat cgctgtgtac gtgagttctg atcctggcac gtacatagtt    1260
cgcattcggt ttaccttcca aaaccgggtg tgacataagt ggtatcaaag ccaggttgac    1320
tgtaggaccg ctgacctaga gtagcactgg tcgtactaag gactattgac ccttccctct    1380
caccttgacc tctgatgtta cttcaaaagt cggtcacctc gcccacccta tgttttacta    1440
catatatata ctatattata ccttggaaaa ttttttatct tatcctggct atgggttatt    1500

<210> SEQ ID NO 22
<211> LENGTH: 1708
<212> TYPE: DNA
```

<213> ORGANISM: Zea mays
<220> FEATURE:
<221> NAME/KEY: misc_feature
<222> LOCATION: (914)..(914)
<223> OTHER INFORMATION: n is a, c, g, or t
<220> FEATURE:
<221> NAME/KEY: misc_feature
<222> LOCATION: (973)..(973)
<223> OTHER INFORMATION: n is a, c, g, or t
<220> FEATURE:
<221> NAME/KEY: misc_feature
<222> LOCATION: (1693)..(1693)
<223> OTHER INFORMATION: n is a, c, g, or t
<220> FEATURE:
<221> NAME/KEY: misc_feature
<222> LOCATION: (1698)..(1698)
<223> OTHER INFORMATION: n is a, c, g, or t

<400> SEQUENCE: 22

```
gctgtctgag aatacgcttg aattcgttct gtgattttg gcacagaggt aggttattac      60
ccatagatgc catcaaaaat aacctctagt gcagaacccc aaccaaatga gggttgtagt    120
acaaagtaac catctaccct tactttgtt attttgcca agattatatc ctaattattc     180
ttaacctcaa atttgtagca taaacaacag tgaccaatag caaccaactg taattttac     240
aacatttttg aaaatttta atcaatata gtagtacaag ttccctttaa aagaacataa     300
atagaaaata aaaagggaa ttctggaagg aattaatatt acataactag atctccctaa    360
gtgcccacta aaacactaag aggatgacta aattcttact tccactcaaa acctaaacta   420
ggtaagtata aagcactaag agcatcatac gataaagaaa ccctagttta cccactgcct   480
taatattgct tcaccataca tcgtatttac taaattggca tatcattaac atgcacgtat   540
cttattcatt gcattcaata gattgtaacc tcgctgacgg agagtacgtc ctcattctag   600
agcaaggagt tgctcaagaa ggagtccagg agccagcacc agagactgcc actgaggatc   660
tccctgcccc agcttttgaa ggcaagcccc agttttatgc ataacgtta tatatgctat    720
tttactgcac ttaatgattg taggcttgta ctgtgcactt aagtgtagga gttgccctaa   780
accatagttg catgaactca ggatcccttg agatggatac gagtatgcta ggtcgagtag   840
ctgctttact aattagggga tctcgtagaa atcagtgat ttttctagca ctcgcgcgag    900
gtcaggaatt ggtngtatcc attttatat cataataatg atggtaggtg gacacgatcc    960
atgaggatgc gtngtctacg ggacggaaat tgaataaagg attaaggtgt ggtatcgtgt  1020
gtcaagcgtt tgaacttact aaacacatgc cgagaaatat ggtaaatcgg caagcctagt  1080
acctgagtga acctgcccgc aaattgacct tctcacggga cctgagatgt ggtctcccat  1140
tccggttatg gtgggtacaa gtgcggtcac tgcacgacga cagtcggtgt cagtgatgca  1200
ttgtacgcca aggcggtgag cctcttctg ttgatgggga atcgatgggg acggttgatg   1260
tgtgtgggga cggagtgcct cgccacgtcg tgtgtttagg tttaccttgc aaggttaaaa  1320
actcgattcg aatcgtctgc ttctcgcagc taatgagact gcttgatcca tgctgctaca  1380
ttgagtgata agtgaaaatg aggtgactgg taaaagatgt tgattgataa aatgtttgat  1440
accatgtatg attagctagg ttctcatcta gttttttgta acacccagtt tgtaatatat  1500
aataaaagag gagaaaagtt attttcctat attttatgtg tgttaaatct acttatcatc  1560
acatgtgaac accatattca aaacaaata agtaataaaa aatatatgcc attaaattat   1620
gcatcatgct ggatattatt tttgtgtgtg cattttgtga caatataaaa ataaagagac  1680
aagaagacga atncctanat gtcaatcc                                     1708
```

<210> SEQ ID NO 23

<211> LENGTH: 118
<212> TYPE: DNA
<213> ORGANISM: Zea mays

<400> SEQUENCE: 23

```
ccacgtattt tgcaagctat ttaactggcg gcgattgcgt acccgacgac caaaattagg      60
gtcaacgcta cctgtaggaa gtgtccgcat aaagtgcacc gcatggaaat gaagacgg      118
```

<210> SEQ ID NO 24
<211> LENGTH: 194
<212> TYPE: DNA
<213> ORGANISM: Zea mays

<400> SEQUENCE: 24

```
ccccttactt gaggataaat tatgtctaat attcaaactg gcgccgagcg tatgccgcat      60
gacctttccc atcttggctt ccttgctggt cagattggtc gtcttattac catttcaact     120
actccggtta tcgctggcga ctccttcgag atggacgccg ttggcgctct ccgtctttct     180
ccattgcgtc gtgg                                                       194
```

<210> SEQ ID NO 25
<211> LENGTH: 1176
<212> TYPE: DNA
<213> ORGANISM: Zea mays

<400> SEQUENCE: 25

```
ccgatgataa gcttgaattc tggtcgtatt atgttcttat gcggatgatg agagccaact      60
tgctttcctg cttggcatgt gctacaaatc ctgtctttct aaaatgaaca tttgttagtc     120
ctaaaatgtg ttctcccttt agaagcttgt gaagattctt catcccaaca tgggctagtc     180
ggcggtgcca gagccaaccc atgttagtct tagcaattaa gcaagtgtcg agttcagctc     240
tatcaaaatc taccaagtat agctgaccct ctaacactcc cttaaatgct attgaatcat     300
cacttcttct aaagacagta acacctacat cagtgaatag acagttgtag cccatttgac     360
acaattgaga tacggaaagc aaattgtaat ctaaagaatc tacaagaaaa acattggaaa     420
tagaatggtc aggagatata gcaattttac ccaaaccttt gaccaaacct tgatttccat     480
ccccgaatgt gatcgctctt tggggatttt ggttttctc atatgaggag aacatctttt     540
tctccccagt catgtggttt gtgcacccgc tgtcgagtat ccaacttgag cccccggatg     600
cataaaccta caaacaagt ttagttcttg actttaggta cccaaatggt tttgggtcct     660
ttggcattag acacaagaac tttgggtacc caaacacaag tctttgaccc cttgtgtttg     720
cccccaacat atttggcaac taatttgccg gattttttg ttaaaacata agatgcatca     780
aaagttttaa atgaaatgct atgttcattt gatgcaatag gaattttctt cttaggcaac     840
ttggcacggg ttggttgcct agagctagat gtctcacttt tatacataaa agcatggtta     900
gaaccagagt gagacttcct agaatgaatt ttcctaattt tgtcctcggg ataaccggca     960
gggtataaaa tgtaaccctc gttatcctga ggcatgggag ccttgccctt aacaaaattg    1020
gacaatcttt taggagggc actaagtttg acattgtctc ccctttggaa gccaatacca    1080
tccttaatgc ccgggcgtct cccattatag agcatacttc tagcaaattt aaatttttca    1140
ttctctaaag aattcaagcg tattctcgga gagtca                              1176
```

<210> SEQ ID NO 26
<211> LENGTH: 731
<212> TYPE: DNA
<213> ORGANISM: Zea mays

```
<400> SEQUENCE: 26
cgtaccaccg cacgaagatt tctattgttc ctgaaggcat attcaaatcg ttttcgttac      60
cgcttgcagg catcatgaca gaacactact tcctataaac gctacacagg ctcctgagat     120
taataatgcg gatctctacg ataatgggag attttcccga ctgtttcgtt cgcttctcag     180
tggataacag ccagcttctc tgtttaacag acaaaaacag catatccact cagttccaca     240
tttccatata aaggccaagg catttattct caggataatt gtttcagcat cgcaaccgca     300
tcagactccg gcatcgcaaa ctgcacccgg tgccgggcag ccacatccag cgcaaaaacc     360
ttcgtgtaga cttccgttga actgatggac ttatgtccca tcaggctttg cagaactttc     420
agcggtatac cggcatacag catgtgcatc gcataggaat ggcggaacgt atgtggtgtg     480
accggaacga agaacgtcac accgtcagca gcagcggcgg caaccgcctc cccaatccag     540
gtcctgaccg ttctgtccgt cacttcccag atccgcgctt tctctgtcct tcctgtgcga     600
cggttacgcc gctccatgag cttatcgcga ataaatacct gtgacggaag atcacttcgc     660
agaataaata aatcctggtg tccctgttga taccgggaag ccctgggcca acttttggcg     720
aaaatgagac g                                                          731

<210> SEQ ID NO 27
<211> LENGTH: 1325
<212> TYPE: DNA
<213> ORGANISM: Zea mays
<220> FEATURE:
<221> NAME/KEY: misc_feature
<222> LOCATION: (1148)..(1148)
<223> OTHER INFORMATION: n is a, c, g, or t

<400> SEQUENCE: 27
tggctgtccg agaatacgct tgaattctta gaccagtttt ggattcacga aggagcaaag      60
tggcaaccga aggccctctg gtctgggagc accggactgt ccggtgtaca ccggacagtg     120
tccggtgcac caccggacag tgtccggtgt accagaggac ttcaactcga actcgccacc     180
ttcgggaatt tccagaggca ctcgcgctat aattcaccgg actgtccggt gtacaccgga     240
cagtgtccgg tgcgccaagg aagatcagcc tcaggaactc gccagcttcg ggaaactcca     300
acggctagtc cgctataatt caccggactg tccggtgtgc accggactgt ccggtgcgac     360
tccagagcaa cggctagtcc acgccaacgg ctacctgcgg cgcattaaat gcgcgcgcag     420
cgcgcgcaga agtcaggcgc gcccatactg gcacaccgga caaggaacag tagatgtccg     480
gtgtgcaccg acacccagg cgggcccaca agtcagaagc tccaacggtc agaatccaac     540
ggcagtgatg acgtggcagg gggcaccgga ctgtctggtg tgcaccggac tgtccggtgc     600
accctctgcc aggtggggcc aggctggtcc ggggcagagg cttttccctcc gcagaaaccc     660
gagagcgcag gtttgggagt tgaattttag tggtgcaccg gacatcgcac cggactgccc     720
ggtgtgcacc ggacagtgac tgttcactgt ccggtgtgcc atgagtccaa cggctagctg     780
tcagaactag ccgttggaaa cgaccgttgg cgcaccggtg gcgcaccgtt ggcgcaccgg     840
tggcgcaccg gactgtccgg tgcgccattg cgcagtgagg tgcctgtaac ggctagttgg     900
tgggtgaggg ctatttatac cccttccacc accatattc aatgtcttgc actccacatt     960
tattccagca cattgctaga gcattgcaac caccaaaagc ctagtgagga gattagagaa    1020
tcttaattcg cgtctgttcc tcattagcgc tagcgagagc cacctagagc acacaccact    1080
tgcattaggc ttctcttggt caagcaaaag tctacggctt gttactcttg gtgattggca    1140
tcacctanac ggcttgttgg cgttgggagc tcggtgatca ccgtgaagat cttgttggtg    1200
```

```
acccgactca agtttgtaag cggtcttgag ggatccaccg ggcccgaagt ggcaaagatc    1260
atctcgtagt gagcccctgg ttcttgcgag gacaaggggg aacgataccc tggcccggtg    1320
cttca                                                                1325
```

<210> SEQ ID NO 28
<211> LENGTH: 77
<212> TYPE: DNA
<213> ORGANISM: Zea mays

<400> SEQUENCE: 28

```
aacggggccg cttttttcaga aaaccaagac cattaacggt tttggggaaa aattccacca     60
acttgggacc gggaata                                                    77
```

<210> SEQ ID NO 29
<211> LENGTH: 153
<212> TYPE: DNA
<213> ORGANISM: Zea mays

<400> SEQUENCE: 29

```
gcgttcaata tcatcgcgat gttcttcgtt atcgcgccag accagcaata cctgcgcttc     60
tcccggctgg cggttctctt ccgctttgtg atgacgtcgc caccagcgtc gtgccgcgct    120
ctgtccaggc aggttttcca gctcaaactg gag                                 153
```

<210> SEQ ID NO 30
<211> LENGTH: 1424
<212> TYPE: DNA
<213> ORGANISM: Zea mays
<220> FEATURE:
<221> NAME/KEY: misc_feature
<222> LOCATION: (1261)..(1261)
<223> OTHER INFORMATION: n is a, c, g, or t
<220> FEATURE:
<221> NAME/KEY: misc_feature
<222> LOCATION: (1267)..(1267)
<223> OTHER INFORMATION: n is a, c, g, or t
<220> FEATURE:
<221> NAME/KEY: misc_feature
<222> LOCATION: (1275)..(1276)
<223> OTHER INFORMATION: n is a, c, g, or t
<220> FEATURE:
<221> NAME/KEY: misc_feature
<222> LOCATION: (1403)..(1403)
<223> OTHER INFORMATION: n is a, c, g, or t

<400> SEQUENCE: 30

```
atgagcaatt agagattcgt gccttggttc accaagtctt gagccggttg tacatgtgtt     60
gtggctcctc ccctttgcga agccggaacc gactgagctc cccctcgatc atttcccgct    120
tggtgatctt tgtaagctca tctccctcgt gcgcggtttt gagcacatcc caaacctcct    180
tggcgctctt caaccccttga actttgttat actcctctct acttaaagag gcgaggagta    240
ttgttgtcgc ttgagagttg aagtgctcga tttgggctac ctcatcctca tcatagtctt    300
tatcccctat agatggtacc tgcgctccaa actcaacaac attccatata cttttgtgga    360
gtgaggttag atgaaatttc attaaatcac tccacctagc ataatcttca ccgtcaaaag    420
ttggcggttt gcctaatgga acggaaagta atggagtatg tctagatgta cgagagtagt    480 gtaggggat attactaaac ttcttacgct cttggcgttt agaagttatg gagggtgcat    540
cggagtcgga ggtcgatgtt gatgaagtgt cggtctcgta gtagaccact ttcctcatcc    600
tcttttgctt atctccactt cgatgtggct tgtgggaaga agattttcc ttcttctctt    660 tgtggtgaga agaagatttc ttctccttcc ctttgttgga ggagatcttc ttcttctccc    720
```

```
tcctcttggt gcgggactct tccgatgaag tgctcccgtg gcttgtagtg ggcttttcgc      780
cggtctccat ctccttcttg gcgtgatctc ccgacatcac ttcgagcggt taggctctaa      840
tgaagcaccg ggctctgata ccaattgaaa gtcgcctaga ggggggggtga atagggcgaa     900 actgaaattt acaaatataa acacaactac aagcccgggtt agcgttagaa atataaacga    960
gtccgcgaga gagggcgcaa aaacaaatcg taagcgaata agcaagtgag acacgtggat     1020
ttgttttacc gaggttcggt tctcgcaaac ctactccccg ttgaggaggc cacaaaggcc     1080
gggtctcttt caacccttcc ctctctcaaa cggtccctcg gaccgagtga gcttttcttc     1140
ttctcaatca aacgggaaca aaacttcccc gcaagggcca ccacacaatt ggtgcctctt     1200
gccttggtta caattgagtt ttgatcacta gaacaagtga gaaagaaaga aagcgatcca     1260
ngcgcangag ctcannagac cacggcaaat ctctctcgct agtcactaaa agcttgagtg     1320
ggattggaga ggatttgatc tctttggtgt gtctagaatt tgatgctaga gctcttgtag     1380
tagttgggaa gtggaaaact tgnatgccat gatgttgggg ttgg                      1424
```

<210> SEQ ID NO 31
<211> LENGTH: 78
<212> TYPE: DNA
<213> ORGANISM: Zea mays

<400> SEQUENCE: 31

```
tggctgtctg agattaagct tgattcgttg ctctttcgct ttaggcagag tcgtcttgat      60
gatttcatga cgaaccag                                                   78
```

<210> SEQ ID NO 32
<211> LENGTH: 1743
<212> TYPE: DNA
<213> ORGANISM: Zea mays

<400> SEQUENCE: 32

```
ggagccagtg tacctatcgg taaggcacag caccctttctg gttgttgtag tcgaatagca     60
caacgtcgac ctccaccta aatcgtagtt atcaggagac ggtgtacctg tcgctcaagg      120
cgccacacca tcttggtgtg gtagtcgggc agccaacgtt gttctcaaac aagttttcca     180
cccccatcat ctctcatcga aagatcggac acccttcttg tgatagaccc tcccaagtca     240
ttaggcccac ctatagttgt ccttgtccaa cggacctcaa acaaccctgc aggtgcacct     300
gatcacttga caagttcggt atctgaattc cttacctttt ccaagagcgt ttcacctatc     360
acacagacat tacaattcat cggagatacg aaagtgtgga agcagttaca ataacttact    420
ttattgaaaa gtaagacaaa gttatatagt tatagaccag aacaaaatat atgagtgcag    480
agtattatta ttcataaca tgggaggcaa aaacccctcc caaataaaca gtaaaagttc      540
tcctaacgga ggacctttcg tcccgcagct ttagtcttga ttctcttctt tcggtaccac     600
cttgaaacag aagcaacaaa agtttgttgt ttcttcacct aaaacaacat gggacaaagc     660
cctgagtatg aagtgtactt tcgcaatact tacccgacaa agtaaaagac tctcaaggat     720
atgctggctt aagggagtc aaggtaaggc ttatcaataa tcaatgactc tgttttgcag       780
aaatgcttac taatagtgga tccttaaaaa tccagttta tttgtcaggt taagtaaaat       840
tacctgcaac tagagttctt tctatcctag ttcaatcact tgacctatac tagccaattt       900
cttaacaacc cttcttattc actggaatgc tacgtgtagg tcagtgacca agtcttcatg        960
tccgcgaagt tacggcgatc cgaatcgatt atactcagct gaggatctcc aatcacacga      1020
catatgtagc atttaacccct tgcatatgtc aactcgccac cgaggttctt aagaccagat   1080
```

```
caggttcagg ccaaccgaga gcatagatac accaccgtcc agcctcttgc cacggagggt    1140
acacgctact ctcgccatct ctccactccc attgcgtgtt atcttattct ggtattagtc    1200
tgcccgaggc aaagcttacc cgtgacgagg catgtgacca gttaaagggt cctcgatcat    1260
caagcctaca tcgagacggt ccttaatcga ctaagacgga gacactccac cgagactctc    1320
ttctcgtgca agtcacccgc ccggtctcag cttaatcatt tcaaacccaa agtttggtac    1380
ctggtagagg tacatatttt ccgatgttga acccatcatg ccatgatgg atccaccatc     1440 aagtttatt ttcgaaaaca ttccacccac tttgaagcat catcttttgt aaaagcaaaa     1500 tattttatt tttctagagc aaagctaagc ataagaaaaa ccatttgtaa aacagggact     1560
taaggagaag taatcaaatc taaggaacgt gttggggcga aggcaaagac gctacccttc    1620
gcttgatgcc cttgccgatc tcgccgcacc aacggaggcg aagcgatcgg cagttttcac    1680
ccttcgtcca acacgctgca agacgaaggc ctacgacgag gtcgcccgt ctcgcgtcct     1740 cgt                                                                  1743

<210> SEQ ID NO 33
<211> LENGTH: 1528
<212> TYPE: DNA
<213> ORGANISM: Zea mays
<220> FEATURE:
<221> NAME/KEY: misc_feature
<222> LOCATION: (1308)..(1308)
<223> OTHER INFORMATION: n is a, c, g, or t

<400> SEQUENCE: 33
atgagcaatt agaaattcgt agttatgaat ttttcaagct ctctacttat ttaaaaagaa      60
taaatcttaa aggtttaaga aaaacagctt tgcgccaggg tccctgggtt atttcttaac     120
taaaacgttc aaaccgtgcc cttgaggaac tgtttcactg agtagtggac ttcgcgaata     180
ccccctggct tttccctctc ttaacccgag ctccctcctc gccggaacag tagccgcaga     240
gagaaatagc ggtggcgcgg cttaccgtg gtaggagagg tccggtggac ggttgggtga      300
ggttcggtgg cttctagcgg tcacgtcgag gggcggatcg ccggcggtga tggccggagt     360
agggctggcc acgcgcgcag gcggtcgagc tcgtcggcga cgcgtgatcc ggcctgctca     420
cggcggtaga gttcaatcaa accgcacgag gagcttcatg ggaggtcact cgtgctgtat     480
gcacaaggaa tcgaagagcg gctcaccgtg tagctcggtc tacgcgcgac ggcggtcggg     540
cgaagtccgg cgacgtcaat ccggcacctc ctatgaggtg gtgttcggtc caagggctca     600
gggagcttca cttagctcta ggaggctag gcgagggttt gatgggtg gcggaggact        660 ggagcggcca gtccatggtg gccggggcta gggcggccgc tggcacgccg tgcgcagagc     720
gattgccggt gaacttgtgc tcgggcgggg ttgagcgga gcggggtgt acggtcaagg       780 ccggggtcgg ctttataggc gtgggcactg gcgtgggcat gtgtggggga cagatatccc     840
ccgggttcac tggaaggata aaagacctca caaaaggccc aagggcccaa tagatcgtaa     900
ggtcactcct tcatgggcct cggaggaac aatcagtaaa gcagattgac ataaggccgg      960
atcggtgcaa gcccggacgg ccccacaacg ttgagcaagc aaccacaaca gaagattcga    1020 cttttctcgcg ctggagcccc gtacgacaga accaggcgaa gataagtcgg cagaactata   1080
ggaagataga ctcaatcagt tcactttctc ttaggtgccg tttgttatct catccgcatg    1140
tattgcctca cggtcgaata tataaggcct agggggcacc ccttcaaatt gatcgatccc    1200
attactcagc catccacccc aactctctac gttctagctt tagagagctc ccttgtaacc    1260
cattacataa agcatactcg ccaggacgta gggtgttacg catctcanag cggcccgaac    1320
```

```
ctgtaaacac tgtccattgt tcttcgtgca tctggcacga accatttagc tatagtcggc    1380
gacaccgtcc tactcctaaa acaccttgag gggcaacccc gggtgtgcgg tcggacccaa    1440
aacatcgaca gctggcgcgc caggtagggg ggtgtgtcgc cgatctaagc tagctcaatt    1500
gccgtcaccc tttcacgcaa gatcaccc                                       1528

<210> SEQ ID NO 34
<211> LENGTH: 460
<212> TYPE: DNA
<213> ORGANISM: Zea mays

<400> SEQUENCE: 34
ctgaacggta gagaaacgta caaatactgg ggtgattttg ttcggatctg agaggaaatc      60
cgctttggta atatcgctta agcttttata tggctggaaa taaccgtgag cggctgatcc     120
gcgtgcatga acaatacgtt ccggaatgcg ctcatggtca aagtgggtga ttttctcgcg    180
cagaataaaa tcttccagca gcgttggacc acggctaccg gcacgcagtg agttttgatc    240
gtcggcgatg cgcacgccct gattagtggt cagcgcataa ttttcactgc ctttgcgtac    300
gtcttccaga gaattaagtt tttcgttacg cgtatcaggg gctttcaggc tccctggggc    360
ggtaggttgt gcacctggcg tgttggttc agccgctgga cgatgagagc cgtcctcagg     420
tgccagtgag tccatccccg gtttcgcttc gctggaatcg                          460

<210> SEQ ID NO 35
<211> LENGTH: 234
<212> TYPE: DNA
<213> ORGANISM: Zea mays

<400> SEQUENCE: 35
ccgtttgaat gttgacggga tgaacataat aagcaatgac ggcagcaata aactcaacag      60
gagcaggaaa gcgagggtat cctacaaagt ccagcgtacc ataaacgcaa gcctcaacgc    120
agcgacgagc acgagagcgg tcagtagcaa tccaaacttt gttactcgtc agaaaatcga    180
aatcatcttc ggttaaatcc aaaacggcag aagcctgaat gagcttaata gagg           234

<210> SEQ ID NO 36
<211> LENGTH: 2303
<212> TYPE: DNA
<213> ORGANISM: Zea mays
<220> FEATURE:
<221> NAME/KEY: misc_feature
<222> LOCATION: (876)..(876)
<223> OTHER INFORMATION: n is a, c, g, or t

<400> SEQUENCE: 36
atgagcaatt agaaattcgt aatttactgc aaagcacaac aaaatcgcaa agtcatcaaa      60
aaaccgcaaa gttgtttaaa ataagagcaa cactacaaaa ggagataaga agagcacata    120
cctcagtcac ttattatcac tagcgctcgc cgcagccgtg taaccgagca tagcgagcga    180
actggcgagg aagcaaagaa gaactgttct gtcagatagc tcttacgctc agcgcaagaa    240
gaaatatcca ccgtgggaaa aactccaggt agaggtacac acgcggatag ccaattcaga    300
gtaataaact gtgataatca accctcatca atgatgacga actaaccccc gatatcaggt    360
cacatgacga agggaaagag aaggaaatca actgtgacaa actgccctca aatttggctt    420
ccttaaaaat tacagttcaa aaagtatgag aaaatccatg caggctgaag gaaacagcaa    480
aactgtgaca aattaccctc agtaggtcag aacaaatgtg acgaaccacc ctcaaatctg    540
tgacagataa ccctcagact atcctgtcgt catggaagtg atatcgcgga aggaaaatac    600
```

```
gatatgagtc gtctggcggc ctttcttttt ctcaatgtat gagaggcgca ttggagttct      660
gctgttgatc tcattaacac agacctgcag gaagcggcgg cggaagtcag gcatacgctg      720
gtaactttga ggcagctggt aacgctctat gatccagtcg attttcagag agacgatgcc      780
tgagccatcc ggcttacgat actgacacag ggattcgtat aaacgcatgg catacggatt      840
ggtgatttct tttgtttcac taagccgaaa ctgcgntaac cggttctgta acccgataaa      900
gaagggaatg agatatgggt tgatatgtac actgtaaagc cctctggatg gactgtgcgc      960
acgtttgata aaccaaggaa aagattcata gccttttctca tcgccggcat cctcttcagg     1020
gcgataaaaa accacttcct tccccgcgaa actcttcaat gcctgccgta tatccttact     1080
ggcttccgca gaggtcaatc cgaatatttc agcatattta gcaacatgga tctcgcagat     1140
accgtcatgt tcctgtaggg tgccatcaga ttttctgatc tggtcaacga acagatacag     1200
catacgtttt tgatcccggg agagactata tgccgcctca gtgaggtcgt ttgactggac     1260
gattcgcggg ctattttttac gtttcttgtg attgataacc gctgtttccg ccatgacaga     1320
tccatgtgaa gtgtgacaag ttttttagatt gtcacactaa ataaaaaga gtcaataagc      1380 agggataact ttgtgaaaaa acagcttctt ctgagggcaa tttgtcacag ggttaagggc      1440
aatttgtcac agacaggact gtcatttgag ggtgatttgt cacactgaaa gggcaatttg     1500
tcacaacacc ttctctagaa ccagcatgga taaaggccta caaggcgctc taaaaagaa      1560 gatctaaaaa ctataaaaaa aataattata aaaatatccc cgtggataag tggataaccc     1620
caagggaagt ttttcaggc atcgtgtgta agcagaatat ataagtgctg ttccctggtg      1680
cttcctcgct cactcgaggg cttcgccctg tcgctcgact gcggcgagca ctactggctg     1740
taaaaggaca gaccacatca tggttctgtg ttcattaggt tgttctgtcc attgctgaca     1800
taatccgctc cacttcaacg taacaccgca cgaagatttc tattgttcct gaaggcatat     1860
tcaaatcgtt ttcgttaccg cttgcaggca tcatgacaga acactacttc ctataaacgc     1920
tacacaggct cctgagatta ataatgcgga tctctacgat aatgggagat tttcccgact     1980
gtttcgttcg cttctcagtg gataacagcc agcttctctg tttaacagac aaaaacagca     2040
tatccactca gttccacatt tccatataaa ggccaaggca tttattctca ggataattgt     2100
ttcagcatcg caaccgcatc agactccggc atcgcaaact gcaccggtg ccgggcagcc       2160 acatccagcg caaaaacctt cgtgtagact tccgttgaac tgatggactt atgtcccatc     2220
aggctttgca gaactttcag cggtataccg gcatacagca tgtgcatcgc atagaacgaa     2280
tcaagcgtat tctcgacagc tca                                             2303

<210> SEQ ID NO 37
<211> LENGTH: 1638
<212> TYPE: DNA
<213> ORGANISM: Zea mays

<400> SEQUENCE: 37
catttagaaa ttcgtccaag taaggggcaa ggaaaagcat gattgaaagg actccccatc      60
tggactctat atgtcatcag cggctaaaaa aaagcatata gcacaacatc agcatcagca      120
tcagcactag agtcatcggc ccggcggtcc gcggtcatcc ccgcggactt tccgtccgcc      180
cggcgggctg tatcagcgtc aactggaacg cgcatatata tacaagacac acataacata      240
gaagcacacc cacgacaata accacacgac aataaccaca cccgcccacc cctcctttcc      300
gtatacaagg cctcggtacc tcttaaaaac tttctctcaa ttctctctac cgtgatcaag      360
gtaaatttct gtgttcctta ttctctcaaa atcttcgatt ttgttttcgt tcgatcccaa      420
```

```
tttcgtatat gttctttggt ttagattctg ttaatcttag atcgaagacg attttctggg      480
tttgatcgtt agatatcatc ttaattctcg attagggttt catagatatc atccgatttg      540
ttcaaataat ttgagttttg tcgaataatt actcttcgat ttgtgatttc tatctagatc      600
tggtgttagt ttctagtttg tgcgatcgaa tttgtcgatt aatctgagtt tttctttttc      660
tttttgcagg tagagttaac gctagccttg gtaccatacg taagaaaatg attgaacaag      720
atggattgca cgcaggttct ccggccgctt gggtggagag gctattcggc tatgactggg      780
cacaacagac aatcggctgc tctgatgccg ccgtgttccg gctgtcagcg caggggcgcc      840
cggttctttt tgtcaagacc gacctgtccg gtgccctgaa tgaactccaa gacgaggcag      900
cgcggctatc gtggctggcc acgacgggcg ttccttgcgc agctgtgctc gacgttgtca      960
ctgaagcggg aagggactgg ctgctattgg gcgaagtgcc ggggcaggat ctcctgtcat     1020
ctcaccttgc tcctgccgag aaagtatcca tcatggctga tgcaatgcgg cggctgcata     1080
cgcttgatcc ggctacctgc ccattcgacc accaagcgaa acatcgcatc gagcgagcac     1140
gtactcggat ggaagccggt cttgtcgatc aggatgatct ggacgaagag catcaggggc     1200
tcgcgccagc cgaactgttc gccaggctca aggcgcggat gcccgacggc gaggatctcg     1260
tcgtgaccca tggcgatgcc tgcttgccga atatcatggt ggaaaatggc cgcttttctg     1320
gattcatcga ctgtgccggc tgggtgtgg cggaccgcta tcaggacata gcgttggcta     1380
cccgtgatat tgctgaagag cttggcggcg aatgggctga ccgcttcctc gtgctttacg     1440
gtatcgccgc tcccgattcg cagcgcatcg ccttctatcg ccttcttgac gagttcttct     1500
gagcgggact ctgggtacgt atgtcgacac aattgcagcg cttgagctct cctaggtccg     1560
cggacaaagc tgggttttt ttttttcaat ttcgattcat ctcaaggtta agaattcaag     1620
cgtattctcg gacagcca                                                    1638

<210> SEQ ID NO 38
<211> LENGTH: 1869
<212> TYPE: DNA
<213> ORGANISM: Zea mays

<400> SEQUENCE: 38
gaattcgtca tcccgggccc cgctcagctt ccacctaacc atgcataccc acaccaccag       60
gaggtacaaa tcgtacctcc cccacccccg cctccacacc cgcaacagcc aaacatccac      120
caccccaacc accccaagc accaaaacaa gaagacttcg ccgatcagct gtatcgcaga      180
gtcattcaca tgatcaccgg ggggtccagc atcgacttcg atacgaagcg acagaagagg      240
gaccactacc gcagcatcaa ccacgttgcc gtcaccggtc cagtcgtgca gacaaagtgg      300
tccatgtgcc attgacccttc gacgcccgag acgtcgacct gcgcagcgca ccccacatcg      360
acgccatggt tatcaactgc atcatggcag gctgggacct acacaaagtc ttagttgaca      420
acagcagcca ggcggatatc attttcctcc acgccttcga ccgcatgggc atcagccaca      480
gctttctcaa accctcggac aacccactat atggcttcgg cggcaagggc acctttcctg      540
tcggcaaaat agagctaccc ctctccttcg gtgtatcacc caatgcacga agcgagaaag      600
tcactttcga catcgtcgac atggtgtacc catacaacgc cataatgggt cgaggctcca      660
tcaacaagtt tgaggcagcc attcacagac tttacctgtg catgaagatc ccgggtccgc      720
aaggcgcgat cacagtctac gacaaccagc aggccgcacg caacatagaa agagacttcg      780
ttcctgggca aggaacgta cactgcctca cggcgaagcg cgaggtcccc gagtctgcca      840
gcccaaccgc caaagaccat gaaaaggcac agctgcagag caacgatggg accaagactg      900
```

| | |
|---|---|
| ttcccctcga ccagacaacg cccaagcaaa cagtcatcat aagcgaagac ctcacttcgc | 960 |
| atgacgaggc gagactcctc tcctgtctat ccaaaaataa agacatcttc gcctggtccg | 1020 |
| ccctcgacct ggtcggagtc aatcgctcta tcatcaagca caacttggga tttgacccttt | 1080 |
| cggtgaggcc gaagaagtag cggctgcgca agatgtctga tgagaagaca gaagccgcca | 1140 |
| aggccgaggt acaccgccta cttgaggcca actttatcga gccagtcgcc taccctacat | 1200 |
| ggctggccaa tgtagtaatg gtgtagaaga agagcggcaa gtggcgaatg tgcattgatt | 1260 |
| tcaatagcct caacaaggcc tgccccaagg acaacttccc gctgcctcgg attgacaaga | 1320 |
| tcgttgatag tgcagccggg tgcgaagtca tgtcactcct tgattgcttc tccggctacc | 1380 |
| accaaatata tatgaaggag gaagacaagg ccagcaccag tttcataaca cccttcggca | 1440 |
| cgtattgctt catcagaatg ccggagggac ttaagaacgc tgggtccaca ttctctcggc | 1500 |
| tcaccaaaat ggtgctcgag agccaagtcg gcagaaacat atttacgtat gtggacgaca | 1560 |
| tcgtcgtcgc catcagaagc aaggaagacc atctggctga cctcgcagaa acgttcgcaa | 1620 |
| acatgcggga cgcacaactt cgcctaaacc ccgaaaagtg tgtattcgac gttcgctagg | 1680 |
| gtaaatactg ggctacctgg tgtcgcaccg cgggatcgaa cccaatccga caaaatccag | 1740 |
| ccatcatcaa catgacgccc ccgcatcagc taaaaacttc aacgactgac cagtaaatgg | 1800 |
| cccgcctcaa cagattattt tcaagtccga aagcgagcct actttcctaa aaacttcgtg | 1860 |
| gcgaaaaaa | 1869 |

<210> SEQ ID NO 39
<211> LENGTH: 2133
<212> TYPE: DNA
<213> ORGANISM: Zea mays

<400> SEQUENCE: 39

| | |
|---|---|
| aatttggaac caatgaggta ttagtaagga cacaagaaga tgcagatgag tggatagaag | 60 |
| gaaagaggct cagaatgtaa ggaaagcacc aaccacaaca ccgtcgggac agacgagaaa | 120 |
| catgggaagc tccaccacaa tcttgggtta agtgcaactt tgatggggca tggccaacag | 180 |
| aaggattaaa atgtggctta gggtgggtgc ttcgcgatca tacagggaag gtgttatggt | 240 |
| taggtgcacg agctgtggta aaagtaagaa gcgtgctgga agtagaagtg gaggctctta | 300 |
| gatgggctgt gctgtcatta tcccgattca attataggaa gatcattttt gaggtggatt | 360 |
| ctcagcaact tgtgtctttg gttacatgaa agttatgctt gtcaagtctc aatccaatta | 420 |
| tccaagacat aaagtatcta cttagcaagt ttgaggattt tatgcttgtg catacaagcc | 480 |
| gagaaggaaa tggagtggca gatagaatag ctaaggaatc tctttctttt gagaattatg | 540 |
| atctaaagtt gtattctatt gtaccaattt gggttaaaag ctctgttgag ctagactgtg | 600 |
| tatccataaa tgggtgaatg gaaagtttgt tgttgagccc accggtggcg cgccataact | 660 |
| tcgtatagca tacattatac gaagttatat tcgatgcggc cgcaaggggt tcgcgtcagc | 720 |
| gggtgttggc gggtgtcggg gctggcttaa ctatgcggca tcagagcaga ttgtactgag | 780 |
| agtgcaccat atgcggtgtg aaataccgca cagatgcgta aggagaaaat accgcatcag | 840 |
| gcgccattcg ccattcagct gcgcaactgt tgggaagggc gatcggtgcg ggcctcttcg | 900 |
| ctattacgcc agctggcgaa aggggatgt gctgcaaggc gattaagttg gtaacgccaa | 960 |
| gggttttccc agtcacgacg ttgtaaaacg acggccagtg aattgtaata cgactcacta | 1020 |
| tagggcgaat tcgagctcgg tacccgggga tcccttcgg ggtatccccc tttcccggtc | 1080 |
| cctgttgcaa gagatagaga aagaggaaaa cggaaaagga tacgaaatcg gacgacgtgg | 1140 |

```
cgtaccttttt ctgacgcggt tattacggcg aaggtgaagc gtcgcgcgct cctcccgtca   1200
gaggcgccgc ctgtcccgcc gcggagttaa tgcgacgggg cgagtggttg gcggggcggc   1260
cgttacgcgt gtgcgagccg tttcgaggaa cggctgtgcc gcttcgcgct tttcgaatct   1320
tgcgtccggt ccaggcggcg tgctggaaac ggtttcgccc tggccttcat atacttgaga   1380
gggggtccgg tgacggttct tcgctctgct cccttctttt ccctttaggt tttcgcaacc   1440
cgggaaactt tagtcggagg agagagaaac cgcccttcct gcccccgcg  ccgccatctt   1500 ctccatcttg gtgatggcgg atcgagtggc tataatcccc ccgcgcgatc cgtggccctt   1560
ctccagggta acggcgagtg atctggagga gctggtcggc gaaggtttgc tccgcccect   1620 caccgacaag cagcggctag agtggattcc tcccgtgggc ggagccgctc cgtccccacc   1680 gccgggtat gtcgtgagct tcgtctcctt ccatgagcgg ggatttggtg tgccggcggg   1740
ccgctttatg cgggccatcc tattccacta cggggtggag ttgcacaacc tctcccccaa   1800
ctccatctcg caggccgcta ttttcgtagc gttatgcgaa gggtacttgg ggatcgctcc   1860
tcattgggat ttgtggactt acttctttct cgccgagcct ttcgccttgt cgacggggga   1920
gaggaggatc cgtgcagcgg tgcgggccgg cggctgcatt ctcttgttga ggcagtcgcg   1980
ggcgttgcag tacattcctg ccattcttgc gtcttcgaac aaggggtggc agcgccggtg   2040
gttctacctc cggaatgacg gtgagttgct cccaccgttt tcccagcgag tagttacggc   2100
tgccaccgaa cgaatcaagc ttatcatcgg cca                                2133

<210> SEQ ID NO 40
<211> LENGTH: 1536
<212> TYPE: DNA
<213> ORGANISM: Zea mays

<400> SEQUENCE: 40
gatgaccatt tagaaattcg tctattcagc aatgacctag gtgcctaagg gcacatgcgt     60
ccttaatcca agatgctggg tactcaggca cctataaata ccctcgcaca gtgcccttga    120
gaggctagat taatagagca attgccttcc tgagctaaaa ccttgtttgc attactttca    180
ctcccccgtt ggatcatctt gctcgggaga gcaagttcca acatttggcg cccaccgttc    240
gtgttacgaa aaaccaccc acgatggcac ccaagagagc tagctcgaag gcagccccat     300
ccgttgacga agcagcgaag gcagcgctgt tggccgagaa aaagggcaat gcccttgtcg    360
acgccaccca ccacgaagcc tgcgaagacg acgcactcag caagaggcag cgcaatgaac    420
aacccacacc cgaaggcagt ctcccgcacct gcagctccgg aggacaaccg caacctcccc    480
caggcttcac tccccggagg gcgcggacgc cactgaggat ggcggagtca tcggtgtttc    540
agcagaggaa caactacaac tgcgggcctt gcgcatcaag aaccgcaacc tccagaagca    600
aaaggagatc ctcaaggcca agcgccaacg tgtctctgcg caggccaagg tgcgccagat    660
gatacacgac gaggagcaga aggctcagga gcttgagcaa agagattgcgc tcatgcagag    720 cgaaggccaa cttggtctac aacaaggacc acccctccaa cagcgtgcgc cattcgaaga    780
cctgttcatt catcagcgtg gacccatccc gcacgccaca gcgttccaag gtgtcaacta    840
ccttgacgag cgaagtccac tggcgccgca cctgcaagtg tcaccatggc cgccaacttt    900
cagggcgggg atctaccccca agtacaacgg cagcacagac ccagcacaat atatcatgag    960
ctaccaagtc gtcgttgcat catccggagg ggacgacgcc acgatggcca aatcattcat   1020
catcgccctc caaggcccgg ctctcacttg gtacaccagg ttgcccccgt tgttcatcga   1080
ctcctggaga ggtctgtggg acaaatttttt gctcaacttc caagggtact gccagacacc   1140
```

```
gacgccttgg ctgaactgtc actctgcaag cagctggaaa gacagactct gcgggagtac   1200
taccgcatgt ttctgactct caagtcgcaa ctgccttcgg ttgatgacca aatcgccatt   1260
cactacgcca tcagtggcct tcaggctggc gttctttaca gccgctgcat cagagatcca   1320
cccaagaacc tccaggagct gtatcagctg ttcgaaaaat atgccagatc tgaagagctc   1380
caccagcgca agtcgagtc ccagaggaaa cccaaagacc ctccgtagtc tagccatacg   1440
tggatgagac cttcgcaagc agactccggt cgggatggcc gcagtcagca gcaggtgcac   1500
aacatcgcac gaatcaagct gaatctcaga cgctca                             1536

<210> SEQ ID NO 41
<211> LENGTH: 1614
<212> TYPE: DNA
<213> ORGANISM: Zea mays

<400> SEQUENCE: 41
gaagataggc gattaatgaa agatcgtagg cgggtagaat tggaaaagat gacaaggtgg     60
tgaaaaccta gaatgcaaat ttgaggggca aaatggagac cggggaaatg gtggaacatt    120
aaaaatatag gacaccagcg gaagggagcc gtttcgggaa ttcttctggg cgattttga    180 agaagggcgc ccaatagggc aaattcagga gttaggaagt tatcggcggg tttcttgccc    240
ggcaccaaat tgcgaggaag ggtgagcaag gtggttccca aaaccccac cagggcgagc     300 gagttgatgg acatcgccac caagttcgcc tctggccagg aggcggtcga ggctatcttc    360
cgaaaggaca gcagcccca gggtcgccca tcggaagaag ctcccgaggc gtctgctccg    420
cgcggcgcca agaagaaagg caagaagaag tcgcaatcga acgcgacgc cgctgacgcg    480 gaccttgtcg ccgccgccga gtataagaac cctcggaagc cccccggagg tgcaaacctc    540
ttcgacaaga tgctcaagga gccgtgcccc taccatcagg ggcccgtcaa gcacaccctc    600
gaggagtgcg ttatgcttcg gcgtcacttc cacagggccg ggccaccgc cgagggtggc    660 agggcccgcg acgaggacaa gaacgaagat cacctagcag gagagttccc cgaggtccgc    720
gactgcttca tgatctatgg agggcatgcg gcgaatacct cggctcggca ccgcaagcaa    780
gagcgccggg aggtctgctc ggtgaaggtg gcggcgccag tctacctaga ctggtccgac    840
aagcccatca ctttcgacca ggccgaccac cccgatcatg tgccgagccc ggggaaatac    900
ccgctcgtcg tcgaccccgt tgtcggcgat gtcaggctca ccaaggtcct gatggatggg    960
ggcagctgcc tcaacatcat ctacgccgag accctcaagc tcctgcgcgt cgatctgtcc   1020
tccgtctgag caggcgctgc gcccttccac gggatcatcc ctgggaagcg cgtccagccc   1080
ctcgggcgac tcgacctccc cgtctgcttc gggacaccct ccaacttccg aagggagacc   1140
ctgacgttcg aggtggtcgg gttccgagga acctaccacg ccgtgctagg gaggccatgc   1200
tacgcgaagt tcatggccgt ccccaactac acctacttga agctcaagat gtcgggcccc   1260 aacgggtca tcaccgtcgg ccccacgtac aaacacgcgt tcgaatgcga cgtggagtgc   1320
gtggagtacg ccgaggccct cgccgagtcc gaggccctca tcgtcgacct ggagaacctc   1380
tccaaggagg tgccagacgt gaagcgccat gccggcaact tcgagccagc ggagacggtc   1440
aaggccgtcc ctctcgaccc cagtggcgac accaccaagc aggtccggat tggttccggg   1500
cttgacccca aataagaagc agtgctcgtc gactttttcc gcgcaaacgc cgacgttttg   1560
ggccggatcc cttcgactgc cccggcttcc cgaggaatgt ccccaaacct tcct         1614

<210> SEQ ID NO 42
<211> LENGTH: 2563
<212> TYPE: DNA
```

```
<213> ORGANISM: Zea mays
<220> FEATURE:
<221> NAME/KEY: misc_feature
<222> LOCATION: (739)..(739)
<223> OTHER INFORMATION: n is a, c, g, or t

<400> SEQUENCE: 42
tgtcgatgat tacgcttgat tcatcagaat tggttaattg gttgtaacac tggcagagca      60
ttacgctgac ttgacgggac ggcggctttg ttgaataaat cgatacggtc cgagtttaaa     120
cactcgagag gccacgtggg ccaacctgca ggaactagtg atatcacatt tagggtcagt     180
ttttttggtc gacaaaacga ggaaagagaa acataacgtc agttttattg gatgccttaa     240
accgacgtta aagtccatat tatttgtagt gaatgttgac aactaggtgt gtaatagcgg     300
attctgacac atttggtctc acaaacagtt aatgagctat aatgtctcca aaaaccacaa     360
tcgtagcaaa gcaaactgaa gaagaagata cagcaaacaa caagtgtgaa tagtacaaga     420
gaagagagac atgcaacgaa aattataacc aaaaacgagg ttctacatat taaagacatc     480
ccatcttaaa agaagctgat atcccgcgga cctaggagag ctcaagcgct gcaattgcat     540
tcattttatg tttcaggttc agggggaggt gtgggaggtt ttttaaagca agtaaaacct     600
ctacaaatgt ggtatggctg attatgatca gttatctaga tccggtggat cctacctttc     660
tcttcttttt tggatctacc tttctcttct tttttggatc tacctttctc ttctttttg      720 gatcagctcg agatctcang aacaggtggt ggcggccctc ggtgcgctcg tactgctcca     780
cgatggtgta gtcctcgttg tgggaggtga tgtccagctt ggcgtccacg tagtagtagc     840
cgggcagctg cacgggcttc ttggccatgt agatggactt gaactccacc aggtagtggc     900
cgccgtcctt cagcttcagg gccttgtggg tctcgccctt cagcacgccg tcgcgggggt     960
acaggcgctc ggtggaggcc tcccagccca tggtcttctt ctgcatcacg gggccgtcgg    1020
aggggaagtt cacgccgatg aacttcacct tgtagatgaa gcagccgtcc tgcagggagg    1080
agtcctgggt cacggtcgcc acgccgccgt cctcgaagtt catcacgcgc tcccacttga    1140
agccctcggg gaaggacagc ttcttgtagt cggggatgtc ggcggggtgc ttcacgtaca    1200
ccttggagcc gtactggaac tggggggaca ggatgtccca ggcgaagggc aggggccgc     1260 ccttggtcac cttcagcttc acggtgttgt ggccctcgta ggggcggccc tcgccctcgc    1320
cctcgatctc gaactcgtgg ccgttcacgg tgccctccat gcgcaccttg aagcgcatga    1380
actcggtgat gacgttctcg gaggaggcca tggtggcgac cggtagcgct agctggtacc    1440
tgttaactct acctgcaaaa agaaaaagaa aaactcagat taatcgacaa attcgatcgc    1500
acaaactaga aactaacacc agatctagat agaaatcaca aatcgaagag taattattcg    1560
acaaaactca aattatttga acaaatcgga tgatatctat gaaaccctaa tcgagaatta    1620
agatgatatc taacgatcaa acccagaaaa tcgtcttcga tctaagatta acagaatcta    1680
aaccaaagaa catatacgaa attgggatcg aacgaaaaca aaatcgaaga ttttgagaga    1740
ataaggaaca cagaaattta ccttgatcac ggtagagaga attgagagaa agttttaag    1800 attttgagaa attgaaatct gaattgtgaa gaagaagagc tctttgggta ttgtttata     1860 gaagaagaag aagaaaagac gaggacgact aggtcacgag aaagctaagg cggtgaagca    1920
atagctaata ataaaatgac acgtgtattg agcgttgttt acacgcaaag ttgttttgg     1980 ctaattgcct tatttttagg ttgaggaaaa gtatttgtgc tttgagttga taaacacgac    2040
tcgtgtgtgc cggctgcaac cactttgacg ccgtttatta ctgactcgtc gacaaccaca    2100
atttctaacg gtcgtcataa gatccagccg ttgagattta acgatcgtta cgatttatat    2160
```

-continued

| | |
|---|---|
| tttttttagca ttatcgtttt atttttaaa tatacggtgg agctgaaaat tggcaataat | 2220 |
| tgaaccgtgg gtcccactgc attgaagcgt atttcgtatt ttctagaatt cttcgtgctt | 2280 |
| tatttctttt cctttttgtt tttttttgcc atttatctaa tgcaagtggg cttataaaat | 2340 |
| cagtgaattt cttggaaaag taacttcttt atcgtataac atattgtgaa attatccatt | 2400 |
| tcttttattt tttagtgtta ttggatattt tggatgatta ttgatttgca taggataatg | 2460 |
| acttttgtat cagttggtga acaagtctcg ttaaaaaagg cagtgtttgg tgactcgatt | 2520 |
| tattcctgta attaattcat aataaatgga tcttatttgg ggc | 2563 |

<210> SEQ ID NO 43
<211> LENGTH: 2753
<212> TYPE: DNA
<213> ORGANISM: Zea mays
<220> FEATURE:
<221> NAME/KEY: misc_feature
<222> LOCATION: (2505)..(2505)
<223> OTHER INFORMATION: n is a, c, g, or t
<220> FEATURE:
<221> NAME/KEY: misc_feature
<222> LOCATION: (2549)..(2549)
<223> OTHER INFORMATION: n is a, c, g, or t

<400> SEQUENCE: 43

| | |
|---|---|
| tcgagattac gcttgattcg tttgtgctat tccggcttca cccgtaggtg acttttgcac | 60 |
| ggagtgtcgc acgcgagggt agttagcgct gcccctcgcg atgactttgg tgtggtcgaa | 120 |
| tgccgaagac catcgatgcg gtcttttcg acattggctt agttttttgc ggggattt | 180 |
| tgcttgtata ttacatggcg ccgcctcatt aaaaaccctca ccccctggg aggaaaagag | 240 |
| tgcgggccgg aataataata tttggtgaat tacaagggcg tgatggccct gaggattcaa | 300 |
| acaaaaaatt tgcgaagatt atctatattc caggaatgtt ccaggtcttc gccagattgt | 360 |
| gttgtcagtc cgtacgcgct gggagacgac ttcgtcttga cgataaatgg tccttcccac | 420 |
| tttggttcca gcttaccccg tgactctgtc cgggttgtgc ggacaagtac gaggtcccct | 480 |
| tcgttgaatt ctcttgggac gactgcgtgg tcgcgccagg ccttcgtttg tgcttgatat | 540 |
| ttgtcgagga cctgcaggc gaagacacag tctccgtcaa tgaggtctttt ggaagttggc | 600 |
| tcgtcgacgt cgggtactgc taaagcgctt gtccgcgggg acccatgttt gattttttgc | 660 |
| ggtgtcatgg cctccgatcc aggggggtgaa atcggtcgcc cgacactcgg tcgtgttcag | 720 |
| tgcccagact gcttcaggta gcaggtcggc ccatttgcgc ttcttgtcgt cgaggagcat | 780 |
| tttcttgatc accgtgaaaa tcttgccatt ggcgcgctcc acgacgccgt tggattgtgg | 840 |
| gtggtacatt gaggcgaagg caagcttggt gccaatggag aagcagaaat ccttgaagtc | 900 |
| ttggctgtca aattgcttgc cattatcgac tgtgagctcg gacgggactc cgaatcgaca | 960 |
| aacaatgttt tgccagaaga atttctaggc agtcttcgat gttatcgtgg atactgccct | 1020 |
| cgcctcgatc cacttggtaa aatactcgac ggtgatgaag gtgaacttga ggttcccttg | 1080 |
| ggccgtgggt agtggcccga caatgtctag gccccagcgc taagggggcc atgtgtgggc | 1140 |
| gattagcttt gtgaattgcg aagggcttcc cgagcgtgga gaaaacttct ggcaggcttc | 1200 |
| gcatgacctt gtgacacgat tgtggtgcca gatcatggcg ggccagtaga agccttgacg | 1260 |
| gatcacctt gcagctaggg ccctaggccc tgcgtgagag ccccaagtcc cgtttggact | 1320 |
| tccgcaggat ttggacgctt tcgttttggt gacacattta agcatgggtg gcctgattcc | 1380 |
| ttcttgtaaa gctggccttc gatgagtgcg aagtcccggc ttcggtgttt gaggcgctgg | 1440 |
| gcttcgttga tgtcggttgg atgatagtac ccctgcagga acagggttat tggtgcccgc | 1500 |

-continued

```
cagtcttcga tcataatgag gttgactatg cggtggccct cgctgtcatt ggttatttgg    1560
aggccctctg ggctgcggac ggctggcgtg ccgatgacat ggtagaatac gtcgaagggc    1620
agggcctcgc tctagcggc tgccttggcc aatgcgtcgg cctcctcatt cttggctcga     1680
tccacgtgct gcaaggtgaa gcctttgaat tgcctctcga gactgcggat agccgcgaga    1740
tactgcatga gtgcggggtc cttcgctgcg aaatatttct cgacttggcc ggcgactacc    1800
ttggagtccg ttctgatgat acaggtagtg acgccaagtg cccttagctt gcgaaggccg    1860
aggatgatag cttcgtattc ttctatattg ttggtgcatc tgtcagactc caaagcaaag    1920
ctgaggcgtg ctgcatattt gtgcttgacc cctgtgggtg aagtaatgac tgcagctgcg    1980
cctgcccccg catggcacca tgcgccgtcg caatggatgg tccacacctt ctctgcggac    2040
gtgtccggct gcgttattgg cccgatccag tcgacgatga agtctgccag gacttgtgac    2100
ttgatggttg tcctgggctc taaggtgata tggtagccgg aaagctcggc tgcccacttg    2160
gcaatccgaa cagatgcctc cggattttta acaattcgc cgagtcccct gtctaaggtg     2220
acccgtacct tgaacgcttc aaaataatgg cgcaatttgc gtgaagccat aacaactgcg    2280
taggcgattt tttccagttc cgtcatgttg cattttgatg tcgtgagtac ttcggagaca    2340
taataaactg acattgcct gatcgtgccc tctctgtcct gctcttgaac cagtgctgcg     2400
ctgatcgcat gcggcgaagc tgcgatgtag agcaataggg gtagcgaggg gttgggctt    2460 gtaagaatcg ccaactctga cagatgctgc tttaatgaag cgaangccgc cgcttgctct    2520
ggtccccatg cgaagtcttt tacgcacgna gtgttttgag aaaaggtagg ctcgctctgc    2580
cgacttggag atgaatctgt tgagggcggc ccatctacct gtcagttcgt ggacgtctct    2640
agctgactgc gggggcgtca ttgtgatgat ggcctggatt ttggtcggat gggctccaat    2700
ccgcggtgcc acaccagtaa cccagttttt accctaacga acgtcgatac cac           2753
```

<210> SEQ ID NO 44
<211> LENGTH: 2816
<212> TYPE: DNA
<213> ORGANISM: Zea mays

<400> SEQUENCE: 44

```
ggggccaacc ccgggggggtt cttccctccc gaaatacgtg aaatttgctc ccccgggttt    60
tcccacggag taagtaaggg ttgcccccaa acgccggggc catggggccc cggcacgaaa    120
gccaaaaaat tcccaagccc cttttttccgg ccccgaagga atttcgggga ggggggactta  180 ccgctgcggg aatgaatgcc gctatccacc gtcggagggt gctcccattg gcggaccgcc    240
ggctgccgct ctgggagatg accccggaaa actgactggg agggctcatg aatgtcccct    300
gatcctctcc ccttcaacgc cctccaatgg cgggtgtcgg ccgcgatggg gaagccggac    360
ccccacgcat attcccagct tcggatgcgc cccgaccagg ggtgcgtgac tttggtgagc    420
gtttgctcct cccttcttcg tatatctggt cgctccgggt ccttatgatc gagttctttt    480 ctccccctcct tttaggatgt ggggtgtcac aaaccctccc tgccacgggt cccggaggac   540
gcggtggacc gtgcagcgcg gcgggtcgcc cggaggagga agaagaaaaa gaaggacgcg    600
gagaaggccc gggccgcga gcggaggcgg gctcgggacg ccttggagaa gcgccgccgc     660
cagcaggagc gggacggact cccgagggag ccgtcgccgg agacgcccga cgacgatgac    720
gacgatgacg atgataatga tgacgacatg gccgcccgtc tcggccttag cctcggcccg    780
gggtgtggcc aggagccgtc gagccagccc ccgagcgagc cgactccgtc agccccgaa    840 gtcggggcgt cgggctcccg acccgaggcg cggggggcgaa ccgagaggtc acctgacccc    900
```

```
tcagccggag gagctgaagt agttccggag gtccaggcca aggcgtctgt tccccagggg      960
ccgccgcttg tgtcggtggc gcatgggggt gaccctcagg tcgtcgcggt cgtgcccggg     1020
gaatctgcct cccaggcgcc ccaagcgccg gtgaagcgga cctcggcggc cgttccgaga     1080
gccaggatac aagaaggctc tccccaggcg cggtggatca tggcccggag tgggtgagta     1140
cctcggaacg tcttcgtctt ggcctcccat tcgtatgtct cggttgtgat cccctttctt     1200
tttcatccag caagcgaagt catggccaga ctgacctggc acctcggaag gccctcaaga     1260
cggcgccgaa ctgtgcggcc agcgccattc agccgaccct ttcgcggggt actccgacat     1320
cgggggctcg ggcgtcgcca atctcggagg agcaggctcc cgaggccggc tcttcagccg     1380
aagcggcgat cgtggttgag gaggcggctg acgcccacgc ggctctgagt tcgcctgtcg     1440
tgtcggtcat gccggcgcct gccaccgccg aggttgccgc cgtccctgtc gaagggtgtc     1500
cagttgccgc cagcgccagg gtggctgatg cgtcggcgcc cgagacctca gaagaggtgg     1560
gcgcggtcgc gcaatccgtc cagccgggtg acagcctcat cgctgtgcgg cggagccccg     1620
aggcccggcg cccattgctc tgattccgga cccgcgaggc ctcggacccc gtcttcgttc     1680
ttgatgatga gcaggaggac cagtcctggg gtgagctcca cgagtgcgca gaggcaacgg     1740
tggggtcgct ccgggcgtcg ctggaggttt tctgcagaga cgtccccaaa atccttcagg     1800
tagcgatttc gggcatacct ttttcccttc tgtgagatac tcgctgtgac gccctgtttc     1860
ctttcccagg atctgacgga ccggagcgcc gccaagtcgt cgttcatccg ccgtgaggtt     1920
gatgtctggg gctcgctgcg atccctgagg tcttcgcttg ccggggctac cacgcgcctt     1980
tctcagcagg atgccaaggt ggcggacctc cagctgctct gcgccgacct gagagccgag     2040
gcggcagcag cgcgtgcgga ggcgcaacag cagcgatcgg agctcgtcca ggtcgtcgag     2100
gaatggaacc gacttcaggg ccggggctgcc gaggccgaaa gccgagccga ccctcgag      2160
gctgacctag ccgcgaccca ggtcgcggcc tcggagcacc gtgcccgagc cggaagtacg     2220
tcttcgtcct ccctagttct ttttcttgtc cgtttccctt gcttgtgctt gaggtatttc     2280
tcctggctac ttgcagagct tgagtccgcc ctcgacgagt ccgccaaggc gcttgctgag     2340
gcgcttgccg gagccgccga gcagagggag gcggacctcg cggccatgtc cgaggccgtc     2400
tcggactttt atcgtgtcct cggctccggc gacgtccctt caggaagctc ccctcagagc     2460
cgccttcgag ccttaggtgg ccacgcccgc ggcagagtcc gcgaagcgct acaccacggc     2520
gtcaggcggg ccttcgccgt gctcgcttct cactacgttg tggacctgga gcgggttagt     2580
gaggggtact gtcttcctga cgaggacgat gctgctctgg cggaggtgca gcggcttgac     2640
gcggtcgccg cgggtccgag cgcggtgctg gcgaccacct ttgaggcgga ggtccttcct     2700
cctgcgacgt caccggaggc cgagatggac cccaccgatg gcggggtgg agctgaaggc     2760
gcggctcctt cccaaggcgg cgcctgatag aattcaagcg tattctcgga cagcca        2816
```

<210> SEQ ID NO 45
<211> LENGTH: 2997
<212> TYPE: DNA
<213> ORGANISM: Zea mays
<220> FEATURE:
<221> NAME/KEY: misc_feature
<222> LOCATION: (918)..(918)
<223> OTHER INFORMATION: n is a, c, g, or t

<400> SEQUENCE: 45

```
atgagcattt aggaattcgt caaattagga attagaataa aacaaaattt tctgcaaagt       60
ataatatata taataaaaca taaaattggt cgatatgacc aaccttgaa gggataccaa       120
```

```
agtcaaggtg ataatagagg tctatagtcc ttagaacgac catcctactc taggttagtg      180
gtcctacagt cagcacgact ttgataccac ctatgtcaca cccggtttta gaaggcaaac      240
cgaatgcgaa ccatgtacgt gcccaggatc agcaattcac gtacacaaca attacataac      300
tggacatcat cacacagtgc tcaaataata acataaaaga tagtaatagt cgattacatc      360
atgatgtccg agacatccac attgtcatta atagttatca aagtgcaaga aagaaacgta      420
gatacacaca gccttcacaa gcagccgact gggggtttgc cgctaaccca cgcctagaac      480
tcatcgcact cttggaactc ctggaagtcc tcctccacga cttcatcttc tcctgagcag      540
tggttgcaac atggacaacc tggggggctt tggtgtgtaa agcaagggtg agtacacatc      600
aacatactca gcaattgtcc cgttttgctg tagtggacta gctttatgtg gggttaagcc      660
aagtagttgc ttttagttgg tcaggttatt attactagta gagagccaga ttttagcatt      720
aacccaagtt gttaacccaa aagtacccctt tccaaatgga aaggataccaa gaaacattac      780 cataagcata atcaaaacca tcatcctcgt caccacctgt aaaccaacca tctctaatca      840
aagtatctct aatcaatgga gctcccttgc cactcataac catgagcaca actgattaat      900
cagtttaata acactcgnaa agagttgggc accttaccca caagccgtga ttccctcttg      960
cctggggccg atcaaacctt taacactgcc atggtgaata ggcagggttt tactacgtag     1020
cctttacaaa gattccctga ggctatagcc gcccattagg ttttctaaat gtaccacact     1080
cctccccaag gggcaatcca ccctcggtag agcgagccgc atacactgag ccccattgac     1140
ggcacgacgg cgaagcgaac tacaccccag ttcctctaat tattcagcta agggcgtccc     1200
ataccaccct catggttgca ctttttttccc gggcggtcat ccaacgaacc aatccttatg     1260
gagaggcact cgagaaacca ctcgagtccc cttaaatgtc acagtatcat catcataatc     1320
aaaaggaaaa atagcgtatg ataaataatc tcatcctgtt cattgattaa tgtgaagcac     1380
tagcataaag ctaaaccaaa ataacccaac caaataggta aacaaggaca agataaacaa     1440
aagctagtca atccttaggt ataaattgtg taaatgcggg gagtgaatta taatgtgagt     1500
aggacataga tgggtcaagg gacacttgcc ttcaccaacc agctgctgct cagggtcttc     1560
acctacaact ccttcagact ctgccaactg accgttatct ataagagttc aaacatacat     1620
tccacaaatt caatataaaa gaacagtaca ccatgcatta aaatagagta aataagtaga     1680
tactcggcgc agggctcgca cctacgacta agcgagaaag agaaagcaac ggtcaaggct     1740
atggtcgatg gacgatcacg ttaagcgatt atagattaaa gtactcgtct aaacataata     1800
gtattaattt gacaatcacg ttatgcatag gataaagtca cgctacagtt taattattat     1860
aaacaattca aagtaaattt aaaaagattg ttgcccagcg aaacgcacga cgacaaacgc     1920
aaacgaaact tagaataaaa tgagtcgtcg cgcggcgaag cgcgcgacac aacacttaga     1980
ctaaaatgaa cataaaacga atcatcgcgt gacgaagcgc gccatgagac acttgaatta     2040
attatgaaaa taacgtcaag cgtcgcgcga cgaagtgcac gacaggatat gtcacttaaa     2100
atgaaattaa aacaaaacgt catgcgacca gacacgcaac gccacacatt aaataattta     2160
agatgaaccg tcgcgtgaca aagtgcgcga cgtagcactt taattaaact aaattcgaaa     2220
ctaattaaac tgaaatttga tcaccgcgcg cgcggaaacg cgctgggcga gccacgaggg     2280
gctgcgcgcc gggtcgggt cgcgcgcact ggagccggga cggccgcgcg caagggccag     2340
gatggccgcg caccaggggt cgggaacgac cgtgcgcagg ggcgccggga cgaccgcgct     2400
cagggggcta ggaacggcca caccgagggg cgccgggaac agccacacat agggggccag     2460
ggcggccgcg cgcaggggc caaggtgccg caccgctagg acacgcgggc ggtgggaaga     2520
```

-continued

| | | |
|---|---|---|
| gaaagggaag ggagagggag agagaggggg aggtgaggct caccttggga tccaaaatcc | 2580 | |
| ggcgataact gtcaccggat cacacctagg gcacgaggtg ggagagaggt ggaagagagg | 2640 | |
| gagagggagt tgctgtgcag gaaaaataaa atgagaggaa gggagaggcg ggcgcgcatg | 2700 | |
| ggggggtttg gggcgccagg ggcacgcggg ggcgcgcagg gccgggacaa gctgggtcac | 2760 | |
| gagccgggat agaagcccac aacgcacacg accactgatc ggaatccagt tgcgaatcga | 2820 | |
| aatccaaaac gaggcgagat gaacgcgtga ttaaacaaaa catcagacaa aataaaaatg | 2880 | |
| ctttggcatg atgcaacacc catgtcaact taggtttttg tttacacgcg atacgtacac | 2940 | |
| cagtcgctat actggtttaa aatggaagaa cgaatcaagc gtattctcgg acactca | 2997 | |

<210> SEQ ID NO 46
<211> LENGTH: 2897
<212> TYPE: DNA
<213> ORGANISM: Zea mays

<400> SEQUENCE: 46

| | |
|---|---|
| tggctctccg agaatacgct tgaattctta tgctttagag gtcagcatta tgtcaccgat | 60 |
| attatgcttt agaggtcagc atgtattttg tcttttgcgg ccgagttcgt gatccgccca | 120 |
| tatcttgcta ggtggtgcaa tttatttgct ctgtgactga ttggacattt gatggacgtt | 180 |
| ccctggctag tcttcatgtc gcttctgtcg ttcagatttt gtacttcacc ggctatattt | 240 |
| ggctttcctt tgatccttac tgatatctca ttttgtctt gaggtattca ttgcatgccc | 300 |
| tgcacggatg tgacagtttt gaaaaatata ctgataattc ctgggcgtcc ctcccaatgg | 360 |
| gtgtgggcaa gggacggctt ggtacgctga gtgttttagc cggctgcttc tgagtagtaa | 420 |
| tgtgatgtga cggtgggtgt aatcatatcg cccgcgcggt tgatctctgt cgtgatattt | 480 |
| attgcaccgt cttaagtcgt tgccgactta agccgattgc tccgttagca gggcatagtg | 540 |
| gtcacctcga gttaagtaag cgcgagcatg ttgcaccgtc ttaagtcatt gccgacttaa | 600 |
| gccgattgct ccgttagcag ggcatagtgg tcaccccgag ttaagtaaga atgccggtca | 660 |
| atcgtgaaca aactgagtat tcttgaagcc cttttttatt gatgacatat ttcccatttt | 720 |
| acaaagtaca ttatcgtccc gatagctttt gaaatacaac tagggataaa acttcctgag | 780 |
| gtgttctata ttccaggagt tcccaattcc tgtgtcgtcc atttgagtga gacgatatga | 840 |
| tcccggccga gtgacttctg ctactatgaa tggtccttcc catgagggcg acaacttgtg | 900 |
| ccgtccctcc cccgttagaa ttcggcggag gacgagatct cccactgtaa aggatcgttg | 960 |
| tcgcacggcc ttgtcgtgat agcatctcag agtctgctgg tatcgtgctg attgaattac | 1020 |
| tgcattcagc cgttcttctt cgagtacatc aatgtcctcc agcctagtag cttcggcttc | 1080 |
| tgctatgctt tcgaaaatca accttggcgc cccaaacttg agatcagcgg gtaatactgc | 1140 |
| ctctgaccca tagaccatga agaaaggagt gtttccatgc agagctcggc taggttgggt | 1200 |
| tcttaggctc caaacgacat agggcaattc cctttatcat ttcctgcga acttttcatt | 1260 |
| cttatcaaag acctttttcc tgagtgcttc ccatatcatc ccgtttgctc gttcaacctg | 1320 |
| cccgttggct ctgggtgtg ctactgaagc atacttgatc tgaatgcttt tttgctcgca | 1380 |
| gaaatcgaag aactctgaaa cttgtgaagt tggatcctaa ggtcagttat gatatggttt | 1440 |
| cggtatcccg accctgaata ataagttctg ttatgaattc cacgggcctt agctgaggtt | 1500 |
| aaagaagtga tgggtttgaa ctctatccat ttagtgaatt tgtcgattgc taccagtaca | 1560 |
| tgagtgtatc ctccttgagc tttcttgaac ggtccaatca tatccagtcc ccagcatgcg | 1620 |
| aagggccaag ttactggtat ggtctgcagc tgttgtgctg gtagatgttg ttgcttttgat | 1680 |

```
aagtactggc aagcctcgca cctttgaact aactgggctg cgtcacttt     tgctgttggc   1740 caatagaatc ctgacctgaa gaccttcccg actagtgtct tggatgctgc    gtgtattcca   1800
cattgcccag catggatctc atctaaaagt cgcttcccag tagatgagag    aatgcacttc   1860
atgaggacgc ctgatgcacc ccttctgtat aatgtctccc caatgagtgt    gtagtgagct   1920
gactgtctag cgatgcgctc ggctgcattt ttgtcatctg gttcctcttc    attctttata   1980
tatttgatga tcggccttct ccagtcatca gagtctgact ctggttgatt    cacgatatta   2040
cactcttctg cctgatccat tgagatgctt gattgtggta tttcttgtac    aaagactcca   2100
ggtgggacct cagttcgact ggatcctagc ttggacagta catcggctgc    cgtgtttcga   2160
tctctttcca cgtgatgaaa ttccagacct tcaaatttat cttctagttt    tcggacggca   2220
gtgcagtact ttcccattga atcgcttgaa caatcccatt ctttgtttat    ctggcttatg   2280
actaccaaag aatccccgta caccatcagt ctcttgatgc ctagtgatat    agcaatgttc   2340
agtccatgaa ttagggcttc atactcggct gcgttgttgg aggctggaaa    tagcaactgg   2400
agggcatatt tgaggtgctc gcctccaggt gcggtgaaga gaattcccgc    gcctgctccc   2460
tgcagcctca gcgagccatc aaaatacatt cgccatactt ctgcagtttc    tgggttatct   2520
ggtacttgtt gttcagtcca ttctgatacg aagtcaacca acgcttgagt    tttgatggca   2580
gtgcgaggtc gaaattcgat gtcatgagat cccagttcac aggcccactt    ggctattcgg   2640
ccaatggctt ccttgttgtg aggaatatcc ccaatcggaa aaccagtgac    tactatgact   2700
ttgtggtcgt caaagtagtg acatagcttg cgggcagtta gaagtactgc    atataatagc   2760
tcctgaactt gaggatactt tttctttgag ggacccagaa cttcactgat    gaaataaaca   2820
ggatgttgta ctgggtaggc atgtccttct tctgctcgct caaatacaac    gaattcaagc   2880
ttattctcag acagcca                                                     2897
```

<210> SEQ ID NO 47
<211> LENGTH: 2845
<212> TYPE: DNA
<213> ORGANISM: Zea mays

<400> SEQUENCE: 47

```
tgagtgtccg agattaagct tgattcgttc gattcgccgt aaactgttga     aaaccagctg     60
taagtcttcg atgaagtttt ctgagttctc cgttttgatt accacatcat     ctacataggc    120
ttccacacgc ttgccccagt gatcggttaa gcatgtttga atggccctct     gataagtcgc    180
tccagcgttt ttgaggccaa acaacatgga ggtatagcag aaagcaccga     acggagtgat    240
gaacgctgtt ttttcctcat cttcccttgc caagctaatc tgatgatatc     cggagtagca    300
atccagaaaa gacagcacaa acatccagcg gtggagtct  accacctggt     ctatccttgg    360
gagcccgaag ggatcctttg gacaattttt gttgagatcc gtatagtcga     cgcacatgcg    420
ccaatccact ttattctttt tgattacaag aacaggggttg gctaaccact    cgggatgtaa    480
cacctctcta ataaacccag ccgcgaccaa gcagccagc  ttagcgcgaa     tggcctctct    540
cttgtcgggc gtgaagcgac gtagttttttg ccgaatcggc cttgcctggg    ggtagaccttt   600 cagtttgtgc tcggccagtt ctctcgggac tcccggcata tccgcaggtt     gccatgcgaa    660
tacgtctcgg ttatccttgca gaaactggac gagcgcgcct tcctatttat    cgcccaggct    720
ggagctgatg atgcaatct  tgcgctcatc agcaaacccc aggttgatcc     ttttagtttc    780
ttcagtcggt cgcatagagg tcgcggcttg agcttcattc gccggtgctg     caaggtcttc    840
ctcaggctta gagtttgcct gcgttgaaga agttgccgat ggtttggtgg     tgagggccgc    900
```

```
ctggatggcc actcggaaac attatgccgc gccttggaag tcagcgcgca cagttatgat    960
tccttgtggt cctagcatct ttaatatcat gtacgtgtaa tgcggaatgg ccatgaattt   1020
tgccaatccc ggcctcccga tgatggcgtt gtacccgcag tcgaagttcg ccacttcgaa   1080
ccttaggaac tcgattctgt agttatccgg agttccgaag gtgacaggca tgtagatgtg   1140
gcccagcggg tattcccctt cagtcagcat gatgccgaag aaaggagtat ctgacttgtg   1200
gagctctttg aggtgaactc ccaagccttg gagtgtccgg gggaaggtga cgttgatgct   1260
gctccccccc gtccactaac accttcttca ccctgctctc tcggatcacc agatcgacga   1320
ggagggata tttgcctggg tggtcgaagt tgagccattg gtctgcccga gtgaaagtga   1380
tcgggtgctc cgaccatcgg tacggagcgg gaggaccggt ggtcgccacc aatatctggc   1440
gatcgttgag cttttgttgt cttctgttct cctgcgatcc gtgtccgttg aagatgacgt   1500
tgacctccct atcaacgcgt gggaaggctc cacctcctcc ctcctcctgc tgctagggtt   1560
gtcgtggttc ttctggtcct ccccgcggcg gaggaggagg tagaggttgg aagggtcggc   1620
cgtgtccgac ggagtgcttg aagtccctgc agttccgaag ggtgtggcgc atgtccttgt   1680
ggtacgggca ctgggcgtcg aggatgtcgt ccagcgtgcg ctcgcctccg cgaggtcctc   1740
cccaggcgcg agaggcaggt ggtccagcgg cgtgcacttc ttcgcgaggt ctcttctccc   1800
agcgtttgtc gggttgctgg ttcgcgtcgc gtcgtggtgc tgccggtgcg ggcttcgctc   1860
ccccgatgag gtcctgagct cgctcgtcgg cggtgatgta gaggtcggct tcccggaaca   1920
gctgctcgga ggtagtcggc gccttctgca atatggctcg gacgaaggcc gagtcattgg   1980
atcctctgta gaagtcctcg atcacgaccg cctccgtaac ctcggggata cgatttctca   2040
tggtctggaa ccttttgagg tacgaccgga gagtttcgtc ccccggcgct tgatggattt   2100
gaggtcccat ggttgcgctg gtttgtcaga gagggattga agttggcgg tgaagcgtcg   2160
actgaagtcg caccagtcgt cgatgcagtg tcggggtaga tgtcgcagcc attgaagtgc   2220
gtcttgcccg aggacaatgg gtaagtatgt agtcatcacg tcctcggacg ctccagcggc   2280
tcgagcggtg gtggtgtaga cggccagcca gcccccctgga tcctgcttag gttcatattt   2340
gtcgacattg ataccttga agttaggcgg ccattgaatg gccctaaggc gtggagtaag   2400
ggcagacact ccacacgtat cttcctgtcg tcagggatga tgtctgtccc ggggagggga   2460
gtagttgttg tggttcctcg actgtccccg ggtagtaccg ccagtcgagg tcgtcgttga   2520
ctcggttctg gtggcctgac tccgagctgg gatgccgtga tccctgtcgt actcctcccg   2580
gcgactgatc tcgttctcat gtcgtcgttc acgcgaagca ttgatggagc ttcgcgcgtc   2640
ccggcgactg ttgatggcgt gtcgtagatc gttcggtggg tgagcaagag gtagatggtt   2700
ggctgcttgg gtgaacaatc gtcgatagcc ctcggcgtcg ggagtccgag ggagtccatc   2760
agctatccga gctagtaacc ctccgacttc actcggcgtg ttcaggctcg ggcgaagtcg   2820
ggaaacgaat caagcttaat ctcga                                        2845
```

<210> SEQ ID NO 48
<211> LENGTH: 3308
<212> TYPE: DNA
<213> ORGANISM: Zea mays

<400> SEQUENCE: 48

```
tgactctctg agaatacgct tgattcgtag ctctggctcc ctctccctcc tctctatttc     60
ttttgagcag agcactccat tcctccccctt tttgcccaaa ttccaaatcc tgtgaaatct   120
tgtgcaacct tgttgtgaaa tgtgttcccc tgtactcctt gagtactcct gcaggttctc   180
```

```
agctccttcg ggagggtttt cacaccttaa atggccattt ctccgaaacc ctaattcctc    240
gccctccaag tgctcggtga aatgcccaaa ctagccaaaa atgcttcaat tgaacccaaa    300
tttttcaggc accttcacaa cacttccagc aatatacttg tcaaatttca cgccaatccg    360 agttccagg cttcaatttc actcaattct ccgtttcgag cgatcgtttc cgagccgagt    420
gcccaaatct cttttcttc gcctaaattc aaaccaagca cacacttcac tcatattcac    480
ctatataaac ctattcatga agtatcggct caattccatg tcgtttcgtg cctcaattcg    540
aattccaaac ctcctatggc actatttatc gttcaaacat cgttttcac gccgtttgac    600 ctatcgatcg tctcgtctcg tgttttctgt gccatatctc tctgtgtgtg tatttattta    660
catttcatat acttatgact atgtgactaa tacgtgctca cctcttttgt catttcagtg    720
accttgattg cccgtgtgcc gtctcctgtc ctgcctggat cgtcacctct cgtgtgagct    780
ttccaggtag tcatctcatc ttttgctaat ctatcggtca ttttcgctct gtgcttagtc    840
actctctctc atttgcagac atcagttcag gatgccgcgc acgaagaatg tgtcggcgcc    900 aggggaggc gatgacgagg atcctcgtcg ccccttcagg caggtcaagg gcaagaccgt    960
ttacttggag cagcaagaag gccgcaagaa gcggcgtaca gacagagcag cccgtgcagc   1020
ggcagcggct acagcagccg cagcgcaggc cgagcttgga gatcagccgc agactccgtc   1080
agatcagatc gcataccgtg ttcgtcgtct cgcctcccgg cctcgctcct ccactcacac   1140
ctccgcttcc actccgccac ccactctgcc tgctcccgtc actcctattg ctccatccac   1200
ctccacagcc ataccgcta cctccactac gccagcttcc actgctcctc ctcctcccgc   1260
tcccgcttta gctcctcctg tccctccacc tcgattccgg gagcgcgatg agactgaggt   1320
tcgacccctg gctacggatc ctcgactgtt tgaccttcag cgtgctacag cggcacgggt   1380
acgtaggttc agatacgtac ctgtggagtc ttggctacca gctcagagag accctgcagc   1440
aggtgaccta ttcagcacac ggattcagga gtcgtttttc agagctcaga tgtctgctca   1500
gatagctctg cgagtgcacc ggcttttgga tcttccagcc tttctgcttg cagccggtgc   1560
tgactctcag gcgcacctca aatatctgcc tggccttctg acccttttga ctaccagcgg   1620
caggtatgtt gaggagtggg ttcgagtctt ctacgcctct gtatggatag acccggatca   1680
tcactggatg aggtttcgtt ttgagcgcga ggatgtcacc attactgccg gtcagatccg   1740
ccagcttttt ggatttcccg agtcgacgac tcgtcttcac agcctctgct acggcacttc   1800
tgatcctcct cgtcgccctc acggcggtgt ggctccgggt acagctcacg tcgcggctct   1860
cttccgcccc cccttctcag atgggtcgcg acgttcaccg gcatattta ctacagcagc   1920 caagtattta tatgagctga tcagacgaac tcttctgccg aggatgggat acagggaggc   1980
taccacacat atacagctct ggctccttgg tgccctggtc tctcactcta gtttgacgt   2040 tgtggacttc ctgatttttg agatcgagga caccgttttg gatgggatct gtgctcgtcg   2100
gcagttgccc tatgctcact acttgtgcca catctttgcg cagctgattc agcctcctcg   2160
gtttcagggc acccttgagg cctcccgcct cgttttggga tcctaccgtc ctgtgcctga   2220
gattcctgtg ccagcttctg ctcctgtttt tgactcttag gccgaggatg cagctcttcg   2280
tcagttcgac actcaggttc cagcagctga tgatgatgat tttggggttc ctcctccgcc   2340
tccgcctcct atgcctccac gctcacatga tcctctagag tcgacctgca ggcatgcaag   2400
cttgagtatt ctatagtgtc acctaaatag cttggcgtaa tcatggtcat agctgtttcc   2460
tgtgtgaaat tgttatccgc tcacaattcc acacaacata cgagccggaa gcataaagtg   2520
taaagcctgg ggtgcctaat gagtgagcta actcacatta attgcgttgc gctcactgcc   2580
```

-continued

| | |
|---|---|
| cgctttccag tcgggaaacc tgtcgtgcca gctgcattaa tgaatcggcc aacgcgaacc | 2640 |
| ccttgcggcc gcccgggccg tcgaccaatt ctcatgtttg acagcttatc atcgaatttc | 2700 |
| tgccattcat ccgcttatta tcacttattc aggcgtagca accaggcgtt taagggcacc | 2760 |
| aataactgcc ttaaaaaaat tacgccccgc cctgccactc atcgcagtac tgttgtaatt | 2820 |
| cattaagcat tctgccgaca tggaagccat cacaaacggc atgatgaacc tgaatcgcca | 2880 |
| gcggcatcag caccttgtcg ccttgcgtat aatatttgcc catggtgaaa acggggcga | 2940 |
| agaagttgtc catattggcc acgtttaaat caaaactggt gaaactcacc cagggattgg | 3000 |
| ctgagacgaa aaacatattc tcaataaacc ctttagggaa ataggccagg ttttcaccgt | 3060 |
| aacacgccac atcttgcgaa tatatgtgta gaaactgccg gaaatcgtcg tggtattcac | 3120 |
| tccagagcga tgaaaacgtt tcagtttgct catggaaaac ggtgtaacaa gggtgaacac | 3180 |
| tatcccatat caccagctca ccgtctttca ttgccatacg aaattccgga tgagcattca | 3240 |
| tcaggcgggc aagaatggaa taaaggccgg ataaaactgt agaattcaag cttatcatcg | 3300 |
| gacactca | 3308 |

<210> SEQ ID NO 49
<211> LENGTH: 4998
<212> TYPE: DNA
<213> ORGANISM: Zea mays

<400> SEQUENCE: 49

| | |
|---|---|
| tggctgtctg agattacgct tgaattctct gcaccgcacc gtgtccggtc agtcgagtca | 60 |
| cctggagaga ctgcaccacc gcctgcgtga ggagcaggaa cgccggcgcc agcacagaga | 120 |
| gcagcagggc tcttcttccc cacctcaacg agaggtggag tccgcgaggc ccgttcctc | 180 |
| tgtggcccag ctggaggcgc ccctgcccc gccgcggac gttccagctg ttggaggagc | 240 |
| tactggagga gatcctggag gagaccccga cgacgacgac tcagaccaca gcacggagtc | 300 |
| ttctgagccg caggaggcgg aaggatgggt cgcccgaccc atcacccgtg acgccgctcg | 360 |
| cggttgtcac ttccacgacg cactcgacac cttgctgcgc caggctttcg accgacacac | 420 |
| ctggtcgatc gagtatcgtt gtgtagtcta ccagcacaat cgcggaggt acccggaccg | 480 |
| ctgggaggct acctgcctag ttcgccgtcc ggaggatgac ctccggggtg cggaggccat | 540 |
| ttcggagcac tattccatct ccgagaggga cactgcagag cggctatgc aggatgcagc | 600 |
| acgacgtgca ctctctcagt actgttcttt gttcggtggc gtggccgacg gtcttaacct | 660 |
| tcggtactac ccccgccgcc ctactagcag caccgagagt gtggttgtct cacccgttgg | 720 |
| tgaggctaac cctaggttga gcagcacagt caacctagtc gcagtgctta acactgagct | 780 |
| ggaccactct ctggacgagc taagcagggc tcgaacggag attgcggagt gcgtgctga | 840 |
| gctggcagag cgccatcacc aggagggtgg ttctcccgct cctgttggga ctcagcaccc | 900 |
| ataccgctca ccgccacgtg gtcaccacac ttatggttcc cctgtctgta agaccaggat | 960 |
| agatctggat ccttagatcg ttagcgtcgt agtttgtaat aattcttaag tcagatgtct | 1020 |
| cagtcttagg tagtcagttt agtttgctta tcagttgctt ccatttaggt tagtttgctt | 1080 |
| atcagttgct ttcatgcttg ttatgatgaa cttgtgctgg attcgaatct ttgtaatgac | 1140 |
| tgttgccaac ctgtgggttt ctgaaaggga attaggctta cacctagtcc ctaattaatt | 1200 |
| ttggtggttg aattgcccaa cacaaataat tggactaact agtttgccca agtgtataga | 1260 |
| ttatacaggt gtaaaggtt cacactcagc caataaaaag accaagtttt ggattcaacg | 1320 |
| aaggagcaaa gtggcaaccg aaggccctct ggtctgggag caccggactg tccggtgtac | 1380 |

-continued

```
acgggacagt gtccggtgca ccaccggaca gtgtccggtg taccagaggt gtcggggacc    1440
ataattaggg gtaccctcaa gacgcctaat tctcagctgg taaccccccat cagcataaag    1500 ctgcaaaggc ctgatgggta cgattaagtc agggatcagt ccacacgagt gactcgatca    1560
cgcttcaccc gagcctagcc tcggccaagg gcagccgacc tcgagagact tccgtctcgc    1620
ccgaggcccc ctttttatgg cggacacatc accggctcgc ccgaggcctt ggcttcgctc    1680
agaagcaacc ttgactaaat cgccacaccg actgaccaaa ttgcaggggc atttaacgca    1740
aaggtggcct gacaccttca tcctgacacg cgcccccggc agagccgaag tgaccgccgt    1800
cactccaccg ctcccactgg cagtctgaca gaaggacagc gccgcctgcg ccactccgac    1860
tgcagtgcca ctcgacagag tgagtctgac aggcagtcag gccttgccaa aggcaccacg    1920
gcgaactccg ccctgcccga ccccaggggct cggactcggg ctaagacccg gaagacggag    1980
aactccgctc cgcccgaccc cagggctcgg actcggcta agacccggaa gacggcgaac    2040
tccgctccgc ccaccctagg gctcggactc gggctaagac ccggaagacg gcgaactccg    2100
ctccgcccga ccctagggct cggactcagg ctaagacccg gaagacggcg aactccgctc    2160
cgcccgaccc cagggctcgg actcggcta agacccggaa gacggcgaac tccgctccgc    2220
ccgaccccag ggctcggact cgggctaaga cccggaagac ggcgaactcc gctccgcccg    2280
accccagggc tcggactcgg gctaagaccc ggaagacggc gaactccgct ccgcccgacc    2340
ccagggctcg gactcgggct aagacccgga agacgacgaa actccgcttc gcccgacccc    2400
agggctcgga ctcgggctaa gacccggaag acgacgaaac tccgcctcgc ccgaccccag    2460
ggctcggact ccgccctggc ctcggccgaa cgacttccgc ctcgcccgac ccatggctc    2520 gggctcggcc acggcaacgg aaggcagact caacctcggc ttcggaggaa cccccacgtc    2580
gccctgccta gggcacagac cgccacgcca acaggaagcg ccatcatcat cctaccccga    2640
atcgactcgg gtcacggaga acaagaccgg cgtcccatcc ggccagctcc gccggagggg    2700
caatgatggc gctccacaag ctctatgacg acggcggccc ccagctctct tacgaaagca    2760
ggacgacgtc agcagggact cgaccgctcc aacagctgtc cctccgccag gctccgccgc    2820
acctccgaca gccacgacat cacgccagca gggtgcccag atctctccgg ctgccacatt    2880
ggcatgtacc tagggcgcta gctctcccctc cgctagacac gtagcactct gctacaccc    2940 ccattgtaca cctggatcct ctccttacga ctataaaagg gaggaccagg gccttcttag    3000
agaaggttgg ccgcgcggga ccgaggacgg gacaggcgct ctcttggggc cgctcgcttc    3060
cctcacccgc gtggacgctt gtaaccccccc tactgcaagc gcacctgacc tgggcgcggg    3120
acgaacacga aggccgcggg acttccaccct ctctcacgct cgactccggc cacctcgcct    3180
ctcccccctt cgcgctcgcc cacgcgctcg acccatctgg gctggggcac gcagcacact    3240
cactcgtcgg cttagggacc ccctgtctc gaaacgccga cagttggcgc gccaggtagg    3300
ggcctgctgc gtgctgacga acagctcccc gtcaagctcc agatgggcag tctccagcaa    3360
cctctccggc ccgggacggt gcttcgtttc gggactcttg agttcatgtc cttcgacggc    3420
agctacgaca tgatacttct tccaccgccg cgcgactacg acaatggcga ccgacaaccc    3480
gcccgccggc ggcggaatcg acgacgtctt ccccgcgtgg tggaagggca acattcgggc    3540
tcgctccgtt ctctccccccg ccaacggagg aggaggcggg gccgtcaagg ccaggtggga    3600
ggccgcgctt cgtcggccgt cgagcgaatc gacgcccccg acgcccgac ggaaggcacg    3660 ccggacgtcg acctcgcgtt caagacggag gcaagcgccg tcccccgcg gcacgctgac    3720 cccgagcaag aagacgacgc cggcgcgctc gcggaaagcc tgcaggacgt cgccctcgaa    3780
```

```
ccagagttga cggtgcaacc agtccccgat gtgactacgt cgctcctcgt cgacaaaaag   3840
gtaccaacta actcccatct tgcgtcattt cgactcggcc tcaacccgcc aaacgacctc   3900
gttttggcgg gcgctctcat tgaggcgagt gcaaccccac tgaggttccg tatgcggtcg   3960
ccttgggacc gactgacgga cgtctcgacc tacgggccct ctgggtccga ggaagatgac   4020
gatcccagca tcgcttggga tttctccgga ctcggcaacc ccagtgccgt gcgggacttc   4080
atgaccgcat gtgactactg cctatccgac tgttccgatg aagccgcag ccttggcgac    4140
gagagctgcg gcccaagccg cgaatgtttc cacatcgagc taggggatcc ctccgaaggc   4200
aaccatcttg gcatgccgga ggacagtgat ctccctaggc cggtgcctcg cgccgacatc   4260
ccacgggagc tagctgtagt ccccgctccg gcgggggtt acgacccaca actcgagcaa    4320
gtccgcgagg cgcaggccag gctcaacgag ggaacaggag cgcttgagcc gatccgtcgg   4380
gacgtcggac aagcatgggt gggccaaccc ctgcccggag aaatacgtca cttgccccaa   4440
ggtctccagc accgcgtcgc caacgatgtc aggatcaggc cgccgcccgc atccagcggg   4500
gttggtcaga acctggcaac cgcagcaatg ctcatccgcg cgatgccgga gccgtcaacc   4560
accgagggtc ggcgaatcca gggagaactc aagaatctcc tggaaggcgc tgcggcccgg   4620
cgggccgaga gcactgcctc ccgaaggcaa ggttatccct cggaacctca tgccgcgact   4680
tcccgattca tgcgggaagc ctcggtctac accgggcgca cgcgcaacac cgcgcctgcg   4740
gccccgggcc acctcggcaa cgagcaccat cgacgcgacc gtcgggctca cctcgacgaa   4800
agggtgcgcc gaggctacca ccccaggcgt gggggcgct acgacagcgg ggaggatcgg    4860
agtccctcgc ccgaaccacc cggtccgcag gccttcagtc gggccatccg acgggcgcca   4920
ttcccgaccc ggttccgacc cccgactact atcacgaagt acttcggggg aaacgagacc   4980
ggaactgtgg ctcgggga                                                 4998

<210> SEQ ID NO 50
<211> LENGTH: 8151
<212> TYPE: DNA
<213> ORGANISM: Zea mays

<400> SEQUENCE: 50
tgagctgtcg agaataagct tgattcgttg tgaaactcac attcaattca aacttgattc     60
aaaataatta tataagataa cagaaaataa aaaaggaaaa gcttaaccgg gcctcagatt    120
cacacttggc ccaccatgaa aaccccctccg cgcggcccaa cttgaatccc ccccgcgca    180
tgactcattg tcaggtgggg ccgtgttgtt ggtcgccgag gcgcgcgcgc tcacgaccgc    240
gtttcgccgc ctggtgggac cccatgttg gctgttcctt cgaccttcag ctcggtgtgt    300
cggttgcaac cactcgccga agattccgcg aatagctcgg gattgacctg accgattccg    360
cgataacttt tgaatgcacc ccgaaatccg ttttcggaat gggtgacgtg cggcaacgaa    420
attgcgcgaa acaaccccaa acatgagttt tggacctaaa gtaatggatt gggcatgttc    480
gttgcgctaa atgaagaaat ggttccggtg gcaaaaactc gtgcttatat gcaccccgac    540
acccgttttc ggaatgggtg atgtgcggca acgaaattgc gcgaaccac cccaaacatg     600
ggttttggac ctaaagtagt ggattgggca tgttcgttgc gaaaaacgaa gaaatgattc    660
cagtggcaaa aactcgtgct tttatgcaac ccgacacccg ttttcggaat gggtgacgtg    720
cggcaacgaa attgcgcgaa accaccccaa acatgagttt tggacctaaa gtagtttagt    780
gggcatattt tttgcgaaaa acgaagaaat ggttccggtg gccaaaactt gtgctttgaa    840
tgcaccccga aatccgtttt cggaatgggt gacgtgcggc aacgaaattg cgcgaaacaa    900
```

```
ccccaaacat gagttttgga cctaaagtaa tggattgggc atgttcgttg cgctaaatga      960
agaaatggtt ccggtggcaa aaactcgtgc ttatatgcac cccgacaccc gttttcggaa     1020
tgggtgatgt gcggcaacaa aattgcgcga aaccacccca aacatgggtt ttggacctaa     1080
agtagtggat tgggcatgtt cgttgcgaaa acgaagaaa tgattccagt ggcaaaaact     1140
cgtgctttta tgcaacccga cacccgtttt cgaaatgggt gacgtgcggc aacgaaattg     1200
cgtgaaacca ccccaaacat tagttttgga cctaaagtag tgtattgggc atgttcgttg     1260
tgaaaaacga agaaatggtt tcggtggcaa aaacacgtcc ttttatgcac cccgacaccc     1320
gttttcggaa tgggtgacgt gctgcaacaa aattgcgtga aaccacccca aacatgagtt     1380
ttggaccttta agtagtggat tgggcatgtt cgttgcgaaa aagaagaaa tggttctggt     1440
ggcaaaaact cgtgctttta tgcactcccg acacccgttt tcggaatggt tgacgtgcgg     1500
caacgaaatt gcgcgaaacc acccaaaaca tgagttttgg acctaaagta gtttagtggg     1560
catatttttt gcgaaaaacg aagaaatggt tccggtggcc aaaacttgtg ctttgaatgc     1620
accccgaaat ccgttttcgg aatgggtgac gtgcggcaac gaaattgcgc gaaacaaccc     1680
caaacatgag ttttggacct aaagtaatgg attgggcatg ttcgttgcgc taaatgaaga     1740
aatggttccg gtggcaaaaa cttgtgctta tatgcacccc gacacccgtt ttcggattgg     1800
gtgatgtgcg gcaacgaaat tgcgggaaac caccccaaac atgggttttg gacctaaagt     1860
agtggattgg gcatgttcgt tgcgaaaaac gaagaaatga ttccagtggc aaaaactcgt     1920
gcttttatgc accccgacac ccgttttcga atgggtgac gtgcggcaac gaaattgcgc     1980
gaaaccaccc caaacatgag ttttggacct aaagtagtgt attgggcatg ttcgttgcga     2040
aaaacgaaga aatggttccg gtggcaaaaa ctcgtgcttt tatgcacccc gacacccgtt     2100
ttcggaatgg gtgacgcgcg gcaacgaaat tgcgcgaaac caccccaaat atgggttttg     2160
gacctaaagt agtggattgg acatgttcgt tgcgaaaaac gaagaaatga ttctggtggc     2220
aaaaactcat gcttttatgc accccgacac ccttttttcgg aatgggtgac gtgcggcaac     2280
gaaattgcgc gaaaccaccc caaacatgag ttttggacct aaagtactgg attgggcatg     2340
ttcgttgcga aaaatgaaga aatggttccg gtggcaaaaa ctcgtgctta tatgcacccc     2400
gacacccgtt ttcggaatgg gtgacgtgcg gcaacgaaat tgcgcgaaac caccccaaac     2460
atgggttttg gacctaaagt agtggattgg catttttcgt tgcgaaaaaa gaagaaatgg     2520
ttctggtggc aaaaactcgt gcttttatgc accccgaca cccgttttta gaatgggtga     2580
cgtgcggcaa cgaaattgcg cgaaaccacc caaacatgg ttttggacc taaagtagtg     2640
gattgtgcat gttcgttgcg aaaaacgaag aaatggttct ggtggcaaaa actcgtgctt     2700
ttatgcaacc cgacacccgt tttcggaatg ggtgacgtgc ggcaacgaaa ttgcgcgaaa     2760
ccaccacaaa catgagtttt ggacctaaag tagtggattg gcatgttcg ttgcgaaaaa     2820
tgaagaaatg gttccggtgg caaaaactcg tgcttttatg caccccgaca cccgttttcg     2880
gaatgggtga cgtgcggcaa cgaaattaag cgaaaccacc caaacatgg ttttggacc     2940
taaagtagtg gattgggcat gttcgttgcg aaaaacaaag aaatgattcc agtggcaaaa     3000
actcgtgctt ttatgcaccc cgacacccgt tttcgaaatg ggtgacgtgc ggcaacgaaa     3060
ttgcgcgaaa ccaccccaaa catgcgtttt ggacctaaag tagtgtattg gcatgttcg     3120
ttgcgaaaaa cgaagaaatg gttccggtgg caaaaactcg tgcattgtat gcaccccgac     3180
acccgttttc ggaatgggtg acgtgcggca acgaaattgc gcgaaaccac ccaaacatg     3240
ggttttggac ctaaagtagt ggattgggca tgttcgttgc gaaaaacgaa gaaatggttc     3300
```

```
cggtggcaaa actcgtgcat tgtatgcacc ccgacacccg ttttcggaat gggtgacgtg    3360
cggcaaccga aattgcgcga aaccacccca aacatgagtt tttggaccta aagtagtgga    3420
ttgggcatgt tcgttgcgaa aaacaaagaa atgattccag tggcaaaaac tcgtgctttt    3480
atgcaccccg acaccgtttt cgaaatgggt gacgtgcgg caacgaaatt gcgcgaaacc    3540
accccaaaca tgcgttttgg acctaaagta gtgtattggg catgttcgtt gcgaaaaacg    3600
aagaaatggt tccggtggca aaaactcgtg cattgtatgc accccgacac ccgttttcgg    3660
aatgggtgac gtgcggcaac gaaattgcgc gaaaccaccc caaacatggg ttttggacct    3720
aaagtagtgg attgggcatg ttcgttgcga aaaacgaaga aatgattctg tggcaaaaa    3780 cacatgcttt tatgcacccc gacacccttt ttcggaatgg gtgacgtgcg gcaacgaaat    3840
tgcgcgaaac caccccaaac atgagttttg acctaaagt agtggattgg gcatgttcgt    3900
tgcgaaaaat gaagaaatgg ttccggtggc aaaaactcgt gcttatatgc accccgacac    3960
ccgttttcgg aatgggtgac gtgcggcaac gaaattgcgc gaaaccaccc caaacatggg    4020
ttttggacct aaagtagtgg attgggcatg ttcgttgcga aaaacgaaga aatggttccg    4080
gtggcaaaac tcgtgcattg tatgcaccca caccccgttt tcggaatggg tgacgtgcgg    4140
caacgaaatt gcgcgaaacc accccaaaca tgagttttgg acctaaagta ggggattggg    4200
catgttcgtt gcgaaaaatg aagaaatggt tccggtggca aaaactcgtg gttttatgca    4260
ccccgacacc cgttttcgga atgggtgacg cgcggcaacg aaattgcgcg aaaccaccca    4320
aaacatgagt tttgggccta aagtagtgga ttgggcatgt tcgttgcgaa aaacaaagaa    4380
atggtttcgg tggcaaaaac tcgtgcattg tatgcacccc gacacccgtt tcggaatgg    4440 gtgacgtgcg gcaacgaaat tgcgcgaaac caccccaaac atgggttttg gacctaaagt    4500
agtggattgg gcatgttcgt tgcgaaaaac gaagaaatga ttctggtggc aaaaactcat    4560
gcttttatgc accccgacac ccttttttcg aatgggtgac gtgcggcaac gaaattgcgc    4620
gaaaccaccc caaacatgag ttttggacct aaagtagtgg attgggcatg ttcgttgcga    4680
aaaatgaaga atggttccg gtggcaaaaa ctcgtgctta tatgcaccccc gacacccgtt    4740 ttcggaatgg gtgacatgcg gcaacgaaat tgcgcgaaac caccccaaac atgggttttg    4800
gacctaaagt agtggattgg gcatgttcgt tgcgaaaaac gaagaaatgg ttccggtggc    4860
aaaaactcgt gcttttaagc accccgacac ccgttttcga atgggtgac gtgcggcaac    4920 gaaattgcgc gaaaccaccc caaacattag ttttggacct aaagtagtgt attgggcatg    4980
ttcgttgcga aaaacgaaga atggttccg gtggcaaaaa cacgtccttt tatgcaccccc    5040 gacacccgtt tcggaatgg gtgacgtgct gcaacaaaat tgcgtgaaac caccccaaac    5100
atgagttttg gacctaaagt agtggattgg gcatgttcgt tgcgaaaaaa gaagaaatgg    5160
ttctggtggc aaaaactcgt gcttttatgc actcccgaca cccgttttcg gaatggttga    5220
cgtgcggcaa cgaaattgcg cgaaacaacc ccaaacatga ttttggacc taaagtaata    5280 gattgggcat gttcgttgcg caaaatgaag aaatggttcc agtggaaaaa actcgtgctt    5340
atatgcaccc cgacacccgt ttcggaatg ggtgatgtgc ggcaacgaaa ttgcgcgaaa    5400
ccaccccaaa catgggtttt ggacctaaag tagtggattg gcatgttcg ttgcaaaaac    5460 gaagaaatgg tttcggtggc aaaaactcgt gaattgtatg caccccgaca cccgttttcg    5520
gaataggtga cgtgtggcaa cgaaattgcg cgaaaccacc ccaaacatga ttttttgacc    5580
taaagtagtg tattgggcat gttcgttgcg aaaaatgaag aaatggttcc ggtggcaaaa    5640
actcgtgctt ttatgcaccg cgataccgt ttcggaatg gatgacgtgc ggcaacgaaa    5700
```

-continued

```
ttgcgcgaaa ccaccccaaa catgggtttt ggacctaaag tagtggattg ggcatgttcg   5760
ttgcgaaaaa cgaagaaatg attccagtgg caaaaactcg tgcttttatg caacccgaca   5820
cccgttttcg gaatgggtga cgtgcggcaa cgaaattgcg cgaaaccacc ccaaacatga   5880
gttttggacc taaagtagtg gattgggcat gttcgttgcg aaaaatgaag aaatggttct   5940
ggtggcaaaa actcgtgctt ttatgcaccc cgacacccgt tttcggaatg ggtgacgtgc   6000
ggcaacgaaa ttaagcgaaa ccaccccaaa catgggtttt ggacctaaag tagtggattg   6060
ggcatgttcg ttgcgaaaaa caagaaatg attccagtgg caaaaactcg tgcttttatg   6120
caccccgaca cccgttttcg aaatgggtga cgtgcggcaa cgaaattgcg cgaaaccacc   6180
ccaaacatga ggtttggacc taaagtagtg tattgggcat gttcgttgcg aaaaacgaag   6240
aaatggttcc gatggcaaaa actcgtgctt ttatgcaccc caacacccgt tttcggaatg   6300
ggtgacgcgc ggcaacgaaa ttgcgcgaaa ccacccaaaa catgagtttt gggcctaaag   6360
tagtggattg ggcatgttcg ttgcgaaaaa caagaaatg gtttcggtgg caaaaactcg   6420
tgcattgtat gcaccccgac acccgttttc ggaatgggtg acgtgcagca acgaaattgc   6480
gcgaaaccac cccaaacatg gttttggac ctaaagtagt ggattgggca tgttcgttgc   6540
gaaaaacgaa gaaatgattc tggtggcaaa aactcatgct tttaagcacc ccgacaccct   6600
ttttcggaat gggtgacgtg cggcaacgaa attgcgcgaa accacccaa acatgagttt   6660 tggacctaaa gtagtggatt gggcatgttc gttgcgaaaa atgaagaaat ggttccggtg   6720
gcaaaaactc gtgcttatat gcaccccgac acccgttttc ggaatgggtg acgtgcggca   6780
acgaaattgc gcgaaaccac cccaaacatg gttttggac ctaaagtagt ggattgggca   6840
tgttcgttgc gaaaaacgaa gaaatggttc cggtggcaaa aactcgtgct tttaagcacc   6900
ccgacacccg ttttcgaaat gggtgacgtg cggcaacgaa attgcgcgaa accacccca   6960 acattagttt tggacctaaa gtagtgtatt gggcatgttc gttgcgaaaa acgaagaaat   7020
ggtttcggtg gcaaaaactc gtgaattgta tgcaccccga cacccgtttt cggaataggt   7080
gacgtgtggc aacgaaattg cgcgaaacca cccccaaacat gagttttgac ctaaagtagt   7140
gtattgggca tgttcgttgc gaaaaatgaa gaaatggttc cggtggcaaa aactcgtgct   7200
tttatgcacc ccgataccccg ttttcggaat ggatgacgtg cggcaacgaa attgcgcgaa   7260 accacccca acatgggttt tggacctaaa gtagtggatt gggcatgttc gttgcgaaaa   7320
acgaagaaat gattccagtg gcaaaaactc gtgcttttat gcaacccgac acccgttttc   7380
ggaatgggtg acgtgcggca acgaaattgc gcgaaaccac cacaaacatg agttttggac   7440
caaaagtagt ggattgggca tgttcgttgc gaaaaacaaa taaatggttc cggtggcaaa   7500
aactcgtgct tttatgcacc cccgacaccc gttttggaa tgggtgacgt gcggcgacga   7560
aattgcacga accaccccca aacatgagtt ttggacctaa agtagtgtat tgggactgtt   7620
cgttgcgaaa acgaagaaa gggttccggt ggcaaaaact cgtgctttta tgcaccccga   7680
caccccgatt cggaatgggt gacgtgcgac aacgaaattg cgcgaaacca cccaaaacat   7740
gagttttgga cctaaagtag tggattgggc atgttcgttg cgaaaaacaa agaaatggtt   7800
tcggtggcaa aaactcgtgc attgtatgca ccccgacacc cgttttcgga tgggtgacg   7860 tgcggcaacg aaattgcgtg aaaccaccccc aacatgagt tttggaccta agcagtgga   7920 ttgggcatgt tcgttgtgaa aaatgaagaa atggttccgg tggcaaaact cgtgctttta   7980
tgcacctcga cacccgtttt cggaatgggt gatgtgcggc aacgaaattg tgcgaaacca   8040
cccccgaaca tgggttttgg acttaaagta gtgcattggg catgttcgtt gtgaaaaacg   8100
```

-continued

| | |
|---|---|
| aagaaatgat tccagggcaa aaactaagaa ttcaagctta ttctcagaca c | 8151 |

<210> SEQ ID NO 51
<211> LENGTH: 10813
<212> TYPE: DNA
<213> ORGANISM: Zea mays

<400> SEQUENCE: 51

| | |
|---|---|
| gactctccga gaataagctt gattcgttaa cgaacatgcc caatacacta ctttaggtca | 60 |
| aaaactcatg tttggggtgg tttcgcgcaa tttcgttgcc acacgtcacc tattccgaaa | 120 |
| acgggtgtcg gggtgcatac aattcacgag ttttgccac cgaaaccatt tcttcgtttt | 180 |
| tcgcaacgaa catgcccaat acactacttt aggtccaaaa ctaatgtttg ggtggtttc | 240 |
| gcgcaatttc gttgccgcac gtcacccatt tcgaaaacgg gtgtcggggt gcttaaaagc | 300 |
| acgagttttt gccaccggaa ccacttcttc gttttttcgca acgaacatgc ccaatccact | 360 |
| actttaggtc caaaacccat gtttggggtg gtttcgcgca atttcgttgc cgcacgtcac | 420 |
| ccattccgaa aacgggtgtc ggggtgcata taagcacgag ttttgccac cggaaccatt | 480 |
| tcttcatttt tcgcaacgaa catgcccaat ccactacttt aggtccaaaa ctcatgtttg | 540 |
| ggtggtttc gcgcaatttc gttgccgcac gtcacccatt ccgaaaaagg gtgtcggggt | 600 |
| gcataaaagc atgagttttt gccaccagaa tcatttcttc gttttttcgca acgaacatgc | 660 |
| ccaatccact actttaggtc caaaacccat atttggggtg gtttcgcgca atttcgttgc | 720 |
| cgcacgtcac ccattccgaa aacgggtgtc ggggtgcata caatgcacga gttttttgcca | 780 |
| ccggaaccat ttcttcgttt ttcgcaacga acatgcccaa tacactactt taggtccaaa | 840 |
| actcatgttt ggggtggttt cgcgcaattt cgttgccgca cgtcacccat ttcgaaaacg | 900 |
| ggtgtcgggg tgcataaaag cacgagtttt tgccactgga atcatttctt tgtttttcgc | 960 |
| aacgaacatg cccaatccac tactttaggt ccaaaaccca tgtttggggt ggtttcgctt | 1020 |
| aatttcgttg ccgcacgtca cccattccga aaacgggtgt cggggtgcat aaaagcacga | 1080 |
| gttttttgcca ccgggaccca tttcttcatt tttcgcaacg aacatgccca atccactact | 1140 |
| ttaggtccaa aactcatgtt tgtggtggtt tcgcgcaatt tcgttgccgc acgtcaccca | 1200 |
| ttccgaaaac gggtgtcggg ttgcataaaa gcacgagttt tgccactgg aatcatttct | 1260 |
| tcgtttttcg caacgaacat gcccaatcca ctactttagg tccaaaaccc atgtttgggg | 1320 |
| tggtttcgcg caatttcgtt gccgcacgtc atccattccg aaaacgggta cggggtgca | 1380 |
| taaaagcacg agttttttgcc accggaacca tttcttcatt tttcgcaacg aacatgccca | 1440 |
| atacactact ttaggtcaaa aactcatgtt tggggtggtt tcgcgcaatt tcgttgccac | 1500 |
| acgtcaccta ttccgaaaac gggtgtcggg gtgcatacaa ttcacgagtt tttgccaccg | 1560 |
| aaaccatttc ttcgtttttc gcaacgaaca tgcccaatac actactttag gtccaaaact | 1620 |
| aatgtttggg gtggtttcgc gcaatttcgt tgccgcacgt cacccatttc gaaaacgggt | 1680 |
| gtcggggtgc ttaaaagcac gagttttttgc caccggaacc acttcttcgt ttttcgcaac | 1740 |
| gaacatgccc aatccactac tttaggtcca aaacccatgt tggggtggt ttcgcgcaat | 1800 |
| ttcgttgccg cacgtcaccc attccgaaaa cgggtgtcgg ggtgcatata agcacgagtt | 1860 |
| tttgccaccg gaaccatttc ttcatttttc acaacgaaca tgcccaatcc actgctttag | 1920 |
| gtccaaaact catgtttggg gtggtttcac gcaatttcgt tgccgcacgt cacccattcc | 1980 |
| gaaaacgggt gtcggggtgc atacaatgca cgagttttttg ccaccgaaac catttctttg | 2040 |
| ttttttcgcaa cgaacatgcc caatccacta ctttaggtcc aaaactcatg ttttgggtgg | 2100 |

```
tttcgcgcaa tttcgttgcc gcacgtcacc cattccgaaa acgggtgtcg gggtgcataa    2160
aagcacgagt ttttgccacc agaaccattt cttcgttttt cgcaacgaac atgcccaata    2220
cactacttaa ggtccaaaac tcatgttttg ggtggtttcg cgcaatttcg ttgccgcacg    2280
tcatccattc cgaaaacgga tgccggggtg catacaatgc acgagttttt gccactggaa    2340
ccatttcttt cttttttcgca acgaacatgc ccaatccact actttaggtc caaaacccat    2400
gtttggggtg gtttcgcgca atttcgttgc cgcacgtcac ccattccaaa acgggtgtc    2460
ggggtgcaga aaagcacggg ttttttgccac cggaaccatt tcttcgtttt tcgcaacgaa    2520
catgccaaat acactacttt aggtccaaaa ctcatgtttg ggtggtttc gcgcaatttc    2580
gttgcagcac gtcacccatt tcaaaaacgg gtgtggtgca taaaagcacg agttttttgcc    2640
accggaacca tttcttcgtt tttgcaacg aacatgccca atccactagt ttaggtccaa    2700
aaccaatgtt tggggtggtt tcgcgcaatt tcgttgccgc acgtcaccca ttccgaaaac    2760
gggtgtcggg gtgcataaaa gcacgagttt ttgccaccgg aaccatttct tcattttcg    2820
caacgaacat gcacaatcca ctactttagg tccaaaactc atgtttgggg tggtttcgcg    2880
caatttcgtt gccgcacgtc acccattccg aaaacgggtg tcggggtgca taaaagcacg    2940
agttttttgcc accggaacca tttcatcatt ttcgcaacg aacatgccca atacactact    3000
ttaggtctaa aactcatgtt tggggtggtt tcgcacaatt tcgttgtcgc acgtcaccca    3060
tttcgaaaac gggtgtcggg gtgcataaaa gcacgagttt ttgccaccag aaccatttct    3120
tcgtttttcg caacgaacat gcccaataca ctactttagg tccaaaactc atgtgttggg    3180
gtggtttcgc gcaatttcgt tgccgcacgt caccccattcc gaaaacgggt gtcgggtgca    3240
tacaatgcac gagttttttgc caccgatacc atttctttgt ttttcgcaac gaacatgccc    3300
aatccactac tttaggtcca aaactcatgt tttgggtggt tcgcgcaat tcgttaccg    3360
cacgtcaccc attccgaaaa cgggtgtcgg ggtgcataaa agcacgagtt tttgccacgg    3420
gaaccatttc ttcatttttc gcaacgaaca tgcccaatcc actactttag gtccaaaact    3480
catgtttggg gttgtttcgc gcaatttcgt tgccgcacgt cacacattcc gaaaacgggt    3540
gtcggggtgc ataaaagcac gagttttttgc caccggaacc atttcttcat tttttcacaac    3600
gaacatgccc aatccactgc tttaggtcca aaactcatgt ttggggtggt tcacgcaat    3660
ttcgttgccg cacatcaccc attccgaaaa cgggtgtcga ggtgcataaa agcacgagtt    3720
ttgccaccgg aaccatttct tcattttttca acgaacat gcccaatcca ctgctttagg    3780
tccaaaactc atgtttgggg tggtttcacg caatttcgtt gccgcacgtc acccattccg    3840
aaaacgggtg tcggggtgca tacaatgcac gagttttttgc caccgaaacc atttctttgt    3900
ttttcgcaac gaacatgccc aatccactac tttaggtcca aaactcatgt ttgggtggt    3960
ttcgcgcaat tcgttgtcg cacgtcaccc attccgaaat cgggtgtcgg ggtgcataaa    4020
agcacgagtt tttgccaccg gaaccctttc ttcgttttc gcaacgaaca gtcccaatac    4080
actactttag gtccaaaact catgtttggg gtggtttcgt gcaatttcgt cgccgcacgt    4140
cacccattcc aaaacgggt gtcggggtg cataaaagca cgagtttttg ccaccggaac    4200
catttatttg ttttttcgcaa cgaacatgcc caatccacta cttttggtcc aaaacccatg    4260
tttggggtgg tttcgcgcaa tttcgttgcc gcacgtcacc cattccgaaa acgggtgtcg    4320
gggtgcataa aagcacgagt ttttgccacc agaaccattt cttcgttttt cgcaacgaac    4380
atgcccaata cactactttta ggtccaaaac tcatgtgttg ggtggtttc gcgcaatttc    4440
gttgccgcac gtcacccatt ccgaaaacgg gtgtcgggt gcattcaaag cacaagtttt    4500
```

-continued

```
tgccaccgga accatttctt cgttttcgc aacaaacatg ccgactaaac tactttaggt    4560
ccaaaactca agttttgggt ggtttcgcgc aatttcgttg ccgcacgtca cccattccga    4620
aaacgggtgt cggggtgcat aacaacacga gttttgcca ccggaaccat ttcttcattt    4680
ttcgcaacga acatgcccaa tccactactt taggtccaaa actcatgttt ggggtggttt    4740
cgcgcaattt cgttgctgca cgtcacccat tccgaaaacg ggtgtcgggt gcatacaatg    4800
cacgagtttt tgccaccgaa accatttctt tgttttcgc aacgaacatg accaatccac    4860
tactttaggt ccaaaactca tgttttgtat ggtttcgcgc aatttcgttg ccgcacgtca    4920
cccataccga aaacgggtgt cggggtgcat aaaagcaaga gttttgcca ccggaaccat    4980
ttttcatttt ttcgcaacga acatgcccac taaactactt taggtccaaa actcatgttt    5040
ggggtggttt cgcgcaattt cgttgtcgca cgtcacccat tccgaaatcg ggtgtcgggg    5100
tgcataaaag cacgagtttt tgccaccgga accctttctt cgttttcgc aacgaacagt    5160
cccaatacac tactttaggt ccaaaactca tgtttgggt ggtttcgtgc aatttcgtcg    5220
ccgcacgtca cccattccaa aaacgggtgt cggggggtgca taaaagcacg agttttgcc    5280
accggaacca tttattgtt tttcgcaacg aacatgccca atccactact tttggtccaa    5340
aacccatgtt tggggtggtt tcgcgcaatt tcgttgccgc acgtcaccca ttccgaaaac    5400
gggtgtcggg gtgcataaaa gcacgagttt ttgccaccag aaccatttct tcgttttcg    5460
caacgaacat gcccaataca ctactttagg tccaaaactc atgtgttggg gtggtttcgc    5520
gcaaatttcgt tgccgcacgt cacccattcc gaaaacgggt gtcggggtgc attcaaagca    5580
caagtttttg ccaccggaac catttcttcg ttttcgcaa caaacatgcc gactaaacta    5640
ctttaggtcc aaaactcaag ttttgggtgg tttcgcgcaa tttcgttgcc gcacgtcacc    5700
cattccgaaa acgggtgtcg gggtgcataa caacacgagt ttttgccacc ggaaccattt    5760
cttcattttt cgcaacgaac atgcccaatc cactacttta ggtccaaaac tcatgtttgg    5820
ggtggtttcg cgcaatttcg ttgctgcacg tcacccattc cgaaaacggg tgtcgggtgc    5880
atacaatgca cgagttttg ccaccgaaac catttctttg ttttcgcaa cgaacatgac    5940
caatccacta ctttaggtcc aaaactcatg ttttgtatgg tttcgcgcaa tttcgttgcc    6000
gcacgtcacc cataccgaaa acgggtgtcg gggtgcataa aagcaagagt ttttgccacc    6060
ggaaccattt ttcattttt gcaacgaaca tgcccaatct actctttag gtccaaaact    6120
catgtttggg gtggtttcgc gcaatttcgt tgccgcacgt cacccattcc gaaaacgggt    6180
gtcgggtgc atacaatgca cgagttttg ccaccgaaac catttctttg ttttcgcaa    6240
cgaacatgcc caatccacta ctttaggtcc aaaactcatg ttttagtgg tttcgcgcaa    6300
tttcgttgcc gcatgtcacc cattccgaaa acgggtgtcg gggtgcataa aagcacgagt    6360
ttttgccacc ggaaccattt cttcgttttt cgcaacgaac acgcccaata cactactata    6420
ggtccaaaac tcattttttt gggtggtttc gcgcaatttc gttgccgcac gtcaccatt    6480
ccgaaaacgg gtgtcaaggg tgcataaaag cacgagtttt tgccaccaga accatttctt    6540
ttttcgcaa cgaacatgct caatccacta cttaaggtcc aactcatgtt tggggtggtt    6600
tcgcgcaatt tcgttgcagc acgtcaccca ttccgacaac aggtgtcggg ggtgcataca    6660
atgcacgagt ttttgccatc ggaaccattt cttcgttttt cgcaatgaac atgcccaatc    6720
cactacttta ggtccaaaac acatgttttg ggtggtttcg cgcaatttcg ttgccacatg    6780
tcacccattc cgaaatgggt gtcggggtgc ataaaagcac gagttttgc caccggaacc    6840
atttcatcat ttttcgcaac gaacatgccc aatacactac tttaggtcta aaactcatgt    6900
```

```
ttggggtggt tcgcacaat ttcgttgtcg cacgtcaccc atttcgaaaa cgggtgtcgg    6960
ggtgcataaa agcacgagtt tttgccaccg gaaccatttc ttcgttttc gcaacgaaca    7020 tgcccaatcc actactttag gtccaaaacc catgtttggg gtggtttcgc gcaatttcgt   7080
tgccgcacgt cacccattct aaaaacggtt gtcggggtgc ataaaagcac gagtttctgc   7140
caccggaacc atttcttcat ttttcgcaac gaacatgccc aatccactac tttaggtcca   7200
aaactcatgt tttgggtggt ttcacgcaat tcgttgccg cacgtcaccc attccgaaaa    7260
cgggtgtcgg ggtgcataaa agcacgagtt tttgccaccg gaatcatttc ttcgttttc    7320 acaacgaaca tgcccaatcc actactttag gtccaaaacc catgtttggg gtggtttcgc   7380
acaatttcgt tgccgcacgt cacccattcc gaaaacgggt gtcggggtgc ataaaagcac   7440 gagttttgc caccggaacc atctcttcat ttttcgcaac gaacatgccc aatccactac    7500
tttaggtcca aaactcatgt ttgggttggt ttcgcgcaat tcgtcgccg cacgtcaccc    7560 attccgaaaa cgggtgtcgg ggtgcataca atgcacgagt ttttgccacc gaaaccattt   7620
ctttgttttt cgcaacgaac atgcccaatc cactacttta ggtccaaaac tcatgttttg   7680
ggtggtttcg cgcaatttcg ttgccgcacg tcacccattc caaaaacggg tgttggggtg   7740
cataaatgca cgagttttg ccaccggaac catttcttcg ttttcgcaa cgaacatgcc     7800 caatacacta ctttaggtcc aaaactcatg tttggggtgg ttatcgcaat tcgtcgccg    7860 cacgtcaccc attccgaaaa cgggtgtcgg ggtgcataaa agcacgagtt tttgccaccg   7920
gaaccatttc ttcgttttc gcaacgaaca tgcccaatcc actactttag gtccaaaact    7980
catgtttggg gtggtttcgc gcaatttcgt tgcagcacgt cacccattcc gaaaacgggt   8040
gtcggggtac atacaatgca cgagttttg ccaccggaac cgtttcttcg ttttcgcaa     8100 tgaacatgcg caatccacta ctttaggtcc aaaacacatg ttttgagtgg tttcgcgcaa   8160
tttcgttgcc gcacgtcacc cattccgaaa acgggtgtcg gggtgcataa agcacaagt    8220 ttttgccacc ggaaccattt cttcgttttt tgcaacgaac atgcccaata cactactta    8280 tgtccaaaac tcatgtttgg agtggttct cgcaatttcg ttgccgcacg tcaaccattc    8340
cgaaaacggg tgtcggggt gcataaaagc acgagttttt gccaccagaa ccatttcttc    8400 ttttcgcaa cgaacatgcc caatccacta cttaaggtcc aaaactcatg tttggggtgg    8460
tttcgcgcaa tttcgttgcc ccacgtcacc cattccgaaa acgggtgtcg gggtgcatac   8520
aatgcacgag ttttgccac gggaaccatt tcttcgtttt tcgcaacgaa catgcccaat    8580
ccactacttt aggtccaaaa catatgtttt gggtggtttc gcgcaatttc gttgccgcac   8640
gtcacccatt ccgaaaatgg gtgtcggggt gcattcaaag cacaagtttt tgccaccgga   8700
accatttctt cgttttcgc aacgaacatg cccaatccac tacttaaagt ccaaaactca    8760
tgttttgggt ggttttgcgc aatttcgttg tcgcacgtca accattccga aacgggtgt    8820 cggggggtgca taaaagcacg agttttgcc accagaacca tttcttcttt tttcgcaacg   8880
aaaatgccca atccactact taaagtccaa aactcatgtt tggggtggtt tcgcgcaatt   8940
tcgttgcagc acgtcaccca ttccgaaaac gggtgtcggg gtgcatacaa tgcacgagtt   9000
tttgccaccg gaaccatttc ttcgttttc gcaacgaaca tgcccaatcc actactttag    9060
gtccaaaaca catgttttgg gtggtttcgc gcaatttctt tgccgcacgt cacccattcc   9120
gaaaacgggt gtcagggtgc gtaaaagcac gagttttgc caccggaacc atttcttcgt    9180
ttttcgcaac gaacatgccc aatacactac tttaggtcta aaactcatgt ttgggtggtt   9240
tcgcgcaatt tcgttgccgc acgtcaccca tttcgaaaac aggtgtcggg gtgcataaaa   9300
```

-continued

```
gcacgagttt ttgccaccag aaccattcct tcgttttttcg caacgaacat gcccaatcca      9360
ctactttagg tccaaaaccc atgtttgggg tggtttcgtg taatttcgtt gccgcacgtc      9420
acccattcta aaacggggtg tcggggtgca taaaagcacg agttttttgcc accggaatca    9480
tttcttcgtt tttcgcaacg aacatgccca atccactact ttaggtccaa aacccatgtt      9540
tggggtggtt tcgcgcaatt tcgttgccgc atgtcaccca ttccaaaaac gggtgtcggg      9600
gtgcatataa gcacgagttt ttgccaccgg aaccatttct tcattttttcg caacgaacat    9660
gcccaatcca ctactttagg tccaaaactc atgtttgggg tggtttcgcg caatttcgtt      9720
gccgcacgtc acccattccg aaacggggtg tggggtgcat acaatgcacg agttttttgcc    9780
accggaacca tttcttcgtt tttcgcaacg aacatgccca atccactact ttaggtccaa      9840
aacacatgtt tggggtggtt tcgcgcaatt tcgttgccgc acgtcaccca ttccaaaaac      9900
gggtgtccgg gtgcatattg ggtggtttcg cgcaatttcg ttgccgcacg tcacccattc      9960
caaaaacggg tgtccgggtg cataaaagca cgagttttttg ccaccggaac catttcttcg    10020
ttttttcgcaa cgaacatgcc caatacacta ctttaggtcc aaaactcatg tttggggtgg    10080
tttcgcgcaa tttcgtcgcc gcacgtcacc cattccgaaa acgggtgttg gggtgcataa    10140
aagcacgagt ttttgccacc ggaacgattt cttcgttttt cgcaacgaac atgcccaatc    10200
cactacttta ggtccaaaac ccatgtttgg ggtggtttcg cgcaatttcg ttccgcacg    10260
tcacccattc cgaaaacggg tgtcgggtgc ataaaaggac gagttttttgc caccagaacc    10320
attacttctt ttttcgcaac gaacatgccc gatccactac tttaggtcca aaactcatgt    10380
ttggggtggt ttcgcgcaat ttcgttgccg cacgtcaccc attccgaaaa acgggtgtcg    10440
gggtgcataa aagcatgagt ttttgccacc agaaccattt cttcgttttt cgcaacgaac    10500
atgcccaata cactacttta ggtccaaaac tcatgtttgg ggtgggttcg cgcaatttcg    10560
ttgccgcacg tcacccattt cgaaaacggg tgtcggggtg cataaaagca cgagttttttg    10620
ccaccggaac catttcttca ttttttcgcaa cgaacatgcc caatccccta cttcaggtcc    10680
aaaactcatg tttggggtgg ttttgcgcaa tttcgttgcc gcacgtcacc catttcgaaa    10740
acgggtgttg ggtgcataca atgcacgagt ttttgccacc ggaacacgaa tcaagcttaa    10800
tctcggacac tca                                                        10813
```

<210> SEQ ID NO 52
<211> LENGTH: 864
<212> TYPE: DNA
<213> ORGANISM: Zea mays

<400> SEQUENCE: 52

```
acgaatcgaa gattcatcgc cactgtgctg gaagcatcag actccggcat cgcaaactgc        60
acccggtgcc gggcagccac atccagcgca aaaaccttcg tgtagacttc cgttgaactg      120
atggacttat gtcccatcag gctttgcaga actttcagcg gtataccggc atacagcatg      180
tgcatcgcat aggaatggcg gaacgtatgt ggtgtgaccg gaacagagaa cgtcacaccg      240
tcagcagcag cggcggcaac cgcctcccca atccaggtcc tgaccgttct gtccgtcact      300
tcccagatcc gcgctttctc tgtccttcct gtgcgacggt tacgccgctc catgagctta      360
tcgcgaataa atacctgtga cggaagatca cttcgcagaa taaataaatc ctggtgtccc      420
tgttgatacc gggaagccct gggccaactt ttggcgaaaa tgagacgttg atcggcactc      480
cgcttattat cacttattca ggcgtagcaa ccaagcgttt aagggcacca ataactgcct      540
taaaaaaatt acgcccgcc ctgccactca tcgcagtact gttgtaattc attaagcatt      600
```

```
ctgccgacat ggaagccatc acaaacggaa tgatgaacct gaatcgccag cggcatcagc    660
acccttgtcg ccttggcgta atatatttgc ccctggtgaa aaacgggggg gaacaagttg    720
gccattttgg gccacgtttt aatccaaacc tgggtgaaac tcccccccagg tattggctga    780 aaaacaaaaa acctaattct ccaataaacc ccttaaggga aaatagggcc cggttttttca   840 ccgtaacacc accccacctt ttgt                                            864
```

<210> SEQ ID NO 53
<211> LENGTH: 835
<212> TYPE: DNA
<213> ORGANISM: Zea mays

<400> SEQUENCE: 53

```
acttctgaag ataatcagct tgattcgctg aagctccaat gtgctggaaa ggttttgaaa     60
tccatgtttt gtagctgtat tgttccttaa ggcaataatt ctatcctcca cgtaatttgt    120
aacctgcaca cgaatttaat acccgacttt gggtttctga tttcaccaca aaccgagtca    180
acatcgtttc cttattttc tccttcggtt acgtcaaaaa aaacagaaa aaacaaaccg      240 agtcaacggc cgtttccttg attttctcct tcggttacga aaaaaaaaca gcaaaaaaaa    300
acaaaccgag tcaaccttcc ttgttttct ccttcggtta cgtcaaaaaa acagaaaaaa     360
aagataacga aggagaaagg atacggttgt ttcatcccgg tcgttttttag aacataactt   420 gaggtacctt ccgtaaaccg ggcataactt ttcgctcggg tgtccaaaaa atctgaaatt    480
tttataggag ctagttgaca ccattctgag gccggccaaa ctcacctacg gtctgtttgg    540
ggttcgacaa aattgtcaaa aaaattcagg aaaataaaga aaaaaatccg tcaaagttct    600
cgcacgcttt tcagagaact tcctgatttt ctgtagacca catctgatat ctgttttagg    660
tgaaacttcg tgtagctcct atcttgttgc ttcttgtgct gagaaaaata tcaaaagaat    720
catacaaaaa agcaaaacaa aatcaccctgt gatttctact agtggctttt ttgcatcact   780
agtacaatat ttacggtact ggccttcctg ctagtttcca tcctcccttt gcacc          835
```

<210> SEQ ID NO 54
<211> LENGTH: 903
<212> TYPE: DNA
<213> ORGANISM: Zea mays

<400> SEQUENCE: 54

```
cgattctaga tatcatcgcc actcgtgctg gaaaggacca gacaaacaca gaaaaattcc     60
agacatattc ctacttattc agtacagtcc ctgaactaaa cccccactat agctctatca    120
ctgttcagtc gccagaatgt cttcgtcaaa acagcctcac caggaggacc atcccgattc    180
ggagcctgaa atgctcgcgg aggatgatgc tcttgaggag attgacgctt ccgaggacgt    240
cgacgttccc atggacagcg acgatgaggg ggagcccgaa gagatcaacc tgcacaacga    300
cggcgtcgcc tactttgacc tacacaagga ctcggttttc gccattgccc aacatccaac    360
ccgcccgaca ctgatcgcaa cgggtggatc agaaggagac tcggacgacg cgccaggcaa    420
gggctacgtc tttgacaccg cacacgttcc ccagcgccct ctattaccac caaactttag    480
cggcgaacct ccgaaccccc cggtagcgct ggaccgtctg tttgagattg atgggcatac    540
cgacagcatc aatgctttga cgttcaccta ccccgaggga gagtatctct tgagcggagg    600
tatggacggc aagcttcgcg cgtacgccgg caaggcggca ccatttcaac cgggagccgc    660
ccatgtcacc agtcgcacaa atccccctcc cttgccgagt cccaggaagt cccccaaatc    720
aacttcctat cttcccttgc cccattgctc catcgtcctc ccttgtcctt agaccttggc    780
```

```
tggcatcctg accggctccg tctggtgtgt acccatggaa gaacgcaggc tccccaatcc    840
cggcgctggt ctaatcccga aagacatttt ccttcttccc taatatgggc cccggaccca    900
cta                                                                  903
```

<210> SEQ ID NO 55
<211> LENGTH: 1110
<212> TYPE: DNA
<213> ORGANISM: Zea mays

<400> SEQUENCE: 55

```
ctccggaatg attcaagctt ggattcgctg aagctccaat gtgctggaaa gatgttcgtt     60
gagaaaaacg aagaaatggt tcctgtggca aaaactcgtg ctttgtatgc accatgacac    120
ccgttttcag aatgggtgac gtgcgacaac gaaattgtgc gaaaccaccc caaacatgag    180
ttttggacct aaagtagtgg attgggcatg ttcgttgcga aaaacgaaga aatggttccg    240
gtggcaaaaa ttcgtgcttt gtatgcacca tgacacccgt tttcggaatg ggtgacgtgc    300
gacaacgaaa ttgtgcgaaa cgacctaaag tagtggattg ggcatgtttg ttacgaaaaa    360
cgaagaaatg gttccggtgg caaaaactcg tgcttttatg caccccgata ccgttttca    420 gaataggtga cgtgtgacaa cgaaattgcg cgaaaccacc tcaaacatga gttttggacc    480
taaagtagtg gattgggcat gttcgttgcg aaaaacgaag aaatggttcc ggtggcaaac    540
actcgtgctt ttatgcaccc gacactcgtt ttcagaatga gtgacgtgcg gcaacgaaat    600
tgcgtgaaac cacccaaaac atgagttttg tacctaaagt agtggattgg gcatgttcgt    660
tgagaaaaac gaagaaatgg ttccagtggc aaaaactcgt gctttgtatg cacccgacac    720
ccgttttcgg aatgggtgac gtgcgacaac gaaattgtgc gaaaccaccc caaacatgag    780
ttttggacct aaagtagtgg attgggcatg tttgttacga aaaacgaaga aatggttccg    840
gtggcaaaaa ctcgtgcttt tatgcacccc gatacccgtt ttcagaatgg gtgacgtgcg    900
acaacgaaat tgcgcgaaac cacctcaaat atgagttttg gacctaaagt agtggattgg    960
gcatgttcgt tgcgaaaaac gaagaaatgg ttccggtggc aaacactcgt gcttttatgc   1020
acccgacact cgttttcgga atgagtgacg tgcggcaacg cttccagca cattggagct   1080 tcagcgaatc aagcttgata ccattctgta                                    1110
```

<210> SEQ ID NO 56
<211> LENGTH: 586
<212> TYPE: DNA
<213> ORGANISM: Zea mays

<400> SEQUENCE: 56

```
ggcctttta cggttcctgg cctttttgctg gccttttgct cacatgttct ttcctgcgtt     60
atcccctgat tctgtggata accgtattac cgcctttgag tgagctgata ccgctcgccg    120
cagccgaacg accgagcgca gcgagtcagt gagcgaggaa gcggaagagc gcccaatacg    180
caaaccgcct ctccccgcgc gttggccgat tcattaatgc agctggcacg acaggtttcc    240
cgactggaaa gcgggcagtg agcgcaacgc aattaatgtg agttagctca ctcattaggc    300
accccaggct ttacacttta tgctcccggc tcgtatgttg tgtggaattg tgagcggata    360
acaatttcac acaggaaaca gctatgacca tgattacgcc aagcgcgcaa ttaaccctca    420
ctaaagggaa caaaagctgg gtaccgggcc cccctcgag gtcgacggta tcgataagct    480
tgatagagta agttgtcgc atgtatcaag tgatccagaa tcgtactgca actttacttt    540
taatggagct atcagcgaat cagagctgat tctcagtagt acaaaa                  586
```

<210> SEQ ID NO 57
<211> LENGTH: 857
<212> TYPE: DNA
<213> ORGANISM: Zea mays
<220> FEATURE:
<221> NAME/KEY: misc_feature
<222> LOCATION: (827)..(827)
<223> OTHER INFORMATION: n is a, c, g, or t
<220> FEATURE:
<221> NAME/KEY: misc_feature
<222> LOCATION: (847)..(847)
<223> OTHER INFORMATION: n is a, c, g, or t

<400> SEQUENCE: 57

```
agaaaaataa gcacaagttt tatccggcct ttattcacat tcttgcccgc ttgatgaatg      60
ctcatccgga attacgtatg gcatgaaaag acggtgagct ggtgatatgg gatagtgttc     120
acccttgtta caccgttttc catgagcaaa ctgaaacgtt ttcatcgctc tggagtgaat     180
accacgacga tttccggcag tttctacaca tatattcgca agatgtggcg tgttacggtg     240
aaaacctggc ctatttccct aaagggttta ttgagaatat gttttttcgtc tcagccaatc    300
cctgggtgag tttcaccagt tttgatttaa acgtggccaa tatggacaac ttcttcgccc     360
ccgttttcac catgggcaaa tattatacgc aaggcgacaa ggtgctgatg ccgctggcga     420
ttcaggttca tcatgccgtt tgtgatggct tccatgtcgg cagaatgctt aatgaattac     480
aacagtactg cgatgagtgg cagggcgggg cgtaatttttt ttaaggcagt tattggtgcc    540
cttaaacgcc tggttgctac gcctgaataa gtgataataa gcggatgaat ggcagaaatt    600
cgaaagcaaa ttcgacccgg tcgtcggttc agggcagggt cgttaaatag ccgcttatgt     660
ctattgctgg tttaccggtt tattgactac cggaagcagt gtgaccgtgt gcttctcaaa    720
tgcctgaggc cagtttgctc aggctctccc cgtggaggta ataattgacg atatgatcct    780
ttttttctga tcaaaaagga tctaggtgaa gatccttttt gcttccnagc acagtggcga    840
tgatatncta gaattcg                                                    857
```

<210> SEQ ID NO 58
<211> LENGTH: 119
<212> TYPE: DNA
<213> ORGANISM: Zea mays

<400> SEQUENCE: 58

```
agctccaatg tgctggaaag gcaacggtgc acttggcgga aaggccttgg gtgcttgctg      60
gcggattgca gtgtcgtttt gcgtggggat aaatcctttc cagcacagtg gcgatgata     119
```

<210> SEQ ID NO 59
<211> LENGTH: 1510
<212> TYPE: DNA
<213> ORGANISM: Zea mays
<220> FEATURE:
<221> NAME/KEY: misc_feature
<222> LOCATION: (1491)..(1491)
<223> OTHER INFORMATION: n is a, c, g, or t

<400> SEQUENCE: 59

```
ggaagattgg gcatgtcctt gcgaaaaacg aagaaatggt tccggtggca aaaactcgtg      60
ctttgtatgc acccgacacc cgttttcgga atgggtgacg tgcgacaacg aaattgtgcg    120
aaaccacccc aaacatgagt tttggaccta agtagtggaa ttcggcatgt tcgttacgaa     180
aaacgaagaa atggttccgg tggcaaaaac tcgtgctttt atgcaccccg atacacgttt    240
tcagaatggg tgacgtgcga caacaaaatt gcgcgaaacc accccaaaca tgagttttgg    300
```

-continued

| | |
|---|---|
| acctaaagta gtggattggg catgtccttg cgaaaaacga agaaatggtt ccggtggcaa | 360 |
| aaactcgtgc tttgtatgca cccgacaccc gttttcggaa tgggtgacgt gcgacaacga | 420 |
| aattgtgcga aaccacccca aacatgagtt ttggacctaa agtagtggat tcggcatgtt | 480 |
| cgttacgaaa aacgaagaaa tggttccggt ggcaaaaact cgtgctttta tgcaccccga | 540 |
| tacacgtttt cagaatgggt gacgtgcgac aacaaaattg cgcgaaacca ccccaaacat | 600 |
| gagttttgga cctaaagtag tggaattggg catgtccttg cgaaaaacga agaaatggtt | 660 |
| ccggtggcaa aaactcgtgc tttgtatgca cccgacaccc gttttcggaa tgggtgacgt | 720 |
| gcgacaacga aattgcgaga aaccacccca aacatgagtt ttggacctaa agtactggat | 780 |
| taggcatgtt cgttgcgaaa aacgaagaaa tggttccggt ggcaaaaact cgtgctttgt | 840 |
| atgcacccga tacccgtttt cggaatgggt gacgtgcgac aactaaattg tgtgaaacca | 900 |
| ccccaaacat gagttttgga cctaaagtag tggattgggc atgttcgtta cgaaaaacga | 960 |
| agaaatggtt ccggtggcaa aaactcgtgc tttgtatgca accccacact cgttttcgga | 1020 |
| atgagtgacg tgcggcaacg aaattgcgca aaccaccca aacatgagt tttgtaccta | 1080 |
| aagtagtgga ttgggcatgt tcgttgagaa aaacgaagaa atggttcctg tggcaaaaac | 1140 |
| tcgtgctttg tatgcaaccc cacacccgtt ttcagaatgg gtgacgtgcg gcaacgaaat | 1200 |
| tgcgcgaaac cacccaaaac atgagttttg gacctaaagt agtggattgg catgttcgtt | 1260 |
| gcgaaaaaca agaaatagt tccggtggca aaaactcgtg ctttgtatgc accatgacac | 1320 |
| ccgttttcag aatgggtgac gtgcgacaac gaaattgtgc gaaaccaccc caaacatgag | 1380 |
| ttttggacct aaagtagtgg attgggcatg ttcgttgcga aaaacgaaga aatggttccg | 1440 |
| gtggcaaaaa ctcgtgcttt cttttccagca cattggagct tcagcgaatc naagctgata | 1500 |
| catacaggga | 1510 |

<210> SEQ ID NO 60
<211> LENGTH: 1785
<212> TYPE: DNA
<213> ORGANISM: Zea mays

<400> SEQUENCE: 60

| | |
|---|---|
| gggttttggg gccgaggatc agcgagctga ttcgtcgcca ctgtgctgga aaggtcatct | 60 |
| aaattgaaac cgccctttta tgttatttga attccagtca tgttctttt tccccttttcg | 120 |
| ttttacaagc cttcatttgt tcagcatatt cattaattta tgatggatag aacttagaag | 180 |
| tagtagcagt aacaagtacg caaataataa acatgtatga caataagtga atgtgttaac | 240 |
| tatatactga ccattatgaa tgtgacataa gaaatagaga aatttcaaag actccatccc | 300 |
| atcatgaatt catggtttac ttacattaaa caagaatagt atacatttgt atagtggtaa | 360 |
| cagaaaaata tggcacagag cagcaattct gctcaagtcc ctagtgttac attataacaa | 420 |
| agaatattca cgttatgcga gtccatttca gctgataaga acaacaagaa gaattcctag | 480 |
| tcaggaactt actcgtggca atagcaattg gtgcagttgt tggccaatgt tccttccatc | 540 |
| ggactagctt agcacttgac agttcaaagc tgcaacactc actcgtccaa cctttcccag | 600 |
| cacattggag cttcagctgc tcgagggggg ggcccggtac ccaattcgcc ctatagtgag | 660 |
| tcgtattacg cgcgctcact ggccgtcgtt ttacaacgtc gtgactggga aaaccctggc | 720 |
| gttacccaac ttaatcgcct tgcagcacat ccccctttcg ccagctggcg taatagcgaa | 780 |
| gaggcccgca ccgatcgccc ttcccaacag ttgcgcagcc tgaatggcga atgggacgcg | 840 |
| ccctgtagcg gcgcattaag cgcggcgggt gtggtggtta cgcgcagcgt gaccgctaca | 900 |

| | | |
|---|---|---|
| cttgccagcg ccctagcgcc cgctcctttc gctttcttcc cttcctttct cgccacgttc | 960 | |
| gccggctttc cccgtcaagc tctaaatcgg gggctccctt tagggttccg atttagtgct | 1020 | |
| ttacggcacc tcgaccccaa aaaacttgat tagggtgatg gttcacgtag tgggccatcg | 1080 | |
| ccctgataga cggttttttcg ccctttgacg ttggagtcca cgttctttaa tagtggactc | 1140 | |
| ttgttccaaa ctggaacaac actcaaccct atctcggtct attcttttga tttataaggg | 1200 | |
| attttgccga tttcggccta ttggttaaaa aatgagctga tttaacaaaa atttaacgcg | 1260 | |
| aattttaaca aaatattaac gcttacaatt taggtggcac ttttcgggga aatgtgcgcg | 1320 | |
| gaacccctat ttgtttattt ttctaaatac attcaaatat gtatccgctc atgagacaat | 1380 | |
| aaccctgata aatgcttcaa taatattgaa aaaggaagag tatgagtatt caacatttcc | 1440 | |
| gtgtcgccct tattcccttt tttgcggcat tttgccttcc tgttttttgct cacccagaaa | 1500 | |
| cgctggtgaa agtaaaagat gctgaagatc agttgggtgc acgagtgggt tacatcgaac | 1560 | |
| tggatctcaa cagcggtaag atccttgaga gttttcgccc cgaagaacgt tttccaattg | 1620 | |
| atgagcactt tttcgaccga ataaatacct gtgacgggaa gatcacttcg caaaaataaa | 1680 | |
| taaaatcctg ggtgtccctg ttgataccgg gaaagccctg gggccaactt ttggcgaaaa | 1740 | |
| tgaaaacgtt gatccggcac gtaagtttct tccccctttc ctcta | 1785 | |

<210> SEQ ID NO 61
<211> LENGTH: 867
<212> TYPE: DNA
<213> ORGANISM: Zea mays

<400> SEQUENCE: 61

| | | |
|---|---|---|
| gtaggcagga cttttcaagt cttgggaagg gttttttcaa tttgcatttc gcttcgaatt | 60 | |
| agatattaac aagttgtttg ggtgttcgaa tttcaacagg taaagttagt tgctagaacc | 120 | |
| catggctcct ttgccgacgc tgagtagatt ttaggtgacg ggtggtgaca atgagtccgt | 180 | |
| gtcgagcgct gattttttcg gcctttagag cgagatttat acaatagaat ttggcatgag | 240 | |
| attggattgc ttttagtcag cctcttatag cctaaagtct ttgagtgact agatgacata | 300 | |
| tcatgtaagt tgctgatagg tttccagttt tccgctccta ggtctgcata ttgtactttt | 360 | |
| cctcttactc gacttaacca gtaccaaccc agcttctcaa cggatttata ccatggcact | 420 | |
| ttaaagccag catcactgac aatgagcggt gtggtgttac tcgtagaat gctcgcaagg | 480 | |
| tcggctagaa attggtcatg agctttcttt gaacattgct ctgaaagcgg gaacgctttc | 540 | |
| tcataaagag taacagaacg accgtgtagt gcgactgaag ctcgcaatac cataagtcgt | 600 | |
| ttttgctcac gaatatcaga ccagtcaaca agtacaatgg gcatcgtatt gcccgaacag | 660 | |
| ataaagctag catgccaacg gtatacagcg agtcgctctt tgtggaggtg acgattacct | 720 | |
| aacaatcggt cgattcgttt gatgttatgt tttgttctcg cttggttgg caggttacgg | 780 | |
| ccaagttcgg taagagtgag agttttacag tcaagtaatg cgtggcaagc cctttccagc | 840 | |
| acagtggcga tgatatctag attcgcg | 867 | |

<210> SEQ ID NO 62
<211> LENGTH: 3369
<212> TYPE: DNA
<213> ORGANISM: Zea mays
<220> FEATURE:
<221> NAME/KEY: misc_feature
<222> LOCATION: (3353)..(3354)
<223> OTHER INFORMATION: n is a, c, g, or t

<400> SEQUENCE: 62

-continued

```
cttcagaatg aatcaaagct tgattcgctg aagctccaat gtgctggaaa gatgcacccg    60 acaccegttt tcggaatggg tgacgtgcga caacaaaatt gcgcgaaacc accccaaaca   120
tgagttttgg acctaaagta gtggattggg catgttcatt gcgaaaaacg aagaaatggt   180
tccggtggca aaaactcgag ctctgtatgc acccgcacac cgttttcgga atgggtgacg   240
tgcgacaacg aaattgcgtg aaaccacccc aaacatgagt tttggaccta agtagtgga   300 ttgggcatgt tcgttgcgaa aaacgaagaa atggttccgg tggcaaaaac tcgtgctttg   360
tatgcacccg acaccegttt tcggaatggg tgacgtgcga caacgaaatt gcgagaaacc   420
acctcaaaca tgagtttgga cctaaagtag tggattgggc atgttcgtta cgaaaaacga   480
agaaatggtt ccggtggcaa aaactcgtgc tttgtatgca cccgacaccc gttttcggaa   540
tgggtgacgt gcgacaacga aattgtgcga accaccccca aacatgagtt tggacctaa   600 agtagtggat tgggcatgtt tgttgcgaaa acaaagaaa tggttccggt ggcaaaaact   660
cgtgctttgt atgcaccatg acaccegttt tcggaatggg taacgtgcga caacaaaatt   720
gcgagaaacc accccaaaca tgagttttgg acctaaagta gtggattagg catgttcgtt   780
gcgaaaaacg aagaaatggt tccggtggca aaaactcgtg ctttgtatgc actccgacac   840
ccgttttcgg aatgggtgac gcgtgacaac aaaattgcgc gaaaccaccc caaacatgag   900
ttttgaacct aaagaagtgg attgggcatg ttccgttaca aaaaacgaag aaatggtttc   960
cggtggcaaa aactcgtgct tttgtatgcc accccgacac ccgttttcg aaatggggtg   1020 acttgcgaca accaaatttc gagaaatccc ccccaacatg agtttggac ctaaagtagt   1080 ggattgagca tgttcgttgc gaaaaacgaa gaaatggttc cggtggcaaa aactcgtgct   1140
ttttattcac ccgacaccg ttttcggaat gggtgacgtg cgacaacgaa attgcgcgaa   1200
accaccccaa acatgagttt tggatgtaaa gtagtggatt gggcatgttc gttgcgaaaa   1260
acgaagaaat ggttccggtg gcaaaaactc gtgctttgta tgcacccgac accegttttc   1320 ggaatgggtg acgtgcgaca cgaaattgt gcgaaaccac cccaaacatg agttttggac   1380
ctaaagtagt ggattcggca tgttcgttac gaaaaacgaa gaaatggttc cggtggcaaa   1440
aactcgtgct tttatgcacc cgacaccegt tttcagaatg ggtgacgtgc gacaacaaaa   1500
ttgcgcgaaa ccaccccaaa catgagtttt ggacctaaag tagtggattc ggcatgttcg   1560
ttgcgaaaaa cgaagaaatg gttccggtgg caaaaactcg tgctttttat gcaccccgat   1620
acccgttttc agaatgggtg acatgcgaca caaaattgc acgaaaccac cccaaacatg   1680
agttttggac ctaaagtagt ggattgggca tgttcgttgc gaaaaacgaa gaaatggttc   1740
cggtggcaaa aactcgtgct tttatgcacc ccgatacect ttttcagaat gggtgacgtg   1800
cgacaacgaa actgtgcgaa accaccccaa acatgagttt tggacctata gtagtggatt   1860
gggcatgttc gttgtgaaaa acgaagaaat ggttccggtg gcaaaaactc gtgctttgta   1920 tgcacccega caacegtttt cggaatgggt gacgtgcggc aacgaaattg cgcgaaacca   1980
ccccaaacat gagttttgga cctaaagtag tggattgggc atgttcgttg cgaaaaacga   2040
agaaatggtt ccggtggcaa aaactcgtgc ttttatgcac cccgataccc gttttcagaa   2100
tgggtgacgt gcgacaacga aattgtgcga aacctcccca aacatgagtt tggacctaa   2160 agtagtggat tgggcatgtt cgttgcgaaa acgaagaaa tggttccggt ggcaaaaact   2220
cgtgctttgt atgcaccccc gacaaccgtt ttcggaatgg gtgacgtgcg gcaacgaaat   2280
tgcgcgaaac cactccaaac atgagttttg gacctaaagt agtggattgg gcatgttcat   2340
tgcgaaaaac gaagaaatgg ttccggtggc aaaaactcgt gctttttatt cacccgacac   2400
```

```
ccgttttcgg aatgggtgac gtgcgacaac gaaattgcgc gaaaccaccc caaacatgag    2460
ttttggatgt aaagtagtgg attgggcatg ttcgttgcga aaaacgaaga aatggttccg    2520
gtggcaaaaa ctcgtgcttt gtatgcaccc gacacccgtt ttcggaatgg gtgacgtgcg    2580
acaaagaaat tgcgcgaaaa ccaccccaaa catgagtttt ggatgtaaag tagtggatgg    2640
ggcatgttcg ttgcgaaaaa cgaagaaatg gttccggtgg caaaaactcg tgcttttatg    2700 cacccccgata cccgttttca gaatgggtga cgtgcgacaa cgaaattgcg cgaaaccacc    2760
ccaaacatga gttttggacc taaagtagtg gattgggcat gttcgttgcg aaaaacgaag    2820
aaatggttcc ggtggcaaaa actcgtgctt ttatgcaccc cgatacccgt tttcagaatg    2880
ggtgacgtgc gacaacgaaa ctgtgcgaaa ccaccccaaa catgagtttt ggacctaaag    2940
tagtggattg ggcatgttcg ttatgaaaaa cgaagaaatg gttccggtgg caaaaactcg    3000
tgctttgtat gcaccccgac aaccgttttc ggaatgggtg acgtgcggca acgaaattgc    3060
gcgaaaccac cccaaacatg agttttggac taaagtagt ggattgggca tgttcgttgc    3120
gaaaaacgaa gaaatggttc cggtggcaaa aactcgtgct ttttattcac ccgacacccg    3180
ttttcggaat gggtgacgtg cgacaacgaa attgcgcgaa accacccccaa acatgagttt    3240 tggatgtaaa gtagtggatt gggcatgttc gttgcgaaaa acgaagaaat ggttccggtg    3300
gcaaaaactc gtgctttctt tccagcacat tggagcttca gcgaatcaag ctnngatatc    3360
attcggaag                                                             3369

<210> SEQ ID NO 63
<211> LENGTH: 5594
<212> TYPE: DNA
<213> ORGANISM: Zea mays

<400> SEQUENCE: 63
cgatatctag aatcatcgcc actgtgctgg aaaggagtgt atagagaaaa ttgaggccat      60
tcttaaggaa cttgaaaagc cagcaccctg atgcgaccac gttttagtct acgtttatct    120
gtctttactt aatgtccttt gttacaggcc agaaagcata actggcctga atattctctc    180
tgggcccact gttccacttg tatcgtcggt ctgataatca gactgggacc acggtcccac    240
tcgtatcgtc ggtctgatta ttagtctggg accacggtcc cactcgtatc gtcggtctga    300
ttattagtct gggaccacgg tcccactcgt atcgtcggtc tgataatcag actgggacca    360
cggtcccact cgtatcgtcg gtctgattat tagtctggga ccatggtccc actcgtatcg    420
tcggtctgat tattagtctg gaccacggt cccactcgta tcgtcggtct gattattagt    480
ctggaaccac ggtccccactc gtatcgtcgg tctgattatt agtctgggac acggtccca    540 ctcgtatcgt cggtctgatt attagtctgg gaccacgatc ccactcgtgt tgtcggtctg    600
attatcggtc tgggaccacg gtcccacttg tattgtcgat cagactatca gcgtgagact    660
acgattccat caatgcctgt caagggcaag tattgacatg tcgtcgtaac ctgtagaacg    720
gattaacctc ggtgtgcggt tgtatgcctg ctgtggattg ctgctgtgtc ctgcttaatc    780
cacaacattt tgcgcacggt ttatgtggac aaaatacctg gttacccagg ccgtgccggc    840
acgttaaccg ggctgcatcc gatgcaagtg tgtcgctgtc gacgagctcg cgagctcgga    900
catgaggttt ccccgtattc agtgtcgctg atttgtattg tctgaagttg tttttacgtt    960
aagttgatgc agatcaatta atacgatacc tgcgtcataa ttgattattt gacgtggttt   1020
gatgccctcc acgcacgttg tgatatgtag atgataatca ttatcacttt acgggtcctt   1080
tccggtgatc cgacaggtta cggggcggcg acctcgcggg ttttcgctat ttatgaaaat   1140
```

```
tttccggttt aaggcgtttc cgttcttctt cgtcataact taatgttttt atttaaaata   1200
ccctctgaaa agaaaggaaa cgacaggtgc tgaaagcgag ctttttggcc tctgtcgttt   1260
cctttctctg tttttgtccg tggaatgaac aatggaagtc cgagctcatc gctaataact   1320
tcgtatagca tacattatac gaagttatag cggccgcaca ccggtgttcc taaggacata   1380
ttccgttcgt acttgagtta ttggatctat gaaatcgctc gctatacacc agtcatgatt   1440
ttgtccctgg taatagggt tttggtttta ttaattatat tttttaatga caacgaagct   1500
tgtgttttca attctgcaat atttgctttt acttctcttg taggtttgtt aataatatta   1560
agtgatggta atccaaagct agtcagtcgt cgaaatttta ggaccgagct tttagtggat   1620
gtcatcacac gtaaaccggc ggtagaaggg aaagaatgga ggatcatcac atacaacatg   1680
aaccaatatt tgtttaatca tgggcaatgg catactccgt attacttta cagcgatgag   1740 gattgctacc gttatttct acgccttgtt gagggagtaa ccccccaagaa gcaaacagcc   1800 acgtcaattg gcaattctcc ggtcaccgct aagcctgaag atgccatcga gtcagcttct   1860
cctagttcca gactgaatta tcaaaacttt ttgctcaagg cagcggagat cgaacgacaa   1920
ggtcaggaaa attactggtg aaggcggcat cccaatatcg atgcgcttct taaaaagatg   1980
gaatagctta gagacattgc cttacgtaaa gggaacataa actagagtat gatatttaat   2040
cagcactaac tggccggaaa acggccgaag gaagcctcga aaagtcgatt cgtgttggac   2100
ccatttgctg aacaaagtgg ttcattgcct acctattatg gtagtagtcg tgataatcgt   2160
gtggttggtt ttgtcaacgg tgcatttgca ttttcatgac aataaaccct gcgttttcgt   2220
tctcgggata ttactttccc tccacttctt tcgcctcaat agctcctata agcattctca   2280
gggcgtatgt cggtgatcga gatttccaag caagctttta gtggaaatca tcgcgcgcaa   2340
gccagcggta aagggaaaag aacggaggac gattacatac aagatgaacg aataaataaa   2400
ttaataataa ataataataa aaagtacagt agcattaaat attattaagt ttaatgatta   2460
aaaattggtt aattgtcaag aaaatctaag gtattaataa ataaataata ctatgacaac   2520
ctgcagcgaa agcatcagcc ccaatgaaaa ttaatcagaa ttgaatctga gcgtatttat   2580
ttgataacgg tttacgtaac tgttggaata aaaatcaact atcatctact aactagtgtt   2640
tacgttacta gtatattatc atatacggtg ttagaagatg acgcaaatga tgagaaatag   2700
tcatcgtttt caacggaagc tgaaatacaa ggattgataa tgtaatagga tcaatgaata   2760
tcaacatata aaacgatgat aataatattt atagaattgt gtagaattgc agattcccctt   2820 ttatggattc ctaaatcctc gagaagaact tctagtatat ctacgtacct aatattattg   2880
ccttattaaa aatggaatcc caacaattat ctcaaaattc ccccaattct catcagtaac   2940
accccacccc gtattacttt taccgtgatg aagattggca tcgttacttt ctaaacgtag   3000
gacgtgcgga atgacaaaac catcagcagt gtcacgatct ctccagtcac aatggcaatc   3060
atgagtgcat agtccaaagt aaaggggcaa ggaaaagcat gattgaaagg actccccatc   3120
tggactctat atgtcatcag cggctaaaaa aaagcatata gcacaacatc agcatcagca   3180
tcagcactag agtcatcggc ccggcggtcc gcggtcatcc ccgcggactt tccgtccgcc   3240
cggcgggctg tatcagcgtc aactggaacg cgcatatata tacaagacac acataacata   3300
gaagcacacc cacgcaaata accacacgac aataaccaca cccgcccacc cctcctttcc   3360
gtatacaagg cctcggtacc tcttaaaaac tttctctcaa ttctctctac cgtgatcaag   3420
gtaaatttct gtgttcctta ttctctcaaa atcttcgatt tgttttcgt tcgatcccaa   3480 tttcgtatat gttctttggt ttagattctg ttaatcttag atcgaagacg attttctggg   3540
```

```
tttgatcgtt agatatcatc ttaattctcg attagggttt catagatatc atccgatttg    3600
ttcaaataat ttgagttttg tcgaataatt actcttcgat ttgtgatttc tatctagatc    3660
tggtgttagt ttctagtttg tgcgatcgaa tttgtcgatt aatctgagtt tttcttttc     3720
tttttgcagg tagagttaac gctagccttg gtaccatacg taagaaaatg attgaacaag    3780
atggattgca cgcaggttct ccggccgctt gggtggagag gctattcggc tatgactggg    3840
cacaacagac aatcggctgc tctgatgccg ccgtgttccg gctgtcagcg caggggcgcc    3900
cggttctttt tgtcaagacc gacctgtccg gtgccctgaa tgaactccaa gacgaggcag    3960
cgcggctatc gtggctggcc acgacgggcg ttccttgcgc agctgtgctc gacgttgtca    4020
ctgaagcggg aagggactgg ctgctattgg gcgaagtgcc ggggcaggat ctcctgtcat    4080
ctcaccttgc tcctgccgag aaagtatcca tcatggctga tgcaatgcgg cggctgcata    4140
cgcttgatcc ggctacctgc ccattcgacc accaagcgaa acatcgcatc gagcgagcac    4200
gtactcggat ggaagccggt cttgtcgatc aggatgatct ggacgaagag catcaggggc    4260
tcgcgccagc cgaactgttc gccaggctca aggcgcggat gcccgacggc gaggatctcg    4320
tcgtgaccca tggcgatgcc tgcttgccga atatcatggt ggaaaatggc cgcttttctg    4380
gattcatcga ctgtggccgg ctgggtgtgg cggaccgcta tcaggacata gcgttggcta    4440
cccgtgatat tgctgaagag cttggcggcg aatgggctga ccgcttcctc gtgctttacg    4500
gtatcgccgc tcccgattcg cagcgcatcg ccttctatcg ccttcttgac gagttcttct    4560
gagcgggact ctgggtacgt atgtcgacac aattgcagcg cttgagctct cctaggtccg    4620
cggacaaagc tgggtttttt tttttcaat ttcgattcat ctcaaggttt ttggagtttt     4680
tgattatgga cttgtgagac tcttagaatt tctgttttat gatttattgg ataactgtga    4740
ttctccaaga acttatgtct tatatgattt tgtcttcatt tcgttgcttc ttatttcttg    4800
cctgtgatgt attgcatctg catagttgga ttgaaagtta ggttcttggg tttataagaa    4860
ggctgtgact tgatgttact tagccatagc tgatcaaata tcgtctaaca aagtggtctg    4920
ttactctgtt atattggttc gcgtaaattt tggttacagt ttgtttccga gttggtatct    4980
cgtaagtcgt aacgtttgtg tacttattca ctggaagcaa gttgtattgt tgttagtctt    5040
ttgttacctc tcctggtacg attttttttg tttgtgaaca agatcagaaa ctgggactgt    5100
gaatttgacc gataaactag tcttaattaa gatttaaatg cgagctcagc ccgggcagcg    5160
atcgcaggcc ggccatcgat ttattcaaca aagccacgtt gtgtctcaaa atctctgatg    5220
ttacattgca caagataaaa atatatcatc atgaacaata aaactgtctg cttacataaa    5280
cagtaataca aggggtgtta tgacgatgga ccgcgcttgt gtgtcgcgtt cagtttggct    5340
tttgccaagc agtagggtag cttcccgcgt cggtaattat atggtatgaa ccatcacctt    5400
ttggctctac atggtatgaa cgtaagatac aaattccaac tacctctagc tcgccgcact    5460
agttcctgca ggtggcccca cgtggcctct cgagtgttta aactcggacc gtatcgattt    5520
attcaacaaa gccgccgtcc cgtcaagtca gcgtaatgct ctgccagtgt tacaaccaat    5580
taaccaaatt ctga                                                      5594
```

<210> SEQ ID NO 64
<211> LENGTH: 5111
<212> TYPE: DNA
<213> ORGANISM: Zea mays

<400> SEQUENCE: 64

```
ctccggaaga aattaagctt gaatttcgct gaagctcaat gtgctggaaa gtggaacacg      60
```

```
agacctgtcc aggttaagca ccattttatc gcccttatac aatactgtcg ctccaggagc      120
aaactgatgt cgtgagctta aactagttct tgatgcagat gacgttttaa gcacagaagt      180
taaaagagtg ataacttctt cagcttcaaa tatcacccca gcttttttct gctcatgaag      240
gttagatgcc tgctgcttaa gtaattcctc tttatctgta aaggcttttt gaagtgcatc      300
acctgaccgg gcagatagtt caccggggtg agaaaaaaga gcaacaactg atttaggcaa      360
tttggcggtg ttgatacagc gggtaataat cttacgtgaa atattttccg catcagccag      420
cgcagaaata tttccagcaa attcattctg caatcggctt gcataacgct gaccacgttc      480
ataagcactt gttgggcgat aatcgttacc caatctggat aatgcagcca tctgctcatc      540
atccagctcg ccaaccagaa cacgataatc actttcggta agtgcagcag ctttacgacg      600
gcgactccca tcggcaattt ctatgacacc agatactctt cgaccgaacg ccggtgtctg      660
ttgaccagtc agtagaaaag aagggatgag atcatccagt gcgtcctcag taagcagctc      720
ctggtcacgt tcattacctg accatacccg agaggtcttc tcaacactat caccccggag      780
cacttcaaga gtaaacttca catcccgacc acatacaggc aaagtaatgg cattaccgcg      840
agccattact cctacgcgcg caattaacga atccaccatc ggggcagctg tgtcgataa       900 cgaagtatct tcaaccggtt gagtattgag cgtatgtttt ggaataacag gcgcacgctt      960
cattatctaa tctcccagcg tggtttaatc agacgatcga aaatttcatt gcagacaggt     1020
tcccaaatag aaagagcatt tctccaggca ccagttgaag agcgttgatc aatggcctgt     1080
tcaaaaacag ttctcatccg gatctgacct ttaccaactt catccgtttc acgtacaaca     1140 tttttttagaa ccatgcttcc ccaggcatcc cgaatttgct cctccatcca cggggactga     1200
gagccattac tattgctgta tttggtaagc aaaatacgta catcaggctc gaacccttta     1260
agatcaacgt tcttgagcag atcacgaagc atatcgaaaa actgcagtgc ggaggtgtag     1320
tcaaacaact cagcaggcgt gggaacaatc agcacatcag cagcacatac gacattaatc     1380
gtgccgatac ccaggttagg cgcgctgtca ataactatga catcatagtc atgagcaaca     1440
gtttcaatgg ccagtcggag catcaggtgt ggatcggtgg gcagtttacc ttcatcaaat     1500
ttgcccatta actcagtttc aatacggtgc agagccagac aggaaggaat aatgtcaagc     1560
cccggccagc aagtgggctt tattgcataa gtgacatcgt cctttccccc aagatagaaa     1620
ggcaggagag tgtcttctgc atgaatatga agatctggta cccatccgtg atacattgag     1680
gctgttccct gggggtcgtt accttccacg agcaaaacac gtagcccctt cagagccaga     1740
tcctgagcaa gatgaacaga aactgaggtt ttgtaaacgc cacctttatg ggcagcaacc     1800
ccgatcaccg gtggaaatac gtcttcagca cgtcgcaatc gcgtaccaaa cacatcacgc     1860
atatgattaa tttgttcaat tgtataacca acacgttgct caacccgtcc tcgaatttcc     1920
atatccgggt gcggtagtcg ccctgctttc tcggcatctc tgatagcctg agaagaaacc     1980
ccaactaaat ccgctgcttc acctattctc cagcgccggg ttattttcct cgcttccggg     2040
ctgtcatcat taaactgtgc aatggcgata gccttcgtca tttcatgacc agcgtttatg     2100
cactggttaa gtgtttccat gagtttcatt ctgaacatcc tttaatcatt gctttgcgtt     2160 ttttttattaa atcttgcaat ttactgcaaa gcaacaacaa aatcgcaaag tcatcaaaaa     2220
accgcaaagt tgtttaaaat aagagcaaca ctacaaaagg agataagaag agcacatacc     2280
tcagtcactt attatcacta gcgctcgccg cagccgtgta accgagcata gcgagcgaac     2340
tggcgaggaa gcaaagaaga actgttctgt cagatagctc ttacgctcag cgcaagaaga     2400
aatatccacc gtgggaaaaa ctccaggtag aggtacacac gcggatagcc aattcagagt     2460
```

```
aataaactgt gataatcaac cctcatcaat gatgacgaac taaccccga tatcaggtca      2520 catgacgaag ggaaagagaa ggaaatcaac tgtgacaaac tgccctcaaa tttggcttcc     2580
ttaaaaatta cagttcaaaa agtatgagaa aatccatgca ggctgaagga aacagcaaaa     2640
ctgtgacaaa ttaccctcag taggtcagaa caaatgtgac gaaccaccct caaatctgtg     2700
acagataacc ctcagactat cctgtcgtca tggaagtgat atcgcggaag gaaaatacga     2760
tatgagtcgt ctggcggcct ttcttttct caatgtatga gaggcgcatt ggagttctgc      2820
tgttgatctc attaacacag acctgcagga agcggcggcg gaagtcaggc atacgctggt     2880
aactttgagg cagctggtaa cgctctatga tccagtcgat tttcagagag acgatgcctg     2940
agccatccgg cttacgatac tgacacaggg attcgtataa acgcatggca tacggattgg     3000
tgatttcttt tgtttcacta agccgaaact gcgtaaaccg gttctgtaac ccgataaaga    3060
agggaatgag atatggggttg atatgtacac tgtaaagccc tctggatgga ctgtgcgcac    3120
gtttgataaa ccaaggaaaa gattcatagc ctttttcatc gccggcatcc tcttcagggc    3180
gataaaaaac cacttccttc cccgcgaaac tcttcaatgc ctgccgtata tccttactgg    3240
cttccgcaga ggtcaatccg aatatttcag catatttagc aacatggatc tcgcagatac   3300
cgtcatgttc ctgtagggtg ccatcagatt ttctgatctg gtcaacgaac agatacagca   3360 tacgttttg atcccgggag agactatatg ccgcctcagt gaggtcgttt gactggacga     3420
ttcgcgggct attttttacgt ttcttgtgat tgataaccgc tgtttccgcc atgacagatc  3480
catgtgaagt gtgacaagtt tttagattgt cacactaaat aaaaaagagt caataagcag    3540
ggataacttt gtgaaaaaac agcttcttct gagggcaatt tgtcacaggg ttaagggcaa    3600
tttgtcacag acaggactgt catttgaggg tgatttgtca cactgaaagg gcaatttgtc    3660
acaacacctt ctctagaacc agcatggata aaggcctaca aggcgctcta aaaagaaga    3720 tctaaaaact ataaaaaaa taattataaa aatatccccg tggataagtg gataacccca    3780
agggaagttt tttcaggcat cgtgtgtaag cagaatatat aagtgctgtt ccctggtgct    3840
tcctcgctca ctcgagggct tcgccctgtc gctcgactgc ggcgagcact actggctgta    3900
aaaggacaga ccacatcatg gttctgtgtt cattaggttg ttctgtccat tgctgacata    3960
atccgctcca cttcaacgta acaccgcacg aagatttcta ttgttcctga aggcatattc    4020 aaatcgttt cgttaccgct tgcaggcatc atgacagaac actacttcct ataaacgcta     4080
cacaggctcc tgagattaat aatgcggatc tctacgataa tgggagattt tcccgactgt    4140
ttcgttcgct tctcagtgga taacagccag cttctctgtt taacagacaa aaacagcata    4200
tccactcagt tccacatttc catataaagg ccaaggcatt tattctcagg ataattgttt    4260
cagcatcgca accgcatcag actccggcat cgcaaactgc acccggtgcc gggcagccac    4320
atccagcgca aaaaccttcg tgtagacttc cgttgaactg atggacttat gtcccatcag    4380
gctttgcaga actttcagcg gtataccggc atacagcatg tgcatcgcat aggaatggcg    4440
gaacgtatgt ggtgtgaccg gaacagagaa cgtcacaccg tcagcagcag cggcggcaac    4500
cgcctcccca atccaggtcc tgaccgttct gtccgtcact tcccagatcc gcgctttctc    4560
tgtccttcct gtgcgacggt tacgccgctc catgagctta tcgcgaataa atacctgtga    4620
cggaagatca cttcgcagaa taaataaatc ctggtgtccc tgttgatacc gggaagccct    4680
gggccaactt ttggcgaaaa tgagacgttg atcggcactg cccgctttcc agtcgggaaa    4740
cctgtcgtgc cagctgcatt aatgaatcgg ccaacgcgaa ccccttgcgg ccgcccgggc    4800
cgacgaccaa ttctcatgtt tgacagctta tcatcaaatt tctgccattc ctccgcttta    4860
```

-continued

| | |
|---|---|
| ttattcaact tattccggcg aagccactat ggcgtttaag ggcaccaata actgccttaa | 4920 |
| aaaatttacc cccccccctg cccctcctt cgcagtactg tttgaaatca ttaaacattt | 4980 |
| ttgccgaact ggaaacccat aaaaacgggc aggatgaacc ttaatccgcc cccggccttc | 5040 |
| ccacccttgg caccttgggg taaaattatt tcccaaggga gaaacagggg cgccaaaaaa | 5100 |
| atcctcccaa t | 5111 |

```
<210> SEQ ID NO 65
<211> LENGTH: 8559
<212> TYPE: DNA
<213> ORGANISM: Zea mays
<220> FEATURE:
<221> NAME/KEY: misc_feature
<222> LOCATION: (8221)..(8222)
<223> OTHER INFORMATION: n is a, c, g, or t
<220> FEATURE:
<221> NAME/KEY: misc_feature
<222> LOCATION: (8225)..(8225)
<223> OTHER INFORMATION: n is a, c, g, or t
<220> FEATURE:
<221> NAME/KEY: misc_feature
<222> LOCATION: (8227)..(8228)
<223> OTHER INFORMATION: n is a, c, g, or t
<220> FEATURE:
<221> NAME/KEY: misc_feature
<222> LOCATION: (8230)..(8230)
<223> OTHER INFORMATION: n is a, c, g, or t
<220> FEATURE:
<221> NAME/KEY: misc_feature
<222> LOCATION: (8234)..(8236)
<223> OTHER INFORMATION: n is a, c, g, or t
<220> FEATURE:
<221> NAME/KEY: misc_feature
<222> LOCATION: (8241)..(8241)
<223> OTHER INFORMATION: n is a, c, g, or t
<220> FEATURE:
<221> NAME/KEY: misc_feature
<222> LOCATION: (8244)..(8245)
<223> OTHER INFORMATION: n is a, c, g, or t
<220> FEATURE:
<221> NAME/KEY: misc_feature
<222> LOCATION: (8250)..(8250)
<223> OTHER INFORMATION: n is a, c, g, or t
<220> FEATURE:
<221> NAME/KEY: misc_feature
<222> LOCATION: (8256)..(8256)
<223> OTHER INFORMATION: n is a, c, g, or t
<220> FEATURE:
<221> NAME/KEY: misc_feature
<222> LOCATION: (8258)..(8258)
<223> OTHER INFORMATION: n is a, c, g, or t
<220> FEATURE:
<221> NAME/KEY: misc_feature
<222> LOCATION: (8269)..(8269)
<223> OTHER INFORMATION: n is a, c, g, or t
<220> FEATURE:
<221> NAME/KEY: misc_feature
<222> LOCATION: (8274)..(8274)
<223> OTHER INFORMATION: n is a, c, g, or t
<220> FEATURE:
<221> NAME/KEY: misc_feature
<222> LOCATION: (8278)..(8278)
<223> OTHER INFORMATION: n is a, c, g, or t
<220> FEATURE:
<221> NAME/KEY: misc_feature
<222> LOCATION: (8290)..(8290)
<223> OTHER INFORMATION: n is a, c, g, or t
<220> FEATURE:
<221> NAME/KEY: misc_feature
<222> LOCATION: (8300)..(8301)
<223> OTHER INFORMATION: n is a, c, g, or t
<220> FEATURE:
<221> NAME/KEY: misc_feature
<222> LOCATION: (8304)..(8304)
<223> OTHER INFORMATION: n is a, c, g, or t
<220> FEATURE:
```

```
<221> NAME/KEY: misc_feature
<222> LOCATION: (8315)..(8315)
<223> OTHER INFORMATION: n is a, c, g, or t
<220> FEATURE:
<221> NAME/KEY: misc_feature
<222> LOCATION: (8319)..(8319)
<223> OTHER INFORMATION: n is a, c, g, or t
<220> FEATURE:
<221> NAME/KEY: misc_feature
<222> LOCATION: (8321)..(8321)
<223> OTHER INFORMATION: n is a, c, g, or t
<220> FEATURE:
<221> NAME/KEY: misc_feature
<222> LOCATION: (8323)..(8323)
<223> OTHER INFORMATION: n is a, c, g, or t
<220> FEATURE:
<221> NAME/KEY: misc_feature
<222> LOCATION: (8343)..(8343)
<223> OTHER INFORMATION: n is a, c, g, or t
<220> FEATURE:
<221> NAME/KEY: misc_feature
<222> LOCATION: (8356)..(8356)
<223> OTHER INFORMATION: n is a, c, g, or t
<220> FEATURE:
<221> NAME/KEY: misc_feature
<222> LOCATION: (8361)..(8361)
<223> OTHER INFORMATION: n is a, c, g, or t
<220> FEATURE:
<221> NAME/KEY: misc_feature
<222> LOCATION: (8372)..(8372)
<223> OTHER INFORMATION: n is a, c, g, or t
<220> FEATURE:
<221> NAME/KEY: misc_feature
<222> LOCATION: (8383)..(8383)
<223> OTHER INFORMATION: n is a, c, g, or t
<220> FEATURE:
<221> NAME/KEY: misc_feature
<222> LOCATION: (8386)..(8387)
<223> OTHER INFORMATION: n is a, c, g, or t
<220> FEATURE:
<221> NAME/KEY: misc_feature
<222> LOCATION: (8391)..(8391)
<223> OTHER INFORMATION: n is a, c, g, or t
<220> FEATURE:
<221> NAME/KEY: misc_feature
<222> LOCATION: (8397)..(8397)
<223> OTHER INFORMATION: n is a, c, g, or t
<220> FEATURE:
<221> NAME/KEY: misc_feature
<222> LOCATION: (8400)..(8400)
<223> OTHER INFORMATION: n is a, c, g, or t
<220> FEATURE:
<221> NAME/KEY: misc_feature
<222> LOCATION: (8404)..(8404)
<223> OTHER INFORMATION: n is a, c, g, or t
<220> FEATURE:
<221> NAME/KEY: misc_feature
<222> LOCATION: (8408)..(8408)
<223> OTHER INFORMATION: n is a, c, g, or t
<220> FEATURE:
<221> NAME/KEY: misc_feature
<222> LOCATION: (8413)..(8413)
<223> OTHER INFORMATION: n is a, c, g, or t
<220> FEATURE:
<221> NAME/KEY: misc_feature
<222> LOCATION: (8421)..(8421)
<223> OTHER INFORMATION: n is a, c, g, or t
<220> FEATURE:
<221> NAME/KEY: misc_feature
<222> LOCATION: (8424)..(8424)
<223> OTHER INFORMATION: n is a, c, g, or t
<220> FEATURE:
<221> NAME/KEY: misc_feature
<222> LOCATION: (8427)..(8427)
<223> OTHER INFORMATION: n is a, c, g, or t
<220> FEATURE:
<221> NAME/KEY: misc_feature
<222> LOCATION: (8433)..(8433)
<223> OTHER INFORMATION: n is a, c, g, or t
<220> FEATURE:
```

```
<221> NAME/KEY: misc_feature
<222> LOCATION: (8435)..(8435)
<223> OTHER INFORMATION: n is a, c, g, or t
<220> FEATURE:
<221> NAME/KEY: misc_feature
<222> LOCATION: (8461)..(8461)
<223> OTHER INFORMATION: n is a, c, g, or t
<220> FEATURE:
<221> NAME/KEY: misc_feature
<222> LOCATION: (8463)..(8465)
<223> OTHER INFORMATION: n is a, c, g, or t
<220> FEATURE:
<221> NAME/KEY: misc_feature
<222> LOCATION: (8472)..(8472)
<223> OTHER INFORMATION: n is a, c, g, or t
<220> FEATURE:
<221> NAME/KEY: misc_feature
<222> LOCATION: (8479)..(8479)
<223> OTHER INFORMATION: n is a, c, g, or t
<220> FEATURE:
<221> NAME/KEY: misc_feature
<222> LOCATION: (8482)..(8483)
<223> OTHER INFORMATION: n is a, c, g, or t

<400> SEQUENCE: 65
gggttctcgt tactgatgat cagcttgatt cgctgaagct ccaatgtgct ggaaagtatg      60
gattttgtgc tgggattgcc taggactagg aagggacgtg atagtgtgtt tgtggttgtt     120
gatagatttt ctaagatggc acatttcata ccatgtcata aaactgacga tgctactcat     180
attgctgatt tgttctttcg tgaaattgtt cgcttgcatg gtgtgcccaa cacaatcgtt     240
tctgatcgtg atgctaaatt tcttagtcat ttttggagga ctttgtgggc aaaattgggg     300
actaagcttt tattttctac tacatgtcat cctcaaactg atggtcaaac tgaagttgtg     360
aatagaactt tgtctactat gttaagggca gttctaaaga agaatattaa gatgtgggag     420
gactgtttgc ctcatgttga atttgcttat aatcgatcat tgcattctac tacaaagatg     480
tgcccatttc agattgtata tggtttgttg cctcgtgctc ctattgattt aatgcctttg     540
ccatcttctg aaaaactaaa ttttgatgct actaggcgtg ctgaattgat gttaaaactg     600
catgaaacta ctaaagaaaa catagagcgt atgaatgcta gatataagtt tgctagtgat     660
aaaggtagaa aggaaataaa ttttgaacct ggagatttag tttggttgca tttgagaaag     720
gaaaggtttc ctgaattgcg aaaatctaag ttgttgcctc gagccgatgg accgtttaaa     780
gtgctagaga aaattaacga caatgcatat aggctagatc tgcctgcaga ctttggggtt     840
agccccacat ttaacattgc agatttaaag ccctacttgg gagaggaagt taagcttgag     900
tcgaggacga ctcaaatgca agaagggag aatgatgaag acatccacac tactgatgca     960
tctataccaa tacaagtacc aatttctggt cccattactc gcgctcgtgc tcgtcaactc    1020
aaccatcagg tgattacact cttgagttca tgtccatcat atttagacca tggagacccg    1080
tgcactcttg ttttgcttag gaatcaggga gaagaccgaa agggaaaagg atttgaacat    1140
gctggattcg gactgcagaa gaacaccaac ttgtgacggt caccacggtc agatgcgggc    1200
tcggattgga atgttcaagc acaacatgga aagcttatca agtctacttt catatggatc    1260
cggaattata gtcatatctg ttctgaggcc gccgtaatca ttgttttatt accgagacat    1320
ttcctgcctt ttctgcccat ggtgctgcgt cacccatttt ggcccaatg ggtcgtgtat    1380
caagttaggt ccattaggga cgcatcctag ggttgcagca cgaccccaat acccttgtgg    1440
tcgtcctccc atgtttataa acccctagc cgccaccaag aacagcgggt tttgtttaga    1500
tcaagtttag ctctcgctac ttgcttgcaa gcgcgcgtgc tagttcagcc gcccgtcttc    1560
ttgtcttcgg aaccccacca tattgtagtt tgatctttaa acctacatt agatctggta    1620
```

```
attcagtact tgttctactt gttcttgcta gttcttcgat tgcttgcagg acgagtgccc    1680
tagtggccag ggtgtcacgc tccacaagat cgtgacagcc ataggagtg gtgtatcggt    1740 tgctaaggcg cagcgtcttt ggaaggctgt agtcgggccg tgaacgtcgt ctcctcccc     1800 aatcgagtta ttccacaccc tctcatcgaa agatcgggca atcacccaac gggtgcacat   1860
cactgaatat cccgtgtacg tcctgtggaa gaagcggcgc ctttggcagg gggcgccact   1920
ggcttggtcg tccctgtgcg cgatgtagtg ctaggcgtag aaggtgcagg gctgaagga    1980 gttgagctgt gtgttggacc ccggcctgca agagagttag tatatgtctt tgatcgtcgt   2040
ccctgcactt cacgttcagc tttgcaagca tattcaaaca atgtggttat atcaaaataa   2100
tccttataat caagtatatc ctgaatttcc ctgttcaaac caccacgaaa acgcgccata   2160
gcagcgtcat ccgactcaac taaaccacaa cgaagcatac ccttttgtaa ctcctggtaa   2220
taatcctcaa cagactgtga accttgttga aaacgctgca ttttgttaag caaatcacga   2280
gcataatagg aaggaacaaa tctgtggcgc atggcagttt ttaattgggt ccaagtaatg   2340
acactgttaa tgggaagttt tgtttatac tcacgccacc aaattaaagc aaaatcagta    2400
aattcactaa tggcagcctt cacttggcta ttagcaggaa tatcatggca tgaaaatttc   2460
tgttctacct ctaattccca atcaagatat gcagcaggat catatttacc attaaaagat   2520
ggaattttaa atttaatctt agaaaataag tcattagggg gatgacgaac cacacgacgt   2580
gcacgaccac ggcgatctcc atcgtcctgc tcagtgtcaa cgccgtattc ctgctccatc   2640
tttgtggtca gtgcatcaag gcgtgccagg atggtgtcga gtgtggtgcg agtcgccgtt   2700
tgagcaaggt caagttggtt gaaacgctcg gtcgtcgaag tgatcgttga atcaagccgt   2760
tcatgcatcg tcctaatgtc agcagcaagt ccatcaactt gtcccttac ttcctgcaac    2820 tgggcatcca ccatgtcgtg tgctcctgcc atagttagcg caaacaccaa aaggagaaaa   2880
accaacgaca caacagggg tgtactgctc acaggcgct cacactagtg ctgttatcaa     2940
gttcttatcc gttcttacca agccacagtg gtgaactgca accaacaggt ggaaccggtg   3000
aaagattgga tgagcgattg cgtggagaaa cagaaacctg ctcgtcgtag aaatatgtgg   3060
agttgtgggt aggctgcact caagtcaagg attagcacga tcaaacaata atgcaaagta   3120
gaattatagt gcaaaacacg aaactatatt gctggccaca ggtgcaaagg atggatggaa   3180
ctagcagaat ggcagtaccg taaatattgt actagtgatg ccaaaaaggc actagtagaa   3240
atcacaggtg attttgtttt tcttttttgt atgattttt tgatatttt ctcagcacaa     3300 gaagcaacaa gataggagct acacgaagtt tcacctaaaa cagatatcag atgtggtcta   3360
cagaaaatca ggaagttctc tgaaaagcgt gcgagaactt tgacggattt ttttcttat    3420 tttcctgaat ttttttgaca attttgtcga accccaaaca gaccgtaggt gagtttggcc   3480
ggcctcagaa tggtgtcaac tagctcctat aaaaatttca gattttttgg acacccgagc   3540
gaaaagttat gcccggttta cggaaggtac ctcaagttat gttctaaaaa cgaccgggat   3600
gaaacaaccg tatccttct ccttcgttat ctttttttc tgttttttg acgtaaccga      3660 aggagaaaaa caaggaaggt tgactcggtt tgttttttt tgctgttttt ttttcgtaac    3720
cgaaggagaa aatcaaggaa acggccgttg actcggttg ttttttctgt tttttttga     3780 cgtaaccgaa ggagaaaaat aaggaaacga tgttgactcg gtttgtggtg tgatcaaatg   3840
ggagatggtg gcggcgctag ggtttgaatg gtggaagaac acaatgcaac cagcaacaaa   3900
tgacgcgaaa gcacacaaat tcaacaatgc agattattga aagaaagtgt gaggctcaaa   3960
agggtgctgg gataagatct aacctgaatt tttatgtggt tttgtggact gtaggaaaaa   4020
```

```
aaacgctcga taaactcacc gatcaacctg gaaatctgat accaattgat gaagctgagg    4080
tgcccgatct ttcggcaagt agagataatt ccgatttggc ggaagatgac ccttgcgatc    4140
cgactacgac gagcaagccc gaggcgccaa tgcaatcgct gaaccaactc cctgtggtta    4200
ccgaccttgc tgatgcgaga tcggcctgat cacgaagatc gtttcctgtg cgcaatcgaa    4260
gaacgaacaa gaacaagatg cgagcaatct aatctattac tcgagggtgg agttctgaat    4320
acacgaagac agcgcagatt tgcgcgtgtt cgagagtagc taaggctaat gtaaaacaaa    4380
actcaggaaa taaggaggc gcagctcctg aataaataga gaggggcgc agcccctagg      4440 ggcggccaac cctaggtcgt ccattatggg ccgcaattgg gctggtcgtc tattctttcg    4500
ggccttcgtt ctttaacaac atgatgtagt tcaattctct tgcacgggcc cgagtcactg    4560
gcccaggtgg aaggggtggc gcctgggctg gagaaggtgc tgctggtgta gatgtgctcg    4620
tgttggtgtt gatgtccgca tcacttgggt tttgtttgat gtaagtttag cctttgctac    4680
ttccttgtaa acgcgtgtgt cggctagacc acccgaatac ttgaaacggg accccaactt    4740
tatcagatcc gtgcgtgttt gcttgttatc ttgttcttgc ttgttctcga ttgcttgcag    4800
gttcaaggct gttcttggca cggcaagagc agcaacaaca ggagccggtg taactatcgc    4860
taaggcgcag caccccttgtg gttgttgtag tcggatagca caacgtcgac ctccaccca    4920 aatcgtagtt atcaggagat ggtgtacctg tcgctcaagg cgccacacca tcttggttgt    4980
ggtagtcggg cagccaacgt cgttctccaa caagttttcc acctccatca tctctcatcg    5040
aaagatcggg caccccttcta cccgttgggt tcatcagttc cggtggcaaa aactcgtgct    5100
ttgtatgcac catgacaccc gttttcggaa tgggtgagac gtgcgacaac gaaattgtgc    5160
gaaaccaccc caacacatga gttttggacc taaagtagtg gattgggcat gttcgttgca    5220
aaaaacaaag aaatggttcc ggtggcaaaa actcgtgctt tgtatgcacc atgacacccg    5280
ttttcggaat gggtgacgtg cgacaacgaa attgcgagaa accaccccaa acatgagttt    5340
tggacctaaa gtactggatt aggcatgttc gttgcgaaaa acgaagaaat ggttccggtg    5400
gcaaaaactc gtgctttgta tgcacccgac accgttttc ggaatgggtg acgtgcgaca    5460
acgaaattgt gtgaaaccac cccaaacatg agttttggac ctaaagtagt ggattgggca    5520
tgttcgttac gaaaaacgaa gaaatggttc cggtggcaaa aactcgtgct tttatgcacc    5580
ccgatacccg ttttcagaat gggtgacatg cgacaacaaa attgcgcgaa accaccccaa    5640
acatgagttt tggacctaaa gtagtggatt gggcatgttc gttgcgaaaa acgaaggaat    5700
ggttccggtg gcaaaaactc gtgctttat gcacccccgat accgttttc agaatgggtg    5760 acgtgcgaca acgaaactgt gcgaaaccac cccaaacatg agttttggac ctatagtagt    5820
ggattgggca tgttcgttgt gaaaaacgaa gaaatggttc cggtgaaaa aactcgtgct    5880 ttgtatgcac cccgacaacc gttttcggaa tgggtgacgt gcggcaacga aattgcgcga    5940
aaccacccca acatgagtt ttggacctaa agtagtggat tgggcatgtt cgttgcgaaa    6000
aacgaagaaa tggttccggt ggcaaaaact cgtgcttttt attcacccga cacccgtttt    6060
cggaatgggt gacgtgcgac aaagaaattg cgcgaaacca ccccaaacat gagttttgga    6120
tgtaaagtag tggattgggc atgttcgttg tgaaaaacga agaaatggtt ccggtggcaa    6180
aaactcgtgc tttgtatgca cccgacaccc gttttcggaa tgggtgacgt gcgacaacga    6240
aattgtgcga accacccca acatgagtt ttggacctaa agtagtggat tcggcatgtt    6300
cgttacgaaa aacgaagaaa tggttccggt ggcaaaaact cgtgctttta tgcacccccga    6360 tacccgtttt cagaatgggt gacgtgcgac aacaaaattg cgcgaaacca ccccaaacat    6420
```

-continued

```
gagttttgga cctaaagtag tggattgggc atgttcgttg cgaaaaacga agaaatggtt    6480
ccggtggcaa aaactcgtgc ttttatgcac cccgataccc gttttcagaa tgggtgacgt    6540
gcgacaacga aactgtgcga aaccacccca aacatgagtt ttggacctat agtagtggat    6600
tgggcatgtt cgttgtgaaa acgaagaaa tggttccggt ggcaaaaact cgtgctttgt    6660
atgcaccccg acaaccgttt tcggaatggg tgacgtgcgg caacgaaatt gcgcgaaacc    6720
accccaaaca tgagttttgg acctaaagta gtggattggg catgttcgtt gcgaaaaacg    6780
aagaaatggt tccggtggca aaaactcgtg cttttatgca ccccgatacc cgttttcgga    6840
atgggtgaca tgcgacaaca aaattgcgcg aaaccacccc aaacatgagt tttggaccta    6900
aagtagtgga ttgggcatgt tcgttgcgaa aaacgaagaa atggttccgg tggcaaaaac    6960
tcgtgctttg tatgcacccg acccgtttt cggaatggg tgacgtgcga caagaaatt      7020 gcgcgaaacc accccaaaca tgagttttgg atgtaaagta gtggattggg catgttcgtt    7080
gcgaaaaacg aagaaatggt tccggtggca aaaactcgtg ctttgtatgc acccgacacc    7140
cgttttcgga atgggtgacg tgcgacaacg aaattgtgcg aaaccacacc aaacatgagt    7200
tttggaccta aagtagtgga ttgggcatgt tcgttacgaa aaacgaagaa atggttccgg    7260
tggcaaaaac tcgtgctttg tatgcacccc cgacaaccgt tttcggaatg ggtgacgtgc    7320
ggcaacgaaa ttgcgcgaaa ccactccaaa catgagtttt ggacctaaag tagtggattg    7380
ggcatgttcg ttgtgtaaaa cgaagaaatg gttccggtgg caaaaactcg tgctttgtat    7440 gcacccgac aaccgttttc ggaatgggtg acgtgcggca acgaaattgc gcgaaaccac    7500
cccaaacatg agttttggac ctaaagtagt ggattgggca tgttcgttgc gaaaaacgaa    7560
gaaatggttc cggtggcaaa aactcgtgct ttgtatgcac ccgacacccg ttttcggaat    7620
gggtgacgtg cgacaaagaa attgcgcgaa accaccccaa acatgagttt tggatgtaaa    7680
gtagtggatt gggcatgttc gttgcgaaaa acgaagaaat ggttccggtg gcaaaaactc    7740
gtgctttgta tgcacccgac acccgttttc ggaatgggtg acgtgcgaca acgaaattgt    7800
gcgaaaccac accaaacatg agttttggac ctaaagtagt ggattgggca tgttcgttac    7860
gaaaaacgaa gaaatggttc cggtggcaaa aactcgtgct tttatgcacc ccgatacccg    7920
ttttcggaat gggtgatgat gaagacatcc acactactga tgcatctata ccaatacaag    7980
taccaatttc tggtcccatt actcgcgctc gtgctcgtca actcaaccat caggtgatta    8040
cactcttgag ttcatgtcca tcatatttag accatggaga cccgtgcact cttgttttgc    8100
ttaggaatca gggagaagac cgaaagggaa aaggatttga acatgctgga ttcggactgc    8160
agaagaacac caacttgtga cggtcaccac ggtcagatgc gggctcggat tggaatgttc    8220
nngcncnncn tggnnngctt ntcnngtctn ctttcntntg gatccggant tatngtcntt    8280
tctgttctgn ggccgccgtn ntcnttgttt tcttnccgng ncntttcctg cctttcctgc    8340
ccntggtgct gcgtcnccct nttttggccc antgggtcgt gtntcnngtt nggtccnttn    8400
gggncgcntc ctngggttgc ngcncgncc cntnccctt gtggtcgtcc taaggtgttt    8460 ntnnncccc tngccgtcnc cnngccccg aaatgtgttt agatcaagtt tctttccagc    8520
agatggagct tcagcgaatc aagcttgatt catcaggag                            8559
```

<210> SEQ ID NO 66
<211> LENGTH: 10771
<212> TYPE: DNA
<213> ORGANISM: Zea mays

<400> SEQUENCE: 66

```
cgtcctcatg atatcaagct tgattcgctg aagctccaat gtgctggaaa gacgaagaaa      60
tggttccggt ggcaaaaact cgtgctttgt gtgcacccga cacccgtttt cggaatgggt     120
gacgtgcgac aacgaaattg cgagaaatca ccccaaacat gagttttgga cctaaagtag     180
tggattgggc atgttcgttg cgaaaaacga agaaatggtt ccggtggcaa aaactcgtgc     240
tttgtatgca accgacaccc gttttcggaa tgggtgacgt gcgacaacga aattgcgcga     300
aaccacccca acatgagttt tggatctaa agtagtggat tgggcatgtt cgttgcgaaa      360
aacgaagaaa tggttccggt ggcaaaaact cgtgctttgt atgcacccga cacccgtttt     420
cggattgggt gatgtgcgac aacgaaatta cgcgaaacca ccccaaacat gagttttgga     480
tgtaaagtag tggattgggc atgttcgttg cgaaaaacga agaaatggtt ctggtggcaa     540
aaactcgtgc tttgtatgca accgacaccc gttttcggaa tgggtgacgt gcgacaacga     600
aattgcgcga aaccatccca acatgagttt ttggatctaa agtagtggaa ttgggcatgt     660
tcgttgcgaa aaacgaagaa atggttccgg tggcaaaaac tcgtgctttt atgcaccccg     720
atgcccgttt tcagaatggg tgacgtgcga caacgaaact gtgcgaaacc accccaaaca     780
tgagttttgg acctaaagta atggattggg catgttcgtt gcgaaaaacg aagaaatggt     840
tccggtggca aaaactcgtg ctttgtatgc accccgaca accgttttcg gaatgggtga     900
cgtgcggcaa cgaaattgcg cgaaaccacc caaacatga gttttggacc tatagtagtg      960
gattgggcat gttcgttgtg aaaaacgaag aaatggttcc ggtggaaaaa actcgtgctt    1020
tgtatgcacc ccgacaaccg ttttcggaat gggtgacgtg cggcaacgaa attgcgcgaa    1080
accaccccaa acatgagttt tggacctaaa gtagtggatt gggcatgttc gttgcgaaaa    1140
acgaagaaat ggttccggtg gcaaaaactc gtgcttttta ttcacccgac acccgttttc    1200
ggaatgggtg acgtgcgaca aagaaattgc gcgaaaccac cccaaacatg agttttggat    1260
gtaaagtagt ggattgggca tgttcgttgc gaaaaacgaa gaaatggttc cggtggcaaa    1320
aactcgtgct ttgtatgcac ccgacacccg ttttcggaat gggtgacgtg cgacaacgaa    1380
attgtgcgaa accacaccaa acatgagttt tggacctaaa gtagtggatt gggcatgttc    1440
gttacgaaaa acgaagaaat ggttccggtg gcaaaaactc gtgcttttat gcaccccgat    1500
acccgttttc agaatgggtg acatgcgaca caaaattgc acgaaaccac cccaaacatg     1560
agttttggac ctaaagtagt ggattgggca tgttcgttgc gaaaaacgaa gaaatggttc    1620
cggtggcaaa aactcgtgct tttatgcacc ccgatacccg ttttcagaat gggtgacgtg    1680
cgacaacgaa actgtgcgaa accaccccaa acatgagttt tggacctaaa gtagtggatt    1740
gggcatgttc gttgtgaaaa acgaagaaat ggttccggtg gcaaaaactc gtgctttgta    1800
tgcaccccga caaccgtttt cggaatgggt gacgtgcggc aacgaaattg cgcgaaacca    1860
ccccaaacat gagttttgga cctaaagtag tggattgggc atgttcgttg cgaaaaacga    1920
agaaatggtt ccggtggcaa aaactcgtgc tttttattca cccgacaccc gttttcggaa    1980
tgggtgacgt gcgacaacga aattgcgcga aaccacccca acatgagttt ttggatgtaa    2040
agtagtggat tgggcatgtt cgttgcgaaa acgaagaaa tggttccggt ggcaaaaact    2100
cgtgctttgt atgcacccga cacccgtttt cggaatgggt gacgtgcgac aacgaaattg    2160
tgcgaaacca ccccaaacat gagttttgga cctaaagtag tggattcggc atgttcgtta    2220
cgaaaaacga agaaatggtt ccggtggcaa aaactcgtgc ttttatgcac cccgatacac    2280
gttttcagaa tgggtgacgt gcgacaacga actgtgcgaa accaccccaa acatgagtt    2340
ttggacctaa agtagtggat tgggcatgtt cgttatgaaa acgaagaaa tggttccggt     2400
```

```
ggcaaaaact cgtgctttgt atgcaccccg acaaccgttt tcggaatggg tgacgtgcgg    2460
caacgaaatt gcgcgaaacc accccaaaca tgagttttgg acctaaagta gtggattggg    2520
catgttcgtt gcgaaaaacg aagaaatggt tccggtggca aaactcgtg cttttattc     2580 acccgacacc cgttttcgga atgggtgacg tgcgacaacg aaattgcgcg aaaccacccc    2640
aaacatgagt tttggatgta aagtagtgga ttgggcatgt tcgttgcgaa aaacgaagaa    2700
atggttccgg tggcaaaaac tcgtgctttg tatgcacccg acaccgtttt cggaatggg    2760 tgacgtgcga caacgaaatt gtgcgaaacc accccaaaca tgagttttgg acctaaagta    2820
gtggattcgg catgttcgtt acgaaaacg aagaaatggt tccggtggca aaaactcgtg    2880
cttttatgca ccccgatacc cgttttcaga atgggtgacg tgcgacaaca aaattgcgcg    2940
aaaccacccc aaacatgagt tttggaccta aagtagtgga ttgggcatgt tcgttgcgaa    3000
aaacgaagaa atggttccgg tggcaaaaac tcgtgctttt atgcaccccg atacccgttt    3060
tcagaatggg tgacgtgcga caacgaaact gtgcgaaacc accccaaaca tgagttttgg    3120
acctaaagta gtggattggg catgttcgtt gtgaaaaacg aagaaatggt tccggtggca    3180
aaaactcgtg ctttgtatgc accccgacaa ccgttttcgg aatgggtgac gtgcggcaac    3240
gaaattgcgc gaaaccaccc caaacatgag ttttggacct aaagtagtgg attgggcatg    3300
ttcgttgcga aaaacgaaga atggttccg gtggcaaaaa ctcgtgcttt gtatgcaccc    3360
gacacccgtt ttcggaatgg gtgacgtgcg acaagaaat gcgcgaaac caccccaaac    3420 atgagttttg gatgtaaagt agtggattgg gcatgttcgt tgcgaaaaac gaagaaatgg    3480
ttccggtggc aaaaactcgt gctttgtatg cacccgacac ccgttttcgg aatgggtgac    3540
gtgcgacaac gaaattgtgc gaaaccacac caaacatgag ttttggacct aaagtagtgg    3600
attgggcatg ttcgttacga aaaacgaaga atggttccg gtggcaaaaa ctcgtgctttt    3660 tatgcaccc gatacccgtt ttcagaatgg gtgacgtgcg acaacaaaat gcgcgaaac    3720 caccccaaac atgagttttg gacctaaagt agtggattgg gcatgttcgt tgcgaaaaac    3780
gaagaaatgg ttccggtggc aaaaactcgt gcttttatgc accccgatac ccgttttcag    3840
aatgggtgac gtgcgacaac gaaactgtgc gaaaccaccc caaacatgag ttttggacct    3900
aaagtagtgg attgggcatg ttcgttgtga aaaacgaaga atggttccg gtggcaaaaa    3960 ctcgtgcttt gtatgcaccc cgacaaccgt tttcggaatg ggtgacgtgc ggcaacgaaa    4020
ttgcgcgaaa ccaccccaaa catgagttt ggacctaaag tagtggattg agcatgttcg    4080
ttgcgaaaaa cgaagaaatg gttccggtgg caaaaactcg tgcttttat cacccgaca    4140 cccgttttcg gaatgggtga cgtgcgacaa cgaaattgcg cgaaaccacc caaacatga    4200 gttttggatg taaagtagtg gattgggcat gttcgttgcg aaaaacgaag aaatggttcc    4260
ggtggcaaaa actcgtgctt tgtatgcacc cgacaccgt tttcggaatg gtgacgtgc     4320 gacaacgaaa ttgtgcgaaa ccaccccaaa catgagtttt ggacctaaag tagtggattc    4380
ggcatgttcg ttacgaaaaa cgaagaaatg gttccggtgg caaaaactcg tgcttttatg    4440
caccccgata cccgttttca gaatgggtga cgtgcgacaa caaattgcg cgaaaccacc    4500 ccaaacatga gttttggacc taaagtagtg gattgggcat gttcgttgcg aaaaacgaag    4560
aaatggttcc ggtggcaaaa actcgtgctt tgtatgcacc cgacacccgt tttcggaatg    4620
ggtgacgtgc gacaacgaaa ttgtgcgaaa ccaccccaaa catgagtttt ggacctaaag    4680
tagtggattg gcatgttcg ttgcgaaaaa cgaagaaatg gttccggtgg caaaaactcg    4740
tgcttttatg caccccgata cccgttttca gaatgggtga catgcgacaa caaattgca    4800
```

```
cgaaaccacc ccaaacatga gttttggacc taaagtagtg gattgggcat gttcgttgcg    4860
aaaaacgaag aaatggttcc ggtggcaaaa actcgtgctt ttatgcaccc cgatacccgt    4920
tttcagaatg ggtgacgtgc gacaacgaaa ctgtgcgaaa ccaccccaaa catgagtttt    4980
ggacctatag tagtggattg ggcatgttcg ttgtgaaaaa cgaagaaatg gttccggtgg    5040
caaaaactcg tgctttgtat gcaccccgac aaccgttttc ggaatggatg acgtgcggca    5100
acgaaattgc gcgaaaccac cccaaacatg agttttggac ctaaagtagt ggattgggca    5160
tgttcgttgc gaaaaacgaa gaaatggttc cggtggcaaa aactcgtgct ttttattcac    5220
ccgacacccg ttttcggaat gggtgacgtg cgacaacgaa attgcgcgaa accaccccaa    5280
acatgagttt tggatgtaaa gtagtggatt gggcatgttc gttgcaaaaa cgaagaaat    5340
ggttccggtg gcaaaaactc gtgctttgta tgcacccgac accgttttc ggaatgggtg     5400
acgtgcgaca acgaaattgt gcgaaaccac cccaaacatg agttttggac ctaaagtagt    5460
ggattaggca tgttcgttgc gaaaaacgaa gaaatggttc cgctggcaaa aactcgtgct    5520
ttgtatgcac tccgacaccc ttttcggaat gggtgacgtg tgacaacgaa attgcgcgaa    5580
accacccaaa catgagtttt gtacctaaag tagtggattg ggcatgttcg ttgcgaaaaa    5640
cgaagaaatg gttccggtgg caaaaacgcg tgctttgtat gcaccccga caaccgtttt    5700
cggaatgggt gacgtgcggc aacgaaattg cgcgaaacca ccccaaacat gagttttgga    5760
cctaaagtag tggattgggc atgttcgttg cgaaaaacga agaaatggtt ccggtggcaa    5820
aaactcgtgc tttgtatgca cccgacaccc gttttcggaa tgggtgacgt gcgacaacga    5880
aattgtgtga accaccccca acatgagtt ttggacctaa agtagtggat tgggcatgtt     5940
cgttacgaaa aacgaagaaa tggttccggt ggcaaaaact cgtgctttta tgcacctgac    6000
actcgttttc ggaatgagtg acgtgcggca acgaaattgc gcaaaccac ccaaaacatg     6060
agttttgtac ctaaagtagt ggattgggca tgttcgttga gaaaaacgaa gaaatggttc    6120
ctgtggcaaa aactcgtgct ttgtatgcaa ccccacaccc gttttcagaa tgggtgacgt    6180
gcggcatcga aattgcgcga aaccacccaa acatgagtt ttggacctaa agtagtggat     6240
tggcatgttc gttgcgaaaa acaaagaaat agttccggtg gcaaaaactc gtgctttgta    6300
tgcaccatga cacccgtttt cagaatgggt gacgtgcgac aacgaaattg tgcgaaacca    6360
ccccaaacat gagttttgga cctaaagtag tggattgggc atgttcgttg cgaaaatga    6420
agaaatggtt ccggtggcaa aaactcgtgc tttgtatgca cccgacaccc gttttcggaa    6480
tgggtgacgt gcgacaacga aattgtgcga accaccccca acatgagtt ttggacctaa     6540
agtagtggat tgggcatgtt cgttgcgaaa acaaagaaa tggttccggt ggcaaaaact     6600
cgtgctttgt atgcaccatg acaccgtt cggaatggg taacgtgcga caacaaaatt       6660
gcgagaaacc accccaaaca tgagttttgg acctaaagta gtgtattagg catgttcgtt    6720
gcgaaaaacg aagaaatggt tccgctggca aaaactcgtg ctttgtatgc actccgacac    6780
ccttttcgga atgggtgacg tgtgacaacg aaattgcgcg aaaccaccca acatgagtt     6840
ttgtacctaa agtagtggat tgggcatgtt cgttgcgaaa aacgaagaaa tggttccggt    6900
ggcaaaaacg cgtgctttgt atgcaccccc gacaaccgtt ttcggaatgg gtgacgtgcg    6960
gcaacgaaat tgcgcgaaac caccccaaac atgagttttg acctaaagt agtggattgg     7020
gcatgttcgt tgcgaaaaac gaagaaatgg ttccggtggc aaaaactcgt gctttgtatg    7080
cacccgacac ccgttttcgg aatgggtgac gtgcgacaac gaaattgcgc aaaccaccc    7140
caaacatgag ttttggacct aaagtagtgg attgggcatg ttcattgcga aaaacgaaga    7200
```

```
aatggttccg gtggcaaaaa ctcgtgcttt gtatgcaccc gacaccgtt ttcggaatga    7260 gtgacatgcg acaacgaaat tgcgcgaaac caccccaaac atgagttttg gacctaaagt    7320
agtggattgg gcatgttcgt tgcgaaaaac gaagaaatgg ttccagtggc aaaaactcgt    7380
gctttgtatg cacccgacac ccgttttcgg aatgggtgac gtgcgacaac gaaattgcgc    7440
gaaaccacct caaacatgag ttttggacct aaagtagtgg attgggcatg ttcgttacga    7500
aaaacaaaga aatggttccg gtggcaaaaa ctcgtgcttt gtatgcaccc gacaccgtt    7560 ttcggaatgg gtgacgtgcg acaacgaaat tgcgagaaac caccccaaac atgagttttg    7620
gacctaaagt agtggattgg gcatgttcgt tgcgaaaaac gaagaaatgg ttccggtggc    7680
aaaaactcgt gctttgtatg cacccccgac aaccgttttc ggaatgggtg acgtgcggca    7740
acgaaattgc gcgaaaccac tccaaacatg agttttggac ctaaagtagt ggattgggca    7800
tgttcgttgc gaaaaacgaa gaaatggttc cgtggcaaa aactcgtgct ttttattcac    7860
ccgacacccg ttttcggaat gggtgacgtg cgacaacgaa attgcgcgaa accaccccaa    7920
acatgagttt tggatgtaaa gtagtggatt gggcatgttc gttgcgaaaa acgaagaaat    7980
ggttccggtg gcaaaaactc gtgctttgta tgcacccgac accgttttc ggaatgggtg    8040 acgtgcgaca agaaattgc gcgaaaccac cccaaacatg agttttggat gtaaagtagt    8100
ggattgggca tgttcgttgc gaaaaacgaa gaaatggttc cgtggcaaa aactcgtgct    8160 ttgtatgcac ccgacacccg ttttcggaat gggtgacgtg cgacaacgaa attgtgcgaa    8220
accaccccaa acatgagttt tggacctaaa gtagtggatt tggcatgttc gttacgaaaa    8280
acgaagaaat ggttccggtg gcaaaaactc gtgcttttat gcaccccgat acccgttttc    8340
agaatgggtg acgtgcgaca acaaaattgc gcgaaaccat cccaaacatg agttttggac    8400
ctaaagtagt ggattgggca tgttcgttgc gaaaaacgaa gaaatggttc cgtggcaaa    8460 aactcgtgct tttatgcacc ccgatgcccg ttttcagaat gggtgacgtg cgacaacgaa    8520
actgtgcgaa accaccccaa acatgagttt tggacctaaa gtaatggatt gggcatgttc    8580
gttgcgaaaa acgaagaaat ggttccggtg gcaaaaactc gtgctttgta tgcacccccg    8640
acaaccgttt tcggaatggg tgacgtgcgg caacgaaatt gcgcgaaacc accccaaaca    8700
tgagttttgg acctaaagta gtggattggg catgttcgtt gcgaaaacg aagaaatggt    8760 tccggtggca aaaactcgtg ctttttattc acccgacacc cgtttttcgga atgggtgacg    8820 tgcgacaacg aaattgcgcg aaaccacccc aaacatgagt tttggatgta aagtagtgga    8880
ttgggcatgt tcgttgcgaa aaacgaagaa atggttccgg tggcaaaaac tcgtgctttg    8940
tatgcacccg acaccgttt tcggaatggg tgacgtgcga caacgaaatt gtgcgaaacc    9000
accccaaaca tgagttttgg acctaaagta gtggattcgg catgttcgtt acgaaaaacg    9060
aagaaatggt tccggtggca aaaactcgtg cttttatgca ccccgatacc gttttcaga    9120 atgggtgacg tgcgacaaca aaattgcgcg aaaccacccc aaacatgagt tttgaccta    9180 aagtaataaa gttgggcatg ttcgttgcga aaacgaaga atggttcca gtggcaaaaa    9240 ctcgtgcttt gtatgcaccc gacaccgttt tcggaatggg tgacgtgcg acaacgaaat    9300 tgcgcgaaac cacctcaaac atgagttttg gacctaaagt agtggattgg gcatgttcgt    9360
tacgaaaaac aagaaatgg ttccggtggc aaaaactcgt gctttgtatg cacccgacac    9420
ccgttttcgg aatgggtgac gtgcgacaac gaaattgcga gaaccaccc caaacatgag    9480 ttttgtacct aaagtactgg attaggcatg ttcgttgcga aaacgaaga aatggttccg    9540 gtggcaaaaa ctcgtgcttt gtatgcaccc gacaccgttt tcggaatggg tgacgtgcg    9600
```

| | |
|---|---|
| acaacaaaat tgtgtgaaac caccccaaac atgagttttg gacctaaagt agtggattgg | 9660 |
| gcatgttcgt tacgaaaaac gaagaaatgg ttccggtggc aaaaactcgt gcttttatgc | 9720 |
| acctgacact cgttttcgga atgagtgacg tgcggcaacg aaattgcgca aaaccaccca | 9780 |
| aaacatgagt tttgtaccta aagtagtgga ttgggcatgt tcgttgagaa aaacgaagaa | 9840 |
| atggttcctg tggcaaaaac tcgtgctttg tatgcaaccc cacaccgtt ttcagaatgg | 9900 |
| gtgacgtgcg gcaacgaaat tgcgcgaaac caccaaaac atgagttttg gacctaaagt | 9960 |
| agtggattgg catgttcgtt gcgaaaaaca agaaatagt tccggtggca aaaactcgtg | 10020 |
| ctttgtatgc accatgacac ccgttttcag aatgggtgac gtgcgacaac gaaattgtgc | 10080 |
| gaaaccaccc caaacatgag ttttggacct aaagtagtgg attgggcatg ttcgttgcga | 10140 |
| aaaactaaga aatggttccg gtggcaaaaa ctcgtgcttt gtatgcaccc gacaccgtt | 10200 |
| ttcggaatgg gtgacgtgcg acaacgaaat tgtgcgaaac caccccaaac atgagttttg | 10260 |
| gacctaaagt agtggattgg gcatgttcgt tgcgaaaaac aaagaaatgg ttccggtggc | 10320 |
| aaaaactcgt gctttgtatg caccatgaca cccgttttcg gaatgggtga cgtgcgacaa | 10380 |
| cgaaattgtg cgaaaccacc caaaacatga gttttggacc taaagtagtg gattgggcat | 10440 |
| gttcgttgcg aaaaacgaag aaatggttcc ggtggcaaaa actcgtgctt tgtatgcacc | 10500 |
| cgacaccgt tttcggaatg ggtgacgtgc gacaacgaaa ttgtgcgaaa ccacccaaaa | 10560 |
| catgagtttt gtacctaaag tagtggattg gcatgttcg ttgagaaaaa cgaagaaatg | 10620 |
| gttccggtgg caaaaactcg tgctttgtat gcacccgaca cccgttttcg gaatgggtga | 10680 |
| cgtgcggcaa cgaaattgcg cgaaaccacc cgaaacatga gtttctttcc agcacatgga | 10740 |
| gctcagcgaa tcaagcttga ttctcagggc c | 10771 |

<210> SEQ ID NO 67
<211> LENGTH: 15540
<212> TYPE: DNA
<213> ORGANISM: Zea mays

<400> SEQUENCE: 67

| | |
|---|---|
| ccgaaatcta gaatcatcgc cactgctgca tggaagatga acatattagg tctttaatcg | 60 |
| tctctaatcc aaagattttg tagtcaagtt gattcagcaa agtatatctc ctagacaaag | 120 |
| cgtcagcaat gatattctct tttcctttct tgtgcttaat aacataagga aacgattcga | 180 |
| taaattcaac ccacttagca tgtctacggt tcagttttcc ttgactacga atatgtttca | 240 |
| aagattcatg atcagaatga ataacaaact ctttgggcca caaataatgc tgccatgttt | 300 |
| ctaatgttcg cacaagagca tataattcct tatcataagt agaataattt agaacagacc | 360 |
| cactcaattt tcactaaaa tatgcaacag gtttgccttc ttgtaacaaa acaccaccca | 420 |
| atccaattcc actagcatca cattcaagct caaaagtctt attaaaatca ggaagttgga | 480 |
| ggagaggtgc atgtgtcaac ttatctttca gcacgttgaa agcgtgctct tgtactttgc | 540 |
| cccaactaaa atgcactccc ttcttcgtaa gctcattcaa aggtgcagca atggtgctaa | 600 |
| agtccttcac aaaacggcga tagaagccag caagtcctag gaaactccgc acctgtgtga | 660 |
| tagtctttgg cataggccat ccatgtatcg cttctacctt ggcttgatca acctcaattc | 720 |
| cctgtggagt cacaacataa ccaagaaacg aaactcgatc ggtgcaaaat gtgcacttct | 780 |
| caaggttacc aaataaacgt gcatctcgta aagcattaaa aacagcacgc atgtgatcaa | 840 |
| catgttcatc catagatttg ctgtagatca atatatcatc aaagtatact accacaaatt | 900 |
| ttccaatgaa ggcacgcaaa acctcgttca ttaatctcat gaaagtgcta ggtgcattag | 960 |

```
ttaacccaaa aggcatgact aaccactcat acaatccgaa cttagttttg aaagcagttt    1020
tccattcatc tcccaatttc atacgaatct ggtggtaccc actacgcaaa tcaactttag    1080
aaaagacaat ggcaccactc aattcatcaa gcatatcatc taaacgtgga atagggtgtc    1140
gataacgtat ggtgatatta ttaatagccc tacaatcaac acacatacgc catgttccat    1200 cttthat ctttcttagg cactaaaata accggaacag cacacggact aagagactca cgcacgtaac    1260
```
```
ctttcttagg cactaaaata accggaacag cacacggact aagagactca cgcacgtaac    1260
ctttgtcgag tagttcttgc acttgtcgct gaatttcttt tgtttcctct ggatttgtcc    1320
tatatggcgc acgattcggc aaagatgcac caggaataag atcaatttgg tgctcaatcc    1380
ctcgtatagg tggcagcccc tctggtatct cacttggaaa tacatcagaa tactcctgca    1440
aaatgttagt aataacagga ggcaaagaat gctgcatatc ttgaattgaa atcaaaacat    1500
ccttgcatac caaggcgtag gcaacagtag tggaagcaaa taattcatta acatcagttt    1560
ttgttgcaag caagcaatgt cctttcaatt ttatcccatc tttgttatta ccaacagctt    1620
taatattctt gttgttctca gttttagctt tggtagcttt agcaacatca tcacacacaa    1680
tagcctcagg ggacatggga agcaaaataa ttttcttatc atggtgtatg agagaatatt    1740
tatttgatct accatgatgc atacaatctg aatcaaattg ccatggtcta cctagcagaa    1800
tattacaagc atccataggc acaacatcac agtcaacaac atcacgatat gaaccaatag    1860
caaaattaat tcgtaccagc ttggttacct tgaccttacc actattgtta agccattgaa    1920
tgtgatatgg atgcgggtgc ggtttggtcg taagtgcaag cttctccacc atgtcgctgc    1980
tagccaagtt gttgcagcta cctccatcaa tgatcaaacg acatgaacgc tccttaatga    2040
cacactttgt ttgaaacaac gtatgtcgct gattctgctc tgccttctcc atttgtgcac    2100
taagcacacg ctgtacaatg aggctctcat aatgctctgc atcatctgca ccaatctgtt    2160
cttcgggtgg ttccttagtg cctgcatcat cagccgcaag caaagcaagt gtagcttcat    2220
ccaaatcact agcagaggaa tacccaccat cgtcttttac caccaaaaca cgctgattag    2280
gacaatcacg ctgcacgtgt ccatagccct tgcatcgata acacagaaca tctcttgttc    2340
tacccgtgga ggctactgaa gaggcactac ctgctggttt ctgggcagat ttggttgctg    2400
aatttgtgga agatgcacgt ggtttgtcgc cggaggaagg cggggtgct ggtcgacttg    2460 gcgagggagt tggtgctggt gtacggccgg tcatggacgt agtcgtgcgc tgttgccatg    2520
gtgtagattt cctgcagaa acattagacc ttgcactagc acgtcgtccc tgcacttccc    2580
tttcagcttt gcaagcaaga tgaaacaatc gggttacatt agcataatct ttataagcaa    2640
ggatgtcctg aatttcccta tttaacccgc ccaaaaatct agccatagca gattcctcac    2700
actcctctat gttacaacgc aacatcccca tttgtaattc ctgataatat tcttctacac    2760
ttttagtacc ctgtctcaat tgttcaact tgtttaacat atcacgtgca taataagaag    2820
gaacaaatct agcccgcatg acccgtttca acgcatccca agtttgtggc atgttattag    2880
gattcttctt accatgttct atccaccaaa cagaagcaaa ttcagtaaac tcactagtag    2940
cagctctaac ccgcacattc tcaggaaatt catggcatgc aaacttttga tcaaccgcaa    3000
tctcccaagt aatgtaagca tcagggtcat atttaccatc aaaaggaggt attttaaatt    3060
taaccttact aaaagcatca tcattaccat gtacctcacg tcggtgaaaa ccacccatac    3120
ctctacggtt agtacgtagt cgccggcgat taggtgcttc ttggtcatct tgttcagtat    3180
cagcaacata gtcatcccag ttaccttcgg cgccctcatc acgcccacca ttgatattag    3240
catgcatctc atcaaaccgc ctcaagagtg cgacaaggct cttgtcaata tgagcaactg    3300
tcatttccac atttgcaagt ttggtgttcg tgtcgatctg tgtggcctcc aattgcccca    3360
```

```
tcttttcatt cgtcacctgc atgtcattat caagaccttc cgtgtgcgtc ttcactagcc    3420
ttacaaagtg ttgtatgata cccttggtgc gaggagagtg tggcatatta cgagaagcat    3480
catcaacctc caatcctgcc atggttagac gaacagaggc aacaagaaaa aaaaacgtga    3540
aggaatgaaa actctacaac tattaggatg tagctactgc aaggcgctca ctctcaacct    3600
gccacacaag ctcttaccaa ttcttacctt gcacaacagg aggggtcagc aaccaacaag    3660
tctgcaaccg tggaataagt gtatcggtgc cgcagcaaca cgacctgtca aactgtagtc    3720
gaaatatgta gagttgtagg tgggctgaag caaggaatac actagtacca cgttagttac    3780
aaaagcaagc tgaataatcg ttcaacggtg gtactgtgct ggtcctaggc taaaccaggt    3840
tagagacgtg agcctaggca caaggtagt cactgaaaaa gaacaactag cacagcacaa     3900
agagaaacaa cagatttaga gattcagccc ccttcttctt cttttccttt ttttttctat    3960 tcttttttt tcttcttctt cttctgtttt tttttgcagg ggcttaaacc ctttttttcac    4020 tatgacaacc caaacaataa agatattgct aacagcccct ttaaatcaga tttaacaaat    4080
cttgttaata tagaaagtcc agaaatctct acgatgattg cggagcgctc agaacgaatt    4140
ttgagataag gtcagatccg ttggaaagaa gataagataa gctttctaga ttgtatttaa    4200
acttccaaat cggatatgat atgtatccgt ggtggcaaaa acgaaccaga tatgttttg     4260 gtgatggtgg atctcgtggt gaccaaaacg tggtagaact caaaactcta aaggaataaa    4320
ctaagaccag caactcgaca caaccgatgc aaccaaaaac tcaacaagcc ctaactaagt    4380
agtactagta aatgctcaat ggtttatagg attgcggtaa aactaatcta ctattttttt    4440 ggcttttct ggactatagg agataagaaa acagcgaaga aaagtaaatc tctcaccgat      4500
aaaccttgct ctgattacca actgatgtgc acccgttggg tgattgcccg atctttcgat    4560
gagagggtgt ggaataactc gattggggga ggagacgacg ttcacggccc gactacagcc    4620
ttccaaagac gctgcgcctt agcaaccgat acaccacctc ctatggctgt cacgatcttg    4680
tggagcgtga caccctggcc actagggcac tcgtcctgca agcaatcgaa gaactagcaa    4740
gaacaagtag aacaagtact gaattaccag atctaaatgt aggtttaaag atcaaactac    4800
aatatggtgg ggttccgaag acaagaagac gggcggctga actagcacgc gcgcttgcaa    4860
gcaagtagcg agagctaaac ttgatctaaa caaacccgc tgttcttggt ggcagctagg      4920
gggtttataa acatgggagg acgaccacaa gggtattggg gtcgtgctgc aaccctagga    4980
tgcgtcccta atggacctaa cttgatacac gacccattgg gccaaaatag ggtgacgcag    5040
caccatgggc agaaaaggca ggaaatgtct cggtaataaa acaatgatta cggcggcctc    5100
agaacagata tgactataat tccggatcca tatgaaagta gacttgataa gctttccatg    5160
ttgtgcttga acattccaat ccgagcccgc atctgaccgt ggtgaccgtc acaagttggt    5220
gttcttctgc agtccgaatc cagcatgttc aaatcctttt cccttcggt cttctccctg      5280 attcctaagc aaaacaagag tgcacgggtc tccatggtct aaatatgatg gacatgaact    5340
caagagtgta atcacctgat ggttgagttg acgagcacga gcgcgagtaa tgggaccaga    5400
aattggtact tgtattggta tagatgcatc agtagtgtgg atgtcttcat cattcagtgc    5460
catcgttgta gagggtttgg gcatatgatt cgggactgcc caaacaagcg taccttgctt    5520
atacgtgaca atggtgagta ctcttcagcc agtgattctg aggaaactag tcatgctatg    5580
attgccacta accatgcaga aaatgaggaa gtccacgttg atcctatcga cgccgatagg    5640
tatgagagtc ttgttgtgca gcgtgttctc agcacacagg ttgcccaggc cgaaaaaaat    5700
cagcgacaca ctctattcca taccaagggc gtcgtgcacg aacggtcgat tcgcatcatc    5760
```

-continued

| | |
|---|---|
| atcgatagtg gcagctgcaa caatttggca agtacagcgt tggtagagaa attatccttg | 5820 |
| cccactcgca cacatccaca tccgtatcac attcaatggc ttaatgatgg tggtaaaata | 5880 |
| aaggtaacac gttcggtacg tgtccccttt tcgctgggtt cttattctga ttatgctgat | 5940 |
| tgcgatgtta ttcctatgga agcatgctct ttgttattag gtcgaccttg gcaatatgat | 6000 |
| actgatagtt tacatcatgg tcgttcaaat cattattctt tcatgtttaa aggccagaaa | 6060 |
| ataattatac atccaatgac ccctgaccaa attttgaaag atgatcttac tagggctgct | 6120 |
| aaaactgcac aacaagtcaa atcgacatca gccgcaccta ttaaatctga atcaagttg | 6180 |
| cactctcctg ttttacttgc tacacgtgct gattttgatg atctccatga agctcatatg | 6240 |
| ccctgttatg cacttgtatg ctcgcgaatg attgttccgc ttgatgatgc aacgtctttg | 6300 |
| gatatacccc ctgctgttgt taaccttttg caggagtatg ctgatgttta tcctacggac | 6360 |
| ttaccaccgg gtcttcctcc cctccgtggc attgagcatc agatcgatct catccccggc | 6420 |
| gcttctcttc cgaaccgcgc cccgtaccgt acaaatccag atgagacgaa ggagatccag | 6480 |
| cgccaggtgc agacgctgct tgataagggt tacattcgtg agtctcttag cccttgctcg | 6540 |
| gttcctgttt tactcgtccc aaagaaagat gggtcatggc gtatgtgcgt agattgtcgt | 6600 |
| gctattaata acatcacagt tcgttatcga tatcctattc cacgccttga tgatatgcta | 6660 |
| gatgagctta gtggtgccgt tattttctct aaggttgatt tgcgtagcgg ttaccatcag | 6720 |
| attagaatga aactcggtga tgaatggaaa acggcttta aaacgaaatt tggtttatat | 6780 |
| gaatggttgg ttatgccatt tggattgact aatgctccca gcacctttat gcgtttaatg | 6840 |
| aacgaagttc tacgggcctt cataggtttg tttgttgttg tttatttcga tgatatccTT | 6900 |
| atttacagca agtctataga ggagcattta gaacatttgc gtgctgtttt tgacgctttg | 6960 |
| cgtgctgctc gcttgtttgg taacatggaa aagtgcacat tttgcacgca acgtgtctcg | 7020 |
| tttcttggtt atgtggttac tccgcagggc attgaggtgg atagcagcaa gattgctgcc | 7080 |
| attcgggagt ggcctacacc gacgacggtc acacaaattc ggagctttct tggacttgcc | 7140 |
| ggtttctacc gcagatttgt tcgtgatttt agctccattg cagcgcctct acatgagctt | 7200 |
| acaaagaaag atgtgccgtt tgcttggagt gattcgcagg aggtagcgtt cagcactttg | 7260 |
| aaagataagt taacccaagc tcccctattg caattgcctg attttaataa agtgtttgag | 7320 |
| cttgaatgcg atgctagcgg tattgggcta ggtgctgttt tgttacaaga aggaaaacca | 7380 |
| gttgcttatt ttagtgaaaa attaagcggt gctagtctga atattctac ttatgataag | 7440 |
| gagctttacg ctttagtgcg cactttgcat acatggcagc actatctttg gcatcgtgag | 7500 |
| tttataatcc attctgatca tgaggcttta aaacatattc gtacccaaac aaatctgaac | 7560 |
| cgtcgtcatg ctaaatgggt agaattcatt gagtcctttc cttacattat taaacacaag | 7620 |
| aacgggaagg acaatgttat tgctgatgct ttgtctcgtc gctataccat gctgtcacag | 7680 |
| ttagattta aaatctttgg tttggacact gtgaaggatc aatatgttga cgatgctgat | 7740 |
| tttaaagatg ctttcggtca ttgtattaat gggaaaccat ggggcaaatt tcacatacag | 7800 |
| gatgggttcc tgtttcgcgc taacaagctg tgtgttccag ctagctcggt tcgtctttg | 7860 |
| ttgttacagg aagcgcatgg aggcggtctc atggggcatt tcggcctcta caagacacat | 7920 |
| gaggttttgg ctgcccattt cttttggcct cggatgcgcg ctgatgtgga gcgccttgtt | 7980 |
| gcacgctgca ctacttgtca gaaagctaag tcacggttga caaccatgg tttgtatatg | 8040 |
| cctttgcctg tccttcttc tccttggctt gatatctcta tggactttgt tttgggcttg | 8100 |
| cctagaacta agaaggggag ggatagtatt tttgtggttg ttgatagatt ctctaaaatg | 8160 |

```
gctcacttta taccttgtca taaaactgat gatgctagca ttgttgctga attgttcttt    8220
agagaaatta ttcgtttaca tggtattcca aaaacaatag tctctgatcg cgatgctaag    8280
tttctaagcc attttggag atctctttgg aataaattgg gaactaaatt gttgtttagc     8340
actacttgtc accctcagac tgatggacaa actgaggtag taaatagaac tttatctacc    8400
atgcttaggg ctgttttaga caagaatttg agacgttggg aggattgctt gcctcatgtt    8460
gaatttgctt acaatcatgc cacgcattct tctacaaaga tgtgcccttt ccagattgtt    8520
tatggttaca ttcctagggc acctattgat ttgatttcac ttaatgctgc gaacgcccca    8580
catgtagatg cttctgcaca tgttaacaa atgattacca tacatgaaca aacgaaacag     8640
aacattgctg ctactaatac aaaaaatcag gttgctggta gtaaaggaag aaaacatgtt    8700
acttttgaac ctggtgatat ggtttggttg catttgagaa aggatcgttt tcctactttg    8760
cgccgttcta aattgatgcc tcgtgctgct ggtccttta  agatactaac caagattaat    8820
gataatgctt atacctcga  cctacctgcg gagtttggtg tttccactag ttttaatgtt    8880
gcagatttga aaccgtatgc gggagaagat gaggagttgc cgtcgaggac gacttcagtt    8940
caagaagggg aggatgatgc ggacatcaac accaacacga gcacatctac accagcagca    9000
ccttctccag cccaggcgcc accccttcca cctgggccag tgactcgggc ccgtgcaaga    9060
gaattgaact acatcatgtt gttaaagaac gaaggcccgg aagaatagac gaccagccca    9120
attgcggccc ataatggacg acctagggtt ggccgcccct aggggctgcg ccccctctct    9180
atttattcag gagctgcgcc tcctttattt cctgagtttt gttttacatt agccttagct    9240
actctcgaac acgcgcaaat ctgcgctgtc ttcgtgtatt cagaactcca ccctcgagta    9300
atagattaga ttgctcgcat cttgttcttg ttcattcttc gattgcgcac aggaaacgat    9360
cttcgtgatc aggccgatct cgcatcagca aggtcggtaa ccacagggag ttggttcagc    9420
gattgcattg gcgcctcggg cttgctcgtc gtagtcggat cgcaagggtc atcttccgcc    9480
aaatcggaat tatctctact tgccgaaaga tcggcacct  cagcttcatc accaagttct    9540
ttggtggctg ctagttgctt aaatagaaa  ataggaagaa ggaattctgg tggagtcatg    9600
aagttccctc ggcagtttct ggacgcctcg ggtgtagtct cccattaatt cttgatccac    9660
cagcaagtag acgaagggag ctttccaaca agtatttatt tgcattaaac ggccttggaa    9720
gttggaagat atgccccatt taaacttgta tttggtgctg ttacgaaatc ctctcgggtg    9780
cagcagcctt tattgccttg ttgccttctc cagtccaaga tggttcacct cccaaacacc    9840
tgagcataat aaagtcatcg caaggcttta gtacctcatt taaagaagaa ttagcttcaa    9900
tagcaaagaa cgagttcacc tgataattaa gtttacgtgc acgggctcgt gtcattggtc    9960
cttgattagc tacgaatggt gaagtggtca ctggtatggt tgtatcaatg atagtgatgt    10020
cctcatcatc ctccccttct tgcaacaaag tcgtcctcga ctcaaacgtg tcattctctc    10080
ccaagtatgt tgttaaatct gcaatgttaa aagaggaact cacccccaaaa tctgcaggca   10140 actgaacttt atatgcatta tcattaattt tgtgaagcac tttgaagggt ccagcagctc    10200
ttggttgtaa tttagatttg cgcatatcag ggaatctatc tttccttaaa tgcacccata    10260
ctaaatcacc aggttcaaag gtaatatgct ttctacccctt gctacctgct tcttcatact   10320
tagcattcat ggctttaata tttgctttag tttgttcatg cagctttata atcagttcag    10380
cacgacgaga agcatcaaaa ttcattattt cagaatgtgg gatggcgata agatcaatag    10440
gagcacgagg gacaaaacca tacacaattt taaagggca  tagtttagtt gtagaatgct    10500
gagaacgatt ataagcaaat tcaatgtgag gcaaacattc ttcccacaat ttgatgttat    10560
```

```
gtttcagaac agccctaagc atggtagata aactacggtt tacgacttcg gtttgtccat   10620
cggtttgagg gtgacaagta gtagaaaaga gcaatttagt tcccaactta gcccataacg   10680
ttttccaaaa atgactaaga aatttggtat cccgatcgga cacaatagtg tttggaaccc   10740
catgcaaacg aacaacttca cgaaagaaca aatcagcaac atgggtagcg tcatcagttt   10800
tgtgacatgg tataaagtgt gccattttg aaaatctgtc cacaacaaca aaaatactat    10860
ccctcccctt ctttgttcta ggtattccta aaacaaagtc catagaaata tcctcccatg   10920
gtgcactggg aactgggaga ggcatgtata aaccatgtga attaaggcga gacttagctt   10980
tttgacatgt agtgcagcga gcaacaaatc gctccacgtc tcttctcatc ttcggccaaa   11040
agaaatggct ggccaggatg tcttatgtct tcttcacacc aaagtgtccc atcaacccac   11100
cgccatgtgc ttgctgtaat aataatatac gcacggaacc agctggaatg cataatttgt   11160
tagcccgaaa cacaaagcca tcagtgagaa caaatttgtt ccatgtcctt ccttctttac   11220
aatgtaatag cacatctttg aaatcagcat cgaaaacata ttcttgttta attgtttcca   11280
agccaaaaat cttaaaatca agttgagaca gcatggtata acggcgagac aaggcatctg   11340
caatgacatt atcttttcct ttcttatgtt tgatgcacata gggaaaagat tcaataaatt   11400
cgacccactt ggcatgccta cggttcagat ttgtttggct ccttagatgc tttaaagatt   11460
catgatcaga atgtataaca aattcttag gccataagta gtgttgccat gtttccaaag    11520
ttcgaactaa ggcatataat tctttatcat aagtggaata gttcagactg ggtccattca   11580
gtttctcact aaaataagca acaggcttcc cttcttgcaa caagacacca cccaaaccaa   11640
taccactagc atcacattcc aattcaaaag tcttactaaa atcaggtaat tggagaaggg   11700
gtgtatgagt taacctatcc ttcaatgttt caaatgcaac ctcttgtgcc ttgccccaag   11760
aaaaaggagc acccttctta gtaagctcgt gcaatggccc tgcgatggtg ctgaaatctt   11820
tcacaaatcg acgatagaac cccgcaagcc cgagaaagct tcggacttgc gtgaccgtgg   11880
tagggactgg ccagctatgt atggcctcca ccttagcctg atcaacttca attccctgcg   11940
gtgtcacaac atagccaaga aaagagacac ggtctgtgca aaatgtgcac ttgtcaaggt   12000
tatcaaataa gcgtgcttca cgtaaagcat tgaaaacaac acgtagatga tcaagatggt   12060
ctactagaca tttgttatag atccccgggt accgagctcg aattcgccct atagtgagtc   12120
gtattacaat tcactggccg tcgttttaca acgtcgtgac tgggaaaacc ctggcgttac   12180
ccaacttaat cgccttgcag cacatccccc tttcgccagc tggcgtaata gcgaagaggc   12240
ccgcaccgat cgcccttccc aacagttgcg cagctgaatg gcgaatggcg cctgatgcgg   12300
tattttctcc ttacgcatct gtgcggtatt tcacaccgca tatggtgcac tctcagtaca   12360
atctgctctg atgccgcata gttaagccag ccccgacacc cgccaacacc cgctgacgcg   12420 aacccccttgc ggccgcatcg aatataactt cgtataatgt atgctatacg aagttatggc   12480
gcgccaccgg tgggatccaa acagtcactt aggatatgtt tggaagcaca ccgacatgtt   12540
tggaagcaca ccagttttaa aaactatttt tctatcctca ctttcttgaa aatgtttat    12600 gaaaaaaatt gggtggggtg tttggaacct agtttctagt tttttataa ggagaatagc    12660 ttcttggttt tagttatggg agagtagctt cttggttttt aagaaactaa gaatccagtt   12720
tttataaact gagacataaa caagtatatt tggaatcact ctagtttgta caaaccaatt   12780
tcttagaaat tggatgctta taaataggcc ctcaatgtcc ttgttgggtt tatgaaattt   12840
acatctatta ccattatttt aaaaatagac gaagaatatg ttagtaatta tgtataaaaa   12900
actagaaact attttaaaaa aaactgagtt ccagttacct ttatctaatt cttttataag   12960
```

```
ctaattttta gacactgagg atagaaactg ttttaaaaa  actggtgtgc ttctgtttaa   13020
ctcttcgtaa gaacagtggt acgtcccgtg tctatatttg gcttttgtta aagccaacag   13080
tacatgcttg cgtgggtgaa aatgtgaaat gccatcgctg tgctacaact tttcggctcc   13140
ctcctgcttc ggtgcttcca catgcccctg cacggcgtct agaaatccta atgatttagc   13200
agcacacctg tccgcctagc cgcctacgcg tacacagaaa acaattttt  tgtccacaca   13260
cgcgcgcgct ccgagccgca gatccgagct agcgcggcgc atccgacggc cacgacagcg   13320
cagtgccgtc ctccgccgcc accgcttggc gattgtccgc accccaccag tccaccacct   13380
cccccacgag cgaaaaccac ggtccacgga ccacggctat gttccactcc aggtggaggc   13440
tgcagccccg gtttcgcaag ccgcgccgtg gtttgcttgc ccacaggcgg ccaaaccgca   13500
ccctccttcc cgtcgtttcc catctcttcc tcctttagag ctaccactat ataaatcagg   13560
gctcattttc tcgctcctca caggctcatc tcgctttgga tcgattggtt tcgtaactgg   13620
tgagggactg agggtctcgg agtggattga tttggggttc tgttcggaga tttgcggagg   13680
gaggccttgg taccggtgat caagtgcaaa ggtccgcctt gtttctcctc tgtctcttga   13740
tctgactaat cttggtttat gattcgttga gtaattttgg ggaaagcttc gtccacagtt   13800
tttttcgat gaacagtgcc gcagtggcgc tgatcttgta tgctatcctg caatcgtggt   13860
gaacttattt cttttatatc ctttactccc atgaaaaggc tagtaatctt tctcgatgta   13920
acatcgtcca gcactgctat taccgtgtgg tccatccgac agtctggctg aacacatcat   13980
acgatctatg gagcaaaaat ctatcttccc tgttctttaa tgaaggacgt cattttcatt   14040
agtatgatct aggaatgttg caacttgcaa ggaggcgttt ctttctttga atttaactaa   14100
ctcgttgagt ggccctgttt tcggacgta  aggcctttgc tgctccacac atgtccattc   14160
gaattttacc gtgtttagca agggcgaaaa gtttgcatct tgatgattta gcttgactat   14220
gcgattgctt tcctggaccc gtgcagctgc ggtggcaagg gaggccggca agcgctagcg   14280
ctaccggtcg ccaccatggc ctcctccgag aacgtcatca ccgagttcat gcgcttcaag   14340
gtgcgcatgg agggcaccgt gaacggccac gagttcgaga tcgagggcga gggcgagggc   14400
cgcccctacg agggccacaa caccgtgaag ctgaaggtga ccaagggcgg ccccctgccc   14460
ttcgcctggg acatcctgtc ccccagttc  cagtacggct ccaaggtgta cgtgaagcac   14520
cccgccgaca tccccgacta caagaagctg tccttccccg agggcttcaa gtgggagcgc   14580
gtgatgaact tcgaggacgg cggcgtggcg accgtgaccc aggactcctc cctgcaggac   14640
ggctgcttca tctacaaggt gaagttcatc ggcgtgaact tccctccga  cggccccgtg   14700
atgcagaaga gaccatggg  ctgggaggcc tccaccgagc gcctgtaccc ccgcgacggc   14760
gtgctgaagg gcgagaccca aaggccctg  aagctgaagg acggcggcca ctacctggtg   14820
gagttcaagt ccatctacat ggccaagaag cccgtgcagc tgcccggcta ctactacgtg   14880
gacgccaagc tggacatcac ctcccacaac gaggactaca ccatcgtgga gcagtacgag   14940
cgcaccgagg gccgccacca cctgttcctg agatctcgag ctgatccaaa aagaagaga    15000
aaggtagatc caaaaagaa  gagaaaggta gatccaaaaa agaagagaaa ggtaggatcc   15060
accggatcta gataactgat cataatcagc cataccacat ttgtagaggt tttacttgct   15120
ttaaaaaacc tcccacacct cccctgaac  ctgaaacata aaatgaatgc aattgcagcg   15180
cttgagctct cctaggtccg cggaggcaat gccagcctgc cctttcgatg aggaggtaca   15240
tacacgctgg cgatggaccg cgcttgtgtg tcgcgttcag tttggctttt gccaagcagt   15300
agggtagctt cccgcgtcgg taattatatg gtatgaacca tcacctttg  gctctacatg   15360
```

```
gtatgaacgt aagatacaaa ttccaactac ctctagctcg ccgcactagt tcctgcaggt      15420
tggcccacgt ggcctctcga gtgtttaaac tcggaccgta tcgatttatt caacaaagcc      15480
gccgtcccgt caagtcagcg taatgctctg ccagtgttac aaccaattaa ccaattctga      15540
```

<210> SEQ ID NO 68
<211> LENGTH: 14443
<212> TYPE: DNA
<213> ORGANISM: Zea mays

<400> SEQUENCE: 68

```
ggaagctttc cagcaatttc gttgccgcac gtcactcatt ccgaaaacga gtgtcaggtg        60
cataaaagca cgagtttttg ccaccggaac catttcttcg ttttcgtaa cgaacatgcc       120 caatccacta ctttaggtcc aaaactcatg tttggggtgg tttcacacaa tttcgttgtc       180
gcacgtcacc cattccgaaa acgggtgtcg ggtgcataca aagcacgagt ttttgccacc       240
ggaaccattt cttcgttttt cgcaacgaac atgcctaatc cagtacttta ggtccaaaac       300
tcatgtttgg ggtggtttct cgcaatttcg ttgtcgcacg tcacccattc cgaaaactgg       360
tgtcatggtg catacaaagc acgagttttt gccaccggaa ccatttcttt gttttttgca       420
acgaacatgc ccaatccact actttaggtc caaaactcat gtgttggggt ggtttcgcac       480
aatttcgttg tcgcacgtct cacccattcc gaaaacgggt gtcatggtgc atacaaagca       540 cgagttttg ccaccggaac catttctttg ttttcgcaa cgaacatgcc caatccacta       600
ctttaggtcc aaaactcatg tttgggtgg tttcgcgcaa tttcgttgcc gcacgtcacc       660
cattccgaaa acgggtgtcg ggtgcataca aagcacgagt ttttgccact ggaaccattt       720
cttcgttttt ctcaacgaac atgcccaatc cactacttta ggtacaaaac tcatgttttg       780
ggtggtttca cgcaatttcg ttgccgcacg tcactcattc tgaaaacgag tgtcgggtgc       840
ataaaagcac gagtgtttgc caccggaacc atttcttcgt ttttcgcaac gaacatgccc       900
aatccactac tttaggtcca aaactcatgt ttgaggtgg ttcgcgcaat ttcgttgtca       960
cacgtcacct attctgaaaa cgggtatcgg ggtgcataaa agcacgagtt tttgccaccg      1020
gaaccatttc ttcgttttc gtaacaaaca tgcccaatcc actactttag gtcgtttcgc      1080
acaatttcgt tgtcgcacgt cacccattcc gaaaacgggt gtcatggtgc atacaaagca      1140
cgaatttttg ccaccggaac catttcttcg ttttcgcaa cgaacatgcc caatccacta      1200
ctttaggtcc aaaactcatg tttggggtgg tttcgcacaa tttcgttgtc gcacgtcacc      1260
cattctgaaa acgggtgtca tggtgcatac aaagcacgag ttttgccac cggaaccatt      1320 tctttgtttt tcgcaacgaa catgcccaac ccactacttt aggtccaaaa ctcatgtttg      1380
gggtggtttc gcgcaatttc gttgtcgcac gtcacccatt ccgaaaacgg tgtcgggtg      1440 catacaaagc acgagttttt gccaccggaa ccatttcttc gttttcgca acgaacatgc      1500 ccaatccact actttaggtc caaaactcat gtttggggtg tttcacgca atttcgttgt      1560 cgcacgtcac ccattccgaa acgggtgtc gggtgcatac agagctcgag ttttgccac      1620 cggaaccatt tcttcgtttt tcgcaatgaa catgcccaat ccactacttt aggtccaaaa      1680
ctcatgtttg gggtggtttc gcgcaatttc gttgtcgcac gtcacccatt ccgaaaacgg      1740
gtgtcgggtg catacaaagc acgagttttt gccaccggaa ccatttcttc gttttcgca      1800 acgaacatgc ccaatccact actttaggtc caaaactcat gtttggggtg atttctcgca      1860
atttcgttgt cgcacgtcac ccattccgaa acgggtgtc gggtgcatac aaagcacgag      1920 ttttgccac cggaaccatt tcttcgtttt ttgtaacgaa catgcccaat ccactacttt      1980
```

-continued

```
aggtccaaaa ctcatgtttg gggtggtttc gcgcaatttc gttgtcacgc gtcacccatt    2040
ccgaaaacgg gtgtcggagt gcatacaaag cacgagtttt tgccaccgga accatttctt    2100
tgttttcgc aacgaacatg cccaatccac tattttaggt ccaaaactca tgtttggggt    2160
ggtttcgcac aatttcgttg tcgcacgtca cctattccga aaacaggtgt catggtgcat    2220
acaaagcacg agttttttgcc accggaacca tttcttcgtt tttcgcaacg aacatgccca    2280
atccactact ttaggtccaa aactcatgtt tggggtggtt tcgaacaatt tcgttgtcgc    2340
acgtcaccca ttccgaaaac gggtgtcatg gtgcatacaa agcacgagtt tttgccaccg    2400
gaaccatttc tttgttttc gcaacgaaca tgcccaatcc actactttag gtccaaaact    2460
catgtttggg gtggtttcgc gcaatttcgt tgccgcatgt cacccattcc gaaaacgggt    2520
atcggggtgc ataaaagcac gagttttttgc caccggaacc atttcttcgt ttttcgcaac    2580
gaacatgccc aatccactac tttaggtcca aaactcatgt ttggggtggt ttcgcgcaat    2640
ttcgttgtcg cacgtcaccc attccgaaaa cgggtgtcgg gtgcatacaa agcacgagtt    2700
tttgccaccg gaaccatttc ttcgttttt gtaacgaaca tgcccaatcc actactttac    2760
atccaaaact catgtttggg gtggtttcgc gcaatttcgt tgtcgcacgt cacccattcc    2820
gaaaacgggt gtcgggtgaa taaaaagcac gagttttttgc caccggaacc atttcttcgt    2880
ttttcgcaac gaacatgctc aatccactac tttaggtcca aaactcatgt ttggggtgat    2940
ttcgcacaat ttcgttgtcg cacgtcaccc attccgaaaa cgggtgtcgg gtgcatacaa    3000
agcacgagtt tttgccaccg gaaccatttc ttcgtttttt gtaacgaaca tgcccaatcc    3060
actactttag gtccaaaact catgtttggg gtggtttcgc gcaatttcgt tgtcgcacgt    3120
cacccattcc gaaaacgggt gtcgggtgaa taaaaagcac gagttttttgc caccggaacc    3180
atttcttcgt ttttcgcaat gaacatgccc aatccactac tttaggtcca aaactcatgt    3240
ttggagtggt ttcgcgcaat ttcgttgccg cacgtcaccc attccgaaaa cggttgtcgg    3300
gggtgcatac aaagcacgag ttttttgccac cggaaccatt tcttcgtttt tcgcaacgaa    3360
catgcccaat ccactacttt aggtccaaaa ctcatgtttg gggaggtttc gcacaatttc    3420
gttgtcgcac gtcacccatt ctgaaaacgg gtatcggggt gcataaaagc acgattttt    3480
gccaccggaa ccatttcttc gttttttcgca cgaacatgc ccaatccact actttaggtc    3540
caaaactcat gtttggggtg gtttcgcgca attttgttgt cgcacgtcac ccattctgaa    3600
aacgtgtatc ggggtgcata aaagcacgag ttttttgccac cggaaccatt tcttcgtttt    3660
tcgtaacgaa catgccgaat ccactacttt aggtccaaaa ctcatgtttg ggtggtttc    3720
gcacaatttc gttgtcgcac gtcacccatt ccgaaaacgg gtgtcgggtg catacaaagc    3780
acgagttttt gccaccggaa ccatttcttc gttttttcgca acgaacatgc ccaatccact    3840
actttacatc caaaactcat gtttggggtg gtttcgcgca atttcgttgt cgcacgtcac    3900
ccattccgaa aacgggtgtc gggtgaataa aagcacgag ttttttgccac ctgaaccatt    3960
tcttcgttt tcgcaacgaa catgcccaat ccactacttt aggtccaaaa ctcatgtttg    4020
gggtggtttc gcgcaatttc gttgccgcac gtcacccatt ccgaaaacgg ttgtcggggg    4080
tgcatacaaa gcacgagttt ttgccaccgg aaccattct tcgttttttcg caacgaacat    4140
gcccaatcca ctactttagg tccaaaactc atgtttgggg tggttttcgca cagtttcgtt    4200
gtcgcacgtc acccattctg aaaacgggta tcggggtgca taaaagcacg agttttttgcc    4260
accggaacca tttcttcgtt tttcgcaacg aacatgccca atccactact ttaggtccaa    4320
aactcatgtt tgggatggtt tcgcgcaatt ttgttgtcgc acgtcaccca ttctgaaaac    4380
```

```
gggtatcggg gtgcataaaa gcacgagttt ttgccaccgg aaccatttct tcgttttttcg    4440 taacgaagat gcagaatcca ctactttagg tccaaaactc atgtttgggg tggtttagca    4500
caatttagtc gttgcacgtc acccattccg aaaacgggtg tcgggtgcat acaaagcacg    4560 agttttttgcc accggaacca tttcttcgtt tttcgcaacg aacatgccga atccactact    4620
ttaggtccaa aactcatgtt tggggtgatt tctcgcaatt tcgttgtcgc acgtcaccca    4680
ttccgaaaac gggtgtcggg tgcatacaaa gcacgagttt ttgccaccgg aaccatttct    4740 tcgttttttcg caacgaacat gcccaaccca ctactttagg tccaaaactc atgtttgggg    4800
tggtttcgcg caatttcgtt gccgcacgtc acccattctg aaaacggttg tcggggtggg    4860
gtgcatacaa agcacgattt ttgccaccgg aaccatttct tcgtttttag caacgaacat    4920
gcccaatcca ctactttagg tacaaaactc ttgtttgggg tggtttcgcg caatttcgtt    4980
gccgcacgtc acccattccg aaaacgggtg tcgggtgcat acaaagcacg agttttttgcc    5040 accggaacca tttcttcgtt tttcgcaacg aacatgccca atccactact ttaggtccaa    5100
aactcatgtt tggggtggtt tcgcgcaatt tcgttgtcgc acgtcaccca ttctgaaaaa    5160
gggtatcggg gtgcataaaa gcacgagttt ttgccaccgg aaccatttct tcgttttttcg    5220 caacgaacat gcccaatcca ctactttagg tccaaaactc atgtttgggg tggtttcgcg    5280
caattttgtt gtcgcacgtc acccattctg aaaacgggta tcggggtgca taaaagcacg    5340 agttttttgcc accggaacca tttcttcgtt tttcgcaacg aacatgccga atccactact    5400
ttaggtccaa aactcatgtt tggggtggtt tcgcacaatt tcgttgtcgc acgtcaccca    5460
ttccgaaaac gggtgtcggg gtgcatacaa agcacgagtt tttgccaccg gaaccatttc    5520
ttcgtttttc acaacgaaca tgcccaatcc actactttag gtccaaaact catgtttggg    5580
gtggtttcgc acagtttcgt tgtcgcacgt cacccattct gaaaacgggt atcggggtgc    5640
ataaaagcac gagttttttgc caccggaacc atttcttcgt ttttcgcaac gaacatgccc    5700
aatccactac tttaggtcca aaactcatgt ttggggtggt ttcgcgcaat ttcgttgccg    5760
cacgtcaccc attccgaaaa cggttgtcgg ggtgcataca aagcacgagt ttttgccacc    5820
ggaaccattt cttcgttttt cacaacgaac atgcccaatc cactacttta ggtccaaaac    5880
tcatgtttgg ggtggtttcg cacagtttcg ttgtcgcacg tcacccattc tgaaaacggg    5940
tatcggggtg cataaaagca cgagttttttg ccaccggaac catttcttcg ttttttcgcaa    6000 cgaacatgcc caatccacta ctttaggtcc aaaactcatg tttggggtgg tttcgcgcaa    6060
ttttgttgtc gcatgtcacc cattccgaaa acgggtatcg gggtgcataa aagcacgagt    6120
ttttgccacc ggaaccattt cttcgttttt cgcaacgaac atgcccaatc cactactttta    6180 ggtccaaaac tcatgtttgg ggtggtttcg cgcaatttcg ttgccgcacg tcacccattc    6240
cgaaaacggt tgtcggggtg catacaaagc acgagttttt gccaccggaa ccatttcttc    6300 gttttttcaca cgaacatgc ccaatccact actttaggtc caaaactcat gtttggggtg    6360
gtttcgcaca gtttcgttgt cgcacgtcac ccattctgaa acgggtatcg gggtgcata    6420 aaagcacgag ttttttgccac cggaaccatt tcttcgtttt tcgcaacgaa catgcccaat    6480
ccactacttt aggtccaaaa tcatgtttg gggtggtttc gcgcaattttt gttgtcgcac    6540 gtcacccatt ctgaaaacgg gtatcggggt gcataaaagc acgagttttttt gccaccggaa    6600 ccatttcttc gttttttcgta acgaacatgc ccaatccact actttaggtc caaaactcat    6660
gtttggtgtg gtttcgcaca atttcgttgt cgcacgtcac ccattccgaa acgggtgtc    6720 gggtgcatac aaagcacgag ttttttgccac cggaaccatt tcttcgtttt tcgcaacgaa    6780
```

```
catgcccaat ccactacttt acatccaaaa ctcatgtttg gggtggtttc gcgcaatttc   6840
gttgtcgcac gtcacccatt ccgaaaacgg gtgtcgggtg catacaaagc acgagttttt   6900
gccaccggaa ccatttcttc gttttttcgca acgaacatgc ccaatccact actttacatc   6960
caaaactcat gtttggggtg gtttcgcgca atttcgttgt cgcacgtcac ccattccgaa   7020
aacgggtgtc gggtgaataa aaagcacgag ttttgccac cggaaccatt tcttcgtttt   7080
tcgcaacgaa catgcccaat ccactacttt aggtccaaaa ctcatgtttg gagtggtttc   7140
gcgcaatttc gttgccgcac gtcacccatt ccgaaaacgg ttgtcggggg tgcatacaaa   7200
gcacgagttt tgccaccgg aaccattct cgttttcg caacgaacat gcccaatcca   7260
ctactttagg tccaaaactc atgtttgggg tggtttcgcg caatttcgtt gtcgcacgtc   7320
acccattctg aaaacgggta tcggggtgca taaaagcacg agttttgcc accggaacca   7380 tttcttcgtt tttcgcaagg acatgcccaa tccactactt taggtccaaa actcatgttt   7440
ggggtggttt cgcgcaattt tgttgtcgca cgtcacccat tctgaaaacg tgtatcgggg   7500
tgcataaaag cacgagtttt tgccaccgga accatttctt cgttttcgt aacgaacatg   7560 ccgaatccac tactttaggt ccaaaactca tgtttggggt ggtttcgcac aatttcgttg   7620
tcgcacgtca cccattccga aaacgggtgt cgggtgcata caaagcacga ttttgcca   7680 ccgaaccat ttcttcgttt ttcgcaacga acatgcccaa tccactactt tacatccaaa   7740
actcatgttt ggggtggttt cgcgcaattt cgttgtcgca cgtcacccat tccgaaaacg   7800
ggtgtcgggt gaataaaaag cacgagtttt tgccaccgga accatttctt cgttttcgc   7860 aacgaacatg cccaatccac tactttaggt ccaaaactca tgtttggggt ggtttcgcac   7920
aatttcgttg tcgcacgtca cccattctga aaacgggtgt catggtgcat acaaagcacg   7980 agttttgcc accgaacta tttctttgtt tttcgcaacg acatgccaa tccactactt   8040 taggtccaaa actcatgttt tgggtggttt cgcgcaattt cgttgccgca cgtcacccat   8100
tctgaaaacg ggtgtggggt tgcatacaaa gcacgagttt tgccacagg aaccatttct   8160 tcgttttct caacgaacat gcccaatcca ctactttagg tacaaaactc atgttttggg   8220
tggttttgcg caatttcgtt gccgcacgtc actcattccg aaaacgagtg tggggttgca   8280
tacaaagcac gagttttgc caccgaacc atttcttcgt tttcgtaac gaacatgccc   8340 aatccactac tttaggtcca aaactcatgt ttggggtggt tcacacaat ttagttgtcg   8400 cacgtcaccc attccgaaaa cgggtatcgg gtgcatacaa agcacgagtt tttgccaccg   8460
gaaccatttc ttcgttttc gcaacgaaca tgcctaatcc agtactttag gtccaaaact   8520
catgtttggg gtggtttctc gcaatttcgt tgtcgcacgt cacccattcc gaaaacgggt   8580
gtcatggtgc atacaaagca cgagtttttg ccaccggaac catttctttg tttttttgcaa   8640 cgaacatgcc caatccacta ctttaggtcc aaaactcatg tgttggggtg gtttcgcaca   8700
atttcgttgt cgcacgtctc acccattccg aaaacgggtg tcatggtgca tacaaagcac   8760 gagttttgc caccggaacc atttctttgt ttttcgcaac gaacatgccc aatccactac   8820
tttaggtcca aaactcatgt ttcgggtggt tcgcgcaat tcgttgccg cacgtcaccc   8880 attccgaaaa cgggtgtcgg gtgcatacaa agcacgagtt tttgccaccg gaaccatttc   8940
ttcgtttttc tcaacgaaca tgcccaatcc actactttag gtacaaaact catgttttgg   9000
gtggtttcgc gcaatttcgt tgccgcacgt cactcattcc gaaaacgagt gtcgggtgca   9060
taaaagcacg agtgttttgcc accggaacca ttttcttcgtt tttcgcaacg aacatgccca   9120
atccactact ttaggtccaa aactcatgtt tgaggtggtt tcgcgcaatt tcgttgtcgc   9180
```

```
acgtcaccca ttctgaaaac gggtatcggg gtgcataaaa gcacgagttt tgccaccgg   9240
aaccatttct tcgttttccg taacaaacat gcccaatcca ctactttagg tccaaaactc  9300
atgtttgggg tggtttcgca caatttcgtt gtcgcacgtc acccattccg aaaacgggtg  9360
tcgggtgcat acaaagcacg agttttttgcc accggaacca tttctttgtt tttcgtaacg 9420
aacatgccca atccactact ttaggtccaa aactcatgtt tgaggtggtt tcgcgcaatt  9480
tcgttgtcgc acgtcaccca ttccgaaaac gggtgtcggg tgcatacaaa gcacgagttt  9540
ttgccaccgg aaccatttct tcgttttcg caacgaacat gcccaatcca ctactttagg   9600
tccaaaactc atgtttgggg tggtttcgcg caatttcgtt gtcgcatgtc actcattccg  9660
aaaacgggtg tcgggtgcat acagagcacg agttttttgcc accggaacca tttcttcgtt 9720
tttcgcaatg aacatgccca atccactact ttaggtccaa aactcatgtt tggggtggtt  9780
tcgcgcaatt tcgttgtcgc acgtcaccca ttccgaaaac gggtgtcggg tgcatacaaa  9840
gcacgagttt ttgccaccgg aaccatttct tcgttttgc gaacatgccc aatccactac   9900
tttaggtcca aaactcatgt ttggggtggt ttcgcgcaat ttcgttgccg cacgtcaccc   9960
attccgaaaa cggttgtcgg gggtgcatac aaagcacgcg tttttgccac cggaaccatt  10020
tcttcgtttt tcgcaacgaa catgcccaat ccactacttt aggtacaaaa ctcatgtttg  10080
ggtggtttcg cgcaatttcg ttgtcacacg tcacccattc cgaaaagggt gtcggagtgc  10140
atacaaagca cgagtttttg ccagcggaac catttcttcg ttttcgcaa cgaacatgcc    10200
taatccacta ctttaggtcc aaaactcatg tttggggtgg tttctcgcaa ttttgttgtc   10260
gcacgttacc cattccgaaa acgggtgtca tggtgcatac aaagcacgag tttttgccac  10320
cggaaccatt tctttgtttt tcgcaacgaa catgcccaac ccactacttt aggtccaaaa  10380
ctcatgtttg ggtggtttc gcgcaatttc gttgtcgcac gtcacccatt ccgaaaacgg    10440
gtgtcgggtg catacagagc acgagttttt gccaccagaa ccatttcttc gtttttcgca  10500
atgaacatgc ccaatccact actttaggtc caaaactcat gtttgggtg tttcgcgca    10560
atttcgttgt cgcacgtcac ccattccgaa aacgggtgtc gggtgcatac aaagcacgag  10620
tttttgccac cggaaccatt tcttcgtttt tcgcaacgaa catgcccaat ccactacttt  10680
aggtccaaaa ctcatgtttg ggtggtttc gcgcaatttc gttgccgcac gtcacccatt    10740
ccgaaaacgg ttgtcggggg tgcatacaaa gcacgcgttt tgccaccgg aaccatttct   10800
tcgttttcg caacgaacat gcccaatcca ctactttagg tacaaaactc atgtttgggt    10860
ggtttcgcgc aatttcgttg tcacacgtca cccattccga aagggtgtc ggagtgcata    10920
caaagcacga gttttttgcca gcggaaccat ttcttcgttt ttcgcaacga acatgcctaa  10980
tccactactt taggtccaaa actcatgttt ggggtggttt ctcgcaattt gttgtcgca   11040
cgttacccat tccgaaaacg gtgtcatgg tgcatacaaa gcacgagttt tgccaccgg    11100
aaccatttct ttgtttttcg caacgaacat gcccaatcca ctactttagg tccaaaactc  11160
atgtttgggg tggtttcgca caatttcgtt gtcgcacgtc acccattccg aaaacgggtg  11220
tcgggtgcat acaaagcacg agtttttgcc accggaacca tttcttcgtt tttcgcaacg  11280
aacatgccca atccactact ttaggtccaa aactcatgtt tggggtggtt tcgcacaatt  11340
tcgttgtcgc acgtcaccca ttctgaaaac gggtgtcatg gtgcatacaa agcacgagtt  11400
tttgccaccg gaactatttc tttgtttttc gcaacgaaca tgccaatcca ctactttagg  11460
tccaaaactc atgttttggg tggtttcgcg caatttcgtt gccgcacgtc acccattctg  11520
aaaacgggtg tggggttgca tacaaagcac gagttttttgc cacaggaacc atttcttcgt 11580
```

```
ttttctcaac gaacatgccc aatccactac tttaggtaca aaactcatgt tttgggtggt    11640
tttgcgcaat ttcgttgccg cacgtcactc attccgaaaa cgagtgtcag gtgcataaaa    11700
gcacgagttt tgccaccgg  aaccatttct tcgttttttcg taacgaacat gcccaatcca    11760
ctactttagg tccaaaactc atgtttgggg tggtttcaca caatttcgtt gtcgcacgtc    11820
acccattccg aaaacggtg  tcgggtgcat acaaagcacg agttttgcc  accggaaccaa   11880 tttcttcgtt tttcgcaacg aacatgccta atccagtact ttaggtccaa aactcatgtt    11940
tggggtggtt tctcgcaatt tcgttgtcgc acgtcaccca ttccgaaaac gggtgtcatg    12000
gtgcatacaa agcacgagtt tttgccaccg gaaccatttc tttgtttttt gcaacgaaca    12060
tgcccaatcc actactttag gtccaaaact catgtgttgg ggtggtttcg cacaatttcg    12120
ttgtcgcacg tctcacccat tccgaaaacg ggtgtcatgg tgcatacaaa gcacgagttt    12180
ttgccaccgg aaccatttct ttgttttttcg caacgaacat gcccaatcca ctactttagg    12240
tccaaaaatc atgtttgggg gggtttcgca caatttcgtt gccgcacgtc acccattccg    12300
aaaacggttg tcggggtgc  atacaaagca cgagttttg  ccaccggaac catttcttcg    12360
tttttcgcaa cgaacatgcc caatccacta ctttaggtcc aaaactcatg tttggggtgg    12420
tttcgcacag tttcgttgtc gcacgtcacc cattctgaaa acgggtatcg gggtgcataa    12480
aagcacgagt ttttgccacc ggaaccattt cttcgttttt cgcaacgaac atgcccaatc    12540
cactacttta ggtccaaaac tcatgtttgg gatggtttcg cgcaattttg ttgtcgcacg    12600
tcacccattc tgaaaacggg tatcggggtg cataaaagca cgagttttg  ccaccggaac    12660 catttcttcg tttttcgtaa cgaagatgca gaatccacta ctttaggtcc aaaactcatg    12720
tttggggtgg tttcgcacaa tttcgttgtc gcacgtcacc cattccgaaa acgggtgtcg    12780
ggtgcataca aagcacgagt ttttgccacc ggaaccattt cttcgttttt cgcaacgaac    12840
atgcccaatc cactacttta catccaaaac ccatgtttgg ggtggtttct cgcaatttcg    12900
ttgtcgcacg ttgaaagctc tcttgtgagt tttggtgttt ggatgacaac tcaattaaag    12960
gactaacaag agtactaagt gttgaacagg tgcttaaggt aaagcctaca gggttcaaca    13020
caagtgaaca aatgtgatgg tccaagaact ggattatgga tacataatgg acatcacaag    13080
taagttggac attgcaaaag tgatactcgg gtgcgtagct cggagacaac tgatcaagcc    13140
aaggacggag gaagaaaagc ttcgaggtac caagtgcacg ggagaaggtc aaggaggctg    13200
aggaacccaa agccaagggc gaagaagaag gcttgcaaag tcaagggtga tcgagttgag    13260
aacagctacg gcacatcaag gatcactata taaggacgcg acttacaacc aatgaggtaa    13320
cagctacagt tatgtggtgt aagtcataag gctcaagacc aagctctaag aaggagatcc    13380
tctagagtcg acctgcaggc atgcaagctt gagtattcta tagtgtcacc taaatagctt    13440
ggcgtaatca tggtcatagc tgtttcctgt gtgaaattgt tatccgctca caattccaca    13500
caacatacga gccggaagca taaagtgtaa agcctgggt  gcctaatgag tgagctaact    13560
cacattaatt gcgttgcgct cactgcccgc tttccagtcg ggaaacctgt cgtgccagct    13620
gcattaatga atcggccaac gcgaacccct tgcggccgcc cgggccgtcg accaattctc    13680
atgtttgaca gcttatcatc gaatttctgc cattcatccg cttattatca cttattcagg    13740
cgtagcaacc aggcgtttaa gggcaccaat aactgcctta aaaaaattac gccccgccct    13800
gccactcatc gcagtactgt tgtaattcat taagcattct gccgacatgg aagccatcac    13860
aaacggcatg atgaacctga atcgccagcg gcatcagcac cttgtcgcct tgcgtataat    13920
atttgcccat ggtgaaaacg ggggcgaaga agttgtccat attggccacg tttaaatcaa    13980
```

```
aactggtgaa actcacccag ggattggctg agacgaaaaa catattctca ataaacccectt    14040 tagggaaata ggccaggttt tcaccgtaac acgccacatc ttgcgaatat atgtgtagaa    14100
actgccggaa atcgtcgtgg tattcactcc agagcgatga aaacgtttca gtttgctcat    14160
ggaaaacggt gtaacaaggg tgaacactat cccatatcac cagctcaccg tctttcattg    14220
ccatacgaaa ttccggatga gcattcatca ggcgggcaag aatgtgaata aaggccggat    14280
aaaacttgtg cttattttc tttacggtct ttaaaaaggc cgtaatatcc agctgaacgg    14340
tctggttata ggtacattga gcaactgact gaaatgcctc aaaatgttct ttacgatgcc    14400
attgggatat atcaacggtg gtatatccag tgattttttt ctc                      14443

<210> SEQ ID NO 69
<211> LENGTH: 20048
<212> TYPE: DNA
<213> ORGANISM: Zea mays

<400> SEQUENCE: 69
cgaatcctag atatcatcgc cactgtgctg gaagttcgtt gtgaaaacga agaaatggtt      60
ccggtggcaa aaactcgtgc tttgtatgca ccccgacaac cgttttcgga atgggtgacg     120
tgcggcaacg aaattgcgcg aaaccacccc aaacatgagt tttggaccta agtagtgga     180 ttgggcatgt tcgttgcgaa aaacgaagaa atggttccgg tggcaaaaac tcgtgctttt     240
tattcacccg acaccgtttt cggaatgggt gacgtgcga caacgaaatt gcgcgaaacc     300
accccaaaca tgagttttgg atgtaaagta gtggattggg catgttcatt gcgaaaaacg     360
aagaaatggt tccggtggca aaaactcgtg ctttgtatgc acccgacacc cgttttcgga     420
atgggtgacg tgcgacaacg aaattgtgcg aaaccaccc aaacatgagt tttggaccta     480
aagtagtgga ttcggcatgt tcgttacgaa aaacgaagaa atggttctgg tggcaaaaac     540
tcgtgctttt atgcaccccg atacccgttt tcagaatggg tgacgtgcga caacaaaatt     600
gcgcgaaacc accccaaaca tgagttttgg acctaaagta gtggattggg catgttcgtt     660
gcgaaaaacg aagaaatggt tccggtggca aaaactcgtg cttttatgca ccccgatacc     720 cttttttcaga atgggtgacg tgcgacaacg aaactgtgcg aaaccacccc aaacatgagt     780
tttggaccta tagtagtgga ttgggcatgt tcgttgtgaa aaacgaagaa atggttccgg     840
tggcaaaaac tcgtgctttg tatgcacccc gacaaccgtt tcggaatgg gtgacgtgcg     900 gcaacgaaat tgcgcgaaac caccccaaac atgagttttg dacctaaagt agtggattgg     960
gcatgttcgt tgcgaaaaac gaagaaatgg ttccggtggc aaaaactcgt gctttttatt    1020
cacccgacac ccgttttcgg aatgggtgac gtgcgacaac gaaattgcgc gaaaccaccc    1080
caaacatgag ttttggatgt aaagtagtgg attgggcatg ttcattgcga aaaacgaaga    1140
aatggttccg gtggcaaaaa ctcgtgcttt gtatgcaccc gacaccgtt tcggaatgg    1200 gtgacgtgcg acaacgaaat tgtgcgaaac caccccaaac atgagttttg dacctaaagt    1260
agtggattgg gcatgttcgt tgagaaaaac gaagaaatgg ttccagtggc aaaaactcgt    1320
gctttgtatg cacccgacac ccgttttcgg aatgggtgac gtgcggcaac gaaattgcgc    1380
gaaaccaccc gaaacatgag ttttggacct aaagtagtgg attgggcatg ttcgttgcga    1440
aaaacaaaga atggttccg gtggcaaaaa ctcgtgcttt gtatgcacca tgacacccgt    1500
tttcggaatg ggtgacgtgc gacaacgaaa ttgttcgaaa ccaccccaaa catgagtttt    1560
ggacctaaag tagtggattg gcatgttcg ttgcgaaaaa cgaagaaatg gttccggtgg    1620
caaaaactcg tgctttgtat gcaccatgac acctgttttc ggaataggtg acgtgcgaca    1680
```

```
acgaaattgt gcgaaaccac cccaaacatg agttttggac ctaaagtagt ggattgggca    1740
tgttcgttgc gaaaaataaa gaaatggttc cggtggcaaa aactcgtgct ttgtatgcac    1800
catgacaccc gttttcggaa tgggtgacgt gcgacaacga aattgcgaga accacccca     1860 aacatgagtt ttggacctaa agtagtggat taggcatgtt cgttgcgaaa aacgaagaaa    1920
tggttccggt ggcaaaaact cgtgctttgt atgcactccg acaccgtttt cggaatggg     1980 tgacgcgtga caacgaaatt gcgcgaaacc accccaaaca tgagttttgg acctaaagta    2040
gtggattggg catgttcgtt acaaaaaacg aagaaatggt tccggtggca aaaactcgtg    2100
ctttgtatgc acccgacacc cgttttcgga atgggtgacg tgcgacaacg aaatatcgag    2160
aaatcacccc aaacatgagt tttggaccta agtagtgga ttgggcatgt tcgttgcgaa     2220
aaacgaagaa atggttccgg tggcaaaaac tcgtgctttg tatgcacccg acaccgtttt    2280
tcggaatggg tgacgtgcga acgaaattg cgcgaaacc accccaaaca tgagttttgg      2340
acctaaagta gtggattggg catgttcatt gtgaaaaacg aagaaatggt tccggtggca    2400
aaaactcgag ctctatatgc acccgacacc cgttttcgga atgggtgacg tgcgacaacg    2460
aaattgcgtg aaaccacccc aaacatgagt tttggaccta agtagtgga ttgggcatgt     2520 tcgttgcgaa aaacgaagaa atggttccgg tggcaaaaac tcgtgctttg tatgcacccg    2580
acaccgtttt tcggaatggg tgacgtgcga acgaaattg cgagaaacc acctcaaaca      2640 tgagttttgg acctaaagta gtggattggg catgttcgtt acgaaaaacg aagaaatggt    2700
tccggtggca aaaactcgtg ctttgtatgc acccgacacc cgttttcgga atgggtgacg    2760
tgcgacaacg aaattgtgcg aaaccacccc aaacatgagt tttggaccta agtagtgga    2820 ttgggcatgt ttgttacgaa aaacgaagaa atggttccgg tggcaaaaac tcgtgctttt    2880
atgcaccccg atacccgttt tcagaatggg tgacgtgcga caacgaaatt gcgcgaaacc    2940
acctcaaaca tgagttttgg acctaaagta gtggattggg catgttcgtt gcgaaaaacg    3000
aagaaatggt tccggtggca aacactcgtg cttttatgca cccgacactc gttttcggaa    3060
tgagtgacgt gcggcaacga aattgcgcga accacccaa acatgagtt ttgtacctaa      3120 agtagtggat tgggcatgtt cgttgagaaa acgaagaaa tggttccggt ggcaaaaact    3180
cgtgctttgt atgcaccccc acccggtttt ttagaatggg tgacgtgcgg caacgaaatt    3240
gcgcgaaacc acccgaaaca tgagttttgg acctaaagta gtggattggg catgttcgtt    3300
gcgaaaaaca agaaatggt tccggtggca aaaactcgtg ctttgtatgc accatgacac    3360
ccgttttcgg aatgggtgac gtgcgacaac gaaattgcga gaaccacccc caaacatgag    3420
ttttggacca aaagtagtgg attaggcatg ttcgttgcga aaaacgaaga atggttccg     3480 gtggcaaaaa ctcgtgcttt gtatgcactc cgacacccgt tttcggaatg ggtgacgtgt    3540
gacaacgaaa ttgcgcgaaa ccacccaaa catgagtttt ggacctaaag tagtggcttg    3600
ggcatgttcg ttacaaaaaa cgaagagatg gttccggtgg caaaaactcg tgctttgtat    3660
gcacccgaca cccgttttcg gaatgggtga cgtgcgacaa cgaaattgcg agaaagcacc    3720
ccaaacatga gttttggacc taaagtagtg gattgggcat tttcgttgcg aaaaacgaag    3780
aaatggttcc ggtggcaaaa actcgtgctt tgtatgcacc ccgacacccg ttttcggaat    3840
gggtgacgtg cgacaacgaa attgcgcgaa accacccaa acatgagttt tggacctaaa    3900
gtagtggatt gggcatgttc gttgcgaaaa acgaagaaat ggttccggtg gcaaaaactc    3960
gtgctttgta tgcaccccga caaccgtttt cagaatgggt gacgtgcggc aacgaaattg    4020
cgcgaaacca ccctaaacat gagttttgga cctaaagtag tggattgggc atgttcgttg    4080
```

```
cgaaaaacga agaaatggtt ccggtggcaa aaactcgtgc tttgtatgca cccgacaccc    4140
gttttcggaa tgggtgacgt ccgacaacga aattgtgcga aaccacccca aacatgagtt    4200
ttggacctaa agtagtggat tgggcatgtt cgttgcgaaa aacgaagaaa tggttccggt    4260
ggcaaaaatt gtgctttgta tgcacccccga caaccgtttt cagaatgggt gacgtgcggc    4320
aacgaaattg cgcgaaacca ccccaaacat gagttttgga cctaaagtag tgggttgggc    4380
atgttcgttg cgaaaaacaa agaaatggtt ccggtggcaa aaactcgtgc tttgtatgca    4440
ccatgacacc cgttttcaga tgggtgacg tgcgacaacg aaattgtgcg aaaccacccc    4500
aaacatgagt tttggaccta aagtagtgga ttgggcatgt tcgttgcgaa aaacgaagaa    4560
atggttccgg tggcaaaaat tcgtgctttg tatgcaccat gacacccgtt ttcggaatgg    4620
gtgacgtgcg acaacgaaat tgtgcgaaac caccccaaac atgagttttg acctaaagt     4680 agtggattgg gcatgttcgt tgcgaaaaac aaagaaatgg ttccggtggc aaaaactcgt    4740
gctttgtatg caccatgaca cccgttttcg gaatgggtga cgtgcgacaa cgaaattgcg    4800
agaaaccacc ccaaacatga gttttggacc taaagtagtg gattaggcat gttcgttgcg    4860
aaaaacgaag aaatggttcc gctggcaaaa actcgtgctt tgtatgcact ccgacaccct    4920
tttcggaatg gctgacgtgt gacaacgaaa ttgcggaaac cacccaaaca tgagttttgt    4980
acctaaagta gtggattggg catgttcgtt gcgaaaaacg aagaaatggt tccggtggca    5040
aaaacgcgtg ctttgtatgc accccgacaa ccgttttcgg aatgggtgac gtgcggcaac    5100
gaaattgcgt gaaaccaccc caaacatgag ttttggacct aaagtagtgg attgggcatg    5160
ttcgttgcga aaaacgaaga aatggttccg gtggaaaaaa actcgtgctt tgtatgcacc    5220
cgacacccgt tttcggaatg ggtgacgtgc gacaacgaaa ttgcgcgaaa ccaccccaaa    5280
catgagtttt ggacctaaag tagtggattg gcatgttca ttgcgaaaaa cgaagaaatg    5340
gttccggtgg caaaaactcg tgctctgtat gcacccgaca cccgttttcg gaatgggtga    5400
cgtgcgacaa cgaaattgcg cgaaaccacc ccaaacatga gttttggacc taaagtagtg    5460
gattgggcat gttcgttgcg aaaaacgaag aaatggttcc ggtggcaaaa actcgtgctt    5520
tgtatgcacc cgacacccgt tttcggaatg ggtgacgtgc gacaacgaaa ttgtgcgaaa    5580 ccacccccaaa catgagtttt ggacctaaag tagtggattg gcatgttcg ttgcgaaaaa    5640 cgaagaaatg gttccggtgg caaaaatcgt gctttgtatg caccccgaca ccgttttca    5700 gaatgggtga cgtgcggcaa cgaaattgcg cgaaaccacc ccaaacatga gttttggacc    5760
taaagtagtg ggttgggcat gttcgttgcg aaaaacgaag aaatggttcc ggtggcaaaa    5820
actcgtgctt tgtgtgcacc cgacacccgt tttcggaatg ggtgacgtgc gacaacgaaa    5880
ttgcgagaaa tcaccccaaa catgagtttt ggacctaaag tagtggattg gcatgttcg    5940 ttgcgaaaaa cgaagaaatg gttccggtgg caaaaactcg tgctttgtat gcaccccgac    6000
acccgttttc ggaatgggtg acgtgttaca cgaaattgc gcaaaaccac cccaaacatg    6060
agttttgtac ctaaagtagt ggattgggca tgttcgttgc gaaaaacgaa gaaatggttc    6120
cggtggcaaa aactcgtgct ttgtatgcac cccaacaccc gttttcggca tgggtgacgt    6180
gcggaaacga aattgcgcga aaccacccca aacctgagtt ttggacctaa agtagtggat    6240
tgggcatgtt cgttgcgaaa aacgaagaaa tggttccggt ggcaaaaact cgtgctttgt    6300
atgcacccga caccgttttc ggaatgggt gacgtgcgac aacgaaatta cgcgaaacca    6360
ctccaaacat gagttttgga tgtaaagtag tggattgggc atgttcgttg cgaaaaacga    6420
agaaatggtt ccagtggcaa aaatcgtgct ttgtatgcac cccgacaacc gttttcagaa    6480
```

```
tgggtgatgt gcggcaacga aattgcgcga aaccacccca aacatgagtt ttgtacctaa    6540
agtagtggat tgggcatgtt cgttgagaaa aacgaagaaa tggttccggt ggcaaaaact    6600
cgtgctttgt atgcacccag acaccgtttt cggaatgggt tgacgtgctg caacgaaatt    6660
gcacgaaacc acccaaaaca tgagttttgg acctaaagta gtggattggg catgttcgtt    6720
gcgaaaaacg aagaaatggt tccggtggca aaaactcgtg ctttgtatgc acccgacacc    6780
cgttttcgga ttgggtgatg tgcgacaacg aaattacgcg aaaccacccc aaacatgagt    6840
tttggatgta aagtagtgga ttgggcatgt tcgttgcgaa aaacgaagaa atggttctgg    6900
tggcaaaaac tcgtgctttg tatgcaaccg acaccgtttt cggaatgggt tgacgtgcga    6960
caacgaaatt gcgcgaaacc accccaaaca tgagttttgg atctaaagta gtggattggg    7020
catgttcgtt gcgaaaaacg aagaaatggt tccggtggca aaaactcgtg ctttgtatgc    7080
acccgacacc cgttttcgga atgagtgacg tgcgaaaacg aaattgtgcg aaaccacccc    7140
aaacatgagt tttggaccta aaaaagtgga ttgggcattt tcgttacgaa aaacgaagaa    7200
atggttccgg tggcaaaaac tcgtgctttt atgcacccca taccgtttt tcagaatggt    7260 ttatgcaccc gacactcgtt ttcggaatgg gtgacgtgcg gcaacgaaat tgcgcgaaac    7320
caccccaaac aagagttttg tacctaaagt agtggattgg gcatgttcgt tgctaaaaac    7380
gaagaaatgg ttccggtggc aaaaatcgtg ctttgtatgc accccacccc gacaaccgtt    7440
ttcagaatgg gtgacgtgcg gcaacgaaat tgcgcgaaac caccccaaac atgagttttg    7500
gacctaaagt agtgggttgg gcatgttcgt tgcgaaaaac gaagaaatgg ttccggtggc    7560
aaaaactcgt gctttgtatg cacccgacac ccgttttcgg aatgggtgac gtgcgacaac    7620
gaaattgcga gaaatcaccc caaacatgag ttttggacct aaagtagtgg attcggcatg    7680
ttcgttgcga aaaacgaaga aatggttccg gtggcaaaaa ctcgtgcttt gtatgcaccc    7740 gacaccgtt ttcggaatgg gtgacgtgtg acaacgaaat tgcgcaaaac caccccaaac    7800
atgagttttg tacctaaagt agtggattgg gcatgttcgt tgcgaaaaac gaagaaatgg    7860
ttccggtggc aaaaactcgt gctttgtatg cacccgacac ccgttttcgg attgggtgat    7920
gtgcgacaac gaaattacgc gaaaccaccc ctgatgagga catcaacacc aacacgagca    7980
catctacacc agcagcacct tctccagccc aggcaccatc ttccccagtc caggcgccac    8040
cccttccacc tgggccagtg actcgggccc gtgcaagaga attgaactac attatgctgt    8100
taaagaacga aggcccggaa gaatagacga ccagcccaac tgcggcccat aatggacgac    8160
ctagggttgg ccgcccctag gggctgcgcc cctctctatt tatccaggag ctgcgcctcc    8220
tttatttctg gagttttgtt ttacgttagc cttagctact ctcgaacacg cgcaaatctg    8280
cgctgtcttc gtgtattcag aactccaccc tcgagtaata gattagattg ctcgcctctt    8340
tttcttgttc gttcttcgat tgcgcacagg aaacgatctt cgtgatcagg ccgatctcgc    8400
atcagcaagg tcgtaacca cagggagttg gttcagcgat tgcattggcg cctcgggctt    8460
gctcgtcgta gtcggatcgc aagggtcatc ttccgccaaa tcggaattat ctctactcgc    8520
cgaaagatcg ggcacctcag ctacatcaat tggtatcaga tttccaggtt gatcggtgag    8580
tttatcgagc gttttttttcc tacagtccac aaaaccacat aaaaattcag gttagatctt    8640
atcccagcac ccttttgagc ctcgcacttt cttttcaataa tctgcattgt tgaatttgtg    8700
tgctttcgcg tttccttgtt gctggttgca ttgtgttctt ccaccattca aatcctagcg    8760
ccgccatcat cttccgtttg atcacgccac aaaccgagtc aacatcgtct ccttgttttt    8820
ctccttcggt tacgaaaaaa aaacagaaaa aaaaaacaaa ccgagtcaac gaccgcttcc    8880
```

```
ttgtttttct ccttcggtta cataaaaaaa acagaaacaa aaaaaaagaa aacgaaggag   8940
aagggatacg gttgtttcat cccgtcgtt tttaaaacat aacttgaggt accttccgta    9000
aaccgggcat aacttttcgc tcgggtgtcc aaaaaatctg aaattttac aggagcttgt    9060
tgacaccatt cggaggccgg ccaaactgac ctttggtctg tttggattcg acaaaattgt   9120
caaaaaatt caggaaaata agaaaaaaa tccgtcaaag ttctcgcacg cttttcagag     9180
aacttcctga ttttctgtag accacatctg atctctgttt tcggtgaaac ttcgtctagc   9240
tcctattttg ttgcttcttg tgctgagaaa aatatcaaaa aatcatacaa aaaagaaaa    9300
acaaaatcac ttgtgattcc tactagtggc ctcgctagta caatatttac ggtactgcca   9360
ttctgctagt tccatccgtc ctttgcactt gtggccagca atatagtttc gtgttctgca   9420
ctataattca actttgcatt attgtttgat cgtgctaatc cttgacttga gtgcagccta   9480
cccaaaactc cacatatttc tacgacgaga cggtttctgt ttctccaggc aatcgctaat   9540
ccaatctttc accggttcca cctgttgatt gcagttcacc actgtggctt ggtaagaacg   9600
gataagaact tgataacaac actagtgtga gcgccttgtg agcagtacac ccctgttttt   9660
gtcgttggtt tttctccttt tggtgttttg gtgtttgcgc taactatggc aggagcacac   9720
gacatggtgg atgcccagtt gcaggaagta aggggacaag ttgatggact tgctgctgac   9780
attcggacga tgcatgaacg gcttgattca acgatcactt cgacgaccga gcgtttcaac   9840
caacttgacc ttgctcaaac ggcgactcgc accacactcg acaccatcct ggcacgcctt   9900
gatgcattga ccacaaagat ggagcaggaa tacggcggtg acactgagca ggacgatgga   9960
gatcgccgtg gtcgtgcacg tcgtgtggtt cgtcatcccc ctaatgactt attttctaag  10020
attaaattta aaattccatc ttttaatggt aaatatgatc ctgctgcata tcttgattgg  10080
gaattagagg tagaacagaa atttttcatgc catgatattc ctgctcatag ccaagtgaag  10140
gctgccatta gtgaatttac tgattttgct ttaatttggt ggcgcgagta taatcaaaaa   10200
cttcccatta acaatgtcat tacttggacc caattaaaaa ctgccatgcg ccacagattt  10260
gttccttcct attatgctcg tgatttgctt aacaaaatgc agcgttttca acaaggttca  10320
cagtctgttg aggaatatta ccaggagtta caaaagggta tgcttcgttg tggtttagtt  10380
gagtcggatg acgctgctat ggcgcgtttt cgtggtggtt tgaacagggga aattcaggat  10440
atacttgatt ataaggatta ttttgatata accacatatt ttgaatatgc ttgcaaagct  10500
gaacgtgaag tgcagggacg ccgctcgaag ccatattcta accctttgc aggacgaagc   10560
tcgacatcca cctcagcacc agttcccct gcgccatcga cgtccaccac tacttcacgc   10620
gagaagacga ccaaaccagc cagcactgcc ccacccacag gtcgtacacg ggatattcag  10680
tgtcatcgct gtagaggatt tggccatgtg attcgggact gcccaaacaa gcgcactttg  10740
ctcattcgtg acgatggtga gtactcttcc gctagtgatt ctgaagaaat tgaacatgca  10800
ctacttgcca cttaccatgc agctaaggcg gaggtacatg tcaacccgag cgacgctgat  10860
aggtatgaaa gtcttgttgt gcagcgtgtt ctcagtacac aggtcgcttt gcccgagaag  10920
aatcagcgac acactctgtt ccatacaaag ggtgttgtgc aggagcggtc aattcgcatc  10980
attatcgaca gtggcagttg caacaatttg gcgagtacca tgctggtcga caagttatcg  11040
ttacccactc gtaagcatcc aaacccatat cacattcaat ggcttaatga tggtggtaaa  11100
ataaaaatca cacgttccgt gcgtgttcct ttctccatgg gtgcttattc tgattttgtt  11160
gattgtgatg ttattcccat ggaagcatgc tctttgttac ttggtcgacc ttggcaatat  11220
gatactgata gcttgcatca tggtcgttcg aatcattatt ctttcatttt taagggtcag  11280
```

```
aaaataatta tacatccaat gacacccgaa caaattgtta aagatgatct tgcccgagct    11340
gctataactg ctaaacaact tgatccatcg ccctctgttc cttctgaaat caagttgaag    11400
gctcctgttt tacttgctac acgtgctgat tttgatgatc tacacggtgc tcatttgcca    11460
tgctatgcac ttatatgctc tagtgtcctc atttcacttg atgatgcacc atctttggct    11520 attccccta tggttgctaa cctttttgcaa gagtacgctg atgtctttcc caaagactta    11580
ccaccgggtc tcccaccact tcgtggcatt gagcaccaga tcgacctcat tcccggcgca    11640
cagcttccga accgcgcacc gtaccgtaca aatccggatg agacgaagga gattcagcgc    11700
caggtacagg cgttgcttga caagggatac attcgtgagt ctcttagccc ttgctctgtt    11760
cctgtgttac ttgttcccaa gaaagatggg tcatggcgta tgtgtgtaga ctgtcgtgct    11820
attaataaca tcactattcg ttatcgatat cctataccac gccttgatga tatgctagat    11880
gagcttagtg gtgccattat tttcactaag attgatttgc gtagtggtta ccaccagatt    11940
agaatgaaac tgggtgatga atggaaaacg cttttaaaa cgaaatttgg tttatatgaa    12000
tggttggtta tgccgtttgg attgactaat gctcccagca cttttatgcg agtgatgaat    12060
gaagttctaa ggcccttcat aggattgttt gtggttgttt attttgatga tattcttatt    12120
tacagcaaat ctacgaaaga gcatttggaa catttacgtg ctgttttga tgcattgcgt    12180 gctgctcagt tatttgctaa catggaaaaa tgcatgtttt gtacacgacg tgtctcgttt    12240
cttggttatg ttgttactcc acagggcatt gaggtggata gcagcaagat tgctgccatt    12300
cgggagtggc ctacaccgac gacggtcaca caaatttgga gctttcttgg acttgccggt    12360
ttctaccgca gatttgttcg tgattttagc tccattgcag cgcctctaca tgagcttaca    12420
aagaaagatg tgccatttgc ttggagtgat tcccaggagg aagcgttcag cactttgaaa    12480
gataagttaa cccaagctcc cctattgcaa ttgcctgatt ttaataaagt gtttgagctt    12540
gaatgcgatg ctagcggtat tgggctaggt gctgttttgt tacaagaagg aaaaccagtt    12600
gcttatttta gtgaaaaatt aagcggtgct agtctgaaat attctactta tgataaggag    12660
ctttacgctt tagtgcgcac tttgcataca tggcagcact atctttggca tcgtgagttt    12720
ataatccatt ctgatcatga ggcttttaaa catattcgta cccaaacaaa tctgaaccgt    12780
cgtcatgcta aatgggtaga attcattgag tcctttcctt acattattaa acacaagaac    12840
gggaaggaca atgttattgc tgatgctttg tctcgtcgct ataccatgct gtcacagtta    12900
gattttaaaa tctttggttt gcacactctg aaagatcaat atgttgatga tgctgatttt    12960
aaagatgctt tcggccattg tattaatggg aaaccatggg gcaaatttca catacaggat    13020
gggttcctgt tcgcgctaa caagctgtgt gttccagcta gctcggttcg tcttttgttg    13080
ttacaggaag cacatggagg cggtctcatg gggcactttg gcgtctacaa gacacatgag    13140
gtgttggctg cccacttctt ttggccctcgg atgcgcgctg atgttgagcg ccttgttgca    13200
cgctgcacta cttgtcagaa agctaagtca cggttgaaca accattgttt gtatatgcct    13260
ttgcctgttc ctactttccc ttggattgat atttcgatgg attttgtttt gggattgcct    13320
agaactaaga agggagggga tagcattttt gtggttgttg atcgattctc caaaatggct    13380
catttcatac cttgtcataa gactgatgat gctagcaatg ttgctgaatt gttttttaga    13440
gagattattc gtttgcacgg tattcccaat acaatagtct cggatcgtga tgctaagttt    13500
ctgagtcatt tttggagatc tctgtggaat aaattgggaa ctaaattgct gtttagcacc    13560
acttgtcacc ctcagactga tggtcaaact gaggtagtta atcgaacttt gtctaccatg    13620
cttagggctg ttttagacaa aaatttgaaa cgttgggagg attgcttgcc tcatgttgag    13680
```

```
tttgcttata atcatgcaac ccattcttct acaaagatgt gcccttttca aattgtttat   13740
ggttacattc ctagggcgcc tattgctttg ttttcgcttg atgctgcgga cgccccacac   13800
atagcttcct cctcccaagt taagcgaggt gggataattc tgaggctcac acggtcaccg   13860
tccgactaca attgggccaa ctggccaatt gcgtctttgc caacgggtaa tagtggagga   13920
tgtcctcatc aaacatcatc acgcacaata gcctcagggg acatgggaag caaaataatt   13980
ttcttatcat ggtgtatgag agaatattga tttgatctac catgatgcat acaatctgaa   14040
tcatattgcc atggtctacc tagcagaata ttacaagcat ccataggcac aacatcacag   14100
tcaacaacat cacgatatga accaatagca aaattaattc gtaccagctt ggttaccttg   14160
accttaccac tattgttgag ccattgaatg tgatatggat gcgggtgtgg tttggtcgta   14220
agtgcaagct tctccaccat gtcgctgcta gccaagttgt tgcagctacc tccatcaatg   14280
atcaaacgac atgaacgctc cttaatgaca cactttgttt gaaacaacgt atgtcgctga   14340
ttctgctctg ccttctccat tgtgcacta agcacacgct gtacaatgag gctctcataa   14400
tgctctgcat catctgcacc aatctgttct tcgggtggtt ccttagtgcc tgcatcatca   14460
gccgcaagca aagcaagtgt agcttcatcc aaatcactag cagaggaata cccaccatcg   14520
tcttttacca ccaaaacacg ctgattagga caatcacgct gcacgtgtcc atagcccttg   14580
catcgataac acagaacatc tcttgttcta cctgtggaag ctactgaaga gccctacct   14640
gcgggttcct gggcagattt ggttgctgaa tttatggaag atgcacgtgg tttgtcgctg   14700
gaggaaggcg ggggtgctgg tcgacttggc gaaggagttg gtgctggtgt acggccggtc   14760
atggacgtag tcgtgcgctg ttgccatggt gtagattttc ctgcagaaac attagacctt   14820
gcactagcac gtcgtccctg cacttccctt tcagctttgc aagcaagatg aaacaatcgg   14880
gttacattag cataatcttt ataagcaagg atgtcctgaa tttccctatt taacccgccc   14940
aaaaatctag ccatagcaga ttcctcaccc tcctctatgt tacaacgcag catacccatt   15000
tgtaattcct gataatattc ttctacactt ttagtaccct gtctcaattg ttgcaacttg   15060
tttaacatat cacgtgcata ataagaagga acaaatctag cccgcatgac ccgtttcaac   15120
gcatcccaag tttgtggcat gttattagga ttcttcttac catgttctat ccaccaaaca   15180
aaagcaaatt cagtaaactc actagtagca gctctaaccc gcgcattctc aggaaattca   15240
tggcatgcaa acttttgatc aaccgcaatc tcccaagtaa tgtaagcatc agggtcatat   15300
ttaccatcaa aaggaggtat tttaaattta accttactaa aagcatcatc attaccatgt   15360
acctcacgtc ggcgaaaacc atccatacct ctacggttag tacgtagtcg ccggcgatta   15420
ggtgcttctt ggtcatcttg ttcagtatca gcaacatagt catcccagtt accttcggcg   15480
ccctcatcac gcccaccatt gatattagca tgcatctcat caaaccgcct caagagtgcg   15540
acaaggctct tgtcaatatg agcaactgtc atttccactt ttgcaagttt ggtgtttgtg   15600
tcgatctgtg tggcctccaa ttgccccatc ttttattcg tcacctgcat gtcattatca   15660
agaccttccg tgtgcgtctt caccagcctt acaaagtgtt gtatgatacc cttggtgcga   15720
ggagagtgtg gcatattatg agaagcatca tcaacctcca atcctgccat ggttagacga   15780
atagaggcaa caagaaaaaa aacgtgaagg aatgaaaact ctacaactat taggatgtag   15840
ctactgcaag gcgctcactc tcaacctgcc acacaagctc ttaccaattc ttaccttgca   15900
caacaggagg ggtcagcaac caacaagtct gcaactgtgg aataagtgta tcggtgccgc   15960
agcaacacga cctgtcaaac tgtagtcgaa atatgtagag ttgtaggtgg gctgaagcaa   16020
ggaatacact agtaccacgt tagttacaaa agcaagctga ataatcgttc aacggtggta   16080
```

```
ctgtgctggt cctaggctaa accaggctag agacgtgagc ctaggcacaa aggtagtcac   16140 tgaaaagaa caactagcac agcacaaaga gaaacaacag atttagagat tcagcccct    16200 tcttcttctt ttcctttttt ttcttttcta ttctttttt ttcttcttct tctgttttt    16260 tttgcagggg cctaaaccct ttttttcact atgacaaccc aaacaataaa gatattgcta   16320
acagcccctt taaatcagat ttaacaaatc ttgttaatat agaaagtcca gaaatctcta   16380
cgatgattgc ggagcgctca gaacgaattt tgagataagg tcagatccat tggaaagaag   16440
ataagataag ctttccagat tgtatttaaa cttccaaatc ggatatgata tgtatccgtg   16500
gtggcaaaaa cgaaccagag atgttttttgg tgatggtgga tctcgtggtg accaaaacgt   16560
ggtagaactc aaaactctaa aggaataaac taagaccagc aactcgacac aaccgatgca   16620
accaaaaact caacaagccc taactaagta gtactagtaa atgctcaatg gtttatagga   16680
ttgcggtaaa actaatctac tatttttttgg cttttttctgg actataggag ataagaaaac   16740
agcgaagaaa agtaaatctc tcaccgataa accttgttct gataccaact gatgtgcacc   16800
cgttgggtga ttgcccgatc tttcgatgag agggtgtgga ataactcgat tggggagga    16860 gacgacgttc acgcccgac tacagccttc caaagacgct cgccttagc aaccgataca    16920 ccacctccta tggctgtcac gatcttgtgg agcgtgacac cctggccact agggcactcg   16980
tcctgcaagc aatcgaagaa ctagcaagaa caagtagaac aagtactgaa ttaccagatc   17040
taaatgtagg tttcaaaatc aaactccaat atggtggggt tccgaagaca agaagacggg   17100
cggctgaact agcacgcgcg cttgcaagca agtagcgaga gctaaacttg atctaaacaa   17160
aacccgctgt tcttggtgac ggctaggggg tttataaaca tgggaggacg accacaaggg   17220
tattggggtc gtgctgcaac cctaggatgc gtccctaatg gacctaactt gatacacgac   17280
ccattgggcc aaaatagggt gacgcagcac catgggcaga aaaggcagga aatgtctcgg   17340
taagaaaaca atgattacgg cggcctcaga acagatatga ctataattcc ggatccatat   17400
gaaagtagac ttgataagct ttccatgttg tgcttgaaca ttccaatccg agcccgcatc   17460
tgaccgtggt gaccgtcaca agttggtgtt cttctgcagt ccgaatccag catgttcaaa   17520
tccttttccc tttcggtctt ctccctgatt cctaagcaaa acaagagtgc acgggtctcc   17580
atggtctaaa tatgatggac atgaactcaa gagtgtaatc acctgatggt tgagttgacg   17640
agcacgagcg cgagtaatgg gaccagaaat tggtacttgt attggtatag atgcatcagt   17700
agtgtggatg tcttcatcat cacccattcc gaaaacgggt gtcgggtgaa taaaaagcac   17760
gagtttttgc caccggaacc atttcttcgt ttttcgcaac gaacatgccc aatccactac   17820
tttaggtcca aaactcatgt ttggggtggt ttcgcgcaat ttcgttgccg cacgtcaccc   17880
attccgaaaa cggttgtcgg ggtgcataca aagcacgagt ttttccacc agaaccattt   17940 cttcgttttt cacaacgaac atgcccaatc cactactata ggtccaaaac tcatgtttgg   18000
ggtggtttcg cacagtttcg ttgtcgcacg tcacccattc tgaaaacggg tatcggggtg   18060
cataaaagca cgagttttg ccaccggaac catttcttcg tttttcgtaa cgaacatgcc   18120
caatccacta ctttaggtcc aaaactcatg tttggtgtgg tttcgcacaa tttcgttgtc   18180
gcacgtcacc cattccgaaa acgggtgtcg ggtgcataca aagcacgagt ttttgccacc   18240
ggaaccattt cttttgttttt cgtaacgaac atgcccaatc cactacttta ggtccaaaac   18300
tcatgtttga ggtggtttcg cgcaatttcg ttgtcgcacg tcacccattc cgaaaacggg   18360
tgtcgggtgc atacaaagca cgagttttg ccaccggaac catttcttcg tttttcgcaa   18420
cgaacatgcc caatccacta ctttaggtcc aaaactcatg tttggggtgg tttcgcgcaa   18480
```

```
tttcgttgtc gcatgtcact cattccgaaa acgggtgtcg ggtgcataca gagcacgagt    18540
ttttgccacc agaaccattt cttcgttttt cgcaatgaac atgcccaatc cactactta     18600 ggtccaaaac tcatgtttgg ggtggtttcg cgcaatttcg ttgtcgcacg tcacccattc    18660
cgaaaacggg tgtcgggtgc atacaaagca cgagttttg ccaccggaac catttcttcg     18720
tttttcgcaa cgaacatgcc caatccacta ctttaggtcc aaaactcatg tttggggtgg    18780
tttcgcgcaa tttcgttgcc gcacgtcacc cattccgaaa acggttgtcg ggggtgcata    18840
caaagcacgc gttttgcca ccggaaccat tcttcgtttt ttcgcaacga acatgcccaa     18900
tccactactt taggtacaaa actcatgttt gggtggtttc gcgcaatttc gttgtcacac    18960
gtcacccatt ccgaaaaggg tgtcggagtg catacaaagc acgagttttt gccagcggaa    19020
ccatttcttc gttttcgca acgaacatgc ctaatccact actttaggtc caaaactcat     19080
gttgggggtg gtttctcgca atttcgttgc cgcacgtcac ccattccgaa acgggtgtc    19140 gggtgcatac aaagcacgag ttttgccac cggaaccatt tcttcgtttt ttgtaacgaa     19200
catgcccaat ccactacttt aggtccaaaa ctcatgtttg ggtggtttc gcgcaatttc     19260 gttgtcacgc gtcacccatt ccgaaaacgg tgtcggagt gcatacaaag cacgagttt     19320 tgccaccgga accatttctt cgttttcgc aacgaacatg cctaatccag tactttaggt    19380
ccaaaactca tgtttggggt ggtttctcgc aatttcgttg tcgcacgtca cccattccga    19440
aaacgggtgt catggtgcat acaaagcacg agttttgcc accggaacca tttctttgtt     19500
ttttgcaacg aacatgccca atccactact ttaggtccaa aactcatgtg ttgggtggt     19560 ttcgcgcaat tttcgttgcc gcacgtcacc cattctgaaa acgggtgtgg ggttgcatac    19620
aaagcacgag ttttgccac aggaaccatt tcttcgtttt tctcaacgaa catgcccaat     19680
ccactacttt aggtacaaaa ctcatgtttt gggtggtttt gcgcaatttc gttgtcgcac    19740
gtcacccatt ccgaaaacgg tgtcggggtg catacaaagc acgagttttt gccaccggaa    19800
ccatttcttc gttttcgca acgaacatgc ctaatccagt actttaggtc caaaactcat    19860
gtttggggtg gtttctcgca atttcgttgt cgcacgtcac ccattccgaa acgggtgtc    19920 atggtgcata caaagcacga gttttgcca ccggaaccat ttctttgtttt ttgcaacgaa    19980 catgcccaat ccactacttt cttccagca catggagctt cagcgaattc aagcttgaat    20040
cttcagga                                                            20048
```

<210> SEQ ID NO 70
<211> LENGTH: 172
<212> TYPE: DNA
<213> ORGANISM: Zea mays

<400> SEQUENCE: 70

```
tggttccggt ggcaaaaact cgtgchttdw mttgcacycc cgacacccgg ttttcgggaa       60
tgggtgacgt gcggcaacga aattgcgcga accaccccca acacaatgag ttttggacct      120
aaagtagtgg attgggcatg ttcgttgcga aaaacgaaga aatgrttcyg gt              172
```

<210> SEQ ID NO 71
<211> LENGTH: 188
<212> TYPE: DNA
<213> ORGANISM: Zea mays
<220> FEATURE:
<221> NAME/KEY: misc_feature
<222> LOCATION: (46)..(46)
<223> OTHER INFORMATION: n is a, c, g, or t

<400> SEQUENCE: 71

```
ccatttcttc gttttkcgc maaacgaacv mmatgcccbh aatccnactw acttttwaagg    60 dtccaaaaac tcatkgtttg gggdtggdtt tcgcgcaart ttcgrtttgt cgcacgtctc   120
acccatttcc gaaaamcggg tgtcgggkkt gcatacaaag cacgagttt tgtccaccgg   180 aaccatct                                                            188

<210> SEQ ID NO 72
<211> LENGTH: 158
<212> TYPE: DNA
<213> ORGANISM: Zea mays

<400> SEQUENCE: 72
tttcatcccg gtcgttttta gaacataact tgaggtacct tccgtaaacc gggcataact    60
tttcgctcgg gtgtccaaaa aatctgaaat ttttatagga gctagttgac accattctga   120
ggccggccaa actcacctac ggtctgtttg gggttcga                            158

<210> SEQ ID NO 73
<211> LENGTH: 176
<212> TYPE: DNA
<213> ORGANISM: Zea mays

<400> SEQUENCE: 73
acaaaccgag tcaacggycg tttccttgtt tttctccttc ggttaaccga aaaaaaaaca    60
gvaaaaaaaa aamcaaaccg agtcmaacga ccggcccttc cttgttttc tccttcggtt   120 acdtaaaaaa aacagaaaca aaaaaaaaga aaacgaagga aagggatac ggttgt        176

<210> SEQ ID NO 74
<211> LENGTH: 193
<212> TYPE: DNA
<213> ORGANISM: Zea mays

<400> SEQUENCE: 74
gacgtaaccg aaggagaaaa ayaaggarac gatgttgact cggtttgtgg ygtgatcaaa    60
yggragatgr tggcggcgct aggrtttgaa tggtggaaga acacaatgca accagcaaca   120
arkraacgcg aaagcacaca aattcaacaa tgcagattat tgaaagaaag tgygaggctc   180
aaaagggtgc tgg                                                      193

<210> SEQ ID NO 75
<211> LENGTH: 147
<212> TYPE: DNA
<213> ORGANISM: Zea mays

<400> SEQUENCE: 75
gcagggacga cgatcaaaga catatactaa ctctcttgca ggccggggtc caacacacag    60
ctcaactcct tccagccctg caccttctac gcctagcact acatcgcgca cagggacgac   120
caagccagtg gcgcccctg ccaaagg                                        147

<210> SEQ ID NO 76
<211> LENGTH: 466
<212> TYPE: DNA
<213> ORGANISM: Zea mays

<400> SEQUENCE: 76
ggttcaggta gtaaaaactc gtgctttgta tgcaccccga tacccgtttt cggaatgggt    60
gacgtgaggc aacgaaattg cgcgaaacca acccaaacat gagttttgga cctaaagtag   120
tggattgggc atgttcgttg caaaaaacaa agaaatggtt ccggtggcaa aaactcgtgc   180
```

-continued

| | |
|---|---|
| tttgtatgca cccgacaccc gttttcggaa tgggtgacgt gcggcaacga aattgcgaga | 240 |
| aaccacctca aacctgagtt ttggacctaa agtagtggat tgggcatgtt tgttgcgaaa | 300 |
| aacgaagaaa tggttccggt ggcaaaaact cgtgctttgt atgcacccga cacccgtttt | 360 |
| cggaatgggt gacgtgcgac aacaaaattg cgcgaaacct ccccaaacat gagttttgga | 420 |
| cctaaagtag tggattaggc atgttcattg cgaaaaacga agaaat | 466 |

<210> SEQ ID NO 77
<211> LENGTH: 7572
<212> TYPE: DNA
<213> ORGANISM: Zea mays
<400> SEQUENCE: 77

| | |
|---|---|
| tgatgaagac atccacacta ctgatgcatc tataccaata caagtaccaa tttctggtcc | 60 |
| cattactcgc gctcgtgctc gtcaactcaa ccatcaggtg attacactct tgagttcatg | 120 |
| tccatcatat ttagaccatg gagacccgtg cactcttgtt ttgcttagga atcagggaga | 180 |
| agaccgaaag ggaaaaggat ttgaacatgc tggattcgga ctgcagaaga acaccaactt | 240 |
| gtgacggtca ccacggtcag atgcgggctc ggattggaat gttcaagcac aacatggaaa | 300 |
| gcttatcaag tctactttca tatggatccg gaattatagt catatctgtt ctgaggccgc | 360 |
| cgtaatcatt gttttcttac cgagacattt cctgcctttt ctgcccatgg tgctgcgtca | 420 |
| ccctattttg gcccaatggg tcgtgtatca agttaggtcc attagggacg catcctaggg | 480 |
| ttgcagcacg accccaatac ccttgtggtc gtcctcccat gtttataaac ccctagccg | 540 |
| ccaccaagaa cagcgggttt tgtttagatc aagtttagct ctcgctactt gcttgcaagc | 600 |
| gcgcgtgcta gttcagccgc ccgtcttctt gtcttcggaa ccccaccata ttggagtttg | 660 |
| atctttaaac ctacatttag atctggtaat tcagtacttg ttctacttgt tcttgctagt | 720 |
| tcttcgattg cttgcaggac gagtgcccta gtggccaggg tgtcacgctc acaagatcg | 780 |
| tgacagccat aggaggtggt gtatcggttg ctaaggcgca gcgtctttgg aaggctgtag | 840 |
| tcgggccgtg aacgtcgtct cctcccccaa tcgagttatt ccacaccctc tcatcgaaag | 900 |
| atcgggcaat cacccaacgg gtgcacatca gttggtaatc agagcaaggt ttatcggtga | 960 |
| gagatttact tttcttcgct gtttttcttat ctcctatagt ccagaaaaag ccaaaaaaat | 1020 |
| agtagattag ttttaccgca atcctataaa ccattgagca tttactagta ctacttagtt | 1080 |
| agggcttgtt gagttttggt ttgcatcggt tgtgtcgagt tgctggtctt agtttattcc | 1140 |
| tttagagttt tgagttctac cacgttttgg tcaccacgag atccaccatc accaaaaaca | 1200 |
| tctctggttc gttttttgcca ccacggatac atatcatatc cgatttggaa gtttaaatac | 1260 |
| aatctggaaa gcttatctta tcttctttcc aacggatctg accttatctc aaaattcgtt | 1320 |
| ctgagcgctc cgcaatcatc gtagagattt ctggactttc tatattaaca agatttgtta | 1380 |
| aatctgattt aaagggggttg ttagcaatat ctttattgtt tgggttgtca tagtgaaaaa | 1440 |
| aagggtttag gccctgcaa aaaaaaacag aagaagaaga aaaaaaaga atagaaaaga | 1500 |
| aaaaaaagga aaagaagaag aaggggggctg aatctctaaa tctgttgttt ctctttgtgc | 1560 |
| tgtgctagtt gttcttttttc agtgactacc tttgtgccta ggctcacgtc tctagcctgg | 1620 |
| tttagcctag gaccagcaca gtaccaccgt tgaacgatta ttcagcttgc ttttgtaact | 1680 |
| aacgtggtac tagtgtattc cttgcttcag cccacctaca actctacata tttcgactac | 1740 |
| agtttgacag gtcgtgttgc tgcggcaccg atacacttat tccacggttg cagacttgtt | 1800 |
| ggttgctgac ccctcctgtt gtgcaaggta agaattggta agagcttgtg tggcaggttg | 1860 |

```
agagtgagcg ccttgcagta gctacatcct aatagttgta gagtttttat tccttcacat    1920 tttttttct tgttgcctct gttcgtctaa ccatggcagg attggaggtt gatgatgctt     1980
ctcgtaatat gccacactct cctcgcacca agggtatcat acaacactttt gtaaggctgg   2040 tgaaaacgca cacggaaggt cttgataatg acatgcaggt gacgaatgaa agatggggc    2100 aattggaggc cacacagatc gacacaaaca ccaaacttgc aaatgtggaa atgacagttg   2160
ctcatattga caagagcctt gtcgcactct gaggcgatt tgatgagatg catgctaata    2220
ccaatggtgg gcgtgatgag ggcgccgaag gtaactggga tgactatgtt gctgatactg   2280
aacaagatga ccaagaagca cctaatcgcc ggcgactacg tactaaccgt agaggtatgg   2340
gtggttttca ccgacgtgag gtacatggta atgatgatgc ttttagtaag gttaaattta   2400
aaatacctcc ttttgatggt aaatatgacc ctgatgctta cattacttgg gagattgcgg   2460
ttgatcaaaa gtttgcatgc catgaatttc ctgagaatgc gcgggttaga gctgctacta   2520
gtgagtttac tgaatttgct tctgtttggt ggatagaaca tggtaagaag aatcctaata   2580
acatgccaca aacttgggat gcgttgaaac gggtcatgcg ggctagattt gttccttctt   2640
attatgcacg tgatatgtta aacaagttgc aacaattgag acagggtact aaaagtgtag   2700
aagaatatta tcaggaatta caaatgggta tgctgcgttg taacatagag gagggtgagg   2760
aatctgctat ggctagattt ttgggcgggt taaataggga aattcaggac atccttgctt   2820
ataaagatta tgctaatgta acccgattgt ttcatcttgc ttgcaaagct gaaagggaag   2880
tgcagggacg acgtgctagt gcaaggtcta atgtttctgc aggaaaatct acaccatggc   2940
aacagcgcac gactacgtcc atgaccggcc gtacactagc accaactccc tcgccaagtc   3000
gaccagcacc cccgccttcc tccagcgaca aaccacgtgc atcttccaca aattcagcaa   3060
ccaaatctgc ccagaaacca gcaggtagtg cctcttcagt agcctccacg ggtagaacaa   3120
gagatgttct gtgttatcga tgcaagggct atggacacgt gcagcgtgat tgtcctaatc   3180
agcgtgtttt ggtggtaaaa gacgatggtg ggtattcctc tgctagtgat ttggatgaag   3240
ctacacttgc tttgcttgcg gctgatgatg caggcactaa ggaaccaccc gaagaacaga   3300
ttggtgcaga tgatgcagag cattatgaga gcctcattgt acagcgtgtg cttagtgcac   3360
aaatggagaa ggcagagcag aatcagcgac atacgttgtt tcaaacaaag tgtgtcatta   3420
aggagcgttc atgtcgtttg atcattgatg gaggtagctg caacaacttg gctagcagcg   3480
acatggtgga gaagcttgca cttacgacca aaccgcaccc gcatccatat cacattcaat   3540
ggctcaacaa tagtggtaag gtcaaggtaa ccaagctggt acgaattaat tttgctattg   3600
gttcatatcg tgatgttgtt gactgtgatg ttgtgcctat ggatgcttgt aatattctgc   3660
taggtagacc atggcaattt gattcagatt gtatgcatca tggtagatca aatcaatatt   3720
ctctcataca ccatgataag aaaattattt tgcttcccat gtcccctgag gctattgtgc   3780
gtgatgatgt tgctaaagct accaaagcta aaactgagaa caacaagaat attaaagttg   3840
ttggtaataa caaagatggg ataaaattga aggacattg cttgcttgca acaaaaactg   3900
atgttaatga attatttgct tccactactg ttgcctacgc cttggtatgc aaggatgctt   3960
tgatttcaat tcaagatatg cagcattctt tgcctcctgt tattactaac attttgcagg   4020
agtattctga tgtatttcca agtgagatac cagaggggct gccacctata cgagggattg   4080
agcaccaaat tgatcttatt cctggtgcat cttttgccgaa tcgtgcgcca tataggacaa   4140
atccagagga aacaaaagaa attcagcgac aagtgcaaga actactcgac aaaggttacg   4200
tgcgtgagtc tcttagtccg tgtgctgttc cggttatttt agtgcctaaa aaagatggaa   4260
```

```
catggcgtat gtgtgttgat tgtagggcta ttaataatat cacgatacgt tatcgacacc    4320
ctattccacg tttagatgat atgcttgatg aattgagtgg tgccattgtc ttttctaaag    4380
ttgatttgcg tagtgggtac caccagattc gtatgaaatt gggagatgaa tggaaaactg    4440
ctttcaaaac taagttcgga ttgtatgagt ggtagtcat gccttttggg ttaactaatg     4500
cacctagcac tttcatgaga ttaatgaacg aggttttgcg tgccttcatt ggaaaatttg    4560
tggtagtata ctttgatgac atattaatct acagcaaatc tatggatgaa catgttgatc    4620
acatgcgtgc tgtttttaat gctttacgag atgcacgttt atttggtaac cttgagaagt    4680
gcacattttg caccgatcga gtttcgtttc ttggttatgt tgtgactcca cagggaattg    4740
aggttgatca agccaaggta gaagcgatac atggatggcc tatgccaaag actatcacac    4800
aggtgcggag tttcctagga cttgctggct tctatcgccg ttttgtgaag gactttagca    4860
ccattgctgc acctttgaat gagcttacga agaagggagt gcattttagt tggggcaaag    4920
tacaagagca cgcttcaac gtgctgaaag ataagttgac acatgcacct ctcctccaac     4980
ttcctgattt taataagact tttgagcttg aatgtgatgc tagtggaatt ggattgggtg    5040
gtgttttgtt acaagaaggc aaacctgttg catattttag tgaaaaattg agtgggtctg    5100
ttctaaatta ttctacttat gataaggaat tatatgctct tgtgcgaaca ttagaaacat    5160
ggcagcatta tttgtggccc aaagagtttg ttattcattc tgatcatgaa tctttgaaac    5220
atattcgtag tcaaggaaaa ctgaaccgta gacatgctaa gtgggttgaa tttatcgaat    5280
cgtttcctta tgttattaag cacaagaaag gaaaagagaa tatcattgct gacgctttgt    5340
ctaggagata tactttgctg aatcaacttg actacaaaat ctttggatta gagacgatta    5400
aagaccaata tgttcatgat gctgatttta aagatgtgtt gctgcattgt aaagatggga    5460
aaggatggaa caaatatatc gttagtgatg ggtttgtgtt tagagctaac aagctatgca    5520
ttccagctag ctccgttcgt ttgttgttgt tacaggaagc acatggaggt ggcttaatgg    5580
gacattttgg agcaaagaaa acggaggaca tacttgctgg tcatttcttt tggcccaaga    5640
tgagaagaga tgtggtgaga ttggttgctc gttgcacgac atgccaaaag gcgaagtcac    5700
ggttaaatcc acacggtttg tatttgcctc tacccgttcc tagtgctcct tgggaagata    5760
tttctatgga ttttgtgctg ggattgccta ggactaggaa gggacgtgat agtgtgtttg    5820
tggttgttga tagattttct aagatggcac atttcatacc atgtcataaa actgacgatg    5880
ctactcatat tgctgatttg ttcttccgtg aaattgttcg cttgcatggt gtgcccaaca    5940
caatcgtttc tgatcgtgat gctaaatttc ttagtcattt ttggaggact ttgtgggcaa    6000
aattggggac taagctttta ttttctacta catgtcatcc tcaaactgat ggtcaaactg    6060
aagttgtgaa tagaactttg tctactatgt taagggcagt tctaaagaag aatattaaga    6120
tgtgggagga ctgtttgcct catattgaat ttgcttataa tcgatcattg cattctacta    6180
caaagatgtg cccatttcag attgtatatg gtttgttacc tcgtgctcct attgatttaa    6240
tgcctttgcc atcttctgaa aaactaaatt ttgatgctac taggcgtgct gaattgatgt    6300
taaaactgca cgaaactact aaagaaaaca tagagcgtat gaatgctaga tataagtttg    6360
ctagtgataa aggtagaaag gaaataaatt ttgaacctgg agatttagtt tggttgcatt    6420
tgagaaagga aaggtttcct gaattacgaa aatctaaatt gttgcctcga gccgatggac    6480
cgtttaaagt gctagagaaa attaacgaca atgcatatag gctagatctg cctgcagact    6540
ttggggttag ccccacattt aacattgcag atttaaagcc ctactggga gaggaagttg     6600
agcttgagtc gaggacgact caaatgcaag aaggggagaa tgatgaagac atccacacta    6660
```

-continued

```
ctgatgcatc tataccaata caagtaccaa tttctggtcc cattactcgc gctcgtgctc    6720
gtcaactcaa ccatcaggtg attacactct tgagttcatg tccatcatat ttagagccat    6780
ggagacccgt gcactcttgt tttgcttagg aatcagggag aagaccgaaa gggaaaagga    6840
tttgaacatg ctggattcgg actgcagaag aacaccaact tgtgacggtc accacggtca    6900
gatgcgggct cggattggaa tgttcaagca caacatggaa agcttatcaa gtctactttc    6960
atatggatcc ggaattatag tcatatctgt tctgaggccg ccgtaatcat tgttttctta    7020
ccgagacatt tcctgccttt tctgcccatg gtgctgcgtc accctatttt ggcccaatgg    7080
gtcgtgtatc aagttaggtc cattagggac gcatcctagg gttgcagcac gaccccaata    7140
cccttgtggt cgtcctccca tgtttataaa cccctagcc gccaccaaga acagcgggtt     7200
ttgtttagat caagtttagc tctcgctact tgcttgtaag cgcgcgtgct agttcagccg    7260
cccgtcttct tgtcttcgga acccaccat attggagttt gattttgaaa cctacattta     7320
gatctggtaa ttcagtactt gttctacttg ttccttgctag ttcttcgatt gcttgcagga   7380
cgagtgccct agtggccagg gtgtcacgct ccacaagatc gtgacagcca taggaggtgg    7440
tgtatcggtt gctaaggcgc agcgtctttg gaaggctgta gtcgggccgt gaacgtcgtc    7500
tcctccccca atcgagttat tccacaccct ctcatcgaaa gatcgggcaa tcacccaacg    7560
ggtgcacatc ag                                                        7572

<210> SEQ ID NO 78
<211> LENGTH: 6682
<212> TYPE: DNA
<213> ORGANISM: Zea mays

<400> SEQUENCE: 78
ggttccggtg gcaaaaactc gtgctttata tgcacccccgt tcaaatcatt attctttcat     60
gtttaaaggc cagaaaataa ttatacatcc aatgaccccct gaccaaattt tgaaagatga   120
tcttactagg gctgctaaaa ctgcacaaca agtcaaatcg acatcagccg cacctattaa    180
atctgaaatc aagttgcact ctcctgtttt acttgctaca cgtgctgatt ttgatgatct    240
ccatgaagct catatgccct gttatgcact tgtatgctcg cgcatgcttg ttccgcttga    300
tgatgcaccg tcttttggata taccccctgc tgttgttaac cttttgcagg agtatgctaa    360
tgtttatcct acggacttac caccgggtct tcctcccctc cgtggcattg agcatcagat    420
cgatctcatc cccggcgctt ctcttccgaa ccgcgcccccg taccgtacaa atccagagga   480
gacgaaggag atcagcgcc aggtgcagac gctgcttgat aagggttaca ttcgtgagtc    540
tcttagccct tgctcggttc ctgttttact cgttccaaag aaagatgggt catggcgaat    600
gtgcgtagat tgtcgtgcta ttaataacat cacagttcgt tatcgatatc ctattccacg    660
ccttgatgat atgttagatg aacttagtgg tgccgttatt ttctctaagg ttgatttgcg    720
tagcggttac catcagatta gaatgaaact cggtgatgaa tggaaaacgg cttttaaaac    780
aaaatttggt ttatatgaat ggttggttat gccatttgga ttgactaatg ctcccagcac    840
ctttatgcgt ttaatgaacg aagttctacg ggccttcata ggtttgtttg ttgttgttta    900
tttcgatgat atccttattt acagcaagtc tatagaggag catttagaac atttgcgtgc    960
tggttttgat gctttgcgtg ctgctcgctt ggttggtaac atggaaaagt gcacattttg   1020
cacgcaacgt gtcttgtttc ttggttatgt ggttactccg cagggcattg aggggatagc   1080
agcaagattg ctgccatcgg gagggcctac accaacgacg gtcacacaaa ttcggagctt   1140
tcttggactt gccggttctct accgcagatt tgttcgtgat tttagctcca ttgcagcgcc   1200
```

```
tctacatgag cttacaaaga aagatgtgcc gtttgcttgg agtgattcac aggaggtagc    1260
gttcagcact ttgaaagata agttaaccca agcttccctc ttgcaattgt gatgagaaca    1320
taacccgcac agatatgacc atgttaatgg ctcctgctac aaagacattg aggaacaaag    1380
aagttgattg gggaccaagt aatgatattt ccaacatttc caacaaagca agcacatcat    1440
caaatttaaa gatatacttg ggtgaggagc atacactaga gtcgaggacg actctattac    1500
aagaagggga ggatgatgag gacatcactg ccatcaatac accacaccag cgacctcctt    1560
caccatttaa taatggacca gtaaacgagt ccgtgcacgt aaatttttatt atcaggtgaa    1620 ctcgttcctt attgttgaag ctaatcattc cttaaatgag gtactaatac cttgtgatta    1680
ctttattaat ctaaggtgtt tgggaggtga accatctaga atttgagaag gcaacaaggc    1740
aataaaagct gctccacttg aggggatttc gaaactacaa caagtgcaag tttaagaggg    1800
catatctttc agctcctaag gttgtttaat gcaaataagc acttgttgga aaggtctctt    1860
tgtctacttt ctagtggatc aagaatcaac gagagatcag acactaagtg tccagaaact    1920
gccgagtgaa ctcctgctct acccaagtca atttcgtaac tgcagcatgc accaaattaa    1980
atggagcata acttttccact cccaaggttg tttagtgcaa ataactactt gttggaaagc    2040
tctcttcgtc tactttcatg tgcatcaata atcaatgaca gaaaccaaac gaggcgtcca    2100
gaaactgccg agagagtttc gttctccatt agaactcctt tctattcctc tatttaagca    2160
actagcagcc accaaagaac ttgggttttt gtttgatgta agtttagcct ttgctacttc    2220
cttgtaaacg catgtgtcgg ctagaccacc cggatacttg aaacagaacc ccaactctat    2280
cagatccgtg agtgtctgct ttttatcttg ttcttgcttg ttctcgattg cttgcaggtt    2340
caaggctgtt cttggcacgg caagggcagc aacaacagga gccgatgtaa ctatcgctaa    2400
ggcgcagcac ccttgtggtt gttgtagtcg gatagcacaa cgtcgacctc cacccccaaat    2460 cgtagttatc aggagacggt gtacctgtcg ctcaaggcgc cacaccatct tggttgtggt    2520
agtcgggcag ccaacgtcgt tctccaacaa gtttccacct ccatcatctc tcatcgaaag    2580
atcgggcacc cttctacccg ttgggtttat caagtggtat caaatttcag gttgctcggt    2640
gagagatctc aatcttcctt gttttgttta cctacagtcc acttttgccc aaagatatat    2700
ttagagcaga aattcaccta aaaacagttt gagcctttgc tttactactt agttttcgac    2760
ttgttgaatt ccggtagctg catttgggtc gagttgctgg tctaaagttt tcttaccgct    2820
agagtttcga gttcgcgcca ccttgtttca atcaccagtt tagacctctt gctgcaattc    2880
aaccaaaaag aagagaaagc aaaaggcgag tgcacaaaaa aagccgcact aatcagcaaa    2940
acaaaaaaag acacgtgcaa aacaaagag agagaaaaaa accagttctg aattttggta    3000
gataaaattt gtaagtgcaa caaaacaaaa ggcagtttgt gtgccttctt tttatagttt    3060
cagaaatcag attgttgttc tgagcttttg gtgatactat ttgtgtaacg gctcgcgtct    3120
ctattacggt ttggactagg accagcacaa caccttgtgg aacgtttatt caacttgttg    3180
tggctaacgt ggtactagct attccttgga actattgttt aaacagccac ctataaatcc    3240
acaaaatttt ctacaacacc accaggttgt gctagcagcc actgttgttg ttgttcgtgc    3300
tgtttgccag cgcctcctgc tttgcgtggt gagaacttgt aagaacttgt ttaaccagtt    3360
tgagagtgag agattacaac aatgattcct agtagtttat agaatcaaag atatttttta    3420
ttgtttcttg tctttactaa acatggcagg tgatatggac atttttgacc caaccgaacg    3480
ttatattgga ggcatcattc aacacttgcc tttatatgcc ggtaaattcg atcctcatgc    3540
atacattgat tgggagctaa agctagataa ggaatttgat aagcatgatc tatctcaaaa    3600
```

```
acaaaagatt tatattgcct ctaatttgtt aactgagcac gcattgatgg aatggaaata   3660
catttgtagg cacaacaaag ttccacaatc ttgggaagac ttcaaacttc attttagaga   3720
tgcattcatt cctgcatact atgctgatca tttgctttct aaattagaca ccttaaagca   3780
gggtgctagg actgtgaaag attattatta tgattttaaa attttttacca tgtttgctcg   3840
tttagatgaa tgcatggaag atgtcatgac taggttcatg aaaggactca attctgaaat   3900
tcagactata gtcatgcatg aagcatacaa acacatttct cacttgtttt tgcttgcatg   3960
taaagctgaa aatgagattc tattatacaa ttatacaagc actgaacatg tgagccataa   4020
ttcctctttt gcatcttctc tacatgctga tcaagaacac aaaataatga aaccagctgt   4080
tgttttttcca tcatcacaag aagaattgat tgctgacact tgtgatagtg aagatttgtg   4140
ggataatgat tcacatgtac taagacaaca actagtaaat gaacatgtta catctattat   4200
tgaaccaaac attttggcta aaaaggaaca tgtaatttgt attgcaaacg aaactgaaga   4260
aataaatttg ctctcttctt taaatacttg gggctatatt gaatttgatg atcttttttga   4320
gctcggtaat ttggaaaata ttttatttgc tagattcaac tataccatgt ccttctcatg   4380
atatattttta tattgctggc aagtacaaca acataggaca atttcttgtg catgaaattt   4440
ctatttcatc tagatatgtt gtttcttcac tttgtgcaaa taagatattg gtatgttctc   4500
aagaagaaaa gaatctcttg tttccatgta cttttagttga agtttcaggt ttatatttga   4560
aagacattaa taaaagctta gtcatcaaca tcaatcatga tgcaaaaccg aggacggttt   4620
gctatcaaga aggggagaat gatgagaaca taacccgcac agatatgacc atgttaatgg   4680
ctcctgctac aaagacatta aggaacaaag aagttgattg gggaccaagt aatgatatttt   4740
tcaacatttc caacaaagca agcacatcat caaatttaaa gatatacttg ggtgaggagc   4800
atacactaga gtcgaggacg actctattac aagaagggga ggacgatgag gacatcactg   4860
ccatcaatac accacaccag cgacctcctt caccatttaa taatggacca gtaaacgagt   4920
ccgtgcacgt aaatttaatt atcaggtgaa ctcgttcctt gttgttgaag ctaatcattc   4980
cttaaatgag gtactaatac cttgtgatta ctttattatt ctaaggtgtt tgggaggtga   5040
accatctaga atttgagaag gcaacaaggc aataaaagtt gctccacttg aggggatttc   5100
gaaactacaa caagtgcaag tttaagaggg catatctttc agctcctaag gttgtttaat   5160
gcaaataagc acttgttgga aaggtctctt tgtctacttt ctagtggatc aagaatcaac   5220
gagagatcag acactaagtg tccagaaact gccgagtgaa ctcctgctct acccaagtca   5280
atttcgtaac tgcagcatgc accaaattaa atggagcata acttttccact cccaaggttg   5340
tttagtgcaa ataactactt gttggaaagc tctcttcgtc tactttcatg tgcatcaata   5400
atcaatgaca gaaaccaaac gaggcgtcca gaaactgccg agagagtttc gttctccatt   5460
agaactcctt tctattcctc tatttaagca actagcagcc accaaagaac ttgggttttt   5520
gtttgatgta agtttagcct ttgctacttc cttgtaaact catgtgtcgg ctagaccacc   5580
cggatacttg aaacaaaacc ccaactctat cagatccgtg agtgtctgct ttttatcttg   5640
ttcttgcttt ttctcgattg cttgcaggtt caaggctgtt cttggcacgg caagagcagc   5700
aacaacagga gccggtgtaa ctatcgctaa ggcgcagcac ccttgtggtt gttgtagtcg   5760
gatagcacaa cgtcgacctc cacccccaaat cgtagttatc aggagacggt gtacctgtcg   5820
ctcaaggcac cacaccatct tggttgtggt agtcgggcag ccaacgtcgt tctccaacaa   5880
gttttccacc tccatcatct ctcatcgaaa gatcgggcac ccttctaccc gttgcgttta   5940
tcaaattgcc tgatttttaat gaagtttttg agcttgaatg cgatgctagc ggtattgggc   6000
```

```
taggtgctgt tttgttacaa gaaggaaaac cagttgctta ttttagtgaa aaattaagcg    6060
gtgctagtct gaaatattct acttatgata aggagcttta cgctttagtg cgcactttgc    6120
atacatggca gcactatctt tggcatcgtg agttcataat tcattctgat catgaggctt    6180
taaaacatat tcgtacccaa acaaatctga accgtcgtca tgctaaatgg gtcgaattca    6240
ttgagtcctt tccttacatt attaaaccca agaccagtaa ggacaacgtt attgctgatg    6300
ctttgtctcg tcgctatacc atgctgtcac aattagattt taaaatcttt ggtttggaca    6360
ctgtgaagga tcaatatgtt gacgatgctg attttaaaga tgctttcggc cattgtatta    6420
atgggatacc atgggcaaa tttcacatac aggatgggtt cctgtttcgc gctaacaagt    6480
tgcgtgttcc agctagttcg gttcgtcttt tgttgttaca ggaggcgcat ggaggcggtc    6540
tcatggggca ttttggcgtc tacaaaacgc atgaggtgtt ggctgcccac ttcttttggc    6600
ctcggatgcg cgctgatgtt gagcgccttg ttgcacgctg aaagtcgcct agaggggggg    6660
tgaatagggc gaaactgaaa tt                                            6682

<210> SEQ ID NO 79
<211> LENGTH: 118
<212> TYPE: DNA
<213> ORGANISM: Zea mays

<400> SEQUENCE: 79
ccacgtattt tgcaagctat ttaactggcg gcgattgcgt acccgacgac caaaattagg      60
gtcaacgcta cctgtaggaa gtgtccgcat aaagtgcacc gcatggaaat gaagacgg       118

<210> SEQ ID NO 80
<211> LENGTH: 194
<212> TYPE: DNA
<213> ORGANISM: Zea mays

<400> SEQUENCE: 80 cccttactt gaggataaat tatgtctaat attcaaactg gcgccgagcg tatgccgcat      60
gacctttccc atcttggctt ccttgctggt cagattggtc gtcttattac catttcaact   120
actccggtta tcgctggcga ctccttcgag atggacgccg ttggcgctct ccgtctttct   180
ccattgcgtc gtgg                                                      194

<210> SEQ ID NO 81
<211> LENGTH: 234
<212> TYPE: DNA
<213> ORGANISM: Zea mays

<400> SEQUENCE: 81
ccgtttgaat gttgacggga tgaacataat aagcaatgac ggcagcaata aactcaacag     60
gagcaggaaa gcgagggtat cctacaaagt ccagcgtacc ataaacgcaa gcctcaacgc    120
agcgacgagc acgagagcgg tcagtagcaa tccaaactt tgttactcgtc agaaaatcga   180 aatcatcttc ggttaaatcc aaaacggcag aagcctgaat gagcttaata gagg          234

<210> SEQ ID NO 82
<211> LENGTH: 400
<212> TYPE: DNA
<213> ORGANISM: Zea mays
<220> FEATURE:
<221> NAME/KEY: misc_feature
<222> LOCATION: (74)..(233)
<223> OTHER INFORMATION: n is a, c, g, or t
<220> FEATURE:
<221> NAME/KEY: misc_feature
<222> LOCATION: (368)..(400)
```

```
<223> OTHER INFORMATION: n is a, c, g, or t

<400> SEQUENCE: 82
tgagctgtcg agaataagct tgattcgttg tgaaactcac attcaattca aacttgattc      60
aaaataatta tatnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnncgaccgc     240
gtttcgccgc ctggtgggac ccccatgttg gctgttcctt cgaccttcag ctcggtgtgt     300
cggttgcaac cactcgccga agattccgcg aatagctcgg gattgacctg accgattccg     360
cgaataannn nnnnnnnnnn nnnnnnnnnn nnnnnnnnnn                           400

<210> SEQ ID NO 83
<211> LENGTH: 903
<212> TYPE: DNA
<213> ORGANISM: Zea mays

<400> SEQUENCE: 83
cgattctaga tatcatcgcc actcgtgctg gaaaggacca gacaaacaca gaaaaattcc      60
agacatattc ctacttattc agtacagtcc ctgaactaaa ccccactat agctctatca     120
ctgttcagtc gccagaatgt cttcgtcaaa acagcctcac caggaggacc atcccgattc     180
ggagcctgaa atgctcgcgg aggatgatgc tcttgaggag attgacgctt ccgaggacgt     240
cgacgttccc atggacagcg acgatgaggg ggagcccgaa gagatcaacc tgcacaacga     300
cggcgtcgcc tactttgacc tacacaagga ctcggttttc gccattgccc aacatccaac     360
ccgcccgaca ctgatcgcaa cgggtggatc agaaggagac tcggacgacg cgccaggcaa     420
gggctacgtc tttgacaccg cacacgttcc ccagcgccct ctattaccac caaactttag     480
cggcgaacct ccgaaccccc cggtagcgct ggaccgtctg tttgagattg atgggcatac     540
cgacagcatc aatgctttga cgttcaccta ccccgaggga gagtatctct tgagcggagg     600
tatggacggc aagcttcgcg cgtacgccgg caaggcggca ccatttcaac cgggagccgc     660
ccatgtcacc agtcgcacaa atcccccttc cttgccgagt cccaggaagt cccccaaatc     720
aacttcctat cttcccttgc cccattgctc catcgtcctc ccttgtcctt agaccttggc     780
tggcatcctg accggctccg tctggtgtgt acccatggaa gaacgcaggc tcccaatcc     840
cggcgctggt ctaatcccga aagacatttt ccttcttccc taatatgggc cccggaccca     900
cta                                                                    903

<210> SEQ ID NO 84
<211> LENGTH: 857
<212> TYPE: DNA
<213> ORGANISM: Zea mays
<220> FEATURE:
<221> NAME/KEY: misc_feature
<222> LOCATION: (1)..(603)
<223> OTHER INFORMATION: n is a, c, g, or t
<220> FEATURE:
<221> NAME/KEY: misc_feature
<222> LOCATION: (779)..(821)
<223> OTHER INFORMATION: n is a, c, g, or t
<220> FEATURE:
<221> NAME/KEY: misc_feature
<222> LOCATION: (827)..(827)
<223> OTHER INFORMATION: n is a, c, g, or t
<220> FEATURE:
<221> NAME/KEY: misc_feature
<222> LOCATION: (847)..(847)
<223> OTHER INFORMATION: n is a, c, g, or t
```

```
<400> SEQUENCE: 84
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnaagcaaa ttcgacccgg tcgtcggttc agggcagggt cgttaaatag ccgcttatgt     660
ctattgctgg tttaccggtt tattgactac cggaagcagt gtgaccgtgt gcttctcaaa     720
tgcctgaggc cagtttgctc aggctctccc cgtggaggta ataattgacg atatgatcnn     780
nnnnnnnnnn nnnnnnnnnn nnnnnnnnnn nnnnnnnnnn ncttccnagc acagtggcga     840
tgatatncta gaattcg                                                   857

<210> SEQ ID NO 85
<211> LENGTH: 119
<212> TYPE: DNA
<213> ORGANISM: Zea mays

<400> SEQUENCE: 85
agctccaatg tgctggaaag gcaacggtgc acttggcgga aaggccttgg gtgcttgctg      60
gcggattgca gtgtcgtttt gcgtggggat aaatcctttc cagcacagtg gcgatgata     119

<210> SEQ ID NO 86
<211> LENGTH: 1802
<212> TYPE: DNA
<213> ORGANISM: Zea mays
<220> FEATURE:
<221> NAME/KEY: misc_feature
<222> LOCATION: (643)..(834)
<223> OTHER INFORMATION: n is a, c, g, or t
<220> FEATURE:
<221> NAME/KEY: misc_feature
<222> LOCATION: (1282)..(1765)
<223> OTHER INFORMATION: n is a, c, g, or t

<400> SEQUENCE: 86
gggttttggg gccgaggatc agcgagctga ttcgtcgcca ctgtgctgga aaggtcatct      60
aaattgaaac cgccctttta tgttatttga attccagtca tgttcttttt tccccttttcg    120 ttttacaagc cttcatttgt tcagcatatt cattaattta tgatggatag aacttagaag    180
tagtagcagt aacaagtacg caaataataa acatgtatga caataagtga atgtgttaac    240
tatatactga ccattatgaa tgtgacataa gaaatagaga aatttcaaag actccatccc    300
atcatgaatt catggtttac ttacattaaa caagaatagt atacatttgt atagtggtaa    360
cagaaaaata tggcacagag cagcaattct gctcaagtcc ctagtgttac attataacaa    420
agaatattca cgttatgcga gtccatttca gctgataaga acaacaagaa gaattcctag    480
tcaggaactt actcgtggca atagcaattg gtgcagttgt tggccaatgt tccttccatc    540
ggactagctt agcacttgac agttcaaagc tgcaacactc actcgtccaa cctttcccag    600
```

```
cacattggag cttcagctgc tcgagggggg ggcccggtac ccnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnngacgcg    840
ccctgtagcg gcgcattaag cgcggcgggt gtggtggtta cgcgcagcgt gaccgctaca    900
cttgccagcg ccctagcgcc cgctcctttc gctttcttcc cttcctttct cgccacgttc    960
gccggctttc cccgtcaagc tctaaatcgg gggctccctt tagggttccg atttagtgct   1020
ttacggcacc tcgaccccaa aaaacttgat tagggtgatg gttcacgtag tgggccatcg   1080
ccctgataga cggttttttcg cccctttgacg ttggagtcca cgttctttaa tagtggactc   1140
ttgttccaaa ctggaacaac actcaaccct atctcggtct attcttttga tttataaggg   1200
attttgccga tttcggccta ttggttaaaa aatgagctga tttaacaaaa atttaacgcg   1260
aattttaaca aaatattaac gnnnnnnnnn nnnnnnnnnn nnnnnnnnnn nnnnnnnnnn   1320
nnnnnnnnnn nnnnnnnnnn nnnnnnnnnn nnnnnnnnnn nnnnnnnnnn nnnnnnnnnn   1380
nnnnnnnnnn nnnnnnnnnn nnnnnnnnnn nnnnnnnnnn nnnnnnnnnn nnnnnnnnnn   1440
nnnnnnnnnn nnnnnnnnnn nnnnnnnnnn nnnnnnnnnn nnnnnnnnnn nnnnnnnnnn   1500
nnnnnnnnnn nnnnnnnnnn nnnnnnnnnn nnnnnnnnnn nnnnnnnnnn nnnnnnnnnn   1560
nnnnnnnnnn nnnnnnnnnn nnnnnnnnnn nnnnnnnnnn nnnnnnnnnn nnnnnnnnnn   1620
nnnnnnnnnn nnnnnnnnnn nnnnnnnnnn nnnnnnnnnn nnnnnnnnnn nnnnnnnnnn   1680
nnnnnnnnnn nnnnnnnnnn nnnnnnnnnn nnnnnnnnnn nnnnnnnnnn nnnnnnnnnn   1740
nnnnnnnnnn nnnnnnnnnn nnnnntttct tccccctttc ctctatgata tctagattcg   1800
cg                                                                  1802

<210> SEQ ID NO 87
<211> LENGTH: 294
<212> TYPE: DNA
<213> ORGANISM: Zea mays
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (157)..(294)
<223> OTHER INFORMATION: n is a, c, g, or t

<400> SEQUENCE: 87
nnncgatgga ccgcgcttgt gtgtcgcgtt cagtttggct tttgccaagc agtagggtag     60
cttcccgcgt cggtaattat atggtatgaa ccatcacctt ttggctctac atggtatgaa    120
cgtaagatac aaattccaac tacctctagc tcgccgnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnnnnnnnn nnnnnnnnnn nnnnnnnnnn nnnnnnnnnn nnnn          294

<210> SEQ ID NO 88
<211> LENGTH: 2540
<212> TYPE: DNA
<213> ORGANISM: Zea mays
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (1274)..(2203)
```

<223> OTHER INFORMATION: n is a, c, g, or t
<220> FEATURE:
<221> NAME/KEY: misc_feature
<222> LOCATION: (2404)..(2540)
<223> OTHER INFORMATION: n is a, c, g, or t

<400> SEQUENCE: 88

| | | | | | |
|---|---|---|---|---|---|
| nnnnnnnnnn | nnntgtttaa | ctcttcgtaa | gaacagtggt | acgtcccgtg | tctatatttg | 60 |
| gcttttgtta | aagccaacag | tacatgcttg | cgtgggtgaa | aatgtgaaat | gccatcgctg | 120 |
| tgctacaact | tttcggctcc | ctcctgcttc | ggtgcttcca | catgcccctg | cacggcgtct | 180 |
| agaaatccta | atgatttagc | agcacacctg | tccgcctagc | cgcctacgcg | tacacagaaa | 240 |
| acaattttt | tgtccacaca | cgcgcgcgct | ccgagccgca | gatccgagct | agcgcggcgc | 300 |
| atccgacggc | cacgacagcg | cagtgccgtc | tccgccgcc | accgcttggc | gattgtccgc | 360 |
| accccaccag | tccaccacct | ccccacgag | cgaaaaccac | ggtccacgga | ccacggctat | 420 |
| gttccactcc | aggtggaggc | tgcagccccg | gtttcgcaag | ccgcgccgtg | gtttgcttgc | 480 |
| ccacaggcgg | ccaaaccgca | ccctccttcc | cgtcgtttcc | catctcttcc | tcctttagag | 540 |
| ctaccactat | ataaatcagg | gctcattttc | tcgctcctca | caggctcatc | tcgctttgga | 600 |
| tcgattggtt | tcgtaactgg | tgagggactg | agggtctcgg | agtggattga | tttggggttc | 660 |
| tgttcggaga | tttgcggagg | gaggccttgg | taccggtgat | caagtgcaaa | ggtccgcctt | 720 |
| gtttctcctc | tgtctcttga | tctgactaat | cttggtttat | gattcgttga | gtaattttgg | 780 |
| ggaaagcttc | gtccacagtt | ttttttcgat | gaacagtgcc | gcagtggcgc | tgatcttgta | 840 |
| tgctatcctg | caatcgtggt | gaacttattt | cttttatatc | ctttactccc | atgaaaaggc | 900 |
| tagtaatctt | tctcgatgta | acatcgtcca | gcactgctat | taccgtgtgg | tccatccgac | 960 |
| agtctggctg | aacacatcat | acgatctatg | gagcaaaaat | ctatcttccc | tgttctttaa | 1020 |
| tgaaggacgt | cattttcatt | agtatgatct | aggaatgttg | caacttgcaa | ggaggcgttt | 1080 |
| ctttctttga | atttaactaa | ctcgttgagt | ggccctgttt | ctcggacgta | aggcctttgc | 1140 |
| tgctccacac | atgtccattc | gaattttacc | gtgtttagca | agggcgaaaa | gtttgcatct | 1200 |
| tgatgattta | gcttgactat | gcgattgctt | tcctggaccc | gtgcagctgc | ggtggcaagg | 1260 |
| gaggccggca | agcnnnnnnn | nnnnnnnnnn | nnnnnnnnnn | nnnnnnnnnn | nnnnnnnnnn | 1320 |
| nnnnnnnnnn | nnnnnnnnnn | nnnnnnnnnn | nnnnnnnnnn | nnnnnnnnnn | nnnnnnnnnn | 1380 |
| nnnnnnnnnn | nnnnnnnnnn | nnnnnnnnnn | nnnnnnnnnn | nnnnnnnnnn | nnnnnnnnnn | 1440 |
| nnnnnnnnnn | nnnnnnnnnn | nnnnnnnnnn | nnnnnnnnnn | nnnnnnnnnn | nnnnnnnnnn | 1500 |
| nnnnnnnnnn | nnnnnnnnnn | nnnnnnnnnn | nnnnnnnnnn | nnnnnnnnnn | nnnnnnnnnn | 1560 |
| nnnnnnnnnn | nnnnnnnnnn | nnnnnnnnnn | nnnnnnnnnn | nnnnnnnnnn | nnnnnnnnnn | 1620 |
| nnnnnnnnnn | nnnnnnnnnn | nnnnnnnnnn | nnnnnnnnnn | nnnnnnnnnn | nnnnnnnnnn | 1680 |
| nnnnnnnnnn | nnnnnnnnnn | nnnnnnnnnn | nnnnnnnnnn | nnnnnnnnnn | nnnnnnnnnn | 1740 |
| nnnnnnnnnn | nnnnnnnnnn | nnnnnnnnnn | nnnnnnnnnn | nnnnnnnnnn | nnnnnnnnnn | 1800 |
| nnnnnnnnnn | nnnnnnnnnn | nnnnnnnnnn | nnnnnnnnnn | nnnnnnnnnn | nnnnnnnnnn | 1860 |
| nnnnnnnnnn | nnnnnnnnnn | nnnnnnnnnn | nnnnnnnnnn | nnnnnnnnnn | nnnnnnnnnn | 1920 |
| nnnnnnnnnn | nnnnnnnnnn | nnnnnnnnnn | nnnnnnnnnn | nnnnnnnnnn | nnnnnnnnnn | 1980 |
| nnnnnnnnnn | nnnnnnnnnn | nnnnnnnnnn | nnnnnnnnnn | nnnnnnnnnn | nnnnnnnnnn | 2040 |
| nnnnnnnnnn | nnnnnnnnnn | nnnnnnnnnn | nnnnnnnnnn | nnnnnnnnnn | nnnnnnnnnn | 2100 |
| nnnnnnnnnn | nnnnnnnnnn | nnnnnnnnnn | nnnnnnnnnn | nnnnnnnnnn | nnnnnnnnnn | 2160 |

```
nnnnnnnnnn nnnnnnnnnn nnnnnnnnnn nnnnnnnnnn nnnaggcaat gccagcctgc    2220
cctttcgatg aggaggtaca tacacgctgg cgatggaccg cgcttgtgtg tcgcgttcag    2280
tttggctttt gccaagcagt agggtagctt cccgcgtcgg taattatatg gtatgaacca    2340
tcaccttttg gctctacatg gtatgaacgt aagatacaaa ttccaactac ctctagctcg    2400
ccgnnnnnnn nnnnnnnnnn nnnnnnnnnn nnnnnnnnnn nnnnnnnnnn nnnnnnnnnn    2460
nnnnnnnnnn nnnnnnnnnn nnnnnnnnnn nnnnnnnnnn nnnnnnnnnn nnnnnnnnnn    2520
nnnnnnnnnn nnnnnnnnnn                                                2540

<210> SEQ ID NO 89
<211> LENGTH: 153
<212> TYPE: DNA
<213> ORGANISM: Zea mays

<400> SEQUENCE: 89
cgatggaccg cgcttgtgtg tcgcgttcag tttggctttt gccaagcagt agggtagctt     60
cccgcgtcgg taattatatg gtatgaacca tcaccttttg gctctacatg gtatgaacgt    120
aagatacaaa ttccaactac ctctagctcg ccg                                 153

<210> SEQ ID NO 90
<211> LENGTH: 2773
<212> TYPE: DNA
<213> ORGANISM: Zea mays

<400> SEQUENCE: 90
gatcctaaag gaagctcatg agacagccta ctccatacac cctggaagtg aaaagatgta     60
tcaggattta aaaaggagat tttggtggta tggcatgaaa agagaaatcg cagaatatgt    120
cgccatctgt gatagctgtc aaagaaccaa agcagagcat caaaagcccg ccggactgtt    180
gcagccattg cagatccctc agtggaagtg ggatgagatc gggatggatt tcatagttgg    240
cctacctcgt acccgggccg gctatgattc catctgggtg gttgtggacc gcttaacaaa    300
ggtagcccat tttatacctg tgaagacaac gtacaccgga gcagcgttag ctgagttata    360
catgtctcga atagtctgcc ttcatggtgt gccgaagaag atagtgtcag atcgaggaac    420
acagtttacc tctcattttt ggcagcagct acaagaagct ttgggcacac atttgaactt    480
cagctcggct tatcacccac agacagacgt cagactgaa agaactaatc agatcctaga    540
agatatgttg agagcctgtg cgttgcaaga caagtcagga tgggacaaaa aggttacctt    600
atgcagaatt ctcctacaac aatagttacc aggccagctt gaagatgaca ccgtttcagg    660
cgctctatgg acggagttgt aggactccgc tgcattggga ccagcctgga gagagacagg    720
tgtttggccc cgacattttg cttgaagccg aagagaatat caaaatggtt cgggagaatc    780
tgaagatagc acaatcaagg cagcgaagct atgctgacag aaggagaaga gaactgagtt    840
ttgaagtggg agattacgtc tatctgaagg tgtcgcctat cagaggagtc agaaggttcg    900
aagtcaaggg caagttagca ccccggtacg ttggaccata tcagattcaa gcaaagcgtg    960
gagaagtggc ctaccagctc aacctaccag aaagtttgtt ggccagtgca caatgtgttc   1020
catgtgtccc aattgaagaa gtgtctgcga gtaccagaag aacagttgcc agtggaggac   1080
ttggaagtcc aagaggatct gacctacata gagaagccaa cgcagattct ggagtttgca   1140
gacagagtca gccggaggaa caccatcaga atgtgcaaag tcagatgggg ccaccactct   1200
gaggaagaag caacctggga acgagaagat gatctgaaag acaaataccc cgaactcttt   1260
gctgaccaac cttgaatctc ggggcgagat tcttttaagg gggataggtt tgtaacaccc   1320
```

```
tgaatttggg gtataaaatt tctttgctca tatccacaaa ttcaggtgtt attcctctca    1380
tctcatcttc tccaatctct tgttttcttt tttatatat agaagaagag tggttatttt    1440
taatcgtaaa ggtaattata atctagtaga aaagagaaca atggttgttg catcatgtta    1500
gaaagcattt gttcttttg gttgatgaat gagttgctca atctttcatc taataattta    1560
ttttcgcata gtgtcaaact gaaataaata gaaagagaa agaaaagaa agaaaagga     1620 aaaacagatt tcagcccagc ccccttccc tggcccagcc agcccaccgc gccagccccc    1680 ccttcccct ctttctcccc ccgctcggc ccaactcccg gcccttcccc cccccacgc     1740 cagaaccccc ctcgcgggcc cgcgcacgcc gcagcccacc ccagctcccg cggcggccca    1800
gcgcgccatt ccaaatcgga acgcctgtgc gaatttccag agaagaaaac cgcccgcgcg    1860
cagttttctt cgctagttgc gcatgatttc ttccacccgt tgtccagttt tctcgccacg    1920
aacgcccacg accccctgc gcagttctcg ccattgctgc ttcgtctcgc cgatccgccg    1980
ccggagcctc gcctcgcccc cgctctctgc gtccccgtcg ccggagtgcc gcgcccgct     2040 gcggccgtcg tcgtgcgcgc cgccgaggta agcccgcccc atcctctctc tccttcca    2100 ttcttcctcc ccgccgtac gcgtctgctg cgtacccgta gcccttgtc gcgccgtttc    2160 acttcgccgg cgagacctcg ctcagtcgct gccggcgtc gcggtcaggg ggacctgcgc    2220
agcgactcgt ccctgccgcg gactcccctc cggccagcgc tgatgaggac atcctccact    2280 attaccccgtt ggcaaagacg caattggccc agttggccca attgtagtcg gacggcgacc    2340
gtgtgagcct cagaattatc ccacctcgct taacttggga ggaggaagcc actttaaaag    2400
ggagagccac ccttccccca ttgggctagt cttttggggc gattgggcct ctccctgagt    2460
tgggtgtgct taatgaacag ttgggctccg ggcaacccta atttgttggg cctcggccaa    2520
ccccacctgg gctgggtgta tcatctggta tcagaactag gcccatttt aagaaggtgg    2580 gaatgatgag gacatcctcc actattaccc gttggcaaag acgcaattgg cccagttggc    2640
ccaattgtag tcggacggcg accgtgtgag cctcagaatt atcccacctc gcttaacttg    2700
ggaggaggaa gccactttaa aagggagagc caccccttccc ccattgggct agtcttttgg    2760
ggcgattggg cct                                                       2773

<210> SEQ ID NO 91
<211> LENGTH: 155
<212> TYPE: DNA
<213> ORGANISM: Zea mays

<400> SEQUENCE: 91
gacgtgcggc aacgaaattg cgcgaaacca ccccaaacat gagttttgga cctaaagtag       60
tggattgggc atgttcgttg cgaaaaacga agaaatggtt ccggtggcaa aaactcgtgc      120
ttttatgcac cccgacaccc gttttcggaa tgggt                                 155

<210> SEQ ID NO 92
<211> LENGTH: 10925
<212> TYPE: DNA
<213> ORGANISM: Zea mays
<220> FEATURE:
<221> NAME/KEY: misc_feature
<222> LOCATION: (550)..(589)
<223> OTHER INFORMATION: n is a, c, g, or t
<220> FEATURE:
<221> NAME/KEY: misc_feature
<222> LOCATION: (8665)..(8677)
<223> OTHER INFORMATION: n is a, c, g, or t
<220> FEATURE:
<221> NAME/KEY: misc_feature
<222> LOCATION: (8681)..(8683)
```

```
<223> OTHER INFORMATION: n is a, c, g, or t
<220> FEATURE:
<221> NAME/KEY: misc_feature
<222> LOCATION: (8685)..(8685)
<223> OTHER INFORMATION: n is a, c, g, or t
<220> FEATURE:
<221> NAME/KEY: misc_feature
<222> LOCATION: (8687)..(8689)
<223> OTHER INFORMATION: n is a, c, g, or t
<220> FEATURE:
<221> NAME/KEY: misc_feature
<222> LOCATION: (8691)..(8691)
<223> OTHER INFORMATION: n is a, c, g, or t
<220> FEATURE:
<221> NAME/KEY: misc_feature
<222> LOCATION: (8696)..(8696)
<223> OTHER INFORMATION: n is a, c, g, or t
<220> FEATURE:
<221> NAME/KEY: misc_feature
<222> LOCATION: (8698)..(8698)
<223> OTHER INFORMATION: n is a, c, g, or t
<220> FEATURE:
<221> NAME/KEY: misc_feature
<222> LOCATION: (8700)..(8700)
<223> OTHER INFORMATION: n is a, c, g, or t
<220> FEATURE:
<221> NAME/KEY: misc_feature
<222> LOCATION: (8704)..(8705)
<223> OTHER INFORMATION: n is a, c, g, or t
<220> FEATURE:
<221> NAME/KEY: misc_feature
<222> LOCATION: (8707)..(8708)
<223> OTHER INFORMATION: n is a, c, g, or t
<220> FEATURE:
<221> NAME/KEY: misc_feature
<222> LOCATION: (8739)..(8739)
<223> OTHER INFORMATION: n is a, c, g, or t
<220> FEATURE:
<221> NAME/KEY: misc_feature
<222> LOCATION: (8750)..(8750)
<223> OTHER INFORMATION: n is a, c, g, or t
<220> FEATURE:
<221> NAME/KEY: misc_feature
<222> LOCATION: (8755)..(8756)
<223> OTHER INFORMATION: n is a, c, g, or t
<220> FEATURE:
<221> NAME/KEY: misc_feature
<222> LOCATION: (8764)..(8764)
<223> OTHER INFORMATION: n is a, c, g, or t
<220> FEATURE:
<221> NAME/KEY: misc_feature
<222> LOCATION: (8779)..(8780)
<223> OTHER INFORMATION: n is a, c, g, or t
<220> FEATURE:
<221> NAME/KEY: misc_feature
<222> LOCATION: (8827)..(8827)
<223> OTHER INFORMATION: n is a, c, g, or t
<220> FEATURE:
<221> NAME/KEY: misc_feature
<222> LOCATION: (9083)..(9122)
<223> OTHER INFORMATION: n is a, c, g, or t

<400> SEQUENCE: 92
tgtaacgccc cgaattttgc agttgaattt tttctttct ttactcgcca aattcgggcg      60 ttacctttc ttttctttt tcccttcgct aaaccttgac cttttccaaa gttctagcgg     120
gattcggttt ggaattcctg tgtaagaaaa accctaaata ctttatgttg tttgatgcac    180
catgccgaac cttgcatttc ttttgattgc tttgaaagtg caaatgcatt catgtagaaa    240
gatcggattt cgaaaatgag gagaagatct tttctttctt tttctctctc tttctctctc    300
ctcttttttt tctctctctc ccgcgccgtg ggccgacccc ggccggccca gccgcccctg    360
cgcgcccccc ccctcttggg ccttggcagg cccaaccgcc cccccctcat ccccccccctt    420 tttccccaaa ccctctcccct ctccctctca ttttctctca tttcatcaa gcggaaagat    480
```

```
accgtcgacc tcgcgcgtgg tactgattta cccaatctcc gccctgatag tgaagttcgt    540
attacgcggn nnnnnnnnnn nnnnnnnnnn nnnnnnnnnn nnnnnnnnnt aaatgtggat    600
ggatgtatgt atgtttgcaa tcgcatagag aacgatccgg tcgaagagcc cgaggaattc    660
gcaggagaag ccctgagca gcagtcgggt ggtggaggca agtgtccttt gacctatctc    720
tgtcctattt attatttaat tcaccccgc atcacacatt tatacctaag gattgactag     780
cttttgttat ccatgtcctt gtttacctat ttggggttgga ttattactgt ttagctttat   840
gctattgctc aactctaatc aatgaacatg atgtggttat ctatgatacg ttgttttccc    900
gttcttattt atgattatac ttgtggcatt taagggggact cgagcggttt ctcgagtgcc   960
tctccgtaag gacctgttct atggatgatc gcccgggaaa acagtgcaac catgagggtg   1020
gaatggggtg cccttagctg aataattaga ggatccggga tgtagttcgc ttcgccgtcg   1080
tgccgtcaat ggggctcggt gtatgcggct cgctctgcca aggttgattt gtcccttggg   1140
gaggagtgcg gtacatttag gaaacctaac gggcggctac agccccgagg aatctttgta   1200
aaggctacat agtgagaccc tgcctattca ccttggtagt gtttaagggt ttgatcggcc   1260
cgaggcaaga gggaatcacg gcttgtgggt aaagtgcaca acctctgcag agtgttatga   1320
aactgatata tcagccgtgc tcacggttat gagcggccaa gggagctcca gtgattagtg   1380
gtacttgatc agagacatta tggtacaggt ggttatgaga tcgatggttc tggttatgac   1440
tatggttctg gttatgacta tggttctggt aagtggtatt ctttccgttt ggaaagggta   1500
catcgggtta ataacttggg ttaatgctaa aacttggctt tctactagta aataatgatc   1560
tgaccaacta aaagcaactg cttgacttat ccccacataa agctagtcca ctacagccaa   1620
acaggatact tgctgagtat gttgatgtgt actcacccct tgctctacaca ccaaaccccc   1680
cccccccagg ttgtcagcat tgcaaccact gctcaggaga agatgaagct gtggaaggag   1740
acttccagga gttccaagac tacgacgagt tctaggtgtg ggttagcggc aacccacagt   1800
cggctgcctg tgaaggccgc gttatctacg tttcttttcc gcactttgat ttattgtaag   1860
aactatatgg acgtctcaga cgtatgatgt aatcgactat ttcccttatt aatactattt   1920
tgagcactgt gtgatgatgt ccatattatg taactgctgt gtacgtgaat aactgatcct   1980
ggcacgtaca tggttcgcat tcggtttgcc ttctaaaacc gggtgtgaca taagtggtat   2040
caaagccgtg ctgactgtag gaccgctaac ctagagtaga atggtcgttc taaggattat   2100
agacctctgt ccctaccttg actttgatat ctcttcaaaa gttggtccta ccgaccaaac   2160
ctatgttcta ctatatatta taccttgcta aaaaattgtg tttcattctg atccttcatt   2220
tacttattac ttgctggtca tattaatttc gttctcaccc ttttgcttgc gatgtctttt   2280
gtagatggct cgacttagac acactgcacg aaagtcagtc atccccttct taccctcccg   2340
ccttgctgag cgtccgcttc gccgtcccgt ggccggacag tccagccact tggagagact   2400
acaccaccgc ctgcgtgagg agcaggagcg tcgacgacag gagcagcaga gctcttcttt   2460
ctcgctccac caggagatag agtctgtgag gagctgctcc cctgtgcttc ctctggagcc   2520
gcccctgca ccaccactgg gcgccccagc ttctggagta gctgctggag gagacccaga    2580
cgacggagat ggcgacgaca gctcaagcca cgacaccgac ttctctgcta accctgagcc   2640
ggaaggatgg gttgctcgac ccatcactcg cgacgctgct cgcgggtgtc acttccatga   2700
tgcgctcgac accctgctac gtcgggcttt tgaccggcat acttggtccg tcgagtatcg   2760
ctgtgtggtc taccagcata gtcgcgggt ctacccggac cgctgggagg cgacttgctt    2820
ggtgcgctgc ccggaggaca gtctccaggg tgcagaggcc tgctcagagc actattctat   2880
```

```
ctctgaacgg gacttagctg aggcagccat gcaagatgct gcacggcgtg cgctttcgca      2940
ctactgctcg gttttcggtg gggtagctga tggtcttgac ctgaagtatt accccgccg       3000 tccatctggc agcacaggag gcgtgattgt ctcacctgtc ggtgagggca atcctaggtt      3060
gagcagcaca gtcaacctag ccgccgtgct aaacacggag ctggaccatg cattagacga     3120
gctgagtagg gctcgtgctg agatcgccct gctgcgggct gagcgcgcgg aacgttgtta     3180
tttggatggt ggttccccg ctcccgttgg gactcagcac ccgtaccgct cacctcagcg      3240
tggacaccag tcttatggca accccgactg caagaccaag ataactctag aaccatagat     3300
cgttagagtt ggatcttgta attaatacga aatatatatg cgtagaagct tcagtcttag     3360
cgttagactc agtcttagtt agtcttagtt agacagggta gtttgctata tcatgtgcat     3420
ttatgtttgt catgatgaac tatgtttggt ttggatcttt gtaatgactg ttaccagagt     3480
gtgggtatcc cctgcatttt ggtttatcta ttatggtaat aaagttagtt atatagttgg     3540 gaaaccctt attctacttt cctctttatc tgagaagctg tgtggtctgt gttggagatc      3600
agtgaagatg ctcatctgtt cagtgctgtt gaagaactct attctctttt ctcatgctgc     3660
aagatttgcc agatcagttc tgatgtgtgg ttgcatcctg cagatgtcag agaacaggcg     3720
tagaggagga aggcgtgctc agcaggagcg agccggtcaa caggaggagg tgccccagca    3780
gcagcacctg ccgccccgc ccccgatgtc gatcgagcag atgtttctga tgcagactca     3840
ggcagttcaa gccatcggtc agactctggc cgccattcag cagcagcagc agcagcagca    3900
agcaccaccc cagcctcaga tgcctcagat gcccagagat aagcgtgttg aattcatgag    3960
aggtcatcca ccaacgttcg ctcactcttc tgaccctatg gatgctgaag attggctgcg    4020
cactgtggag cggagttgc ataccgctca gtgcgatgac agggagaaag ttctgtatgg     4080
tccccgtctg ttgagaggag cagcccagtc atggtgggag tcttacctcg ccacccatgc    4140
ccatcctgac gccatcactt gggaagagtt cagaggtagc tttcgtcagt accatgttcc    4200
tgcaggtctg atgacagtga agaaggagga gttcctggcc ctcaagcaag ggccattgtc    4260
tgtcagtgag taccgggaca gtttctgca attgtctcgc tatgctcctg aggatgtcaa     4320
cactgacgcc aagcgacagt accgtttcct gagaggcttg gttgaccctc tgcattacca    4380
actgatgaat cacaccttcc cgacattcca gcacctgatt gatagagcga tcatgacaga    4440
aaggaagcgt aaggagatgg aagatcgtaa gcgcaagatc agtggacccc agcctggaag    4500
cagcagccgt cctcgtttct caggcaatca acctcagcag ttcaggcaga atcagcgtcc    4560
acctcagcag catcagcagt ttcaaaggca gtatcctcag cacccgtacc agaaccgtca    4620
gagcaatcag tcaggaggtc agtttcaaag gcagaatcag caggcccctc gtcttcctgc    4680
cccagcaacc cagcagagca atcaggcagt accagctcaa gttggaaaca gggcatgttt    4740
ccactgtgga gagcaaggcc actgggtgat ccaatgtccg aagaaggcag cccagcagca    4800
gtcaggcccc aatgccccag cgaagcagaa tgtgcctcaa cctggatcag caatcgctc    4860 tcagccgcgc tataatcatg aaggctgaa ccatttggaa gctgaagcag ttcaggagac     4920
ccccggcatg atagtaggta tgttcccagt cgactccat attgcagaag tgttatttga    4980
tactggagca acgcattctt tcattactgc atcatgggta gaagcacata atcttccaat    5040
tactaccatg tcaaccccca ttcaaattga ctcagccggt ggtagaattc gagccgatag    5100
catttgtttg aatataagtg tgaaaataag ggggatagca tttcccgcca accttatagt    5160
aatgggtact cagggaatag atgtcatcct agggatgaat tggctagata agtatcaggc    5220
agttatcagt tgtgataaaa ggacaatcaa gttggtgtct ccattaggag aggaaatggt    5280
```

```
gaccgagtta gtcccgcctg agccaaagaa aggaagttgt tatcagacag ctgttgatag    5340
tagtgaagca gacccaattg aaagtatcaa ggttgtgtct gaattcccag atgtgtttcc    5400
caaggattta ccgggtatgc caccagagcg gaaagttgag tttgccatag agcttcttcc    5460
tggaaccgcc cctatcttta agagagctta cagaatatct ggaccagagt tggatgaact    5520
taagaagcaa attgatgagc tgtcagagaa aggttacatt tggccaagca cctcgccttg    5580
ggccgcccct gtcctatttg tggaggagaa agatggcacc aagaggatgt gtattgatta    5640
tcgagctttg aatgaggtca cgatcaagaa caagtatccc ttgcccagaa tagaagatct    5700
gttcgaccag ttgagaggag ccagtgtgtt ctccaagatt gatctgaggt caggttatca    5760
tcagctcagg atccgacctt cggacattcc gaagacggca ttcatttcca gtatgggtt     5820 gtacgagttc acagtgatgt cttttggttt gaccaatgcg ccagcattct ttatgaactt    5880
gatgaacagt gtattcatgg attaccttga taagtttgtg gtggtattca ttgatgatat    5940
tctggtttat tctcaaagcg aagaagagca tgcagatcat ttgaggatgg tgttgcagag    6000
attgcgagag caccagttgt atgcaaagtt gagtaaatgt gagttctgga tcagtgaagt    6060
cctgttcttg ggtcacataa tcaacaaaga aggattggct gtggatccaa agaaagtggc    6120
agacattctg aactggaaag cgccaacaga tgctagagga atcaagagct tcattggaat    6180
ggccggatat tatcggcgat tcattgaagg gttttcgaag attgcgaaac caatgacagc    6240
gttgctaggc aacaaagttg agttcaagtg gacctagaaa tgtcaagagg cctttgaagc    6300
gctgaaagag aggttgacta cagcgcctgt cctagtcttg cccgatgtgc acaagccctt    6360
ctcggtgtat tgcgatgctt gttacacagg tttgggatgt gtgttgatgc aagagggaag    6420
agttgtggct tactcatccc gacagctgaa ggttcatgag aagaactacc caatccatga    6480
tctagagttg gcagcagtgg ttcacgcact gaagtcatgg aggcactatc tgtatggaca    6540
gaaatgcgat gtttacacag atcacaagag tctgaagtac atattcactc agtcagagtt    6600
gaacatgagg caacgaagat ggttagagat gatcaaagac tatgagttgg agattcatta    6660
ccatccaggc aaagcaaacg tagtggcaga tgctttgagc agaaagagtc aagtcaatct    6720
gatggtcgct cgcccgatgc cttatgagtt ggccaaggag tttgacaggt tgagtctcgg    6780
gtttctgaac aattcgcgag gagtcacagt tgagttggaa cctaccttgg agcgcgaaat    6840
caaagaagcg cagaagaatg atgagaaaat cagtgagatt cggcgattga ttctagatgg    6900
caaaggcaaa gattttcgag aagatgcaga aggcgtgata tggttcaaag accgcttgtg    6960
tgttcccaat gtccagtcta ttcgagagtt gattctcaag gaagctcatg agacggctta    7020
ttcgattcac cctggtagtg agaagatgta tcaggatctg aagaggaaat tctggtggta    7080
cggaatgaag agggaaatcg cagagcatgt ggctatgtgc gatagttgcc gaagaattaa    7140
ggcagagcac cagagaccag ctggattgtt gcaaccgttg cagatccctc agtggaaatg    7200
ggatgaaatt ggtatggatt tcatagtcgg attgcctcgc actcgagccg gctacgattc    7260
catttgggta gtagtggacc gtttgaccaa gtcagcccac ttcatacctg tcaagaccaa    7320
ctatagcagc gccgtattgg cagaattgta tatgtctcgg atcgtttgtc ttcatggtgt    7380
gccaaagaag atagtgtcag acagaggaac gcagttcacc tctcatttct ggcagcagtt    7440
gcatgaagct ttgggcacgc atctgaattt cagttcagct tatcacccgc agacagatgg    7500
ccagaccgaa aggaccaatc aaattcttga agatatgttg agagcctgtg cgttgcaaga    7560
tcagtccgga tgggacaagc gattgcctta tgcagagttt cctataaca acagctacca     7620 ggccagtttg aagatgtcac catttcaggc gctttatgga aggagttgca gaactccgtt    7680
```

-continued

```
gcaatgggat cagcctggag aaaagcaagt gtttgggcca gacattttgc ttgaagctga    7740
agagaacatc aagatggttc gagagaatct gaagatagcg caatcgaggc agcgaagcta    7800
tgcagacacc agaagaagag agctgagttt cgaagtcggg gactttgtct atctgaaagt    7860
gtcaccgatc agaggagtca gaagattcgg agtgaaaggc aaactagcac cccgctacat    7920
tggtccgtat cagattcttg caaagcgtgg agaagtggcc tatcagctca gtttgcccga    7980
gaatttgtct gctgtgcata atgtctttca tgtgtctcag ttgaagaagt gcttgcgtgt    8040
gccagaagag cagttgccag tggaaggtct ggaagtccag gaggacttga cctatgttga    8100
gaagccagct cagatccttg agattgcaga cagagtcacc cgaaggaaga ccatcagaat    8160
gtgcaaggtc agatggaatc accactctga ggaagaagca acctgggagc gtgaagatga    8220
tctgatggcc aagtacccag agctctttgc tagccagccc tgaatctcga gggcgagatt    8280
cttttaaggg ggataggttt gtaacgcccc gaattttgca gttgaatttt ttcttttctt    8340
tactcgccaa attcgggcgt tacctttcct ttttctttt cccttcgcta aaccttgacc     8400
ttttccaaag ttctagcggg attcggtttg gaattcccgt gtaagaaaaa ccctaaatac    8460
tttatgttgt ttgatgcacc atgccgaacc ttgcatttct tttgattgct ttgaaagtgc    8520
aaatgcattc atgtagaaag atcggatttc gaaaatgagg agaagatctt ttcttttctt    8580
ttctctctcc tcttttttt ctctctctcc cgcgccgtgg gccgacctcg gccgcccag      8640 ccgcccctgc gccccccccc cccnnnnnn nnnnnnnccc nnngncnnnc ncccncncn      8700 cccncnncc cccccccccc cccccccccc cccccccnc cccccccccn ccccnnccc       8760 cccnccgccc ccccccccnn cccccccccc ccccacgccc ccgcgcgccc gcggcccgcc    8820
gcgcggngcg cggcggcggg cgcccccccgc ccccgccgg gcggccgggg gcggcggggc    8880
cgggcggggc ggccgccggg ggcccgggcg cgcgggggggg ggcggggcgc gggcgggcgc   8940
ggcggggcgg gcggagcggc ggcggcccgg ggggccgcgc ggacaggggga gagagcagag   9000 aagagggcaa gaaaaagcag agaaacagaa agagggggggc ggaacacggg cgacagacgc   9060
ggggcacaca agaaccagag acnnnnnnnn nnnnnnnnn nnnnnnnnnn nnnnnnnnnn     9120
nntttttatt ttatttatt tactttctgt gatcatagct attttatttt aggtaggcta     9180
atcattgttc atgccattga ataggaagt ttaatttaaa attccgttat gctagttgat     9240
tcatgtagtt aattgtttac ctcgtgtaat gttgatcaac ttaaaatgat taggtttcca    9300
ttagtgtata tgtaacagaa ttcttttgtt aagaaccaat tgtaattgat cgttagtgca    9360
taagatttaa cccctgcga gacccttttcc cgtttctttc taaccataac aaatgcgata   9420
tcgaatgtca tacttgatgc atactcactt tatttgttcc cttgtatggt gtactgttct    9480
tttgtattaa atttggatgg atgtatgtat gtttgcaatc gcatagagaa cgatccggtc    9540
gaagagcccg aggaattcgc aggagaagcc cctgagcagc agtcgggtgg tggaggcaag    9600
tgtcctttga cctatctctg tcctatttat tatttaattc acccccccgca tcacacattt   9660 atacctaagg attgactagc ttttgttatc catgtccttg tttacctatt tgggttggat    9720
tattactgtt tagcttatg ctattgctca actctaatca atgaacatga tgtggttatc     9780
tatgatacgc tgtttttcccg ttcttattta tgattatact tgtggcattt aagggggactc  9840 gagcggtttc tcgagtgcct ctccgtaaag acctgttcta tggatgaccg cccgggaaaa    9900
cagtgcaacc atgagggtgg aatgggggtgc ccttagctga ataattagag gatccgggat   9960
gtagttcgct tcgccgtcgt gccgtcaatg gggctcggtg tatgcggctc gctctgccaa   10020
ggttgatttg tcccttgggg aggagtgcgg tacatttagg aaacctaacg ggcggctaca   10080
```

```
gccccgagga atctttgtaa aggctacgta gtgagaccct gcctattcac cttggtagtg    10140
tttaagggtt tgatcggccc gaggcaagag ggaatcacgg cttgtgggta aagtgcacaa    10200
cctctgcaga gtgttatgaa actgatatat cagtcgtgct cacggttatg agcggccaag    10260
ggagctccag tgattagtgg tacttgatca gagacattat ggtacaggtg gttatgagat    10320
cgatggttct ggttatgact atggttctgg ttatgactat ggttctggta agtggtattc    10380
tttccgtttg gaaagggtac atcggggttaa taacttgggt taatgctaaa acttggcttt    10440
ctactagtaa ataatgatct gaccaactaa aagcaactgc ttgacttatc cccacataaa    10500
gctagtccac tacagccaaa caggatactt gctgagtatg ttgatgtgta ctcacccttg    10560
ctctacacac caaaccccccc ccaggttgtc agcattgcaa ccactgctca ggagaagatg    10620
aagctgtgga aggagacttc caggagttcc aagactacga cgagttctag gtgtgggtta    10680
gcggcaaccc ccagtcggct gcctgtgaag gccgcgttat ctacgtttct tttccgcact    10740
ttgatttatt gtaagaacta tatggacgtc tcagacgtat gatgtaatcg actatttccc    10800
ttattaatac tattttgagc actgtgtgat gatgtccata ttatgtaact gctgtgtacg    10860
tgaataactg atcctggcac gtacatggtt cgcattcggt ttgccttcta aaaccgggtg    10920
tgaca                                                                10925
```

<210> SEQ ID NO 93
<211> LENGTH: 8458
<212> TYPE: DNA
<213> ORGANISM: Zea mays
<400> SEQUENCE: 93

```
tgttggggtt tttctccgcc gaaggtcttc aaggcaaaaa caccttcgac aaaatgatac      60
aaaatcttac tgaagttatc ttcagcctcg gctcaactcc tcgagacaaa gctcaagggc     120
tttggcgaca gtgcaagaag ccgaaggtca atagcttcgg cccagaccaa gcaaagaagg     180
aaaaatgact agatagacct tattattttt aattacttat aaacaaatgt ttgagggcat     240
gaatgtaatt gtaccggggc tgcgtcccgc gcctttaaat atatgaacag tacctcgtac     300
tattcacgct ggattgtatt cactctcacg tcattcttgc atccatacct tctgccaagc     360
cgaatgtatc aatgtaacac aaatattatt catattttct catattcact gaatatataa     420
atatgaatat attgttgatt tataattgtg atctttattt ccttatattt tattgcttaa     480
ttgttcacat gataaaatga tgaaggtatt cccttcatga ccttcgtctg aagatcatta     540
tatccaaagg gaaataatac ttcgaaggat gaaggtcttt aaccaataac aactgtgttg     600
ctttgttctt catttatagc atctgagaac aagtggccaa cattggcgcc cacctacgat     660
gaactcactt ctacagctat aacaatggct tcgcaaagca accaagttgt agcatctttg     720
gccacgaagc tagtgtttcc aatcacaggc ggctcaagtt ctgaaccagc caacaagaaa     780
cagaagaagg aagcacatag aagggtacat catgttggag ttcaaggacc tttcatcaag     840
tccaagtagt cgcatattcc aatcacctttt tctcaggaag accttcagct taaagattat     900
cctcacaacg atgcaatggt catatattgc atcatcaagg attttttggt ccataatgtc     960
ttagtggaca catgcagtgc aacagataac atctttgcga aggccttcag gcaaatgcaa    1020
gagctagatg ataagataca tgatgcaaca caccctcttt gtggtttcgg agggagatag    1080
atagtggcac ttggcaagat aacaatgcca gtcaccttcg gctacgttaa caacacaagg    1140
acatagcaag ttgtctttga tattgttgat atagagtacc catacaatgc aatcattggt    1200
cgagggacgc tcaatgcctt cgaagcaata ctccacccag catacccttg catgaagata    1260
```

```
ccttcggaac aagggcccat tgctgtacat gggagtcaag aagctgtcag gagagccgaa    1320
ggaagttgga tggattctaa ggctattcat aatatagatg aagtcgaagc ttatcagtag    1380
tataagcaca aaagagaaaa ggttgcttcg gtagaccaac caaagcctat gctcttgtgt    1440
ggagacatag ccgagcaaaa agtattgctg ggatctcaac tatctgatga acaagaaaag    1500
accttgctaa gattttttgtt taacaacaaa gatgttttg cttggacagc caatgacctc    1560
tgcggtgtca atagagacat cattgagcac tcactcaatg tggactcatc ctttagacca    1620
agaaagcaaa ggcttcagag aatgtctgat gacaaagccg aaggaccacg aaatgaagta    1680
aaaagacttc taagtgccga cgttattaga gaagtaacat acctagagtg gttggccaac    1740
actgtcatgg tgaagaaagc taacggaaaa tggagaatgt gtattaattt tacagatctt    1800
aacaaggcat gtccgaagga tgaattccca ttgccaagaa tagattcctt agtggatgca    1860
gcagccactt cgaaactcat gagcttattg gattgatact caggctatca tcaaatctgg    1920
atgaaaaagg acgatgagcc gaagacaagc ttcataactc ctagtggcac ttattgttat    1980
ctttagatgc ctgaggggct caagaatgct ggaggaagct tcagcagaat gactgccaaa    2040
gttcttcact ctcaaattgg caaaaatatg ctaacatatg tcgatgacat catagtaaaa    2100
agcacaaaac aagagaacca tgttgctgat ttgcaagaga catttgccaa tttcagacaa    2160
gctggtctta agttaaatcc agagaaatgt gtcttcggag taaagaatga caagtttctt    2220
ggctgcttgg tgtcaacaaa gggtattgaa gctaacctaa gcaaaatcga agctatcctt    2280
cggatagagc cgccaaattc gaaaggggg gctcaaggt tagcaggaag ctggtatca    2340
ttgaacagat tcatttcaag atcaacagag aggaatctac ctttctttga aatattgaaa    2400
tcagccgaag tcttccaatg gggtccaacc caacaaaaag cctttgaaga gatgaagcag    2460
tatttgatag atataacaac tttaactcca ccttcatcag gaacccccatt gcttctatac    2520
gtggttgttt ctcatactgc ggtcagtgca gcacttgtac aagagaaaca agatggccac    2580
ataaaaaagc aagcaccgat atacttcgtc tccgaagtac tcagcccatc taagaagaat    2640
tacacataat tggagaaggt attgtatgtt gtattgatgg cctccagaaa gcttcgacac    2700
tacttccaaa catatcatat aatagtgcct tcatcacaac ccctgaagga cataatgagg    2760
aacagagaag ccacaggaag ggtcgaaaaa tgggccgcag aactcaatga attcaccatt    2820
gattatgtac ataggtcttc gattcaatct caggcgttgt cagacttcat tgtcgattaa    2880
acgctagggg ctcaggatga agatagaata aatgatatcg aagcttggat ggtattttgt    2940
gatgggtcct ggggaacctt cggtgcaggg gcaactgttg tcctagtagc accatccaaa    3000
gttagaactc gttatgcagt acaattggat tttagctgca caaataatat tgtagagtac    3060
gaagccctcc tcttggggct tcgaaaactt aaggcaatga gtataagaag gcagttttc    3120
aagactgatt cacaagttat atcaggtcat gtggacaaaa gtagcaaggc aagagatccg    3180
aagcttgaaa aatatctaga tgcagtccga aggttggaag cttcttttga aggtttcttt    3240
gtaaagaaca tcccaagggg agaaaatgag catgcagact tattggctaa atcagtggca    3300
cagggcttc cgctaccttc ggaggtgttt tttgaaataa taaaagcacc atcagttgag    3360
ctcatggaaa gagcggtgct cacgatttca ctggtacata gtgaagattg gaggactgag    3420
attgtatctt tcctccaggg caactgtctt tcagatgacg aaggttataa taacagaatg    3480
gatgcatgga caagaccata tgtaataata gaagggggagt tatataagca cggagtttgc    3540
tccccattgc tcaagtgttt atccagaact gaagggcaag aactactgaa ggagatacat    3600
gcaggactat gtgggcccca cattggatct aggcccctat tggggaaggt tttcagacaa    3660
```

```
ggtttctact gggcgaaggc agcttcggat gtagcagaat tagtacaaaa atgtgaaaat   3720
tgccaaagat gcgccagaga ccagaagcaa ccttcgtctt tgactcaact aatacaaccg   3780
acttggccac tgcaaagatg gggtttggat ctgttaggac cactcccacc ggcacagggc   3840
aacttgaaat atgttgtggt ggcggtggaa tattttctta agtggattga agcaaagtct   3900
ttggctacaa taacttcggc cacagtacaa aaattcttct ggcaaaacat cgtttgtcgc   3960
ttcagcgtgc cgaaggctat cactgttgat aatggaactc agttcgatgt cgaaactttc   4020
aaagcctttt gtagccaaat tggtacaaaa atacacttcg catcagcgag tcatctggag   4080
tcaaatggat tggtagaaag ggcaaatgga attgtaataa caggaataat gaagtcaatc   4140
ttcaatcagc ctaagggaaa gtggccagat gaattaataa agtggtctc gaaccacaac    4200
actgctgtat caaggtcaat gggatttact ccattcaaac ttctgttcgg tgacgaaaca   4260
attacaccgg aagaagaaag aacgagttca ataagaactt tagcttcgac agaggacgaa   4320
ggtgactgcc aagtaacaaa ggataccata gaagagacca ggcttcaagt catagagcac   4380
attaataaat accaggctga aacagtcaaa tggcgtgaca gaaaagtaag attgaaaaac   4440
accaagccag gtcacttggt gcttcgaagg gtggccaacc ctgatatagt ggggaagctt   4500
catcttaaat gggaaggagc ctttctggtt gtatcttcgt caagacctgg ctcttacagg   4560
ttgaaagaca tggatggaaa tgacattcca agatcttgga atgcagatga gcttcgaaga   4620
tattatgtgt aaacaatgta atttcttat tatttcctta tggcacccctt tcctttcaa     4680
gttgggagaa aggtttttaa cggggccata ggttgtaatt tttattcttt gttttggcct   4740
atgcaatata aaggcaaaat tcccccatat gtaaattgta acatccagat tcgcaccttc   4800
gagtgcaaaa agggacatgg agaagctcaa aagtcgtccc taggggatg cagagccaaa    4860
atatcacctg aaaggtgaag aagctacaaa gtcgttccta agggagcgca aagtaagttc   4920
cgaagctcaa aagttgttcc taagggaatg tagagctaag atgacaccta agtaaaggt    4980
gaagaagctc aaaagtcgtt tctaagggga tgtagagctt gaatgccacc taagtaaaag   5040
gtggagaagc tccaaagtcg ttcctaaggg gattctgagc ttggctccaa agtcgttcct   5100
aagggggatga agagctgaaa taccacctaa gtaaaaggtg aagagactcc aaagtcgttc   5160
ctaagggat gcagagtttg ggtgtgtttt tggcatacat ttgcatagct cattacatca    5220
ttcattgcat tcatacaagc attcattagc cattcttagg atcatcatca tcatcatgac   5280
ataaagtact aacaggaaaa gacagaagat gtctgtcttc gctggaaaaa atgcttcgtt   5340
gaaaatggag atgctttgtc tcagacaaaa cttcatggca tatgaaggtg attcgtcttt   5400
gataaaaaaa tgcttcaatg tgaacgaaaa gaatggaagg tgttttttcgc ctatggctca   5460
aaaattgcaa gtgttggttt cgtccatatc aaagcaattc atacaggagc aaataggtaa   5520
aattatatta caagatattc acaaatttgt acaatatttt gttcaactaa caattacaat   5580
tccttgcaaa gtaatgcaaa gagacccctaa gttttctaca gatagataca aaagaatgtc   5640
ctaagagtct tcaggccttc agaacaagct tcggctcagc aaccttcctg caaacagatg   5700
aaggtataag gtaatcagaa atttaataaa ggaaaaccaa ggtaaaaaga caggtaaaat   5760
agtcatactg aattgagcaa tttcctagct tcatcccag ccaactcacg tccgcccttta   5820
gcccaaattt gtgtaatgaa tctgttccct atacttcggg cttcggcggg gatatcaact   5880
atatctgacg tcgaaagatt gaaagttggc ttgttgactg tcttggcatg agtacatcca   5940
gccttcataa aagcagcagc tgtgcctcga gaagctacca gggcacaaaa atctctatgc   6000
ccgcttataa cttcgtcaag ggcttcaact ttgttttcaa tatgattaaa ggctctagga   6060
```

```
tatcttcggt cgaaggggta aacttttcag aagcagctcc aaatgagttg aatatcccct    6120
taagccggtc agcacaccga gtcgcaaaat ctacacactt gttccgaagg tccttaatag    6180
actcgtacaa cttcgtattc ttctcagttt tggcctcgac tctttttta agtttcttcg    6240 tctcctggtc gaagcaccgt gaactctcat ccaagatcga tcgagcttca tttagttcct    6300
cgcttaactt ggtattttgg gatcgtgatt ctgcgaggga actttcagct atttgcagta    6360
ggatagtttt ttcttctaga taagtttcaa gttcctttat tttttcctct aatccttta     6420 ctataacttt gtgtttcatg tcctcactat cctgctgcat tctcagcgct ttgcttagca    6480
gcatgctctg caaacaaatt aaagttagaa cactcaatct atctcgaagg taataaaaat    6540
cttgatgaag atcttacctt aaaattagaa taaaataggc taccaacaat gtgttgtcat    6600
cggtaaccac tgatgtttgc ctcgagcttc gggaatccga cactcttaga aagagtgccg    6660
attatctttg ccccggcgcg gtcgcttata catcctaaaa tttcttcatc aaccctaccg    6720
aagagcaaag atcccggctg gtaaccacaa gatattacat attctttcag ctcttccttg    6780
tcttcctcgg aaagctcctg gccgcccacg tgacgaaggt caaaatcccc ttcatccgaa    6840
ggagttttaa caatttcttt ttctttatca ggcactgtgg ccatggtttc ttctggagct    6900
acatttgtct ccacagtcac atctgcaaat acgtctgaca caagcctatc aatatctgac    6960
attgttgttt cggcttcatc agcatctttg gcttcggcag caccttcagc ttcagctttg    7020
gtatccgcat gaatcgctac tttggccgcc gaagctgagg acagtgtttg ttcaattgct    7080
tccattacat ttacaattcg ttgcttcttt tgttctttaa ctttctcctc tgtagccgaa    7140
ggctgttctt ttctctgtaa aatttttgtc agttctcatc ccagaggact tagcagcttg    7200
aagggtgggg attcagtcat taccttcagg atttcggctg cttcagcagc agagggcgtc    7260
agaggagctt cttctcctgt ctcatctact tcggtccgaa gagggtattg tgtcaagctt    7320 ccactttta gaaattgttg tcttaagttc aggagttgtt ttttatttct tcgaaacttt    7380
ttcatcctcc ttcactaccc gagcagcttg cctactcagg atgctaacaa tccttttcct    7440
ttttacccct tcggccccttt tgtcaagcct cttgtaatcc gggtattcga agtttaacgt    7500
gtccatcacc cgattcagcc ttcgtttcgg ccgggtgccg aaggcggtag tcattaattg    7560
gtcttccttt ttggtgtagt tgccaaggat ttcgttgcac attgtttcga tcatttctag    7620
caactctttg catggcttct tgaattgctt ctcaaattta aatcagtaag ggagccgaac    7680
aagttcgtac ttttaccccc ccccttcttt ttcttaggca ttccccagcc actagaggtc    7740
ggaaatattc tatttgccag gtactcttgt actagatctc taatgctgat ttcggctgcc    7800
accactttga attctacttc ggctaactgg catgggaac caagctgcat gtggcacaag     7860
ggccttgtca ttccgaagct taacttcaat ggactcatga ccatagtcat tagcttctcc    7920
cttttcttct cgtctgcttt tatgtagaac cattcgcttg tccaaccggt cggccacttg    7980
gtacgatagc caattaccgg ggccttcgta tctttctgat atgcgaagtt gtagcagccg    8040
aagttattat gaagaccatc cgctctgccc ttcgtttgat agtgcagctc atgcacttgg    8100
cagaaagctt cgacattagg actcataccc tggcttcgga gagcccatat gtagacttgt    8160
gtaacgattg cattaggtgt caactgatga agtatatctc caaaattctt taaaacctct    8220
ccaatcatct cacgaaaagg gaatcaaagc cctgccctaa agaagctctt aaaaacaacg    8280
atttaagcct cccttggctg cggaactacc tcctcccgg caaaccggac aagcttgctc     8340
tcgacttcgc caaagtagcc caattttttt atcataacca tgtcgtctgc cgtcacagta    8400
gatttaccaa attcaatatg gctaggtttc attaggctca gaatggtgtt gtcctcttt    8458
```

<210> SEQ ID NO 94
<211> LENGTH: 9535
<212> TYPE: DNA
<213> ORGANISM: Zea mays
<220> FEATURE:
<221> NAME/KEY: misc_feature
<222> LOCATION: (543)..(582)
<223> OTHER INFORMATION: n is a, c, g, or t
<220> FEATURE:
<221> NAME/KEY: misc_feature
<222> LOCATION: (8766)..(8805)
<223> OTHER INFORMATION: n is a, c, g, or t

<400> SEQUENCE: 94

```
cccgggtgaa agtcgcctag aggggggtg aatagggcga aactgaaatt tacaaatata      60
aacacaacta caagccgggg ttagcgttag taataaagaa atgagtccgc gagagagggc     120
gcgaaacaaa tcccaagcga ataagcaagt gagacacgga gatttgtttt accgaggttc     180
ggttcttgca aacctactcc ccgttgagga ggccacaaag gccgggtctc tttcaaccct     240
tccctctctc aaacggtccc tcagaccgag tgagcttttcc ttcttctcaa tcaaacggga    300
acaaaacttc cccgcaaggg ccaccacaca attggtgcct cttgccttgg ttacaattga     360
gttttgatca caagaacaag tgagaaagaa acaaagcgat ccaagcgcaa gagctcaaaa     420
gaacacggca aatctctctc gctagtcact aaaggcttga gtggaattgg agaggatttg     480
atctctttgg agtgtctaga attgaatgct agagctcttg tagtagttgg aagtggaaa     540
acnnnnnnnn nnnnnnnnnn nnnnnnnnnn nnnnnnnnnn nnagccccaa ccaccaaatg     600
tggccgttgg gaggctgtct gctcgatggc gcaccggaca gtccggtgca caccgaacag     660
tccggtgccc cctgccacgt catcactgcc gttggattct agccgttgga gcttctgact     720
tgtgggcccg cctggatgtc cggtgcacac cggacatgta ctgtttgctg tccggtgtgc     780
cagtatgggc gcgcctgact tctgcgcgcg ctgcgcgcgc aattaatgcg ccgcaggtag     840
ccgttgctcc ggagtcgcac cggacagtcc ggtgcacacc ggacagtccg gtgaattata     900
gcggactagc cgttggagtt ccccgaagct ggcgagttcc tgaggccgac ctcccttggc     960
gcaccggaca ctgtccggtg tacaccggac agtccggtga attatagcgc gccggccttg    1020
gaaattcccg aaggtagcga gttcgagttg gagtcctctg gtgcactgga cactgtccgg    1080
tggcgcaccg gacattgtcc ggtgtacacc ggacagtccg gtgctcccag accagagggc    1140
cttcggttcc cactttgctc ttttgttgaa tccaaaactt ggtcttttta ttggctgagt    1200
gtgaaccttt tacacctgtg taatttatac actcgggcaa acttagttag tccaaatgtt    1260
tgtgttgggc aattcaacca ccaaaattaa ttagggacta ggtgtaagcc taattccctt    1320
acaatctccc ccttttttggt gattgatgcc aacacaaacc aaagcaaata tagaagtgca    1380
taattgaact agtttgcata atgtaagtgt aaaggttgct tagaattgag ccaatataac    1440
tacttacgag atatgcaagg aatgtttctt tcttatttag tattttggac cacgcttgca    1500
ccacgagttt tgttttttgca aacttttttgt aaatccttttt caaagttctt ttgcaaatag    1560
tcaaaggtga atgaataaga ttttgcaaag catttccaag atttgaaatt ttctcccccct    1620
gtttcaaatg cttttccttt gactaaacaa aactcccccct aaaagagatc ctcctcttag    1680
tgttcaagag ggttttgatg tatcattttg aaatactact ttctccccct tttgaacaca    1740
ataggatacc aaatgaaaaa tattcaatac tgagttttttg aaatttgaaa taggtggtgg    1800
tgcggtccctt ttgctttggg ctcatttctc ccccttttttg gcatgaatcg ccaaaaacgg    1860
aatcattaga gcccttgaag tgcttttctt cctctttggt cgtaaataaa tgagttaaga    1920
```

```
ttataccaaa ggtgaagtac ggtcctgttg ctttgggctc ttactttctc ccccaaagac    1980
aaagtccttt tctttgatgc tcatgctttt ctccccaaga atggagagtt gcttggagcg    2040
acggcgaagg atgagttacg tagtggaagc ctttgtcttc gccgaagact ccaattccct    2100
ttcaatacac ctatgacttg gtttgaaata gacttgaaaa cacattagtc atagcatatg    2160
aaggagacat gatcaaaggt atataaatga gctatgtgtg caatttaaca aaagaaattc    2220
ctagaatcaa gaatattgag ctcatgccta agtttgttaa aagattgttc atcaagaggc    2280
ttggtaaaga tatcgactaa ttgatcttta gtattaatgt atgaaatctc gatatctccc    2340
ttttgttggt gatccctaag aaaatgatac cgaatggcta tgtgcttagt gcggctatgc    2400
tcgacgggat tgtcggccat tttgattgca ctctcattat cacatagcaa agggactttg    2460
gttaatttgt aaccgtagtc ccgcagggtt tgcctcatcc aaagcaactg cgcgcaacaa    2520
tggcctgcgg caatatactc ggcttcagcg gtggaaagag cgaccgaatt ttgcttcttt    2580
gaagcccaag acaccaagga tcttcccaag aactggcaag tccccgatgt gctcttccta    2640
ttgattttac accccgccca atcggcatcc gaatatccaa tcaaatcaaa tgtggatccc    2700
ctaggatacc aaagcccaaa cttaggagta taagccaaat atctcaagat tcgtttcacg    2760
gccgtaaggt gagcttcctt agggtcggct tgaaatcttg cacacatgca tacagaaagc    2820
ataatatccg gtcgagatgc acaaagataa agtaatgaac ctatcatcga ccggtatacc    2880
ttttgatcca cggatttacc tcccgtgtcg aggtcgagat gcccattggt tcccatgggt    2940
gtcttgatgg gcttggcatc cttcatccca aacttggtta aatgtcttg agtgtacttc    3000 gtttggctga tgaaggttcc ctcttggagt tgtttaactt ggaatcctaa gaaatacttc    3060
aactccccca tcatagacat ctcgaacttt tgtgtcataa tcctactaaa ctcttcacat    3120
gtagactcgt tagtagaccc aaatataata tcatcaacat aaatttgaca tacaaacaag    3180
tcattttcaa gagtttttagt aaagagtgta ggatcggcct ttccgacttt gaatccattt    3240
gcaataagaa aatctctaag gcattcatac cacgctcttg gggcttgctt gagcccataa    3300
agcgccttag atagcttata gacatggtta ggatactcac tgtcttcaaa gccgggaggt    3360
tgctcaacat agacctcttc cttgattggt ccattgagga aggcactttt cacgtccatt    3420
tgaaaaagct taaagccatg gtaagtagca taggccaata atatgcgaat tgactcaagc    3480
ctagctacgg gtgcataggt ttcaccgaaa tccaaacctt cgactgggga gtatcccttg    3540
gccacaagtc gagctttgtt ccttgtcacc acaccatgct catcttgctt gttgcggaag    3600
acccatttgg ttcctacaac attttggtta ggacgtggaa ctaaatgcca tacctcattc    3660
ctagtgaagt tgttgagctc ctcttgcatc gccaccaccc aatccgaatc taggagtgct    3720
tcctctaccc tgtgtggctc aatagaggaa acaaacgagt aatgttcaca aaaatgggca    3780
acacgagatc gagtagttac ccccttatga atgtcgccga ggatggtgtc gacggggtga    3840
tctcgttgga ttgcttggtg gactcttggg tgtggcggcc ttggttcttc atcctccttg    3900
tcttgatcgt ttgcatctcc cccttgatct atgtcgtcat cttgaggtgg ctcatttgat    3960
tgatcttctt cttcatcaac ttgagcttca tcctcatttt gagttggtgg agatgcttgc    4020
gtggaggagg atggttgatc ttgtgctttt ggaggctctt cggattcctt aggacacaca    4080
tccccaatgg acatgttcct tagtgctatg cacggagcct cttcatcacc tatctcatca    4140
agatcaactt gctctacttg agagccgtta gtttcatcaa acacaacgtc acatgagact    4200
tcaactagtc cagtggactt gttaaagacc ctatatgccc ttgtgtttga gtcataacca    4260
agaaaaaaac cttctacagt cttaggagca aatttagatt ttctacctct tttaacaaga    4320
```

```
ataaagcatt tgctaccaaa gactctgaaa tatgaaatgt tgggctttttt accggtaagg   4380 agttcatatg atgtcttctt gaggattcgg tgaagatata accggttgat ggcgtagcag   4440
gcggtgttga ccgcctcggc ccaaaaccga tccgaagtct tgtattcatc aagcatggtt   4500
cttgccatgt ccaatagagt tctattcttc ctctccacta caccattttg ttgtggcgtg   4560
tagggagaag agaactcatg cttgatgccc tcctcctcaa ggaagccttc gatttgagag   4620
ttcttgaact ccgttccgtt gtcgcttctt attttcttga tccttaaggc gaactcattt   4680
tgagcccgtc tcaagaatcc ctttaaggtc tcttgggttt gagattttc ctgtaaaaag     4740 aatacccaag tgaagcgaga ataatcatcc acaataacta gacagtactt actcccgccg   4800
atgcttatgt aagcgatcgg gccgaataga tccatgtgta ggagctccag tggcctgtcg   4860
gtcgtcatta tgttcttatg cggatgatga gtgccaactt gctttcctgc ttggcatgcg   4920
ctacaaaccc tgtgtttctc aaaatgaaca tttgttagtc ctaaaatgtg ttctcccttt   4980
agaagtttat gaagattctt catcccaaca tgtgccagtc ggcggtgcca gagccaaccc   5040
atgttagtct tagcaattaa gcaagtgtcg agttcagctc tatcaaaatc taccaagtaa   5100
agctgaccct ctaacactcc cttaaatgct attgaatcat cacttcttct aaagacagtg   5160
acaccaatat cagtaaaaag acagttgtag cccatttgac ataattgaga aacagaaagc   5220
aaattgtaat ctagagaatc tacaagaaaa acattggaaa tagaatggtc aggagatata   5280 gcaatttac caagacctt gaccaaacct tgatttccat ccccgaatgt gatcgctctt     5340
tggggatctt ggttttctc atatgaggag aacatctttt tctccccagt catgtggttt    5400
gtgcacccgc tgtcgagtat ccaacttgag cccccggatg cataaaccta caaaacaagt   5460
ttagttcttg actttaggta cccaaatggt tttgggtcct ttggcattag acacaagaac   5520
tttgggtacc caaacacaag tctttgatcc cttgtgcttg cccctaacat acttggcaac   5580
tactttgccg gatttgttag ttaaaacata ggatgcatca aaagttttaa atgaaatgtt   5640
atgctcattt gatgcactag gagttttcct tttaggcaac ttggcacggg ttggttgcct   5700
agagctagat gtctcaccct tatacatgaa tgcatgatta gggccagagt gagacttcct   5760
agaatgaatt cccctaattt tgctctcagg ataaccggca gggtacaaaa tgtaaccctc   5820
gttatcctga ggcatgggag ccttgcccct tacaaaatta gacaatcttt taggaggggc   5880
actaagtttg acattgtctc ccctttggaa gccaatgcca tccttgatgc cagggcgtct   5940
cccactatag agcatacttc tagcaaattt aaatttttca ttttctaagt tatgctcggc   6000
aattttagca tctagttttg ctatatgatc attttgttgt ttaattaaag ccatatgatc   6060
atgaatagca tcaatgttaa tatctctaca tctagtgcaa atagaagtgt gctcaacgat   6120
agatgtgagg ggtttgcaag attttagttc tacaacctta gcatgcaata tttcattttt   6180
atttctaagg tcggaaatag tagcattgca acatcaaaaa tctttagcct tagcaagcaa   6240
tttttcattc tcaattctaa ggctagcaag agaaatgttc agttcttcaa tcctagcaag   6300
caaatcctca tcattatctc tagggttggg aattgaaaca ttgcaaacat gtgaatcaac   6360
cttagcattt aaactagtat tttcattcct aaggttgtca atcatctcac gacaagtgct   6420
tagctcacta gacaattttt cacattttc tacttctaga gcataagcat ttttaacctt    6480
aacatgtttc ttgttttcct taataagata tcctcttgg gaatccaaaa ggtcatcctt    6540
ttcatgaata gcactaatta attcatttaa ttttttttg ttccatgtta agattggcaa    6600
aaagggtacg caagttatcc tcctcatcac tagcattttc atcactagag gtttcatatt   6660
tagtggagga tcttgatttt accttcttcc ttttgtcgtc ctttgccatg aggcacttgt   6720
```

```
ggccgacgtt gggggaagaga agtcccttgg tgacggcgat gttggcggcg tcctcgtcgt    6780
cggaggagtc gctagagctt tcgtcggagt cccactcccg acaaacgtgg gcatcgccgc    6840
ccttcttctt gtagtacctt ttcttctcct ttcttctccc cttcttgtcg tcgcctcggt    6900
cactgtcact tgatatagga tatttagcaa taaaatgacc gggcttacca catttgtagc    6960
aaaccttctt ggagcgggac ttgtagtctt tccctctcct ttgcttgagg atttggcgga    7020
agctcttgat gatgagcgcc atttcctcat tgtcaagctt ggaggcgtcg attggttgtc    7080
tacttggtgt agactcctcc ttcttttctt ccgtcgcctt gaatgcgacg ggttgagctt    7140
cggatgtggt gggttcgtca agctcgttga ttttcctcga gccttcgatc atgcactcaa    7200
aacttacaaa atgcccgatt acttcctcgg gggtcatttt agtatatcta ggattaccac    7260
gaattaattg aacttgagta gggttaagga aaataagaga tcttagaata accttaacca    7320
cctcatggtc atcccacttt acgctcccga ggttgcgcac ttggttcacc aaggtcttga    7380
gccggttgta catgtgttgt ggctcctctc ctttgcgaag ccggaaccga ccgagctccc    7440
cctcgatcgt ttcccgcttg gtgatcttgg tgagctcatc tccctcgtgc gcggttttga    7500
gcacatccca aacctccttg gcgctcttca acccttgcac tttgttatac tcctctctac    7560
ttaaagaggc gaggagtatc gttgtcgctt gagagttgaa gtgctcgatt tgggccacct    7620
catcctcatc ataatcttca tccctacgg atggtacctg tgcaccaaac tcaacaacat    7680
cccatatgct tttgtggagc gaggttagat gaaatcgcat taaatcgctc cacctagcgt    7740
aatcttcacc atcaaaagtt ggtggtttgc ctaatgggac ggaaagtaaa ggtgtatgtt    7800
tggaaatacg agggtagcgt aggggggatct tactatactt cttgcgctct tggcgcttag    7860
aagtgacgga tgccgcgtcg gagccggagg tggatgccga tgaagaatcg gtctcgtagt    7920
agaccacctt cctcattctt ttcttcttgt ccccaatccg atgcggcttg tgggaagaag    7980
atttttcctt cttctccttg tggtgagaag aagatttctt ctccttccct ttgttggagg    8040
agatcttctt cttctccttc ctcttggtgc gggactcttc cgatgaagtg ctcccgtggc    8100
ttgtagtggg cttttcgccg gtctccatct ccttcttggc gtgatctccc gacatcactt    8160
cgagcggtta ggctctaatg aagcaccggg ctctgatacc aattgaaagt cgcctagagg    8220
gggggggtgaa tagggcgaaa ctgaaattta caaatataaa cacaactaca agccggggtt    8280
agcgttagta ataaagaaat gagtccgcga gagagggcgc gaaacaaatc ccaagcgaat    8340
aagcaagtga gacacggaga tttgttttac cgaggttcgg ttcttgcaaa cctactcccc    8400
gttgaggagg ccacaaaggc cgggtctctt tcaacccttc cctctctcaa acggtccctc    8460
ggaccgagtg agcttttcctt cttctcaatc aaacgggaac aaaacttccc cgcaagggcc    8520
accacacaat tggtgcctct tgccttggtt acaattgagt tttgatcaca agaacaagtg    8580
agaaagaaac aaagcgatcc aagcgcaaga gctcaaaaga acacggcaaa tctctctcgc    8640
tagtcactaa aggcttgagt ggaattggag aggatttgat ctctttggag tgtctagaat    8700
tgaatgctag agctcttgta gtagttggga agtggaaaac ttggatgcaa tgaatggtgg    8760
ggtggnnnnn nnnnnnnnnn nnnnnnnnnn nnnnnnnnnn nnnnnccacc aaatgtggcc    8820
gttgggaggc tgtctgctcg atggcgcacc ggacagtccg gtgcacaccg aacagtccgg    8880
tgcccccctgc cacgtcatca ctgccgttgg attctagccg ttggagcttc tgacttgtgg    8940
gcccgcctgg atgtccggtg cacaccggac atgtactgtt tgctgtccgg tgtgccagta    9000
tgggcgcgcc tgacttctgc gcgcgctgca cgcgcaatta atgcgccgca ggtagccgtt    9060
ggcgccgcag gtagccgttg ctccggagtc gcaccggaca gtccggtgca taccgtacag    9120
```

```
tccggtgaat tatagcggac tagccgttgg agtttcccga agctggcgag ttcctgaggc    9180
cgacctctct tggcgcaccg gacactgtcc ggtgtacacc ggacagtccg gtgaattata    9240
gcgcgccgac cttggaaatt cccgaaggta gcgagttcga gttggagtcc tctggtgcac    9300
cggacactgt ccggtgtaca ccggacagtc cggtgctccc agaccagagg ccttcggtt     9360 cccactttgc tcttttgttg aatccaaaac ttggtctttt tattggctga gtgtgaacct    9420
tttacacctg tgtaatttat acactcgggc aaacttagtt agtccaaatg tttgtgttgg    9480
gcaattcaac caccaaaatt aattagggac taggtgtaag cctaattccc ttaca          9535

<210> SEQ ID NO 95
<211> LENGTH: 91
<212> TYPE: DNA
<213> ORGANISM: Zea mays

<400> SEQUENCE: 95
aaawtcaaac gacaataact tttkactcgg atgtccgatt gwgtcccgta rtatatcgag    60
acgctcgwaa ttgaaaacwg aagctctrag m                                   91

<210> SEQ ID NO 96
<211> LENGTH: 127
<212> TYPE: DNA
<213> ORGANISM: Glycine max

<400> SEQUENCE: 96
tccagaggcg gcgggcccga tgacaagcag agaccaagtt tggtcattct gcacccttgt    60
atcatccaga ggcggcgggc ccgatgatac gcggagatac cttacggtta ccgcaccct    120 tttgtca                                                              127

<210> SEQ ID NO 97
<211> LENGTH: 100
<212> TYPE: DNA
<213> ORGANISM: Glycine max

<400> SEQUENCE: 97
tccagaggcg gcgggcccga tgacaagcag agaccaagtt tggtcattct gcacccawga    60
tacgcggaga taccttaygg ttatycgcac ccttttgtca                          100

<210> SEQ ID NO 98
<211> LENGTH: 91
<212> TYPE: DNA
<213> ORGANISM: Glycine max

<400> SEQUENCE: 98
aaattcaaac gacaataact ttttactcgg atgtcygatt gagtcccgta atatatcgag    60
acgctcgaaa ttgaatrytg aagctctgag c                                   91

<210> SEQ ID NO 99
<211> LENGTH: 91
<212> TYPE: DNA
<213> ORGANISM: Glycine max

<400> SEQUENCE: 99
aaawtcaaac gacaataact tttdactcgg atgtccgatt gwgtcccgta rtatatcgag    60
acgctcgwaa ttgaaaacwg aagctctgag m                                   91

<210> SEQ ID NO 100
<211> LENGTH: 19760
<212> TYPE: DNA
```

<213> ORGANISM: Zea mays
<220> FEATURE:
<221> NAME/KEY: misc_feature
<222> LOCATION: (1810)..(1819)
<223> OTHER INFORMATION: n is a, c, g, or t

<400> SEQUENCE: 100

```
gatcctaaag gaagctcatg agacagccta ctccatacac cctggaagtg aaaagatgta      60
tcaggattta aaaggagat tttggtggta tggcatgaaa agagaaatcg cagaatatgt     120
cgccatctgt gatagctgtc aaagaaccaa agcagagcat caaaagcccg ccggactgtt     180
gcagccattg cagatccctc agtggaagtg ggatgagatc gggatggatt tcatagttgg     240
cctacctcgt acccgggccg gctatgattc catctgggtg gttgtggacc gcttaacaaa     300
ggtagcccat tttatacctg tgaagacaac gtacaccgga gcagcgttag ctgagttata     360
catgtctcgg atagtctgcc ttcatggtgt gccgaagaag atagtgtcag atcgaggaac     420
acagtttacc tctcattttt ggcagcagct acaagaagct ttgggcacac atttgaactt     480
cagctcggct tatcacccac agacagacgg tcagactgaa agaactaatc agatcctaga     540
agatatgttg agagcctgtg cgttgcaaga caagtcagga tgggacaaaa aggttacctt     600
atgcagaatt ctcctacaac aatagttacc aggccagctt gaagatgaca ccgtttcagg     660
cgctctatgg acggagttgt aggactccgc tgcattggga ccagcctgga gagagacagg     720
tgtttggccc cgacattttg cttgaagccg aagagaatat caaaatggtt cgggagaatc     780
tgaagatagc acaatcaagg cagcgaagct atgctgacag aaggagaaga gaactgagtt     840
ttgaagtggg agattacgtc tatctgaagg tgtcgcctat cagaggagtc agaaggttcg     900
aagtcaaggg caagttagca ccccggtacg ttggaccata tcagattcaa gcaaagcgtg     960
gagaagtggc ctaccagctc aacctaccag aaagtttgtt ggccagtgca caatgtgttc    1020
catgtgtccc aattgaagaa gtgtctgcga gtaccagaag aacagttgcc agtggaggac    1080
ttggaagtcc aagaggatct gacctacata gagaagccaa cgcagattct ggagtttgca    1140
gacagagtca gccggaggaa caccatcaga atgtgcaaag tcagatgggg ccaccactct    1200
gaggaagaag caacctggga acgagaagat gatctgaaag acaaatacc  cgaactcttt    1260
gctgaccaac cttgaatctc ggggcgagat tcttttaagg gggataggtt tgtaacaccc    1320
tgaatttggg gtataaaatt tctttgctca tatccacaaa ttcaggtgtt attcctctca    1380
tctcatcttc tccaatctct tgttttcttt ttttatatat agaagaagag tggttatttt    1440
taatcgtaaa ggtaattata atctagtaga aaagagaaca atggttgttg catcatgtta    1500
gaaagcattt gttctttttg gttgatgaat gagttgctca atctttcatc taataattta    1560
ttttcgcata gtgtcaaact gaaataaata gaaaagagaa agaaaaagaa aagaaaagga    1620
aaaacagatt tcagcccagc ccccttccc  tggcccagcc agcccaccgc gccagccccc    1680
ccttccccct ctttctcccc ccgctcggc  ccaactcccg gccctttcccc cccccacgc    1740
cagaaccccc ctcgcgggcc cgcgcacgcc gcagcccacc ccagctcccg ggcggccca     1800
gcgcgccatn nnnnnnnnnt ccaaatcgga acgcctgtgc gaatttccag agaagaaaac    1860
cgcccgcgcg cagttttctt cgctagttgc gcatgatttc ttccacccgt tgtccagttt    1920
tctcgccacg aacgcccacg acccccctgc gcagttctcg ccattgctgc ttcgtctcgc    1980
cgatccgccg ccggagcctc gcctcgcccc cgctctctgc gtccccgtcg ccggagtgcc    2040
gcgcccgct  gcggccgtcg tcgtgcgcgc gccgaggta  agcccgcccc atcctctctc    2100
tccttttccca ttcttcctcc ccgccgtac  gcgtctgctg cgtacccgta gcccttgtc    2160
```

```
gcgccgtttc acttcgccgg cgagacctcg ctcagtcgct gcccggcgtc gcggtcaggg   2220
ggacctgcgc agcgactcgt ccctgccgcg gactcccctc cggccagcgc tgatgaggac   2280
atcctccact attacccgtt ggcaaagacg caattggccc agttggccca attgtagtcg   2340
gacggcgacc gtgtgagcct cagaattatc ccacctcgct taacttggga ggaggaagcc   2400
actttaaaag ggagagccac ccttccccca ttgggctagt cttttggggc gattgggcct   2460
ctccctgagt tgggtgtgct taatgaacag ttgggctccg ggcaacccta atttgttggg   2520
cctcggccaa ccccacctgg gctgggtgta tcatctggta tcagaactag ggcccatttt   2580
aagaaggtgg gaatgatgag gacatcctcc actattaccc gttggcaaag acgcaattgg   2640
cccagttggc ccaattgtag tcggacggcg accgtgtgag cctcagaatt atcccacctc   2700
gcttaacttg ggaggaggaa gccactttaa aagggagagc cacccttccc ccattgggct   2760
agtcttttgg ggcgattggg cctctccctg agttgggtgt gcttaatgaa ctgttgggct   2820 ccggcaacc ctaatttgtt gggcctcggc caaccccacc tgggctgggt gtatcaagcg   2880
cgcagcccag ctcccttgtg cgcgactgaa ctccctgcta tcgcggcttg cagcgcgcag   2940
caagcccgat ccccgacgt gcagacccg cgcgccctcg cctcgtccct gcgtgcagcg   3000
gccgagtagc tgcgcactcg gcgcgctcag accgtcccc atgccgcgca gcccaatccc   3060
agcgctcaca cgcagcacgc ccagccgcgt tgacgtttag cgccgtagca gccgttcgtc   3120
gtcgaacctc gccctgcgc gtcgcagctg tgttgctgcg cgctcgccgc tgcccagctc   3180
gccctggccg ttcgtctacc ctcgtcgtgc ctcgttacgg tcacctagcg cattgcgtac   3240
tcgtcagtct cgcgtgcgca gtttcacacg tgatcacggg tatcgcgcgc gccgtcgtca   3300
ttgtttgtag aatcctcgcg ctgtttcgcg cgtgtcgcgc gcgcattctg cgcgcaataa   3360
ttaattattt cgtgatgatc gtccatacgc gttagtcaat tagttctcgt attaatcatc   3420
gatttattga taattcattt ttttatctaa aatattccac acaagtagtt tacgtcaact   3480
aaattgaact tagaaatata attttcgcgt ttaaacgtaa tataggttgt tcgtcgtcac   3540
gtcattaatt agccgcggtt tgctaattat ttaatgtgtc gtgcgtcgcg caactagtgc   3600
acgcactcgc gtttgcttgc gcgcagtgcg tcgacggac tctgtctacg ttcgcctacc   3660
cttcgtctac ccctagacga ctctcgtcta ccccgtcta cccccccccc cccccgtcta   3720
cccccgtcta accccgtgcg cgttcgtgtc gttcgccatc gcccgcgcgt cgcgcaataa   3780
atcgtcgcgt gctgtccgcg cgcgttgtgc atactgttca cacgtgtcgt cgtgcgtttt   3840
acgcacgcta atgattcatc tcacctagaa tagctcgcgc taagtaaata tatatttaag   3900
caacggttat tcgaacaaca cactaatcgg gactaagtag taattttact cggcatgtga   3960
ttattgtctg ttaatatgat taagccgaat taaatattat aattcatatt cgcttagtat   4020
acatgtgata tccctcgacc gtagtatcag tcgtctcggt tccgttctcg cgtagtcgta   4080
gatgcgaatt ctttgtcgcg tgcatattta tttgatctat actgttgtat ggtgtactgt   4140
tttctaccat ttcaagaatg ttggatgtat gtttgcactc gcgtagatat cgggccgttc   4200
gtggagtctg agggaattgc aggagaagac cctgagcagc agcagcttgg tgaaggcaag   4260
tgtcctctga cccattatgt cctattcact tataattcac tttcccgcag tatttaattg   4320
aaatctaagg attgactagc tttatacttt accttatcct tgatgacctt tttgggtgat   4380
tatggttagc attttgctat tgccttaatt ttaatcaatg aacatgatgt gactatctat   4440
gatacgatac tgttatcctg attatattgt tgatcttgtg atactctagg gggctcaggc   4500
tgtttcctga gtacctctcc gtaaggacct gttcgttgag agaccacccg ggataacagt   4560
```

```
gcaaccatga gggtggaatg gggtgccctt agctaattaa ttagaggaac tagaagtgta    4620
gttgcttcgc cgtcgtgccg tcaatgggtt ccaggcacag tgcttgctct gccgaggctg    4680
agtgccgagg ttctttcgtt ttgtttttta gtcaccctcc tgcggggagg aggtactgtg    4740
tttatcaaac tggagaaacc taacgggcag ctatgacctc tagggaatct ttgtaaaggc    4800
ttcgtagtga atccctggcc attcaccttg ggagtgaata agggtcttga caagcccggg    4860
ctagagaggg aatcacggct catgggtaaa gtgtgcgacc tctgcagagg gtagtgaaac    4920
tgatatatca gctgtgctca cggttaagag cagccttggg atcctctttg attagagata    4980
cgaatggttc gagatacaat ggttctattt atgattttgg ttcgatgatg ataatgatat    5040
tcctcgatga ggaaatgatt cacgggttag ttattgataa aacctggctt cactaataat    5100
aaatacctga ccaactaaaa gcaactgctt gagcctaacc ccacataaag ctagtccact    5160
tcagccaaac ggggcatttg ctgagtacgt tgatgtgtac tcatccttgc tttaccacaa    5220
aacaccaggt tgtccacatt gcaaccactt ctcaggagaa gactcagtcg tggaaggaga    5280
cttccaggag ttccaagact acgacgagtt ttaggtgtgg gttggcggca accccagtc     5340 agctgcctgt gaaggcctta tctttactgc gtttcgctag cactttgatt taactgttaa    5400
gttgatgact atgtggatgt ctatgactct gtgatgtaat aagttaatac ccttttatgt    5460
tattattcga acactgtgcg atgatgttca tttatgtaat cgctgtgtac gtgaattatg    5520
atccaggcat gtacatagtt cgcattcggt ttgccttctg aaacgggtgt gacaatgcac    5580
cccgacaccc gttttcggaa tggttgacgt gcggcaacga aattgcgcga accaccccta    5640
aacatgagtt ttggacctaa agtagtttag tgggcatgtt tgttgggaaa acgaagaaa     5700 tggttctggc ggcaaaaact tgtgcttttgt atgcacccca acaccctgttt tcagaatggg    5760 tgacgtgcgg ctacgaaatt gcgcgaaacc accccaaaca tgagttttgg accttaaata    5820
gtggattggg catgttcgtt gcgataaaag aagaaatgca aggtggcaaa aactcgtgct    5880
tttatgcacc ccgcacaccc gttttcggaa tggttgacgt gcggcaacga aattgcacga    5940
aaccacccaa aacatgagtt ttggacctaa agtagtttag tgggcatgtt tgttgcaaaa    6000
acgaagaaat ggttccggtg gcaaaaactt gtgcttttgaa tgcaccccga caccccgttt    6060
tcggaatggg tgacgtgcgg caacgaaatt gcgcgaaacc accccaaaca tgagttttgg    6120
acctaaatta gtggattagg catgttcgtt gcgaaaatg aagaaatggt tccggtggca    6180
aaaactcgtg ctttttatgca ccccgacact cgttttcgga atgggtgacg tgcggcaacg    6240
aaattgcgcg aaaccacccc aaacatgagt tttggaccta aattagtgga ttaggcatgt    6300
tcgttgcgaa aaatgaagaa atggttccgg tggcaaaaac acgtgctttt atgccacccc    6360
gacacccgtt ttcggaatgg gtgacgtgcg gcaacgaaat tgcgcgaaac caccgcaaac    6420
atgggttttg gtcctaaagt agtggattgg gcatgttcgt tgtagaaaaa cgaagaaatg    6480
gttccagtgg acaaaaactc gtgctttttat gcaccgcaac cccgttttc cgaatgggtg    6540 acgtgcggca acgaaattgc gcgaaaccac cccaaacttg agttttggac ctaaagtagt    6600
ggattgggca tattcgttgc gaaaaatgaa gaaatggttc cggtggcaaa aactcgtgct    6660
tttatgcacc ccgacactcg ttttcggaat gggtgacgtg cggcaacgaa attgcgcgaa    6720 accacccaa atatgagttt tggacctaaa ttagtggatt gggcatgttc gtttcgaaaa    6780
atgaagaaat ggttccggtg gcaaaaactc gtgcttttat gcaccccgac acctgttttc    6840
ggaatgggtg acgtgcggca acgaaattgc gcgaaaccac cccaaacatg gttttggtc     6900 ctaaagtagt ggattgggca tgttcgttgc gaaaaacgaa gaaatggttc cggtggcaaa    6960
```

```
aactcgagca tttatgcacc cgacacccgt tttcggaatg ggtgacgtgc ggcaacgaaa    7020
ttgcgcgaaa ccaccccaaa cttgagtttt ggacctaaag tagtggattg ggcatgttcg    7080
ttgcgaaaaa cgaagaaatg gtttcggtgg caaaaactcg tgcattgtat gcaccccgag    7140
acccgttttc ggaatgggtg acgtgcggca acgaaattgc gcgaaccac cccaaacatg    7200
agttttggac cttaagtagt ggattgggca tgttcgttgc gaaaaagaa gaaatggttc    7260
tggtggcaaa aactcgtgct tttatgcacc ccgacaccc gttttcggaa tggttgacgt    7320
gcggcaacga aattctcgcg aaaccaccca aacatgagt tttggaccta aagtagttta    7380
gtgggcatgt tgttgcaaa aacgaagaaa tggttccgt ggcaaaaact gtgctttga    7440
atgcacccg acacccgtt ttcggaatgg gtgacgtgcg gcaacgaaat tgcgcgaaac    7500
caccccaaac atgagttttg gacctaaatt agtggattag gcatgttcgt tgcgaaaaat    7560
gaagaaatgg ttctggtgga caaaaactcg tgcttttatg caccccgaca ctcgttttcg    7620
gaatgggtga cgtgcggcaa cgaaattgcg cgaaaccacc ccaaacatga gttttggacc    7680
taaattagtg gattaggcat gttcgttgcg aaaaatgaag aaatggttcc ggtggcaaaa    7740
acacgtgctt ttatgcaccc cgacacccgt tttcggaatg ggtgacgtgc ggcaacgaaa    7800
ttgcgcgaaa ccaccgcaaa catgggtttt ggtcctaaag tagtggattg ggcatgttcg    7860
ttgtgaaaaa cgaagaaatg gttccagtgg caaaaactcg tgcttttatg caccgcaaca    7920
cccgttttcc gaatgggtga cgtgcggcaa cgaaattgcg cgaaaccacc ccaaacttga    7980
gttttggacc taaagtagtg gattgggcat attcgttgcg aaaaatgaag aaatggttcc    8040
ggtggcaaaa actcgtgctt ttatgcaccc cgacactcgt tttcggaatg ggtgacgtgc    8100
gacaacgaaa ttgcgcgaaa ccaccccaaa catgagtttt ggaccttaag tagtggattg    8160
ggcatattcg ttgcgaaaaa cgaagaaatg gttccgatgg caaaaactcg tgcttttatg    8220
caccccgcac acccgttttc ggaatgggtg acgtgcggca acgaaaatt gcgcgaaacc    8280
accccaatct tgagttttgg acctaaagta gtggattggg catattcgtt gcgaaaaaat    8340
gaagaaaatg gttccggtgg caaaaactcg tgcttttatg cacccgacac ccgttttgga    8400
atgggtgacg tgcggcaacg aaattgagcg aaaccaccca aacatgagt tttggaccta    8460
aagtagttta gtgggcatgt tgttgcgaa aaacgaagaa atggttccgg tggcaaaaaa    8520
cttgtgcttt gaatgcaccg cgacacccgt tttcggaatg ggtgacgtgc ggcaacgaaa    8580
ttgcgcgaaa ccaccccaaa catgagtttt ggacctaaat tagtggattg ggcatgttcg    8640
ttgcaaaaaa tgaagaaatg gttctggtgg caaaaactcg tgcttttatg caccccgaca    8700
cccgttttcg gaatgggtga cgtgcggcaa cgaaattgag cgaacccacc caaacatga    8760
gttttggacc taaagtagtt tagtgggcat gtttgttgcg aaaacgaaga atggttccg    8820
gtggcaaaaa cttgtgcttt gaatgcaccc cgacacccgt tttcggaatg ggtgacgtgc    8880
ggcaacgaaa ttgcacgaaa ccaccacgaa cttgagtttt ggacctaaag tagtggattg    8940
ggcatattcg ttgcgaaaaa tgaagaaaat ggttccggtg gcaaaaactc gtgctttat    9000
gcaccccgac acccgttttc ggaatgggtg acgtgcggca acgaaattgc gcgaaaccac    9060
cccaaacatg agttttggac cttaagtagt ggattgggca tgttcgttgc gaaaaagaa    9120
gaaatggttc tggtggcaaa aactcgtgct tttatgcacc ccgacacccg ttttcggaat    9180
ggttgacgtg ctgcaacaaa attgcgcgaa accacccaaa acatgagttt tggacctaaa    9240
gtagtttagt gggcatgttt gctgcgaaaa acgaagaaat ggttccggtg gcaaaaactt    9300
gtgctttgaa tgcaccccga cacccgtttt cggaatgggt gacgtgcggc aacgaaattg    9360
```

```
cgcaaaacca ccccaaacat gagttttgga cctaaattac tggattgggc atgttcgttg   9420
cgaaaaatag aagaaatggt tccggtggca aaaactcgtg cttttatgca cccggacacc   9480
cgttttcgca atgggtgacg tgcggcaacg aaattgcgtg aaaccacccc caaacatggg   9540
ttttggtcct aaggtagtgg attgggcatg ttcgttgcaa aaaacgaaga aatggttccg   9600
gtggcaaaaa acttgtgctt ttatgcaccc caacaccegt tttcggaatg ggtgacgtgc   9660
ggcaacgaaa ttgcgagaaa ccaccccaaa cttgagtttt ggacctaaag tagtggactg   9720
ggcatgttcg ttgcgaaaaa acgaagaaat ggttccggtg gcaaaaactc gtgcattaga   9780
tgcaccccga cacccgtttt cggaatgggt gacgtgcggc aacgaaattg gcgaaacca   9840 ccccaaacat gagttttgga ccttaagtag tggattgggc atgttcgttg cgaaaaaaca   9900
agaaatggtt ctggtggcaa aaactcgtgc tttatgcacc ccgacacccg ttttcggaat   9960
gggtgacgtg cggcaacgaa attgcgcgaa accacccccaa acttgagttt tggacctaaa  10020
gtagtggatt gggcatgttc gttgcgaaaa acgaagaaat ggttccggtg gcaaaaacta  10080
cgtgctttga atgcaccccg acaccgtttt cggaatggt tgacgtgcgg caacgaaatt  10140
gcgcgaaacc ccccaaaaca tgagttttgg accttaagta gtggattggg catgttcgtt  10200
gcgaaaaaag aagaaatggt tctggtggca aaaactcgtg ctttatgcac cccgacaccc  10260
gttttcggaa tggtgacgt gcggcaacga aattgcgcga aaccacccca aacttgagtt  10320
ttggacctaa agtagtggat tgggcatgtt cgttgcgaaa aacgaagaaa tggttccggt  10380
ggcaaaaact cgtgctttga atgcaccccg cacccgtttt cggaatggt tgacgtgcgg  10440 caacgaaatt gcgcgaaacc accccaaaca tgagttttgg accttaagta gtggattggg  10500
catgttcgtt gcgaaaaaag aagaaatggt tctggtggca aaaactcgtg ctttatgcac  10560
cccgacaccc gttttcggaa tggtgacgt gcggcaacga aattgcgcga aaccacccca  10620
aacttgagtt ttggacctaa agtagtggat tgggcatgtt cgttgcgaaa aacgaagaaa  10680
tggttccggt ggcaaaaact cgtgctttta tgcaccccga cacccgtttt cggaatgggt  10740
gacatccggc aacgaaattg cgcaaaacca ccccaaacat gagttttgga cctaaattag  10800
tggattgggc atgttcgttg cgaaaaaaat gaagaaatgg ttccggtggc aaaaacacgt  10860
gcttttatgc accccgacac ccgttttcgg aatgggtgac gtgcggcaa cgaaattgcg  10920 cgaaaccacc ccaaacttga gttttgcacc taaagtagtg gattgggat attcgttgcg  10980 aaaaatgaag aatggttccg gtggcaaaaa ctcgtgctt tatgcacccc gacacccgtt  11040 tttgaatgg gtgacgtgcg gcaacgaaat tgagcgaaac cacccaaaac atgtagttt  11100 ggacctaaag tagtttagtg ggcatgtttg ttgcgaaaaa cgaagaaatg gtaacggtgg  11160
caaaaacttg tgctttgaat gcaccccgac accgtttc ggaatgggtg acgtgcggca  11220
acgaaattgc gcgaaaccac cccaaacatg agttttggac ctaaattagt ggattgggca  11280
tgttcgttgc gaaaaatgaa gaaattgtt ccggtgtcaa aaactcgtgc ttttatgctc  11340
cccgacaccc gttttcggaa tggtgacat gcggcaacga aattacgcga aaccacccca  11400
aacatgggtt ttggtcctaa agtagtggat tgggcatgtt cgttgcgaaa acgaagaaa  11460 tggttccggt ggcaaaaact cgagctttta tgcaccctga cacccgtttt cggaatgggt  11520
gacgtgcgga acgaaattg cgagaaacca ccccaaactt gagttttgga cctaaagtag  11580
tggattgggc atgttcgttg tgaaaaacga agaaatggtt tcgctggcaa aaactcgtgc  11640
attgtgtgca ccccgacacc cgttttcgga atgggtgacg tgcggcaaag aaattgcgcg  11700
aaaccacccc aaacatgagt tttggaccta agtagtgga ttgggcatat tcgttgcgaa  11760
```

| | | | | | |
|---|---|---|---|---|---|
| aaacgaagaa | atggttccga | tggcaaaaac | tcgtgctttt | atgcaccccg | acaccgttt  11820 |
| tcggaatggg | tgacgtgcgg | caacgaaatt | gtgcgaaacc | accccaaaca | tgagttttgg  11880 |
| acctaaagta | gtgtattggg | catgttcgtt | gcgaaaaacg | aagaaatggt | tccggtggca  11940 |
| aaaactcctc | cttttatgca | ccccgacacc | cgttttcgga | atgggtgacg | tgtgacatca  12000 |
| atattgcgcg | aaaccaccta | aacatgagt  | tttggaccta | aagtagttta | gtgggcatgt  12060 |
| tcattgcgaa | aaatgaagaa | atggtttcgg | tggcaaaaac | tcgtgcattg | tatgcacccc  12120 |
| gacaaccgtt | ttcggaatgg | gtgacgtgcg | acaacgaaat | tgtgcgaaac | caccccaaac  12180 |
| atgagttttg | gaccttaagt | agtggattgg | gcatgttcgt | tgcgaaaaaa | gaagaaatgg  12240 |
| ttccggtggc | aaaaactcgt | gcttttatgc | accacgacac | ccgttctcgg | aatgggtgac  12300 |
| gtgcggcaac | gaaattgcgc | gaaaccaccc | caaacatgag | ttttggacct | aaagtagtgg  12360 |
| attgggcatg | ttcgttgcaa | aaacgaaga  | aatggtttcg | gtggcaaaaa | cttgtgcatt  12420 |
| gtatgcaccc | cgacaaccgt | tttcggaatg | ggtgacgtgc | ggcaacgaaa | ttgagtgaaa  12480 |
| ccaccccaaa | catgagtttt | ggaccttaag | tagtggattg | gcatgttcg  | ttgcgaaaaa  12540 |
| agaagaaatg | gttctggtgg | caaaaactcg | tgcttttatg | cacccccgac | accgttttc   12600 |
| ggaatggttg | acgtgcggca | acgaaattgc | gcgaaaccac | cctaaacatg | agttttggac  12660 |
| ctaaagtagt | ttagtgggca | tgtttgttgc | aaaaaacgaa | gaaatggttc | cggtggcaaa  12720 |
| aactcctgct | ttgaatgcac | cccaacaccc | gttttcggaa | tgggtgacgt | gcggcaaaga  12780 |
| aattgcgcga | aaccacccca | aacatgagtt | ttggacctaa | agtagtggat | tgggcatatt  12840 |
| cgttgcgaaa | aacgaagaaa | tggttccggt | ggcaaaaact | cgtgctttta | tgcacccga   12900 |
| cacccgtttt | cggaatgggt | gacgtgcggc | aacgaaattg | cgcgaaacca | ccccaaacat  12960 |
| gagttttgga | cctaaagtag | tgtattggc  | atgttcattc | gaaaaacga  | agaaatggtt  13020 |
| ccggtggcaa | aaactcctgc | ttttatgcac | cccgacaccc | gttttcggaa | tgggtgacgt  13080 |
| gcgacatcga | tattgcggtg | aaaccaccca | aacatgagt  | tttggaccta | aagtagttta  13140 |
| gtgggcatgt | tcgttgcgaa | aaatgaagaa | atggttcgg  | tggcaaaaac | tcgtgcattg  13200 |
| tatgcacgac | aaccgttttc | ggaatgtgtg | acgtgcggca | acgaaattgc | gtgaaaccac  13260 |
| cccaaacatg | agttttggac | ctaaattagt | ggatttggca | tgttcgttgc | aaaaaacgaa  13320 |
| gaaatggttt | cggtggcaaa | aactcgtgca | ttgtatgcac | cccgacaacc | gttttcggaa  13380 |
| tgggtgacgt | gcagcaacga | aattgcgcga | aaccacccca | aacatgagtt | tggaccttta  13440 |
| agtagtggat | tgggcatgtt | cattgcgaaa | aagaagaaa  | tggttctgat | agcaaaaact  13500 |
| cgtgctttta | tgcacccga  | cacccgtttt | cggaatggtt | gacgtgcggc | aacgaaattg  13560 |
| cgcgaaacca | ccctaaacat | gagttttggc | cctaaagtag | tttagtgggc | atgtttgttg  13620 |
| cgaaaaacga | agaaatggtt | ccggtggcaa | aaacttgtgc | tttgaatgca | ccccgacacc  13680 |
| catttttgga | atgggtgacg | tgcggcaacg | aaattgcgcg | aaaccacccc | aaacttgagt  13740 |
| tttggaccta | agtagtgga  | ttgggcatat | tcgttgcgaa | aaacgaagaa | atggttccag  13800 |
| tggcaaaaac | tcgtgctttt | atgcaccccg | acacctgttt | tcggaatggg | tgacgtgcgg  13860 |
| caacgaaatt | gcgtgaaacc | acacgaaata | tgagttttga | acctaaagta | gtggattggg  13920 |
| catgttcgtt | gcgaaaaacg | aagaaatggt | tccagtggca | aaaactcgtg | cttttatgca  13980 |
| ccctgacacc | cgttctcgga | atgggtgatg | tgcgacaacg | aaattgcgcg | aaaccacccc  14040 |
| aaacatgagt | tttggaccta | agtagtgga  | ttgggcatgt | tcgttgcaaa | aacgaagaa   14100 |
| atggtttcgg | tggcaaaaac | tcgtgcattg | tatgcacccc | gacaaccgtt | ttcggaatgg  14160 |

```
gtgacgtgcg gcaacgaaat tgcgcgaaac caccccaaac aagagttttg gaccttaaat    14220
agtggattgg gcatgttcat tgcgaaaaaa gaaagaaatg gttctggtag caaaaactcg    14280
tgcttttatg caccccgaca cccgttttcg gaatggttga cgtgcggcaa cgaaattgcg    14340
cgaaaccacc ctaaacatga gttttggacc taaagtagtt tagtgggcat gtttgttgcg    14400
aaaaacgaag aaatggttcc ggtggcaaaa acttgtgctt tgaatgcacc ccgacacccg    14460
tttttggaat gggtgacgtg cggcaacgaa attgcgcgaa accacccaa acttgagttt    14520 tggacctaaa gtagtggatt gggcatattc gttgcgaaaa acgaagaaat ggttccagtg    14580
gcaaaaactc gtgcttttat gcaccccgac acccgttttc ggaatgggtg acgtgcgaca    14640
acgaaattgc gtgaaaccca ccccaaacat gagttttgaa cctaaagtag tggattgggc    14700
atgttcgttg cgaaaaacga gaaatggtt ccggtggcaa aaactcgtgc ttttatgcac    14760
cccgacaccc gttctcggaa tgggtgacgt gcggcaacga aattgcgcga accacccaa    14820 aacatgagtt ttggaccaaa agtagtggat tgggcatgtt cgttgcgaaa aacgaagaaa    14880
tggtttcggt ggcaaaaaca cgtgcattgt atgcaccccg acaactgttg ggcctatgct    14940
tcgtcgccga aggtcttaca ggaagaagcg gtcttcgact gaagttgttt gtataagatg    15000
gccgaaggtt cctcttcgtg gagcttcggt attacaaacc gacttaaaga tagaatgacc    15060
ttttagtcca taaaggtctg agtcaatgtt gtaagctttt ataagggggta tacttgtaat    15120 ttctcacagg ctgcgtcctg tgcctataaa tagtgaacag tattcccttta ctgttcacgc    15180 attctggtaa ttaccatcgc atcttctgga atccaacctt tgtcaaggca gaggtattat    15240
tgtattcaat gattcaatat attaagtaaa tataatataa ttcgtttatg atttatttac    15300 cccttttttat acctttaatt ttatgttgtc tcacaatatg tattgaaatt tttttacgaa    15360
gacttaagct tcgtaatttt actctcatca accttcgtcc aaggcccatt atcctcaagg    15420
gaataatgtt tcatggacga aggacgttaa catttaacac tttatgttgc cttgttctta    15480
attcatagca cttgagaaca agtccccaac attggcgccc acctccggtg aactcacttc    15540
cactttttga gctgatggct tcgttcaacg atcaagctgg agctgcttcg gacccgaagc    15600
tggtgctccc gatcacaggt ggttcgtcct cagagccagc taacaagaaa caaagaaag    15660 aagcacagag aagggtacat catgttgggg tgcaaggacc cttcatcaag tcaagatggt    15720
ctcacattcc tattccttc tcccaagagg accttcagct caaggattac ccacacaacg    15780
atgccatggt tatctcttgt gttatcaaag gatttctggt ccacaatgtc ctggttgaca    15840
taggcagtgc agctgacatc atatttgcta aggccttcag acaaatgcaa gagccagaag    15900
ataagattca tgatgctaca catcctctct gtggcttcgg aggaagacag attgtagcac    15960
tgggcaagat caccatgtca gtgaccttcg ggttcatcaa caacactaga actgagcaag    16020
ttgtgtttga cattgttgac atggaatacc cttacaatgc aattattggt cgtggcaccc    16080
tcaatgcttt cgaagcaatt cttcatcctg cctatctttg catgaagata ccttcggatc    16140
aaggacccat cgctatccat ggaagtcagg aagctgccag aagggccgaa ggcaattgga    16200
ctgactcaaa aagcaatcca taacatagat ggagctgaag cttgtgaaca gtacaaattc    16260
agaagggaga aagcagcttc agcagatcag ccgaagccta tgctcttatg tgaggacata    16320
gcagaggcag aaggtgctgt taggctctca attatccgaa gagcaggaga aaaccttgat    16380
aaggtttttt gttcaacaac aaagatgttt ttgcatggtc agctaatgat ctctgcggag    16440 taaatagggga tgttattgaa cactcgctca atgttgaccc atccttcaga cccgaaaagc    16500
agaggcttcg gaaaatgtca gatgataagg ccgaaggtgc tcgtaacgaa gtacaaaaga    16560
```

```
cttctcagtg caggagttat cagagaagta aagtacccag aatggctagc taacactgtt   16620
atggtaaaaa aggccaatgg taagtggcga atgtgtatcg attttacaga tcttaacaag   16680
gcttgtccga aggatgaatt cccattgcca aggatagact ctttagttga tgcagcagct   16740
tcttcagagc tcatgagtct gttagactgt tattcaggct accatcaaat ctggatgaag   16800
aaggaagatg agccaaagac tagcttcata actccaaggg gcacatattg ctatcttcgg   16860
atgcctgagg ggctcaaaaa cgctggagga gtttcagca gaatgactgc gaaggttctc    16920
cagtctcaga taggcagaaa tgtgctaact tatgttgatg acatcattgt aaaaagcacg   16980
aaacaggaga atcatattgc tgatctgcag gagaccttcg ccagtttcag acaagctggt   17040
ttaaagctga atccagaaaa atgcgtcttc ggagtaaaga aggggaaatt tcttggatgc   17100
ttggtttcaa caagggaat tgaagctaat ccaagtaaaa ttgaagctat acttcggatg    17160
gagccaccaa ctacaaagaa gggggctcaa agattgacag gaaggttggc atctctcaat   17220
agattcatat ccagatcagc agaaagaaac ttaccattct tcgaagtgct gaagtcagcc   17280
gaagtctttc aatgggacc aattcagcag aaggccttcg aagagctgaa acagtatttg     17340
atagatctaa cagcactaac cccacctacg ccagggggctc ctttgttatt atatgtggca   17400
gcttcgcact cagcggtaag tgcagcactt gtccaggaga agcttgatgg ccaagtcaga   17460
aagcaggtcc gagtgtattt tgtatctgaa gttcttagta tatcaaagaa aaactacaca   17520
gaattggaga aggtgtttga aagggaatta ggcttacacc tagtccctaa ttaattttgg   17580
tggttgaatt gcccaacaca aaatattgaa ctaactagtt tgcccaagtg tatagattat   17640
acaggtgtaa aaggttcaca ctcagccaat aaaaagatca agtgttggat tcaacaaaag   17700
agcaaagggc caaccgaagg cacctctggt ctggcgcacc ggactgtccg gtgtgccacc   17760
ggacagtgtc cggtgcacca ccggacatgt ccggtgcacc agaggactcc aactcaaact   17820
cggcaccttc gggaatttcc agaggcgact ccgctaaaat tcaccggact gtccggtgta   17880
caccggacag tgtccggtgc tccaagggaa gtcggcctca ggaactcgcc agcttcggga   17940
aacgccaacg gctagtccgc tataattcac cggacatgtc cggtgcaact ccggagcaac   18000
ggctacctcc gcgccaacag ctacccgcgg cgcattaaaa tgcgcgcgca gcgcgcgcag   18060
aagtcaggcg cgcccatact ggcacaccgg acagcaaaca gtacctgtcc ggtgtgcacc   18120
ggacacccag gcgggcccac aagtcagaag ctccaacggt cagaatccaa cggcagtgat   18180
gacgtggcag ggggcaccgg actgtccggt gtgcaccgga ctgtctggtg cgccatcgag   18240
cagacagcct cccaacggcc acttttggtg gttggggcta taaataccc aaccaccca     18300
ccattcattg catccaagtt ttccacttcc caactactac aagagctcta gaattcaatt   18360
ctagacacac taaagagatc aaatcctctc caaattccac acaacgccat agtgattaga   18420
gagagagatt tgcttgtgtt ctttcgagct cttgcgcttg gattgctttc gtctttcttg   18480
attctttcat tgcgatcaaa ctcacttgta aattgagaca agagacacca aacttgtggt   18540
gatccttgtg ggaactttgt gttccaagtg attgagaaaa gaaagctcac tcgatccgtg   18600
gatcgtttga gagagagaag ggttgaaaga gacccggcct ttgtggcctc ctcaacgggg   18660
agtaggtttg caagaaccga acctcggtaa aacaaatctc cgtatctcac ttgcttattc    18720
gcttgggatt tgttttgcgc cctctctcgc ggacttgttt ccttattact aacgctaacc   18780
cggcttgtag ttgtgtttat atttgtaaat ttcagtttcg ccctattcac cccccccct    18840
ctaggcgact ttcaattggt atcagagctc ggtgcttcat tagagcctaa ccgctcgaag   18900
tgatgtcggg agatcacgcc aagaaggaga tggagaccgg cgaaaagccc actacaagcc   18960
```

```
                                                       -continued
acgggagcac ttcatcggaa aagtcccgca ccaagaggaa ggagaagaag aagatctcct  19020
ccaacaaagg gaaggagaag aaatcctcct ctcaccacaa agagaagaag gaaaaaatct  19080
tcttcccaca agccgcatcg gagtggggac aagaagaaaa ggatgaggaa ggtggtctac  19140
tacgagaccg attcttcatc ggcatccacc tccggatccg acgcggcatc cgtcacttct  19200
aagcgccaag agcgcaagaa gtatagtaag attccctac gctaccctcg catttccaaa  19260
catacacctt tactttccgt cccattaggc aaaccaccaa cttttgatgg tgaagattac  19320
gctagttgga gcgatttaat gcgatttcat ctaacctcgc tccacaaaag catatgggat  19380
gttgttgagt ttggtgcaca ggtaccatcc gtaggggatg aagactatga tgaggatgag  19440
gtggcccaaa tcgagcactt caactctcaa gcgacaacaa tactactcgc ctctctaagt  19500
agagaggagt acaacaaagt acaagggttg aagagtgcca aggaggtttg ggatgtgctc  19560
aaaaccgcgc acgagggaga cgagctcacc aagatcacca agcgggaaac gatcgagggg  19620
gagctcggtc ggttccggct tcgcaaaggg gaagagccac aacacatgta caaccggctc  19680
aagaccttgg tgaaccaagt gcgcaacctc gggagtgtaa agtgggatga ccatgaaatg  19740
gttaaggtta ttctaagatc                                              19760
```